(12) United States Patent
Molino et al.

(10) Patent No.: US 7,956,050 B2
(45) Date of Patent: Jun. 7, 2011

(54) ARYL- AND HETEROARYL-SUBSTITUTED TETRAHYDROBENZAZEPINES AND USE THEREOF TO BLOCK REUPTAKE OF NOREPINEPHRINE, DOPAMINE, AND SEROTONIN

(75) Inventors: Bruce F. Molino, Slingerlands, NY (US); Shuang Liu, Schenectady, NY (US); Aruna Sambandam, Delmar, NY (US); Peter R. Guzzo, Niskayuna, NY (US); Min Hu, Watervliet, NY (US); Congxiang Zha, Schenectady, NY (US); Kassoum Nacro, Albany, NY (US); David D. Manning, Duanesburg, NY (US); Matthew L. Isherwood, Delmar, NY (US); Kristen N. Fleming, Clifton Park, NY (US); Wenge Cui, Clifton Park, NY (US); Richard E. Olson, Orange, CT (US)

(73) Assignee: Albany Molecular Research, Inc., Albany, NY (US)

( * ) Notice: Subject to any disclaimer, the term of this patent is extended or adjusted under 35 U.S.C. 154(b) by 241 days.

(21) Appl. No.: 11/487,884

(22) Filed: Jul. 17, 2006

(65) Prior Publication Data

US 2007/0021408 A1 Jan. 25, 2007
US 2008/0207595 A9 Aug. 28, 2008

Related U.S. Application Data

(60) Provisional application No. 60/700,057, filed on Jul. 15, 2005.

(51) Int. Cl.
*A61P 25/00* (2006.01)
*A61K 31/55* (2006.01)
*C07D 223/16* (2006.01)
(52) U.S. Cl. .................. 514/213.01; 540/593
(58) Field of Classification Search ............ 514/213.01; 540/593
See application file for complete search history.

(56) References Cited

U.S. PATENT DOCUMENTS

| 3,225,011 A | 12/1965 | Preston et al. |
| 3,225,031 A | 12/1965 | Sherlock |
| 3,642,993 A | 2/1972 | Harcourt et al. |
| 3,655,651 A | 4/1972 | Harcourt et al. |
| 3,666,763 A | 5/1972 | Grethe et al. |

(Continued)

FOREIGN PATENT DOCUMENTS

CA 2015114 10/1990

(Continued)

OTHER PUBLICATIONS

Euerby et al., Methylthio Activating Groups in the Synthesis of Tetrahydroisoquinolines and Tetrahydro-2-benzazepines from N-Allyl- and N-Cinnamyl-benzylamines, Journal of Chemical Research, vol. 2, pp. 40-41, 1987.*
Aihara et al., "Increasing 5-Lipoxygenase Inhibitory Activities by Oxidative Conversion of o-Methoxyphenols to Catechols Using a $Cu^{2+}$-Ascorbic Acid-$O_2$ System," *Chem. Pharm. Bull.* 38(3):842-844 (1990).
Berge et al., "Pharmaceutical Salts," *J. Pharm. Sci.* 66(1):1-19 (1977).
Banerji et al., "Studies on Single-Electron Transfer Reagents. Part IV Reaction of Nitrogen Heterocycles with Sodium Naphthalenide," *Tetrahedron* 50(30):9079-9096 (1994).
Blomberg et al., "The Barbier Reaction—A One Step Alternative for Syntheses via Organomagnesium Compounds," *Synthesis* pp. 18-30 (1977).
Bobowski & Gottlieb, "4-Substituted 1,2,3,4-tetrahydro-3,3-dimethylisoquinolines. II.," *J. Heterocyclic Chem.* 19(1):21-27 (1982).
Brown & Dyke, "1,2-Dihydroisoquinolines. II. Berbine Synthesis," *Tetrahedron* 22(8):2429-35 (1966).
Brown & Dyke, "1,2-Dihydroisoquinolines. III. Dimerization," *Tetrahedron* 22(8):2437-2443 (1966).
Bundgaard, "Means to Enhance Penetration," *Adv. Drug Delivery Rev.* 8:1-38 (1992).
Burrows et al., "Antidepressant Efficacy and Tolerability of the Selective Norepinephrine Reuptake Inhibitor Reboxetine: A Review," *J. Clin. Psychiatry* 59(Suppl. 14):4-7 (1998) (98819-76-2 Registry (Reboxetine)).
Chandrasekhar et al., "Highly Efficient Synthesis of 3-alkyl/aryl-4-aryl-1,2,3,4-tetrahydroisoquinolines from N,N-dibenzylaminols," *Tetrahedron Lett.* 43(10):1885-1888 (2002).

(Continued)

*Primary Examiner* — Brenda L Coleman
(74) *Attorney, Agent, or Firm* — LeClairRyan

(57) ABSTRACT

The compounds of the present invention are represented by the following aryl- and heteroaryl-substituted tetrahydrobenzazepine and dihydrobenzazepine derivatives having formulae I(A-E) and formula (II):

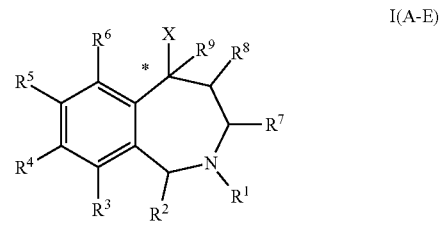

I(A-E)

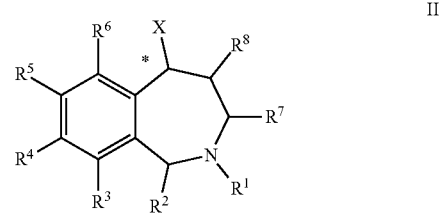

II where the carbon atom designated * is in the R or S configuration, and the substituents X and $R^1$-$R^9$ are as defined herein.

28 Claims, No Drawings

U.S. PATENT DOCUMENTS

| | | | |
|---|---|---|---|
| 3,947,456 | A | 3/1976 | Rheiner |
| 4,080,449 | A | 3/1978 | Croisier et al. |
| 4,113,869 | A | 9/1978 | Gardner |
| 4,340,600 | A | 7/1982 | Brenner et al. |
| 4,564,613 | A | 1/1986 | Boltze et al. |
| 4,843,071 | A | 6/1989 | Hohenwarter |
| 4,902,710 | A | 2/1990 | Foster et al. |
| 5,098,901 | A | 3/1992 | Johnson et al. |
| 5,440,033 | A | 8/1995 | Berger et al. |
| 5,444,070 | A | 8/1995 | Moldt et al. |
| 5,532,244 | A | 7/1996 | Wong et al. |
| 5,607,939 | A | 3/1997 | Kato et al. |
| 5,654,296 | A | 8/1997 | Kato et al. |
| 5,789,449 | A | 8/1998 | Norden |
| 6,015,791 | A | 1/2000 | Gyorkos et al. |
| 6,121,261 | A | 9/2000 | Glatt et al. |
| 6,136,803 | A | 10/2000 | Freedman et al. |
| 6,579,885 | B2 | 6/2003 | Beck et al. |
| 6,911,453 | B2 | 6/2005 | Hofmeister et al. |
| 7,084,152 | B2 | 8/2006 | Beck et al. |
| 7,622,462 | B2 | 11/2009 | Schoenfeld et al. |
| 2003/0203920 | A1 | 10/2003 | Beck et al. |
| 2004/0002495 | A1 | 1/2004 | Sher et al. |
| 2005/0020597 | A1 | 1/2005 | Beck et al. |
| 2006/0025435 | A1 | 2/2006 | Beck et al. |
| 2006/0052378 | A1 | 3/2006 | Molino et al. |
| 2006/0063766 | A1 | 3/2006 | Molino et al. |
| 2006/0111385 | A1 | 5/2006 | Molino et al. |
| 2006/0111386 | A1 | 5/2006 | Molino et al. |
| 2006/0111393 | A1 | 5/2006 | Molino et al. |
| 2006/0111394 | A1 | 5/2006 | Molino et al. |
| 2006/0111395 | A1 | 5/2006 | Molino et al. |
| 2006/0111396 | A1 | 5/2006 | Molino et al. |
| 2006/0217409 | A1 | 9/2006 | Beck et al. |
| 2007/0281920 | A1 | 12/2007 | Schoenfeld et al. |

FOREIGN PATENT DOCUMENTS

| | | | |
|---|---|---|---|
| CH | 538 477 | | 8/1973 |
| CS | 192861 | B1 | 9/1979 |
| DE | 2 062 001 | | 7/1971 |
| EP | 0 002 624 | A1 | 6/1979 |
| EP | 0 140 070 | A1 | 5/1985 |
| EP | 0 360 390 | A1 | 3/1990 |
| EP | 0 394 989 | B1 | 10/1990 |
| EP | 0 400 319 | A1 | 12/1990 |
| EP | 0 428 434 | A2 | 5/1991 |
| EP | 0 429 366 | B1 | 5/1991 |
| EP | 0 430 771 | B1 | 6/1991 |
| EP | 0 436 334 | B1 | 7/1991 |
| EP | 0 443 132 | B1 | 8/1991 |
| EP | 0 463 810 | A1 | 1/1992 |
| EP | 0 482 539 | B1 | 4/1992 |
| EP | 0 498 069 | B1 | 8/1992 |
| EP | 0 499 313 | B1 | 8/1992 |
| EP | 0508425 | A1 | 10/1992 |
| EP | 0 512 901 | B1 | 11/1992 |
| EP | 0 512 902 | A1 | 11/1992 |
| EP | 0 514 273 | A1 | 11/1992 |
| EP | 0 514 274 | A1 | 11/1992 |
| EP | 0 514 275 | A1 | 11/1992 |
| EP | 0 514 276 | A1 | 11/1992 |
| EP | 0 515 681 | A1 | 12/1992 |
| EP | 0 517 589 | B1 | 12/1992 |
| EP | 0 520 555 | A1 | 12/1992 |
| EP | 0 522 808 | A2 | 1/1993 |
| EP | 0 528 495 | A1 | 2/1993 |
| EP | 0 532 456 | B1 | 3/1993 |
| EP | 0 533 280 | B1 | 3/1993 |
| EP | 0 536 817 | A1 | 4/1993 |
| EP | 0 545 478 | A1 | 6/1993 |
| EP | 0 558 156 | A2 | 9/1993 |
| EP | 0 577 394 | B1 | 1/1994 |
| EP | 0 585 913 | B1 | 3/1994 |
| EP | 0 599 338 | A2 | 6/1994 |
| EP | 0 599 538 | A1 | 6/1994 |
| EP | 0 610 793 | A1 | 8/1994 |
| EP | 0 634 402 | A1 | 1/1995 |
| EP | 0679642 | A1 | 11/1995 |
| EP | 0 686 629 | A2 | 12/1995 |
| EP | 0 693 489 | A1 | 1/1996 |
| EP | 0 694 535 | A1 | 1/1996 |
| EP | 0 699 674 | A1 | 3/1996 |
| EP | 0 707 006 | B1 | 4/1996 |
| EP | 0 708 101 | B1 | 4/1996 |
| EP | 0 709 375 | A2 | 5/1996 |
| EP | 0 709 376 | A2 | 5/1996 |
| EP | 0 714 891 | A1 | 6/1996 |
| EP | 0 723 959 | A1 | 7/1996 |
| EP | 0 733 632 | A1 | 9/1996 |
| EP | 0 776 893 | A1 | 6/1997 |
| EP | 0 699 655 | B1 | 9/1997 |
| EP | 0 520 555 | B1 | 9/1999 |
| EP | 1 122 252 | A1 | 8/2001 |
| FR | 2848210 | A1 | 6/2004 |
| GB | 1242963 | | 8/1971 |
| GB | 2 266 529 | A | 11/1993 |
| GB | 2 268 931 | A | 1/1994 |
| GB | 2 269 170 | A | 2/1994 |
| GB | 2 269 590 | A | 2/1994 |
| GB | 2 271 566 | A | 4/1994 |
| GB | 2 271 774 | A | 4/1994 |
| GB | 2 292 144 | A | 2/1996 |
| GB | 2 293 168 | A | 3/1996 |
| GB | 2 293 169 | A | 3/1996 |
| GB | 2 302 689 | A | 1/1997 |
| JP | 59013761 | A | 1/1984 |
| JP | 63094239 | A | 4/1988 |
| JP | 04193867 | | 7/1992 |
| JP | 9301953 | A | 11/1997 |
| RU | 2149158 | C1 | 5/2000 |
| WO | WO 90/05525 | | 5/1990 |
| WO | WO 90/05729 | | 5/1990 |
| WO | WO 91/09844 | | 7/1991 |
| WO | WO 91/18899 | | 12/1991 |
| WO | WO 92/01688 | | 2/1992 |
| WO | 92/08173 | A1 | 4/1992 |
| WO | WO 92/06079 | | 4/1992 |
| WO | WO 92/12151 | | 7/1992 |
| WO | WO 92/15585 | | 9/1992 |
| WO | WO 92/17449 | | 10/1992 |
| WO | WO 92/20661 | | 11/1992 |
| WO | WO 92/20676 | | 11/1992 |
| WO | WO 92/21677 | | 12/1992 |
| WO | WO 92/22569 | | 12/1992 |
| WO | WO 93/00330 | | 1/1993 |
| WO | WO 93/00331 | | 1/1993 |
| WO | WO 93/01159 | | 1/1993 |
| WO | WO 93/01165 | | 1/1993 |
| WO | WO 93/01169 | | 1/1993 |
| WO | WO 93/01170 | | 1/1993 |
| WO | 93/08174 | A1 | 4/1993 |
| WO | WO 93/06099 | | 4/1993 |
| WO | WO 93/09116 | | 5/1993 |
| WO | WO 93/10073 | | 5/1993 |
| WO | WO 93/14084 | | 7/1993 |
| WO | WO 93/14113 | | 7/1993 |
| WO | WO 93/18023 | | 9/1993 |
| WO | WO 93/19064 | | 9/1993 |
| WO | WO 93/21155 | | 10/1993 |
| WO | WO 93/21181 | | 10/1993 |
| WO | WO 93/23380 | | 11/1993 |
| WO | WO 93/24465 | | 12/1993 |
| WO | WO 94/00440 | | 1/1994 |
| WO | WO 94/01402 | | 1/1994 |
| WO | WO 94/02461 | | 2/1994 |
| WO | WO 94/02595 | | 2/1994 |
| WO | WO 94/03429 | | 2/1994 |
| WO | WO 94/03445 | | 2/1994 |
| WO | WO 94/04494 | | 3/1994 |
| WO | WO 94/04496 | | 3/1994 |
| WO | WO 94/05625 | | 3/1994 |
| WO | WO 94/07843 | | 4/1994 |
| WO | WO 94/08997 | | 4/1994 |
| WO | WO 94/10165 | | 5/1994 |
| WO | WO 94/10167 | | 5/1994 |
| WO | WO 94/10168 | | 5/1994 |

| | | |
|---|---|---|
| WO | WO 94/10170 | 5/1994 |
| WO | WO 94/11368 | 5/1994 |
| WO | WO 94/13639 | 6/1994 |
| WO | WO 94/13663 | 6/1994 |
| WO | 94/14776 A2 | 7/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |
| WO | WO 94/29309 | 12/1994 |
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | 96/06067 A1 | 2/1996 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | 96/26190 A1 | 8/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |
| WO | WO 97/21702 | 6/1997 |
| WO | WO 97/23458 | 7/1997 |
| WO | WO 97/36876 | 10/1997 |
| WO | WO 97/49710 | 12/1997 |
| WO | 98/02432 A1 | 1/1998 |
| WO | 98/21186 A1 | 5/1998 |
| WO | WO 98/40358 | 9/1998 |
| WO | 99/01434 A1 | 1/1999 |
| WO | 99/61414 A1 | 2/1999 |
| WO | 99/45013 A1 | 9/1999 |
| WO | 00/27802 A1 | 5/2000 |
| WO | 00/38618 A2 | 7/2000 |
| WO | 00/46215 A1 | 8/2000 |
| WO | 01/03680 A2 | 1/2001 |
| WO | 01/55118 A1 | 2/2001 |
| WO | WO 01/32624 A1 | 5/2001 |
| WO | 01/96312 A1 | 12/2001 |
| WO | 02/06241 A1 | 1/2002 |
| WO | WO 02/04455 A3 | 1/2002 |
| WO | 02/057257 A1 | 7/2002 |
| WO | 02/100860 A2 | 12/2002 |
| WO | 2004/037788 A1 | 5/2004 |
| WO | 2004/087131 A1 | 10/2004 |
| WO | 2004/089919 A1 | 10/2004 |
| WO | 2005/087235 A1 | 9/2005 |
| WO | 2007/011820 A2 | 1/2007 |
| WO | WO 2007/137953 A1 | 12/2007 |

OTHER PUBLICATIONS

Cherpillod et al., "A Controlled Trial with Diclofensine, A New Psychoactive Drug, in the Treatment of Depression," *J. Int. Med. Res.* 9(5):324-329 (1981).

Cliffe et al., "(*S*)-*N-tert*-Butyl-3-(4-(2-methoxyphenyl)-piperazin-l-yl)-2-phenylpropanamide [(*S*)-WAY—100135]: A Selective Antagonist at Presynaptic and Postsynaptic-5-HT$_{1A}$ Receptors," *J. Med. Chem.* 36:1509-10 (1993).

Dandridge et al., "Synthesis, Resolution, Absolute Stereochemistry, and Enantioselectivity of 3', 4'-Dihydroxynomifensine," *J. Med. Chem.* 27:28-35 (1984).

Desai et al., "Relationship Between in Vivo Occupancy at the Dopamine Transporter and Behavioral Effects of Cocaine, GBR 12909 [1-{2-[Bis-(4-fluorophenyl)methoxy]ethyl}-4-(3-phenylpropyl)piperazine], and Benztropine Analogs," *J. Pharmacol. Exp. Ther.* 315(1):397-404 (2005).

Dudley et al., "The Actions of Xylamine on Central Noradrenergic Neurons," *J. Pharm. Exp. Ther.* 217(3):834-840 (1981).

Gao et al., "Asymmetric Hetero Diels-Alder Reaction Catalyzed by Stable and Easily Prepared CAB Catalysts," *Tetrahedron* 50(4):979-988 (1994).

Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," *J. Org. Chem.* 56(10):3362-3369 (1991).

Hudlicky, "Fluorination with Diethylaminosulfur Trifluoride and Related Aminofluorosulfuranes," *Organic Reactions* 35:513-637 (1985).

Hyttel, "Pharmacological Characterization of Selective Serotonin Reuptake Inhibitors (SSRIs)," *Int. Clin. Psychopharmacol.* 9(Suppl. 1):19-26 (1994) (61869-08-7 Registry (Paroxetine); 59729-32-7 Registry (Citalopram); 79559-97-0 Registry (Sertraline); 54910-89-3 Registry (Fluoxetine); 54739-18-3 Registry (Fluvoxamine)).

Ishikura et al., "The Synthesis of 4-Substituted Isoquinoline Derivatives from Diethyl (4-Isoquinolyl) Borane," *Heterocycles* 26:1603-1610 (1987).

Jacob et al., "Dopamine Agonist Properties of N-Alkyl-4-(3,4-dihydroxyphenyl)-1,2,3,4-tetrahydroisoquinolines," *J. Med. Chem.* 24:1013-1015 (1981).

Kakeya et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(*Z*)-2-Methoxyiminoacetamido]-3-Methyl-3-Cephem-4-Carboxylic Acid," *Chem. Pharm. Bull.* 32(2):692-698 (1984).

Kametani et al., "Studies on the Synthesis of Heterocyclic Compounds," *Tetrahedron* 31:235-238 (1975).

Kihara et al., "A Convenient Synthesis of 4-Substituted 1,2,3,4-Tetrahydroisoquinolin-4-OLS by a Novel Intramolecular Barbier Reaction and by an Insertion Reaction: Reaction Scope and Limitations," *Tetrahedron* 48(1):67-78 (1992).

Kihara et al., "Synthesis and Enantioselectivity of Optically Active 1- and 3-Substituted 4-Phenyl-1,2,3,4-Tetrahydroisoquinolin-4-ols and Related Compounds As Norepinephrine Potentiators," *Chem. Pharm. Bull.* 43(9):1543-1546 (1995).

Kihara et al., "Synthesis and Pharmacological Evaluation of Phenolic 2-Methyl-4-Phenyl-1,2,3,4,-Tetrahydroisoquinolin-4-ols As New Norepinephrine Potentiator," *Drug Design Dis.* 11(3):175-183 (1994).

Knabe & Herbort, "Dehydrogenation of Tertiary Amines with Aercury (II) Acetate in the Presence of EDTA. XIII. Oxidative Dimerization of 6,7-dimethoxy-2-methyl-1,1-diethyl-1,2,3,4- tetrahydroisoquinoline," *Archiv. der Pharmazie. und Berichte der Deutschen Pharmazeutischen Gesellschaft* 300(9):774-783 (1967).

Knabe & Renz, "Synthesis of 3,4'-Biisoquinolines,"*Archiv. der Pharmazie.* (Weinheim, Germany) 307(8):612-622 (1974).

Maryanoff et al., "Pyrroloisoquinoline Antidepressants. 2. In-Depth Exploration of Structure-Activity Relationships," *J. Med. Chem.* 30(8):1433-1454 (1987).

Middlemiss et al., "Centrally Active 5-HT Receptor Agonists and Antagonists," *Neurosci. Biobehavioral Rev.* 16:75-82 (1992).

Miller et al., "An Efficient Synthesis of 4-Aryl-1,2,3,4-Tetrahydroisoquinolines," *Synthetic Com.* 24(8):1187-1193 (1994).

Mondeshka et al., "Synthesis, Antiulcer and Antidepressive Activity of 4-(4-Halophenyl)-2-Phenyl-1,2,3,4-Tetrahydroisoquinolines," *Il Farmaco* 49:475-480 (1994).

Müller, "Current St. John's Wort Research from Mode of Action to Clinical Efficacy," *Pharmacological Research* 47:101-109 (2003).

Nielsen et al., "Glycolamide Esters as Biolabile Prodrugs of Carboxylic Acid Agents: Synthesis, Stability, Bioconversion, and Physicochemical Properties," *J. Pharm. Sci.* 77(4):285-298 (1988).

Salama et al., "Antigenic Determinants Responsible for the Reactions of Drug-Dependent Antibodies with Blood Cells," *Br. J. Haematol.* 78:535-539 (1991).

Seebach et al., "Alkylation of Amino Acids without Loss of the Optical Activity: Preparation of α-Substituted Proline Derivatives. A Case of Self-Reproduction of Chirality," *J. American Chem. Soc.* 105(16):5390-5398 (1983).

Stille, "Zur pharmakologischen Prufung von Antidepressiva am Beispiel eines Dibenzodiazepins," *Arzneimittel-Forschung* 14:534-537 (1964) (English summary included).

Sugiura & Hamada, "Studies on Nitrogen-Containing Heterocyclic Compounds XXXV. Syntheses and Reduction of 4-Amino-2-cyano-1,3-dimethoxy-1,2,3,4-tetrahydroisoquinolines," *Yakugaku Zasshi* 99(6):556-563 (1979).

Sugiura et al., "Synthesis and Stereochemistry of 3,7-Diazatricyclo[4.2.2.2$^{2,5}$]dodeca-9,11-dienes Derived By [4+4] Cyclodimerization of 2,3-Dihydroisoquinoline Derivatives," *Chem. Pharm. Bull.* 46(12):1862-1865 (1998).

Tirelli et al., "Differential Effects of Direct and Indirect Dopamine Agonists on the Induction of Gnawing in C57BI/6J Mice," *J. Pharm. Exp. Therapy* 273(1):7-15 (1995).

Trepanier et al., "3,4-Dihydroisocarbostyril and 1,2,3,4-Tetrahydroisoquinoline Derivatives of Ephedrine," *J. Med. Chem.* 16(4):342-347 (1973).

Uno & Okada, "A Novel Method for the Synthesis of 4-Isoquinolinols," *J. Heterocyclic Chem.* 28(2):341-346 (1991).

Venkov et al., "A New Synthesis of 1,2,3,4-Tetrahydro-2-Methyl-4-Phenylisoquinolines," *Synthesis* 253-255 (1990).

Zára-Kaczián et al., "8-Amino-4-Aryl-2Methyl-1,2,3,4-Tetrahydroisoquitilines: Reactions of the Amino Group Via the Diazonium Salts," *Acta Chimica Hungarica*, 12(4):573-584 (1989).

CAS No. 53885-32-8, Nov. 1984.
CAS No. 53885-23-7, Nov. 1984.
Beilstein No. 455853 (CAS 71730-66-0), 1979.
Beilstein No. 4048047 (CAS 17074-38-3, 17074-39-4), 1967.
Beilstein No. 4102323 (CAS 53885-34-0), 1974.
Beilstein No. 4341479 (CAS 134021-24-2), 1991.
Beilstein No. 4494373 (CAS 82416-61-3), 1982.
Beilstein No. 4774688 (CAS 133160-36-8), 1991.
Beilstein No. 4787749 (CAS 133043-12-6, 133160-34-6, 133160-35-7), 1991.
Beilstein No. 4787750 (CAS 133043-12-6, 133160-34-6, 133160-35-7), 1991.
Beilstein No. 4787836 (CAS 133043-20-6, 133043-31-9), 1991.
Beilstein No. 4787837 (CAS 133043-20-6, 133043-31-9), 1991.
Beilstein No. 4788234 (CAS 133043-19-3, 133043-30-8), 1991.
Beilstein No. 4788235 (CAS 133043-19-3, 133043-30-8), 1991.
Beilstein No. 4789758 (CAS 133043-21-7, 133043-22-8), 1991.

Ackerman et al., "A New Synthesis of 5-phenyl-2,3-dihydro- and 2,3,4,5-tetrahydro-1H-2-benzazepin-1-ones," *Canadian Journal of Chemistry* 50(23):3886-91 (1972).

Arany et al., "1,7-Electrocydization of Non-Stabilized Azomethine Ylides," *Tetrahedron Letters* 39(20):3267-8 (1998).

Arany et al., "1,7-Electrocyclization of Nonstabilized a,B:y,&-unsaturated azomethine Ylides," *Journal of the Chemical Society, Perkin Transactions 1: Organic and Bio-Organic Chemistry* 18:2605-8 (1999).

Armesto et al., "Novel Photoreactions of 2-aza-1,4-dienes in the Triplet Excited State and Via Radical-Cation Intermediates. 2-Aza-di-pi-methane Rearrangements Yielding Cyclopropylimines and N-vinylaziridines," *Journal of Organic Chemistry* 68(17):6661-71 (2003).

Brooks et al., "Cyclization of N-prop-2-ynylbenzylamines: Preparation of a 1,2-dihydroisoquinoline and a 2-benzazepine", *Journal of the Chemical Society [Section] C: Organic* 4:625-7 (1969).

Eberbach, "Azomethine Ylides. Synthesis of Product Class 11," *Science of Synthesis* 27:441-98 (2004).

Euerby et al., "A Convenient Procedure for the Reductive Desulfurization of Thioethers with Nickel Boride," *Synthetic Communications* 16(7):779-84 (1986).

Gast et al., "Cyclization Reactions with 2-(B-styryl)benzylamines. 5-Phenyl-1H-2-benzazepines," *Helvetica Chimica Acta* 60(5):1644-9 (1977) (Abstract).

International Search Report for International Patent Application No. PCT/US06/27574 (May 15, 2008).

Korkhova et al., "Derivatives of 2-benzazepine From 3-substituted 2-methylamino-1,4-naphthoquinones," *Zhurnal Organicheskoi Khimii* 11(10):2140-4 (1975).

Kuznetsov et al., "Skeletal Transformation of 2-methylamino-1,4-naphthoquinone Leading to 2-benzazepine Derivatives," *Zhurnal Organicheskoi Khimii* 11(4):808-23 (1975).

Pedrosa et al., "Diastereoselective Tandem 6-exo Carbolithiation Intramolecular Ring Opening in (-)-8-aminomenthol-derived Perhydrobenzoxazines. A New Synthesis of Enantiopure 4-substituted Tetrahydroisoquinolines and 2-azabenzonorbomanes," *Journal of the American Chemical Society* 123(9):1817-21 (2001).

Rajsner et al., "4,4-Bis(4-fluorophenyl)butylamines and Their Cyclic Analogs; An Efficient Synthesis of the Neuroleptic Penfluridol," *Collection of Czechoslovak Chemical Communications* 43(7):1760-77 (1978).

STN Registration No. 312614-52-2 (Jan. 3, 2001).
STN Registration No. 33643-70-8 (Nov. 16, 1984).

Takayama et al., "Triflic Acid Catalyzed Double-Cyclization of N,N-dibenzyl-2-propynylamine and Related Compounds," *Chemistry Letters* 8:865-6 (1978).

Thomas et al., "Voltammetric Electrochemical Detection for Normal-Phase High-Performance Liquid Chromatography," *Anal. Chem.* 60:2158-61 (1988).

Toda et al., "A Conformational Restriction Approach to the Development of Dual Inhibitors of Acetylcholinesterase and Serotonin Transporter as Potential Agents for Alzheimer's Disease," *Bioorganic and Medicinal Chemistry* 11 (20):4389-415 (2003).

Vogel et al., "Synthesis of Benzazepines and Their Rearrangement to Quinolines and pyrrolo[2,3-b] Quinolines," *Helvetica Chimica Acta* 52(7):1929-39 (1969) (Abstract).

Matthews et al., "Structure-Activity Relationships of Phenothiazines in Inhibiting Lymphocyte Motility as Determined by a Novel Flow Cytometric Assay," *Biochemical Pharmacology* 50(7):1053-1061 (1995).

Sanchez et al., "Total Synthesis of Racemic Lycoramine," *Journal of Organic Chemistry* 49(1):157-163 (1984).

Sawa et al., "Studies on the Syntheses of Analgesics. IV. Syntheses of 1,2,3,4-tetrahydro-5H-benzazepine Derivatives," *Chemical & Pharmaceutical Bulletin* 23(9):1917-1927 (1975).

International Search Report and Written Opinion for PCT/US06/27574 (May 15, 2008).

Extended European Search Report for EP 06787476.8 (Jul. 15, 2010).

Supplementary European Search Report for EP 06787476 (Sep. 27, 2010).

Office Action for Ukraine Patent Application No. 200801920 (Sep. 14, 2010).

* cited by examiner

ARYL- AND HETEROARYL-SUBSTITUTED TETRAHYDROBENZAZEPINES AND USE THEREOF TO BLOCK REUPTAKE OF NOREPINEPHRINE, DOPAMINE, AND SEROTONIN

This application claims the benefit of U.S. Provisional Patent Application Ser. No. 60/700,057, filed Jul. 15, 2005, which is hereby incorporated by reference in its entirety.

FIELD OF THE INVENTION

The present invention relates to compounds, compositions, methods for the treatment of various neurological and psychological disorders, and the use of the compounds in combination therapy. In particular, the present invention relates to such compounds, compositions, and methods, where the compounds are novel aryl- and heteroaryl-substituted tetrahydrobenzazepine derivatives.

BACKGROUND OF THE INVENTION

It is well known that the neurotransmitters, dopamine (DA), norepinephrine (NE), and serotonin (5-HT), regulate a number of biological processes and that decreased levels of DA, NE, and 5-HT are associated with a number of neurological disorders and their physical manifestations. Significant effort has been expended on devising methods for adjusting the levels of these neurotransmitters in order to produce a desired pharmacological effect. Preventing the reuptake of these neurotransmitters in any combination of one, two, or all three of them is likely to be effective in treating these disorders. Targeting the dopamine transporter (DAT), norepinephrine transporter (NET), and the serotonin transporter (SERT) proteins has proven to be an effective way of increasing the levels of the respective monoamines.

Methylphenidate, currently used for the treatment of attention deficit-hyperactivity disorder, is known to be selective for inhibition of the DAT. Also, U.S. Pat. No. 5,444,070 discloses selective inhibitors of the dopamine reuptake as treatments for Parkinson's disease, drug addiction or abuse including cocaine and amphetamines.

Selective norepinephrine reuptake inhibitors (NARI) have also been disclosed. U.S. Pat. No. 6,352,986 describes methods of treating attention deficit-hyperactivity disorder (ADHD), addictive disorders, and psychoactive substance use disorders with Reboxetine. Also, Atomoxetine (Strattera®) is currently marketed as a selective NET reuptake inhibitor for ADHD.

The use of selective serotonin reuptake inhibitors (SSRI) has been shown to be effective in treating depressive disorders. Sertraline, Citalopram, and Paroxetine are well known examples of SSRIs used to treat disorders, such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy.

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1A antagonist for the treatment of a wide variety of conditions.

Also advantageous is the use of compounds that inhibit one or more of the neurotransmitters at the same time. The antidepressant qualities of the dual NET and SERT reuptake inhibitor duloxetine is disclosed in European Patent No. EP 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are also disclosed in U.S. Pat. No. 6,136,083 for the treatment of depression. It is also recognized that compounds which inhibit the reuptake of NE, DA, and 5-HT in varying ratios not specifically mentioned here would also be advantageous.

Treating illnesses by inhibiting the reuptake of all three of the monoamines either through combination therapy or "triple inhibitors" may have clinical benefit as well. Rationale for inclusion of a dopamine enhancing component in anti-depressant therapy includes observed deficits in dopaminergic function, the success of combination therapy with dopamine agonists and traditional anti-depressants, and an increased sensitivity in dopamine receptors due to chronic anti-depressant administration (Skolnick et al., *Life Sciences*, 73:3175-3179 (2003)). Combination therapy with an SSRI and a noradrenaline and dopamine reuptake inhibitor was shown to be more efficacious in patients with treatment-resistant depression (Lam et al, *J. Clin. Psychiatry*, 65(3):337-340 (2004)). Another study using a combination of a serotonin and norepinephrine reuptake inhibitor with a norepinephrine and dopamine reuptake inhibitor reported a significant decrease in depressive symptoms in patients with refractory major depressive disorder who had failed to respond previously to either agent alone (Papkostas, G. I., *Depression and Anxiety*, 23:178-181 (2006)). In addition, the combination of bupropion-SR with either SSRIs or norepinephrine and dopamine reuptake inhibitors was found to induce less sexual dysfunction than monotherapy (Kennedy et al, *J. Clin. Psychiatry*, 63(3):181-186 (2002)). As such, inhibitory activity against DA reuptake, in addition to NE and 5-HT reuptake, is expected to provide a more rapid onset of anti-depressant effect than other mixed inhibitors which are selective for NET and SERT over DAT. PCT International Publication Nos. WO 03/101453 and WO 97/30997 disclose a class of compounds which are active against all three monoamine transporters. Also, PCT International Patent Publication No. WO 03/049736 discloses a series of 4-substituted piperidines, each of which displays similar activity against DA, NE, and 5-HT transporters. Bicyclo[2.2.1]heptanes (Axford et al., *Bioorg. Med. Chem. Lett.*, 13:3277-3280 (2003)) and azabicyclo[3.1.0]hexanes (Skolnick et al., *Eur. J. Pharm.*, 461:99-104 (2003)) are also described as triple inhibitors of the three monoamine transporters.

U.S. Pat. No. 3,225,031 discloses phenyl tetrahydrobenzazepines of formula 1 (where R is a member of the group consisting of H, lower alkyl and phenyl-lower alkyl, and X is a member of the group consisting of H and methyl), which are said to be useful in elevating mood or establishing wakefulness. At higher doses, these compounds are said to elicit analgesic response, while their non-toxic quaternary salts are said to be useful as anticholinergic or parasympathetic blocking agents.

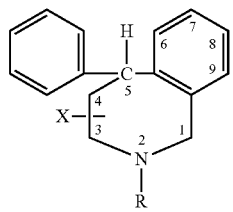

1

Phenyl tetrahydrobenzazepines of formula 2, (where R is a member of the group consisting of H, lower alkyl, lower alkenyl, and isocyclic-lower alkyl having 3-6 cyclic carbon atoms, $R_1$ is lower alkyl, and X is a member of the group consisting of hydrogen and lower alkyl) described in U.S. Pat. No. 3,242,164 are said to possess analgesic activity. The compound of formula 2 possesses an ester functionality at the 5-position of the 2,3,4,5-tetrahydro-1H-benzo[c]azepine core.

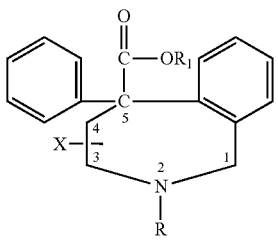

2

Japanese Patent Application No. 590113761 discloses the use of phenyl tetrahydrobenzazepines of formula 3 (where R represents a halogen, a hydroxy group, a nitro group, or an amino group) as analgesics.

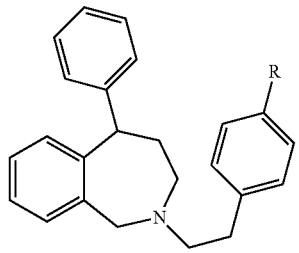

3

Compounds, 8-(methylthio)-5-phenyl-2,3,4,5-tetrahydro-1H-benzo[c]azepine (4), 6-(methylthio)-5-phenyl-2,3,4,5-tetrahydro-1H-benzo[c]azepine (5), and 2,3,4,5-tetrahydro-1H-benzo[c]azepine (6), are described in Euerby et al., *Synth. Commun.*, 16:779-784 (1986) and in Euerby et al., *J. Chem. Research (S)*, pp. 40-41 (1987) as substrates (4 and 5) and product (6) in reductive desulphurization of thioethers with nickel bromide. No usage or activity was reported in those references.

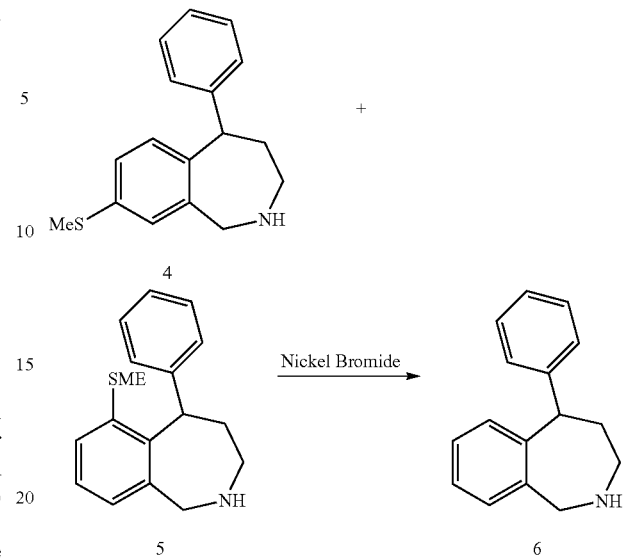

PCT International Patent Publication No. WO 2001/003680 discloses compounds of formula 7 (where C is a carbon; N is a nitrogen; H is a hydrogen; $A^1, A^2, A^3, A^4, A^5$, and $A^6$ are independently alkyl, O, S, or —NH; m and n (for each individual A group) are independently 0 or 1; p, q, and l are independently 0, 1, or 2; $R^7, R^8, R^9, R^{10}, R^{11}, R^{12}$, and each $R^{14}$ are independently hydrogen, alkyl, alicyclyl, heterocyclyl, or aryl, each $R^{13}$ is independently hydrogen, alkyl, alicyclyl, heterocycyl, aryl, or an anionic group, and adjacent R groups (e.g., $R^7$ and $R^8$) may form an unsubstituted or substituted cyclic or heterocyclic ring) as inhibitors of islet amyloid polypeptide (IAPP) associated amyloidosis. These compounds are suggested for use in disorders in which such amyloid deposition occurs, such as diabetes.

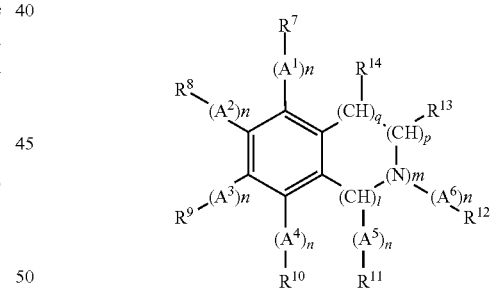

7

U.S. Pat. No. 5,607,939 discloses compounds of formula 8 (where ring A represents a benzene ring; Ar represents an aromatic group; $R^1$ and $R^2$ independently represent hydrogen, acyl, or hydrocarbon group, or $R^1$ and $R^2$ taken together with the adjacent nitrogen atom represent a nitrogen-containing heterocyclic group; m represents an integer of 1 to 6; n represents an integer of 2 to 3; ═══ represents a single bond or a double bond; X stands for —O— or —$NR^3$— in which $R^3$ represents hydrogen, acyl, or hydrocarbon group where ─── is a single bond or ═N— where ─── is a double bond) as gonadotropin-releasing hormone (GnRH) receptor antagonists and suggests their use in acute and chronic CNS disorders, such as dysmnesia. This reference discloses 5-aryl 2,3,4,5-tetrahydro-1H-benzo[c]azepines with particular cyclic aminoalkyl groups at the 5-position of the 2,3,4,5-tetrahydro-1H-benzo[c]azepines.

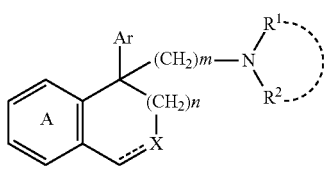

8

Great Britain Patent No. GB 2271566 discloses compounds of formula 9 (where n is 0-3; p is 1-2; q is 1-2; X is $CH_2$, O, or N—$R^1$, and $R^1$ is H, $C_{1-4}$ alkyl or $C_{3-5}$ cycloalkyl; R is (a) $C_{1-6}$ alkyl, (b) $C_{1-6}$ alkoxy, (c) hydroxyl, (d) halogen, (e) CN, (f) $NO_2$, (g) $NHSO_2CH_3$, or (h) COOH; G is H or R) as HIV integrase inhibitors.

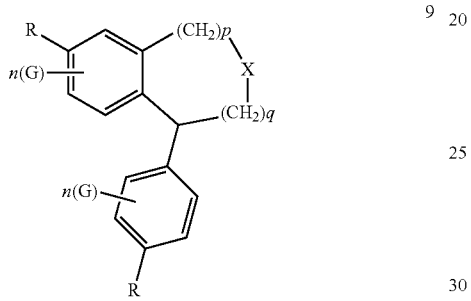

9

PCT International Patent Publication No. WO 99/045013 discloses compounds of formula 10 (where A together with the double bond of formula 10 forms a cyclic system selected from the group consisting of benzene, thiophene, furan, pyridine, pyrimidine, pyrazine, pyridazine, pyrrole, indole, pyrazole, imidazole, oxazole, isoxazole, and thiazole; $R^2$ is an optionally substituted $C_{1-6}$-alkyl, optionally substituted heterocyclyl; $R^1$ is heteroaryl, optionally substituted; $R^4$ and $R^5$ are independently hydrogen, halogen, perhalomethyl, optionally substituted $C_{1-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy, or carbamoyl; m is 0, 1, or 2; n is 0, 1, or 2) for the treatment or prevention of diseases of the endocrinological system.

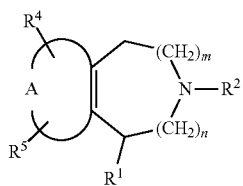

10

Brooks et al., *Journal of Chemical Society [Section] C: Organic*, pp. 625-627 (1969) describes the synthesis of compound of formula 11 and formula 12 via acid catalyzed ring-closure method. No biological activity of these compounds is reported in the above-mentioned reference. U.S. Pat. Nos. 3,655,651 and 3,642,993 disclose a single compound of formula 11 and suggest its sedative-hypnotic effect.

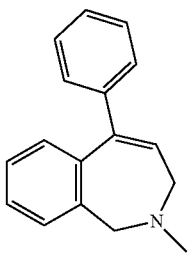

11

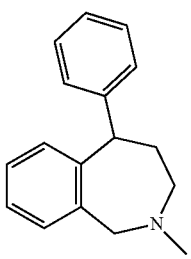

12

Arany et al., *J. Chem. Soc, Perkin Trans.* I: 2605-2608 (1999) and Arany et al., *Tetrahedron Letters* 39:3267-3268 (1998) describe compounds of formula 13 as products of electrocyclisation of azomethine ylides. No biological activity of these compounds is reported in the above mentioned references.

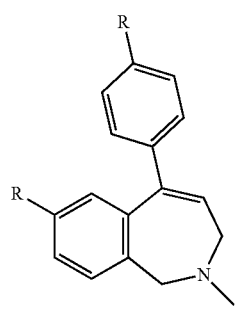

13

R=H, OMe, OBn

Gast et al., *Helvetica Chimica Acta*, 60(5):1644-1649 (1977) describes compounds of formula 14 as products of the cyclization of 2-(β-styryl)benzylamine derivatives. No biological activity is disclosed in the above mentioned reference.

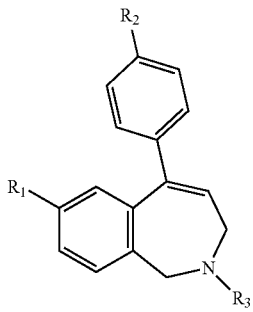

R1, R2=H, Cl
R3=H, CH3

14

Toda et al., *Bioorganic and Medicinal Chemistry*, 11 (20): 4389-4415 (2003) describes compounds of formula 15 as dual inhibitors of acetylcholinesterase and serotonin transporter and potential agents for Alzheimer's disease. The IC$_{50}$s for the serotonin transporter for the three compounds of formula 15 are reported to be >1000 nM in the above mentioned reference.

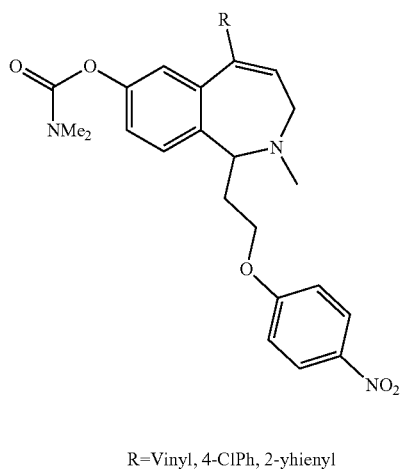

15

R=Vinyl, 4-ClPh, 2-yhienyl

There is still a large need for compounds that block the reuptake of norepinephrine, dopamine, and serotonin and treat various neurological and psychological disorders.

The present invention is directed to achieving this objective.

SUMMARY OF THE INVENTION

The present invention relates to compounds represented by the formulae I(A-E) having the following structure:

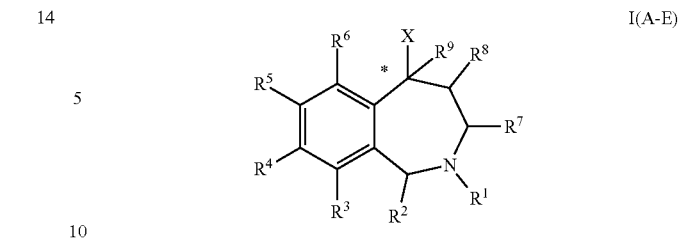

I(A-E)

where:
the carbon atom designated * is in the R or S configuration; and

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$;

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or X is an alkene or alkyne, optionally substituted from 1 to 4 times with substitutents as defined below in $R^{15}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted phenyl and $R^4$ is H, —$OR^{12}$, —$S(O)_nR^{13}$, $C(O)R^{13}$, —$NR^{10}R^{11}$, —CN, halogen, or $C_1$-$C_6$ alkyl, where each of the $C_1$-$C_6$ alkyl is optionally substituted from 1 to 3 times with substituents as defined below in $R^{15}$;

provided that for compounds of formula ID, X is substituted bicyclic aryl or heteroaryl and $R^4$ is H, —$OR^{12}$, —$S(O)_nR^{13}$, $C(O)R^{13}$, —$NR^{10}R^{11}$, —CN, halogen, or $C_1$-$C_6$ alkyl, where each of the $C_1$-$C_6$ alkyl is optionally substituted from 1 to 3 times with substituents as defined below in $R^{15}$; and provided that for compounds of formula IE, X is substituted monocyclic heteroaryl and $R^4$ is substituted monocyclic or bicyclic aryl or heteroaryl;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, —$OR^{12}$, —$S(O)_nR^{13}$, —CN, —$C(O)R^{13}$, —$NR^{10}R^{11}$, $C_1$-$C_6$ alkyl $C_{2-C6}$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, —$OR^{12}$, —$SR^{10}$, $C_1$-$C_6$ alkyl, —CN, or —$NR^{10}R^{11}$, where each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, where each of C$_1$-C$_4$ alkyl is optionally substituted from 1 to 3 times with substituents as defined below in R$^{15}$;

R$^{10}$ and R$^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, or on the additional nitrogen atom from 1 to 3 times with a substituent selected independently at each occurrence thereof from the group consisting of S(O)$_n$R$^{13}$, —C(O)R$^{13}$, and C$_1$-C$_4$ alkyl, wherein each of C$_1$-C$_4$ alkyl is optionally substituted from 1 to 3 times with substituents as defined below in R$^{15}$;

R$^{10}$ and R$^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in R$^{14}$; or when R$^4$ is —NR$^{10}$R$^{11}$ or —C(O)NR$^{10}$R$^{11}$, either R$^{10}$ or R$^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of C$_1$-C$_3$ alkyl, —C(O)R$^{13}$, and —S(O)$_n$R$^{13}$, or either R$^{10}$ or R$^{11}$ is a C$_1$-C$_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of C$_1$-C$_3$ alkyl, —C(O)R$^{13}$, and —S(O)$_n$R$^{13}$;

R$^{12}$ is selected from the group consisting of H, C$_1$-C$_4$ alkyl, C$_3$-C$_6$ cycloalkyl, C$_4$-C$_7$ cycloalkylalkyl, and —C(O)R$^{13}$, where each of C$_1$-C$_6$ alkyl, C$_3$-C$_6$ cycloalkyl, and C$_4$-C$_7$ cycloalkylalkyl is optionally substituted from 1 to 3 times with substituents as defined below in R$^{15}$;

R$^{13}$ is selected from the group consisting of H, —NR$^{10}$R$^{11}$, C$_1$-C$_4$ alkyl, C$_3$-C$_6$ cycloalkyl, and C$_4$-C$_7$ cycloalkylalkyl, where each of C$_1$-C$_6$ alkyl, C$_3$-C$_6$ cycloalkyl, and C$_4$-C$_7$ cycloalkylalkyl is optionally substituted from 1 to 3 times with substituents as defined below in R$^{15}$; or R$^{12}$ and R$^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in R$^{14}$; or R$^{12}$ and R$^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —OR$^{10}$, —S(O)$_n$R$^{10}$, —C(O)R$^{10}$, —C(O)NR$^{10}$R$^{11}$ and C$_1$-C$_4$ alkyl, where each of C$_1$-C$_4$ alkyl is optionally substituted from 1 to 3 times with substituents as defined below in R$^{15}$;

n is 0, 1, or 2;

R$^{14}$ is independently selected at each occurrence from a substituent in the group consisting of halogen, —NO$_2$, —OR$^{12}$, —NR$^{10}$R$^{11}$, —NR$^{12}$C(O)$_2$R$^{13}$, —NR$^{12}$C(O)NR$^{12}$R$^{13}$, —S(O)$_n$R$^{13}$, —CN, —C(O)R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{15}$; and R$^{15}$ is independently selected at each occurrence from a substituent in the group consisting of —CN, halogen, C(O)R$^{13}$, C$_1$-C$_3$ alkyl, —OR$^{12}$, —NR$^{10}$R$^{11}$, —S(O)$_n$R$^{13}$, aryl, and heteroaryl, where each of the aryl or heteroaryl groups is optionally substituted from 1 to 4 times with substituents as defined above in R$^{14}$;

with the following provisos that (1) when R$^4$ is H, X cannot be phenyl; (2) when R$^4$ is (a) C$_{1-6}$ alkyl, (b) C$_{1-6}$ alkoxy, (c) hydroxyl, (d) halogen, (e) CN, (f) NO$_2$, (g) NHSO$_2$CH$_3$, or (h) COOH, X cannot be a phenyl substituted at the para-position with the same R$^4$; (3) when any one of R$^3$, R$^4$, R$^5$, and R$^6$ is hydrogen, halogen, perhalomethyl, optionally substituted C$_{1-6}$-alkyl, hydroxy, optionally substituted C$_{1-6}$-alkoxy, nitro, cyano, amino, optionally substituted mono- or optionally substituted di-C$_{1-6}$-alkylamino, acylamino, C$_{1-6}$-alkoxycarbonyl, carboxy, or carbamoyl, X cannot be furanyl, thienyl, pyrazolyl, tetrazolyl, isoxazolyl, isothiazolyl, 1,2,3-oxadiazolyl, 1,2,3-thiadiazolyl, 1,2,4-oxadiazolyl, 1,2,4-thiadiazolyl, 1,3,4-oxadiazolyl, 1,3,4-thiadiazolyl, 1,2,5-oxadiazolyl, 1,2,5-thiadiazolyl, benzo[d]isoxazolyl, or benzo[d]isothiazolyl; (4) when R$^4$ is —S(O)$_n$R$^{13}$, n cannot be 0; and (5) when R$^9$ is a substituted alkyl, R$^{15}$ cannot be —NR$^{10}$R$^{11}$;

or an oxide thereof, or a pharmaceutically acceptable salt thereof.

Another aspect of the present invention relates to a compound represented by the formula (II) having the following structure:

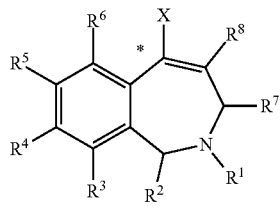

where:

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$;

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or X is an alkene or alkyne, optionally substituted from 1 to 4 times with substituents as defined below in $R^{15}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ is gem-dimethyl;

$R^8$ is H or $C_1$-$C_6$ alkyl, where each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, where each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, or on the additional nitrogen atom from 1 to 3 times with a substituent selected independently at each occurrence thereof from the group consisting of $S(O)_nR^{13}$, $-C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{14}$; or when $R^4$ is $-NR^{10}R^{11}$ or $-C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and $-C(O)R^{13}$, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, $-NR^{10}R^{11}$, $C_1$-$C_4$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, $-OR^{10}$, $-S(O)_nR^{10}$, $-C(O)R^{10}$, $-C(O)NR^{10}R^{11}$ and $C_1$-$C_4$ alkyl, where each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of $-CN$, halogen, $C(O)R^{13}$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$;

with the following provisos that (1) when $R^4$ is H, X cannot be phenyl or a phenyl substituted at the para-position with Cl; (2) when $R^4$ is H, OMe, or O-benzyl, X cannot be a phenyl substituted at the para-position with the same $R^4$; and (3) when $R^2$ is a 2-(4-nitrophenoxy)ethyl, $R^5$ cannot be OC(O)NMe$_2$;

or an oxide thereof, or a pharmaceutically acceptable salt thereof.

Results of recent clinical investigations with drugs, such as duloxetine, venlafaxine, atomoxetine, and others that work mechanistically through transporter reuptake inhibition, provide evidence that potency and selectivity are important factors in leading to drugs with an improved efficacy, improved therapeutic index, and utility for treatment of new clinical indications. Duloxetine, a dual action transporter reuptake inhibitor, is a selective inhibitor for serotonin transporter protein and norepinephrine transporter protein reuptake (Sorbera et al., *Drugs of the Future*, 25(9):907-916 (2000), which is hereby incorporated by reference in its entirety) and is in clinical development for the treatment of depression and stress urinary incontinence. In clinical studies, researchers attribute the effect of the medication on a broad spectrum of depression symptoms, which include emotional and painful physical symptoms as well as anxiety, to its dual reuptake inhibition of both serotonin and norepinephrine. Venlafaxine, which is also reported to be a selective serotonin and norepinephrine reuptake inhibitor (SNRI class), has been reported to exhibit a more rapid onset of action. The late onset of action has been a drawback with the first generation antidepressants, i.e., the single action serotonin selective reuptake inhibitors (SSRI class). For example, Prozac®, the prototype drug in this class, can take four weeks or longer for full anti-depressive activity to take effect.

Atomoxetine (Strattera®) was recently approved for the treatment of ADHD. Atomoxetine is a norepinephrine selective transporter reuptake inhibitor. Unlike Ritalin®, one of the most frequently used drugs for treatment of ADHD, atomoxetine has little or no activity at the dopamine transporter. As a result, atomoxetine has the advantage that it is not scheduled as a controlled substance because it has minimal potential for substance abuse.

In a manner similar to the newer clinical agents like atomoxetine, duloxetine, and venlafaxine, the compounds of the present invention may exhibit improved efficacy towards broader symptoms of depression. The compounds of the present invention may also exhibit more rapid onset of action in the treatment of central nervous system (CNS) diseases, such as depression. In addition to providing improved efficacy, the compounds of the present invention may also exhibit fewer undesirable side effects. Finally, because the compounds of the present invention possess a diverse transporter reuptake inhibition profile, they are expected to be useful for a wider variety of CNS disorders.

DETAILED DESCRIPTION OF THE INVENTION

The present invention relates to compounds represented by the formulae I(A-E) having the following structure:

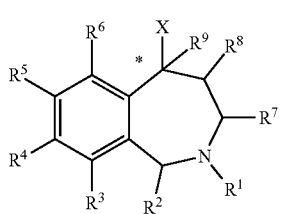

I(A-E)

where:
the carbon atom designated * is in the R or S configuration; and
X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$;
X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or X is an alkene or alkyne, optionally substituted from 1 to 4 times with substitutents as defined below in $R^{15}$;
$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;
$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or
$R^2$ is gem-dimethyl;
$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or
$R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;
$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;
$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{13}$, and —S(O)$_n$$R^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or nonaromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic aryl or heteroaryl and $R^4$ is substituted monocyclic or bicyclic aryl or heteroaryl;

provided that for compounds of formula IC, X is substituted phenyl and $R^4$ is H, —O$R^{12}$, —S(O)$_n$$R^{13}$, C(O)$R^{13}$, —N$R^{10}$$R^{11}$, —CN, halogen, or $C_1$-$C_6$ alkyl, where each of the $C_1$-$C_6$ alkyl is optionally substituted from 1 to 3 times with substituents as defined below in $R^{15}$;

provided that for compounds of formula ID, X is substituted bicyclic aryl or heteroaryl and $R^4$ is H, —O$R^{12}$, —S(O)$_n$$R^{13}$, C(O)$R^{13}$, —N$R^{10}$$R^{11}$, —CN, halogen, or $C_1$-$C_6$ alkyl, where each of the $C_1$-$C_6$ alkyl is optionally substituted from 1 to 3 times with substituents as defined below in $R^{15}$; and provided that for compounds of formula IE, X is substituted monocyclic heteroaryl and $R^4$ is substituted monocyclic or bicyclic aryl or heteroaryl;

$R^7$ is selected from the group consisting of H, —S(O)$_n$$R^{13}$, —C(O)$R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, —O$R^{12}$, —S(O)$_n$$R^{13}$, —CN, —C(O)$R^{13}$, —N$R^{10}$$R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, —O$R^{12}$, —S$R^{10}$, $C_1$-$C_6$ alkyl, —CN, or —N$R^{10}$$R^{11}$, where each of $C_1$-$C_6$ alkyl is optionally substituted from 1 to 3 times with substituents as defined below in $R^{15}$;

$R^{10}$ and $R^{11}$ are each independently selected from the group consisting of H, —C(O)$R^{13}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —O$R^{12}$, —N$R^{12}$$R^{13}$, —S(O)$_n$$R^{13}$, —C(O)$R^{13}$, and $C_1$-$C_4$ alkyl, where each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, —O$R^{12}$, —N$R^{12}$$R^{13}$, —S(O)$_n$$R^{13}$, —C(O)$R^{13}$, and $C_1$-$C_4$ alkyl, or on the additional nitrogen atom from 1 to 3 times with a substituent selected independently at each occurrence thereof from the group consisting of S(O)$_n$$R^{13}$, —C(O)$R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{14}$; or when $R^4$ is —$NR^{10}R^{11}$ or —$C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_n R^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{13}$, and —$S(O)_n R^{13}$;

$R^{12}$ is selected from the group consisting of H, $C_1$-$C_4$ alkyl, $C_3$-$C_6$ cycloalkyl, $C_4$-$C_7$ cycloalkylalkyl, and —$C(O)R^{13}$, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —$NR^{10}R^{11}$, $C_1$-$C_4$ alkyl, $C_3$-$C_6$ cycloalkyl, and $C_4$-$C_7$ cycloalkylalkyl, where each of $C_1$-$C_6$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^{10}$, $S(O)_n R^{10}$, —$C(O)R^{10}$, —$C(O)NR^{10}R^{11}$ and $C_1$-$C_4$ alkyl, where each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2 R^{13}$, —$NR^{12}C(O)NR^{12}R^{13}$, —$S(O)_n R^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, —$NR^{10}R^{11}$, —$S(O)_n R^{13}$, aryl, and heteroaryl, where each of the aryl or heteroaryl groups is optionally substituted from 1 to 4 times with substituents as defined above in $R^{14}$;

with the following provisos that (1) when $R^4$ is H, X cannot be phenyl; (2) when $R^4$ is (a) $C_{1-6}$ alkyl, (b) $C_{1-6}$ alkoxy, (c) hydroxyl, (d) halogen, (e) CN, (f) $NO_2$, (g) $NHSO_2CH_3$, or (h) COOH, X cannot be a phenyl substituted at the para-position with the same $R^4$; (3) when any one of $R^3$, $R^4$, $R^5$, and $R^6$ is hydrogen, halogen, perhalomethyl, optionally substituted $C_{1-6}$-alkyl, hydroxy, optionally substituted $C_{1-6}$-alkoxy, nitro, cyano, amino, optionally substituted mono- or optionally substituted di-$C_{1-6}$-alkylamino, acylamino, $C_{1-6}$-alkoxycarbonyl, carboxy, or carbamoyl, X cannot be furanyl, thienyl, pyrazolyl, tetrazolyl, isoxazolyl, isothiazolyl, 1,2,3-oxadiazolyl, 1,2,3-thiadiazolyl, 1,2,4-oxadiazolyl, 1,2,4-thiadiazolyl, 1,3,4-oxadiazolyl, 1,3,4-thiadiazolyl, 1,2,5-oxadiazolyl, 1,2,5-thiadiazolyl, benzo[d]isoxazolyl, or benzo[d]isothiazolyl; (4) when $R^4$ is —$S(O)_n R^{13}$, n cannot be 0; and (5) when $R^9$ is a substituted alkyl, $R^{15}$ cannot be —$NR^{10}R^{11}$;

or an oxide thereof, or a pharmaceutically acceptable salt thereof.

As used above, and throughout the description of the invention, the following terms, unless otherwise indicated, shall be understood to have the following meanings:

The term "monocyclic carbocycle" means a monocyclic ring system of 5 to about 8 ring carbon atoms, preferably 5 or 6. The ring is nonaromatic, but may contain one or more carbon-carbon double bonds. Representative monocyclic carbocycles include cyclopentyl, cyclohexyl, cyclopentenyl, cyclohexenyl, and the like.

The term "monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is nonaromatic, but may be fused to an aromatic ring. Representative monocyclic heterocycles include pyrrolidine, piperidine, piperazine, and the like.

The term "aromatic monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is aromatic. Representative aromatic monocyclic heterocycles include pyrrole, pyridine, oxazole, thiazole, and the like.

The term "fused bicyclic carbocycle" means a bicyclic ring system consisting of about 8 to 11 ring carbon atoms, preferably 9 or 10. One or both of the rings is/are aromatic. Representative fused bicyclic carbocycles include indenyl, indanyl, naphthyl, dihydronaphthyl, tetrahydronaphthyl, benzocycloheptenyl, dihydrobenzocycloheptenyl, tetrahydrobenzocycloheptenyl, and the like.

The term "fused bicyclic heterocycle" means a bicyclic ring system consisting of about 8 to 13 ring atoms, preferably 9 or 10, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. Representative fused bicyclic heterocycles include benzofuranyl, benzothiophenyl, benzoisothiazolyl, benzoisoxazolyl, indazolyl, indolyl, isoindolyl, indolizinyl, benzoimidazolyl, benzooxazolyl, benzothiazolyl, benzotriazolyl, imidazo[1,2-a]pyridinyl, pyrazolo[1,5-a]pyridinyl,

[1,2,4]triazolo[4,3-a]pyridinyl, 5,6,7,8-tetrahydro-[1,2,4]triazolo[4,3-a]pyrazinyl, [1,2,4]triazolo[4,3-a]pyrazinyl, thieno[2,3-b]pyridinyl, thieno[3,2-b]pyridinyl, 1H-pyrrolo[2,3-b]pyridinyl, chromenyl, dihydrobenzothiophenyl, dihydrobenzofuranyl, indolinyl, quinolinyl, isoquinolinyl, 4H-quinolizinyl, 9aH-quinolizinyl, quinazolinyl, cinnolinyl, quinoxalinyl, benzo[1,2,3]triazinyl, benzo[1,2,4]triazinyl, and the like.

The term "bridged bicyclic ring" means a bridged bicyclic ring containing 6-12 carbon atoms and optionally containing one or more heteroatoms selected from the group consisting of oxygen, nitrogen, and sulfur. Representative bridged bicyclic rings include quinuclidine, 9-azabicyclo[3.3.1]nonane, 7-azabicyclo[2.2.1]heptane, 2,5-diazabicyclo[2.2.2]octane, and the like.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Representative alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Representative alkenyl groups include ethenyl, propenyl, n-butenyl, and i-butenyl.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Representative alkynyl groups include ethynyl, propynyl, n-butynyl, 2-butynyl, 3-methylbutynyl, and n-pentynyl.

The term "cycloalkyl" means a non-aromatic mono- or multicyclic ring system of about 3 to about 7 carbon atoms, preferably of about 5 to about 7 carbon atoms. Representative monocyclic cycloalkyl include cyclopentyl, cyclohexyl, cycloheptyl, and the like.

The term "cycloalkylalkyl" means a cycloalkyl-alkyl-group in which the cycloalkyl and alkyl are as defined herein. Representative cycloalkylalkyl groups include cyclopropylmethyl and cyclopentylmethyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "heteroaryl" means an aromatic monocyclic or multicyclic ring system of 6 to about 14 ring atoms, preferably of 6 to about 10 ring atoms, in which one or more of the atoms in the ring system is/are element(s) other than carbon, for example, nitrogen, oxygen or sulfur. Representative heteroaryl groups include pyridinyl, pyridazinyl and quinolinyl.

The term "alkoxy" means an alkyl-O-group where the alkyl group is as herein described. Representative alkoxy groups include methoxy, ethoxy, n-propoxy, i-propoxy, n-butoxy and heptoxy.

The term "halo" or "halogen" means fluoro, chloro, bromo, or iodo.

The term "haloalkyl" means both branched and straight-chain alkyl substituted with 1 or more halogen, where the alkyl group is as herein described.

The term "haloalkoxy" means a $C_{1-4}$ alkoxy group substituted by at least one halogen atom, where the alkoxy group is as herein described.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compounds of the invention", and equivalent expressions, are meant to embrace compounds of general formulae I(A-E), as well as formula (II), as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example Berge et al., *J Pharm Sci,* 66:1-sup.19 (1977) and *Remington's Pharmaceutical Sciences,* 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethylsilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., *Methods in Enzymology*, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, "*Advanced Drug Delivery Reviews*," 8:1-38 (1992); Bundgaard et al., *Journal of Pharmaceutical Sciences*, 77:285 (1988); Nakeya et al., *Chem Pharm Bull*, 32:692 (1984); Higuchi, "Pro-drugs as Novel Delivery Systems" Roche, ed., A.C.S. Symposium Series, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate and benzoate derivatives of alcohol and amine functional groups in the compounds of the invention.

The term "therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formulae I(A-E) and formula II and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

One embodiment of the present invention relates to the compound of formula (IA), where X is substituted phenyl and $R^4$ is substituted monocyclic or bicyclic aryl or heteroaryl.

Another embodiment of the present invention relates to the compound of formula (IB), where X is substituted bicyclic aryl or heteroaryl and $R^4$ is substituted monocyclic or bicyclic aryl or heteroaryl.

Another embodiment of the present invention relates to the compound of formula (IC), where X is substituted phenyl and $R^4$ is H, —$OR^{12}$, —$S(O)_n R^{13}$, $C(O)R^{13}$, —$NR^{10}R^{11}$, —CN, halogen, and $C_1$-$C_6$ alkyl, where each of the $C_1$-$C_6$ alkyl is optionally substituted from 1 to 3 times with substituents as defined below in $R^{15}$.

Another embodiment of the present invention relates to the compound of formula (ID), where X is substituted bicyclic aryl or heteroaryl and $R^4$ is H, —$OR^{12}$, —$S(O)_n R^{13}$, $C(O)R^{13}$, —$NR^{10}R^{11}$, —CN, halogen, or $C_1$-$C_6$ alkyl, where each of the $C_1$-$C_6$ alkyl is optionally substituted from 1 to 3 times with substituents as defined below in $R^{15}$.

Another embodiment of the present invention relates to the compound of formula (IE), where X is substituted monocyclic heteroaryl and $R^4$ is substituted monocyclic or bicyclic aryl or heteroaryl.

Another embodiment of the present invention relates to the compound of formulae (IA-E) where:

X is phenyl, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is H, halogen, —$OR^{12}$, —$S(O)_nR^{13}$, —CN, $C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$;

$R^5$ is H, fluoro, chloro, methyl, trifluoromethyl, trifluoromethoxy, cyano, hydroxy or methoxy;

$R^6$ is H, fluoro, chloro, methyl, trifluoromethyl, trifluoromethoxy, cyano, hydroxy or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxy, fluoro, chloro, methyl, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X is phenyl, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_{1-4}$ alkyl is optionally substituted from 1 to 3 times with substituents as defined below in $R^{15}$;

$R^8$ is H, hydroxy, fluoro, chloro, methyl, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, $C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X represents a 5- or 6-membered monocyclic heterocycle selected from the group consisting of pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$; or X, in compounds represented by formula (I), is an alkene or alkyne, optionally substituted from 1 to 4 times with substituents as defined below in $R^{15}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is H, halogen, $-OR^{12}$, $-S(O)_nR^{13}$, $-CN$, $-C(O)R^{13}$, $-NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{13}$, and $-S(O)_nR^{13}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxy, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, $-C(O)R^{13}$, $-CN$, $C_1$-$C_3$ alkyl, $-OR^{12}$, $-NR^{10}R^{11}$, $-S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X represents a 5- or 6-membered monocyclic heterocycle selected from the group consisting of pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$; or X, in compounds represented by formula (I), is an alkene or alkyne, optionally substituted from 1 to 4 times with substituents as defined below in $R^{15}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxy, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl or cyano;

$R^{14}$ is independently selected at each occurrence from a substituent in the group consisting of halogen, $-NO_2$, $-OR^{12}$, $-NR^{10}R^{11}$, $-NR^{12}C(O)_2R^{13}$, $-NR^{12}C(O)NR^{12}R^{13}$, $-S(O)_nR^{13}$, $-CN$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, $-C(O)R^{13}$, $-CN$, $C_1$-$C_3$ alkyl, $-OR^{12}$, $-NR^{12}R^{13}$, $-S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is H, halogen, —$OR^{12}$, —$S(O)_n R^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_n R^{13}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxy, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_n R^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_n R^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo

[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_1$-$C_4$ alkyl is optionally substituted from 1 to 3 times with substituents as defined below in $R^{15}$;

$R^8$ is H, hydroxy, fluoro, chloro, $C_1$-$C_3$ alkyl optionally substituted with hydroxyl or amino, or amino optionally substituted with $C_1$-$C_3$ alkyl;

$R^9$ is H, fluoro, chloro, methyl, hydroxyl, or cyano;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formulae (IA-E) where:

X is thiophenyl, thiazolyl, pyridinyl, phenyl, naphthyl, benzo[b]thiophenyl, benzofuranyl, benzo[d][1,3]dioxolyl, 2,3-dihydrobenzo[b][1,4]dioxinyl, 3,4-dihydro-2H-benzo[b][1,4]oxazinyl, or 4-methyl-3,4-dihydro-2H-benzo[b][1,4]oxazinyl, optionally substituted with from 1 to 3 substituents selected independently from the group consisting of halogen, methoxy, cyano, trifluoromethyl, trifluoromethoxy, difluoromethoxy, substituted $C_1$-$C_3$ alkyl, methanesulfonyl, carbamoyl, $C_1$-$C_3$ alkyl-substituted carbamoyl, and acetamido;

$R^1$ is H, methyl, ethyl, isopropyl, 2-hydroxyethyl, 2,2,2-trifluoroethyl, 2-fluoroethyl, or benzyl;

$R^2$ is H or gem-dimethyl;

$R^3$ is H or fluoro;

$R^4$ is H, methoxy, hydroxyl, methyl, fluoro, bromo, cyano, trifluoromethyl, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, piperidin-2-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-pyridazin-3-yloxy, 1,2,4-oxadiazol-3-yl, 3,5-dimethylisoxazol-4-yl, 1H-pyrazol-4-yl, 2-cyanophenyl, 3-cyanophenyl, 4-cyanophenyl, (methanesulfonyl)phenyl, pyridinyl, aminopyridinyl, pyridazin-3-yl, 6-methylpyridazin-3-yl, 6-(trifluoromethyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, (6-(hydroxymethyl)pyridazin-3-yl, 6-(methoxycarbonyl)pyridazin-3-yl, pyrimidin-2-yl, pyrimidin-4-yl, pyrimidin-5-yl, pyrazin-2-yl, 2-oxopyridin-1(2H)-yl, 6-oxo-1,6-dihydropyridazin-3-yl, imidazo[1,2-a]pyridin-6-yl, imidazo[1,2-a]pyrazin-3-yl, 3-oxo-[1,2,4]triazolo[4,3-a]pyridin-2(3H)-yl, 5,6-dihydroimidazo[1,2-a]pyrazin-7(8H)-yl, 3-(trifluoromethyl)-5,6-dihydro-[1,2,4]triazolo[4,3-a]pyrazin-7(8H)-yl, [1,2,4]triazolo[1,5-a]pyridin-6-yl, [1,2,4]triazolo[4,3-a]pyridin-6-yl, 3,3-dimethyl-2-oxoindolin-5-yl, 5,6-dihydroimidazo[1,2-a]pyrazin-7(8H)-yl, 3-methyl-[1,2,4]triazolo[4,3-b]-pyridazinyl, or [1,2,4]triazolo[4,3-b]-pyridazinyl;

$R^5$ is H or fluoro;

$R^6$ is H or fluoro;

$R^7$ is H;

$R^8$ is H, fluoro, methyl, or hydroxy;

$R^9$ is H or hydroxy;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of halogen, —$C(O)R^{13}$, —CN, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Other specific compounds of formulae I(A-E) of the present invention are the following 5-carbocyclic/5-heterocyclic-8-heteroaryl tetrahydrobenzazepine compounds:

4-(8-methoxy-2-methyl-2,3,4,5-tetrahydro-1H-benzo[c]azepin-5-yl)morpholine;

4-(2-methyl-8-(6-methylpyridazin-3-yl)-2,3,4,5-tetrahydro-1H-benzo[c]azepin-5-yl)morpholine;

8-methoxy-2-methyl-5-(4-methylpiperazin-1-yl)-2,3,4,5-tetrahydro-1H-benzo[c]azepine;

2-methyl-5-(4-methylpiperazin-1-yl)-8-(6-methylpyridazin-3-yl)-2,3,4,5-tetrahydro-1H-benzo[c]azepine;

5-cyclohexyl-2-methyl-8-(pyridazin-3-yl)-2,3,4,5-tetrahydro-1H-benzo[c]azepine; and 5-cyclohexyl-2-methyl-8-(6-methylpyridazin-3-yl)-2,3,4,5-tetrahydro-1H-benzo[c]azepine.

Other specific compounds of formulae I(A-E) of the present invention are the following tetrahydrobenzazepine compounds with mono- or bicyclic carbocycles or heterocycles at the X substituent and simple (noncyclic) substituents at $R^4$ (or $R^6$):

5-(3,4-difluorophenyl)-2-methyl-2,3,4,5-tetrahydro-1H-benzo[c]azepine;

5-(3,5-difluorophenyl)-2-methyl-2,3,4,5-tetrahydro-1H-benzo[c]azepine;

2-methyl-5-phenyl-2,3,4,5-tetrahydro-1H-benzo[c]azepin-4-ol;

2,4-dimethyl-5-phenyl-2,3,4,5-tetrahydro-1H-benzo[c]azepine;

4-fluoro-2-methyl-5-phenyl-2,3,4,5-tetrahydro-1H-benzo[c]azepine;
8-methoxy-5-phenyl-2,3,4,5-tetrahydro-1H-benzo[c]azepine;
8-methoxy-2-methyl-5-phenyl-2,3,4,5-tetrahydro-1H-benzo[c]azepine;
2-ethyl-8-methoxy-5-phenyl-2,3,4,5-tetrahydro-1H-benzo[c]azepine;
2-isopropyl-8-methoxy-5-phenyl-2,3,4,5-tetrahydro-1H-benzo[c]azepine;
6-methoxy-2-methyl-5-phenyl-2,3,4,5-tetrahydro-1H-benzo[c]azepine;
6-fluoro-8-methoxy-2-methyl-5-phenyl-2,3,4,5-tetrahydro-1H-benzo[c]azepine;
7-fluoro-8-methoxy-2-methyl-5-phenyl-2,3,4,5-tetrahydro-1H-benzo[c]azepine;
9-fluoro-8-methoxy-5-phenyl-2,3,4,5-tetrahydro-1H-benzo[c]azepine;
9-fluoro-8-methoxy-2-methyl-5-phenyl-2,3,4,5-tetrahydro-1H-benzo[c]azepine;
9-fluoro-8-methoxy-2-methyl-5-phenyl-2,3,4,5-tetrahydro-1H-benzo[c]azepin-5-ol;
5-(4-fluorophenyl)-8-methoxy-2-methyl-2,3,4,5-tetrahydro-1H-benzo[c]azepine;
5-(4-bromophenyl)-8-methoxy-2-methyl-2,3,4,5-tetrahydro-1H-benzo[c]azepine;
5-(4-chlorophenyl)-8-methoxy-2-methyl-2,3,4,5-tetrahydro-1H-benzo[c]azepine;
5-(2-chlorophenyl)-8-methoxy-2-methyl-2,3,4,5-tetrahydro-1H-benzo[c]azepine;
5-(3-chlorophenyl)-8-methoxy-2-methyl-2,3,4,5-tetrahydro-1H-benzo[c]azepine;
8-methoxy-2-methyl-5-(4-(trifluoromethyl)phenyl)-2,3,4,5-tetrahydro-1H-benzo[c]azepine;
8-methoxy-2-methyl-5-(4-(trifluoromethyl)phenyl)-2,3,4,5-tetrahydro-1H-benzo[c]azepin-5-ol;
5-(3,4-difluorophenyl)-8-methoxy-2-methyl-2,3,4,5-tetrahydro-1H-benzo[c]azepine;
5-(3,4-difluorophenyl)-8-methoxy-2-methyl-2,3,4,5-tetrahydro-1H-benzo[c]azepin-5-ol;
5-(3-chloro-4-fluorophenyl)-8-methoxy-2-methyl-2,3,4,5-tetrahydro-1H-benzo[c]azepine;
2-fluoro-4-(8-methoxy-2-methyl-2,3,4,5-tetrahydro-1H-benzo[c]azepin-5-yl)phenol;
2,6-difluoro-4-(8-methoxy-2-methyl-2,3,4,5-tetrahydro-1H-benzo[c]azepin-5-yl)phenol;
2,6-difluoro-4-(8-methoxy-2-methyl-2,3,4,5-tetrahydro-1H-benzo[c]azepin-5-yl)benzonitrile;
5-(4-fluorophenyl)-2-methyl-2,3,4,5-tetrahydro-1H-benzo[c]azepin-8-ol;
5-(4-fluorophenyl)-2,8-dimethyl-2,3,4,5-tetrahydro-1H-benzo[c]azepine;
8-ethynyl-2-methyl-5-phenyl-2,3,4,5-tetrahydro-1H-benzo[c]azepine;
8-ethynyl-5-(2-fluorophenyl)-2-methyl-2,3,4,5-tetrahydro-1H-benzo[c]azepine;
5-(2-fluorophenyl)-2-methyl-8-(pyridin-2-ylethynyl)-2,3,4,5-tetrahydro-1H-benzo[c]azepine;
5-(2-fluorophenyl)-2-methyl-8-((6-methylpyridazin-3-yl)ethynyl)-2,3,4,5-tetrahydro-1H-benzo[c]azepine;
1-(2-methyl-5-phenyl-2,3,4,5-tetrahydro-1H-benzo[c]azepin-8-yl)ethanone;
2-(2-methyl-5-phenyl-2,3,4,5-tetrahydro-1H-benzo[c]azepin-8-yl)propan-2-ol;
N-methyl-2-(2-methyl-5-phenyl-2,3,4,5-tetrahydro-1H-benzo[c]azepin-8-yl)ethanesulfonamide;
N,N-dimethyl-2-(2-methyl-5-phenyl-2,3,4,5-tetrahydro-1H-benzo[c]azepin-8-yl)ethanesulfonamide;
8-(2-(1H-1,2,4-triazol-1-yl)ethyl)-2-methyl-5-phenyl-2,3,4,5-tetrahydro-1H-benzo[c]azepine;
8-(2-(1H-1,2,3-triazol-1-yl)ethyl)-2-methyl-5-phenyl-2,3,4,5-tetrahydro-1H-benzo[c]azepine;
8-(2-(1H-1,2,4-triazol-1-yl)ethyl)-5-(2-fluorophenyl)-2-methyl-2,3,4,5-tetrahydro-1H-benzo[c]azepine;
8-(2-(1H-1,2,3-triazol-1-yl)ethyl)-5-(2-fluorophenyl)-2-methyl-2,3,4,5-tetrahydro-1H-benzo[c]azepine;
2-methyl-5-phenyl-2,3,4,5-tetrahydro-1H-benzo[c]azepine-8-carbonitrile;
5-(4-chlorophenyl)-2-methyl-2,3,4,5-tetrahydro-1H-benzo[c]azepine-8-carbonitrile;
(2-methyl-5-phenyl-2,3,4,5-tetrahydro-1H-benzo[c]azepin-8-yl)methanamine;
1-(2-methyl-5-phenyl-2,3,4,5-tetrahydro-1H-benzo[c]azepin-8-yl)cyclopropanamine;
4-((2-methyl-5-phenyl-2,3,4,5-tetrahydro-1H-benzo[c]azepin-8-yl)methyl)morpholine;
5-(2-fluorophenyl)-2-methyl-2,3,4,5-tetrahydro-1H-benzo[c]azepine-8-carboxamide;
5-(2-fluorophenyl)-N,2-dimethyl-2,3,4,5-tetrahydro-1H-benzo[c]azepine-8-carboxamide;
5-(2-fluorophenyl)-N,N,2-trimethyl-2,3,4,5-tetrahydro-1H-benzo[c]azepine-8-carboxamide;
(2-methyl-5-phenyl-2,3,4,5-tetrahydro-1H-benzo[c]azepin-8-yl)(morpholino)methanone;
N-(5-(2-fluorophenyl)-2-methyl-2,3,4,5-tetrahydro-1H-benzo[c]azepin-8-yl)acetamide;
N-(5-(2-fluorophenyl)-2-methyl-2,3,4,5-tetrahydro-1H-benzo[c]azepin-8-yl)isobutyramide;
N-(5-(2-fluorophenyl)-2-methyl-2,3,4,5-tetrahydro-1H-benzo[c]azepin-8-yl)picolinamide;
N-(5-(2-fluorophenyl)-2-methyl-2,3,4,5-tetrahydro-1H-benzo[c]azepin-8-yl)morpholine-3-carboxamide;
N-(5-(2-fluorophenyl)-2-methyl-2,3,4,5-tetrahydro-1H-benzo[c]azepin-8-yl)methanesulfonamide;
8-fluoro-2-methyl-5-phenyl-2,3,4,5-tetrahydro-1H-benzo[c]azepine;
2-methyl-5-phenyl-8-(trifluoromethyl)-2,3,4,5-tetrahydro-1H-benzo[c]azepine;
5-(4-chlorophenyl)-8-(trifluoromethoxy)-2,3,4,5-tetrahydro-1H-benzo[c]azepine;
2-(2-methyl-5-phenyl-2,3,4,5-tetrahydro-1H-benzo[c]azepin-8-ylamino)ethanol;
2-methyl-2-(2-methyl-5-phenyl-2,3,4,5-tetrahydro-1H-benzo[c]azepin-8-ylamino)propan-1-ol;
N1,N2-dimethyl-N1-(2-methyl-5-phenyl-2,3,4,5-tetrahydro-1H-benzo[c]azepin-8-yl)ethane-1,2-diamine;
8-methoxy-2-methyl-5-(thiophen-2-yl)-2,3,4,5-tetrahydro-1H-benzo[c]azepine;
5-(3-chlorothiophen-2-yl)-8-methoxy-2-methyl-2,3,4,5-tetrahydro-1H-benzo[c]azepine;
2-(8-methoxy-2-methyl-2,3,4,5-tetrahydro-1H-benzo[c]azepin-5-yl)thiazole;
8-methoxy-2-methyl-5-(pyridin-3-yl)-2,3,4,5-tetrahydro-1H-benzo[c]azepine;
8-methoxy-2-methyl-5-(pyridin-4-yl)-2,3,4,5-tetrahydro-1H-benzo[c]azepine;
4-(2-(5-(4-fluorophenyl)-2-methyl-2,3,4,5-tetrahydro-1H-benzo[c]azepin-8-yloxy)ethyl)morpholine;
5-(benzo[b]thiophen-2-yl)-2-methyl-2,3,4,5-tetrahydro-1H-benzo[c]azepine;
8-methoxy-2-methyl-5-(naphthalen-2-yl)-2,3,4,5-tetrahydro-1H-benzo[c]azepine;

5-(benzo[b]thiophen-5-yl)-8-methoxy-2-methyl-2,3,4,5-tetrahydro-1H-benzo[c]azepine;
5-(3-fluoro-1H-indol-5-yl)-8-methoxy-2-methyl-2,3,4,5-tetrahydro-1H-benzo[c]azepine; and
5-(3-chloro-1H-indol-5-yl)-8-methoxy-2-methyl-2,3,4,5-tetrahydro-1H-benzo[c]azepine.

Other specific compounds of formulae I(A-E) of the present invention are the following 5-substituted phenyl-8-hetero (aryl/cyclic) tetrahydrobenzazepine compounds:

4-(2-methyl-5-phenyl-2,3,4,5-tetrahydro-1H-benzo[c]azepin-8-yl)benzonitrile;
3-(2-methyl-5-phenyl-2,3,4,5-tetrahydro-1H-benzo[c]azepin-8-yl)benzonitrile;
2-methyl-8-(4-(methylsulfonyl)phenyl)-5-phenyl-2,3,4,5-tetrahydro-1H-benzo[c]azepine;
2-methyl-5-phenyl-8-(1H-pyrazol-4-yl)-2,3,4,5-tetrahydro-1H-benzo[c]azepine;
5-methyl-3-(2-methyl-5-phenyl-2,3,4,5-tetrahydro-1H-benzo[c]azepin-8-yl)-1,2,4-oxadiazole;
2-methyl-5-phenyl-8-(pyridin-4-yl)-2,3,4,5-tetrahydro-H-benzo[c]azepine;
6-(2-methyl-5-phenyl-2,3,4,5-tetrahydro-1H-benzo[c]azepin-8-yl)pyridin-2-amine;
2-methyl-5-phenyl-8-(pyridazin-3-yl)-2,3,4,5-tetrahydro-1H-benzo[c]azepine;
2-methyl-8-(6-methylpyridazin-3-yl)-5-phenyl-2,3,4,5-tetrahydro-1H-benzo[c]azepine;
6-fluoro-8-(6-methylpyridazin-3-yl)-5-phenyl-2,3,4,5-tetrahydro-1H-benzo[c]azepine;
6-fluoro-2-methyl-8-(6-methylpyridazin-3-yl)-5-phenyl-2,3,4,5-tetrahydro-1H-benzo[c]azepine;
7-fluoro-2-methyl-8-(6-methylpyridazin-3-yl)-5-phenyl-2,3,4,5-tetrahydro-1H-benzo[c]azepine;
9-fluoro-2-methyl-5-phenyl-8-(pyridazin-3-yl)-2,3,4,5-tetrahydro-1H-benzo[c]azepine;
9-fluoro-5-phenyl-8-(pyridazin-3-yl)-2,3,4,5-tetrahydro-1H-benzo[c]azepine;
9-fluoro-2-methyl-5-phenyl-8-(pyridazin-3-yl)-2,3,4,5-tetrahydro-1H-benzo[c]azepine;
9-fluoro-8-(6-methylpyridazin-3-yl)-5-phenyl-2,3,4,5-tetrahydro-1H-benzo[c]azepine;
6-(9-fluoro-5-phenyl-2,3,4,5-tetrahydro-1H-benzo[c]azepin-8-yl)pyridazin-3-amine;
6-(9-fluoro-2-methyl-5-phenyl-2,3,4,5-tetrahydro-1H-benzo[c]azepin-8-yl)pyridazin-3-amine;
9-fluoro-2-methyl-5-phenyl-8-(6-(trifluoromethyl)pyridazin-3-yl)-2,3,4,5-tetrahydro-1H-benzo[c]azepine;
9-fluoro-5-phenyl-8-(6-(trifluoromethyl)pyridazin-3-yl)-2,3,4,5-tetrahydro-1H-benzo[c]azepine;
9-fluoro-2-methyl-8-(6-methylpyridazin-3-yl)-5-phenyl-2,3,4,5-tetrahydro-1H-benzo[c]azepine;
4-(6-(5-phenyl-2,3,4,5-tetrahydro-1H-benzo[c]azepin-8-yl)pyridazin-3-yl)morpholine;
4-(6-(2-methyl-5-phenyl-2,3,4,5-tetrahydro-1H-benzo[c]azepin-8-yl)pyridazin-3-yl)morpholine;
N,N-dimethyl-6-(2-methyl-5-phenyl-2,3,4,5-tetrahydro-1H-benzo[c]azepin-8-yl)pyridazin-3-amine;
N-methyl-6-(2-methyl-5-phenyl-2,3,4,5-tetrahydro-1H-benzo[c]azepin-8-yl)pyridazin-3-amine;
6-(2-methyl-5-phenyl-2,3,4,5-tetrahydro-1H-benzo[c]azepin-8-yl)pyridazin-3-amine;
(6-(2-methyl-5-phenyl-2,3,4,5-tetrahydro-1H-benzo[c]azepin-8-yl)pyridazin-3-yl)methanol;
6-(2-methyl-5-phenyl-2,3,4,5-tetrahydro-1H-benzo[c]azepin-8-yl)pyridazin-3-ol;
2-methyl-8-(6-methylpyridazin-3-yloxy)-5-phenyl-2,3,4,5-tetrahydro-1H-benzo[c]azepine;
2-methyl-5-phenyl-8-(pyridazin-3-yloxy)-2,3,4,5-tetrahydro-1H-benzo[c]azepine;
1-(methyl(6-(2-methyl-5-phenyl-2,3,4,5-tetrahydro-1H-benzo[c]azepin-8-yl)pyridazin-3-yl)amino)propan-2-ol;
2-(6-(2-methyl-5-phenyl-2,3,4,5-tetrahydro-1H-benzo[c]azepin-8-yl)pyridazin-3-ylamino)butan-1-ol;
2-methyl-5-phenyl-8-(pyrimidin-2-yl)-2,3,4,5-tetrahydro-1H-benzo[c]azepine;
2-methyl-5-phenyl-8-(pyrimidin-5-yl)-2,3,4,5-tetrahydro-1H-benzo[c]azepine;
2-methyl-5-phenyl-8-(pyrazin-2-yl)-2,3,4,5-tetrahydro-1H-benzo[c]azepine;
2-methyl-5-phenyl-8-(1,2,4-triazin-3-yl)-2,3,4,5-tetrahydro-1H-benzo[c]azepine;
2-methyl-5-phenyl-8-(1,3,5-triazin-2-yl)-2,3,4,5-tetrahydro-1H-benzo[c]azepine;
8-(imidazo[1,2-a]pyridin-6-yl)-2-methyl-5-phenyl-2,3,4,5-tetrahydro-1H-benzo[c]azepine;
2-(2-methyl-5-phenyl-2,3,4,5-tetrahydro-1H-benzo[c]azepin-8-yl)-[1,2,4]triazolo[4,3-a]pyridin-3(2H)-one;
2-methyl-5-phenyl-8-(3-(trifluoromethyl)-5,6-dihydro-[1,2,4]triazolo[4,3-a]pyrazin-7(8H)-yl)-2,3,4,5-tetrahydro-1H-benzo[c]azepine;
8-(5,6-dihydroimidazo[1,2-a]pyrazin-7(8H)-yl)-2-methyl-5-phenyl-2,3,4,5-tetrahydro-1H-benzo[c]azepine;
1-(2-methyl-5-phenyl-2,3,4,5-tetrahydro-1H-benzo[c]azepin-8-yl)pyridin-2(1H)-one;
1-(2-methyl-5-phenyl-2,3,4,5-tetrahydro-1H-benzo[c]azepin-8-yl)pyrrolidin-2-one;
1-(2-methyl-5-phenyl-2,3,4,5-tetrahydro-1H-benzo[c]azepin-8-yl)piperidin-2-one;
2-methyl-5-phenyl-8-(piperidin-2-yl)-2,3,4,5-tetrahydro-1H-benzo[c]azepine;
4-(5-phenyl-2,3,4,5-tetrahydro-1H-benzo[c]azepin-8-yl)morpholine;
4-(1,1-dimethyl-5-phenyl-2,3,4,5-tetrahydro-1H-benzo[c]azepin-8-yl)morpholine;
2-methyl-8-(4-methylpiperazin-1-yl)-5-phenyl-2,3,4,5-tetrahydro-1H-benzo[c]azepine;
8-(4-(ethylsulfonyl)piperazin-1-yl)-2-methyl-5-phenyl-2,3,4,5-tetrahydro-1H-benzo[c]azepine;
N-isopropyl-2-(4-(2-methyl-5-phenyl-2,3,4,5-tetrahydro-1H-benzo[c]azepin-8-yl)piperazin-1-yl)acetamide;
5-phenyl-8-(4-(pyridin-2-yl)piperazin-1-yl)-2,3,4,5-tetrahydro-1H-benzo[c]azepine;
2-methyl-5-phenyl-8-(4-(pyridin-2-yl)piperazin-1-yl)-2,3,4,5-tetrahydro-1H-benzo[c]azepine;
2-methyl-5-phenyl-8-(4-(pyrimidin-2-yl)piperazin-1-yl)-2,3,4,5-tetrahydro-1H-benzo[c]azepine;
4-(2-methyl-5-phenyl-2,3,4,5-tetrahydro-1H-benzo[c]azepin-8-yl)morpholine;
4-(2-ethyl-5-phenyl-2,3,4,5-tetrahydro-1H-benzo[c]azepin-8-yl)morpholine;
4-(2-isopropyl-5-phenyl-2,3,4,5-tetrahydro-1H-benzo[c]azepin-8-yl)morpholine;
2-(8-morpholino-5-phenyl-4,5-dihydro-1H-benzo[c]azepin-2(3H)-yl)ethanol;
4-(2-(2-fluoroethyl)-5-phenyl-2,3,4,5-tetrahydro-1H-benzo[c]azepin-8-yl)morpholine;
4-(2-benzyl-5-phenyl-2,3,4,5-tetrahydro-1H-benzo[c]azepin-8-yl)morpholine;
4-(5-phenyl-2-(2,2,2-trifluoroethyl)-2,3,4,5-tetrahydro-1H-benzo[c]azepin-8-yl)morpholine;
5-(4-chlorophenyl)-8-(pyridazin-3-yl)-2,3,4,5-tetrahydro-1H-benzo[c]azepine;
5-(4-chlorophenyl)-8-(6-methylpyridazin-3-yl)-2,3,4,5-tetrahydro-1H-benzo[c]azepine;

5-(4-chlorophenyl)-2-methyl-8-(6-methylpyridazin-3-yl)-2, 3,4,5-tetrahydro-1H-benzo[c]azepine;
5-(4-chlorophenyl)-2-methyl-8-(6-methylpyridazin-3-yl)-2, 3,4,5-tetrahydro-1H-benzo[c]azepin-4-ol;
5-(4-chlorophenyl)-2-methyl-8-(pyridazin-3-yl)-2,3,4,5-tetrahydro-1H-benzo[c]azepine;
5-(4-chlorophenyl)-2-methyl-8-(pyrazin-2-yl)-2,3,4,5-tetrahydro-1H-benzo[c]azepine;
4-(5-(4-chlorophenyl)-2-methyl-2,3,4,5-tetrahydro-1H-benzo[c]azepin-8-yl)-3,5-dimethylisoxazole;
5-(4-chlorophenyl)-2-methyl-8-(pyrimidin-2-yl)-2,3,4,5-tetrahydro-1H-benzo[c]azepine;
6-(5-(4-chlorophenyl)-2-methyl-2,3,4,5-tetrahydro-1H-benzo[c]azepin-8-yl)-N,N-dimethylpyridazin-3-amine;
6-(5-(4-chlorophenyl)-2-methyl-2,3,4,5-tetrahydro-1H-benzo[c]azepin-8-yl)-N-methylpyridazin-3-amine;
6-(5-(4-chlorophenyl)-2-methyl-2,3,4,5-tetrahydro-1H-benzo[c]azepin-8-yl)pyridazin-3-amine;
4-(5-(4-chlorophenyl)-2-methyl-2,3,4,5-tetrahydro-1H-benzo[c]azepin-8-yl)morpholine;
5-(4-chlorophenyl)-9-fluoro-8-(pyridazin-3-yl)-2,3,4,5-tetrahydro-1H-benzo[c]azepine;
5-(4-chlorophenyl)-9-fluoro-2-methyl-8-(pyridazin-3-yl)-2, 3,4,5-tetrahydro-1H-benzo[c]azepine;
6-(5-(4-chlorophenyl)-9-fluoro-2,3,4,5-tetrahydro-1H-benzo[c]azepin-8-yl)pyridazin-3-amine;
6-(5-(4-chlorophenyl)-9-fluoro-2-methyl-2,3,4,5-tetrahydro-1H-benzo[c]azepin-8-yl)pyridazin-3-amine;
6-(5-(4-chlorophenyl)-9-fluoro-2,3,4,5-tetrahydro-1H-benzo[c]azepin-8-yl)pyridazin-3-amine;
5-(3,4-dichlorophenyl)-9-fluoro-2-methyl-8-(pyridazin-3-yl)-2,3,4,5-tetrahydro-1H-benzo[c]azepine;
6-(5-(3,4-dichlorophenyl)-9-fluoro-2,3,4,5-tetrahydro-1H-benzo[c]azepin-8-yl)pyridazin-3-amine;
6-(5-(3,4-dichlorophenyl)-9-fluoro-2-methyl-2,3,4,5-tetrahydro-1H-benzo[c]azepin-8-yl)pyridazin-3-amine;
5-(3,4-dichlorophenyl)-9-fluoro-8-(6-(trifluoromethyl)pyridazin-3-yl)-2,3,4,5-tetrahydro-1H-benzo[c]azepine;
5-(3,4-dichlorophenyl)-9-fluoro-2-methyl-8-(6-(trifluoromethyl)pyridazin-3-yl)-2,3,4,5-tetrahydro-1H-benzo[c]azepine;
5-(2-chlorophenyl)-2-methyl-8-(pyridazin-3-yl)-2,3,4,5-tetrahydro-1H-benzo[c]azepine;
2-(5-(2-fluorophenyl)-2-methyl-2,3,4,5-tetrahydro-1H-benzo[c]azepin-8-yl)benzonitrile;
3-(5-(2-fluorophenyl)-2-methyl-2,3,4,5-tetrahydro-1H-benzo[c]azepin-8-yl)benzonitrile;
4-(5-(2-fluorophenyl)-2-methyl-2,3,4,5-tetrahydro-1H-benzo[c]azepin-8-yl)benzonitrile;
1-(5-(2-fluorophenyl)-2-methyl-2,3,4,5-tetrahydro-1H-benzo[c]azepin-8-yl)pyridin-2(1H)-one;
5-(2-fluorophenyl)-8-(pyridazin-3-yl)-2,3,4,5-tetrahydro-1H-benzo[c]azepine;
5-(2-fluorophenyl)-2-methyl-8-(pyridazin-3-yl)-2,3,4,5-tetrahydro-1H-benzo[c]azepine;
5-(2-fluorophenyl)-8-(6-methylpyridazin-3-yl)-2,3,4,5-tetrahydro-1H-benzo[c]azepine;
5-(2-fluorophenyl)-2-methyl-8-(6-methylpyridazin-3-yl)-2, 3,4,5-tetrahydro-1H-benzo[c]azepine;
2-ethyl-5-(2-fluorophenyl)-8-(6-methylpyridazin-3-yl)-2,3, 4,5-tetrahydro-1H-benzo[c]azepine;
6-(5-(2-fluorophenyl)-2,3,4,5-tetrahydro-1H-benzo[c]azepin-8-yl)pyridazin-3-amine;
6-(5-(2-fluorophenyl)-2-methyl-2,3,4,5-tetrahydro-1H-benzo[c]azepin-8-yl)pyridazin-3-amine;
(6-(5-(2-fluorophenyl)-2-methyl-2,3,4,5-tetrahydro-1H-benzo[c]azepin-8-yl)pyridazin-3-yl)methanol;
6-fluoro-5-(2-fluorophenyl)-8-(6-methylpyridazin-3-yl)-2, 3,4,5-tetrahydro-1H-benzo[c]azepine;
6-fluoro-5-(2-fluorophenyl)-2-methyl-8-(6-methylpyridazin-3-yl)-2,3,4,5-tetrahydro-1H-benzo[c]azepine;
7-fluoro-5-(2-fluorophenyl)-8-(pyridazin-3-yl)-2,3,4,5-tetrahydro-1H-benzo[c]azepine;
7-fluoro-5-(2-fluorophenyl)-2-methyl-8-(pyridazin-3-yl)-2, 3,4,5-tetrahydro-1H-benzo[c]azepine;
7-fluoro-5-(2-fluorophenyl)-8-(6-methylpyridazin-3-yl)-2, 3,4,5-tetrahydro-1H-benzo[c]azepine;
7-fluoro-5-(2-fluorophenyl)-2-methyl-8-(6-methylpyridazin-3-yl)-2,3,4,5-tetrahydro-1H-benzo[c]azepine;
6-(7-fluoro-5-(2-fluorophenyl)-2,3,4,5-tetrahydro-1H-benzo[c]azepin-8-yl)pyridazin-3-amine;
6-(7-fluoro-5-(2-fluorophenyl)-2-methyl-2,3,4,5-tetrahydro-1H-benzo[c]azepin-8-yl)pyridazin-3-amine;
9-fluoro-5-(2-fluorophenyl)-8-(6-methylpyridazin-3-yl)-2, 3,4,5-tetrahydro-1H-benzo[c]azepine;
9-fluoro-5-(2-fluorophenyl)-2-methyl-8-(6-methylpyridazin-3-yl)-2,3,4,5-tetrahydro-1H-benzo[c]azepine;
6-(9-fluoro-5-(2-fluorophenyl)-2,3,4,5-tetrahydro-1H-benzo[c]azepin-8-yl)pyridazin-3-amine;
6-(9-fluoro-5-(2-fluorophenyl)-2-methyl-2,3,4,5-tetrahydro-1H-benzo[c]azepin-8-yl)pyridazin-3-amine;
5-(2-fluorophenyl)-2-methyl-8-(pyridin-2-yloxy)-2,3,4,5-tetrahydro-1H-benzo[c]azepine;
5-(2-fluorophenyl)-2-methyl-8-(6-methylpyridazin-3-yloxy)-2,3,4,5-tetrahydro-1H-benzo[c]azepine;
5-(2-fluorophenyl)-2-methyl-8-(pyridazin-3-yloxy)-2,3,4,5-tetrahydro-1H-benzo[c]azepine;
5-(2-fluorophenyl)-2-methyl-8-(pyrimidin-2-yloxy)-2,3,4, 5-tetrahydro-1H-benzo[c]azepine;
5-(2-fluorophenyl)-2-methyl-8-(4-(pyrimidin-2-yl)piperazin-1-yl)-2,3,4,5-tetrahydro-1H-benzo[c]azepine;
5-(2-fluorophenyl)-8-(6-(trifluoromethyl)pyridazin-3-yl)-2, 3,4,5-tetrahydro-1H-benzo[c]azepine;
5-(2-fluorophenyl)-2-methyl-8-(6-(trifluoromethyl)pyridazin-3-yl)-2,3,4,5-tetrahydro-1H-benzo[c]azepine;
5-(2-fluorophenyl)-2-methyl-8-(2-(trifluoromethyl)pyrimidin-5-yl)-2,3,4,5-tetrahydro-1H-benzo[c]azepine;
2-(5-(2-fluorophenyl)-2-methyl-2,3,4,5-tetrahydro-1H-benzo[c]azepin-8-yl)pyrimidine-5-carbonitrile;
5-(2-fluorophenyl)-2-methyl-8-(5-(trifluoromethyl)pyrimidin-2-yl)-2,3,4,5-tetrahydro-1H-benzo[c]azepine;
5-(2-fluorophenyl)-2-methyl-8-(1,2,4-triazin-3-yl)-2,3,4,5-tetrahydro-1H-benzo[c]azepine;
5-(2-fluorophenyl)-2-methyl-8-(1,3,5-triazin-2-yl)-2,3,4,5-tetrahydro-1H-benzo[c]azepine;
5-(2-fluorophenyl)-2-methyl-8-(4-methylpiperazin-1-yl)-2, 3,4,5-tetrahydro-1H-benzo[c]azepine;
9-fluoro-5-(2-fluorophenyl)-8-(4-methylpiperazin-1-yl)-2, 3,4,5-tetrahydro-1H-benzo[c]azepine;
9-fluoro-5-(2-fluorophenyl)-8-(piperazin-1-yl)-2,3,4,5-tetrahydro-1H-benzo[c]azepine;
9-fluoro-5-(2-fluorophenyl)-2-methyl-8-(4-methylpiperazin-1-yl)-2,3,4,5-tetrahydro-1H-benzo[c]azepine;
5-(2-fluorophenyl)-2-methyl-8-(4-(pyrimidin-2-yl)piperazin-1-yl)-2,3,4,5-tetrahydro-1H-benzo[c]azepine;
5-(2-fluorophenyl)-8-(imidazo[1,2-a]pyridin-6-yl)-2-methyl-2,3,4,5-tetrahydro-1H-benzo[c]azepine;
8-([1,2,4]triazolo[1,5-a]pyridin-6-yl)-5-(2-fluorophenyl)-2-methyl-2,3,4,5-tetrahydro-1H-benzo[c]azepine;
8-([1,2,4]triazolo[4,3-a]pyridin-6-yl)-5-(2-fluorophenyl)-2-methyl-2,3,4,5-tetrahydro-1H-benzo[c]azepine;
6-(5-(2-fluorophenyl)-2-methyl-2,3,4,5-tetrahydro-1H-benzo[c]azepin-8-yl)benzo[d]oxazol-2(3H)-one;

5-(5-(2-fluorophenyl)-2-methyl-2,3,4,5-tetrahydro-1H-benzo[c]azepin-8-yl)benzo[c][1,2,5]thiadiazole;
5-(3-fluorophenyl)-2-methyl-8-(6-methylpyridazin-3-yl)-2,3,4,5-tetrahydro-1H-benzo[c]azepine;
5-(3-fluorophenyl)-2-methyl-8-(piperazin-1-yl)-2,3,4,5-tetrahydro-1H-benzo[c]azepine;
5-(3-fluorophenyl)-2-methyl-8-(4-methylpiperazin-1-yl)-2,3,4,5-tetrahydro-1H-benzo[c]azepine;
9-fluoro-5-(3-fluorophenyl)-8-(pyridazin-3-yl)-2,3,4,5-tetrahydro-1H-benzo[c]azepine;
9-fluoro-5-(3-fluorophenyl)-2-methyl-8-(pyridazin-3-yl)-2,3,4,5-tetrahydro-1H-benzo[c]azepine;
6-(9-fluoro-5-(3-fluorophenyl)-2,3,4,5-tetrahydro-1H-benzo[c]azepin-8-yl)pyridazin-3-amine;
6-(9-fluoro-5-(3-fluorophenyl)-2-methyl-2,3,4,5-tetrahydro-1H-benzo[c]azepin-8-yl)pyridazin-3-amine;
5-(4-fluorophenyl)-2-methyl-8-(6-methylpyridazin-3-yl)-2,3,4,5-tetrahydro-1H-benzo[c]azepine;
5-(4-fluorophenyl)-2-methyl-8-(6-methylpyridazin-3-yl)-2,3,4,5-tetrahydro-1H-benzo[c]azepin-4-ol;
9-fluoro-5-(4-fluorophenyl)-8-(pyridazin-3-yl)-2,3,4,5-tetrahydro-1H-benzo[c]azepine;
9-fluoro-5-(4-fluorophenyl)-2-methyl-8-(pyridazin-3-yl)-2,3,4,5-tetrahydro-1H-benzo[c]azepine;
9-fluoro-5-(4-fluorophenyl)-8-(6-methylpyridazin-3-yl)-2,3,4,5-tetrahydro-1H-benzo[c]azepine;
9-fluoro-5-(4-fluorophenyl)-2-methyl-8-(6-methylpyridazin-3-yl)-2,3,4,5-tetrahydro-1H-benzo[c]azepine;
6-(9-fluoro-5-(4-fluorophenyl)-2,3,4,5-tetrahydro-1H-benzo[c]azepin-8-yl)pyridazin-3-amine;
6-(9-fluoro-5-(4-fluorophenyl)-2-methyl-2,3,4,5-tetrahydro-1H-benzo[c]azepin-8-yl)pyridazin-3-amine;
9-fluoro-5-(4-fluorophenyl)-8-(6-(trifluoromethyl)pyridazin-3-yl)-2,3,4,5-tetrahydro-1H-benzo[c]azepine;
9-fluoro-5-(4-fluorophenyl)-2-methyl-8-(6-(trifluoromethyl)pyridazin-3-yl)-2,3,4,5-tetrahydro-1H-benzo[c]azepine;
5-(4-fluorophenyl)-2-methyl-8-(6-(trifluoromethyl)pyridazin-3-yl)-2,3,4,5-tetrahydro-1H-benzo[c]azepine;
5-(4-fluorophenyl)-2-methyl-8-(6-(4-methylpiperazin-1-yl)pyridazin-3-yl)-2,3,4,5-tetrahydro-1H-benzo[c]azepine;
1-(6-(5-(4-fluorophenyl)-2-methyl-2,3,4,5-tetrahydro-1H-benzo[c]azepin-8-yl)pyridazin-3-yl)piperidin-4-ol;
5-(4-fluorophenyl)-2-methyl-8-(pyrimidin-5-yl)-2,3,4,5-tetrahydro-1H-benzo[c]azepine;
5-(4-fluorophenyl)-2-methyl-8-(1,2,4-triazin-3-yl)-2,3,4,5-tetrahydro-1H-benzo[c]azepine;
5-(4-fluorophenyl)-2-methyl-8-(1,3,5-triazin-2-yl)-2,3,4,5-tetrahydro-1H-benzo[c]azepine;
4-(5-(4-fluorophenyl)-2-methyl-2,3,4,5-tetrahydro-1H-benzo[c]azepin-8-yl)morpholine;
9-fluoro-5-(4-fluorophenyl)-8-(piperazin-1-yl)-2,3,4,5-tetrahydro-1H-benzo[c]azepine;
9-fluoro-5-(4-fluorophenyl)-8-(4-methylpiperazin-1-yl)-2,3,4,5-tetrahydro-1H-benzo[c]azepine;
9-fluoro-5-(4-fluorophenyl)-2-methyl-8-(4-methylpiperazin-1-yl)-2,3,4,5-tetrahydro-1H-benzo[c]azepine;
5-(5-(4-fluorophenyl)-2-methyl-2,3,4,5-tetrahydro-1H-benzo[c]azepin-8-yl)-3,3-dimethylindolin-2-one;
5-(4-fluorophenyl)-8-(imidazo[1,2-a]pyrazin-3-yl)-2-methyl-2,3,4,5-tetrahydro-1H-benzo[c]azepine;
5-(4-fluorophenyl)-2-methyl-8-(2-(trifluoromethyl)pyrimidin-5-yl)-2,3,4,5-tetrahydro-1H-benzo[c]azepine;
5-(4-fluorophenyl)-2-methyl-8-(5-(trifluoromethyl)pyrimidin-2-yl)-2,3,4,5-tetrahydro-1H-benzo[c]azepine;
8-(6-methylpyridazin-3-yl)-5-p-tolyl-2,3,4,5-tetrahydro-1H-benzo[c]azepine;
2-methyl-8-(4-(pyrimidin-2-yl)piperazin-1-yl)-5-p-tolyl-2,3,4,5-tetrahydro-1H-benzo[c]azepine;
2-methyl-8-(6-methylpyridazin-3-yl)-5-p-tolyl-2,3,4,5-tetrahydro-1H-benzo[c]azepine;
2-methyl-8-(6-methylpyridazin-3-yl)-5-o-tolyl-2,3,4,5-tetrahydro-1H-benzo[c]azepine;
5-(2-methoxyphenyl)-2-methyl-8-(6-methylpyridazin-3-yl)-2,3,4,5-tetrahydro-1H-benzo[c]azepine;
5-(4-methoxyphenyl)-2-methyl-8-(6-methylpyridazin-3-yl)-2,3,4,5-tetrahydro-1H-benzo[c]azepine;
4-(2-methyl-8-(6-methylpyridazin-3-yl)-2,3,4,5-tetrahydro-1H-benzo[c]azepin-5-yl)phenol;
2-(2-methyl-8-(6-methylpyridazin-3-yl)-2,3,4,5-tetrahydro-1H-benzo[c]azepin-5-yl)phenol;
2-methyl-8-(6-methylpyridazin-3-yl)-5-(4-(trifluoromethoxy)phenyl)-2,3,4,5-tetrahydro-1H-benzo[c]azepine;
4-(2-methyl-5-(4-(trifluoromethyl)phenyl)-2,3,4,5-tetrahydro-1H-benzo[c]azepin-8-yl)morpholine;
2-methyl-8-(6-methylpyridazin-3-yl)-5-(3-(trifluoromethyl)phenyl)-2,3,4,5-tetrahydro-1H-benzo[c]azepine;
2-(2-methyl-8-(6-methylpyridazin-3-yl)-2,3,4,5-tetrahydro-1H-benzo[c]azepin-5-yl)benzonitrile;
4-(2-methyl-8-(6-methylpyridazin-3-yl)-2,3,4,5-tetrahydro-1H-benzo[c]azepin-5-yl)benzonitrile;
N,N-dimethyl-4-(2-methyl-8-(6-methylpyridazin-3-yl)-2,3,4,5-tetrahydro-1H-benzo[c]azepin-5-yl)benzamide;
2-methyl-8-(6-methylpyridazin-3-yl)-5-(4-(methylsulfonyl)phenyl)-2,3,4,5-tetrahydro-1H-benzo[c]azepine;
4-(2-methyl-5-(4-(methylsulfonyl)phenyl)-2,3,4,5-tetrahydro-1H-benzo[c]azepin-8-yl)morpholine;
5-(2,3-difluorophenyl)-2-methyl-8-(6-methylpyridazin-3-yl)-2,3,4,5-tetrahydro-1H-benzo[c]azepine;
5-(2,3-difluorophenyl)-9-fluoro-8-(pyridazin-3-yl)-2,3,4,5-tetrahydro-1H-benzo[c]azepine;
5-(2,3-difluorophenyl)-9-fluoro-2-methyl-8-(pyridazin-3-yl)-2,3,4,5-tetrahydro-1H-benzo[c]azepine;
6-(5-(2,3-difluorophenyl)-9-fluoro-2,3,4,5-tetrahydro-1H-benzo[c]azepin-8-yl)pyridazin-3-amine;
6-(5-(2,3-difluorophenyl)-9-fluoro-2-methyl-2,3,4,5-tetrahydro-1H-benzo[c]azepin-8-yl)pyridazin-3-amine;
5-(2,4-difluorophenyl)-2-methyl-8-(6-methylpyridazin-3-yl)-2,3,4,5-tetrahydro-1H-benzo[c]azepine;
5-(2,4-difluorophenyl)-9-fluoro-2-methyl-8-(6-methylpyridazin-3-yl)-2,3,4,5-tetrahydro-1H-benzo[c]azepine;
5-(2,4-difluorophenyl)-2-methyl-8-(4-methylpiperazin-1-yl)-2,3,4,5-tetrahydro-1H-benzo[c]azepine;
5-(2,4-difluorophenyl)-9-fluoro-8-(pyridazin-3-yl)-2,3,4,5-tetrahydro-1H-benzo[c]azepine;
5-(2,4-difluorophenyl)-9-fluoro-2-methyl-8-(pyridazin-3-yl)-2,3,4,5-tetrahydro-1H-benzo[c]azepine;
6-(5-(2,4-difluorophenyl)-9-fluoro-2,3,4,5-tetrahydro-1H-benzo[c]azepin-8-yl)pyridazin-3-amine;
6-(5-(2,4-difluorophenyl)-9-fluoro-2-methyl-2,3,4,5-tetrahydro-1H-benzo[c]azepin-8-yl)pyridazin-3-amine;
5-(2,5-difluorophenyl)-2-methyl-8-(6-methylpyridazin-3-yl)-2,3,4,5-tetrahydro-1H-benzo[c]azepine;
5-(2,6-difluorophenyl)-2-methyl-8-(6-methylpyridazin-3-yl)-2,3,4,5-tetrahydro-1H-benzo[c]azepine;
5-(2,5-difluorophenyl)-9-fluoro-8-(pyridazin-3-yl)-2,3,4,5-tetrahydro-1H-benzo[c]azepine;
5-(2,5-difluorophenyl)-9-fluoro-2-methyl-8-(pyridazin-3-yl)-2,3,4,5-tetrahydro-1H-benzo[c]azepine;
6-(5-(2,5-difluorophenyl)-9-fluoro-2,3,4,5-tetrahydro-1H-benzo[c]azepin-8-yl)pyridazin-3-amine;
6-(5-(2,5-difluorophenyl)-9-fluoro-2-methyl-2,3,4,5-tetrahydro-1H-benzo[c]azepin-8-yl)pyridazin-3-amine;

5-(3,4-difluorophenyl)-8-(6-methylpyridazin-3-yl)-2,3,4,5-tetrahydro-1H-benzo[c]azepine;
5-(3,4-difluorophenyl)-2-methyl-8-(6-methylpyridazin-3-yl)-2,3,4,5-tetrahydro-1H-benzo[c]azepine;
5-(3,4-difluorophenyl)-9-fluoro-8-(pyridazin-3-yl)-2,3,4,5-tetrahydro-1H-benzo[c]azepine;
5-(3,4-difluorophenyl)-9-fluoro-2-methyl-8-(pyridazin-3-yl)-2,3,4,5-tetrahydro-1H-benzo[c]azepine;
6-(5-(3,4-difluorophenyl)-9-fluoro-2,3,4,5-tetrahydro-1H-benzo[c]azepin-8-yl)pyridazin-3-amine;
6-(5-(3,4-difluorophenyl)-9-fluoro-2-methyl-2,3,4,5-tetrahydro-1H-benzo[c]azepin-8-yl)pyridazin-3-amine;
5-(3,5-difluorophenyl)-2-methyl-8-(pyridazin-3-yl)-2,3,4,5-tetrahydro-1H-benzo[c]azepine;
5-(3,5-difluorophenyl)-2-methyl-8-(6-methylpyridazin-3-yl)-2,3,4,5-tetrahydro-1H-benzo[c]azepine;
5-(3,5-difluorophenyl)-9-fluoro-2-methyl-8-(6-methylpyridazin-3-yl)-2,3,4,5-tetrahydro-1H-benzo[c]azepine;
4-(5-(3,5-difluorophenyl)-2-methyl-2,3,4,5-tetrahydro-1H-benzo[c]azepin-8-yl)morpholine;
5-(3,5-difluorophenyl)-2-methyl-8-(piperazin-1-yl)-2,3,4,5-tetrahydro-1H-benzo[c]azepine;
5-(3,5-difluorophenyl)-2-methyl-8-(4-methylpiperazin-1-yl)-2,3,4,5-tetrahydro-1H-benzo[c]azepine;
5-(3,5-difluorophenyl)-9-fluoro-8-(pyridazin-3-yl)-2,3,4,5-tetrahydro-1H-benzo[c]azepine;
5-(3,5-difluorophenyl)-9-fluoro-2-methyl-8-(pyridazin-3-yl)-2,3,4,5-tetrahydro-1H-benzo[c]azepine;
6-(5-(3,5-difluorophenyl)-9-fluoro-2,3,4,5-tetrahydro-1H-benzo[c]azepin-8-yl)pyridazin-3-amine;
6-(5-(3,5-difluorophenyl)-9-fluoro-2-methyl-2,3,4,5-tetrahydro-1H-benzo[c]azepin-8-yl)pyridazin-3-amine;
5-(3,5-difluorophenyl)-6-fluoro-8-(pyridazin-3-yl)-2,3,4,5-tetrahydro-1H-benzo[c]azepine;
5-(3,5-difluorophenyl)-6-fluoro-2-methyl-8-(pyridazin-3-yl)-2,3,4,5-tetrahydro-1H-benzo[c]azepine;
6-(5-(3,5-difluorophenyl)-6-fluoro-2,3,4,5-tetrahydro-1H-benzo[c]azepin-8-yl)pyridazin-3-amine;
6-(5-(3,5-difluorophenyl)-6-fluoro-2-methyl-2,3,4,5-tetrahydro-1H-benzo[c]azepin-8-yl)pyridazin-3-amine;
5-(3-chloro-2-fluorophenyl)-2-methyl-8-(6-methylpyridazin-3-yl)-2,3,4,5-tetrahydro-1H-benzo[c]azepine;
5-(4-chloro-2-fluorophenyl)-9-fluoro-8-(pyridazin-3-yl)-2,3,4,5-tetrahydro-1H-benzo[c]azepine;
5-(4-chloro-2-fluorophenyl)-9-fluoro-2-methyl-8-(pyridazin-3-yl)-2,3,4,5-tetrahydro-1H-benzo[c]azepine;
5-(4-chloro-2-fluorophenyl)-9-fluoro-8-(6-methylpyridazin-3-yl)-2,3,4,5-tetrahydro-1H-benzo[c]azepine;
5-(4-chloro-2-fluorophenyl)-2-methyl-8-(6-methylpyridazin-3-yl)-2,3,4,5-tetrahydro-1H-benzo[c]azepine;
6-(5-(4-chloro-2-fluorophenyl)-9-fluoro-2,3,4,5-tetrahydro-1H-benzo[c]azepin-8-yl)pyridazin-3-amine;
6-(5-(4-chloro-2-fluorophenyl)-9-fluoro-2-methyl-2,3,4,5-tetrahydro-1H-benzo[c]azepin-8-yl)pyridazin-3-amine;
9-fluoro-5-(2-fluoro-4-methylphenyl)-8-(6-methylpyridazin-3-yl)-2,3,4,5-tetrahydro-1H-benzo[c]azepine;
5-(2-fluoro-4-methylphenyl)-2-methyl-8-(6-methylpyridazin-3-yl)-2,3,4,5-tetrahydro-1H-benzo[c]azepine;
6-(9-fluoro-5-(2-fluoro-4-methylphenyl)-2,3,4,5-tetrahydro-1H-benzo[c]azepin-8-yl)pyridazin-3-amine;
6-(9-fluoro-5-(2-fluoro-4-methylphenyl)-2-methyl-2,3,4,5-tetrahydro-1H-benzo[c]azepin-8-yl)pyridazin-3-amine;
9-fluoro-5-(2-fluoro-4-methylphenyl)-8-(6-(trifluoromethyl)pyridazin-3-yl)-2,3,4,5-tetrahydro-1H-benzo[c]azepine;
9-fluoro-5-(2-fluoro-4-methylphenyl)-2-methyl-8-(6-(trifluoromethyl)pyridazin-3-yl)-2,3,4,5-tetrahydro-1H-benzo[c]azepine;
5-(2-fluoro-3-methylphenyl)-2-methyl-8-(6-methylpyridazin-3-yl)-2,3,4,5-tetrahydro-1H-benzo[c]azepine;
5-(2-fluoro-4-methoxyphenyl)-2-methyl-8-(6-methylpyridazin-3-yl)-2,3,4,5-tetrahydro-1H-benzo[c]azepine;
5-(2-fluoro-3-methoxyphenyl)-2-methyl-8-(6-methylpyridazin-3-yl)-2,3,4,5-tetrahydro-1H-benzo[c]azepine; and
2-fluoro-4-(2-methyl-8-(6-methylpyridazin-3-yl)-2,3,4,5-tetrahydro-1H-benzo[c]azepin-5-yl)benzonitrile.

Other specific compounds of formulae I(A-E) of the present invention are the following 5-bicyclic aryl-8-hetero (aryl/cyclic) tetrahydrobenzazepine compounds:
5-(naphthalen-2-yl)-8-(pyridazin-3-yl)-2,3,4,5-tetrahydro-1H-benzo[c]azepine;
2-methyl-5-(naphthalen-2-yl)-8-(pyridazin-3-yl)-2,3,4,5-tetrahydro-1H-benzo[c]azepine;
5-(1-fluoronaphthalen-2-yl)-2-methyl-8-(6-methylpyridazin-3-yl)-2,3,4,5-tetrahydro-1H-benzo[c]azepine;
5-(3-fluoronaphthalen-2-yl)-2-methyl-8-(6-methylpyridazin-3-yl)-2,3,4,5-tetrahydro-1H-benzo[c]azepine;
6-(5-(naphthalen-2-yl)-2,3,4,5-tetrahydro-1H-benzo[c]azepin-8-yl)pyridazin-3-amine;
6-(2-methyl-5-(naphthalen-2-yl)-2,3,4,5-tetrahydro-1H-benzo[c]azepin-8-yl)pyridazin-3-amine;
4-(2-methyl-5-(naphthalen-2-yl)-2,3,4,5-tetrahydro-1H-benzo[c]azepin-8-yl)morpholine;
5-(1-fluoronaphthalen-2-yl)-8-(pyridazin-3-yl)-2,3,4,5-tetrahydro-1H-benzo[c]azepine;
5-(1-fluoronaphthalen-2-yl)-2-methyl-8-(pyridazin-3-yl)-2,3,4,5-tetrahydro-1H-benzo[c]azepine;
9-fluoro-5-(naphthalen-2-yl)-8-(pyridazin-3-yl)-2,3,4,5-tetrahydro-1H-benzo[c]azepine;
9-fluoro-2-methyl-5-(naphthalen-2-yl)-8-(pyridazin-3-yl)-2,3,4,5-tetrahydro-1H-benzo[c]azepine;
9-fluoro-5-(1-fluoronaphthalen-2-yl)-8-(pyridazin-3-yl)-2,3,4,5-tetrahydro-1H-benzo[c]azepine;
9-fluoro-5-(1-fluoronaphthalen-2-yl)-2-methyl-8-(pyridazin-3-yl)-2,3,4,5-tetrahydro-1H-benzo[c]azepine;
6-(9-fluoro-5-(1-fluoronaphthalen-2-yl)-2,3,4,5-tetrahydro-1H-benzo[c]azepin-8-yl)pyridazin-3-amine; and
6-(9-fluoro-5-(1-fluoronaphthalen-2-yl)-2-methyl-2,3,4,5-tetrahydro-1H-benzo[c]azepin-8-yl)pyridazin-3-amine.

Other specific compounds of formulae I(A-E) of the present invention are the following 5-bicyclic heteroaryl-8-hetero (aryl/cyclic) tetrahydrobenzazepine compounds:
4-(5-(benzo[b]thiophen-5-yl)-2-methyl-2,3,4,5-tetrahydro-1H-benzo[c]azepin-8-yl)morpholine;
5-(benzo[b]thiophen-5-yl)-2-methyl-8-(pyrimidin-5-yl)-2,3,4,5-tetrahydro-1H-benzo[c]azepine;
5-(benzo[b]thiophen-5-yl)-2-methyl-8-(pyrazin-2-yl)-2,3,4,5-tetrahydro-1H-benzo[c]azepine;
5-(benzo[b]thiophen-5-yl)-2-methyl-8-(6-methylpyridazin-3-yl)-2,3,4,5-tetrahydro-1H-benzo[c]azepine;
5-(benzo[b]thiophen-5-yl)-2-methyl-8-(pyridazin-3-yl)-2,3,4,5-tetrahydro-1H-benzo[c]azepine;
4-methyl-7-(2-methyl-8-(6-methylpyridazin-3-yl)-2,3,4,5-tetrahydro-1H-benzo[c]azepin-5-yl)-3,4-dihydro-2H-benzo[b][1,4]oxazine;
4-methyl-7-(2-methyl-8-morpholino-2,3,4,5-tetrahydro-1H-benzo[c]azepin-5-yl)-3,4-dihydro-2H-benzo[b][1,4]oxazine;
4-(5-(benzo[d][1,3]dioxol-5-yl)-2-methyl-2,3,4,5-tetrahydro-1H-benzo[c]azepin-8-yl)morpholine;
5-(benzo[d][1,3]dioxol-5-yl)-2-methyl-8-(6-methylpyridazin-3-yl)-2,3,4,5-tetrahydro-1H-benzo[c]azepine;

4-(5-(2,3-dihydrobenzo[b][1,4]dioxin-6-yl)-2-methyl-2,3,4,5-tetrahydro-1H-benzo[c]azepin-8-yl)morpholine;

5-(2,3-dihydrobenzo[b][1,4]dioxin-6-yl)-2-methyl-8-(6-methylpyridazin-3-yl)-2,3,4,5-tetrahydro-1H-benzo[c]azepine;

5-(3-chloro-1H-indol-5-yl)-2-methyl-8-(6-methylpyridazin-3-yl)-2,3,4,5-tetrahydro-1H-benzo[c]azepine; and 5-(3-fluoro-1H-indol-5-yl)-2-methyl-8-(6-methylpyridazin-3-yl)-2,3,4,5-tetrahydro-1H-benzo[c]azepine.

Other specific compounds of formulae I(A-E) of the present invention are the following aryl- or heteroaryl-substituted tetrahydrobenzazepine compounds:

5-phenyl-8-(pyrimidin-2-yl)-2,3,4,5-tetrahydro-1H-benzo[c]azepine;

5-phenyl-8-(pyrimidin-5-yl)-2,3,4,5-tetrahydro-1H-benzo[c]azepine;

5-phenyl-8-(pyrazin-2-yl)-2,3,4,5-tetrahydro-1H-benzo[c]azepine;

6-fluoro-5-(2-fluorophenyl)-8-(pyridazin-3-yl)-2,3,4,5-tetrahydro-1H-benzo[c]azepine;

6-fluoro-5-(2-fluorophenyl)-2-methyl-8-(pyridazin-3-yl)-2,3,4,5-tetrahydro-1H-benzo[c]azepine;

6-(6-fluoro-5-(2-fluorophenyl)-2,3,4,5-tetrahydro-1H-benzo[c]azepin-8-yl)pyridazin-3-amine;

6-(6-fluoro-5-(2-fluorophenyl)-2-methyl-2,3,4,5-tetrahydro-1H-benzo[c]azepin-8-yl)pyridazin-3-amine;

7-fluoro-5-(2-fluorophenyl)-8-(pyridazin-3-yl)-2,3,4,5-tetrahydro-1H-benzo[c]azepine;

9-fluoro-5-(2-fluorophenyl)-8-(pyridazin-3-yl)-2,3,4,5-tetrahydro-1H-benzo[c]azepine;

9-fluoro-5-(2-fluorophenyl)-2-methyl-8-(pyridazin-3-yl)-2,3,4,5-tetrahydro-1H-benzo[c]azepine;

9-fluoro-5-(2-fluorophenyl)-8-(6-(trifluoromethyl)pyridazin-3-yl)-2,3,4,5-tetrahydro-1H-benzo[c]azepine;

9-fluoro-5-(2-fluorophenyl)-2-methyl-8-(6-(trifluoromethyl)pyridazin-3-yl)-2,3,4,5-tetrahydro-1H-benzo[c]azepine;

5-(2-fluorophenyl)-8-(pyridin-2-yloxy)-2,3,4,5-tetrahydro-1H-benzo[c]azepine;

5-(2-fluorophenyl)-8-(6-methylpyridazin-3-yloxy)-2,3,4,5-tetrahydro-1H-benzo[c]azepine;

5-(2-fluorophenyl)-8-(pyridazin-3-yloxy)-2,3,4,5-tetrahydro-1H-benzo[c]azepine;

9-fluoro-5-(2-fluorophenyl)-8-(pyridazin-3-yloxy)-2,3,4,5-tetrahydro-1H-benzo[c]azepine;

9-fluoro-5-(2-fluorophenyl)-2-methyl-8-(pyridazin-3-yloxy)-2,3,4,5-tetrahydro-1H-benzo[c]azepine;

6-(9-fluoro-5-(2-fluorophenyl)-2-methyl-2,3,4,5-tetrahydro-1H-benzo[c]azepin-8-yloxy)pyridazin-3-amine;

6-(9-fluoro-5-(2-fluorophenyl)-2,3,4,5-tetrahydro-1H-benzo[c]azepin-8-yloxy)pyridazin-3-amine;

9-fluoro-5-(2-fluorophenyl)-8-(6-methylpyridazin-3-yloxy)-2,3,4,5-tetrahydro-1H-benzo[c]azepine;

9-fluoro-5-(2-fluorophenyl)-2-methyl-8-(6-methylpyridazin-3-yloxy)-2,3,4,5-tetrahydro-1H-benzo[c]azepine;

9-fluoro-5-(2-fluorophenyl)-8-(6-(trifluoromethyl)pyridazin-3-yloxy)-2,3,4,5-tetrahydro-1H-benzo[c]azepine;

9-fluoro-5-(2-fluorophenyl)-2-methyl-8-(6-(trifluoromethyl)pyridazin-3-yloxy)-2,3,4,5-tetrahydro-1H-benzo[c]azepine;

7-fluoro-5-(2-fluorophenyl)-8-(pyridazin-3-yloxy)-2,3,4,5-tetrahydro-1H-benzo[c]azepine;

7-fluoro-5-(2-fluorophenyl)-2-methyl-8-(pyridazin-3-yloxy)-2,3,4,5-tetrahydro-1H-benzo[c]azepine;

6-fluoro-5-(2-fluorophenyl)-8-(pyridazin-3-yloxy)-2,3,4,5-tetrahydro-1H-benzo[c]azepine;

6-fluoro-5-(2-fluorophenyl)-2-methyl-8-(pyridazin-3-yloxy)-2,3,4,5-tetrahydro-1H-benzo[c]azepine;

5-(2-fluorophenyl)-8-(pyrimidin-2-yloxy)-2,3,4,5-tetrahydro-1H-benzo[c]azepine;

5-(4-fluorophenyl)-8-(6-methylpyridazin-3-yl)-2,3,4,5-tetrahydro-1H-benzo[c]azepine;

5-(4-fluorophenyl)-8-(pyridazin-3-yl)-2,3,4,5-tetrahydro-1H-benzo[c]azepine;

5-(4-fluorophenyl)-2-methyl-8-(pyridazin-3-yl)-2,3,4,5-tetrahydro-1H-benzo[c]azepine;

6-(5-(4-fluorophenyl)-2,3,4,5-tetrahydro-1H-benzo[c]azepin-8-yl)pyridazin-3-amine;

6-(5-(4-fluorophenyl)-2-methyl-2,3,4,5-tetrahydro-1H-benzo[c]azepin-8-yl)pyridazin-3-amine;

7-fluoro-5-(4-fluorophenyl)-8-(pyridazin-3-yl)-2,3,4,5-tetrahydro-1H-benzo[c]azepine;

7-fluoro-5-(4-fluorophenyl)-2-methyl-8-(pyridazin-3-yl)-2,3,4,5-tetrahydro-1H-benzo[c]azepine;

7-fluoro-5-(4-fluorophenyl)-8-(6-methylpyridazin-3-yl)-2,3,4,5-tetrahydro-1H-benzo[c]azepine;

7-fluoro-5-(4-fluorophenyl)-2-methyl-8-(6-methylpyridazin-3-yl)-2,3,4,5-tetrahydro-1H-benzo[c]azepine;

6-(7-fluoro-5-(4-fluorophenyl)-2,3,4,5-tetrahydro-1H-benzo[c]azepin-8-yl)pyridazin-3-amine;

6-(7-fluoro-5-(4-fluorophenyl)-2-methyl-2,3,4,5-tetrahydro-1H-benzo[c]azepin-8-yl)pyridazin-3-amine;

7-fluoro-5-(4-fluorophenyl)-8-(6-(trifluoromethyl)pyridazin-3-yl)-2,3,4,5-tetrahydro-1H-benzo[c]azepine;

7-fluoro-5-(4-fluorophenyl)-2-methyl-8-(6-(trifluoromethyl)pyridazin-3-yl)-2,3,4,5-tetrahydro-1H-benzo[c]azepine;

6-fluoro-5-(4-fluorophenyl)-8-(pyridazin-3-yl)-2,3,4,5-tetrahydro-1H-benzo[c]azepine;

6-fluoro-5-(4-fluorophenyl)-2-methyl-8-(pyridazin-3-yl)-2,3,4,5-tetrahydro-1H-benzo[c]azepine;

6-fluoro-5-(4-fluorophenyl)-8-(6-methylpyridazin-3-yl)-2,3,4,5-tetrahydro-1H-benzo[c]azepine;

6-fluoro-5-(4-fluorophenyl)-2-methyl-8-(6-methylpyridazin-3-yl)-2,3,4,5-tetrahydro-1H-benzo[c]azepine;

6-(6-fluoro-5-(4-fluorophenyl)-2,3,4,5-tetrahydro-1H-benzo[c]azepin-8-yl)pyridazin-3-amine;

6-(6-fluoro-5-(4-fluorophenyl)-2-methyl-2,3,4,5-tetrahydro-1H-benzo[c]azepin-8-yl)pyridazin-3-amine;

6-fluoro-5-(4-fluorophenyl)-8-(6-(trifluoromethyl)pyridazin-3-yl)-2,3,4,5-tetrahydro-1H-benzo[c]azepine;

6-fluoro-5-(4-fluorophenyl)-2-methyl-8-(6-(trifluoromethyl)pyridazin-3-yl)-2,3,4,5-tetrahydro-1H-benzo[c]azepine;

5-(4-fluorophenyl)-8-(pyridin-2-yloxy)-2,3,4,5-tetrahydro-1H-benzo[c]azepine;

5-(4-fluorophenyl)-2-methyl-8-(pyridin-2-yloxy)-2,3,4,5-tetrahydro-1H-benzo[c]azepine;

5-(4-fluorophenyl)-8-(6-methylpyridazin-3-yloxy)-2,3,4,5-tetrahydro-1H-benzo[c]azepine;

5-(4-fluorophenyl)-2-methyl-8-(6-methylpyridazin-3-yloxy)-2,3,4,5-tetrahydro-1H-benzo[c]azepine;

5-(4-fluorophenyl)-8-(pyridazin-3-yloxy)-2,3,4,5-tetrahydro-1H-benzo[c]azepine;

5-(4-fluorophenyl)-2-methyl-8-(pyridazin-3-yloxy)-2,3,4,5-tetrahydro-1H-benzo[c]azepine;

9-fluoro-5-(4-fluorophenyl)-8-(pyridazin-3-yloxy)-2,3,4,5-tetrahydro-1H-benzo[c]azepine;

9-fluoro-5-(4-fluorophenyl)-2-methyl-8-(pyridazin-3-yloxy)-2,3,4,5-tetrahydro-1H-benzo[c]azepine;

5-(4-fluorophenyl)-8-(pyrimidin-2-yloxy)-2,3,4,5-tetrahydro-1H-benzo[c]azepine;

5-(4-fluorophenyl)-2-methyl-8-(pyrimidin-2-yloxy)-2,3,4,5-tetrahydro-1H-benzo[c]azepine;
5-(4-fluorophenyl)-8-(6-(trifluoromethyl)pyridazin-3-yl)-2,3,4,5-tetrahydro-1H-benzo[c]azepine;
5-(2,4-difluorophenyl)-8-(6-methylpyridazin-3-yl)-2,3,4,5-tetrahydro-1H-benzo[c]azepine;
5-(2,4-difluorophenyl)-8-(pyridazin-3-yl)-2,3,4,5-tetrahydro-1H-benzo[c]azepine;
5-(2,4-difluorophenyl)-2-methyl-8-(pyridazin-3-yl)-2,3,4,5-tetrahydro-1H-benzo[c]azepine;
6-(5-(2,4-difluorophenyl)-2,3,4,5-tetrahydro-1H-benzo[c]azepin-8-yl)pyridazin-3-amine;
6-(5-(2,4-difluorophenyl)-2-methyl-2,3,4,5-tetrahydro-1H-benzo[c]azepin-8-yl)pyridazin-3-amine;
5-(2,4-difluorophenyl)-8-(6-(trifluoromethyl)pyridazin-3-yl)-2,3,4,5-tetrahydro-1H-benzo[c]azepine;
5-(2,4-difluorophenyl)-2-methyl-8-(6-(trifluoromethyl)pyridazin-3-yl)-2,3,4,5-tetrahydro-1H-benzo[c]azepine;
5-(2,4-difluorophenyl)-7-fluoro-8-(pyridazin-3-yl)-2,3,4,5-tetrahydro-1H-benzo[c]azepine;
5-(2,4-difluorophenyl)-7-fluoro-2-methyl-8-(pyridazin-3-yl)-2,3,4,5-tetrahydro-1H-benzo[c]azepine;
6-(5-(2,4-difluorophenyl)-7-fluoro-2,3,4,5-tetrahydro-1H-benzo[c]azepin-8-yl)pyridazin-3-amine;
6-(5-(2,4-difluorophenyl)-7-fluoro-2-methyl-2,3,4,5-tetrahydro-1H-benzo[c]azepin-8-yl)pyridazin-3-amine;
5-(2,4-difluorophenyl)-8-(6-methylpyridazin-3-yl)-2,3,4,5-tetrahydro-1H-benzo[c]azepine;
5-(2,4-difluorophenyl)-9-fluoro-8-(6-(trifluoromethyl)pyridazin-3-yl)-2,3,4,5-tetrahydro-1H-benzo[c]azepine;
5-(2,4-difluorophenyl)-9-fluoro-2-methyl-8-(6-(trifluoromethyl)pyridazin-3-yl)-2,3,4,5-tetrahydro-1H-benzo[c]azepine;
5-(2,3-difluorophenyl)-8-(6-methylpyridazin-3-yl)-2,3,4,5-tetrahydro-1H-benzo[c]azepine;
5-(2,3-difluorophenyl)-8-(pyridazin-3-yl)-2,3,4,5-tetrahydro-1H-benzo[c]azepine;
5-(2,3-difluorophenyl)-2-methyl-8-(pyridazin-3-yl)-2,3,4,5-tetrahydro-1H-benzo[c]azepine;
6-(5-(2,3-difluorophenyl)-2,3,4,5-tetrahydro-1H-benzo[c]azepin-8-yl)pyridazin-3-amine;
6-(5-(2,3-difluorophenyl)-2-methyl-2,3,4,5-tetrahydro-1H-benzo[c]azepin-8-yl)pyridazin-3-amine;
5-(2,3-difluorophenyl)-8-(6-(trifluoromethyl)pyridazin-3-yl)-2,3,4,5-tetrahydro-1H-benzo[c]azepine;
5-(2,3-difluorophenyl)-2-methyl-8-(6-(trifluoromethyl)pyridazin-3-yl)-2,3,4,5-tetrahydro-1H-benzo[c]azepine;
5-(2,3-difluorophenyl)-7-fluoro-8-(pyridazin-3-yl)-2,3,4,5-tetrahydro-1H-benzo[c]azepine;
5-(2,3-difluorophenyl)-7-fluoro-2-methyl-8-(pyridazin-3-yl)-2,3,4,5-tetrahydro-1H-benzo[c]azepine;
6-(5-(2,3-difluorophenyl)-7-fluoro-2,3,4,5-tetrahydro-1H-benzo[c]azepin-8-yl)pyridazin-3-amine;
6-(5-(2,3-difluorophenyl)-7-fluoro-2-methyl-2,3,4,5-tetrahydro-1H-benzo[c]azepin-8-yl)pyridazin-3-amine;
5-(2,3-difluorophenyl)-7-fluoro-8-(6-(trifluoromethyl)pyridazin-3-yl)-2,3,4,5-tetrahydro-1H-benzo[c]azepine;
5-(2,3-difluorophenyl)-7-fluoro-2-methyl-8-(6-(trifluoromethyl)pyridazin-3-yl)-2,3,4,5-tetrahydro-1H-benzo[c]azepine;
5-(2,3-difluorophenyl)-9-fluoro-8-(6-methylpyridazin-3-yl)-2,3,4,5-tetrahydro-1H-benzo[c]azepine;
5-(2,3-difluorophenyl)-9-fluoro-2-methyl-8-(6-methylpyridazin-3-yl)-2,3,4,5-tetrahydro-1H-benzo[c]azepine;
5-(2,3-difluorophenyl)-9-fluoro-8-(6-(trifluoromethyl)pyridazin-3-yl)-2,3,4,5-tetrahydro-1H-benzo[c]azepine;
5-(2,3-difluorophenyl)-9-fluoro-2-methyl-8-(6-(trifluoromethyl)pyridazin-3-yl)-2,3,4,5-tetrahydro-1H-benzo[c]azepine;
5-(3,4-difluorophenyl)-8-(pyridazin-3-yl)-2,3,4,5-tetrahydro-1H-benzo[c]azepine;
5-(3,4-difluorophenyl)-2-methyl-8-(pyridazin-3-yl)-2,3,4,5-tetrahydro-1H-benzo[c]azepine;
6-(5-(3,4-difluorophenyl)-2,3,4,5-tetrahydro-1H-benzo[c]azepin-8-yl)pyridazin-3-amine;
6-(5-(3,4-difluorophenyl)-2-methyl-2,3,4,5-tetrahydro-1H-benzo[c]azepin-8-yl)pyridazin-3-amine;
5-(3,4-difluorophenyl)-8-(6-(trifluoromethyl)pyridazin-3-yl)-2,3,4,5-tetrahydro-1H-benzo[c]azepine;
5-(3,4-difluorophenyl)-2-methyl-8-(6-(trifluoromethyl)pyridazin-3-yl)-2,3,4,5-tetrahydro-1H-benzo[c]azepine;
5-(3,4-difluorophenyl)-7-fluoro-8-(pyridazin-3-yl)-2,3,4,5-tetrahydro-1H-benzo[c]azepine;
5-(3,4-difluorophenyl)-7-fluoro-2-methyl-8-(pyridazin-3-yl)-2,3,4,5-tetrahydro-1H-benzo[c]azepine;
5-(3,4-difluorophenyl)-7-fluoro-8-(6-methylpyridazin-3-yl)-2,3,4,5-tetrahydro-1H-benzo[c]azepine;
5-(3,4-difluorophenyl)-7-fluoro-2-methyl-8-(6-methylpyridazin-3-yl)-2,3,4,5-tetrahydro-1H-benzo[c]azepine;
6-(5-(3,4-difluorophenyl)-7-fluoro-2,3,4,5-tetrahydro-1H-benzo[c]azepin-8-yl)pyridazin-3-amine;
6-(5-(3,4-difluorophenyl)-7-fluoro-2-methyl-2,3,4,5-tetrahydro-1H-benzo[c]azepin-8-yl)pyridazin-3-amine;
5-(3,4-difluorophenyl)-9-fluoro-8-(6-methylpyridazin-3-yl)-2,3,4,5-tetrahydro-1H-benzo[c]azepine;
5-(3,4-difluorophenyl)-9-fluoro-2-methyl-8-(6-methylpyridazin-3-yl)-2,3,4,5-tetrahydro-1H-benzo[c]azepine;
5-(3,4-difluorophenyl)-9-fluoro-8-(6-(trifluoromethyl)pyridazin-3-yl)-2,3,4,5-tetrahydro-1H-benzo[c]azepine;
5-(3,4-difluorophenyl)-9-fluoro-2-methyl-8-(6-(trifluoromethyl)pyridazin-3-yl)-2,3,4,5-tetrahydro-1H-benzo[c]azepine;
5-(2,5-difluorophenyl)-8-(6-methylpyridazin-3-yl)-2,3,4,5-tetrahydro-1H-benzo[c]azepine;
5-(2,5-difluorophenyl)-8-(pyridazin-3-yl)-2,3,4,5-tetrahydro-1H-benzo[c]azepine;
5-(2,5-difluorophenyl)-2-methyl-8-(pyridazin-3-yl)-2,3,4,5-tetrahydro-1H-benzo[c]azepine;
6-(5-(2,5-difluorophenyl)-2,3,4,5-tetrahydro-1H-benzo[c]azepin-8-yl)pyridazin-3-amine;
6-(5-(2,5-difluorophenyl)-2-methyl-2,3,4,5-tetrahydro-1H-benzo[c]azepin-8-yl)pyridazin-3-amine;
5-(2,5-difluorophenyl)-8-(6-(trifluoromethyl)pyridazin-3-yl)-2,3,4,5-tetrahydro-1H-benzo[c]azepine;
5-(2,5-difluorophenyl)-2-methyl-8-(6-(trifluoromethyl)pyridazin-3-yl)-2,3,4,5-tetrahydro-1H-benzo[c]azepine;
5-(2,5-difluorophenyl)-7-fluoro-8-(pyridazin-3-yl)-2,3,4,5-tetrahydro-1H-benzo[c]azepine;
5-(2,5-difluorophenyl)-7-fluoro-2-methyl-8-(pyridazin-3-yl)-2,3,4,5-tetrahydro-1H-benzo[c]azepine;
6-(5-(2,5-difluorophenyl)-7-fluoro-2,3,4,5-tetrahydro-1H-benzo[c]azepin-8-yl)pyridazin-3-amine;
6-(5-(2,5-difluorophenyl)-7-fluoro-2-methyl-2,3,4,5-tetrahydro-1H-benzo[c]azepin-8-yl)pyridazin-3-amine;
5-(2,5-difluorophenyl)-9-fluoro-8-(6-(trifluoromethyl)pyridazin-3-yl)-2,3,4,5-tetrahydro-1H-benzo[c]azepine;
5-(2,5-difluorophenyl)-9-fluoro-2-methyl-8-(6-(trifluoromethyl)pyridazin-3-yl)-2,3,4,5-tetrahydro-1H-benzo[c]azepine;
5-(2,6-difluorophenyl)-8-(6-methylpyridazin-3-yl)-2,3,4,5-tetrahydro-1H-benzo[c]azepine;
5-(2,6-difluorophenyl)-8-(pyridazin-3-yl)-2,3,4,5-tetrahydro-1H-benzo[c]azepine;

5-(2,6-difluorophenyl)-2-methyl-8-(pyridazin-3-yl)-2,3,4,5-tetrahydro-1H-benzo[c]azepine;
6-(5-(2,6-difluorophenyl)-2,3,4,5-tetrahydro-1H-benzo[c]azepin-8-yl)pyridazin-3-amine;
6-(5-(2,6-difluorophenyl)-2-methyl-2,3,4,5-tetrahydro-1H-benzo[c]azepin-8-yl)pyridazin-3-amine;
5-(2,6-difluorophenyl)-8-(6-(trifluoromethyl)pyridazin-3-yl)-2,3,4,5-tetrahydro-1H-benzo[c]azepine;
5-(2,6-difluorophenyl)-2-methyl-8-(6-(trifluoromethyl)pyridazin-3-yl)-2,3,4,5-tetrahydro-1H-benzo[c]azepine;
5-(2,6-difluorophenyl)-7-fluoro-8-(pyridazin-3-yl)-2,3,4,5-tetrahydro-1H-benzo[c]azepine;
5-(2,6-difluorophenyl)-7-fluoro-2-methyl-8-(pyridazin-3-yl)-2,3,4,5-tetrahydro-1H-benzo[c]azepine;
6-(5-(2,6-difluorophenyl)-7-fluoro-2,3,4,5-tetrahydro-1H-benzo[c]azepin-8-yl)pyridazin-3-amine;
6-(5-(2,6-difluorophenyl)-7-fluoro-2-methyl-2,3,4,5-tetrahydro-1H-benzo[c]azepin-8-yl)pyridazin-3-amine;
5-(2,6-difluorophenyl)-9-fluoro-8-(6-(trifluoromethyl)pyridazin-3-yl)-2,3,4,5-tetrahydro-1H-benzo[c]azepine;
5-(2,6-difluorophenyl)-9-fluoro-2-methyl-8-(6-(trifluoromethyl)pyridazin-3-yl)-2,3,4,5-tetrahydro-1H-benzo[c]azepine;
5-(3,5-difluorophenyl)-9-fluoro-8-(6-(trifluoromethyl)pyridazin-3-yl)-2,3,4,5-tetrahydro-1H-benzo[c]azepine;
5-(3,5-difluorophenyl)-9-fluoro-2-methyl-8-(6-(trifluoromethyl)pyridazin-3-yl)-2,3,4,5-tetrahydro-1H-benzo[c]azepine;
5-(3,5-difluorophenyl)-8-(6-methylpyridazin-3-yl)-2,3,4,5-tetrahydro-1H-benzo[c]azepine;
5-(3,5-difluorophenyl)-8-(pyridazin-3-yl)-2,3,4,5-tetrahydro-1H-benzo[c]azepine;
6-(5-(3,5-difluorophenyl)-2,3,4,5-tetrahydro-1H-benzo[c]azepin-8-yl)pyridazin-3-amine;
6-(5-(3,5-difluorophenyl)-2-methyl-2,3,4,5-tetrahydro-1H-benzo[c]azepin-8-yl)pyridazin-3-amine;
5-(3,5-difluorophenyl)-8-(6-(trifluoromethyl)pyridazin-3-yl)-2,3,4,5-tetrahydro-1H-benzo[c]azepine;
5-(3,5-difluorophenyl)-2-methyl-8-(6-(trifluoromethyl)pyridazin-3-yl)-2,3,4,5-tetrahydro-1H-benzo[c]azepine;
5-(3,5-difluorophenyl)-9-fluoro-8-(pyridazin-3-yl)-2,3,4,5-tetrahydro-1H-benzo[c]azepine;
5-(3,5-difluorophenyl)-9-fluoro-2-methyl-8-(pyridazin-3-yl)-2,3,4,5-tetrahydro-1H-benzo[c]azepine;
6-(5-(3,5-difluorophenyl)-9-fluoro-2,3,4,5-tetrahydro-1H-benzo[c]azepin-8-yl)pyridazin-3-amine;
6-(5-(3,5-difluorophenyl)-9-fluoro-2-methyl-2,3,4,5-tetrahydro-1H-benzo[c]azepin-8-yl)pyridazin-3-amine;
5-(3,5-difluorophenyl)-9-fluoro-8-(6-(trifluoromethyl)pyridazin-3-yl)-2,3,4,5-tetrahydro-1H-benzo[c]azepine;
5-(3,5-difluorophenyl)-9-fluoro-2-methyl-8-(6-(trifluoromethyl)pyridazin-3-yl)-2,3,4,5-tetrahydro-1H-benzo[c]azepine;
2-(2-methyl-5-phenyl-2,3,4,5-tetrahydro-1H-benzo[c]azepin-8-yl)benzonitrile;
2-methyl-8-(4-(methylsulfonyl)phenyl)-5-phenyl-2,3,4,5-tetrahydro-1H-benzo[c]azepine;
2-methyl-8-(3-(methylsulfonyl)phenyl)-5-phenyl-2,3,4,5-tetrahydro-1H-benzo[c]azepine;
2-methyl-8-(2-(methylsulfonyl)phenyl)-5-phenyl-2,3,4,5-tetrahydro-1H-benzo[c]azepine;
4-(5-(2-fluorophenyl)-2-methyl-2,3,4,5-tetrahydro-1H-benzo[c]azepin-8-yl)benzonitrile;
3-(5-(2-fluorophenyl)-2-methyl-2,3,4,5-tetrahydro-1H-benzo[c]azepin-8-yl)benzonitrile;
2-(5-(2-fluorophenyl)-2-methyl-2,3,4,5-tetrahydro-1H-benzo[c]azepin-8-yl)benzonitrile;
5-(2-fluorophenyl)-2-methyl-8-(4-(methylsulfonyl)phenyl)-2,3,4,5-tetrahydro-1H-benzo[c]azepine;
5-(2-fluorophenyl)-2-methyl-8-(3-(methylsulfonyl)phenyl)-2,3,4,5-tetrahydro-1H-benzo[c]azepine;
5-(2-fluorophenyl)-2-methyl-8-(2-(methylsulfonyl)phenyl)-2,3,4,5-tetrahydro-1H-benzo[c]azepine;
5-(5-fluoronaphthalen-2-yl)-2-methyl-8-(6-pyridazin-3-yl)-2,3,4,5-tetrahydro-1H-benzo[c]azepine;
5-(6-fluoronaphthalen-2-yl)-2-methyl-8-(6-pyridazin-3-yl)-2,3,4,5-tetrahydro-1H-benzo[c]azepine;
5-(7-fluoronaphthalen-2-yl)-2-methyl-8-(6-pyridazin-3-yl)-2,3,4,5-tetrahydro-1H-benzo[c]azepine;
5-(8-fluoronaphthalen-2-yl)-2-methyl-8-(6-pyridazin-3-yl)-2,3,4,5-tetrahydro-1H-benzo[c]azepine;
5-(5-fluoronaphthalen-2-yl)-8-(6-pyridazin-3-yl)-2,3,4,5-tetrahydro-1H-benzo[c]azepine;
5-(6-fluoronaphthalen-2-yl)-8-(6-pyridazin-3-yl)-2,3,4,5-tetrahydro-1H-benzo[c]azepine;
5-(7-fluoronaphthalen-2-yl)-8-(6-pyridazin-3-yl)-2,3,4,5-tetrahydro-1H-benzo[c]azepine;
5-(8-fluoronaphthalen-2-yl)-8-(6-pyridazin-3-yl)-2,3,4,5-tetrahydro-1H-benzo[c]azepine;
5-(1-fluoronaphthalen-2-yl)-8-(6-pyridazin-3-yl)-2,3,4,5-tetrahydro-1H-benzo[c]azepine;
5-(2-fluoronaphthalen-2-yl)-8-(6-pyridazin-3-yl)-2,3,4,5-tetrahydro-1H-benzo[c]azepine;
5-(1-fluoronaphthalen-2-yl)-8-(6-methylpyridazin-3-yl)-2,3,4,5-tetrahydro-1H-benzo[c]azepine;
5-(2-fluoronaphthalen-2-yl)-8-(6-methylpyridazin-3-yl)-2,3,4,5-tetrahydro-1H-benzo[c]azepine;
9-fluoro-5-(naphthalen-2-yl)-8-(6-(trifluoromethyl)pyridazin-3-yl)-2,3,4,5-tetrahydro-1H-benzo[c]azepine;
9-fluoro-2-methyl-5-(naphthalen-2-yl)-8-(6-(trifluoromethyl)pyridazin-3-yl)-2,3,4,5-tetrahydro-1H-benzo[c]azepine;
5-(1-fluoronaphthalen-2-yl)-8-(6-(trifluoromethyl)pyridazin-3-yl)-2,3,4,5-tetrahydro-1H-benzo[c]azepine;
5-(1-fluoronaphthalen-2-yl)-2-methyl-8-(6-(trifluoromethyl)pyridazin-3-yl)-2,3,4,5-tetrahydro-1H-benzo[c]azepine;
5-(3-fluoronaphthalen-2-yl)-8-(6-(trifluoromethyl)pyridazin-3-yl)-2,3,4,5-tetrahydro-1H-benzo[c]azepine;
5-(3-fluoronaphthalen-2-yl)-2-methyl-8-(6-(trifluoromethyl)pyridazin-3-yl)-2,3,4,5-tetrahydro-1H-benzo[c]azepine;
6-(5-(1-fluoronaphthalen-2-yl)-2,3,4,5-tetrahydro-1H-benzo[c]azepin-8-yl)pyridazin-3-amine;
6-(5-(1-fluoronaphthalen-2-yl)-2-methyl-2,3,4,5-tetrahydro-1H-benzo[c]azepin-8-yl)pyridazin-3-amine;
6-(5-(3-fluoronaphthalen-2-yl)-2,3,4,5-tetrahydro-1H-benzo[c]azepin-8-yl)pyridazin-3-amine;
6-(5-(3-fluoronaphthalen-2-yl)-2-methyl-2,3,4,5-tetrahydro-1H-benzo[c]azepin-8-yl)pyridazin-3-amine;
7-fluoro-5-(naphthalen-2-yl)-8-(pyridazin-3-yl)-2,3,4,5-tetrahydro-1H-benzo[c]azepine;
7-fluoro-2-methyl-5-(naphthalen-2-yl)-8-(pyridazin-3-yl)-2,3,4,5-tetrahydro-1H-benzo[c]azepine;
7-fluoro-5-(1-fluoronaphthalen-2-yl)-8-(pyridazin-3-yl)-2,3,4,5-tetrahydro-1H-benzo[c]azepine;
7-fluoro-5-(1-fluoronaphthalen-2-yl)-2-methyl-8-(pyridazin-3-yl)-2,3,4,5-tetrahydro-1H-benzo[c]azepine;
4-(5-(benzo[b]thiophen-2-yl)-2,3,4,5-tetrahydro-1H-benzo[c]azepin-8-yl)morpholine;
5-(benzo[b]thiophen-5-yl)-8-(pyrimidin-5-yl)-2,3,4,5-tetrahydro-1H-benzo[c]azepine;
5-(benzo[b]thiophen-5-yl)-8-(pyrazin-2-yl)-2,3,4,5-tetrahydro-1H-benzo[c]azepine;

5-(benzo[b]thiophen-5-yl)-8-(6-methylpyridazin-3-yl)-2,3, 4,5-tetrahydro-1H-benzo[c]azepine;
5-(benzo[b]thiophen-2-yl)-8-(pyridazin-3-yl)-2,3,4,5-tetrahydro-1H-benzo[c]azepine;
4-(5-(benzo[b]thiophen-2-yl)-2-methyl-2,3,4,5-tetrahydro-1H-benzo[c]azepin-8-yl)morpholine;
5-(benzo[b]thiophen-2-yl)-2-methyl-8-(pyrimidin-5-yl)-2,3, 4,5-tetrahydro-1H-benzo[c]azepine;
5-(benzo[b]thiophen-2-yl)-2-methyl-8-(pyrazin-2-yl)-2,3,4, 5-tetrahydro-1H-benzo[c]azepine;
5-(benzo[b]thiophen-2-yl)-2-methyl-8-(6-methylpyridazin-3-yl)-2,3,4,5-tetrahydro-1H-benzo[c]azepine;
5-(benzo[b]thiophen-2-yl)-2-methyl-8-(pyridazin-3-yl)-2,3, 4,5-tetrahydro-1H-benzo[c]azepine;
6-(5-(benzo[b]thiophen-2-yl)-2,3,4,5-tetrahydro-1H-benzo [c]azepin-8-yl)pyridazin-3-amine;
5-(benzo[b]thiophen-2-yl)-8-(6-(trifluoromethyl)pyridazin-3-yl)-2,3,4,5-tetrahydro-1H-benzo[c]azepine;
6-(5-(benzo[b]thiophen-2-yl)-2-methyl-2,3,4,5-tetrahydro-1H-benzo[c]azepin-8-yl)pyridazin-3-amine;
5-(benzo[b]thiophen-2-yl)-2-methyl-8-(6-(trifluoromethyl) pyridazin-3-yl)-2,3,4,5-tetrahydro-1H-benzo[c]azepine;
5-(benzo[b]thiophen-2-yl)-9-fluoro-8-(pyridazin-3-yl)-2,3, 4,5-tetrahydro-1H-benzo[c]azepine;
5-(benzo[b]thiophen-2-yl)-9-fluoro-2-methyl-8-(pyridazin-3-yl)-2,3,4,5-tetrahydro-1H-benzo[c]azepine;
5-(benzo[b]thiophen-2-yl)-9-fluoro-8-(6-methylpyridazin-3-yl)-2,3,4,5-tetrahydro-1H-benzo[c]azepine;
5-(benzo[b]thiophen-2-yl)-9-fluoro-2-methyl-8-(6-methylpyridazin-3-yl)-2,3,4,5-tetrahydro-1H-benzo[c] azepine;
6-(5-(benzo[b]thiophen-2-yl)-9-fluoro-2,3,4,5-tetrahydro-1H-benzo[c]azepin-8-yl)pyridazin-3-amine;
6-(5-(benzo[b]thiophen-2-yl)-9-fluoro-2-methyl-2,3,4,5-tetrahydro-1H-benzo[c]azepin-8-yl)pyridazin-3-amine;
5-(benzo[b]thiophen-2-yl)-9-fluoro-8-(6-(trifluoromethyl) pyridazin-3-yl)-2,3,4,5-tetrahydro-1H-benzo[c]azepine;
5-(benzo[b]thiophen-2-yl)-9-fluoro-2-methyl-8-(6-(trifluoromethyl)pyridazin-3-yl)-2,3,4,5-tetrahydro-1H-benzo[c] azepine;
5-(benzo[b]thiophen-2-yl)-7-fluoro-8-(pyridazin-3-yl)-2,3, 4,5-tetrahydro-1H-benzo[c]azepine;
5-(benzo[b]thiophen-2-yl)-7-fluoro-2-methyl-8-(pyridazin-3-yl)-2,3,4,5-tetrahydro-1H-benzo[c]azepine;
5-(benzo[b]thiophen-2-yl)-7-fluoro-8-(6-methylpyridazin-3-yl)-2,3,4,5-tetrahydro-1H-benzo[c]azepine;
5-(benzo[b]thiophen-2-yl)-7-fluoro-2-methyl-8-(6-methylpyridazin-3-yl)-2,3,4,5-tetrahydro-1H-benzo[c] azepine;
6-(5-(benzo[b]thiophen-2-yl)-7-fluoro-2,3,4,5-tetrahydro-1H-benzo[c]azepin-8-yl)pyridazin-3-amine;
6-(5-(benzo[b]thiophen-2-yl)-7-fluoro-2-methyl-2,3,4,5-tetrahydro-1H-benzo[c]azepin-8-yl)pyridazin-3-amine;
5-(benzo[b]thiophen-2-yl)-7-fluoro-8-(6-(trifluoromethyl) pyridazin-3-yl)-2,3,4,5-tetrahydro-1H-benzo[c]azepine;
5-(benzo[b]thiophen-2-yl)-7-fluoro-2-methyl-8-(6-(trifluoromethyl)pyridazin-3-yl)-2,3,4,5-tetrahydro-1H-benzo[c] azepine;
5-(benzo[b]thiophen-2-yl)-6-fluoro-8-(pyridazin-3-yl)-2,3, 4,5-tetrahydro-1H-benzo[c]azepine;
5-(benzo[b]thiophen-2-yl)-6-fluoro-2-methyl-8-(pyridazin-3-yl)-2,3,4,5-tetrahydro-1H-benzo[c]azepine;
5-(benzo[b]thiophen-6-yl)-8-(pyridazin-3-yl)-2,3,4,5-tetrahydro-1H-benzo[c]azepine;
5-(benzo[b]thiophen-6-yl)-2-methyl-8-(pyridazin-3-yl)-2,3, 4,5-tetrahydro-1H-benzo[c]azepine;
5-(benzo[b]thiophen-7-yl)-8-(pyridazin-3-yl)-2,3,4,5-tetrahydro-1H-benzo[c]azepine; and
5-(benzo[b]thiophen-7-yl)-2-methyl-8-(pyridazin-3-yl)-2,3, 4,5-tetrahydro-1H-benzo[c]azepine.

Other embodiments of the present invention are compounds of formulae I(A-E) where the carbon atom designated * is in the R configuration.

Other embodiments of the present invention are compounds of formulae I(A-E) where the carbon atom designated * is in the S configuration.

Another embodiment of the present invention is a mixture of stereoisomeric compounds of formulae I(A-E) where * is in the S or R configuration.

Within these embodiments, the selection of a particular preferred substituent at any one of $R^1$-$R^9$ does not affect the selection of a substituent at any of the others of $R^1$-$R^8$. That is, preferred compounds provided herein have any of the preferred substituents at any of the positions. For example, as described hereinabove, $R^1$ is preferably $C_1$-$C_6$ alkyl; the selection of $R^1$ as any one of $C_1$, $C_2$, $C_3$, $C_4$, $C_5$, or $C_6$ alkyl, does not limit the choice of $R^2$ in particular to any one of H, $C_1$-$C_6$ alkyl, or $C_1$-$C_6$ haloalkyl. Rather, for $R^1$ as any of $C_1$, $C_2$, $C_3$, $C_4$, $C_5$, or $C_6$ alkyl, $R^2$ is any of H, $C_1$, $C_2$, $C_3$, $C_4$, $C_5$, or $C_6$ alkyl or $C_1$, $C_2$, $C_3$, $C_4$, $C_5$, or $C_6$ haloalkyl. Similarly, the selection of $R^2$ as any of H, $C_1$, $C_2$, $C_3$, $C_4$, $C_5$, or $C_6$ alkyl or $C_1$, $C_2$, $C_3$, $C_4$, $C_5$, or $C_6$ haloalkyl does not limit the selection of $R^3$ in particular to any one of H, halogen, —$OR^{11}$, —$S(O)_nR^{12}$, —CN, —$C(O)R^{12}$, $C_1$-$C_6$ alkyl, $C_3$-$C_6$ cycloalkyl, $C_4$-$C_7$ cycloalkylalkyl, or substituted $C_4$-$C_7$ cycloalkylalkyl.

Another aspect of the present invention relates to a compound represented by the formula (II) having the following structure:

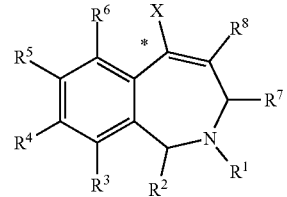

II where:

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in $R^{14}$;

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or X is an alkene or alkyne, optionally substituted from 1 to 4 times with substituents as defined below in $R^{15}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ is gem-dimethyl;

$R^8$ is H or $C_1$-$C_6$ alkyl, where each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, where each of C$_1$-C$_4$ alkyl is optionally substituted from 1 to 3 times with substituents as defined below in R$^{15}$;

R$^{10}$ and R$^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on a ring carbon with from 1 to 3 times with a substituent selected independently at each occurrence thereof from the group consisting of halogen, cyano, —OR$^{12}$, —NR$^{12}$R$^{13}$, —S(O)$_n$R$^{13}$, —C(O)R$^{13}$, and C$_1$-C$_4$ alkyl, or on the additional nitrogen atom from 1 to 3 times with a substituent selected independently at each occurrence thereof from the group consisting of S(O)$_n$R$^{13}$, —C(O)R$^{13}$, and C$_1$-C$_4$ alkyl, wherein each of C$_1$-C$_4$ alkyl is optionally substituted from 1 to 3 times with substituents as defined below in R$^{15}$;

R$^{10}$ and R$^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in R$^{14}$; or when R$^4$ is —NR$^{10}$R$^{11}$ or —C(O)NR$^{10}$R$^{11}$, either R$^{10}$ or R$^{11}$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of C$_1$-C$_3$ alkyl, —C(O)R$^{13}$, and —S(O)$_n$R$^{13}$, or either R$^{10}$ or R$^{11}$ is a C$_1$-C$_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of C$_1$-C$_3$ alkyl, —C(O)R$^{13}$, and —S(O)$_n$R$^{13}$;

R$^{12}$ is selected from the group consisting of H, C$_1$-C$_4$ alkyl, C$_3$-C$_6$ cycloalkyl, C$_4$-C$_7$ cycloalkylalkyl, and —C(O)R$^{13}$, where each of C$_1$-C$_6$ alkyl, C$_3$-C$_6$ cycloalkyl, and C$_4$-C$_7$ cycloalkylalkyl is optionally substituted from 1 to 3 times with substituents as defined below in R$^{15}$;

R$^{13}$ is selected from the group consisting of H, —NR$^{10}$R$^{11}$, C$_1$-C$_4$ alkyl, C$_3$-C$_6$ cycloalkyl, and C$_4$-C$_7$ cycloalkylalkyl, where each of C$_1$-C$_6$ alkyl, C$_3$-C$_6$ cycloalkyl, and C$_4$-C$_7$ cycloalkylalkyl is optionally substituted from 1 to 3 times with substituents as defined below in R$^{15}$; or R$^{12}$ and R$^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in R$^{14}$; or R$^{12}$ and R$^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —OR$^{10}$, —S(O)$_n$R$^{10}$, —C(O)R$^{10}$, —C(O)NR$^{10}$R$^{11}$ and C$_1$-C$_4$ alkyl, where each of C$_1$-C$_4$ alkyl is optionally substituted from 1 to 3 times with substituents as defined below in R$^{15}$;

n is 0, 1, or 2;

R$^{14}$ is independently selected at each occurrence from a substituent in the group consisting of halogen, —NO$_2$, —OR$^{12}$, —NR$^{10}$R$^{11}$, —NR$^{12}$C(O)$_2$R$^{13}$, —NR$^{12}$C(O) NR$^{12}$R$^{13}$, —S(O)$_n$R$^{13}$, —CN, —C(O)R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined below in R$^{15}$; and R$^{15}$ is independently selected at each occurrence from a substituent in the group consisting of —CN, halogen, C(O) R$^{13}$, C$_1$-C$_3$ alkyl, —OR$^{12}$, —NR$^{10}$R$^{11}$, —S(O)$_n$R$^{13}$, aryl, and heteroaryl, where each of the aryl or heteroaryl groups is optionally substituted from 1 to 4 times with substituents as defined above in R$^{14}$;

with the following provisos that (1) when R$^4$ is H, X cannot be phenyl or a phenyl substituted at the para-position with Cl; (2) when R$^4$ is H, OMe, or O-benzyl, X cannot be a phenyl substituted at the para-position with the same R$^4$; and (3) when R$^2$ is a 2-(4-nitrophenoxy)ethyl, R$^5$ cannot be OC(O) NMe$_2$;

or an oxide thereof, or a pharmaceutically acceptable salt thereof.

One embodiment of the present invention relates to the compound of formula (II) where:

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in R$^{14}$, or other 5- or 6-membered aromatic or non-aromatic monocyclic carbocycles or heterocycles containing 1-4 heteroatoms selected from the group consisting of oxygen, nitrogen, and sulfur, optionally substituted from 1 to 4 times with substituents as defined below in R$^{14}$;

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, indolyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo [1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4] triazolo[4,3-a]pyridinyl, thieno[2,3-b]furanyl, thieno[2,3- b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$, or other [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or X is an alkene or alkyne, optionally substituted from 1 to 4 times with substituents as defined below in $R^{15}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^4$ is H, halogen, —$OR^{13}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{13}$, and —$S(O)_nR^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, or other 5- or 6-membered aromatic or non-aromatic monocyclic carbocycles or heterocycles or [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, where each of the $C_{1-4}$ alkyl is optionally substituted from 1 to 3 times with substituents as defined below in $R^{15}$;

$R^8$ is H or $C_1$-$C_3$ alkyl;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Another embodiment of the present invention relates to the compound of formula (II) where:

X is thiophenyl, thiazolyl, pyridinyl, phenyl, naphthyl, benzo[b]thiophenyl, benzofuranyl, benzo[d][1,3]dioxolyl, 2,3-dihydrobenzo[b][1,4]dioxinyl, 3,4-dihydro-2H-benzo[b][1,4]oxazinyl or 4-methyl-3,4-dihydro-2H-benzo[b][1,4]oxazinyl, optionally substituted with from 1 to 3 substituents selected independently from the group consisting of halogen, methoxy, cyano, trifluoromethyl, trifluoromethoxy, difluoromethoxy, substituted $C_1$-$C_3$ alkyl, methanesulfonyl, carbamoyl, $C_1$-$C_3$ alkyl-substituted carbamoyl, and acetamido;

$R^1$ is H, methyl, ethyl, isopropyl, 2-hydroxyethyl, 2,2,2-trifluoroethyl, 2-fluoroethyl, or benzyl;

$R^2$ is H or gem-dimethyl;

$R^3$ is H or fluoro;

$R^4$ is H, methoxy, hydroxyl, methyl, fluoro, bromo, cyano, trifluoromethyl, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, piperidin-2-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-pyridazin-3-yloxy, 1,2,4-oxadiazol-3-yl, 3,5-dimethylisoxazol-4-yl, 1H-pyrazol-4-yl, 2-cyanophenyl, 3-cyanophenyl, 4-cyanophenyl, (methanesulfonyl)phenyl, pyridinyl, aminopyridinyl, pyridazin-3-yl, 6-methylpyridazin-3-yl, 6-(trifluoromethyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, (6-(hydroxymethyl)pyridazin-3-yl, 6-(methoxycarbonyl)pyridazin-3-yl, pyrimidin-2-yl, pyrimidin-4-yl, pyrimidin-5-yl, pyrazin-2-yl, 2-oxopyridin-1(2H)-yl, 6-oxo-1,6-dihydropyridazin-3-yl, imidazo[1,2-a]pyridin-6-yl, imidazo

[1,2-a]pyrazin-3-yl, 3-oxo-[1,2,4]triazolo[4,3-a]pyridin-2 (3H)-yl, 5,6-dihydroimidazo[1,2-a]pyrazin-7(8H)-yl, 3-(trifluoromethyl)-5,6-dihydro-[1,2,4]triazolo[4,3-a] pyrazin-7(8H)-yl, [1,2,4]triazolo[1,5-a]pyridin-6-yl, [1,2,4]triazolo[4,3-a]pyridin-6-yl, 3,3-dimethyl-2-oxoindolin-5-yl, 5,6-dihydroimidazo[1,2-a]pyrazin-7(8H)-yl, 3-methyl-[1,2,4]triazolo[4,3-b]-pyridazinyl, or [1,2,4]triazolo[4,3-b]-pyridazinyl;

$R^5$ is H or fluoro;
$R^6$ is H or fluoro;
$R^7$ is H;
$R^8$ is H, or $C_1$-$C_3$ alkyl;
$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and
$R^{15}$ is independently selected at each occurrence from a substituent in the group consisting of —CN, halogen, C(O)$R^{13}$, $C_1$-$C_3$ alkyl, —$OR^{12}$, —$NR^{10}R^{11}$, —$S(O)_nR^{13}$, aryl, and heteroaryl, where each of the aryl or heteroaryl groups is optionally substituted from 1 to 4 times with substituents as defined above in $R^{14}$.

Other specific compounds of formula (II) of the present invention are the following compounds:
(Z)-8-methoxy-5-phenyl-2,3-dihydro-1H-benzo[c]azepine;
(Z)-5-(4-chlorophenyl)-8-methoxy-2,3-dihydro-1H-benzo[c]azepine;
(Z)-5-(4-fluorophenyl)-8-methoxy-2,3-dihydro-1H-benzo[c]azepine;
(Z)-5-(3-fluorophenyl)-8-methoxy-2,3-dihydro-1H-benzo[c]azepine;
(Z)-5-(2-fluorophenyl)-8-methoxy-2,3-dihydro-1H-benzo[c]azepine;
(E)-5-(2,4-difluorophenyl)-8-methoxy-2,3-dihydro-1H-benzo[c]azepine;
(E)-5-(2,3-difluorophenyl)-8-methoxy-2,3-dihydro-1H-benzo[c]azepine;
(E)-5-(2,5-difluorophenyl)-8-methoxy-2,3-dihydro-1H-benzo[c]azepine;
(E)-5-(2,6-difluorophenyl)-8-methoxy-2,3-dihydro-1H-benzo[c]azepine;
(E)-5-(3,4-difluorophenyl)-8-methoxy-2,3-dihydro-1H-benzo[c]azepine;
(E)-5-(3,5-difluorophenyl)-8-methoxy-2,3-dihydro-1H-benzo[c]azepine;
(Z)-8-methoxy-2-methyl-5-phenyl-2,3-dihydro-1H-benzo[c]azepine;
(Z)-5-(4-chlorophenyl)-8-methoxy-2-methyl-2,3-dihydro-1H-benzo[c]azepine;
(Z)-5-(4-fluorophenyl)-8-methoxy-2-methyl-2,3-dihydro-1H-benzo[c]azepine;
(Z)-5-(3-fluorophenyl)-8-methoxy-2-methyl-2,3-dihydro-1H-benzo[c]azepine;
(Z)-5-(2-fluorophenyl)-8-methoxy-2-methyl-2,3-dihydro-1H-benzo[c]azepine;
(E)-5-(2,4-difluorophenyl)-8-methoxy-2-methyl-2,3-dihydro-1H-benzo[c]azepine;
(E)-5-(2,3-difluorophenyl)-8-methoxy-2-methyl-2,3-dihydro-1H-benzo[c]azepine;
(E)-5-(2,5-difluorophenyl)-8-methoxy-2-methyl-2,3-dihydro-1H-benzo[c]azepine;
(E)-5-(2,6-difluorophenyl)-8-methoxy-2-methyl-2,3-dihydro-1H-benzo[c]azepine;
(E)-5-(3,4-difluorophenyl)-8-methoxy-2-methyl-2,3-dihydro-1H-benzo[c]azepine;
(E)-5-(3,5-difluorophenyl)-8-methoxy-2-methyl-2,3-dihydro-1H-benzo[c]azepine;
(Z)-5-phenyl-8-(pyridazin-3-yl)-2,3-dihydro-1H-benzo[c]azepine;
(Z)-5-(4-chlorophenyl)-8-(pyridazin-3-yl)-2,3-dihydro-1H-benzo[c]azepine;
(Z)-5-(4-fluorophenyl)-8-(pyridazin-3-yl)-2,3-dihydro-1H-benzo[c]azepine;
(Z)-5-(3-fluorophenyl)-8-(pyridazin-3-yl)-2,3-dihydro-1H-benzo[c]azepine;
(Z)-5-(2-fluorophenyl)-8-(pyridazin-3-yl)-2,3-dihydro-1H-benzo[c]azepine;
(E)-5-(2,4-difluorophenyl)-8-(pyridazin-3-yl)-2,3-dihydro-1H-benzo[c]azepine;
(E)-5-(2,3-difluorophenyl)-8-(pyridazin-3-yl)-2,3-dihydro-1H-benzo[c]azepine
(E)-5-(2,5-difluorophenyl)-8-(pyridazin-3-yl)-2,3-dihydro-1H-benzo[c]azepine;
(E)-5-(2,6-difluorophenyl)-8-(pyridazin-3-yl)-2,3-dihydro-1H-benzo[c]azepine;
(E)-5-(3,4-difluorophenyl)-8-(pyridazin-3-yl)-2,3-dihydro-1H-benzo[c]azepine;
(E)-5-(3,5-difluorophenyl)-8-(pyridazin-3-yl)-2,3-dihydro-1H-benzo[c]azepine;
(Z)-2-methyl-5-phenyl-8-(pyridazin-3-yl)-2,3-dihydro-1H-benzo[c]azepine;
(Z)-5-(4-chlorophenyl)-2-methyl-8-(pyridazin-3-yl)-2,3-dihydro-1H-benzo[c]azepine;
(Z)-5-(4-fluorophenyl)-2-methyl-8-(pyridazin-3-yl)-2,3-dihydro-1H-benzo[c]azepine;
(Z)-5-(3-fluorophenyl)-2-methyl-8-(pyridazin-3-yl)-2,3-dihydro-1H-benzo[c]azepine;
(Z)-5-(2-fluorophenyl)-2-methyl-8-(pyridazin-3-yl)-2,3-dihydro-1H-benzo[c]azepine;
(E)-5-(2,4-difluorophenyl)-2-methyl-8-(pyridazin-3-yl)-2,3-dihydro-1H-benzo[c]azepine;
(E)-5-(2,3-difluorophenyl)-2-methyl-8-(pyridazin-3-yl)-2,3-dihydro-1H-benzo[c]azepine;
(E)-5-(2,5-difluorophenyl)-2-methyl-8-(pyridazin-3-yl)-2,3-dihydro-1H-benzo[c]azepine;
(E)-5-(2,6-difluorophenyl)-2-methyl-8-(pyridazin-3-yl)-2,3-dihydro-1H-benzo[c]azepine;
(E)-5-(3,4-difluorophenyl)-2-methyl-8-(pyridazin-3-yl)-2,3-dihydro-1H-benzo[c]azepine;
(E)-5-(3,5-difluorophenyl)-2-methyl-8-(pyridazin-3-yl)-2,3-dihydro-1H-benzo[c]azepine;
(Z)-8-(6-methylpyridazin-3-yl)-5-phenyl-2,3-dihydro-1H-benzo[c]azepine;
(Z)-5-(4-chlorophenyl)-8-(6-methylpyridazin-3-yl)-2,3-dihydro-1H-benzo[c]azepine;
(Z)-5-(4-fluorophenyl)-2-methyl-8-(6-methylpyridazin-3-yl)-2,3-dihydro-H-benzo[c]azepine;
(Z)-5-(3-fluorophenyl)-8-(6-methylpyridazin-3-yl)-2,3-dihydro-1H-benzo[c]azepine;
(Z)-5-(2-fluorophenyl)-8-(6-methylpyridazin-3-yl)-2,3-dihydro-1H-benzo[c]azepine;
(E)-5-(2,4-difluorophenyl)-2-methyl-8-(6-methylpyridazin-3-yl)-2,3-dihydro-1H-benzo[c]azepine;
(E)-5-(2,3-difluorophenyl)-8-(6-methylpyridazin-3-yl)-2,3-dihydro-1H-benzo[c]azepine;
(E)-5-(2,5-difluorophenyl)-8-(6-methylpyridazin-3-yl)-2,3-dihydro-1H-benzo[c]azepine;

(E)-5-(2,6-difluorophenyl)-8-(6-methylpyridazin-3-yl)-2,3-dihydro-1H-benzo[c]azepine;
(E)-5-(3,4-difluorophenyl)-8-(6-methylpyridazin-3-yl)-2,3-dihydro-1H-benzo[c]azepine;
(E)-5-(3,5-difluorophenyl)-8-(6-methylpyridazin-3-yl)-2,3-dihydro-1H-benzo[c]azepine;
(Z)-2-methyl-8-(6-methylpyridazin-3-yl)-5-phenyl-2,3-dihydro-1H-benzo[c]azepine;
(Z)-5-(4-chlorophenyl)-2-methyl-8-(6-methylpyridazin-3-yl)-2,3-dihydro-1H-benzo[c]azepine;
(Z)-5-(4-fluorophenyl)-2-methyl-8-(6-methylpyridazin-3-yl)-2,3-dihydro-1H-benzo[c]azepine;
(Z)-5-(3-fluorophenyl)-2-methyl-8-(6-methylpyridazin-3-yl)-2,3-dihydro-1H-benzo[c]azepine;
(Z)-5-(2-fluorophenyl)-2-methyl-8-(6-methylpyridazin-3-yl)-2,3-dihydro-1H-benzo[c]azepine;
(E)-5-(2,4-difluorophenyl)-2-methyl-8-(6-methylpyridazin-3-yl)-2,3-dihydro-1H-benzo[c]azepine;
(E)-5-(2,3-difluorophenyl)-2-methyl-8-(6-methylpyridazin-3-yl)-2,3-dihydro-1H-benzo[c]azepine;
(E)-5-(2,5-difluorophenyl)-2-methyl-8-(6-methylpyridazin-3-yl)-2,3-dihydro-1H-benzo[c]azepine;
(E)-5-(2,6-difluorophenyl)-2-methyl-8-(6-methylpyridazin-3-yl)-2,3-dihydro-1H-benzo[c]azepine;
(E)-5-(3,4-difluorophenyl)-2-methyl-8-(6-methylpyridazin-3-yl)-2,3-dihydro-1H-benzo[c]azepine;
(E)-5-(3,5-difluorophenyl)-2-methyl-8-(6-methylpyridazin-3-yl)-2,3-dihydro-1H-benzo[c]azepine;
(Z)-6-(5-phenyl-2,3-dihydro-1H-benzo[c]azepin-8-yl)pyridazin-3-amine;
(Z)-6-(5-(4-chlorophenyl)-2,3-dihydro-1H-benzo[c]azepin-8-yl)pyridazin-3-amine;
(Z)-6-(5-(4-fluorophenyl)-2,3-dihydro-1H-benzo[c]azepin-8-yl)pyridazin-3-amine;
(Z)-6-(5-(3-fluorophenyl)-2,3-dihydro-1H-benzo[c]azepin-8-yl)pyridazin-3-amine;
(Z)-6-(5-(2-fluorophenyl)-2,3-dihydro-1H-benzo[c]azepin-8-yl)pyridazin-3-amine;
(E)-6-(5-(2,4-difluorophenyl)-2,3-dihydro-1H-benzo[c]azepin-8-yl)pyridazin-3-amine;
(E)-6-(5-(2,3-difluorophenyl)-2,3-dihydro-1H-benzo[c]azepin-8-yl)pyridazin-3-amine;
(E)-6-(5-(2,5-difluorophenyl)-2,3-dihydro-1H-benzo[c]azepin-8-yl)pyridazin-3-amine;
(E)-6-(5-(2,6-difluorophenyl)-2,3-dihydro-1H-benzo[c]azepin-8-yl)pyridazin-3-amine;
(E)-6-(5-(3,4-difluorophenyl)-2,3-dihydro-1H-benzo[c]azepin-8-yl)pyridazin-3-amine;
(E)-6-(5-(2,5-difluorophenyl)-2,3-dihydro-1H-benzo[c]azepin-8-yl)pyridazin-3-amine;
(Z)-6-(2-methyl-5-phenyl-2,3-dihydro-1H-benzo[c]azepin-8-yl)pyridazin-3-amine;
(Z)-6-(5-(4-chlorophenyl)-2-methyl-2,3-dihydro-1H-benzo[c]azepin-8-yl)pyridazin-3-amine;
(Z)-6-(5-(4-fluorophenyl)-2-methyl-2,3-dihydro-1H-benzo[c]azepin-8-yl)pyridazin-3-amine;
(Z)-6-(5-(3-fluorophenyl)-2-methyl-2,3-dihydro-1H-benzo[c]azepin-8-yl)pyridazin-3-amine;
(Z)-6-(5-(2-fluorophenyl)-2-methyl-2,3-dihydro-1H-benzo[c]azepin-8-yl)pyridazin-3-amine;
(E)-6-(5-(2,4-difluorophenyl)-2-methyl-2,3-dihydro-1H-benzo[c]azepin-8-yl)pyridazin-3-amine;
(E)-6-(5-(2,3-difluorophenyl)-2-methyl-2,3-dihydro-1H-benzo[c]azepin-8-yl)pyridazin-3-amine;
(E)-6-(5-(2,5-difluorophenyl)-2-methyl-2,3-dihydro-1H-benzo[c]azepin-8-yl)pyridazin-3-amine;
(E)-6-(5-(2,6-difluorophenyl)-2-methyl-2,3-dihydro-1H-benzo[c]azepin-8-yl)pyridazin-3-amine;
(E)-6-(5-(3,4-difluorophenyl)-2-methyl-2,3-dihydro-1H-benzo[c]azepin-8-yl)pyridazin-3-amine;
(E)-6-(5-(2,5-difluorophenyl)-2-methyl-2,3-dihydro-1H-benzo[c]azepin-8-yl)pyridazin-3-amine;
(Z)-2-methyl-5-phenyl-8-(6-(trifluoromethyl)pyridazin-3-yl)-2,3-dihydro-1H-benzo[c]azepine;
(Z)-5-(4-chlorophenyl)-2-methyl-8-(6-(trifluoromethyl)pyridazin-3-yl)-2,3-dihydro-1H-benzo[c]azepine;
(Z)-5-(4-fluorophenyl)-2-methyl-8-(6-(trifluoromethyl)pyridazin-3-yl)-2,3-dihydro-1H-benzo[c]azepine;
(Z)-5-(3-fluorophenyl)-2-methyl-8-(6-(trifluoromethyl)pyridazin-3-yl)-2,3-dihydro-1H-benzo[c]azepine;
(Z)-5-(2-fluorophenyl)-2-methyl-8-(6-(trifluoromethyl)pyridazin-3-yl)-2,3-dihydro-1H-benzo[c]azepine;
(E)-5-(2,4-difluorophenyl)-2-methyl-8-(6-(trifluoromethyl)pyridazin-3-yl)-2,3-dihydro-1H-benzo[c]azepine;
(E)-5-(2,3-difluorophenyl)-2-methyl-8-(6-(trifluoromethyl)pyridazin-3-yl)-2,3-dihydro-1H-benzo[c]azepine;
(E)-5-(2,5-difluorophenyl)-2-methyl-8-(6-(trifluoromethyl)pyridazin-3-yl)-2,3-dihydro-1H-benzo[c]azepine;
(E)-5-(2,6-difluorophenyl)-2-methyl-8-(6-(trifluoromethyl)pyridazin-3-yl)-2,3-dihydro-1H-benzo[c]azepine;
(E)-5-(3,4-difluorophenyl)-2-methyl-8-(6-(trifluoromethyl)pyridazin-3-yl)-2,3-dihydro-1H-benzo[c]azepine;
(E)-5-(3,5-difluorophenyl)-2-methyl-8-(6-(trifluoromethyl)pyridazin-3-yl)-2,3-dihydro-1H-benzo[c]azepine;
(Z)-5-phenyl-8-(6-(trifluoromethyl)pyridazin-3-yl)-2,3-dihydro-1H-benzo[c]azepine;
(Z)-5-(4-chlorophenyl)-8-(6-(trifluoromethyl)pyridazin-3-yl)-2,3-dihydro-1H-benzo[c]azepine;
(Z)-5-(4-fluorophenyl)-8-(6-(trifluoromethyl)pyridazin-3-yl)-2,3-dihydro-1H-benzo[c]azepine;
(Z)-5-(3-fluorophenyl)-8-(6-(trifluoromethyl)pyridazin-3-yl)-2,3-dihydro-1H-benzo[c]azepine;
(Z)-5-(2-fluorophenyl)-8-(6-(trifluoromethyl)pyridazin-3-yl)-2,3-dihydro-1H-benzo[c]azepine;
(E)-5-(2,4-difluorophenyl)-8-(6-(trifluoromethyl)pyridazin-3-yl)-2,3-dihydro-1H-benzo[c]azepine;
(E)-5-(2,3-difluorophenyl)-8-(6-(trifluoromethyl)pyridazin-3-yl)-2,3-dihydro-1H-benzo[c]azepine;
(E)-5-(2,5-difluorophenyl)-8-(6-(trifluoromethyl)pyridazin-3-yl)-2,3-dihydro-1H-benzo[c]azepine;
(E)-5-(2,6-difluorophenyl)-8-(6-(trifluoromethyl)pyridazin-3-yl)-2,3-dihydro-1H-benzo[c]azepine;
(E)-5-(3,4-difluorophenyl)-8-(6-(trifluoromethyl)pyridazin-3-yl)-2,3-dihydro-1H-benzo[c]azepine;
(E)-5-(3,5-difluorophenyl)-8-(6-(trifluoromethyl)pyridazin-3-yl)-2,3-dihydro-1H-benzo[c]azepine;
(Z)-2-methyl-5-phenyl-8-(6-(trifluoromethyl)pyridazin-3-yl)-2,3-dihydro-1H-benzo[c]azepine;
(Z)-5-(4-chlorophenyl)-2-methyl-8-(6-(trifluoromethyl)pyridazin-3-yl)-2,3-dihydro-1H-benzo[c]azepine;
(Z)-5-(4-fluorophenyl)-2-methyl-8-(6-(trifluoromethyl)pyridazin-3-yl)-2,3-dihydro-1H-benzo[c]azepine;
(Z)-5-(3-fluorophenyl)-2-methyl-8-(6-(trifluoromethyl)pyridazin-3-yl)-2,3-dihydro-1H-benzo[c]azepine;
(Z)-5-(2-fluorophenyl)-2-methyl-8-(6-(trifluoromethyl)pyridazin-3-yl)-2,3-dihydro-1H-benzo[c]azepine;
(E)-5-(2,4-difluorophenyl)-2-methyl-8-(6-(trifluoromethyl)pyridazin-3-yl)-2,3-dihydro-1H-benzo[c]azepine;
(E)-5-(2,3-difluorophenyl)-2-methyl-8-(6-(trifluoromethyl)pyridazin-3-yl)-2,3-dihydro-1H-benzo[c]azepine;
(E)-5-(2,5-difluorophenyl)-2-methyl-8-(6-(trifluoromethyl)pyridazin-3-yl)-2,3-dihydro-1H-benzo[c]azepine;

(E)-5-(2,6-difluorophenyl)-2-methyl-8-(6-(trifluoromethyl)pyridazin-3-yl)-2,3-dihydro-1H-benzo[c]azepine;
(E)-5-(3,4-difluorophenyl)-2-methyl-8-(6-(trifluoromethyl)pyridazin-3-yl)-2,3-dihydro-1H-benzo[c]azepine;
(E)-5-(3,5-difluorophenyl)-2-methyl-8-(6-(trifluoromethyl)pyridazin-3-yl)-2,3-dihydro-1H-benzo[c]azepine;
(E)-9-fluoro-5-(2-fluorophenyl)-8-(pyridazin-3-yl)-2,3-dihydro-1H-benzo[c]azepine;
(E)-9-fluoro-5-(2-fluorophenyl)-2-methyl-8-(pyridazin-3-yl)-2,3-dihydro-1H-benzo[c]azepine;
(E)-6-(9-fluoro-5-(2-fluorophenyl)-2,3-dihydro-1H-benzo[c]azepin-8-yl)pyridazin-3-amine;
(E)-9-fluoro-5-(2-fluorophenyl)-8-(6-(trifluoromethyl)pyridazin-3-yl)-2,3-dihydro-1H-benzo[c]azepine;
(E)-6-(9-fluoro-5-(2-fluorophenyl)-2-methyl-2,3-dihydro-1H-benzo[c]azepin-8-yl)pyridazin-3-amine;
(E)-9-fluoro-5-(2-fluorophenyl)-2-methyl-8-(6-(trifluoromethyl)pyridazin-3-yl)-2,3-dihydro-1H-benzo[c]azepine;
(E)-9-fluoro-5-(2-fluorophenyl)-8-(6-methylpyridazin-3-yl)-2,3-dihydro-1H-benzo[c]azepine;
(E)-9-fluoro-5-(2-fluorophenyl)-2-methyl-8-(6-methylpyridazin-3-yl)-2,3-dihydro-1H-benzo[c]azepine;
(E)-9-fluoro-5-(4-fluorophenyl)-8-(pyridazin-3-yl)-2,3-dihydro-1H-benzo[c]azepine;
(E)-9-fluoro-5-(4-fluorophenyl)-2-methyl-8-(pyridazin-3-yl)-2,3-dihydro-1H-benzo[c]azepine;
(E)-6-(9-fluoro-5-(4-fluorophenyl)-2,3-dihydro-1H-benzo[c]azepin-8-yl)pyridazin-3-amine;
(E)-9-fluoro-5-(4-fluorophenyl)-8-(6-(trifluoromethyl)pyridazin-3-yl)-2,3-dihydro-1H-benzo[c]azepine;
(E)-6-(9-fluoro-5-(4-fluorophenyl)-2-methyl-2,3-dihydro-1H-benzo[c]azepin-8-yl)pyridazin-3-amine;
(E)-9-fluoro-5-(4-fluorophenyl)-2-methyl-8-(6-(trifluoromethyl)pyridazin-3-yl)-2,3-dihydro-1H-benzo[c]azepine;
(E)-9-fluoro-5-(4-fluorophenyl)-8-(6-methylpyridazin-3-yl)-2,3-dihydro-1H-benzo[c]azepine;
(E)-9-fluoro-5-(4-fluorophenyl)-2-methyl-8-(6-methylpyridazin-3-yl)-2,3-dihydro-1H-benzo[c]azepine;
(E)-5-(2,4-difluorophenyl)-9-fluoro-8-(pyridazin-3-yl)-2,3-dihydro-1H-benzo[c]azepine;
(E)-6-(5-(2,4-difluorophenyl)-9-fluoro-2,3-dihydro-1H-benzo[c]azepin-8-yl)pyridazin-3-amine;
(E)-5-(2,4-difluorophenyl)-9-fluoro-8-(6-(trifluoromethyl)pyridazin-3-yl)-2,3-dihydro-1H-benzo[c]azepine;
(E)-5-(2,4-difluorophenyl)-9-fluoro-8-(6-methylpyridazin-3-yl)-2,3-dihydro-1H-benzo[c]azepine;
(E)-5-(2,4-difluorophenyl)-9-fluoro-2-methyl-8-(pyridazin-3-yl)-2,3-dihydro-1H-benzo[c]azepine;
(E)-6-(5-(2,4-difluorophenyl)-9-fluoro-2-methyl-2,3-dihydro-1H-benzo[c]azepin-8-yl)pyridazin-3-amine;
(E)-5-(2,4-difluorophenyl)-9-fluoro-2-methyl-8-(6-(trifluoromethyl)pyridazin-3-yl)-2,3-dihydro-1H-benzo[c]azepine;
(E)-5-(2,4-difluorophenyl)-9-fluoro-2-methyl-8-(6-methylpyridazin-3-yl)-2,3-dihydro-1H-benzo[c]azepine;
(E)-5-(3,4-difluorophenyl)-9-fluoro-8-(pyridazin-3-yl)-2,3-dihydro-1H-benzo[c]azepine;
(E)-6-(5-(3,4-difluorophenyl)-9-fluoro-2,3-dihydro-1H-benzo[c]azepin-8-yl)pyridazin-3-amine;
(E)-5-(3,4-difluorophenyl)-9-fluoro-8-(6-(trifluoromethyl)pyridazin-3-yl)-2,3-dihydro-1H-benzo[c]azepine;
(E)-5-(3,4-difluorophenyl)-9-fluoro-8-(6-methylpyridazin-3-yl)-2,3-dihydro-1H-benzo[c]azepine;
(E)-5-(3,4-difluorophenyl)-9-fluoro-2-methyl-8-(pyridazin-3-yl)-2,3-dihydro-1H-benzo[c]azepine;
(E)-6-(5-(3,4-difluorophenyl)-9-fluoro-2-methyl-2,3-dihydro-1H-benzo[c]azepin-8-yl)pyridazin-3-amine;
(E)-5-(3,4-difluorophenyl)-9-fluoro-2-methyl-8-(6-(trifluoromethyl)pyridazin-3-yl)-2,3-dihydro-1H-benzo[c]azepine;
(E)-5-(3,4-difluorophenyl)-9-fluoro-2-methyl-8-(6-methylpyridazin-3-yl)-2,3-dihydro-1H-benzo[c]azepine;
(E)-5-(3,5-difluorophenyl)-9-fluoro-8-(pyridazin-3-yl)-2,3-dihydro-1H-benzo[c]azepine;
(E)-6-(5-(3,5-difluorophenyl)-9-fluoro-2,3-dihydro-1H-benzo[c]azepin-8-yl)pyridazin-3-amine;
(E)-5-(3,5-difluorophenyl)-9-fluoro-8-(6-(trifluoromethyl)pyridazin-3-yl)-2,3-dihydro-1H-benzo[c]azepine;
(E)-5-(3,5-difluorophenyl)-9-fluoro-8-(6-methylpyridazin-3-yl)-2,3-dihydro-1H-benzo[c]azepine;
(E)-5-(3,5-difluorophenyl)-9-fluoro-2-methyl-8-(pyridazin-3-yl)-2,3-dihydro-1H-benzo[c]azepine;
(E)-6-(5-(3,5-difluorophenyl)-9-fluoro-2-methyl-2,3-dihydro-1H-benzo[c]azepin-8-yl)pyridazin-3-amine;
(E)-5-(3,5-difluorophenyl)-9-fluoro-2-methyl-8-(6-(trifluoromethyl)pyridazin-3-yl)-2,3-dihydro-1H-benzo[c]azepine;
(E)-5-(3,5-difluorophenyl)-9-fluoro-2-methyl-8-(6-methylpyridazin-3-yl)-2,3-dihydro-1H-benzo[c]azepine;
(E)-5-(2,3-difluorophenyl)-9-fluoro-8-(pyridazin-3-yl)-2,3-dihydro-1H-benzo[c]azepine;
(E)-5-(2,3-difluorophenyl)-9-fluoro-2-methyl-8-(pyridazin-3-yl)-2,3-dihydro-1H-benzo[c]azepine;
(E)-5-(2,6-difluorophenyl)-9-fluoro-8-(pyridazin-3-yl)-2,3-dihydro-1H-benzo[c]azepine;
(E)-5-(2,6-difluorophenyl)-9-fluoro-2-methyl-8-(pyridazin-3-yl)-2,3-dihydro-1H-benzo[c]azepine;
(E)-5-(2,5-difluorophenyl)-9-fluoro-8-(pyridazin-3-yl)-2,3-dihydro-1H-benzo[c]azepine;
(E)-5-(2,5-difluorophenyl)-9-fluoro-2-methyl-8-(pyridazin-3-yl)-2,3-dihydro-1H-benzo[c]azepine;
(E)-7-fluoro-5-(2-fluorophenyl)-8-(pyridazin-3-yl)-2,3-dihydro-1H-benzo[c]azepine;
(E)-7-fluoro-5-(2-fluorophenyl)-2-methyl-8-(pyridazin-3-yl)-2,3-dihydro-1H-benzo[c]azepine;
(E)-7-fluoro-5-(4-fluorophenyl)-8-(pyridazin-3-yl)-2,3-dihydro-1H-benzo[c]azepine;
(E)-7-fluoro-5-(4-fluorophenyl)-2-methyl-8-(pyridazin-3-yl)-2,3-dihydro-1H-benzo[c]azepine;
(E)-5-(2,3-difluorophenyl)-7-fluoro-8-(pyridazin-3-yl)-2,3-dihydro-1H-benzo[c]azepine;
(E)-5-(2,3-difluorophenyl)-7-fluoro-2-methyl-8-(pyridazin-3-yl)-2,3-dihydro-1H-benzo[c]azepine;
(E)-5-(2,4-difluorophenyl)-7-fluoro-8-(pyridazin-3-yl)-2,3-dihydro-1H-benzo[c]azepine;
(E)-5-(2,4-difluorophenyl)-7-fluoro-2-methyl-8-(pyridazin-3-yl)-2,3-dihydro-1H-benzo[c]azepine;
(E)-5-(2,5-difluorophenyl)-7-fluoro-8-(pyridazin-3-yl)-2,3-dihydro-1H-benzo[c]azepine;
(E)-5-(2,5-difluorophenyl)-7-fluoro-2-methyl-8-(pyridazin-3-yl)-2,3-dihydro-1H-benzo[c]azepine;
(E)-5-(2,6-difluorophenyl)-7-fluoro-8-(pyridazin-3-yl)-2,3-dihydro-1H-benzo[c]azepine;
(E)-5-(2,6-difluorophenyl)-7-fluoro-2-methyl-8-(pyridazin-3-yl)-2,3-dihydro-1H-benzo[c]azepine;
(E)-5-(3,4-difluorophenyl)-7-fluoro-8-(pyridazin-3-yl)-2,3-dihydro-1H-benzo[c]azepine;
(E)-5-(3,4-difluorophenyl)-7-fluoro-2-methyl-8-(pyridazin-3-yl)-2,3-dihydro-1H-benzo[c]azepine;
(E)-5-(3,5-difluorophenyl)-7-fluoro-8-(pyridazin-3-yl)-2,3-dihydro-1H-benzo[c]azepine
(E)-5-(3,5-difluorophenyl)-7-fluoro-2-methyl-8-(pyridazin-3-yl)-2,3-dihydro-1H-benzo[c]azepine;

(E)-6-fluoro-5-(2-fluorophenyl)-8-(pyridazin-3-yl)-2,3-dihydro-1H-benzo[c]azepine;
(E)-6-fluoro-5-(2-fluorophenyl)-2-methyl-8-(pyridazin-3-yl)-2,3-dihydro-1H-benzo[c]azepine;
(E)-6-fluoro-5-(4-fluorophenyl)-8-(pyridazin-3-yl)-2,3-dihydro-1H-benzo[c]azepine;
(E)-6-fluoro-5-(4-fluorophenyl)-2-methyl-8-(pyridazin-3-yl)-2,3-dihydro-1H-benzo[c]azepine;
(E)-5-(3,5-difluorophenyl)-6-fluoro-8-(pyridazin-3-yl)-2,3-dihydro-1H-benzo[c]azepine;
(E)-5-(3,5-difluorophenyl)-6-fluoro-2-methyl-8-(pyridazin-3-yl)-2,3-dihydro-1H-benzo[c]azepine;
(Z)-5-(naphthalen-2-yl)-8-(pyridazin-3-yl)-2,3-dihydro-1H-benzo[c]azepine;
(Z)-2-methyl-5-(naphthalen-2-yl)-8-(pyridazin-3-yl)-2,3-dihydro-1H-benzo[c]azepine;
(Z)-8-(6-methylpyridazin-3-yl)-5-(naphthalen-2-yl)-2,3-dihydro-1H-benzo[c]azepine;
(Z)-2-methyl-8-(6-methylpyridazin-3-yl)-5-(naphthalen-2-yl)-2,3-dihydro-1H-benzo[c]azepine;
(Z)-6-(5-(naphthalen-2-yl)-2,3-dihydro-1H-benzo[c]azepin-8-yl)pyridazin-3-amine;
(Z)-6-(2-methyl-5-(naphthalen-2-yl)-2,3-dihydro-1H-benzo[c]azepin-8-yl)pyridazin-3-amine;
(Z)-2-methyl-5-(naphthalen-2-yl)-8-(6-(trifluoromethyl)pyridazin-3-yl)-2,3-dihydro-1H-benzo[c]azepine;
(Z)-5-(naphthalen-5-yl)-8-(pyridazin-3-yl)-2,3-dihydro-1H-benzo[c]azepine;
(Z)-2-methyl-5-(naphthalen-5-yl)-8-(pyridazin-3-yl)-2,3-dihydro-1H-benzo[c]azepine;
(Z)-5-(naphthalen-6-yl)-8-(pyridazin-3-yl)-2,3-dihydro-1H-benzo[c]azepine;
(Z)-2-methyl-5-(naphthalen-6-yl)-8-(pyridazin-3-yl)-2,3-dihydro-1H-benzo[c]azepine;
(Z)-5-(naphthalen-7-yl)-8-(pyridazin-3-yl)-2,3-dihydro-1H-benzo[c]azepine;
(Z)-2-methyl-5-(naphthalen-7-yl)-8-(pyridazin-3-yl)-2,3-dihydro-1H-benzo[c]azepine;
(E)-5-(1-fluoronaphthalen-2-yl)-8-(pyridazin-3-yl)-2,3-dihydro-1H-benzo[c]azepine;
(E)-5-(1-fluoronaphthalen-2-yl)-2-methyl-8-(pyridazin-3-yl)-2,3-dihydro-1H-benzo[c]azepine;
(E)-6-(5-(1-fluoronaphthalen-2-yl)-2,3-dihydro-1H-benzo[c]azepin-8-yl)pyridazin-3-amine;
(E)-6-(5-(1-fluoronaphthalen-2-yl)-2-methyl-2,3-dihydro-1H-benzo[c]azepin-8-yl)pyridazin-3-amine;
(E)-5-(1-fluoronaphthalen-2-yl)-8-(6-(trifluoromethyl)pyridazin-3-yl)-2,3-dihydro-1H-benzo[c]azepine;
(E)-5-(1-fluoronaphthalen-2-yl)-2-methyl-8-(6-(trifluoromethyl)pyridazin-3-yl)-2,3-dihydro-1H-benzo[c]azepine;
(E)-5-(3-fluoronaphthalen-2-yl)-8-(pyridazin-3-yl)-2,3-dihydro-1H-benzo[c]azepine;
(E)-5-(3-fluoronaphthalen-2-yl)-2-methyl-8-(pyridazin-3-yl)-2,3-dihydro-1H-benzo[c]azepine;
(E)-6-(5-(3-fluoronaphthalen-2-yl)-2,3-dihydro-1H-benzo[c]azepin-8-yl)pyridazin-3-amine;
(E)-6-(5-(3-fluoronaphthalen-2-yl)-2-methyl-2,3-dihydro-1H-benzo[c]azepin-8-yl)pyridazin-3-amine;
(E)-5-(3-fluoronaphthalen-2-yl)-8-(6-(trifluoromethyl)pyridazin-3-yl)-2,3-dihydro-1H-benzo[c]azepine;
(E)-5-(3-fluoronaphthalen-2-yl)-2-methyl-8-(6-(trifluoromethyl)pyridazin-3-yl)-2,3-dihydro-1H-benzo[c]azepine;
(E)-5-(5-fluoronaphthalen-2-yl)-8-(pyridazin-3-yl)-2,3-dihydro-1H-benzo[c]azepine;
(E)-5-(5-fluoronaphthalen-2-yl)-2-methyl-8-(pyridazin-3-yl)-2,3-dihydro-1H-benzo[c]azepine;
(E)-5-(6-fluoronaphthalen-2-yl)-8-(pyridazin-3-yl)-2,3-dihydro-1H-benzo[c]azepine;
(E)-5-(6-fluoronaphthalen-2-yl)-2-methyl-8-(pyridazin-3-yl)-2,3-dihydro-1H-benzo[c]azepine;
(E)-5-(7-fluoronaphthalen-2-yl)-8-(pyridazin-3-yl)-2,3-dihydro-1H-benzo[c]azepine;
(E)-5-(7-fluoronaphthalen-2-yl)-2-methyl-8-(pyridazin-3-yl)-2,3-dihydro-1H-benzo[c]azepine;
(Z)-9-fluoro-5-(naphthalen-2-yl)-8-(pyridazin-3-yl)-2,3-dihydro-1H-benzo[c]azepine;
(Z)-9-fluoro-2-methyl-5-(naphthalen-2-yl)-8-(pyridazin-3-yl)-2,3-dihydro-1H-benzo[c]azepine;
(Z)-6-(9-fluoro-5-(naphthalen-2-yl)-2,3-dihydro-1H-benzo[c]azepin-8-yl)pyridazin-3-amine;
(Z)-6-(9-fluoro-2-methyl-5-(naphthalen-2-yl)-2,3-dihydro-1H-benzo[c]azepin-8-yl)pyridazin-3-amine;
(Z)-9-fluoro-5-(naphthalen-2-yl)-8-(6-(trifluoromethyl)pyridazin-3-yl)-2,3-dihydro-1H-benzo[c]azepine;
(Z)-9-fluoro-2-methyl-5-(naphthalen-2-yl)-8-(6-(trifluoromethyl)pyridazin-3-yl)-2,3-dihydro-1H-benzo[c]azepine;
(Z)-9-fluoro-8-(6-methylpyridazin-3-yl)-5-(naphthalen-2-yl)-2,3-dihydro-1H-benzo[c]azepine;
(Z)-9-fluoro-2-methyl-8-(6-methylpyridazin-3-yl)-5-(naphthalen-2-yl)-2,3-dihydro-1H-benzo[c]azepine;
(E)-9-fluoro-5-(1-fluoronaphthalen-2-yl)-8-(pyridazin-3-yl)-2,3-dihydro-1H-benzo[c]azepine;
(E)-9-fluoro-5-(1-fluoronaphthalen-2-yl)-2-methyl-8-(pyridazin-3-yl)-2,3-dihydro-1H-benzo[c]azepine;
(E)-9-fluoro-5-(3-fluoronaphthalen-2-yl)-8-(pyridazin-3-yl)-2,3-dihydro-1H-benzo[c]azepine;
(E)-9-fluoro-5-(3-fluoronaphthalen-2-yl)-2-methyl-8-(pyridazin-3-yl)-2,3-dihydro-1H-benzo[c]azepine;
(E)-9-fluoro-5-(5-fluoronaphthalen-2-yl)-8-(pyridazin-3-yl)-2,3-dihydro-1H-benzo[c]azepine;
(E)-9-fluoro-5-(5-fluoronaphthalen-2-yl)-2-methyl-8-(pyridazin-3-yl)-2,3-dihydro-1H-benzo[c]azepine;
(E)-9-fluoro-5-(6-fluoronaphthalen-2-yl)-8-(pyridazin-3-yl)-2,3-dihydro-1H-benzo[c]azepine;
(E)-9-fluoro-5-(6-fluoronaphthalen-2-yl)-2-methyl-8-(pyridazin-3-yl)-2,3-dihydro-1H-benzo[c]azepine;
(E)-9-fluoro-5-(7-fluoronaphthalen-2-yl)-8-(pyridazin-3-yl)-2,3-dihydro-1H-benzo[c]azepine;
(E)-9-fluoro-5-(7-fluoronaphthalen-2-yl)-2-methyl-8-(pyridazin-3-yl)-2,3-dihydro-1H-benzo[c]azepine;
(E)-7-fluoro-5-(1-fluoronaphthalen-2-yl)-8-(pyridazin-3-yl)-2,3-dihydro-1H-benzo[c]azepine;
(E)-7-fluoro-5-(1-fluoronaphthalen-2-yl)-2-methyl-8-(pyridazin-3-yl)-2,3-dihydro-1H-benzo[c]azepine;
(E)-7-fluoro-5-(3-fluoronaphthalen-2-yl)-8-(pyridazin-3-yl)-2,3-dihydro-1H-benzo[c]azepine;
(E)-7-fluoro-5-(3-fluoronaphthalen-2-yl)-2-methyl-8-(pyridazin-3-yl)-2,3-dihydro-1H-benzo[c]azepine;
(E)-7-fluoro-5-(5-fluoronaphthalen-2-yl)-8-(pyridazin-3-yl)-2,3-dihydro-1H-benzo[c]azepine;
(E)-7-fluoro-5-(5-fluoronaphthalen-2-yl)-2-methyl-8-(pyridazin-3-yl)-2,3-dihydro-1H-benzo[c]azepine;
(E)-7-fluoro-5-(6-fluoronaphthalen-2-yl)-8-(pyridazin-3-yl)-2,3-dihydro-1H-benzo[c]azepine;
(E)-7-fluoro-5-(6-fluoronaphthalen-2-yl)-2-methyl-8-(pyridazin-3-yl)-2,3-dihydro-1H-benzo[c]azepine;
(E)-7-fluoro-5-(7-fluoronaphthalen-2-yl)-8-(pyridazin-3-yl)-2,3-dihydro-1H-benzo[c]azepine;
(E)-7-fluoro-5-(7-fluoronaphthalen-2-yl)-2-methyl-8-(pyridazin-3-yl)-2,3-dihydro-1H-benzo[c]azepine;
(E)-6-fluoro-5-(5-fluoronaphthalen-2-yl)-8-(pyridazin-3-yl)-2,3-dihydro-1H-benzo[c]azepine;

(E)-6-fluoro-5-(5-fluoronaphthalen-2-yl)-2-methyl-8-(pyridazin-3-yl)-2,3-dihydro-1H-benzo[c]azepine;
(E)-6-fluoro-5-(6-fluoronaphthalen-2-yl)-8-(pyridazin-3-yl)-2,3-dihydro-1H-benzo[c]azepine;
(E)-6-fluoro-5-(6-fluoronaphthalen-2-yl)-2-methyl-8-(pyridazin-3-yl)-2,3-dihydro-1H-benzo[c]azepine;
(E)-6-fluoro-5-(7-fluoronaphthalen-2-yl)-8-(pyridazin-3-yl)-2,3-dihydro-1H-benzo[c]azepine;
(E)-6-fluoro-5-(7-fluoronaphthalen-2-yl)-2-methyl-8-(pyridazin-3-yl)-2,3-dihydro-1H-benzo[c]azepine;
(E)-5-(benzo[b]thiophen-2-yl)-8-(pyridazin-3-yl)-2,3-dihydro-1H-benzo[c]azepine;
(E)-5-(benzo[b]thiophen-2-yl)-2-methyl-8-(pyridazin-3-yl)-2,3-dihydro-1H-benzo[c]azepine;
(E)-6-(5-(benzo[b]thiophen-2-yl)-2,3-dihydro-1H-benzo[c]azepin-8-yl)pyridazin-3-amine;
(E)-6-(5-(benzo[b]thiophen-2-yl)-2-methyl-2,3-dihydro-1H-benzo[c]azepin-8-yl)pyridazin-3-amine;
(E)-5-(benzo[b]thiophen-2-yl)-8-(6-(trifluoromethyl)pyridazin-3-yl)-2,3-dihydro-1H-benzo[c]azepine;
(E)-5-(benzo[b]thiophen-2-yl)-2-methyl-8-(6-(trifluoromethyl)pyridazin-3-yl)-2,3-dihydro-1H-benzo[c]azepine;
(E)-5-(benzo[b]thiophen-2-yl)-9-fluoro-8-(pyridazin-3-yl)-2,3-dihydro-1H-benzo[c]azepine;
(E)-5-(benzo[b]thiophen-2-yl)-9-fluoro-2-methyl-8-(pyridazin-3-yl)-2,3-dihydro-1H-benzo[c]azepine;
(E)-5-(benzo[b]thiophen-2-yl)-7-fluoro-8-(pyridazin-3-yl)-2,3-dihydro-1H-benzo[c]azepine;
(E)-5-(benzo[b]thiophen-2-yl)-7-fluoro-2-methyl-8-(pyridazin-3-yl)-2,3-dihydro-1H-benzo[c]azepine;
(E)-5-(benzo[b]thiophen-2-yl)-6-fluoro-8-(pyridazin-3-yl)-2,3-dihydro-1H-benzo[c]azepine; and
(E)-5-(benzo[b]thiophen-2-yl)-6-fluoro-2-methyl-8-(pyridazin-3-yl)-2,3-dihydro-1H-benzo[c]azepine.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

Another embodiment of the present invention is a mixture of compounds of formulae I(A-E), or formula (II), where the compound of formulae I(A-E), or formula (II), is radiolabeled, i.e., where one or more of the atoms described are replaced by a radioactive isotope of that atom (e.g., C replaced by $^{14}C$ and H replaced by $^{3}H$). Such compounds have a variety of potential uses, e.g., as standards and reagents in determining the ability of a potential pharmaceutical to bind to neurotransmitter proteins.

Another embodiment of the present invention is a pharmaceutical composition containing a therapeutically effective amount of the compound of formulae I(A-E), or formula (II), and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of formulae I(A-E), or formula (II), or a pharmaceutically acceptable salt thereof. The method of the present invention is capable of treating subjects afflicted with various neurological and psychiatric disorders including, without limitation: lower back pain, attention deficit hyperactivity disorder (ADHD), cognition impairment, anxiety disorders especially generalized anxiety disorder (GAD), panic disorder, bipolar disorder, also known as manic depression or manic-depressive disorder, obsessive compulsive disorder (OCD), posttraumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, supranuclear palsy, eating disorders, especially obesity, anorexia nervosa, bulimia nervosa, and binge eating disorder, analgesia, substance abuse disorders (including chemical dependencies) such as nicotine addiction, cocaine addiction, alcohol and amphetamine addiction, Lesch-Nyhan syndrome, neurodegenerative diseases such as Parkinson's disease, late luteal phase syndrome or narcolepsy, psychiatric symptoms such as anger, rejection sensitivity, movement disorders such as extrapyramidal syndrome, Tic disorders and restless leg syndrome (RLS), tardive dyskinesia, supranuclear palsy, sleep related eating disorder (SRED), night eating syndrome (NES), stress urinary incontinence (SUI), migraine, neuropathic pain, especially diabetic neuropathy, fibromyalgia syndrome (FS), chronic fatigue syndrome (CFS), sexual dysfunction, especially premature ejaculation and male impotence, and thermoregulatory disorders (e.g., hot flashes associated with menopause).

The compounds provided herein are particularly useful in the treatment of these and other disorders due, at least in part, to their ability to selectively bind to the transporter proteins for certain neurochemicals with a greater affinity than to the transporter proteins for other neurochemicals.

In another embodiment of the present invention, the above method further involves administering a therapeutically effective amount of a serotonin 1A receptor antagonist or a pharmaceutically acceptable salt thereof. Suitable serotonin 1A receptor antagonists include WAY 100135 and spiperone. WAY 100135 (N-(t-butyl)-3-[a-(2-methoxyphenyl)piperazin-1-yl]-2 phenylpropanamide) is disclosed as having an affinity for the serotonin 1A receptor in U.S. Pat. No. 4,988,814 to Abou-Gharbia et al., which is hereby incorporated by reference in its entirety. Also, Cliffe et al., *J Med Chem* 36:1509-10 (1993), which is hereby incorporated by reference in its entirety, showed that the compound is a serotonin 1A antagonist. Spiperone (8-[4-(4-fluorophenyl)-4-oxobutyl]-1-phenyl-1,3,8-triazaspiro[4,5]decan-4-one) is a well-known compound and is disclosed in U.S. Pat. Nos. 3,155,669 and 3,155,670, which are hereby incorporated by reference in their entirety. The activity of spiperone as a serotonin 1A antagonist is described in Middlemiss et al., *Neurosc and Biobehav Rev.* 16:75-82 (1992), which is hereby incorporated by reference in its entirety.

In another embodiment of the present invention, the above method further involves administering a therapeutically effective amount of a selective neurokinin-1 receptor antagonist or pharmaceutically acceptable salt thereof. Neurokinin-1 receptor antagonists that can be used in combination with the compound of formulae I(A-E), or formula (II), in the present invention are fully described, for example, in U.S. Pat. Nos. 5,373,003, 5,387,595, 5,459,270, 5,494,926, 5,162,339, 5,232,929, 5,242,930, 5,496,833, and 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293 168, 2 293 169, and 2 302 689; European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0 733 632 and 0 776 893, which are hereby incorporated by reference in their entirety. The preparations of such compounds are fully described in the aforementioned patents and publications.

In another embodiment of the present invention, the above method further involves administering a therapeutically effective amount of a norepinephrine precursor or a pharmaceutically acceptable salt thereof. Suitable norepinephrine precursors include L-tyrosine and L-phenylalanine.

Another aspect of the present invention is a method of inhibiting synaptic norepinephrine uptake in a patient in need thereof. The method involves administering a therapeutically effective inhibitory amount of a compound of formulae I(A-E), or formula (II).

Another aspect of the present invention is a method of inhibiting synaptic serotonin uptake in a patient in need thereof. The method involves administering a therapeutically effective inhibitory amount of a compound of formulae I(A-E), or formula (II).

Another aspect of the present invention is a method of inhibiting synaptic dopamine uptake in a patient in need thereof. The method involves administering a therapeutically effective inhibitory amount of a compound of formulae I(A-E), or formula (II).

Another aspect of the present invention is a therapeutic method described herein, where the (+)-stereoisomer of the compound of formulae I(A-E) is employed.

Another aspect of the present invention is a therapeutic method described herein, where the (−)-stereoisomer of the compound of formulae I(A-E) is employed.

Another aspect of the present invention is a kit comprising a compound of formulae I(A-E), or formula (II), and at least one compound selected from the group consisting of: a serotonin 1A receptor antagonist compound, a selective neurokinin-1 receptor antagonist compound, and a norepinephrine precursor compound.

Another aspect of the present invention relates to a method of treating a disorder referred to in the above-mentioned embodiments in a patient in need thereof. The method involves inhibiting synaptic serotonin and norepinephrine uptake by administering a therapeutically effective inhibitory amount of the compound of formulae I(A-E), or formula (II), which functions as both a dual acting serotonin and norepinephrine uptake inhibitor.

Another aspect of the present invention relates to a method of treating a disorder referred to in the above-mentioned embodiments in a patient in need thereof. The method involves inhibiting synaptic serotonin and dopamine uptake by administering a therapeutically effective inhibitory amount of the compound of formulae I(A-E), or formula (II), which functions as both a dual acting serotonin and dopamine uptake inhibitor.

Another aspect of the present invention relates to a method of treating a disorder referred to in the above-mentioned embodiments in a patient in need thereof. The method involves inhibiting synaptic dopamine and norepinephrine uptake by administering a therapeutically effective inhibitory amount of the compound of formulae I(A-E), or formula (II), which functions as both a dual acting dopamine and norepinephrine uptake inhibitor.

Another aspect of the present invention relates to a method of treating a disorder referred to in the above-mentioned embodiments in a patient in need thereof. The method involves inhibiting synaptic norepinephrine, dopamine and serotonin uptake by administering a therapeutically effective inhibitory amount of the compound of formulae I(A-E), or formula (II), which functions as a triple acting norepinephrine, dopamine, and serotonin uptake inhibitor.

Another aspect of the present invention relates to a method for inhibiting serotonin uptake in mammals. The method involves administering to a mammal requiring increased neurotransmission of serotonin a pharmaceutically effective amount of the compound of formulae I(A-E), or formula (II).

Another aspect of the present invention relates to a method for inhibiting dopamine uptake in humans. The method involves administering to a human requiring increased neurotransmission of dopamine a pharmaceutically effective amount of the compound of formulae I(A-E), or formula (II).

Another aspect of the present invention relates to a method for inhibiting norepinephrine uptake in humans. The method involves administering to a human requiring increased neurotransmission of norepinephrine a pharmaceutically effective amount of the compound of formulae I(A-E), or formula (II).

Another aspect of the present invention relates to a method of suppressing the desire of humans to smoke. The method involves administering to a human in need of such suppression an effective dose, to relieve the desire to smoke, of the compound of formulae I(A-E), or formula (II).

Another aspect of the present invention relates to a method of suppressing the desire of humans to consume alcohol. The method involves administering to a human in need of such suppression an effective dose, to relieve the desire to consume alcohol, of the compound of formulae I(A-E), or formula (II).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example those described by Larock, R. C.,

*Comprehensive Organic Transformations*, VCH publishers, (1989), which is hereby incorporated by reference in its entirety.

A compound of formulae I(A-E), or formula (II), including a group containing one or more nitrogen ring atoms, may be converted to the corresponding compound where one or more nitrogen ring atom of the group is oxidized to an N-oxide, preferably by reacting with a peracid, for example, peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice; for examples, see Green, *Protective Groups in Organic Chemistry*, John Wiley and Sons (1991) and McOmie, *Protective Groups in Organic Chemistry*, Plenum Press (1973), which are hereby incorporated by reference in their entirety.

In the reaction schemes described hereinafter, the synthesis of tetrahydrobenzazepines of the formulae I(A-E) functionalized at $R^4$ with aryl, heteroaryl, or heterocylic groups is described. The synthesis of tetrahydrobenzazepines of the formulae I(A-E) functionalized at $R^3$, $R^5$ or $R^6$ with aryl, heteroaryl, or heterocyclic groups may be achieved via similar routes, apparent to one skilled in the art of organic synthesis.

The novel tetrahydrobenzazepine reuptake inhibitors of formula (I; $R^4$=aryl, heteroaryl, or heterocyclic) of the present invention can be prepared by the general scheme outlined below (Scheme 1). The $R^1$-substituted N-benzyl amines of formula (IV) may be purchased from commercial sources, or alternatively, obtained from a simple reductive amination protocol. Thus, carbonyl containing compounds of formula (III) may be treated with $H_2N-R^1$ in lower alkyl alcoholic solvents (preferably methanol or ethanol) at temperatures at or below room temperature. The resulting imine may be reduced most commonly with alkali earth borohydrides (preferably sodium borohydride) to provide the desired amine intermediates of formula (IV).

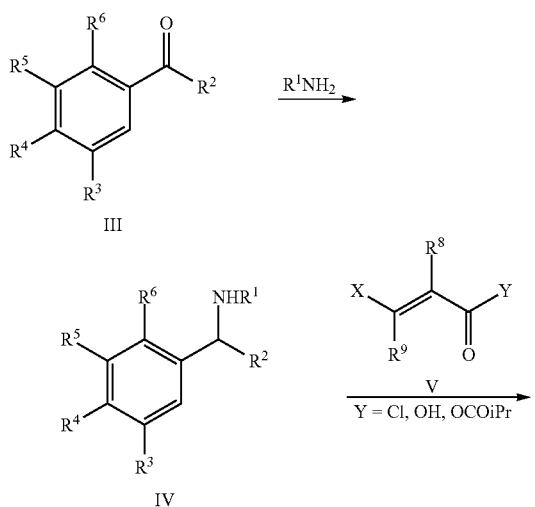

Scheme 1

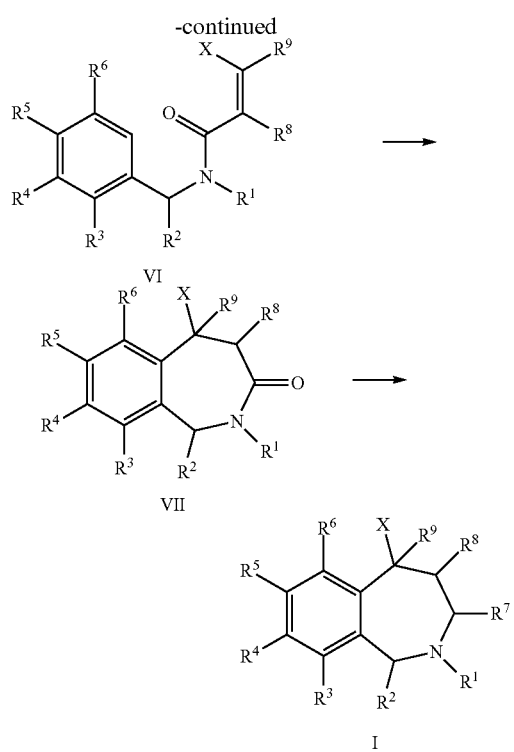

$R^7 = H$

Treatment of intermediates of formula (IV) with cinnamyl chloride, cinnamic acid or cinnamic acid anhydride intermediates of formula (V; Y=Cl, OH, or OCOiPr respectively) cleanly generates the amide products of formula (VI). Amide formation reactions may be run under a wide variety of conditions familiar to one skilled in the art of organic synthesis. Typical solvents include dimethylformamide and methylene chloride. The reactions may be successfully run at temperatures ranging from 0° C. up to room temperature. Reaction progress is conventionally monitored by standard chromatographic and spectroscopic methods.

Several of the aforementioned intermediates of formula (V; Y=OH) are commercially available. Cinnamic acid anhydrides of the formula (V; Y=OCOiPr) are readily prepared from the corresponding cinnamic acid on treatment with an aliphatic chloroformate such as, but not limited to, isopropyl chloroformate, while cinnamyl chloride intermediates of the formula (V; Y=Cl) are obtained on treatment of an appropriate cinnamic acid with oxalyl chloride or thionyl chloride.

Compounds of formula (VI) may be cyclized to the dihydrobenzazepinone compounds of formula (VII) by treatment with a strong acid. Suitable acids include, but are not limited to, concentrated sulfuric acid, polyphosphoric acid, methanesulfonic acid, and trifluoroacetic acid. The reactions are run neat or in the optional presence of a co-solvent such as, for example, methylene chloride or 1,2-dichloroethane. The cyclizations may be conducted at temperatures ranging from 0° C. up to the reflux point of the solvent employed. One skilled in the art of heterocyclic chemistry will readily understand these conditions or may consult the teachings of Euerby et al., *J. Chem. Research* (S), 40-41 (1987), which is hereby incorporated by reference in its entirety. Cyclizations may also be effected by treatment of compounds of formula (VI) with strong Lewis acids, such as for example, aluminum trichloride, typically in halogenated solvents, such as methylene chloride.

Reductions of compounds of formula (VII) to the tetrahydrobenzazepines of formula I of the present invention proceed with reducing agents including, for example, borane and lithium aluminum hydride. The reductions are carried out for a period of time between 1 hour to 3 hours at room temperature or elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from Larock, R. C., *Comprehensive Organic Transformations*, VCH publishers, (1989), which is hereby incorporated by reference in its entirety.

The compounds of formula (I; $R^4$=aryl, heteroaryl) of the present invention may be prepared from the corresponding 8-methoxy, 8-Cl, 8-Br, or 8-I tetrahydrobenzazepine of formula (I; $R^4$=OCH$_3$, Cl, Br, I). The 8-methoxy tetrahydrobenzazepine (I; $R^4$=OCH$_3$) may be converted to the corresponding phenol of formula (I; $R^4$=OH) on treatment with a strong acid or a Lewis acid, such as, but not limited to, hydrobromic acid or boron tribromide. Alternatively, the phenol of formula I ($R^4$=OH) may be obtained from the corresponding 8-methoxy tetrahydrobenzazepine of formula I ($R^4$=OCH$_3$) on treatment with the sodium salt of an alkyl thiol, preferably ethane thiol. The phenol intermediate of formula (I; $R^4$=OH) may be converted into the corresponding triflate of formula (I; $R^4$=OSO$_2$CF$_3$) on treatment with a triflating reagent such as, but not limited to, trifluromethanesulfonic anhydride, in the presence of a base, such as, but not limited to, triethylamine or pyridine. The reaction is carried out in an inert solvent, such as, but not limited to dichloromethane, at temperatures ranging from 0° C. to room temperature. Treatment of compounds of formula (I; $R^4$=Br, I, OSO$_2$CF$_3$) with aryl or heteroaryl boronic acids or aryl or heteroaryl boronic acid esters, of formula $R^4$—Z where Z is equivalent to B(OH)$_2$ or B(OR$^a$)(OR$^b$) (where $R^a$ and $R^b$ are lower alkyl, i.e., $C_1$-$C_6$, or taken together, $R^a$ and $R^b$ are lower alkylene, i.e., $C_2$-$C_{12}$) and $R^4$ is the corresponding aryl or heteroaryl group in the presence of a metal catalyst with or without a base in an inert solvent gives benzazepine compounds of formula (I; $R^4$=aryl, heteroaryl). Metal catalysts include, but are not limited to, salts or phosphine complexes of Cu, Pd, or Ni (e.g., Cu(OAc)$_2$, PdCl$_2$(PPh$_3$)$_2$, NiCl$_2$(PPh$_3$)$_2$, Pd(PPh$_3$)$_4$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao et al., *Tetrahedron*, 50:979-988 (1994), which is hereby incorporated by reference in its entirety.

It will also be appreciated by one skilled in the art that compounds of formula (I; $R^4$=Cl, Br, I, OSO$_2$CF$_3$) may be converted to the boronic acid or boronate ester and subsequently treated with the desired optionally substituted aryl or heteroaryl halide in discrete steps or in tandem as described by Baudoin et al., *J. Org. Chem.* 67:1199-1207 (2002), which is hereby incorporated by reference in its entirety.

The compounds of formula (I; $R^4$=—NR$^{10}$R$^{11}$, —NR$^{12}$C(O)R$^{13}$) of the present invention may be prepared from the compounds of formula (I; $R^4$=Cl, Br, I, OSO$_2$CF$_3$) on reaction with an appropriate amine, amide or lactam, in the presence of a metal catalyst, with or without a base in an inert solvent. Metal catalysts include, but are not limited to, salts or complexes of Cu, Pd, or Ni (e.g., CuI, Cu(OAc)$_2$, PdCl$_2$(dppf), NiCl(OAc)$_2$, Ni(COD)$_2$). Bases may include, but are not limited to, alkali metal carbonates, alkali metal hydrides (preferably sodium hydride), alkali metal alkoxides (preferably, sodium tert-butoxide), and alkali metal bis(trialkylsilyl) amides (preferably, lithium bis(trimethylsilyl)amide). A supporting ligand, such as, but not limited to L-proline or dimethylethylenediamine is often used. Inert solvents may include, but are not limited to, cyclic ethers (preferably, tetrahydrofuran or 1,4-dioxane), N,N-dialkylformamides (preferably, dimethylformamide), dialkylsulfoxides (preferably, dimethylsulfoxide), or aromatic hydrocarbons (preferably, benzene or toluene). Preferred reaction temperatures range from room temperature up to the boiling point of the solvent employed. The reactions may be run in conventional glassware or in a sealed reaction vessel.

Compounds of formula (I) where $R^4$ is aryl, heteroaryl, or heterocyclic, $R^7$=H, $R^8$=H, and $R^9$=H may be obtained by using the route outlined in Scheme 2. Amide intermediate (X) may be prepared by the coupling of an appropriately substituted benzylamine of formula (IX; $R^4$=Br, I, OCH$_3$) with 3,3-diethoxypropanoic acid (VIII; $R^8$=H). Amide formation reactions may be run under a wide variety of conditions familiar to one skilled in the art of organic synthesis. Typical solvents include dimethylformamide and methylene chloride. Typical reagents include, but are not limited to, dicyclohexylcarbodiimide, and 1-ethyl-(3-(3-(dimethylamino)propyl)carbodiimide. The reactions may be successfully run at temperatures ranging from 0° C. up to room temperature. Reaction progress is conventionally monitored by standard chromatographic and spectroscopic methods.

Scheme 2

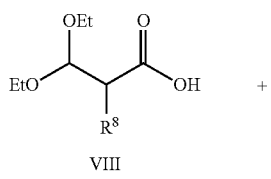

VIII +

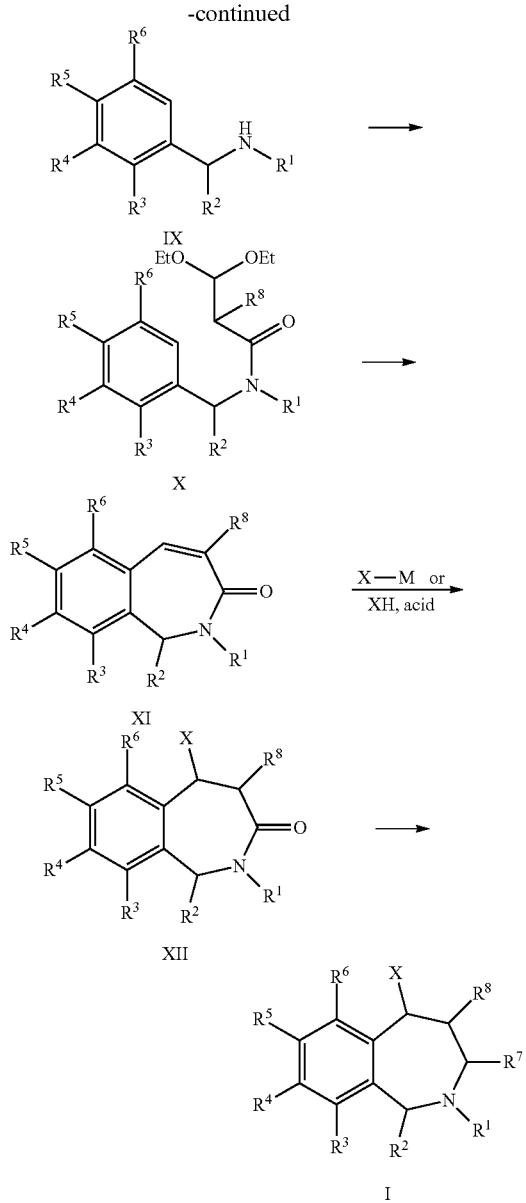

R[7] = R[9] = H

Compounds of formula (X) may be cyclized to give intermediates with the formula (XI) on treatment with a strong acid. Suitable acids include, but are not limited to, concentrated sulfuric acid, polyphosphoric acid, methanesulfonic acid and trifluoroacetic acid. Alternatively, cyclization may be effected by the use of a suitable Lewis acid such as, but not limited to, aluminum trichloride and boron trifluoride etherate. The reactions are run neat or in the optional presence of a co-solvent such as, for example, methylene chloride or 1,2-dichloroethane. The cyclizations may be conducted at temperatures ranging from 0° C. up to the reflux point of the solvent employed.

Treatment of intermediates with the formula (XI) with an aryl or heteroaryl Grignard or an aryl or heteroaryl lithium reagent X-M generates intermediates with the formula (XII), where X is the corresponding aryl or heteroaryl group. This reaction may be catalyzed by a Lewis acid, such as, but not limited to, trimethylsilyl iodide. Alternatively, intermediates with the formula (XI) may be treated with an arene or heterarene X—H in the presence of a strong acid to generate compounds with the formula (XII), where X is the aryl or heteroaryl group. Suitable acids include, but are not limited to, trifluoromethanesulfonic acid, concentrated sulfuric acid and polyphosphoric acid. Alternatively, a suitable Lewis acid such as, but not limited to, aluminum trichloride and boron trifluoride etherate may be used for the preparation of compounds with the formula (XII) from intermediates with the formula (XI). The reactions are run neat or in the optional presence of a co-solvent such as, for example, methylene chloride or 1,2-dichloroethane, at temperatures ranging from 0° C. up to the reflux point of the solvent employed.

Reduction of compounds of formula (XII) to the tetrahydrobenzazepines of formula (I) of the present invention proceeds with reducing agents including, for example, borane and lithium aluminum hydride. The reductions are carried out for a period of time between 1 hour to 3 hours at room temperature or elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from Larock, R. C., *Comprehensive Organic Transformations*, VCH publishers, (1989), which is hereby incorporated by reference in its entirety.

Finally, the compounds of formula (I; $R^4$=aryl, heteroaryl or heterocyclic) of the present invention may be prepared from intermediates of formula (I; $R^4$=Br, I, $OCH_3$) as described above for Scheme 1.

Compounds of formula (I) of the present invention may be prepared by the general scheme outlined in Scheme 3. The acetal-bearing bromoarene intermediate of formula (XIII) may be converted to the intermediate of formula (XIV) on treatment with an alkyl lithium reagent, followed by reaction of the aryl lithium generated thus with an appropriate aryl or heteroaryl aldehyde X—CHO, where X is the aryl or heteroaryl group. The secondary alcohol of the formula (XIV) may be converted to the corresponding chloride of the formula (XV) on treatment with, for example, methanesulfonyl chloride.

Scheme 3

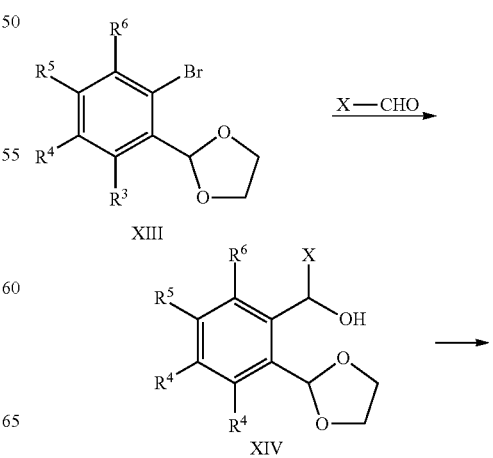

-continued

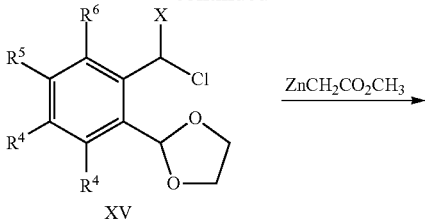
XV

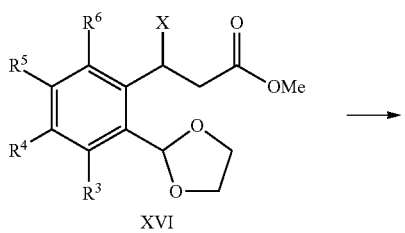
XVI

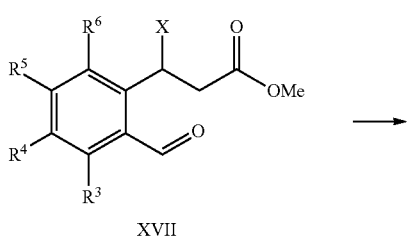
XVII

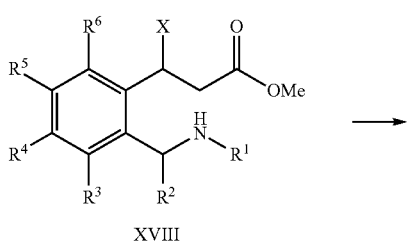
XVIII

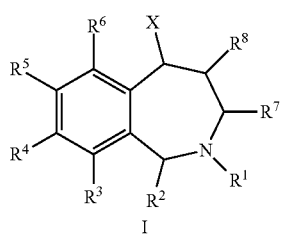
I $R^7 = R^8 = R^9 = H$

Alternatively, the secondary alcohol of the formula (XIV) may also be converted into the corresponding mesylate, tosylate, bromide, or iodide using various methods familiar to one skilled in the art of organic synthesis. Treatment of the intermediate with the formula (XV) with an organozinc reagent such as (2-methoxy-2-oxoethyl)zinc gives the ester of the formula (XVI). One skilled in the art will be familiar with synthetic routes toward the preparation of the aforementioned organozinc reagent. Removal of the acetal protecting group from the intermediate of formula (XVI) may be effected on treatment with, but not limited to, hydrochloric acid, to give the aldehyde with the formula (XVII).

Reductive amination of the aldehyde intermediate (XVII) with primary amines of the formula $R^1NH_2$ generates the benzylamine intermediate (XVIII). Reductive amination may involve the use of various reducing agents including, but not limited to, sodium triacetoxyborohydride, and sodium borohydride, and may be catalyzed by various reagents including, but not limited to, magnesium sulfate and titanium isopropoxide.

Compounds of formula (XVIII) may be converted to the corresponding tetrahydrobenzazepine (I) via hydrolysis of the ester, followed by intramolecular condensation with the benzylamine moiety and reduction of the benzazepinone obtained thus using aforementioned methods. Alternatively, compounds of the formula (XVIII), on heating in an appropriate solvent, can be converted into the corresponding dihydrobenzazepinone, which, on reduction using aforementioned methods, gives the tetrahydrobenzazepine of the formula (I). Direct conversion of the intermediate of formula (XVIII) to the tetrahydrobenzazepine of formula (I) may be effected by a one-pot procedure using diisobutylaluminum hydride, followed by sodium borohydride, according to the teachings of Kato et al, *J. Heterocyclic Chemistry*, 32:637-642 (1995), which is hereby incorporated by reference in its entirety.

Finally, the target compounds of formula (I; $R^4$=aryl, heteroaryl, or heterocyclic) of the present invention may be prepared from compounds of formula I ($R^4$=Cl, $OCH_3$) as described above for Scheme 1.

Compounds of formula (I) where $R^4$ is aryl, heteroaryl or heterocyclic and $R^9$=H may be obtained by using the route outlined in Scheme 4. An appropriately functionalized benzyl amine of the formula (XIX) may be converted to intermediate (XX) on reaction with acrylic acid using methods familiar to one skilled in the art of organic synthesis. The acid with the formula (XX) may be cyclized to give the corresponding 5-benzazepinone of the formula (XXI) on treatment with a strong acid such as, but not limited to, polyphosphoric acid or Eaton's reagent. The 5-benzazepinone of the formula (XXI) may be converted to the secondary alcohol intermediate (XXII) on reaction with an aryl or heteroaryl Grignard reagent or an aryl or heteroaryl lithium reagent. Dehydration and reduction of the intermediate of formula (XXII) using a metal-catalyzed reduction in an acidic medium results in the benzazepine of formula (I). Metal catalysts include, but are not limited to, palladium on carbon, palladium hydroxide, and Raney nickel. Acids used in the reduction include, but are not limited to, acetic acid, formic acid, and trifluoroacetic acid. Finally, the compounds of formula (I; $R^4$=aryl, heteroaryl or heterocyclic) of the present invention may be prepared from intermediates of formula I ($R^4$=Cl, Br, I, $OCH_3$) as described above for Scheme 1.

Scheme 4

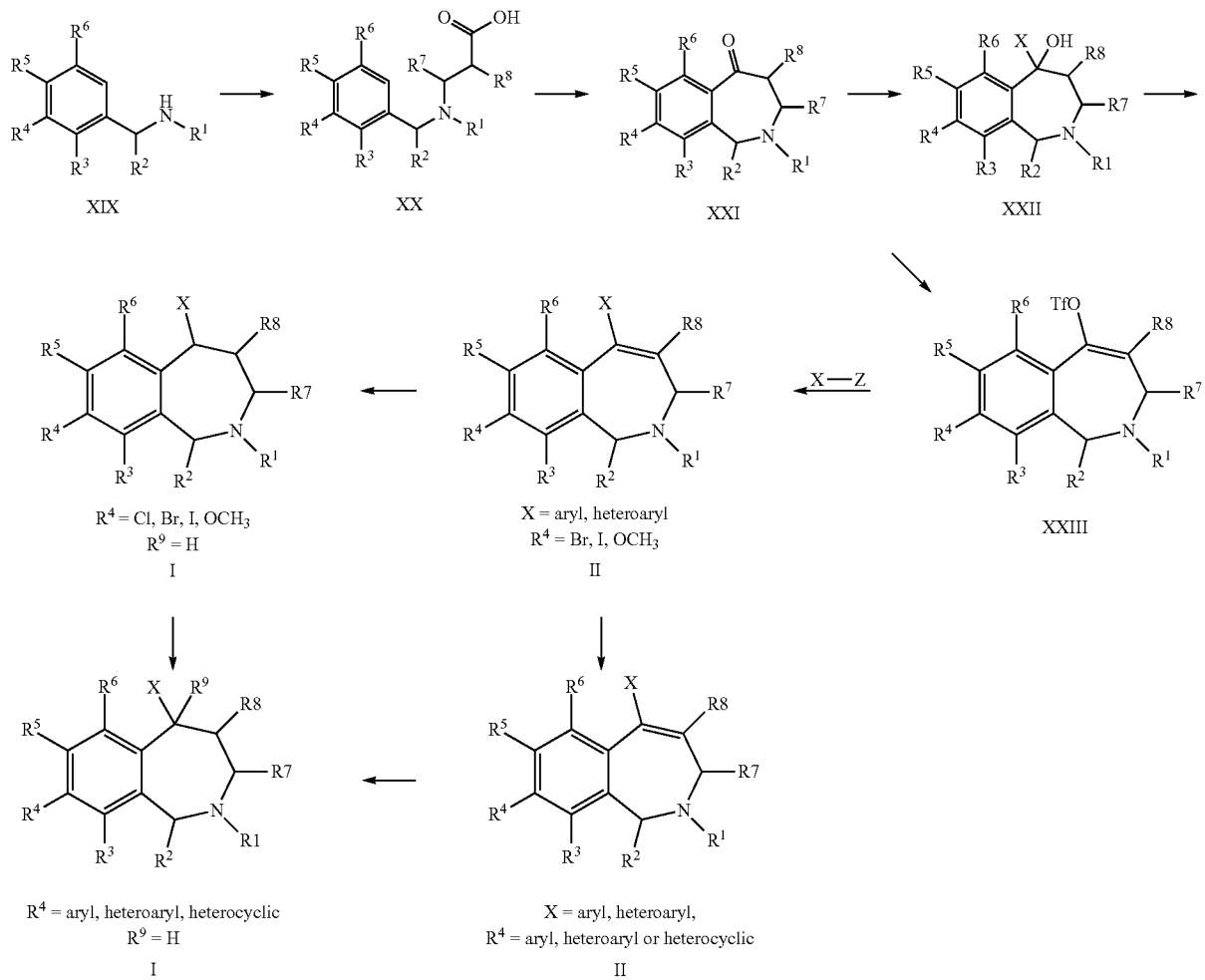

Alternatively, the 5-benzazepinone of formula (XXI) may be converted into the corresponding vinyl triflate of formula (XXIII) on treatment with a strong base and a triflating reagent, such as, but not limited to, trifluoromethanesulfonic anhydride and N-phenyltrifluoromethanesulfonimide. Bases may include, but are not limited to, sodium hydride, lithium hexamethyldisilazide, pyridine, and lithium diisopropylamide. Dihydrobenzazepine intermediates of the formula (II; X=aryl or heteroaryl) may be obtained by the coupling of the vinyl triflate intermediate of formula (XXIII) with aryl or heteroaryl boronic acids or aryl or heteroaryl boronic acid esters of the formula X-Z, where X is the aryl or heteroaryl group, and where Z is equivalent to $B(OH)_2$ or $B(OR^a)(OR^b)$ (where $R^a$ and $R^b$ are lower alkyl, i.e., $C_1$-$C_6$, or taken together, $R^a$ and $R^b$ are lower alkylene, i.e., $C_2$-$C_{12}$) in the presence of a metal catalyst, with or without a base in an inert solvent, using the aforementioned methods. Reduction of the dihydrobenzazepine intermediates of the formula (II; X=aryl or heteroaryl) using metal-catalyzed reduction or transfer hydrogenation gives the benzazepines of formula (I). Finally, the compounds of formula (I; $R^4$=aryl, heteroaryl or heterocyclic) of the present invention may be prepared from intermediates of formula (I; $R^4$=Cl, Br, I, $OCH_3$) as described above for Scheme 1. The reductions may be run under a wide variety of conditions familiar to one skilled in the art of organic synthesis. The reductions may be carried out using chiral catalysts, which may afford the benzazepine enantiomer of choice based on catalyst selection. Alternatively, the sequence of steps may be reversed, with conversion of the intermediates of formula (II; X=aryl or heteroaryl, $R^4$=Br, I, $OCH_3$) to compounds with formula (II; X=aryl or heteroaryl, $R^4$=aryl, heteroaryl, or heterocyclic) using methods described in Scheme 1, followed by reduction to give the target compounds of formula (I; $R^4$=aryl, heteroaryl or heterocyclic), also using aforementioned methods.

Compounds of formula (I) where $R^4$ is aryl, heteroaryl or heterocyclic, $R^7$=H, $R^8$=H and $R^9$=H may be obtained by using the route outlined in Scheme 5. An appropriately functionalized benzyl amine of the formula (XXIV) may be converted to intermediate (XXV) on reaction with a boron reagent, such as, but not limited to, bis(pinacolato)diboron, in the presence of a metal catalyst and a base in an inert solvent. Catalysts include, but are not limited to, dichloro[1,1'-bis(diphenylphosphino)ferrocene]palladium(II) dichloromethane complex, while the base used includes, but is not limited to, potassium acetate in solvents such as, but not limited to, dimethylsulfoxide and dimethylformamide. Reaction of intermediates with the formula (XXV) with methyl 3-iodo aryl (or heteroaryl) acrylates, where X is the aryl or heteroaryl group, gives intermediates of the formula (XXVI).

The synthesis of the iodo aryl (or heteroaryl) acrylates may be accomplished by a variety of methods familiar to one skilled in the art of organic synthesis. Reduction and cyclization of intermediates with the formula (XXVI) may be accomplished by catalytic hydrogenation, followed by heating in an appropriate solvent, such as, but not limited to, toluene, to give the dihydrobenzazepinone intermediate of formula (XXVII). Dihydrobenzazepinones of formula (XXVII) may be reduced using aforementioned methods to give the intermediates of formula (I). Finally, the compounds of formula (I; $R^4$=aryl, heteroaryl or heterocyclic) of the present invention may be prepared from intermediates of formula (I; $R^4$=Cl, Br, I, $OCH_3$) as described above for Scheme 1.

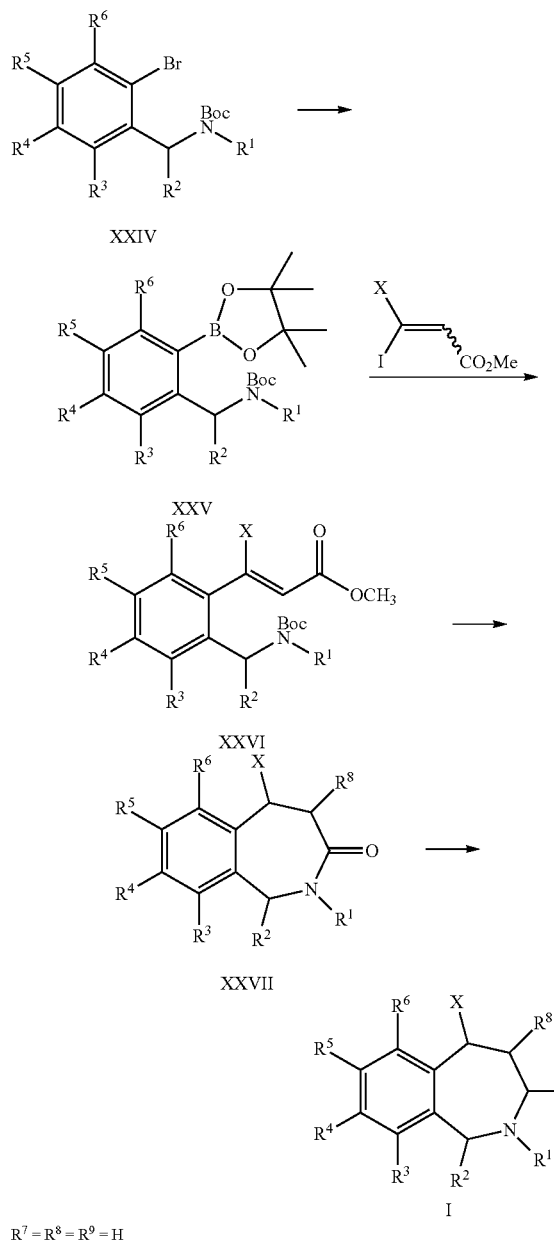

$R^7 = R^8 = R^9 = H$

Compounds of formula (I) where $R^4$ is aryl, heteroaryl, or heterocyclic, $R^7$=H, $R^8$=H, and $R^9$=H may be obtained by using the route outlined in Scheme 6. Appropriately functionalized intermediates of formula (XXVIII) bearing a chiral auxiliary may be prepared by following the teachings of Frey et al, *J. Org. Chem.* 63:3120-3124 (1998) and Song et al, *J. Org. Chem.* 64:9658-9667 (1999), which are hereby incorporated by reference in their entirety. The choice of the chiral auxiliary is dictated by the enantiomer of the benzazepine of the formula (I) that is desired, and includes, but is not limited to, (1R,2R)-(−)-psuedoephedrine, and (1S,2S)-(−)-psuedoephedrine. One skilled in the art of organic synthesis will be capable of making the optimal choice of the chiral auxiliary to be incorporated into the intermediate of the formula (XXVIII). The intermediate of formula (XXVIII), on treatment with an aryl or heteroaryl Grignard or aryl or heteroaryl lithium reagent, gives the enantiomerically enriched or enantiopure compound of formula (XXIX), depending upon the appropriate choice of the chiral auxiliary and the aryl or heteraryl Grignard or lithium reagent used in the reaction; one may also seek guidance from the teachings of Frey et al, *J. Org. Chem.* 63:3120-3124 (1998) and Song et al, *J. Org. Chem.* 64:9658-9667 (1999), which are hereby incorporated by reference in their entirety. Removal of the chiral auxiliary from the intermediate of formula (XXIX) gives the aldehyde (XXX). The removal of the auxiliary is effected by the use of acids such as, but not limited to, acetic acid and citric acid.

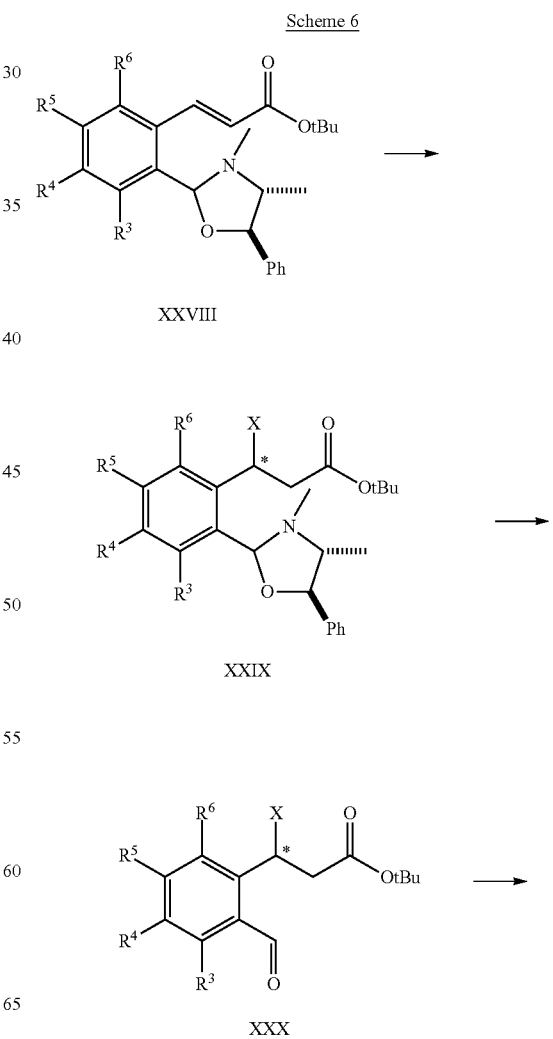

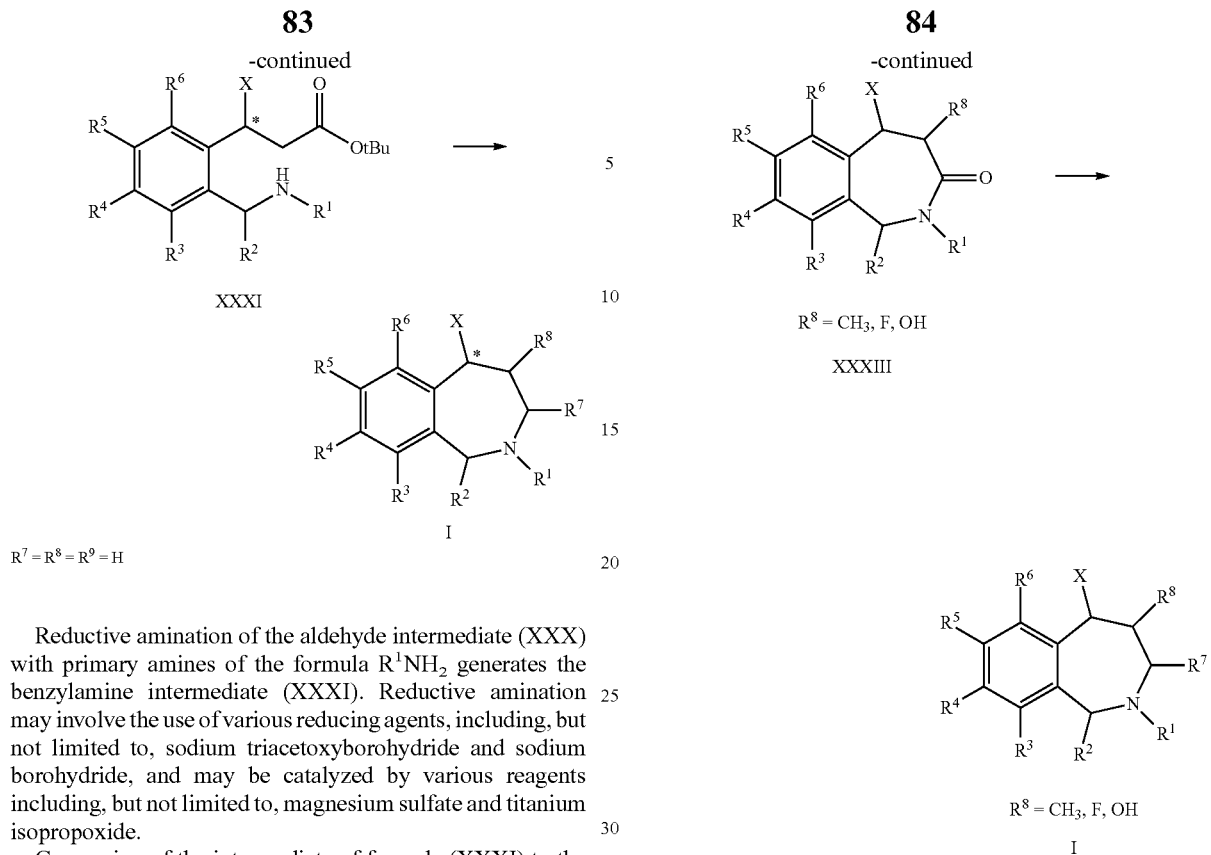

Reductive amination of the aldehyde intermediate (XXX) with primary amines of the formula R¹NH₂ generates the benzylamine intermediate (XXXI). Reductive amination may involve the use of various reducing agents, including, but not limited to, sodium triacetoxyborohydride and sodium borohydride, and may be catalyzed by various reagents including, but not limited to, magnesium sulfate and titanium isopropoxide.

Conversion of the intermediate of formula (XXXI) to the tetrahydrobenzazepine of formula (I) may be effected by a one-pot procedure according to the aforementioned teachings of Kato et al, *J. Heterocyclic Chemistry*, 32:637-642 (1995), which is hereby incorporated by reference in its entirety. Finally, the target compounds of formula (I; R⁴=aryl, heteroaryl or heterocyclic) of the present invention may be prepared from intermediates of formula I (R⁴=Cl, Br, I, OCH₃) as described above for Scheme 1.

Compounds of formula (XXXII; R⁸=H) may be conveniently converted into compounds of formula (XXXIII, R⁸=CH₃, F or OH) as shown in Scheme 7 on treatment with a base such as, but not limited to, lithium diisopropylamide, lithium hexamethyldisilazide, and potassium hexamethyldisilazide, followed by trapping with an electrophile such as, but not limited to, iodomethane, oxidodiperoxymolybdenum (pyridine)(hexamethylphosphoric triamide) and N-fluorobenzenesulfonimide. Finally, the target compounds of formula (I; R⁴=aryl, heteroaryl or heterocyclic) of the present invention may be prepared from intermediates of formula (I; R⁴=Cl, Br, I, OCH₃) as described above for Scheme 1.

Target compounds (I; R⁴=aryl or heteroaryl) of the present invention may be obtained from intermediates of formula (XXXIV; R⁴=OH) on treatment with a base such as, but not limited to, cesium carbonate, sodium hydride, potassium carbonate, and sodium tert-butoxide, followed by reaction with an aryl or heteroaryl halide, where X is the aryl or heteroaryl group (Scheme 8). The reactions are run in solvents such as, but not limited to, DMF, 1,4-dioxane and acetonitrile, at temperatures ranging from room temperature up to the reflux point of the solvent employed. Alternatively, the target compounds of formula (I) of the present invention may be prepared from compounds of formula (XXXIV, R⁴=Br, I, OSO₂CF₃) by coupling with phenols or heteroaryl alcohols in the presence of a metal catalyst, with or without a base in an inert solvent, using literature methods familiar to one skilled in the art of organic synthesis.

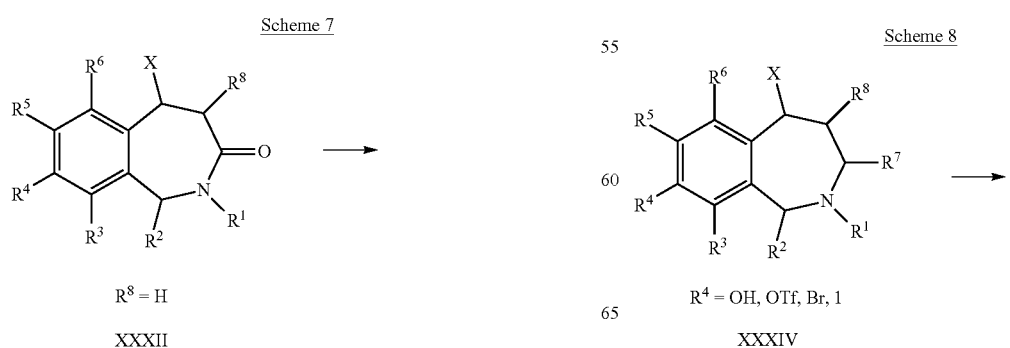

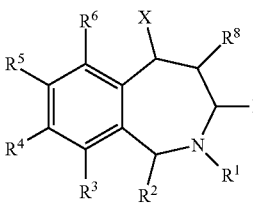

$R^4$ = aryl or heteroaryl

I

Compounds of formula (I) where $R^4$ is aryl, heteroaryl, or heterocyclic, $R^7$=H, $R^8$=H, and $R^9$=H may be obtained by using the route outlined in Scheme 9. As shown in Scheme 9, appropriately functionalized benzyl chlorides of formula (XXXV) may be reacted with amines of the formula (XXXVI) to give tertiary amines of the formula (XXXVII). The aforementioned benzyl chlorides of formula (XXXV) may be obtained from the corresponding lactones via methods familiar to one skilled in the art of organic synthesis. Cyclization of intermediates of formula (XXXVII) to give compounds of formula (XXVIII) may be carried out using a variety of bases, such as, but not limited to, potassium tert-butoxide. Hydrolysis and decarboxylation of compounds of the formula (XXXVIII) may be carried out using acids such as, but not limited to, hydrochloric acid and hydrobromic acid, to give the benzazepinones of formula (XXXIX). Finally, the target compounds of formula (I; $R^4$=aryl, heteroaryl, or heterocyclic) of the present invention may be prepared from intermediates of formula (I; $R^4$=Cl, Br, I, $OCH_3$) as described above for Scheme 4.

Scheme 9

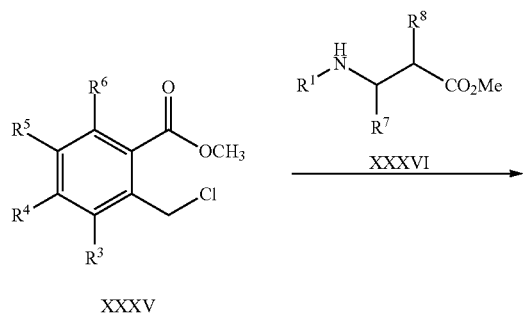

XXXV

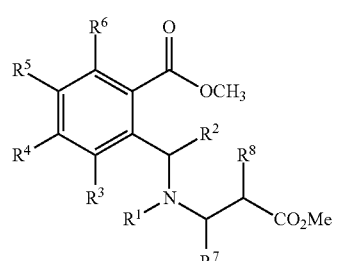

XXXVII

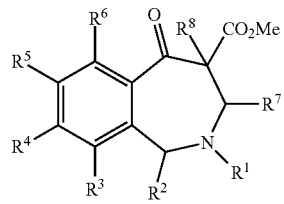

XXXVIII

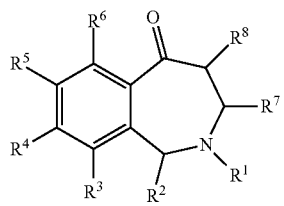

XXXIX

Compounds of formula (I) where $R^4$ is aryl, heteroaryl, or heterocyclic and $R^7$=$R^8$=$R^9$=H may be obtained by using the route outlined in Scheme 10. Appropriately functionalized benzyl amines of the formula (XL) may be reacted with ketones of the formula (XLI) and paraformaldehyde in the presence of an acid such as, but not limited to hydrochloric acid, to give ketones of the formula (XLII). Reduction of the ketone of formula (XLII), followed by cyclization of the resulting alcohol in the presence of acids such as, but not limited to aluminum trichloride results in the formation of benzazepines of formula (I). Finally, the target compounds of formula (I; $R^4$=aryl, heteroaryl, or heterocyclic) of the present invention may be prepared from intermediates of formula (I; $R^4$=Cl, Br, I, $OCH_3$) as described above for Scheme 1.

Scheme 10

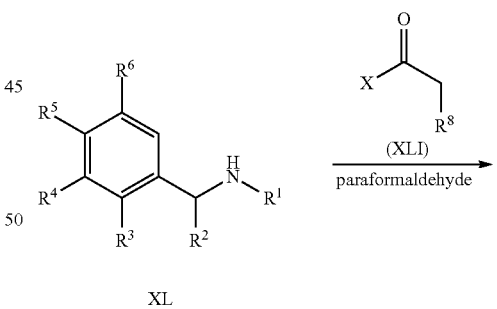

XL

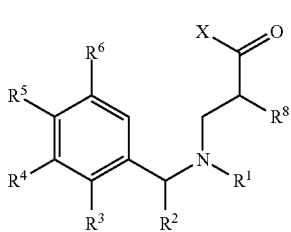

XLII

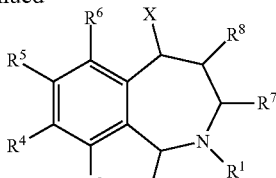

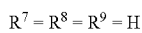

I

Compounds of formulae I(A-E) may be obtained in enantiomerically pure (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formulae I(A-E), or formula (II), hereinabove. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of means well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine, or serotonin transporters and their uptake mechanism are implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formulae I(A-E), or formula (II), and the additional active ingredient (alone or in combination with diluent or carrier) selected from a serotonin 1A receptor antagonist, a selective neurokinin-1 receptor antagonist, and a norepinephrine precursor.

In practice, the compounds of the present invention may generally be administered parenterally, intravenously, subcutaneously, intramuscularly, colonically, nasally, intraperitoneally, rectally, or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formulae I(A-E), or formula II.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine, and serotonin uptake and are, therefore, believed to be useful in treating a disorder which is created by or is dependent upon decreased availability of serotonin, norepinephrine or dopamine. Although the compounds of formulae I(A-E), or formula II, inhibit synaptic norepinephrine, dopamine, and serotonin uptake, in any individual compound, these inhibitory effects may be manifested at the same or vastly different concentrations or doses. As a result, some compounds of formulae I(A-E), or formula II, are useful in treating such a disorder at doses at which synaptic norepinephrine uptake may be substantially inhibited but at which synaptic serotonin uptake or dopamine uptake is not substantially inhibited, or vice versa. Also, some compounds of formulae I(A-E), or formula II, are useful in treating such a disorder at doses at which synaptic dopamine uptake may be substantially inhibited but at which synaptic norepinephrine or serotonin uptake is not substantially inhibited, or vice versa. And, conversely, some compounds of formulae I(A-E), or formula II, are useful in treating such a disorder at doses at which synaptic serotonin uptake may be substantially inhibited but at which synaptic norepinephrine or dopamine uptake is not substantially inhibited, or vice versa. Other compounds of formulae I(A-E), or formula II, are useful in treating such a disorder at doses at which synaptic norepinephrine, dopamine, and serotonin uptake are substantially inhibited.

The present invention provides compounds where the inhibitory effects on serotonin and norepinephrine uptake occurs at similar or even the same concentrations of these compounds, while the effects on inhibition of dopamine uptake occurs at vastly different concentrations or doses. As a result, some compounds of formulae I(A-E), or formula II, are useful in treating such a disorder at doses at which synaptic serotonin and norepinephrine uptake may be substantially inhibited but at which synaptic dopamine uptake is not substantially inhibited, or vice versa.

The present invention provides compounds where the inhibitory effects on serotonin and dopamine uptake occurs at similar or even the same concentrations of these compounds while the effects on inhibition of norepinephrine uptake occurs at vastly different concentrations or doses. As a result, some compounds of formulae I(A-E), or formula II, are useful in treating such a disorder at doses at which synaptic serotonin and dopamine uptake may be substantially inhibited but at which synaptic norepinephrine uptake is not substantially inhibited, or vice versa.

The present invention provides compounds where the inhibitory effects on norepinephrine and dopamine uptake occurs at similar or even the same concentrations of these compounds while the effects on inhibition of dopamine uptake occurs at vastly different concentrations or doses. As a result, some compounds of formulae I(A-E), or formula II, are useful in treating such a disorder at doses at which synaptic norepinephrine and dopamine uptake may be substantially inhibited but at which synaptic serotonin uptake is not substantially inhibited, or vice versa.

The present invention provides compounds where the inhibitory effects on norepinephrine, dopamine and serotonin uptake occur at similar or even the same concentration. As a result, some compounds of formulae I(A-E), or formula II, are useful in treating such a disorder at doses at which synaptic norepinephrine, dopamine, and serotonin uptake may all be substantially inhibited.

The concentrations or doses at which a test compound inhibits synaptic norepinephrine, dopamine, and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther* 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds having higher binding affinities for one or two of the neurotransmitter transporters, e.g., selectivity towards the norepinephrine transporter protein ("NET") over the transporters for other neurochemicals, e.g., the dopamine transporter protein ("DAT") and the serotonin transporter protein ("SERT").

Other compounds of the present invention may demonstrate selectivity towards the SERT over the transporters for other neurochemicals, e.g., the DAT and the NET.

Still other compounds of the present invention may demonstrate selectivity towards the DAT over the transporters for other neurochemicals, e.g., the SERT and the NET.

Other compounds of the present invention may demonstrate selectivity towards the SERT and the NET over the transporter for other neurochemical, e.g., the DAT.

Still other compounds of the present invention may demonstrate selectivity towards the SERT and the DAT over the transporter for other neurochemical, e.g., the NET.

Still other compounds of the present invention may demonstrate selectivity towards the NET and the DAT over the transporter for other neurochemical, e.g., the SERT.

Finally other compounds possess nearly identical affinity towards the NET, the DAT, and the SERT.

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of the present invention; said reversibility, as described below, provides a means of measuring the compounds' binding affinities for the proteins (Ki). A higher Ki value for a compound is indicative that the compound has less binding affinity for a protein than is so for a compound with a lower Ki; conversely, lower Ki values are indicative of greater binding affinities.

Accordingly, the difference in compound selectivity for proteins is indicated by a lower Ki for the protein for which the compound is more selective, and a higher Ki for the protein for which the compound is less selective. Thus, the higher the ratio in Ki values of a compound for protein A over protein B, the greater is the compounds' selectivity for the latter over the former (the former having a higher Ki and the latter a lower Ki for that compound). Compounds provided herein possess a wide range of selectivity profiles for the norepinephrine, dopamine, and serotonin transporters as reflected by the ratios of the experimentally determined Ki values.

Selected compounds ("mono action transporter reuptake inhibitors") of the present invention have potent binding affinity for each of the biogenic amine transporters NET, DAT or SERT. For example, selected compounds of the present invention possess potent (NET Ki<100 nM) and selective binding affinity for NET, where the Ki ratio of DAT/NET and SERT/NET is greater than 10:1. Other selected compounds of the present invention possess potent (SERT Ki<100 nM) and selective binding affinity for SERT, where the Ki ratio of NET/SERT and DAT/SERT is greater than 10:1. Other selected compounds of the present invention possess potent (DAT Ki<100 nM) and selective binding affinity for DAT, where the Ki ratio of NET/DAT and SERT/DAT is greater than 10:1.

Selected compounds ("dual action transporter reuptake inhibitors") of the present invention have potent binding affinity for two of the biogenic amine transporters, NET, DAT or SERT. For example, selected compounds of the present invention possess potent (NET & SERT Ki values<100 nM) and selective binding affinity for NET and SERT, where the Ki ratio of DAT/NET and DAT/SERT is greater than 10:1 while the Ki ratio of SERT/NET or NET/SERT is less than 10:1. Other selected compounds of the present invention possess potent (NET & DAT Ki values<100 nM) and selective binding affinity for NET and DAT, where the Ki ratio of SERT/NET and SERT/DAT is greater than 10:1 while the Ki ratio of DAT/NET or NET/DAT is less than 10:1. Other selected compounds of this invention possess potent (DAT & SERT Ki values<100 nM) and selective binding affinity for DAT and SERT, where the Ki ratio of NET/DAT and SERT/DAT is greater than 10:1 while the Ki ratio of SERT/NET or NET/SERT is less than 10:1.

Selected compounds ("triple action transporter reuptake inhibitors") of the present invention have potent binding affinity simultaneously for all three of the biogenic amine transporters, NET, DAT or SERT. For example, selected compounds of this invention possess potent (NET, DAT & SERT Ki values<100 nM) where the Ki ratios of NET/DAT, NET/SERT, DAT/NET, DAT/SERT, SERT/NET and SERT/DAT are all less than 10:1.

Selected compounds of the present invention have potent binding affinity (Ki values<100 nM) for one, two, or three of the biogenic amine transporters, NET, DAT and SERT where the Ki ratios for any of NET/SERT, NET/DAT, DAT/NET, DAT/SERT, SERT/NET, and SERT/DAT fall outside of the bounds defined for the "Mono-, Dual or Triple action transporter reuptake inhibitors" defined above.

Selected compounds of the present invention have less potent binding affinity (Ki values between 100 nM and 1000 nM) for one, two, or three of the biogenic amine transporters, NET, DAT and SERT, where the Ki ratios for any of NET/SERT, NET/DAT, DAT/NET, DAT/SERT, SERT/NET, and SERT/DAT fall within the bounds defined for the "Mono-, Dual or Triple action transporter reuptake inhibitors" defined above.

Finally, selected compounds of the present invention have less potent binding affinity (Ki values between 100 nM and 1000 nM) for one, two, or three of the biogenic amine transporters, NET, DAT, and SERT, where the Ki ratios for any of NET/SERT, NET/DAT, DAT/NET, DAT/SERT, SERT/NET, and SERT/DAT fall outside of the bounds defined for the "mono-, dual or triple action transporter reuptake inhibitors" defined above.

EXAMPLES

The following examples are provided to illustrate embodiments of the present invention but are by no means intended to limit its scope.

Example 1

Preparation of (+/−)-8-methoxy-2-methyl-5-phenyl-2,3,4,5-tetrahydro-1H-benzo[c]azepine, fumarate salt Step A: To a mixture of (3-methoxybenzyl) methylamine (3.02 g, 20 mmol) and cesium carbonate (7.82 g, 24 mmol) in DMF (50 mL) was added cinnamyl bromide (4.47 g, 22 mmol). The reaction mixture was stirred at room temperature for 15 hours. The reaction mixture was diluted with water and extracted with 1:1 hexanes/ethyl acetate (3×). The combined organic extracts were washed with brine, dried over anhydrous sodium sulfate, and concentrated to provide the desired product (3.1 g, 58%): $^1$H NMR (CDCl$_3$, 500 MHz) δ 7.39-7.37 (m, 2H), 7.32-7.29 (m, 2H), 7.23-7.20 (m, 2H), 6.93-6.91 (m, 2H), 6.81-6.78 (m, 1H), 6.54 (d, J=15.9 Hz, 1H), 6.31 (dt, J=15.9, 6.6 Hz, 1H), 3.81 (s, 3H), 3.52 (s, 2H), 3.19 (dd, J=6.6, 1.2 Hz, 2H), 2.25 (s, 3H); ESI MS m/z=268 [M+H]$^+$. This crude product was used in the next step without further purification.

Step B: A mixture of the product from step A (1.0 g, 3.74 mmol) and pyrophosphoric acid (25 g) in 1,2-dichloroethane (5 mL) was heated at 100° C. for 1 hour. The reaction mixture was cooled, mixed with ice and adjusted to pH 9 with ammonium hydroxide. The reaction mixture was extracted with ethyl acetate (3×). The combined extracts were washed with brine, dried over anhydrous sodium sulfate and concentrated. Purification via MPLC (30% to 50% ethyl acetate/hexanes) provided 6-methoxy-2-methyl-5-phenyl-2,3,4,5-tetrahydro- 1H-benzo[c]azepine (350 mg, 35%) and 8-methoxy-2-methyl-5-phenyl-2,3,4,5-tetrahydro-1H-benzo[c]azepine (280 mg, 28%); 6-methoxy-2-methyl-5-phenyl-2,3,4,5-tetrahydro-1H-benzo[c]azepine: $^1$H NMR (CDCl$_3$, 300 MHz) δ 7.28-7.21 (m, 2H), 7.19-7.13 (m, 2H), 7.06 (d, J=8.0 Hz, 2H), 6.85 (d, J=8.1 Hz, 1H), 6.80 (d, J=7.5 Hz, 1H), 5.12 (t, J=4.9 Hz, 1H), 3.82 (d, J=14.3 Hz, 1H), 3.72 (s, 3H), 3.45 (d, J=13.6 Hz, 1H), 2.92-2.85 (m, 1H), 2.75-2.70 (m, 1H), 2.34-2.29 (m, 2H), 2.27 (s, 3H); ESI MS m/z=268 [M+H]$^+$; 8-methoxy-2-methyl-5-phenyl-2,3,4,5-tetrahydro-1H-benzo[c]azepine: $^1$H NMR (CDCl$_3$, 500 MHz) δ 7.34 (t, J=7.5 Hz, 2H), 7.26-7.23 (m, 1H), 7.17 (d, J=7.5 Hz, 2H), 6.74 (d, J=2.7 Hz, 1H), 6.61-6.59 (m, 2H), 4.26 (d, J=8.6 Hz, 1H), 3.91-3.90 (m, 1H), 3.76 (s, 3H), 3.70 (d, J=14.1 Hz, 1H), 3.12-3.09 (m, 1H), 2.98-2.93 (m, 1H), 2.35 (s, 3H), 2.32-2.27 (m, 1H), 2.11-2.10 (m, 1H). ESI MS m/z=268 [M+H]$^+$.

Step C: To a solution of 8-methoxy-2-methyl-5-phenyl-2,3,4,5-tetrahydro-1H-benzo[c]azepine from step B (260 mg, 0.97 mmol) in ethanol (4 mL) was added fumaric acid (123 mg, 0.97 mmol) in methanol (2 mL). The solvent was removed under reduced pressure. The residue was triturated with ethyl acetate and diethyl ether. The resulting precipitate was collected by filtration, washed with diethyl ether, and dried at 50° C. under vacuum to provide (+/−)-8-methoxy-2-methyl-5-phenyl-2,3,4,5-tetrahydro-1H-benzo[c]azepine, fumarate salt (250 mg, 67%, >99% AUC HPLC) as an off-white solid: mp 171-173° C.; $^1$H NMR (CD$_3$OD, 500 MHz) δ 7.38 (t, J=7.5 Hz, 2H), 7.29 (t, J=7.4 Hz, 1H), 7.18 (d, J=7.5 Hz, 2H), 7.02 (d, J=2.7 Hz, 1H), 6.86-6.78 (m, 2H), 6.67 (s, 2H), 4.50 (dd, J=8.9, 1.9 Hz, 2H), 4.25 (d, J=13.9 Hz, 1H), 3.80 (s, 3H), 3.52-3.51 (m, 2H), 2.85 (s, 3H), 2.57-2.56 (m, 1H), 2.40-2.36 (m, 1H); ESI MS m/z=268 [C$_{18}$H$_{21}$NO+H]$^+$.

Example 2

Preparation of (+/−)-6-methoxy-2-methyl-5-phenyl-2,3,4,5-tetrahydro-1H-benzo[c]azepine, fumarate salt Step A: To a mixture of (3-methoxybenzyl)methylamine (3.02 g, 20 mmol) and cesium carbonate (7.82 g, 24 mmol) in DMF (50 mL) was added cinnamyl bromide (4.47 g, 22 mmol). The reaction mixture was stirred at room temperature for 15 hours. The reaction mixture was diluted with water and extracted with 1:1 hexanes/ethyl acetate (3×). The combined organic extracts were washed with brine, dried over anhydrous sodium sulfate and concentrated to provide the desired product (3.1 g, 58%): $^1$H NMR (CDCl$_3$, 500 MHz) δ 7.39-7.37 (m, 2H), 7.32-7.29 (m, 2H), 7.23-7.20 (m, 2H), 6.93-6.91 (m, 2H), 6.81-6.78 (m, 1H), 6.54 (d, J=15.9 Hz, 1H), 6.31 (dt, J=15.9, 6.6 Hz, 1H), 3.81 (s, 3H), 3.52 (s, 2H), 3.19 (dd, J=6.6, 1.2 Hz, 2H), 2.25 (s, 3H); ESI MS m/z=268 [M+H]$^+$. This crude product was used in the next step without further purification.

Step B: A mixture of the product from step A (1.0 g, 3.74 mmol) and pyrophosphoric acid (25 g) in 1,2-dichloroethane (5 mL) was heated at 100° C. for 1 hour. The reaction mixture was cooled, mixed with ice and adjusted to pH 9 with ammonium hydroxide. The reaction mixture was extracted with ethyl acetate (3×). The combined extracts were washed with brine, dried over anhydrous sodium sulfate and concentrated. Purification via MPLC (30% to 50% ethyl acetate/hexanes) provided 6-methoxy-2-methyl-5-phenyl-2,3,4,5-tetrahydro-1H-benzo[c]azepine (350 mg, 35%) and 8-methoxy-2-methyl-5-phenyl-2,3,4,5-tetrahydro-1H-benzo[c]azepine (280 mg, 28%): 6-methoxy-2-methyl-5-phenyl-2,3,4,5-tetrahydro-1H-benzo[c]azepine: $^1$H NMR (CDCl$_3$, 300 MHz) δ 7.28-7.21 (m, 2H), 7.19-7.13 (m, 2H), 7.06 (d, J=8.0 Hz, 2H), 6.85 (d, J=8.1 Hz, 1H), 6.80 (d, J=7.5 Hz, 1H), 5.12 (t, J=4.9 Hz, 1H), 3.82 (d, J=14.3 Hz, 1H), 3.72 (s, 3H), 3.45 (d, J=13.6 Hz, 1H), 2.92-2.85 (m, 1H), 2.75-2.70 (m, 1H), 2.34-2.29 (m, 2H), 2.27 (s, 3H); ESI MS m/z=268 [M+H]$^+$; 8-methoxy-2-methyl-5-phenyl-2,3,4,5-tetrahydro-1H-benzo[c]azepine: $^1$H NMR (CDCl$_3$, 500 MHz) δ 7.34 (t, J=7.5 Hz, 2H), 7.26-7.23 (m, 1H), 7.17 (d, J=7.5 Hz, 2H), 6.74 (d, J=2.7 Hz, 1H), 6.61-6.59 (m, 2H), 4.26 (d, J=8.6 Hz, 1H), 3.91-3.90 (m, 1H), 3.76 (s, 3H), 3.70 (d, J=14.1 Hz, 1H), 3.12-3.09 (m, 1H), 2.98-2.93 (m, 1H), 2.35 (s, 3H), 2.32-2.27 (m, 1H), 2.11-2.10 (m, 1H); ESI MS m/z=268 [M+H]$^+$.

Step C: To a solution of 6-methoxy-2-methyl-5-phenyl-2,3,4,5-tetrahydro-1H-benzo[c]azepine from step B (334 mg, 1.25 mmol) in ethanol (5 mL) was added fumaric acid (145 mg, 1.25 mmol) in methanol (3 mL). The solvent was removed under reduced pressure. The residue was triturated with ethyl acetate and diethyl ether. The resulting precipitate was collected by filtration, washed with diethyl ether, and dried at 50° C. under vacuum to provide (+/−)-6-methoxy-2-methyl-5-phenyl-2,3,4,5-tetrahydro-1H-benzo[c]azepine, fumarate salt (250 mg, 67%, 96.6% AUC HPLC) as an off-white solid: mp 154-156° C.; $^1$H NMR (CD$_3$OD, 500 MHz) δ 7.41-7.37 (m, 1H), 7.30 (t, J=7.6 Hz, 2H), 7.23-7.17 (m, 2H), 7.05-7.03 (m, 3H), 6.68 (s, 2H), 5.25-5.24 (m, 1H), 4.29-4.27 (m, 1H), 4.11 (d, J=13.9 Hz, 1H), 3.79 (s, 3H), 3.44-3.39 (m, 1H), 3.33-3.32 (m, 1H), 2.81 (s, 3H), 2.68-2.67 (m, 1H), 2.46-2.41 (m, 1H). ESI MS m/z=268 [C$_{18}$H$_{21}$NO+H]$^+$.

Example 3

Preparation of (+/−)-5-(4-fluorophenyl)-8-methoxy-2-methyl-2,3,4,5-tetrahydro-1H-benzo[c]azepine, hydrochloride salt Step A: A solution of 4-fluorocinnamic acid (2.0 g, 12.0 mmol) and N-methylmorpholine (1.9 mL, 16.9 mmol) in anhydrous methylene chloride (100 mL) was cooled to −20° C. Isobutyl chloroformate (1.7 mL, 12.8 mmol) was added dropwise. After 15 minutes, a solution of (3-methoxybenzyl)methylamine (1.8 g, 12.0 mmol) in anhydrous methylene chloride (20 mL) was added dropwise. The reaction was allowed to warm to room temperature and stir under N$_2$ for 3 hours. The reaction mixture was then washed with 1 M NaH$_2$PO$_4$.2H$_2$O (2×), H$_2$O (2×), and brine, then dried over sodium sulfate, filtered, and concentrated in vacuo. Purification via flash column chromatography (1:1 ethyl acetate/hexanes) yielded the desired amide (2.7 g, 79%) as a white solid: $^1$H NMR (300 MHz, CDCl$_3$) δ 7.72 (dd, J=15.3, 4.5 Hz, 1H), 7.56-7.42 (m, 2H), 7.33-7.23 (m, 1H), 7.10-7.00 (m, 2H), 6.88-6.80 (m, 2H), 6.83 (s, 1H), 6.78 (d, J=15.3 Hz, 1H), 4.70-4.66 (m, 2H), 3.80 (s, 3H), 3.09-3.07 (m, 3H); ESI MS m/z=300 [C$_{18}$H$_{18}$FNO$_2$+H]$^+$.

Step B: An excess of polyphosphoric acid (1.5 g) in 1,2-dichloroethane (10 mL) was heated to 100° C. A solution of the product from Step A (614 mg, 2.1 mmol) in 1,2-dichloroethane (5 mL) was added dropwise. The reaction was then allowed to stir at 100° C. overnight under N$_2$. After cooling to room temperature, the reaction was mixed with ice and the pH adjusted to 10 using 6 N NaOH. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (289 mg) as a yellow oil: $^1$H NMR (300 MHz, CDCl$_3$) δ 7.09-6.94 (m, 2H), 7.03-6.93 (m, 2H), 6.85 (d, J=8.4 Hz, 1H) 6.72 (dd, J=8.7, 2.7 Hz, 1H), 6.67 (d, J=2.7 Hz, 1H), 4.92 (d, J=16.2 Hz, 1H), 4.46 (dd, J=10.8, 5.1 Hz, 1H), 4.19 (d, J=16.5 Hz, 1H), 3.79 (s, 3H), 3.17 (dd, J=13.8, 10.8 Hz, 1H), 3.05 (s, 3H), 2.98 (dd, J=13.8, 5.1 Hz, 1H).

Step C: To a stirred solution of lithium aluminum hydride (1 M solution in THF, 0.61 mL, 0.61 mmol) at 0° C. under $N_2$ was added a solution of the product of Step B (167 mg, 0.56 mmol) in anhydrous THF (5 mL) dropwise via an addition funnel. The reaction mixture was heated to reflux and allowed to stir for 2 hours. The reaction was then cooled back down to 0° C. and quenched slowly with 1 N NaOH (2 mL). After diluting with $H_2O$, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (110 mg, 32% two steps) as a yellow oil: $^1$H NMR (300 MHz, CDCl$_3$) δ 7.15-7.11 (m, 2H), 7.06-7.00 (m, 2H), 6.75 (d, J=2.7 Hz, 1H), 6.61 (dd, J=8.4, 2.7 Hz, 1H), 6.57-6.50 (m, 1H), 4.24 (d, J=9.3 Hz, 1H), 3.92-3.82 (m, 1 H), 3.77 (s, 3H), 3.67 (d, J=14.1 Hz, 1H), 3.14-3.06 (m, 1H), 2.95 (ddd, J=12.6, 9.6, 2.7 Hz, 1H), 2.35 (s, 3H), 2.29-2.20 (m, 1H), 2.12-2.02 (m, 1H).

Step D: The product of Step C (110 mg, 0.39 mmol) was converted to its hydrochloride salt by dissolving the oil in a minimum amount of ether, adding one equivalent of HCl (1 M solution in ether), and sonicating the solution for a few minutes until salt precipitation occurred. Filtration yielded (+/−)-5-(4-fluorophenyl)-8-methoxy-2-methyl-2,3,4,5-tetrahydro-1H-benzo[c]azepine, hydrochloride salt (91 mg, 73%, >99% AUC HPLC) as a white solid: mp 149-150° C. 149-150° C.; ESI MS m/z=286 $[C_{18}H_{20}FNO+H]^+$.

Example 4

Preparation of (+)-5-(4-fluorophenyl)-8-methoxy-2-methyl-2,3,4,5-tetrahydro-1H-benzo[c]azepine, hydrochloride salt, and (−)-5-(4-fluorophenyl)-8-methoxy-2-methyl-2,3,4,5-tetrahydro-1H-benzo[c]azepine, hydrochloride salt Pursuant to the general method described above in Example 3, the following products were prepared: (+)-5-(4-fluorophenyl)-8-methoxy-2-methyl-2,3,4,5-tetrahydro-1H-benzo[c]azepine, hydrochloride salt: mp 246-248° C.; ESI MS m/z=286 $[C_{18}H_{20}FNO+H]^+$; (−)-5-(4-fluorophenyl)-8-methoxy-2-methyl-2,3,4,5-tetrahydro-1H-benzo[c]azepine, hydrochloride salt: mp 246-248° C.; ESI MS m/z=286 $[C_{18}H_{20}FNO+H]^+$.

Example 5

Preparation of (+/−)-5-(4-methoxyphenyl)-8-methoxy-2-methyl-2,3,4,5-tetrahydro-1H-benzo[c]azepine, hydrochloride salt Pursuant to the general method described above in Example 3, the following product was prepared: (+/−)-5-(4-methoxyphenyl)-8-methoxy-2-methyl-2,3,4,5-tetrahydro-1H-benzo[c]azepine, hydrochloride salt: mp 165-166° C.; ESI MS m/z=298 $[C_{19}H_{23}NO_2+H]^+$.

Example 6

Preparation of (+)-5-(4-methoxyphenyl)-8-methoxy-2-methyl-2,3,4,5-tetrahydro-1H-benzo[c]azepine, hydrochloride salt and (−)-5-(4-methoxyphenyl)-8-methoxy-2-methyl-2,3,4,5-tetrahydro-1H-benzo[c]azepine, hydrochloride salt Pursuant to the general method described above in Example 3, the following products were prepared: (+)-5-(4-methoxyphenyl)-8-methoxy-2-methyl-2,3,4,5-tetrahydro-1H-benzo[c]azepine, hydrochloride salt: mp 193-194° C.; ESI MS m/z=298 $[C_{19}H_{23}NO_2+H]^+$; (−)-5-(4-methoxyphenyl)-8-methoxy-2-methyl-2,3,4,5-tetrahydro-1H-benzo[c]azepine, hydrochloride salt: mp 193-194° C.; ESI MS m/z=298 $[C_{19}H_{23}NO_2+H]^+$.

Example 7

Preparation of (+/−)-5-(4-chlorophenyl)-8-methoxy-2-methyl-2,3,4,5-tetrahydro-1H-benzo[c]azepine, hydrochloride salt Pursuant to the general method described above in Example 3, the following product was prepared: (+/−)-5-(4-chlorophenyl)-8-methoxy-2-methyl-2,3,4,5-tetrahydro-1H-benzo[c]azepine, hydrochloride salt: mp=152-153° C.; ESI MS m/z 302 $[C_{18}H_{20}ClNO+H]^+$.

Example 8

Preparation of (+)-5-(4-chlorophenyl)-8-methoxy-2-methyl-2,3,4,5-tetrahydro-1H-benzo[c]azepine, hydrochloride salt, and (−)-5-(4-chlorophenyl)-8-methoxy-2-methyl-2,3,4,5-tetrahydro-1H-benzo[c]azepine, hydrochloride salt Pursuant to the general method described above in Example 3, the following products were prepared: (+)-5-(4-chlorophenyl)-8-methoxy-2-methyl-2,3,4,5-tetrahydro-1H-benzo[c]azepine, hydrochloride salt: mp 210-211° C.; ESI MS m/z=302 $[C_{18}H_{20}ClNO+H]^+$; (−)-5-(4-chlorophenyl)-8-methoxy-2-methyl-2,3,4,5-tetrahydro-1H-benzo[c]azepine, hydrochloride salt: mp 210-211° C.; ESI MS m/z=302 $[C_{18}H_{20}ClNO+H]^+$.

Example 9

(+/−)-5-(3,4-difluorophenyl)-8-methoxy-2-methyl-2,3,4,5-tetrahydro-1H-benzo[e]azepine, hydrochloride salt Pursuant to the general method described above in Example 3, the following product was prepared: (+/−)-5-(3,4-difluorophenyl)-8-methoxy-2-methyl-2,3,4,5-tetrahydro-1H-benzo[c]azepine, hydrochloride salt: mp 139-141° C.; ESI MS m/z=304 $[C_{18}H_{19}F_2NO+H]^+$.

Example 10

Preparation of (+/−)-5-(2-chlorophenyl)-8-methoxy-2-methyl-2,3,4,5-tetrahydro-1H-benzo[c]azepine, hydrochloride salt Pursuant to the general method described above in Example 3, the following product was prepared: (+/−)-5-(2-chlorophenyl)-8-methoxy-2-methyl-2,3,4,5-tetrahydro-1H-benzo[c]azepine, hydrochloride salt: mp 129-132° C.; ESI MS m/z=302 $[C_{18}H_{20}ClNO+H]^+$.

Example 11

Preparation of (+/−)-5-(3-chloro-4-fluorophenyl)-8-methoxy-2-methyl-2,3,4,5-tetrahydro-1H-benzo[c]azepine, hydrochloride salt Pursuant to the general method described above in Example 3, the following product was prepared: (+/−)-5-(3- chloro-4-fluorophenyl)-8-methoxy-2-methyl-2,3,4,5-tetrahydro-1H-benzo[c]azepine, hydrochloride salt: mp 167-169° C.; ESI MS m/z=320 [C$_{18}$H$_{19}$ClFNO+H]$^+$.

Example 12

Preparation of (+)-8-methoxy-2-methyl-5-phenyl-2,3,4,5-tetrahydro-1H-benzo[c]azepine, hydrochloride salt, and (−)-8-methoxy-2-methyl-5-phenyl-2,3,4,5-tetrahydro-1H-benzo[c]azepine, hydrochloride salt Pursuant to the general method described above in Example 3, the following products were prepared: (+)-8-methoxy-2-methyl-5-phenyl-2,3,4,5-tetrahydro-1H-benzo[c]azepine, hydrochloride salt: ESI MS m/z 268 [M+H]$^+$; (−)-8-methoxy-2-methyl-5-phenyl-2,3,4,5-tetrahydro-1H-benzo[c]azepine, hydrochloride salt: ESI MS m/z 268 [M+H]$^+$.

Example 13

Preparation of (+)-5-(4-fluorophenyl)-2-methyl-2,3,4,5-tetrahydro-1H-benzo[c]azepin-8-ol, hydrochloride salt Step A: A mixture of (+)-5-(4-fluorophenyl)-8-methoxy-2-methyl-2,3,4,5-tetrahydro-1H-benzo[c]azepine (367 mg, 1.3 mmol) and HBr (48% solution in H$_2$O, 10 mL) was heated to reflux and allowed to stir for two hours. The solvent and excess HBr were removed under reduced pressure and the resulting solid was partitioned between ethyl acetate and saturated NaHCO$_3$ (aq). After separating the two layers, the aqueous phase was extracted with ethyl acetate (3×). The combined extracts were dried over sodium sulfate, filtered, and concentrated in vacuo to provide the desired phenol (347 mg, 99%) as a tan solid: [α]$^{25}_D$ −9.1° (c 0.3, methanol); $^1$H NMR (500 MHz, CDCl$_3$) δ 7.13-7.10 (m, 2H), 7.04-7.01 (m, 2H), 6.60 (d, J=2.5 Hz, 1H), 6.50-6.49 (m, 1H), 6.43 (br s, 1H), 4.21 (d, J=9.5 Hz, 1H), 3.86-3.78 (m, 1H), 3.63 (d, J=14.0 Hz, 1H), 3.13-3.06 (m, 1H), 2.91 (ddd, J=12.8, 10.0, 2.5 Hz, 1H), 2.40 (s, 3H), 2.32-2.25 (m, 1H), 2.13-2.06 (m, 1H); ESI MS m/z=272 [C$_{17}$H$_{18}$FNO+H]$^+$.

Step B: The product of Step A (25 mg, 0.09 mmol) was converted to its hydrochloride salt by dissolving the oil in a minimum amount of ether, adding one equivalent of HCl (1 M solution in ether), and sonicating the solution for a few minutes until salt precipitation occurred. Filtration yielded (+)-5-(4-fluorophenyl)-2-methyl-2,3,4,5-tetrahydro-1H-benzo[c]azepin-8-ol, hydrochloride salt (21 mg, 74%, 96.6% AUC HPLC) as an off-white solid: mp 159-161° C.; ESI MS m/z=272 [C$_{17}$H$_{18}$FNO+H]$^+$.

Example 14

Preparation of (−)-5-(4-fluorophenyl)-2-methyl-2,3,4,5-tetrahydro-1H-benzo[c]azepin-8-ol, hydrochloride salt Pursuant to the general method described above in Example 13, the following product was prepared: (−)-5-(4-fluorophenyl)-2-methyl-2,3,4,5-tetrahydro-1H-benzo[c]azepin-8-ol, hydrochloride salt: mp 159-161° C.; ESI MS m/z=272 [C$_{17}$H$_{18}$FNO+H]$^+$.

Example 15

Preparation of (−)-5-(4-fluorophenyl)-2,8-dimethyl-2,3,4,5-tetrahydro-1H-benzo[c]azepine, hydrochloride salt Step A: To a stirred mixture of (−)-5-(4-fluorophenyl)-2-methyl-2,3,4,5-tetrahydro-1H-benzo[c]azepin-8-ol (252 mg, 0.93 mmol) and pyridine (90 μL, 1.1 mmol) in anhydrous CH$_2$Cl$_2$ (9.3 mL) at 0° C. under N$_2$ was added triflic anhydride (0.19 mL, 1.1 mmol). Stirring was continued at 0° C. for one hour at which time TLC analysis indicated that the reaction had gone to completion. The mixture was then diluted with CH$_2$Cl$_2$, washed with saturated NaHCO$_3$ (aq) and brine, dried over sodium sulfate, filtered, and concentrated in vacuo. Purification via flash column chromatography (1:1 ethyl acetate/hexanes) provided the desired triflate (259 mg, 69%) as a yellow oil: ESI MS m/z=404 [C$_{18}$H$_{17}$F$_4$NO$_3$S+H]$^+$.

Step B: To a stirred mixture of the product of Step A (125 mg, 0.31 mmol) and PdCl$_2$(dppf).CH$_2$Cl$_2$ (2.5 mg, 0.0031 mmol) in anhydrous dioxane (1.8 mL) was added Zn(CH$_3$)$_2$ (2 M solution in toluene, 0.3 mL, 0.62 mmol) dropwise under N$_2$. The reaction was heated to reflux and allowed to stir for two hours. The reaction was then quenched methanol (a few drops), diluted with ethyl acetate, and washed with H$_2$O and brine. The organic phase was dried over sodium sulfate, filtered, and concentrated in vacuo. Purification via flash column chromatography (1:1 ethyl acetate/hexanes) yielded the desired product (85 mg, quantitative yield) as a yellow solid: [α]$^{25}_D$ −6.1° (c 0.3, methanol); $^1$H NMR (500 MHz, CDCl$_3$) δ 7.12 (dd, J=8.0, 5.5 Hz, 2H), 7.05-7.01 (m, 2H), 6.99 (d, J=1.5 Hz, 1H), 6.89 (d, J=8.0 Hz, 1H), 6.51 (br s, 1H), 4.26 (d, J=9.5 Hz, 1H), 3.91-3.83 (m, 1H), 3.68 (d, J=14.5 Hz, 1H), 3.13-3.06 (m, 1H), 2.93 (ddd, J=12.8, 9.5, 2.5 Hz, 1H), 2.34 (s, 3H), 2.28 (s, 3H), 2.24 (dd, J=9.5, 3.0 Hz, 1H), 2.10-2.06 (m, 1H); ESI MS m/z=270 [C$_{18}$H$_{20}$FN+H]$^+$.

Step C: The product of Step B (85 mg, 0.32 mmol) was converted to its hydrochloride salt by dissolving the oil in a minimum amount of ether, adding one equivalent of HCl (1 M solution in ether), and sonicating the solution for a few minutes until salt precipitation occurred. Filtration yielded (−)-5-(4-fluorophenyl)-2,8-dimethyl-2,3,4,5-tetrahydro-1H-benzo[c]azepine, hydrochloride salt (79 mg, 82%, 95.3% AUC HPLC) as an off-white solid: mp 243-244° C.; ESI MS m/z=270 [C$_{18}$H$_{20}$FN+H]$^+$.

Example 16

Preparation of (+)-5-(4-fluorophenyl)-2,8-dimethyl-2,3,4,5-tetrahydro-1H-benzo[c]azepine, hydrochloride salt Pursuant to the general method described above in Example 15, the following product was prepared: (+)-5-(4-fluorophenyl)-2,8-dimethyl-2,3,4,5-tetrahydro-1H-benzo[c]azepine, hydrochloride salt: mp 243-244° C.; ESI MS m/z=270 [C$_{18}$H$_{20}$FN+H]$^+$.

Example 17

Preparation of (+)-2-methyl-5-phenyl-2,3,4,5-tetrahydro-1H-benzo[c]azepine-8-carbonitrile, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol)

as a solution in methanol (50 mL) dropwise over 20 minutes. The reaction was stirred at room temperature under $N_2$ for 15 h, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under $N_2$ for 3 h. The mixture was washed with 1M sodium dihydrogen phosphate dihydrate (2×), $H_2O$ (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 hours under $N_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under $N_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate (aq). After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under $N_2$ was added triflic anhydride (0.46 mL, 2.8 mmol). The reaction was stirred at 0° C. for 1 h, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (249 mg, 0.65 mmol) in DMF (3 mL) at room temperature was added zinc cyanide (152 mg, 1.3 mmol). The reaction mixture was degassed with argon for 2 minutes, then tris(dibenzylideneacetone)-dipalladium(0) (24 mg, 0.026 mmol) and 1,1'-bis(diphenylphosphino)ferrocene (57 mg, 0.10 mmol) were added under argon. The reaction was heated to 130° C. and stirred for 4 hours. After cooling to room temperature, the mixture was diluted with ethyl acetate and washed with saturated sodium bicarbonate. The aqueous phase was extracted with additional ethyl acetate (2×), then the combined extracts were washed with brine, dried over sodium sulfate, filtered, and concentrated in vacuo. Purification by flash column chromatography (2%-10% methanol/methylene chloride) followed by charcoal treatment yielded the desired nitrile (75 mg, 44%) as a light yellow oil: [α]$^{23}_D$−4.00° (c 0.08, methanol);

$^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: To a stirred solution of the nitrile from Step G above (72 mg, 0.27 mmol) in methanol (2.5 mL) at room temperature was added maleic acid (32 mg, 0.27 mmol). The mixture was stirred at room temperature for 1 h and then the solvent was concentrated to approximately 0.5 mL. After diluting with $H_2O$ (2 mL), the mixture was lyophilized for 15 h to provide (+)-2-methyl-5-phenyl-2,3,4,5-tetrahydro-1H-benzo[c]azepine-8-carbonitrile, maleate salt (110 mg, 99%, 99.0% AUC HPLC) as an off-white solid: mp 67-69° C.; $^1$H NMR (500 MHz, $CD_3OD$) δ 7.86 (m, 1H), 7.70-7.69 (m, 1H), 7.45-7.42 (m, 2H), 7.36-7.34 (m, 1H), 7.23-7.21 (m, 2H), 7.06-6.88 (br, 1H), 6.25 (s, 2H), 4.71-4.69 (m, 2H), 4.44-4.42 (m, 1H), 3.66-3.62 (m, 2H), 3.00-2.92 (br, 3H), 2.64-2.53 (br, 1H), 2.46-2.43 (m, 1H); ESI MS m/z 263 $[M+H]^+$.

Example 18

Preparation of (+)-2-(2-methyl-5-phenyl-2,3,4,5-tetrahydro-1H-benzo[c]azepin-8-yl)propan-2-ol, L-tartrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR ($CDCl_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, $CDCl_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, $CDCl_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, $CDCl_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR ($CDCl_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6N HCl (100 mL) and the mixture was heated under reflux for 2 hours. Additional volumes of 1,4-dioxane (60 mL) and 6N HCl (30 mL) were added to the reaction mixture, which was heated under reflux for 1 hour. The mixture was cooled to room temperature and then in an ice-bath, and a solution of 2N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR ($CDCl_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer $[[\alpha]^{25}_D+3.66°$ (c 0.41, methanol)] and (−)-enantiomer $[[\alpha]^{25}_D-1.16°$ (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 h. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step I: To a stirred mixture of the phenol from Step H above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 h, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a stirred solution of the triflate from Step I above (516 mg, 1.3 mmol) in anhydrous DMF (6.5 mL) was added lithium chloride (170 mg, 4.0 mmol). The mixture was degassed with argon for 2 minutes, then dichlorobis(triphenylphosphine)palladium(II) (47 mg, 0.067 mmol) was added. After degassing briefly with argon again, tributyl(1-ethoxyvinyl)tin (0.54 mL, 1.6 mmol) was added and the mixture was degassed briefly with argon one more time. The reaction was heated to 90° C. and stirred for 3.5 hours, at which time TLC and ESI MS analyses both indicated complete consumption of the starting material and formation of the desired intermediate. The solvent was removed in vacuo and the crude material was purified by flash column chromatography (50%-100% ethyl acetate/hexanes) to provide the desired intermediate as a yellow oil. The oil was stirred in 1N HCl (20 mL) at room temperature for 1 hour, solid potassium carbonate was added to adjust the pH to 9, and then the solution was extracted with ethyl acetate (3×). The combined extracts were washed with water and brine, dried over sodium sulfate, filtered, and concentrated in vacuo to provide the desired methyl ketone (354 mg, 95%) as a yellow oil: $^1$H NMR (500 MHz, CDCl$_3$) δ 7.78 (s, 1H), 7.67-7.65 (m, 1H), 7.37 (t, J=7.5 Hz, 2H), 7.30-7.29 (m, 1H), 7.17 (d, J=7.5 Hz, 2H), 6.78-6.70 (br, 1H), 4.38-4.36 (m, 1H), 4.01-3.95 (m, 1H), 3.82-3.79 (m, 1H), 3.17-3.11 (m, 1H), 3.00-2.95 (m, 1H), 2.56 (s, 3H), 2.37 (s, 3H), 2.37-2.30 (m, 1H), 2.17-2.11 (m, 1H).

Step K: To a stirred solution of the methyl ketone from Step J above (121 mg, 0.43 mmol) in anhydrous THF (4 mL) at −78° C. under N$_2$ was added methylmagnesium iodide (3M solution in diethyl ether, 0.17 mL, 0.52 mmol) dropwise. The reaction was stirred at −78° C. for 15 minutes, then warmed to 0° C. and stirred for 3 hours. ESI MS indicated the presence of remaining starting material so additional methylmagnesium iodide solution (0.05 mL) was added and the reaction was stirred at 0° C. for an additional 2 hours. The reaction was quenched with aqueous saturated ammonium chloride solution, then extracted with methylene chloride (3×). The combined extracts were washed with water and brine, dried over sodium sulfate, filtered, and concentrated in vacuo. Purification by flash column chromatography (9.4:0.5:0.1 methylene chloride/methanol/concentrated ammonium hydroxide) yielded the desired alcohol (40 mg, 31%) as a colorless oil: [α]$^{23}_D$ −3.16° (c 0.10, methanol); $^1$H NMR (500 MHz, CDCl$_3$) δ 7.36 (t, J=7.5 Hz, 2H), 7.32-7.31 (m, 1H), 7.28-7.25 (m, 1H), 7.18 (d, J=7.5 Hz, 2H), 7.17-7.15 (m, 1H), 6.62-6.55 (br, 1H), 4.31-4.29 (m, 1H), 3.93-3.88 (m, 1H), 3.74-3.71 (m, 1H), 3.15-3.09 (m, 1H), 2.95-2.89 (m, 1H), 2.38 (s, 3H), 2.36-2.29 (m, 1H), 2.14-2.09 (m, 1H), 1.55 (s, 6H); ESI MS m/z 296 [M+H]$^+$.

Step L: To a stirred solution of the alcohol from Step K above (33 mg, 0.11 mmol) in methanol (3 mL) at room temperature was added L-tartaric acid (17 mg, 0.11 mmol). The mixture was stirred at room temperature for 1 hour and then the solvent was concentrated to approximately 0.5 mL. After diluting with water (2 mL), the mixture was lyophilized for 15 hours to provide (+)-2-(2-methyl-5-phenyl-2,3,4,5-tetrahydro-1H-benzo[c]azepin-8-yl)propan-2-ol, L-tartrate salt (53 mg, 99%, 98.9% AUC HPLC) as a white powder: mp 103-105° C.; $^1$H NMR (500 MHz, CD$_3$OD) δ 7.56 (s, 1H), 7.42-7.37 (m, 1H), 7.39 (t, J=7.5 Hz, 2H), 7.30 (t, J=7.5 Hz, 1H), 7.19 (d, J=7.5 Hz, 2H), 6.88-6.76 (br, 1H), 4.63-4.52 (m, 1H), 4.56-4.55 (m, 1H), 4.39 (s, 2H), 4.32-4.30 (m, 1H), 3.57-3.51 (m, 2H), 2.85 (s, 3H), 2.62-2.53 (m, 1H), 2.42-2.37 (m, 1H), 1.53 (s, 6H); ESI MS m/z 296 [M+H]$^+$.

Example 19

Preparation of (+)-(2-methyl-5-phenyl-2,3,4,5-tetrahydro-1H-benzo[c]azepin-8-yl)(morpholino)methanone, L-tartrate salt Step A: To a stirred solution of methylamine (40% in water) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 h, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 hours under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under N$_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (2.60 g, 6.8 mmol) in anhydrous DMF (30 mL) at room temperature was added zinc cyanide (1.58 g, 13.5 mmol). The reaction mixture was degassed with argon for 5 minutes, then 1,1'-bis(diphenylphosphino)ferrocene (599 mg, 1.1 mmol) and tris(dibenzylideneacetone)dipalladium(0) (247 mg, 0.27 mmol) were added under argon. The reaction was heated to 130° C. and stirred for 4 hours, at which time ESI MS indicated the reaction went to completion. After cooling to room temperature, the mixture was diluted with ethyl acetate and washed with saturated sodium bicarbonate. The aqueous phase was extracted with additional ethyl acetate (3×), then the combined extracts were washed with brine, dried over sodium sulfate, filtered, and concentrated in vacuo. Purification by flash column chromatography (2.5%-10% methanol/methylene chloride) yielded the desired nitrile (1.1 g, 60%) as a dark brown oil: $^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: A mixture of the nitrile from Step G above (290 mg, 1.1 mmol) and an excess of concentrated hydrochloric acid (3.5 mL) was stirred at 100° C. for 15 hours, at which time ESI MS indicated the reaction went to completion. The water and excess hydrochloric acid were removed in vacuo to provide the desired carboxylic acid as a dark brown solid which was used in the next step without further purification: ESI MS m/z 282 [M+H]$^+$.

Step I: To a stirred solution of the carboxylic acid from Step H above (353 mg, 1.1 mmol, theoretical) in methylene chloride (10 mL) at 0° C. were added triethylamine (0.19 mL, 1.3 mmol), morpholine (0.11 mL, 1.2 mmol), and 4-dimethylaminopyridine (14 mg, 0.11 mmol). After stirring at 0° C. for 10 minutes, N-(3-dimethylaminopropyl)-N'-ethylcarbodiimide hydrochloride (234 mg, 1.2 mmol) was added, then the reaction was warmed to room temperature and stirred for approximately 2 days. The reaction mixture was partitioned between ethyl acetate and saturated sodium bicarbonate. After separating the layers, the aqueous phase was extracted with additional ethyl acetate (3×) and the combined extracts were washed with brine, dried over sodium sulfate, filtered, and concentrated in vacuo. Purification by flash column chromatography (2.5%-10% methanol/methylene chloride) yielded the desired amide (171 mg, 44% for two steps) as a yellow oil: [α]$^{23}_D$−4.62° (c 0.065, methanol); $^1$H NMR (500 MHz, CDCl$_3$) δ 7.37 (t, J=7.5 Hz, 2H), 7.29 (d, J=7.0 Hz, 1H), 7.26-7.25 (m, 1H), 7.16 (d, J=7.5 Hz, 2H), 7.10 (d, J=8.0 Hz, 1H), 6.73-6.65 (br, 1H), 4.35-4.33 (m, 1H), 3.96-3.88 (m, 1H), 3.82-3.39 (br, 8H), 3.75-3.72 (m, 1H), 3.16-3.10 (m, 1H), 2.98-2.94 (m, 1H), 2.38 (s, 3H), 2.38-2.31 (m, 1H), 2.18-2.11 (m, 1H); ESI MS m/z 351 [M+H]$^+$.

Step J: To a stirred solution of the amide from Step I above (164 mg, 0.47 mmol) in methanol (4 mL) at room temperature was added L-tartaric acid (70 mg, 0.47 mmol). The mixture was stirred at room temperature for 1 hour and then the solvent was concentrated to approximately 0.5 mL. After diluting with water (2 mL), the mixture was lyophilized for 15 hours to provide (+)-(2-methyl-5-phenyl-2,3,4,5-tetrahydro-1H-benzo[c]azepin-8-yl)(morpholino)methanone, L-tartrate salt (220 mg, 94%, 97.4% AUC HPLC) as a light brown powder: $^1$H NMR (500 MHz, CD$_3$OD) δ 7.51-7.50 (m, 1H), 7.41 (t, J=7.5 Hz, 2H), 7.35 (d, J=8.0 Hz, 1H), 7.32 (t, J=7.5 Hz, 1H), 7.22 (d, J=7.5 Hz, 2H), 6.95-6.86 (br, 1H), 4.63-4.62 (m, 2H), 4.39 (s, 2H), 4.36-4.33 (m, 1H), 3.79-3.67 (br, 4H), 3.75-3.54 (br, 2H), 3.59-3.52 (m, 2H), 3.52-3.38 (m, 2H), 2.85 (s, 3H), 2.63-2.54 (m, 1H), 2.43-2.38 (m, 1H); ESI MS m/z 351 [M+H]$^+$.

Example 20

Preparation of (+)-(2-methyl-5-phenyl-2,3,4,5-tetrahydro-1H-benzo[c]azepin-8-yl)methanamine, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 h, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 h under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under N$_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.2144.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (2.60 g, 6.8 mmol) in anhydrous DMF (30 mL) at room temperature was added zinc cyanide (1.58 g, 13.5 mmol). The reaction mixture was degassed with argon for 5 minutes, then 1,1'-bis(diphenylphosphino)ferrocene (599 mg, 1.1 mmol) and tris(dibenzylideneacetone)dipalladium(0) (247 mg, 0.27 mmol) were added under argon. The reaction was heated to 130° C. and stirred for 4 hours, at which time ESI MS indicated the reaction went to completion. After cooling to room temperature, the mixture was diluted with ethyl acetate and washed with saturated sodium bicarbonate. The aqueous phase was extracted with additional ethyl acetate (3×), then the combined extracts were washed with brine, dried over sodium sulfate, filtered, and concentrated in vacuo. Purification by flash column chromatography (2.5%-10% methanol/methylene chloride) yielded the desired nitrile (1.1 g, 60%) as a dark brown oil: $^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: To a stirred solution of the nitrile from Step G above (154 mg, 0.59 mmol) in anhydrous THF (7 mL) was added lithium aluminum hydride (1M in THF, 1.8 mL) at 0° C. under N$_2$. The reaction was allowed to warm to room temperature and stirred for approximately 2 days. ESI MS indicated the reaction went to completion, so the mixture was poured slowly over ice water, then extracted with methylene chloride (3×). The combined extracts were washed with brine, dried over sodium sulfate, filtered, and concentrated in vacuo. Purification by flash column chromatography (9.5:0.45:0.05 methylene chloride/methanol/concentrated ammonium hydroxide) yielded the desired amine (99 mg, 63%) as a light brown oil: [α]$^{23}_D$+2.22° (c 0.050, methanol); $^1$H NMR (500 MHz, CDCl$_3$) δ 7.37-7.34 (m, 2H), 7.28-7.25 (m, 1H), 7.18 (d, J=7.5 Hz, 2H), 7.14-7.13 (m, 1H), 7.01 (d, J=7.5 Hz, 1H), 6.65-6.57 (br, 1H), 4.32-4.30 (m, 1H), 3.95-3.89 (m, 1H), 3.81 (s, 2H), 3.75-3.72 (m, 1H), 3.15-3.09 (m, 1H), 2.97-2.92 (m, 1H), 2.36 (s, 3H), 2.36-2.29 (m, 1H), 2.16-2.10 (m, 1H); ESI MS m/z 267 [M+H]$^+$.

Step I: To a stirred solution of the amine from Step H above (28 mg, 0.11 mmol) in methanol (3 mL) at room temperature was added maleic acid (12 mg, 0.11 mmol). The mixture was stirred at room temperature for 1 hour and then the solvent was concentrated to approximately 0.5 mL. After diluting with water (2 mL), the mixture was lyophilized for 15 h to provide (+)-(2-methyl-5-phenyl-2,3,4,5-tetrahydro-1H-benzo[c]azepin-8-yl)methanamine, maleate salt (39 mg, 97%, 97.6% AUC HPLC) as a light brown powder: $^1$H NMR (500 MHz, CD$_3$OD) δ 7.36 (t, J=7.5 Hz, 2H), 7.35-7.34 (m, 1H), 7.28 (t, J=7.5 Hz, 1H), 7.23 (t, J=7.5 Hz, 1H), 7.17 (d, J=7.5 Hz, 2H), 6.84-6.73 (br, 1H), 6.24 (s, 2H), 4.47-4.46 (m, 1H), 4.18-4.06 (m, 1H), 4.07 (s, 2H), 3.91-3.88 (m, 1H), 3.26-3.19 (m, 1H), 3.17-3.11 (m, 1H), 2.49 (s, 3H), 2.46-2.39 (m, 1H), 2.26-2.19 (m, 1H); ESI MS m/z 267 [M+H]$^+$.

Example 21

Preparation of (+)-1-(2-methyl-5-phenyl-2,3,4,5-tetrahydro-1H-benzo[c]azepin-8-yl)cyclopropanamine, maleate salt Step A: To a stirred solution of methylamine (40% in water) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 hours, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 h under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H), 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under N$_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 h, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (2.60 g, 6.8 mmol) in anhydrous DMF (30 mL) at room temperature was added zinc cyanide (1.58 g, 13.5 mmol). The reaction mixture was degassed with argon for 5 minutes, then 1,1'-bis(diphenylphosphino)ferrocene (599 mg, 1.1 mmol) and tris(dibenzylideneacetone)dipalladium(0) (247 mg, 0.27 mmol) were added under argon. The reaction was heated to 130° C. and stirred for 4 hours, at which time ESI MS indicated the reaction went to completion. After cooling to room temperature, the mixture was diluted with ethyl acetate and washed with saturated sodium bicarbonate. The aqueous phase was extracted with additional ethyl acetate (3×), then the combined extracts were washed with brine, dried over sodium sulfate, filtered, and concentrated in vacuo. Purification by flash column chromatography (2.5%-10% methanol/methylene chloride) yielded the desired nitrile (1.1 g, 60%) as a dark brown oil: $^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: To a stirred solution of the nitrile from Step G above (143 mg, 0.55 mmol) in anhydrous THF (3 mL) were added titanium(IV) isopropoxide (0.18 mL, 0.60 mmol) and ethylmagnesium bromide (3M in diethyl ether, 0.40 mL, 1.2 mmol) at −78° C. The reaction was stirred for 10 minutes at −78° C. and then warmed to room temperature over 1 hour. Boron trifluoride-diethyl etherate (0.14 mL, 1.1 mmol) was added slowly and the reaction was stirred at room temperature for 1 hour. 1N HCl (1.5 mL) and THF (8 mL) were added, then the mixture was basified using 1N NaOH (6 mL). After extracting the mixture with ethyl acetate (3×), the combined extracts were dried over sodium sulfate, filtered, and concentrated in vacuo. Purification by flash column chromatography (9.5:0.45:0.05 methylene chloride/methanol/concentrated ammonium hydroxide) yielded the desired cyclopropylamine (22 mg, 14%) as a light brown oil: [α]$^{23}_D$+6.67° (c 0.030, methanol); $^1$H NMR (500 MHz, CDCl$_3$) δ 7.35 (t, J=7.5 Hz, 2H), 7.27-7.25 (m, 1H), 7.18 (d, J=7.5 Hz, 2H), 7.12-7.11 (m, 1H), 7.00-6.98 (m, 1H), 6.59-6.53 (br, 1H), 4.30-4.28 (m, 1H), 3.92-3.85 (m, 1H), 3.72-3.69 (m, 1H), 3.14-3.08 (m, 1H), 2.95-2.90 (m, 1H), 2.37 (s, 3H), 2.35-2.28 (m, 1H), 2.15-2.08 (m, 1H), 1.03-1.01 (m, 2H), 0.94-0.92 (m, 2H); ESI MS m/z 293 [M+H]$^+$.

Step I: To a stirred solution of the cyclopropylamine from Step H above (19 mg, 0.065 mmol) in methanol (3 mL) at room temperature was added maleic acid (7.5 mg, 0.065 mmol). The mixture was stirred at room temperature for 1 hour and then the solvent was concentrated to approximately 0.5 mL. After diluting with water (2 mL), the mixture was lyophilized for 15 hours to provide (+)-1-(2-methyl-5-phenyl-2,3,4,5-tetrahydro-1H-benzo[c]azepin-8-yl)cyclopropanamine, maleate salt (25 mg, 94%, 93.0% AUC HPLC) as a light brown powder: $^1$H NMR (500 MHz, CD$_3$OD) δ 7.39-7.36 (m, 3H), 7.30-7.28 (m, 2H), 7.18-7.17 (m, 2H), 6.86-6.75 (br, 1H), 6.24 (s, 2H), 4.52-4.50 (m, 1H), 4.37-4.29 (m, 1H), 4.09-4.07 (m, 1H), 3.45-3.38 (m, 2H), 2.67 (s, 3H), 2.53-2.43 (m, 1H), 2.33-2.26 (m, 1H), 1.28-1.25 (m, 2H), 1.21-1.18 (m, 2H); ESI MS m/z 293 [M+H]$^+$.

Example 22

Preparation of (+)-4-((2-methyl-5-phenyl-2,3,4,5-tetrahydro-1H-benzo[c]azepin-8-yl)methyl)morpholine, L-tartrate salt Step A: To a stirred solution of methylamine (40% in water) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 hours, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1 N HCl (3×) and the combined HCl extracts adjusted to pH 10 by addition of 6 N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A (5.1 g, 33.8 mmol) in anhydrous methylene chloride (30 mL) was added dropwise, then the reaction was allowed to warm to room temperature and stir under N$_2$ for 3 hours. The mixture was washed with 1 M sodium dihydrogen phosphate dihydrate (2×), H$_2$O (2×), and brine, dried over sodium sulfate, filtered, and concentrated in vacuo. Purification via flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B (3.8 g, 13.5 mmol) in 1,2-dichloroethane (15 mL) was added dropwise and the reaction was stirred at 100° C. for 15 hours under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1 M solution in THF, 14.7 mL, 14.7 mmol) at 0° C. under N$_2$ was added a solution of the product of Step C (3.8 g, 13.4 mmol) in anhydrous THF (100 mL) dropwise. The reaction mixture was heated to reflux and stirred for 2 hours. The reaction was then cooled back down to 0° C. and quenched slowly with 1 N NaOH (30 mL). After diluting with water, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/triethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D (1.19 g, 4.5 mmol) and hydrobromic acid (48% solution in H$_2$O, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid.: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.2144.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification via flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F (2.60 g, 6.8 mmol) in anhydrous DMF (30 mL) at room temperature was added zinc cyanide (1.58 g, 13.5 mmol). The reaction mixture was degassed with argon for 5 minutes, then 1,1'-bis(diphenylphosphino)-ferrocene (599 mg, 1.1 mmol) and tris(dibenzylideneacetone)dipalladium(0) (247 mg, 0.27 mmol) were added under argon. The reaction was heated to 130° C. and stirred for 4 hours, at which time ESI MS indicated the reaction went to completion. After cooling to room temperature, the mixture was diluted with ethyl acetate and washed with saturated sodium bicarbonate. The aqueous phase was extracted with additional ethyl acetate (3×), then the combined extracts were washed with brine, dried over sodium sulfate, filtered, and concentrated in vacuo. Purification via flash column chromatography (2.5%-10% methanol/methylene chloride) yielded the desired nitrile (1.1 g, 60%) as a dark brown oil: $^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: To a stirred solution of the nitrile from Step G (154 mg, 0.59 mmol) in anhydrous THF (7 mL) was added lithium aluminum hydride (1 M in THF, 1.8 mL) at 0° C. under N$_2$. The reaction was allowed to warm to room temperature and stirred for approximately 2 days. ESI MS indicated the reaction went to completion, so the mixture was poured slowly over ice water, then extracted with methylene chloride (3×). The combined extracts were washed with brine, dried over sodium sulfate, filtered, and concentrated in vacuo. Purification via flash column chromatography (9.5:0.45:0.05 methylene chloride/methanol/concentrated ammonium hydroxide) yielded the desired amine (99 mg, 63%) as a light brown oil: [α]$^{23}_D$+2.22° (c 0.050, methanol); $^1$H NMR (500 MHz, CDCl$_3$) δ 7.37-7.34 (m, 2H), 7.28-7.25 (m, 1H), 7.18 (d, J=7.5 Hz, 2H), 7.14-7.13 (m, 1H), 7.01 (d, J=7.5 Hz, 1H), 6.65-6.57 (br, 1H), 4.32-4.30 (m, 1H), 3.95-3.89 (m, 1H), 3.81 (s, 2H), 3.75-3.72 (m, 1H), 3.15-3.09 (m, 1H), 2.97-2.92 (m, 1H), 2.36 (s, 3H), 2.36-2.29 (m, 1H), 2.16-2.10 (m, 1H); ESI MS m/z 267 [M+H]$^+$.

Step I: To a stirred solution of the amine from Step H (115 mg, 0.43 mmol) in acetonitrile (30 mL) at room temperature were added di(ethylene glycol)di-p-tosylate (179 mg, 0.43 mmol) and sodium carbonate (137 mg, 1.3 mmol). The reaction mixture was heated to reflux and stirred for 15 h, then cooled to room temperature and filtered to remove the precipitate. The filtrate was then diluted with methylene chloride, washed with brine, dried over sodium sulfate, filtered, and concentrated in vacuo. Flash column chromatography (18.8:1:0.2 methylene chloride/methanol/concentrated ammonium hydroxide) yielded the desired product (16 mg, 11%) as a colorless oil, plus some unreacted starting material (9 mg): [α]23$_D$ −8.00° (c 0.025, methanol); $^1$H NMR (500 MHz, CDCl$_3$) δ 7.35 (t, J=7.5 Hz, 2H), 7.27-7.25 (m, 1H), 7.18-7.17 (m, 2H), 7.14-7.13 (m, 1H), 7.01 (d, J=7.5 Hz, 1H), 6.61-6.54 (br, 1H), 4.31-4.29 (m, 1H), 3.93-3.86 (m, 1H), 3.70-3.68 (m, 5H), 3.43-3.42 (m, 2H), 3.14-3.09 (m, 1H), 2.96-2.91 (m, 1H), 2.44-2.41 (m, 4H), 2.36 (s, 3H), 2.36-2.29 (m, 1H), 2.14-2.09 (m, 1H); ESI MS m/z 337 [M+H]$^+$.

Step J: To a stirred solution of the morpholine product from Step I (20 mg, 0.059 mmol) in methanol (3 mL) at room temperature was added maleic acid (9 mg, 0.059 mmol). The mixture was stirred at room temperature for 1 hour and then the solvent was concentrated to approximately 0.5 mL. After diluting with water (1.5 mL), the mixture was lyophilized for 2 days to provide (+)-4-(2-methyl-5-phenyl-2,3,4,5-tetrahydro-1H-benzo[c]azepin-8-yl)methyl)morpholine, L-tartrate salt (31 mg, 99%, 96.3% AUC HPLC) as an off-white solid: mp 124-127° C.; $^1$H NMR (500 MHz, CD$_3$OD) δ 7.49 (s, 1H), 7.39 (t, J=7.5 Hz, 2H), 7.32-7.29 (m, 2H), 7.19 (d, J=7.0 Hz, 2H), 6.89-6.77 (br, 1H), 4.58-4.57 (m, 2H), 4.40 (s, 2H), 4.33-4.30 (m, 1H), 3.74-3.72 (m, 4H), 3.70 (s, 2H), 3.57-3.51 (m, 2H), 2.88 (s, 3H), 2.65-2.60 (m, 3H), 2.63-2.54 (m, 2H), 2.43-2.37 (m, 1H); ESI MS m/z 337 [M+H]$^+$.

Example 23

Preparation of (+)-5-(4-chlorophenyl)-2-methyl-2,3,4,5-tetrahydro-1H-benzo[c]azepine-8-carbonitrile, maleate salt and (−)-5-(4-chlorophenyl)-2-methyl-2,3,4,5-tetrahydro-1H-benzo[c]azepine-8-carbonitrile, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 h, then cooled to 0° C. and sodium borohydride (6.19 g, 163.8 mmol) was added in portions. After warming to room temperature, the reaction was stirred for 3 hours. The mixture was then concentrated under reduced pressure, dissolved in H$_2$O, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×) and the combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of 4-chlorocinnamic acid (2.0 g, 10.9 mmol) and N-methylmorpholine (1.7 mL, 15.3 mmol) in anhydrous methylene chloride (80 mL) was cooled to −20° C. and isobutyl chloroformate (1.5 mL, 11.6 mmol) was added dropwise. After 15 minutes, a solution of the amine from Step A above (1.66 g, 10.9 mmol) in anhydrous methylene chloride (20 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification via flash column chromatography (1:1 ethyl acetate/hexanes) yielded the desired amide (2.82 g, 82%) as a white solid: $^1$H NMR (300 MHz, CDCl$_3$) δ 7.70 (dd, J=15.3, 4.8 Hz, 1H), 7.48 (d, J=8.4 Hz, 1H), 7.39 (d, J=8.4 Hz, 1H), 7.35 (d, J=8.4 Hz, 1H), 7.30 (d, J=8.4 Hz, 1H), 7.40-7.26 (m, 1H), 6.91 (d, J=15.3 Hz, 1H), 6.83 (s, 1H), 6.83 (d, J=12.3 Hz, 1H), 6.77 (d, J=15.3 Hz, 1H), 4.67 (d, J=12.3 Hz, 2H), 3.80 (s, 3H), 3.08 (d, J=4.2 Hz, 3H); ESI MS m/z 316 [M+H]$^+$.

Step C: An excess of polyphosphoric acid (2 g) in 1,2-dichloroethane (10 mL) was heated to 100° C. A solution of the amide from Step B above (527 mg, 1.7 mmol) in 1,2-dichloroethane (5 mL) was added dropwise and the reaction was stirred at 100° C. for 15 hours under N$_2$. After cooling to room temperature, the reaction was mixed with ice and the pH adjusted to 10 using 6N NaOH. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (199 mg) as a yellow foam: $^1$H NMR (500 MHz, CDCl$_3$) δ 7.24 (d, J=8.5 Hz, 2H), 7.00 (d, J=8.5 Hz, 2H), 6.83 (d, J=8.5 Hz, 1H) 6.72 (dd, J=8.5, 2.5 Hz, 1H), 6.67 (d, J=3.0 Hz, 1H), 4.91 (d, J=16.5 Hz, 1H), 4.44 (dd, J=10.5, 5.0 Hz, 1H), 4.19 (d, J=16.5 Hz, 1H), 3.79 (s, 3H), 3.16 (dd, J=13.5, 11.0 Hz, 1H), 3.05 (s, 3H), 2.98 (dd, J=13.5, 5.0 Hz, 1H).

Step D: To a stirred solution of lithium aluminum hydride (1M solution in THF, 0.48 mL, 0.48 mmol) at 0° C. under N$_2$ was added a solution of the product of Step C above (139 mg, 0.44 mmol) in anhydrous THF (4 mL) dropwise. The reaction mixture was heated to reflux and allowed to stir for 2 hours. The reaction was then cooled back down to 0° C. and quenched slowly with 1N NaOH (1 mL). After diluting with H$_2$O, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (67 mg, 19% two steps) as a light yellow oil: $^1$H NMR (500 MHz, CDCl$_3$) δ 7.31 (d, J=8.5 Hz, 2H), 7.10 (d, J=8.5 Hz, 2H), 6.74 (d, J=3.0 Hz, 1H), 6.61 (dd, J=8.5, 2.5 Hz, 1H), 6.55 (br, 1H), 4.24-4.22 (m, 1H), 3.86-3.84 (m, 1H), 3.77 (s, 3H), 3.68-3.65 (m, 1H), 3.10-3.07 (m, 1H), 2.96-2.91 (m, 1H), 2.34 (s, 3H), 2.30-2.23 (m, 1H), 2.10-2.03 (m, 1H); ESI MS m/z 302 [M+H]$^+$. This compound was resolved by preparative chiral HPLC (CHIRALPAK AD column, using 9:1:0.01 heptane/ethanol/diethylamine as the eluent) to give the (+)-enantiomer [[α]$^{25}_D$+5.00 (c 0.1, methanol)] and the (−)-enantiomer [[α]$^{25}_D$−20.0° (c 0.1, methanol)].

Step E: A mixture of the benzazepine from Step D above (1.40 g, 4.6 mmol) and hydrobromic acid (48% solution in water, 30 mL) was heated to reflux and stirred for 2 hours. The solvent and excess hydrobromic acid were removed under reduced pressure and the resulting solid was partitioned between ethyl acetate and saturated sodium bicarbonate (aq). After separating the two layers, the aqueous phase was extracted with ethyl acetate (3×). The combined extracts were dried over sodium sulfate, filtered, and concentrated in vacuo to provide the desired phenol (1.09 g, 82%) as a tan solid: $^1$H NMR (500 MHz, CDCl$_3$) δ 7.31 (d, J=8.0 Hz, 2H), 7.09 (d, J=8.5 Hz, 2H), 6.57-6.56 (m, 1H), 6.48-6.47 (m, 1H), 6.48-6.39 (m, 1H), 4.20 (d, J=8.5 Hz, 1H), 3.84-3.74 (m, 1H), 3.64-3.61 (m, 1H), 3.12-3.05 (m, 1H), 2.93-2.88 (m, 1H), 2.41 (s, 3H), 2.34-2.26 (m, 1H), 2.14-2.06 (m, 1H); ESI MS m/z 288 [M+H]$^+$.

Step F: To a stirred mixture of the phenol from Step E above (552 mg, 1.9 mmol) and pyridine (0.2 mL, 2.3 mmol) in anhydrous methylene chloride (19 mL) at 0° C. under N$_2$ was added triflic anhydride (0.4 mL, 2.3 mmol). The reaction was stirred at 0° C. for 1 hour, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification via flash column chromatography (1:1 ethyl acetate/hexanes) provided the desired triflate (457 mg, 57%) as a yellow oil: $^1$H NMR (500 MHz, CDCl$_3$) δ 7.35 (d, J=8.5 Hz, 2H), 7.10 (d, J=10.0 Hz, 2H), 7.09 (s, 1H), 6.97 (dd, J=8.5, 2.5 Hz, 1H), 6.70-6.63 (m, 1H), 4.30 (d, J=9.5 Hz, 1H), 3.96 (d, J=14.0 Hz, 1H), 3.72 (d, J=14.5 Hz, 1H), 3.14-3.11 (m, 1H), 2.99 (ddd, J=13.3, 10.0, 3.0 Hz, 1H), 2.35 (s, 3H), 2.28 (m, 1H), 2.09-2.03 (m, 1H); ESI MS m/z 420 [M+H]$^+$.

Step G: To a mixture of the triflate (0.55 g, 1.31 mmol) from step F, zinc cyanide (0.31 g, 2.62 mmol) and 1,1'-bis(diphenylphosphino)ferrocene (87 mg, 0.16 mmol) was added DMF (8.7 mL). The solution was purged with argon for 7 minutes, and tris(dibenzylideneacetone)dipalladium (0) (36 mg, 0.04 mmol) was added to it. The reaction mixture was heated at 130° C. for 2 hours, then cooled to room temperature, and partitioned between saturated sodium bicarbonate and ethyl acetate. The aqueous layer was separated and washed with ethyl acetate (3×). The combined organic extract was dried over sodium sulfate, filtered and concentrated under reduced pressure. Purification by flash column chromatography (ethyl acetate, then 99:1 to 95:5 ethyl acetate/methanol) gave the nitrile (0.15 g, 38%): $^1$H NMR (500 MHz, CDCl$_3$) δ 7.47 (d, J=1.4 Hz, 1H), 7.39-7.35 (m, 3H), 7.09-7.05 (m, 2H), 6.73 (br, 1H), 4.33 (d, J=9.1 Hz, 1H), 4.00-3.94 (m, 1H), 3.74 (d, J=14.1 Hz, 1H), 3.20-3.05 (m, 1H), 3.00-2.90 (m, 1H), 2.36 (s, 3H), 2.55-2.36 (m, 1H), 2.15-2.05 (m, 1H).

Step H: The free base of the benzazepine from step G (0.15 g) was resolved by preparative chiral HPLC (CHIRALCEL OD column, using 97:3:0.1 heptanes/isopropanol/diethylamine as the eluent) to give the (−)-enantiomer [[α]$^{25}_D$−7.11° (c 0.23, methanol)] and the (+)-enantiomer [[α]$^{25}_D$+5.95° (c 0.22, methanol)]. Both enantiomers were washed with water to remove residual diethylamine. To a solution of the (−)-enantiomer (54 mg, 0.18 mmol) in methanol (10 mL) was added maleic acid (21 mg, 0.18 mmol). The solution was concentrated to dryness and the residue was re-dissolved in methanol (1 mL) and water (5 mL). The resultant solution was lyophilized overnight to give (−)-5-(4-chlorophenyl)-2-methyl-2,3,4,5-tetrahydro-1H-benzo[c]azepine-8-carbonitrile, maleate salt (74 mg, 97%, AUC HPLC >99%) as an off-white solid: $^1$H NMR (500 MHz, CD$_3$OD) δ 7.86 (d, J=1.6 Hz, 1H), 7.70 (d, J=7.8 Hz, 1H), 7.44 (d, J=6.3 Hz, 2H), 7.24-7.19 (m, 2H), 6.92 (br, 1H), 6.25 (s, 2H), 4.83-4.41 (m, 2H), 4.40 (d, J=12.8 Hz, 1H), 3.68-3.47 (m, 2H), 2.94 (s, 3H), 2.63-2.47 (m, 1H), 2.43-2.38 (m, 1H); ESI MS m/z 297 [M+H]$^+$.

To a solution of the (+)-enantiomer (53 mg, 0.18 mmol) in methanol (10 mL) was added maleic acid (21 mg, 0.18 mmol). The solution was concentrated to dryness, and the residue was re-dissolved in methanol (1 mL) and water (5 mL). The resultant solution was lyophilized overnight to give (+)-5-(4-chlorophenyl)-2-methyl-2,3,4,5-tetrahydro-1H-benzo[c]azepine-8-carbonitrile, maleate salt (71 mg, 97%, AUC HPLC 98.9%) as an off-white solid: $^1$H NMR (500 MHz, CD$_3$OD) δ 7.86 (d, J=1.6 Hz, 1H), 7.70 (d, J=7.8 Hz, 1H), 7.44 (d, J=6.3 Hz, 2H), 7.24-7.19 (m, 2H), 6.92 (br, 1H), 6.25 (s, 2H), 4.83-4.41 (m, 2H), 4.40 (d, J=12.8 Hz, 1H), 3.68-3.47 (m, 2H), 2.94 (s, 3H), 2.63-2.47 (m, 1H), 2.43-2.38 (m, 1H); ESI MS m/z 297 [M+H]$^+$.

Example 24

Preparation of (+)-2-methyl-8-(6-methyl-pyridazin-3-yl)-5-phenyl-2,3,4,5-tetrahydro-1H-benzo[c]azepine, hydrochloride salt Step A: A solution of trans-cinnamic acid (5.0 g, 33.8 mmol) and N-methylmorpholine (5.2 mL, 47.3 mmol) in anhydrous methylene chloride (120 mL) was cooled to −20° C. Isobutyl chloroformate (4.8 mL, 35.8 mmol) was added dropwise. After 15 minutes, a solution of (3-methoxybenzyl)methylamine (5.1 g, 33.8 mmol) in anhydrous methylene chloride (30 mL) was added dropwise. The reaction was allowed to warm to room temperature and stir under N$_2$ for 3 hours. The reaction mixture was then washed with 1 M NaH$_2$PO$_4$·2H$_2$O (2×), H$_2$O (2×), and brine, dried over sodium sulfate, filtered, and concentrated in vacuo. Purification via flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.55 (d, J=6.5 Hz, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z=282 [C$_{18}$H$_{19}$NO$_2$+H]$^+$.

Step B: An excess of polyphosphoric acid (11 g) in 1,2-dichloroethane (10 mL) was heated to 100° C. A solution of the product from Step A (3.8 g, 13.5 mmol) in 1,2-dichloroethane (15 mL) was added dropwise. The reaction was then allowed to stir at 100° C. overnight under N$_2$. After cooling to room temperature, the reaction was mixed with ice and the pH was adjusted to 9 using concentrated NH$_4$OH. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (1.77 g) as a yellow oil: $^1$H NMR (500 MHz, CDCl$_3$) δ 7.50 (dd, J=7.5, 2.0 Hz, 1H), 7.37-7.35 (m, 1H), 7.29-7.28 (m, 1H), 7.09-7.06 (m, 2H), 6.87 (d, J=9.0 Hz, 1H), 6.71 (dd, J=8.5, 2.5 Hz, 1H), 6.66 (d, J=3.0 Hz, 1H), 5.03 (d, J=16.5 Hz, 1H), 4.46 (dd, J=11.0, 5.0 Hz, 1H), 4.09 (d, J=16.5 Hz, 1H), 3.79 (s, 3H), 3.25 (dd, J=14.0, 12.0 Hz, 1H), 3.05 (s, 3H), 2.97-2.93 (m, 1H).

Step C: To a stirred solution of lithium aluminum hydride (1 M solution in THF, 14.7 mL, 14.7 mmol) at 0° C. under N$_2$ was added a solution of the product of Step B (3.8 g, 13.4 mmol) in anhydrous THF (100 mL) dropwise. The reaction mixture was heated to reflux and allowed to stir for 2 hours. The reaction was then cooled back down to 0° C. and quenched slowly with 1 N NaOH (30 mL). After diluting with H$_2$O, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (2.93 g, 38% over two steps) as a yellow oil: $^1$H NMR (500 MHz, CDCl$_3$) δ 7.36-7.33 (m, 2H), 7.29-7.23 (m, 1H), 7.17 (d, J=7.0 Hz, 2H), 6.74 (d, J=2.5 Hz, 1H), 6.60 (dd, J=8.0, 2.5 Hz, 1H), 6.59-6.52 (br, 1H), 4.26 (d, J=9.0 Hz, 1H), 3.91-3.86 (m, 1H), 3.77 (s, 3H), 3.72 (d, J=10.0 Hz, 1H), 3.13-3.09 (m, 1H), 2.95 (ddd, J=12.8, 10.0, 2.5 Hz, 1H), 2.35 (s, 3H), 2.33-2.28 (m, 1H), 2.12-2.06 (m, 1H); ESI MS m/z=268 [C$_{18}$H$_{21}$NO+H]$^+$. This compound was resolved by preparative chiral HPLC (CHIRALCEL OJ column, using 9:1:0.01 heptane/ethanol/triethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step D: A mixture of the (+)-enantiomer of Step C (1.19 g, 4.5 mmol) and HBr (48% solution in H$_2$O, 34 mL) was heated to reflux and allowed to stir for 2 hours. The solvent and excess HBr were removed under reduced pressure and the resulting solid was partitioned between ethyl acetate and saturated NaHCO$_3$ (aq). After separating the two layers, the aqueous phase was extracted with ethyl acetate (3×). The combined extracts were dried over sodium sulfate, filtered, and concentrated in vacuo to provide the desired phenol (1.10 g, 86%) as a tan solid.: $^1$H NMR (500 MHz, CDCl$_3$) δ 7.36-7.33 (m, 2H), 7.28-7.23 (m, 1H), 7.16 (d, J=7.5 Hz, 2H), 6.54 (s, 1H), 6.48-6.35 (m, 2H), 4.23 (d, J=9.0 Hz, 1H), 3.87-3.77 (m, 1H), 3.64 (d, J=13.5 Hz, 1H), 3.17-3.08 (m, 1H), 2.91 (ddd, J=12.8, 10.0, 2.5 Hz, 1H), 2.42 (s, 3H), 2.35-2.31 (m, 1H), 2.18-2.09 (m, 1H); ESI MS m/z=254 [C$_{17}$H$_{19}$NO+H]$^+$.

Step E: To a stirred mixture of the product of Step D (581 mg, 2.3 mmol) and pyridine (0.22 mL, 2.8 mmol) in anhydrous CH$_2$Cl$_2$ (23 mL) at 0° C. under N$_2$ was added triflic anhydride (0.46 mL, 2.8 mmol). Stirring was continued at 0° C. for one hour at which time TLC analysis indicated that the reaction had gone to completion. The mixture was then diluted with CH$_2$Cl$_2$, washed with saturated NaHCO$_3$ (aq) and brine, dried over sodium sulfate, filtered, and concentrated in vacuo. Purification via flash column chromatography (1:1 ethyl acetate/hexanes) provided the desired triflate (650 mg, 74%) as a yellow oil: $^1$H NMR (500 MHz, CDCl$_3$) δ 7.40-7.37 (m, 2H), 7.31-7.28 (m, 1H), 7.17 (d, J=7.0 Hz, 2H), 7.09 (d, J=2.5 Hz, 1H), 6.97-6.93 (m, 1H), 6.70-6.64 (br, 1H), 4.32 (d, J=9.5 Hz, 1H), 4.03-3.94 (m, 1H), 3.73 (d, J=14.0 Hz, 1H), 3.18-3.13 (m, 1H), 3.03-3.27 (m, 1H), 2.36 (s, 3H), 2.34-2.29 (m, 1H), 2.12-2.06 (m, 1H); ESI MS m/z=386 [C$_{18}$H$_{18}$F$_3$NO$_3$S+H]$^+$.

Step F: To a disposable sealed tube were added bis(pinacolato)diboron (471 mg, 1.7 mmol), potassium acetate (498 mg, 5.1 mmol), and the product of Step E (650 mg, 1.7 mmol) as a solution in anhydrous DMSO (8 mL). The reaction mixture was degassed by a subsurface purge with Ar for one minute. PdCl$_2$(dppf).CH$_2$Cl$_2$ (41 mg, 0.051 mmol) was then added under Ar. The reaction was heated to 80° C. and allowed to stir for 3 hours, at which time ESI MS showed that the reaction had gone to completion. After cooling to room temperature, the reaction mixture was diluted with H$_2$O, then extracted with ethyl acetate (3×). The combined extracts were dried over sodium sulfate, filtered, and concentrated in vacuo to provide the desired boronate ester (crude) as a dark brown oil, which was taken on to the next step without further purification: ESI MS m/z=364 [C$_{23}$H$_{30}$BNO$_2$+H]$^+$.

Step G: To a disposable sealed tube were added the product of Step F (200 mg, 0.55 mmol, theoretical) as a solution in anhydrous DMF (4.5 mL), sodium carbonate (175 mg, 1.7 mmol) as a solution in H$_2$O (1 mL), and 3-chloro-6-methylpyridazine (85 mg, 0.66 mmol). The reaction mixture was degassed by a subsurface purge with Ar for one minute. PdCl$_2$(dppf).CH$_2$Cl$_2$ (27 mg, 0.033 mmol) was then added under Ar. The reaction was heated to 100° C. and allowed to stir overnight. TLC analysis showed that the reaction went to completion. After cooling to room temperature, the reaction mixture was diluted with H$_2$O, then extracted with ethyl acetate (3×). The combined extracts were dried over sodium sulfate, filtered, and concentrated in vacuo. Purification via flash column chromatography (95:5 CH$_2$Cl$_2$/MeOH) yielded the desired pyridazine (74 mg, 41% over two steps) as a brown oil: [α]$^{25}$$_D$ -2.0° (c 0.05, methanol); $^1$H NMR (500 MHz, CDCl$_3$) δ 7.96 (d, J=2.0 Hz, 1H), 7.75 (d, J=7.5 Hz, 1H), 7.72 (d, J=9.0 Hz, 1H), 7.40-7.33 (m, 3H), 7.30-7.27 (m, 1H), 7.21 (d, J=7.5 Hz, 2H), 6.85-6.78 (br, 1H), 4.40 (d, J=8.5 Hz, 1H), 4.06-4.04 (m, 1H), 3.89 (d, J=14.5 Hz, 1H), 3.20-3.16 (m, 1H), 3.03 (ddd, J=12.5, 9.8, 2.5 Hz, 1H), 2.75 (s, 3H), 2.41 (s, 3H), 2.40-2.35 (m, 1H), 2.21-2.15 (m, 1H); ESI MS m/z=330 [C$_{22}$H$_{23}$N$_3$+H]$^+$.

Step H: The product of Step G (70 mg, 0.21 mmol) was converted to its hydrochloride salt by dissolving the oil in a minimum amount of ether, adding one equivalent of HCl (1 M solution in ether), and sonicating the solution for a few minutes until salt precipitation occurred. Filtration yielded (+)-2-methyl-8-(6-methyl-pyridazin-3-yl)-5-phenyl-2,3,4,5-tetrahydro-1H-benzo[c]azepine, hydrochloride salt (69 mg, 89%, >99% AUC HPLC) as a light brown solid: mp 168-170° C.; ESI MS m/z=330 [C$_{22}$H$_{23}$N$_3$+H]$^+$.

Example 25

Preparation of (+)-2-methyl-5-phenyl-8-(pyridazin-3-yl)-2,3,4,5-tetrahydro-1H-benzo[c]azepine, hydrochloride salt Pursuant to the general method described above in Example 24, the following product was prepared: (+)-2-methyl-5-phenyl-8-(pyridazin-3-yl)-2,3,4,5-tetrahydro-1H-benzo[c]azepine, hydrochloride salt: mp 154-156° C.; ESI MS m/z=316 [C$_{21}$H$_{21}$N$_3$+H]$^+$.

Example 26

Preparation of (+)-dimethyl-[6-(2-methyl-5-phenyl-2,3,4,5-tetrahydro-1H-benzo[c]azepine-8-yl)-pyridazin-3-yl]-amine, maleate salt Pursuant to the general method described above in Example 24, the following product was prepared: (+)-dimethyl-[6-(2-methyl-5-phenyl-2,3,4,5-tetrahydro-1H-benzo[c]azepine-8-yl)-pyridazin-3-yl]-amine, maleate salt: mp 99-102° C.; $^1$H NMR (500 MHz, CD$_3$OD) δ 8.08 (d, J=1.5 Hz, 1H), 7.93 (d, J=10.0 Hz, 1H), 7.88-7.83 (m, 1H), 7.44-7.41 (m, 2H), 7.35-7.31 (m, 2H), 7.25 (d, J=6.0 Hz, 2H), 7.08-6.85 (br, 1H), 6.25 (s, 2H), 4.80-4.70 (br, 1H), 4.67 (d, J=10.5 Hz, 1H), 4.50-4.42 (m, 1H), 3.70-3.60 (m, 2H), 3.25 (s, 6H), 3.01-2.94 (br, 3H), 2.70-2.50 (m, 1H), 2.49-2.46 (m, 1H); ESI MS m/z=359 [C$_{23}$H$_{26}$N$_4$+H]$^+$.

Example 27

Preparation of (+)-2-methyl-5-phenyl-8-(pyrimidin-2-yl)-2,3,4,5-tetrahydro-1H-benzo[c]azepine, maleate salt Pursuant to the general method described above in Example 24, the following product was prepared: (+)-2-methyl-5-phenyl-8-(pyrimidin-2-yl)-2,3,4,5-tetrahydro-1H-benzo[c]azepine, maleate salt: mp 76-78° C.; $^1$H NMR (500 MHz, CD$_3$OD) δ 8.85 (d, J=4.5 Hz, 2H), 8.53 (s, 1H), 8.40-8.30 (br, 1H), 7.45-7.42 (m, 2H), 7.39 (t, J=5.0 Hz, 1H), 7.36-7.33 (m, 1H), 7.28-7.21 (br, 2H), 7.04-6.71 (br, 1H), 6.26 (s, 2H), 4.70-4.68 (m, 2H), 4.59-4.38 (br, 1H), 3.77-3.62 (m, 2H), 3.11-2.84 (m, 3H), 2.54-2.41 (m, 2H); ESI MS m/z 316 [M+H]$^+$.

Example 28

Preparation of (+)-2-methyl-5-phenyl-8-(pyrimidin-5-yl)-2,3,4,5-tetrahydro-1H-benzo[c]azepine, maleate salt Pursuant to the general method described above in Example 24, the following product was prepared: (+)-2-methyl-5-phenyl-8-(pyrimidin-5-yl)-2,3,4,5-tetrahydro-1H-benzo[c]azepine, maleate salt: mp 93-96° C.; $^1$H NMR (500 MHz, CD$_3$OD) δ 9.16 (s, 1H), 9.10 (s, 2H), 7.86 (m, 1H), 7.73-7.71 (m, 1H), 7.45-7.42 (m, 2H), 7.36-7.33 (m, 1H), 7.26-7.24 (m, 2H), 7.14-6.93 (br, 1H), 6.24 (s, 2H), 4.70-4.68 (m, 2H), 4.48-4.46 (m, 1H), 3.71-3.64 (m, 2H), 3.03-2.92 (br, 3H), 2.73-2.55 (m, 1H), 2.51-2.43 (m, 1H); ESI MS m/z 316 [M+H]$^+$.

Example 29

Preparation of (+)-2-methyl-5-phenyl-8-(pyrazin-2-yl)-2,3,4,5-tetrahydro-1H-benzo[c]azepine, maleate salt Pursuant to the general method described above in Example 24, the following product was prepared: (+)-2-methyl-5-phenyl-8-(pyrazin-2-yl)-2,3,4,5-tetrahydro-1H-benzo[c]azepine, maleate salt: mp 67-69° C.; $^1$H NMR (500 MHz, CD$_3$OD) δ 9.14 (s, 1H), 8.69 (d, J=1.5 Hz, 1H), 8.56 (m, 1H), 8.24 (d, J=1.5 Hz, 1H), 8.09-8.03 (m, 1H), 7.45-7.42 (m, 2H), 7.36-7.33 (m, 1H), 7.30-7.23 (m, 2H), 7.18-6.82 (br, 1H), 6.26 (s, 2H), 4.71-4.69 (m, 2H), 4.55-4.45 (m, 1H), 3.71-3.63 (m, 2H), 3.05-2.92 (m, 3H), 2.78-2.55 (br, 1H), 2.50-2.43 (m, 1H); ESI MS m/z 316 [M+H]$^+$.

Example 30

Preparation of (+)-6-(2-methyl-5-phenyl-2,3,4,5-tetrahydro-1H-benzo[c]azepin-8-yl)pyridazin-3-amine, maleate salt and (−)-6-(2-methyl-5-phenyl-2,3,4,5-tetrahydro-1H-benzo[c]azepin-8-yl)pyridazin-3-amine, L-tartrate salt Pursuant to the general method described above in Example 24, the following products were prepared: (+)-6-(2-methyl-5-phenyl-2,3,4,5-tetrahydro-1H-benzo[c]azepin-8-yl)pyridazin-3-amine, maleate salt: mp 120-122° C.; $^1$H NMR (500 MHz, CD$_3$OD) δ 8.06 (s, 1H), 7.89 (d, J=9.5 Hz, 1H), 7.84-7.82 (m, 1H), 7.44-7.41 (m, 2H), 7.35-7.32 (m, 1H), 7.25-7.24 (m, 2H), 7.11 (d, J=9.5 Hz, 1H), 7.05-6.91 (br, 1H), 6.24 (s, 2H), 4.82-4.65 (m, 1H), 4.68-4.66 (m, 1H), 4.47-4.44 (m, 1H), 3.69-3.60 (m, 2H), 3.00-2.92 (br, 3H), 2.70-2.53 (br, 1H), 2.48-2.45 (m, 1H); ESI MS m/z 331 [M+H]$^+$; (−)-6-(2-methyl-5-phenyl-2,3,4,5-tetrahydro-1H-benzo[c]azepin-8-yl)pyridazin-3-amine, L-tartrate salt: $^1$H NMR (500 MHz, CD$_3$OD) δ 8.03-8.02 (m, 1H), 7.83 (d, J=9.0 Hz, 1H), 7.81 (d, J=8.0 Hz, 1H), 7.41 (t, J=7.5 Hz, 2H), 7.32 (t, J=7.5 Hz, 1H), 7.24 (d, J=7.5 Hz, 2H), 7.04 (d, J=9.0 Hz, 1H), 6.99-6.92 (br, 1H), 4.71-4.64 (m, 1H), 4.64 (d, J=7.5 Hz, 1H), 4.42-4.40 (m, 1H), 4.40 (s, 2H), 3.61-3.58 (m, 2H), 2.89 (s, 3H), 2.65-2.58 (m, 1H), 2.46-2.42 (m, 1H); ESI MS m/z 331 [M+H]$^+$.

Example 31

Preparation of (+)-2-methyl-5-phenyl-8-(pyridin-4-yl)-2,3,4,5-tetrahydro-1H-benzo[c]azepine, maleate salt Pursuant to the general method described above in Example 24, the following product was prepared: (+)-2-methyl-5-phenyl-8-(pyridin-4-yl)-2,3,4,5-tetrahydro-1H-benzo[c]azepine, maleate salt: mp 91-93° C.; $^1$H NMR (500 MHz, CD$_3$OD) δ 8.62 (d, J=6.0 Hz, 2H), 7.92-7.91 (m, 1H), 7.77 (d, J=6.0 Hz, 3H), 7.43 (t, J=7.5 Hz, 2H), 7.34 (t, J=7.5 Hz, 1H), 7.26-7.25 (m, 2H), 7.16-6.85 (br, 1H), 6.25 (s, 2H), 4.70-4.68 (m, 2H), 4.53-4.43 (m, 1H), 3.72-3.57 (m, 2H), 3.04-2.90 (m, 3H), 2.74-2.52 (br, 1H), 2.51-2.44 (m, 1H); ESI MS m/z 315 [M+H]$^+$.

Example 32

Preparation of (+)-6-(2-methyl-5-phenyl-2,3,4,5-tetrahydro-1H-benzo[c]azepin-8-yl)pyridine-2-amine, maleate salt Pursuant to the general method described above in Example 24, the following product was prepared: (+)-6-(2-methyl-5-phenyl-2,3,4,5-tetrahydro-1H-benzo[c]azepin-8-yl)pyridine-2-amine, maleate salt: mp 112-114° C.; $^1$H NMR (500 MHz, CD$_3$OD) δ 7.98-7.97 (m, 1H), 7.80 (d, J=7.5 Hz, 1H), 7.57 (t, J=7.5 Hz, 1H), 7.42 (d, J=7.5 Hz, 2H), 7.33 (t, J=7.5 Hz, 1H), 7.24 (d, J=7.0 Hz, 2H), 7.06 (d, J=7.0 Hz, 1H), 7.00-6.89 (br, 1H), 6.60 (d, J=8.5 Hz, 1H), 6.24 (s, 2H), 4.76-4.67 (m, 1H), 4.65 (d, J=8.5 Hz, 1H), 4.44-4.41 (m, 1H), 3.66-3.62 (m, 2H), 2.95 (br s, 3H), 2.69-2.57 (m, 1H), 2.47-2.43 (m, 1H); ESI MS m/z 330 [M+H]$^+$.

Example 33

Preparation of (+)-5-methyl-3-(2-methyl-5-phenyl-2,3,4,5-tetrahydro-1H-benzo[c]azepin-8-yl)-1,2,4-oxadiazole, L-tartrate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 hours, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 hours under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under $N_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate (aq). After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under $N_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (2.60 g, 6.8 mmol) in DMF (30 mL) at room temperature was added zinc cyanide (1.58 g, 13.5 mmol). The reaction mixture was degassed with argon for 2 minutes, then tris(dibenzylideneacetone)-dipalladium(0) (247 mg, 0.27 mmol) and 1,1'-bis(diphenylphosphino)ferrocene (599 mg, 1.1 mmol) were added under argon. The reaction was heated to 130° C. and stirred for 4 hours. After cooling to room temperature, the mixture was diluted with ethyl acetate and washed with saturated sodium bicarbonate. The aqueous phase was extracted with additional ethyl acetate (3×), and then the combined extracts were washed with brine, dried over sodium sulfate, filtered, and concentrated in vacuo. Purification by flash column chromatography (2.5%-10% methanol/methylene chloride) yielded the desired nitrile (1.07 g, 60%) as a dark brown oil: $^1$H NMR (500 MHz, CDCl$_3$) δ 7.47-7.46 (m, 1H), 7.40-7.34 (m, 1H), 7.38 (d, J=8.0 Hz, 2H), 7.32-7.29 (m, 1H), 7.15 (d, J=7.5 Hz, 2H), 6.77-6.67 (br, 1H), 4.37-4.35 (m, 1H), 3.99-3.97 (m, 1H), 3.77-3.74 (m, 1H), 3.19-3.12 (m, 1H), 3.02-2.98 (m, 1H), 2.37 (s, 3H), 2.37-2.29 (m, 1H), 2.16-2.10 (m, 1H); ESI MS m/z 263 [M+H]$^+$.

Step H: To a stirred solution of hydroxylamine hydrochloride (467 mg, 6.7 mmol) in water (8.5 mL) was added sodium carbonate (712 mg, 6.7 mmol) and the nitrile from Step G above (235 mg, 0.90 mmol). The reaction was stirred at reflux for 16 hours, at which time ESI MS indicated the reaction went to completion. After cooling to room temperature, the reaction mixture was partitioned between methylene chloride and water. After separating the layers, the aqueous phase was extracted with additional methylene chloride (2×) and the combined extracts were dried over sodium sulfate, filtered, and concentrated in vacuo to provide the desired amidoxime (231 mg, 87%) as a brown solid: $^1$H NMR (500 MHz, CDCl$_3$) δ 7.48-7.47 (m, 1H), 7.36 (t, J=7.5 Hz, 2H), 7.31-7.26 (m, 2H), 7.17 (d, J=7.5 Hz, 2H), 6.74-6.66 (m, 1H), 4.79 (br, 2H), 4.35-4.33 (m, 1H), 3.97-3.93 (m, 1H), 3.80-3.77 (m, 1H), 3.15-3.11 (m, 1H), 3.00-2.95 (m, 1H), 2.36-2.30 (m, 1H), 2.35 (s, 3H), 2.15-2.11 (m, 1H); ESI MS m/z 296 [M+H]$^+$.

Step I: The amidoxime from Step H above (230 mg, 0.78 mmol) and N,-dimethylacetamide dimethylacetal (1.4 mL, 9.4 mmol) were heated at reflux for 4 hours, at which time ESI MS indicated the reaction went to completion. The reaction mixture was concentrated in vacuo and then purified by flash column chromatography (3×) using 9:0.9:0.1 methylene chloride/methanol/concentrated ammonium hydroxide as eluent) and then by preparative HPLC to provide the desired oxadiazole (27 mg, 11%) as a colorless oil: [α]$^{23}_D$−7.50° (c 0.040, methanol); $^1$H NMR (500 MHz, CDCl$_3$) δ 7.89-7.88 (m, 1H), 7.78-7.76 (m, 1H), 7.37 (t, J=7.5 Hz, 2H), 7.29 (d, J=7.5 Hz, 1H), 7.19 (d, J=7.0 Hz, 2H), 6.81-6.74 (br, 1H), 4.39-4.37 (m, 1H), 4.00 (d, J=14.0 Hz, 1H), 3.83 (d, J=14.0 Hz, 1H), 3.18-3.13 (m, 1H), 3.02-2.97 (m, 1H), 2.64 (s, 3H), 2.39-2.32 (m, 1H), 2.36 (s, 3H), 2.17-2.11 (m, 1H); ESI MS m/z 320 [M+H]$^+$.

Step J: To a stirred solution of the oxadiazole from Step I above (25 mg, 0.078 mmol) in methanol (2 mL) at room temperature was added L-tartaric acid (12 mg, 0.078 mmol). The mixture was stirred at room temperature for 1 hour and then the solvent was concentrated to approximately 0.5 mL. After diluting with H$_2$O (1.5 mL), the mixture was lyophilized for 15 hours to provide (+)-5-methyl-3-(2-methyl-5-phenyl-2,3,4,5-tetrahydro-1H-benzo[c]azepin-8-yl)-1,2,4-oxadiazole, L-tartrate salt (37 mg, 99%, 97.8% AUC HPLC) as an off-white solid: mp 102-104° C.; $^1$H NMR (500 MHz, CD$_3$OD) δ 8.14-8.13 (m, 1H), 7.97-7.95 (m, 1H), 7.42 (t, J=7.5 Hz, 2H), 7.33 (t, J=7.5 Hz, 1H), 7.24 (d, J=8.0 Hz, 2H), 7.03-6.94 (br, 1H), 4.66 (d, J=7.5 Hz, 2H), 4.43 (s, 2H), 4.43-4.37 (m, 1H), 3.60-3.56 (m, 2H), 2.86 (br s, 3H), 2.65 (s, 3H), 2.65-2.55 (m, 1H), 2.45-2.41 (m, 1H); ESI MS m/z 320 [M+H]$^+$.

Example 34

Preparation of (+)-4-(2-methyl-5-phenyl-2,3,4,5-tetrahydro-1H-benzo[c]azepin-8-yl)morpholine, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 hours, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 hours. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 hours under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (1.77 g) as a yellow oil: $^1$H NMR.

(500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under N$_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer [[α]$^{25}_D$+3.66° (c 0.41, methanol)] and the (−)-enantiomer [[α]$^{25}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate (aq). After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a stirred solution of the triflate from Step F above (260 mg, 0.68 mmol) in anhydrous toluene (6 mL) at room temperature were added morpholine (0.12 mL, 1.4 mmol), cesium carbonate (660 mg, 2.0 mmol), and 2-dicyclohexylphosphino-2',4',6'-triisopropylbiphenyl (97 mg, 0.20 mmol). The reaction mixture was degassed with argon for 2 minutes, then palladium(II) acetate (23 mg, 0.10 mmol) was added under argon. The reaction was heated to reflux and stirred for 15 hours, at which time ESI MS indicated the reaction went to completion. After cooling to room temperature, the mixture was diluted with methylene chloride and filtered through Celite. The filtrate was washed with saturated ammonium chloride and brine, dried over sodium sulfate, filtered, and concentrated in vacuo. Purification by flash column chromatography (2%-10% methanol/methylene chloride) yielded the desired morpholine (168 mg, 77%) as a light yellow solid: $[\alpha]^{23}{}_D$+3.000 (c 0.10, methanol); $^1$H NMR (500 MHz, CDCl$_3$) δ 7.41-7.35 (m, 1H), 7.34 (t, J=7.5 Hz, 2H), 7.16 (d, J=7.5 Hz, 2H), 6.76-6.75 (m, 1H), 6.64-6.53 (m, 2H), 4.27-4.25 (m, 1H), 3.96-3.85 (m, 1H), 3.85 (t, J=5.0 Hz, 4H), 3.75-3.73 (m, 1H), 3.30-3.18 (m, 1H), 3.12 (t, J=5.0 Hz, 4H), 3.01-2.96 (m, 1H), 2.38 (s, 3H), 2.36-2.29 (m, 1H), 2.16-2.09 (m, 1H); ESI MS m/z 323 [M+H]$^+$.

Step H: To a stirred solution of the morpholine from Step G above (160 mg, 0.50 mmol) in methanol (4 mL) at room temperature was added maleic acid (57 mg, 0.50 mmol). The mixture was stirred for 1 hour and then the solvent was concentrated to approximately 0.5 mL. After diluting with water (2 mL), the mixture was lyophilized for 15 hours to provide (+)-4-(2-methyl-5-phenyl-2,3,4,5-tetrahydro-1H-benzo[c]azepin-8-yl)morpholine, maleate salt (208 mg, 96%, 98.1% AUC HPLC) as an off-white solid: mp 88-89° C.; $^1$H NMR (500 MHz, CD$_3$OD) δ 7.40-7.37 (m, 2H), 7.30-7.28 (m, 1H), 7.20-7.15 (br, 2H), 7.06-7.05 (m, 1H), 6.93-6.85 (br, 2H), 6.25 (s, 2H), 4.50-4.48 (m, 2H), 4.34-4.23 (br, 1H), 3.83-3.81 (m, 4H), 3.63-3.52 (m, 2H), 3.16-3.14 (m, 4H), 2.97-2.82 (m, 3H), 2.43-2.35 (m, 2H); ESI MS m/z 323 [M+H]$^+$.

Example 35

Preparation of (+)-2-methyl-8-(4-methylpiperazin-1-yl)-5-phenyl-2,3,4,5-tetrahydro-1H-benzo[c]azepine, L-tartrate salt Pursuant to the general method described above in Example 34, the following product was prepared: (+)-2-methyl-8-(4-methylpiperazin-1-yl)-5-phenyl-2,3,4,5-tetrahydro-1H-benzo[c]azepine, L-tartrate salt: $^1$H NMR (500 MHz, CD$_3$OD) δ 7.37 (t, J=7.5 Hz, 2H), 7.27 (t, J=7.5 Hz, 1H), 7.17 (d, J=7.5 Hz, 2H), 7.07-7.06 (m, 1H), 6.89 (d, J=7.0 Hz, 1H), 6.79-6.67 (br, 1H), 4.46-4.45 (m, 2H), 4.33 (s, 2H), 4.24-4.21 (m, 1H), 3.51-3.47 (m, 2H), 3.38-3.34 (m, 4H), 3.05-3.02 (m, 4H), 2.81 (s, 3H), 2.66 (s, 3H), 2.59-2.50 (m, 1H), 2.39-2.33 (m, 1H); ESI MS m/z 336 [M+H]$^+$.

Example 36

Preparation of (+)-1-(2-methyl-5-phenyl-2,3,4,5-tetrahydro-1H-benzo[c]azepin-8-yl)pyrrolidin-2-one, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under N$_2$ for 15 hours, then cooled to 0° C. and sodium borohydride (6.19 g, 163.8 mmol) was added in portions. After warming to room temperature, the reaction was stirred for 3 hours. The mixture was then concentrated under reduced pressure, dissolved in water, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of trans-cinnamic acid (5.0 g, 33.8 mmol) and N-methylmorpholine (5.2 mL, 47.3 mmol) in anhydrous methylene chloride (120 mL) was cooled to −20° C., and then isobutyl chloroformate (4.8 mL, 35.8 mmol) was added dropwise. After 15 minutes, a solution of the amine from Step A above (5.1 g, 33.8 mmol) in anhydrous methylene chloride (30 mL) was added dropwise, then the reaction was allowed to warm to room temperature and stir under N$_2$ for 3 h. The mixture was washed with 1M sodium dihydrogen phosphate dihydrate (2×), H$_2$O (2×), and brine, dried over sodium sulfate, filtered, and concentrated in vacuo. Purification by flash column chromatography (1:1 ethyl acetate/hexanes) yielded the desired amide (8.3 g, 87%) as a colorless oil: $^1$H NMR (500 MHz, CDCl$_3$) δ 7.76 (dd, J=15.5, 7.5 Hz, 1H), 7.56-7.54 (m, 1H), 7.47-7.46 (m, 1H), 7.36 (dd, J=14.5, 7.5 Hz, 2H), 7.39-7.33 (m, 1H), 7.31-7.24 (m, 1H), 6.95-6.76 (m, 4H), 4.70-4.66 (m, 2H), 3.80 (s, 3H), 3.09-3.07 (m, 3H); ESI MS m/z 282 [M+H]$^+$.

Step C: An excess of polyphosphoric acid (11 g) in 1,2-dichloroethane (10 mL) was heated to 100° C. A solution of the amide from Step B above (3.8 g, 13.5 mmol) in 1,2-dichloroethane (15 mL) was added dropwise and the reaction was stirred at 100° C. for 15 hours under N$_2$. After cooling to room temperature, the reaction was mixed with ice and the pH adjusted to 9 using concentrated ammonium hydroxide. The reaction mixture was then extracted with ethyl acetate (3×) and the combined extracts were dried over sodium sulfate, filtered, and concentrated in vacuo. Partial purification by flash column chromatography (30-100% ethyl acetate/hexanes) yielded the desired product (1.77 g) as a yellow oil: $^1$H NMR (500 MHz, CDCl$_3$) δ 7.51-7.49 (m, 1H), 7.37-7.35 (m, 1H), 7.29-7.28 (m, 1H), 7.09-7.06 (m, 2H), 6.87 (d, J=9.0 Hz, 1H) 6.71 (dd, J=8.5, 2.5 Hz, 1H), 6.66 (d, J=3.0 Hz, 1H), 5.03 (d, J=16.5 Hz, 1H), 4.48-4.44 (m, 1H), 4.09 (d, J=16.5 Hz, 1H), 3.79 (s, 3H), 3.28-3.22 (m, 1H), 3.05 (s, 3H), 2.97-2.93 (m, 1H).

Step D: To a stirred solution of lithium aluminum hydride (1M solution in THF, 14.7 mL, 14.7 mmol) at 0° C. under N$_2$ was added a solution of the product of Step C above (3.8 g, 13.4 mmol) in anhydrous THF (100 mL) dropwise. The reaction mixture was heated to reflux and stirred for 2 hours. The reaction was then cooled back down to 0° C. and quenched slowly with 1N NaOH (30 mL). After diluting with water, the aqueous phase was extracted with ethyl acetate (3×) and the combined extracts were washed with brine, dried over sodium sulfate, filtered, and concentrated in vacuo. Purification by flash column chromatography (1:1 ethyl acetate/hexanes) yielded the desired benzazepine (2.93 g, 38% two steps) as a yellow oil: $^1$H NMR (500 MHz, CDCl$_3$) δ 7.35 (t, J=7.5 Hz, 2H), 7.27-7.24 (m, 1H), 7.17 (d, J=7.5 Hz, 2H), 6.75-6.74 (m, 1H), 6.61-6.60 (m, 1H), 6.61-6.53 (br, 1H), 4.27-4.26 (m, 1H), 3.91-3.86 (m, 1H), 3.77 (s, 3H), 3.73-3.70 (m, 1H), 3.16-3.09 (m, 1H), 2.99-2.94 (m, 1H), 2.35 (s, 3H), 2.33-2.28 (m, 1H), 2.13-2.07 (m, 1H); ESI MS m/z 268 [M+H]$^+$. This compound was resolved by preparative chiral HPLC (CHIRALCEL OJ column, using 9:1:0.01 heptane/ethanol/diethylamine as the eluent) to give the (+)-enantiomer $[[\alpha]^{25}{}_D$+3.66° (c 0.41, methanol)] and the (−)-enantiomer $[[\alpha]^{25}{}_D$−1.16° (c 0.43, methanol)].

Step E: A mixture of the (+)-enantiomer from Step D above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step F: To a stirred mixture of the phenol from Step E above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step G: To a sealed tube were added 9,9-dimethyl-4,5-bis(diphenylphosphino)xanthene (21 mg, 0.036 mmol), cesium carbonate (275 mg, 0.84 mmol) and the triflate from Step F above (232 mg, 0.60 mmol) in 1,4-dioxane (2.5 mL), and 2-pyrrolidinone (55 μL, 0.72 mmol). The reaction mixture was degassed with argon for 2 minutes, then tris(dibenzylideneacetone)dipalladium(0) (11 mg, 0.012 mmol) was added under argon. The reaction was heated to 100° C. and stirred for 15 hours, at which time TLC analysis indicated the reaction went to completion. After cooling to room temperature, the mixture was diluted with methylene chloride, filtered through Celite, and concentrated in vacuo. Purification by flash column chromatography (2%-10% methanol/methylene chloride) yielded the desired pyrrolidinone (155 mg, 80%) as a light yellow oil: $[α]^{23}{}_D$ –2.08° (c 0.24, methanol); $^1$H NMR (500 MHz, CDCl$_3$) δ 7.50-7.49 (m, 1H), 7.35 (t, J=7.0 Hz, 2H), 7.27-7.24 (m, 2H), 7.16 (t, J=7.0 Hz, 2H), 6.71-6.63 (br, 1H), 4.31-4.30 (m, 1H), 3.98-3.89 (m, 1H), 3.85-3.81 (m, 2H), 3.79-3.76 (m, 1H), 3.17-3.11 (m, 1H), 3.01-2.96 (m, 1H), 2.59 (t, J=8.0 Hz, 2H), 2.36 (s, 3H), 2.35-2.29 (m, 1H), 2.18-2.13 (m, 1H), 2.14 (t, J=8.0 Hz, 2H); ESI MS m/z 321 [M+H]$^+$.

Step H: To a stirred solution of the pyrrolidinone from Step G above (142 mg, 0.44 mmol) in methanol (4 mL) at room temperature was added maleic acid (51 mg, 0.44 mmol). The mixture was stirred at room temperature for 1 h and then the solvent was concentrated to approximately 0.5 mL. After diluting with water (2 mL), the mixture was lyophilized for 15 h to provide (+)-1-(2-methyl-5-phenyl-2,3,4,5-tetrahydro-1H-benzo[c]azepin-8-yl)pyrrolidin-2-one, maleate salt (189 mg, 98%, 98.3% AUC HPLC) as a light yellow powder: $^1$H NMR (500 MHz, CD$_3$OD) δ 7.86-7.85 (m, 1H), 7.51-7.41 (m, 1H), 7.42-7.39 (m, 2H), 7.33-7.29 (m, 1H), 7.24-7.15 (br, 2H), 7.05-6.55 (br, 1H), 6.25 (s, 2H), 4.73-4.58 (m, 2H), 4.40-4.29 (m, 1H), 3.93-3.90 (m, 2H), 3.66-3.57 (m, 2H), 3.02-2.84 (m, 3H), 2.60 (t, J=8.0 Hz, 2H), 2.48-2.39 (m, 2H), 2.19 (t, J=7.5 Hz, 2H); ESI MS m/z 321 [M+H]$^+$.

Example 37

Preparation of (−)-1-(2-methyl-5-phenyl-2,3,4,5-tetrahydro-1H-benzo[c]azepin-8-yl)pyrrolidin-2-one, maleate salt Pursuant to the general method described above in Example 36, the following product was prepared: (−)-1-(2-methyl-5-phenyl-2,3,4,5-tetrahydro-1H-benzo[c]azepin-8-yl)pyrrolidin-2-one, maleate salt: $^1$H NMR (500 MHz, CD$_3$OD) δ 7.86-7.85 (m, 1H), 7.51-7.41 (m, 1H), 7.42-7.39 (m, 2H), 7.33-7.29 (m, 1H), 7.24-7.15 (br, 2H), 7.05-6.55 (br, 1H), 6.25 (s, 2H), 4.73-4.58 (m, 2H), 4.40-4.29 (m, 1H), 3.94-3.90 (m, 2H), 3.66-3.57 (m, 2H), 3.02-2.84 (m, 3H), 2.60 (t, J=8.0 Hz, 2H), 2.48-2.39 (m, 2H), 2.19 (t, J=7.5 Hz, 2H); ESI MS m/z 321 [M+H]$^+$.

Example 38

Preparation of (+)-1-(2-methyl-5-phenyl-2,3,4,5-tetrahydro-1H-benzo[c]azepin-8-yl)piperidin-2-one, maleate salt Pursuant to the general method described above in Example 36, the following product was prepared: (+)-1-(2-methyl-5-phenyl-2,3,4,5-tetrahydro-1H-benzo[c]azepin-8-yl)piperidin-2-one, maleate salt: $^1$H NMR (500 MHz, CD$_3$OD) δ 7.42-7.39 (m, 3H), 7.33-7.31 (m, 1H), 7.27-7.19 (m, 3H), 7.06-6.69 (br, 1H), 6.25 (s, 2H), 4.69-4.61 (m, 2H), 4.39-4.30 (m, 1H), 3.69-3.63 (m, 2H), 3.70-3.48 (m, 2H), 3.01-2.88 (m, 3H), 2.54-2.51 (m, 2H), 2.48-2.40 (m, 2H), 2.01-1.92 (m, 4H); ESI MS m/z 335 [M+H]$^+$.

Example 39

Preparation of (+)-5-(4-chlorophenyl)-2-methyl-8-(6-methyl-pyridazin-3-yl)-2,3,4,5-tetrahydro-1H-benzo[c]azepine, hydrochloride salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction mixture was allowed to stir at room temperature under N$_2$ overnight. The reaction was then cooled to 0° C. and sodium borohydride (6.19 g, 163.8 mmol) was added in portions. After warming to room temperature, the reaction was allowed to stir for 3 hours. The mixture was then concentrated under reduced pressure, dissolved in H$_2$O, and extracted with methylene chloride (3×). The combined methylene chloride extracts were then extracted with 1 N HCl (3×) and the pH of the combined HCl extracts was adjusted to 10 by addition of 6 N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, CDCl$_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of 4-chlorocinnamic acid (2.0 g, 10.9 mmol) and N-methylmorpholine (1.7 mL, 15.3 mmol) in anhydrous methylene chloride (80 mL) was cooled to −20° C. Isobutyl chloroformate (1.5 mL, 11.6 mmol) was added dropwise. After 15 minutes, a solution of the product from Step A (1.66 g, 10.9 mmol) in anhydrous methylene chloride (20 mL) was added dropwise. The reaction was allowed to warm to room temperature and stir under N$_2$ for 3 hours. The reaction mixture was then washed with 1 M NaH$_2$PO$_4$.2H$_2$O (2×), H$_2$O (2×), and brine, then dried over sodium sulfate, filtered, and concentrated in vacuo. Purification via flash column chromatography (1:1 ethyl acetate/hexanes) yielded the desired amide (2.82 g, 82%) as a white solid: $^1$H NMR (300 MHz, CDCl$_3$) δ 7.70 (dd, J=15.3, 4.8 Hz, 1H), 7.48 (d, J=8.4 Hz, 1H), 7.39 (d, J=8.4 Hz, 1H), 7.35 (d, J=8.4 Hz, 1H), 7.30 (d, J=8.4 Hz, 1H), 7.29 (m, 1H), 6.91 (d, J=15.3 Hz, 1H), 6.83

(s, 1H), 6.80 (m, 1H), 6.77 (d, J=15.3 Hz, 1H), 4.69-4.65 (m, 2H), 3.80 (s, 3H), 3.09-3.07 (m, 3H); ESI MS m/z=316 [$C_{18}H_{18}ClNO_2$+H]$^+$.

Step C: An excess of polyphosphoric acid (10 g) in 1,2-dichloroethane (40 mL) was heated to 100° C. A solution of the product from Step B (6.1 g, 19.3 mmol) in 1,2-dichloroethane (35 mL) was added dropwise. The reaction was then allowed to stir at 100° C. overnight under $N_2$. After cooling to room temperature, the reaction was mixed with ice and the pH adjusted to 10 using 6 N NaOH. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (1.9 g) as a yellow foam: $^1$H NMR (500 MHz, CDCl$_3$) δ 7.24 (d, J=8.5 Hz, 2H), 7.00 (d, J=8.5 Hz, 2H), 6.83 (d, J=8.5 Hz, 1H) 6.72 (dd, J=8.5, 2.5 Hz, 1H), 6.67 (d, J=3.0 Hz, 1H), 4.91 (d, J=16.5 Hz, 1H), 4.44 (dd, J=10.5, 5.0 Hz, 1H), 4.19 (d, J=16.5 Hz, 1H), 3.79 (s, 3H), 3.16 (dd, J=13.5, 11.0 Hz, 1H), 3.05 (s, 3H), 2.98 (dd, J=13.5, 5.0 Hz, 1H).

Step D: To a stirred solution of lithium aluminum hydride (1 M solution in THF, 6.6 mL, 6.6 mmol) at 0° C. under $N_2$ was added a solution of the product of Step C (1.89 g, 6.0 mmol) in anhydrous THF (40 mL) dropwise. The reaction mixture was heated to reflux and allowed to stir for 2 hours. The reaction was then cooled back down to 0° C. and quenched slowly with 1 N NaOH (15 mL). After diluting with $H_2O$, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (829 mg, 14% over two steps) as a light yellow oil: $^1$H NMR (500 MHz, CDCl$_3$) δ 7.31 (d, J=8.5 Hz, 2H), 7.10 (d, J=8.5 Hz, 2H), 6.74 (d, J=3.0 Hz, 1H), 6.61 (dd, J=8.5, 2.5 Hz, 1H), 6.55 (br s, 1H), 4.23 (d, J=8.0 Hz, 1H), 3.86-3.84 (m, 1H), 3.77 (s, 3H), 3.67 (d, J=14.0 Hz, 1H), 3.10-3.07 (m, 1H), 2.94 (ddd, J=12.8, 9.5, 2.5 Hz, 1H), 2.34 (s, 3H), 2.30-2.23 (m, 1H), 2.10-2.03 (m, 1H); ESI MS m/z=302 [$C_{18}H_{20}ClNO$+H]$^+$. This compound was resolved by preparative chiral HPLC (CHIRALPAK AD column, using 9:1:0.01 heptane/ethanol/triethylamine as the eluent) to give the (+)-enantiomer [[α]$^{25}_D$+5.00 (c 0.1, methanol)] and the (−)-enantiomer [[α]$^{25}_D$−20.00 (c 0.1, methanol)].

Step E: A mixture of (+)-5-(4-chlorophenyl)-8-methoxy-2-methyl-2,3,4,5-tetrahydro-1H-benzo[c]azepine (252 mg, 0.84 mmol) and HBr (48% solution in $H_2O$, 6.5 mL) was heated to reflux and allowed to stir for 2 hours. The solvent and excess HBr were removed under reduced pressure and the resulting solid was partitioned between ethyl acetate and saturated NaHCO$_3$ (aq). After separating the two layers, the aqueous phase was extracted with ethyl acetate (3×). The combined extracts were dried over sodium sulfate, filtered, and concentrated in vacuo to provide the desired phenol (228 mg, 95%) as a tan solid.: $^1$H NMR (500 MHz, CDCl$_3$) δ 7.31 (d, J=8.0 Hz, 2H), 7.09 (d, J=8.5 Hz, 2H), 6.57 (d, J=2.5 Hz, 1H), 6.48-6.47 (m, 1H), 6.48-6.39 (m, 1H), 4.20 (d, J=8.5 Hz, 1H), 3.84-3.74 (m, 1H), 3.62 (d, J=14.0 Hz, 1H), 3.12-3.05 (m, 1H), 2.90 (ddd, J=12.8, 9.5, 2.5 Hz, 1H), 2.41 (s, 3H), 2.30 (m, 1H), 2.14-2.06 (m, 1H); ESI MS m/z=288 [$C_{17}H_{18}ClNO$+H]$^+$.

Step F: To a stirred mixture of the product of Step E (226 mg, 0.78 mmol) and pyridine (76 µL, 0.94 mmol) in anhydrous CH$_2$Cl$_2$ (8 mL) at 0° C. under $N_2$ was added triflic anhydride (0.16 mL, 0.94 mmol). Stirring was continued at 0° C. for one hour at which time TLC analysis indicated that the reaction had gone to completion. The mixture was then diluted with CH$_2$Cl$_2$, washed with sat. NaHCO$_3$ (aq) and brine, dried over sodium sulfate, filtered, and concentrated in vacuo. Purification via flash column chromatography (1:1 ethyl acetate/hexanes) provided the desired triflate (265 mg, 80%) as a yellow oil: $^1$H NMR (500 MHz, CDCl$_3$) δ 7.35 (d, J=8.5 Hz, 2H), 7.10 (d, J=10.0 Hz, 2H), 7.09 (s, 1H), 6.97 (dd, J=8.5, 2.5 Hz, 1H), 6.70-6.63 (m, 1H), 4.30 (d, J=9.5 Hz, 1H), 3.96 (d, J=14.0 Hz, 1H), 3.72 (d, J=14.5 Hz, 1H), 3.14-3.11 (m, 1H), 2.99 (ddd, J=13.3, 10.0, 3.0 Hz, 1H), 2.35 (s, 3H), 2.28 (m, 1H), 2.09-2.03 (m, 1H); ESI MS m/z=420 [$C_{18}H_{17}ClF_3NO_3S$+H]$^+$.

Step G: To a disposable sealed tube were added bis(pinacolato)diboron (173 mg, 0.68 mmol), potassium acetate (182 mg, 1.86 mmol), and the product of Step F (260 mg, 0.62 mmol) as a solution in anhydrous DMSO (5 mL). The reaction mixture was degassed by a subsurface purge with Ar for one minute. PdCl$_2$(dppf).CH$_2$Cl$_2$ (15 mg, 0.019 mmol) was then added under Ar. The reaction was heated to 80° C. and allowed to stir for 2 hours, at which time ESI MS showed that the reaction had gone to completion. After cooling to room temperature, the reaction mixture was diluted with H$_2$O, δ then extracted with ethyl acetate (3×). The combined extracts were dried over sodium sulfate, filtered, and concentrated in vacuo. Partial purification via flash column chromatography (95:5 CH$_2$Cl$_2$MeOH) provided the desired boronate ester (246 mg) as a dark brown oil: $^1$H NMR (500 MHz, CDCl$_3$) δ 7.66 (s, 1H), 7.68-7.64 (m, 1H), 7.32 (d, J=8.5 Hz, 2H), 7.04 (d, J=7.0 Hz, 2H), 6.85-6.77 (m, 1H), 4.36 (d, J=8.5 Hz, 1H), 4.13-4.07 (m, 1H), 3.99 (d, J=14.5 Hz, 1H), 3.29-3.23 (m, 1H), 3.20-3.13 (m, 1H), 2.49 (s, 3H), 2.42-2.34 (m, 1H), 2.31-2.24 (m, 1H), 1.34 (s, 6H), 1.24 (s, 6H); ESI MS m/z=398 [$C_{23}H_{29}BClNO_2$+H]$^+$.

Step H: To a disposable sealed tube were added the product of Step G (123 mg, 0.31 mmol) as a solution in anhydrous DMF (2.6 mL), sodium carbonate (98 mg, 0.93 mmol) as a solution in H$_2$O (0.6 mL), and 3-chloro-6-methylpyridazine (48 mg, 0.37 mmol). The reaction mixture was degassed by a subsurface purge with Ar for one minute. PdCl$_2$(dppf).CH$_2$Cl$_2$ (15 mg, 0.019 mmol) was then added under Ar. The reaction was heated to 100° C. and allowed to stir overnight. TLC analysis showed that the reaction had gone to completion. After cooling to room temperature, the reaction mixture was diluted with H$_2$O, and then extracted with ethyl acetate (3×). The combined extracts were dried over sodium sulfate, filtered, and concentrated in vacuo. Purification via flash column chromatography (95:5 CH$_2$Cl$_2$/MeOH) yielded the desired pyridazine (58 mg, 52% for two steps) as a brown oil: [α]$^{25}_D$−7.14° (c 0.14, methanol); $^1$H NMR (500 MHz, CDCl$_3$) δ 7.96 (d, J=2.0 Hz, 1H), 7.75 (d, J=8.0 Hz, 1H), 7.71 (d, J=8.5 Hz, 1H), 7.36 (d, J=8.5, 1H), 7.34 (d, J=8.5 Hz, 2H), 7.14 (d, J=8.5 Hz, 2H), 6.80 (br s, 1H), 4.37 (d, J=8.5 Hz, 1H), 4.03-3.98 (m, 1H), 3.85 (d, J=14.0 Hz, 1H), 3.16-3.11 (m, 1H), 3.00 (ddd, J=12.5, 9.5, 2.0 Hz, 1H), 2.75 (s, 3H), 2.38 (s, 3H), 2.37-2.30 (m, 1H), 2.17-2.11 (m, 1H); ESI MS m/z=364 [$C_{22}H_{22}ClN_3$+H]$^+$.

Step I: The product of Step H (43 mg, 0.12 mmol) was converted to its hydrochloride salt by dissolving the oil in a minimum amount of ether, adding one equivalent of HCl (1 M solution in ether), and sonicating the solution for a few minutes until salt precipitation occurred. Filtration yielded (+)-5-(4-chlorophenyl)-2-methyl-8-(6-methyl-pyridazin-3-yl)-2,3,4,5-tetrahydro-1H-benzo[c]azepine, hydrochloride salt (34 mg, 72%, 98.8% AUC HPLC) as a light brown solid: mp 179-181° C. (dec); ESI MS m/z=364 [$C_{22}H_{22}ClN_3$+H]$^+$.

Example 40

Preparation of (+)-5-(4-chlorophenyl)-2-methyl-8-pyridazin-3-yl-2,3,4,5-tetrahydro-1H-benzo[c]azepine, hydrochloride salt Pursuant to the general method described above in Example 39, the following product was prepared: (+)-5-(4-chlorophenyl)-2-methyl-8-pyridazin-3-yl-2,3,4,5-tetrahydro-1H-benzo[c]azepine, hydrochloride salt: mp 187-189° C. (dec); ESI MS m/z=350 $[C_{21}H_{20}ClN_3+H]^+$.

Example 41

Preparation of (+)-5-(4-chlorophenyl)-2-methyl-8-(pyrazin-2-yl)-2,3,4,5-tetrahydro-1H-benzo[c]azepine, maleate salt and (−)-5-(4-chlorophenyl)-2-methyl-8-(pyrazin-2-yl)-2,3,4,5-tetrahydro-1H-benzo[c]azepine, maleate salt Pursuant to the general method described above in Example 39, the following products were prepared: (+)-5-(4-chlorophenyl)-2-methyl-8-(pyrazin-2-yl)-2,3,4,5-tetrahydro-1H-benzo[c]azepine, maleate salt: mp=87-89° C.; $^1$H NMR (500 MHz, CDCl$_3$) δ 9.14 (s, 1H), 8.69 (s, 1H), 8.56 (s, 1H), 8.25 (s, 1H), 8.11-8.05 (m, 1H), 7.45 (d, J=8.0 Hz, 2H), 7.29-7.22 (m, 2H), 7.15-6.85 (br, 1H), 6.25 (s, 2H), 4.85-4.74 (br, 1H), 4.72-4.68 (m, 1H), 4.53-4.44 (br, 1H), 3.70-3.63 (m, 2H), 3.02-2.93 (br, 3H), 2.70-2.50 (br, 1H), 2.49-2.42 (m, 1H); ESI MS m/z=350 $[C_{21}H_{20}ClN_3+H]^+$; (−)-5-(4-chlorophenyl)-2-methyl-8-(pyrazin-2-yl)-2,3,4,5-tetrahydro-1H-benzo[c]azepine, maleate salt: mp 82-84° C.; $^1$H NMR (500 MHz, CDCl$_3$) δ 9.14 (s, 1H), 8.69 (s, 1H), 8.56 (s, 1H), 8.25 (s, 1H), 8.11-8.05 (m, 1H), 7.45 (d, J=8.0 Hz, 2H), 7.29-7.22 (m, 2H), 7.15-6.85 (br, 1H), 6.25 (s, 2H), 4.85-4.74 (br, 1H), 4.72-4.68 (m, 1H), 4.53-4.44 (br, 1H), 3.70-3.63 (m, 2H), 3.02-2.93 (br, 3H), 2.70-2.50 (br, 1H), 2.49-2.42 (m, 1H); ESI MS m/z=350 $[C_{21}H_{20}ClN_3+H]^+$.

Example 42

Preparation of (−)-5-(4-chlorophenyl)-8-(3,5-dimethylisoxazol-4-yl)-2-methyl-2,3,4,5-tetrahydro-1H-benzo[c]azepine, maleate salt Pursuant to the general method described above in Example 39, the following product was prepared: (−)-5-(4-chlorophenyl)-8-(3,5-dimethylisoxazol-4-yl)-2-methyl-2,3,4,5-tetrahydro-1H-benzo[c]azepine, maleate salt: mp 66-68° C.; $^1$H NMR (500 MHz, CD$_3$OD) δ 7.47 (s, 1H), 7.44 (d, J=8.0 Hz, 2H), 7.36-7.30 (m, 1H), 7.29-7.21 (m, 2H), 7.04-6.78 (br, 1H), 6.25 (s, 2H), 4.77-4.70 (br, 1H), 4.66 (d, J=9.0 Hz, 1H), 4.46-4.39 (br, 1H), 3.69-3.58 (m, 2H), 3.02-2.89 (br, 3H), 2.70-2.50 (br, 1H), 2.48-2.42 (m, 1H), 2.41 (s, 3H), 2.25 (s, 3H); ESI MS m/z=367 $[C_{22}H_{23}ClN_2O+H]^+$.

Example 43

Preparation of (+)-5-(4-chlorophenyl)-8-(3,5-dimethylisoxazol-4-yl)-2-methyl-2,3,4,5-tetrahydro-1H-benzo[c]azepine, maleate salt Pursuant to the general method described above in Example 39, the following product was prepared: (+)-5-(4-chlorophenyl)-8-(3,5-dimethylisoxazol-4-yl)-2-methyl-2,3,4,5-tetrahydro-1H-benzo[c]azepine, maleate salt: mp 196-198° C.; $^1$H NMR (500 MHz, CD$_3$OD) δ 7.47 (s, 1H), 7.44 (d, J=8.0 Hz, 2H), 7.36-7.30 (m, 1H), 7.29-7.21 (m, 2H), 7.04-6.78 (br, 1H), 6.25 (s, 2H), 4.77-4.70 (br, 1H), 4.66 (d, J=9.0 Hz, 1H), 4.46-4.39 (br, 1H), 3.69-3.58 (m, 2H), 3.02-2.89 (br, 3H), 2.70-2.50 (br, 1H), 2.48-2.42 (m, 1H), 2.41 (s, 3H), 2.25 (s, 3H); ESI MS m/z=367 $[C_{22}H_{23}ClN_2O+H]^+$.

Example 44

Preparation of (+)-5-(4-chlorophenyl)-2-methyl-8-pyrimidin-2-yl-2,3,4,5-tetrahydro-1H-benzo[c]azepine, maleate salt Pursuant to the general method described above in Example 39, the following product was prepared: (+)-5-(4-chlorophenyl)-2-methyl-8-pyrimidin-2-yl-2,3,4,5-tetrahydro-1H-benzo[c]azepine, maleate salt: mp 84-85° C.; $^1$H NMR (500 MHz, CD$_3$OD) δ 8.85 (d, J=5.0 Hz, 2H), 8.53 (d, J=1.5 Hz, 1H), 8.41-8.35 (m, 1H), 7.44 (d, J=8.5 Hz, 2H), 7.39 (d, J=5.0 Hz, 1H), 7.27-7.21 (m, 2H), 7.15-6.78 (br, 1H), 6.26 (s, 2H), 4.71-4.69 (m, 1H), 4.53-4.41 (br, 2H), 3.69-3.59 (m, 2H), 3.02-2.91 (br, 3H), 2.71-2.50 (br, 1H), 2.49-2.42 (m, 1H); ESI MS m/z=350 $[C_{21}H_{20}ClN_3+H]^+$.

Example 45

Preparation of {6-[5-(4-chlorophenyl)-2-methyl-2,3,4,5-tetrahydro-1H-benzo[c]azepine-8-yl]-pyridazin-3-yl}-dimethylamine, maleate salt, single enantiomer Pursuant to the general method described above in Example 39, the following product was prepared: {6-[5-(4-chlorophenyl)-2-methyl-2,3,4,5-tetrahydro-1H-benzo[c]azepine-8-yl]-pyridazin-3-yl}-dimethylamine, maleate salt, single enantiomer: mp 96-98° C.; $^1$H NMR (500 MHz, CD$_3$OD) δ 8.09 (s, 1H), 7.99 (d, J=9.0 Hz, 1H), 7.91-7.86 (m, 1H), 7.44-7.39 (m, 3H), 7.27-7.22 (m, 2H), 7.05-6.85 (br, 1H), 6.23 (s, 2H), 4.03-4.69 (br, 1H), 4.68 (d, J=7.0 Hz, 1H), 4.50-4.43 (m, 1H), 3.67-3.58 (m, 2H), 3.26 (s, 6H), 3.01-2.95 (br, 3H), 2.68-2.53 (br, 1H), 2.47-2.42 (m, 1H); ESI MS m/z=393 $[C_{23}H_{25}ClN_4+H]^+$.

Example 46

Preparation of (−)-{6-[5-(4-chlorophenyl)-2-methyl-2,3,4,5-tetrahydro-1H-benzo[c]azepine-8-yl]-pyridazin-3-yl}-dimethylamine, maleate salt Pursuant to the general method described above in Example 39, the following product was prepared: (−)-{6-[5-(4-chlorophenyl)-2-methyl-2,3,4,5-tetrahydro-1H-benzo[c]azepine-8-yl]-pyridazin-3-yl}-dimethylamine, maleate salt: mp 109-110° C.; $^1$H NMR (500 MHz, CD$_3$OD) δ 8.08 (m, 1H), 7.86 (d, J=9.5 Hz, 2H), 7.43 (d, J=8.5 Hz, 2H), 7.27-7.20 (br, 1H), 7.22 (d, J=9.5 Hz, 2H), 7.14-6.78 (br, 1H), 6.24 (s, 2H), 4.82-4.62 (br, 1H), 4.67 (d, J=10.0 Hz, 1H), 4.46-4.43 (m, 1H), 3.68-3.54 (m, 2H), 3.22 (s, 6H), 2.99-2.94 (m, 3H), 2.70-2.52 (br, 1H), 2.46-2.41 (m, 1H); ESI MS m/z 393 [M+H]$^+$.

Example 47

Preparation of (−)-4-(5-(4-chlorophenyl)-2-methyl-2,3,4,5-tetrahydro-1H-benzo[c]azepin-8-yl)morpholine, maleate salt Step A: To a stirred solution of methylamine (40% in H$_2$O) (28.2 mL, 327.6 mmol) in methanol (100 mL) at room temperature was added m-anisaldehyde (20.6 mL, 163.8 mmol) as a solution in methanol (50 mL) dropwise over 20 minutes. The reaction was stirred at room temperature under $N_2$ for 15 hours, then cooled to 0° C. and sodium borohydride (6.19 g, 163.8 mmol) was added in portions. After warming to room temperature, the reaction was stirred for 3 hours, then the mixture was concentrated under reduced pressure, dissolved in $H_2O$, and extracted with methylene chloride (3×). The combined methylene chloride extracts were extracted with 1N HCl (3×) and the combined HCl extracts adjusted to pH 10 by addition of 6N NaOH. The aqueous mixture was then extracted with methylene chloride (3×). The combined methylene chloride extracts were dried over sodium sulfate, filtered, and concentrated in vacuo to give the desired amine (25.0 g, quantitative yield) as a light yellow oil: $^1$H NMR (300 MHz, $CDCl_3$) δ 7.27-7.22 (m, 1H), 6.91-6.89 (m, 1H), 6.89 (s, 1H), 6.82-6.79 (m, 1H), 3.81 (s, 3H), 3.74 (s, 2H), 2.46 (s, 3H).

Step B: A solution of 4-chlorocinnamic acid (2.0 g, 10.9 mmol) and N-methylmorpholine (1.7 mL, 15.3 mmol) in anhydrous methylene chloride (80 mL) was cooled to –20° C. and isobutyl chloroformate (1.5 mL, 11.6 mmol) was added dropwise. After 15 minutes, a solution of the amine from Step A above (1.66 g, 10.9 mmol) in anhydrous methylene chloride (20 mL) was added dropwise, then the reaction was allowed to warm to room temperature and stir under $N_2$ for 3 hours. The mixture was washed with 1M sodium dihydrogen phosphate dihydrate (2×), $H_2O$ (2×), and brine, dried over sodium sulfate, filtered, and concentrated in vacuo. Purification via flash column chromatography (1:1 ethyl acetate/hexanes) yielded the desired amide (2.82 g, 82%) as a white solid: $^1$H NMR (300 MHz, $CDCl_3$) δ 7.70 (dd, J=15.3, 4.8 Hz, 1H), 7.48 (d, J=8.4 Hz, 1H), 7.39 (d, J=8.4 Hz, 1H), 7.35 (d, J=8.4 Hz, 1H), 7.30 (d, J=8.4 Hz, 1H), 7.40-7.26 (m, 1H), 6.91 (d, J=15.3 Hz, 1H), 6.83 (s, 1H), 6.83 (d, J=12.3 Hz, 1H), 6.77 (d, J=15.3 Hz, 1H), 4.67 (d, J=12.3 Hz, 2H), 3.80 (s, 3H), 3.08 (d, J=4.2 Hz, 3H); ESI MS m/z 316 [M+H]$^+$.

Step C: An excess of polyphosphoric acid (2 g) in 1,2-dichloroethane (10 mL) was heated to 100° C. A solution of the amide from Step B above (527 mg, 1.7 mmol) in 1,2-dichloroethane (5 mL) was added dropwise. The reaction was stirred at 100° C. for 15 hours under $N_2$. After cooling to room temperature, the reaction was mixed with ice and the pH adjusted to 10 using 6N NaOH. The reaction mixture was then extracted with ethyl acetate (3×) and the combined extracts were dried over sodium sulfate, filtered, and concentrated in vacuo. Partial purification via flash column chromatography (30-100% ethyl acetate/hexanes) yielded the desired product (199 mg) as a yellow foam: $^1$H NMR (500 MHz, $CDCl_3$) δ 7.24 (d, J=8.5 Hz, 2H), 7.00 (d, J=8.5 Hz, 2H), 6.83 (d, J=8.5 Hz, 1H) 6.72 (dd, J=8.5, 2.5 Hz, 1H), 6.67 (d, J=3.0 Hz, 1H), 4.91 (d, J=16.5 Hz, 1H), 4.44 (dd, J=10.5, 5.0 Hz, 1H), 4.19 (d, J=16.5 Hz, 1H), 3.79 (s, 3H), 3.16 (dd, J=13.5, 11.0 Hz, 1H), 3.05 (s, 3H), 2.98 (dd, J=13.5, 5.0 Hz, 1H).

Step D: To a stirred solution of lithium aluminum hydride (1M solution in THF, 0.48 mL, 0.48 mmol) at 0° C. under $N_2$ was added a solution of the product from Step C above (139 mg, 0.44 mmol) in anhydrous THF (4 mL) dropwise. The reaction mixture was heated to reflux and allowed to stir for 2 hours. The reaction was then cooled back down to 0° C. and quenched slowly with 1N NaOH (1 mL). After diluting with $H_2O$, the aqueous phase was extracted with ethyl acetate (3×) and the combined extracts were washed with brine, dried over sodium sulfate, filtered, and concentrated in vacuo. Purification via flash column chromatography (1:1 ethyl acetate/hexanes) yielded the desired benzazepine (67 mg, 19% two steps) as a light yellow oil: $^1$H NMR (500 MHz, $CDCl_3$) δ 7.31 (d, J=8.5 Hz, 2H), 7.10 (d, J=8.5 Hz, 2H), 6.74 (d, J=3.0 Hz, 1H), 6.61 (dd, J=8.5, 2.5 Hz, 1H), 6.55 (br, 1H), 4.24-4.22 (m, 1H), 3.86-3.84 (m, 1H), 3.77 (s, 3H), 3.68-3.65 (m, 1H), 3.10-3.07 (m, 1H), 2.96-2.91 (m, 1H), 2.34 (s, 3H), 2.30-2.23 (m, 1H), 2.10-2.03 (m, 1H); ESI MS m/z 302 [M+H]$^+$. This compound was resolved by preparative chiral HPLC (CHIRALPAK AD column, using 9:1:0.01 heptane/ethanol/diethylamine as the eluent) to give the (+)-enantiomer [[α]$^{25}_D$+5.0° (c 0.1, methanol)] and the (–)-enantiomer [[α]$^{25}_D$–20.0° (c 0.1, methanol)].

Step E: A mixture of the benzazepine from Step D above (1.40 g, 4.6 mmol) and hydrobromic acid (48% solution in $H_2O$, 30 mL) was heated to reflux and stirred for 2 hours. The solvent and excess hydrobromic acid were removed under reduced pressure and the resulting solid was partitioned between ethyl acetate and saturated sodium bicarbonate (aq). After separating the two layers, the aqueous phase was extracted with ethyl acetate (3×). The combined extracts were dried over sodium sulfate, filtered, and concentrated in vacuo to provide the desired phenol (1.09 g, 82%) as a tan solid: $^1$H NMR (500 MHz, $CDCl_3$) δ 7.31 (d, J=8.0 Hz, 2H), 7.09 (d, J=8.5 Hz, 2H), 6.57-6.56 (m, 1H), 6.48-6.47 (m, 1H), 6.48-6.39 (m, 1H), 4.20 (d, J=8.5 Hz, 1H), 3.84-3.74 (m, 1H), 3.64-3.61 (m, 1H), 3.12-3.05 (m, 1H), 2.93-2.88 (m, 1H), 2.41 (s, 3H), 2.34-2.26 (m, 1H), 2.14-2.06 (m, 1H); ESI MS m/z 288 [M+H]$^+$.

Step F: To a stirred mixture of the phenol from Step E above (552 mg, 1.9 mmol) and pyridine (0.2 mL, 2.3 mmol) in anhydrous methylene chloride (19 mL) at 0° C. under $N_2$ was added triflic anhydride (0.4 mL, 2.3 mmol). The reaction was stirred at 0° C. for 1 hour, at which time TLC analysis indicated the reaction went to completion. The mixture was then diluted with methylene chloride, washed with saturated sodium bicarbonate (aq) and brine, dried over sodium sulfate, filtered, and concentrated in vacuo. Purification via flash column chromatography (1:1 ethyl acetate/hexanes) provided the desired triflate (457 mg, 57%) as a yellow oil: $^1$H NMR (500 MHz, $CDCl_3$) δ 7.35 (d, J=8.5 Hz, 2H), 7.10 (d, J=10.0 Hz, 2H), 7.09 (s, 1H), 6.97 (dd, J=8.5, 2.5 Hz, 1H), 6.70-6.63 (m, 1H), 4.30 (d, J=9.5 Hz, 1H), 3.96 (d, J=14.0 Hz, 1H), 3.72 (d, J=14.5 Hz, 1H), 3.14-3.11 (m, 1H), 2.99 (ddd, J=13.3, 10.0, 3.0 Hz, 1H), 2.35 (s, 3H), 2.28 (m, 1H), 2.09-2.03 (m, 1H); ESI MS m/z 420 [M+H]$^+$.

Step G: To a stirred solution of the triflate from Step F above (252 mg, 0.60 mmol) in anhydrous toluene (6 mL) at room temperature were added morpholine (0.10 mL, 1.2 mmol), cesium carbonate (586 mg, 1.8 mmol), and 2-(dicyclohexylphosphino)-2',4',6'-tri-i-isopropyl-1,1'-biphenyl (86 mg, 0.18 mmol). The reaction mixture was degassed with argon for 2 minutes, then palladium(II) acetate (20 mg, 0.09 mmol) was added under argon. The reaction was heated to reflux and stirred for 24 hours, at which time ESI MS indicated the reaction went to completion. After cooling to room temperature, the mixture was diluted with methylene chloride and filtered through Celite. The filtrate was washed with saturated ammonium chloride (aq) and brine, dried over sodium sulfate, filtered, and concentrated in vacuo. Purification via flash column chromatography (2%-10% methanol/methylene chloride) yielded the desired morpholine (73 mg, 34%) as a light yellow oil: [α]$^{23}_D$–2.80° (c 0.18, methanol); $^1$H NMR (500 MHz, $CDCl_3$) δ 7.31 (d, J=8.5 Hz, 2H), 7.10 (d, J=8.0 Hz, 2H), 6.76-6.75 (m, 1H), 6.63-6.60 (m, 1H), 6.58-6.49 (br, 1H), 4.22 (d, J=9.0 Hz, 1H), 3.90-3.84 (m, 1H), 3.85 (t, J=5.0 Hz, 4H), 3.69-3.66 (m, 1H), 3.12 (t, J=5.0 Hz, 4H), 3.11-3.05 (br, 1H), 2.96-2.92 (m, 1H), 2.35 (s, 3H), 2.30-2.23 (m, 1H), 2.09-2.04 (m, 1H); ESI MS m/z 357 [M+H]$^+$.

Step H: To a stirred solution of the morpholine from Step G above (125 mg, 0.35 mmol) in methanol (3 mL) at room temperature was added maleic acid (41 mg, 0.35 mmol). The mixture was stirred for 1 hour and then the solvent was concentrated to approximately 0.5 mL. After diluting with H$_2$O (2 mL), the mixture was lyophilized for 15 hours to provide (−)-4-(5-(4-chlorophenyl)-2-methyl-2,3,4,5-tetrahydro-1H-benzo[c]azepin-8-yl)morpholine, maleate salt (163 mg, 98%, 96.0% AUC HPLC) as a light purple solid: mp 99-100° C.; $^1$H NMR (500 MHz, CD$_3$OD) δ 7.40-7.38 (m, 2H), 7.20-7.14 (br, 2H), 7.06 (s, 1H), 6.94-6.88 (br, 2H), 6.25 (s, 2H), 4.66-4.48 (m, 2H), 4.35-4.20 (br, 1H), 3.83-3.81 (m, 4H), 3.69-3.51 (m, 2H), 3.16-3.14 (m, 4H), 3.02-2.82 (m, 3H), 2.41-2.32 (m, 2H); ESI MS m/z 357 [M+H]$^+$.

Example 48

Preparation of (+)-5-(4-chlorophenyl)-2-methyl-8-morpholin-4-yl-2,3,4,5-tetrahydro-1H-benzo[c] azepine, maleate salt Pursuant to the general method described above in Example 47, the following product was prepared: (+)-5-(4-chlorophenyl)-2-methyl-8-morpholin-4-yl-2,3,4,5-tetrahydro-1H-benzo[c]azepine, maleate salt: mp 94-96° C.; $^1$H NMR (500 MHz, CD$_3$OD) δ 7.39 (d, J=8.5 Hz, 2H), 7.20-7.15 (m, 2H), 7.06 (d, J=2.5 Hz, 1H), 6.93-6.88 (br, 1H), 6.80-6.50 (br, 1H), 6.25 (s, 2H), 4.63-4.45 (br, 1H), 4.49 (d, J=11.0 Hz, 1H), 4.31-4.25 (br, 1H), 3.82 (t, J=5.0 Hz, 4H), 3.61-3.55 (br, 2H), 3.16 (t, J=4.5 Hz, 4H), 2.95-2.85 (br, 3H), 2.41-2.36 (m, 2H); ESI MS m/z 357 [C$_{21}$H$_{25}$ClN$_2$O+H]$^+$.

Example 49

Preparation of (+)-8-methoxy-2-methyl-5-naphthalen-2-yl-2,3,4,5-tetrahydro-1H-benzo[c]azepine, maleate salt and (−)-8-methoxy-2-methyl-5-naphthalen-2-yl-2,3,4,5-tetrahydro-1H-benzo[c]azepine, maleate salt Step A: A solution of 2-naphthylacrylic acid (10.0 g, 50.4 mmol) and N-methylmorpholine (7.8 mL, 70.6 mmol) in anhydrous methylene chloride (307 mL) was cooled to −20° C. Isobutyl chloroformate (7.0 mL, 53.5 mmol) was added dropwise. After 90 minutes, a solution of (3-methoxybenzyl) methylamine (7.63 g, 50.45 mmol) in anhydrous methylene chloride (50 mL) was added dropwise. The reaction was allowed to warm to room temperature and stirred overnight. The reaction mixture was then washed with 1 M NaH$_2$PO$_4$.2H$_2$O (2×), H$_2$O (2×), and brine, dried over sodium sulfate, filtered, and concentrated in vacuo. Purification via flash column chromatography (40:60 to 70:30 ethyl acetate/hexanes) yielded the desired amide (8.60 g, 51%) as a white solid: $^1$H NMR (300 MHz, CDCl$_3$) δ 7.95-7.55 (m, 6H), 7.52-7.45 (m, 2H), 7.35-7.20 (m, 1H), 7.10-6.75 (m, 4H), 4.73-4.69 (m, 2H), 3.81 (s, 3H), 3.14-3.08 (m, 3H).

Step B: An excess of polyphosphoric acid (4 g) was heated to 80° C. A solution of the product from step A (2 g, 6.0 mmol) in 1,2-dichloroethane (10.5 mL) was added dropwise to the hot acid. The reaction mixture was maintained at this temperature for 1 hour, and then chlorobenzene (7 mL) was added to it. The reaction mixture was then heated gradually to 120° C. over the next one hour and 15 minutes, and then allowed to stir at 120° C. overnight. After cooling to room temperature, the reaction was diluted with ethyl acetate and concentrated ammonium hydroxide and stirred for 2 hours. The reaction mixture was then diluted further with water and extracted with dichloromethane (4×). The combined extract was dried over sodium sulfate, filtered, and concentrated in vacuo. Partial purification by flash column chromatography (dichloromethane, then 99:1 to 97:3 methylene chloride/methanol) yielded the desired product (1.20 g) as an inseparable mixture with the undesired regioisomer. The mixture was used in the next step without further purification or characterization.

To a solution of the lactam from above (1.20 g, 3.62 mmol) in tetrahydrofuran (20 mL) at 0° C. was added lithium aluminum hydride (4 mL, 4 mmol, 1 M solution in THF) dropwise. The reaction mixture was warmed to room temperature, and stirred for 45 minutes. The reaction was then cooled back down to 0° C. and quenched carefully with water (3 mL), followed by sodium hydroxide (3 mL, 15% solution in water) and finally, water (9 mL). The mixture was stirred for 20 minutes, and the precipitate formed was removed by filtration. The filtrate was dried over sodium sulfate, filtered, and concentrated in vacuo.

The above steps were repeated once more, using the amide from step A (6.6 g, 19.9 mmol). The two batches of the crude amine were then combined. Partial purification of the crude product via flash column chromatography (90:10 methylene chloride/hexanes, then methylene chloride, and finally, 99:0.9:0.1 to 95:4.5:0.5 methylene chloride/methanol/concentrated ammonium hydroxide) yielded the desired benzazepine as an inseparable mixture with the undesired regioisomer (1.97 g). The regioisomers were separated and resolved by preparative chiral HPLC (CHIRALCEL OJ column, using 90:9:1 heptane/IPA/triethylamine as the eluent) to give the (+)-enantiomer [[α]$^{25}_D$+10° (c 0.12, methanol)] and the (−)-enantiomer [[α]$^{25}_D$−13° (c 0.18, methanol)]: (+)-Enantiomer: $^1$H NMR (500 MHz, CDCl$_3$) δ 7.84-7.68 (m, 3H), 7.58 (br s, 1H), 7.47-7.45 (m, 2H), 7.35 (dd, J=5.1, 1.6 Hz, 1H), 6.77 (s, 1H), 6.57 (br s, 2H), 4.43 (d, J=8.3 Hz, 1H), 4.00-3.84 (m, 1H), 3.77 (s, 3H), 3.77-3.75 (m, 1H), 3.21-3.05 (m, 1H), 3.03-2.89 (m, 1H), 2.47-2.31 (m, 1H), 2.41 (s, 3H), 2.21-2.10 (m, 1H); (−)-Enantiomer: $^1$H NMR (300 MHz, CDCl$_3$) δ 7.85-7.68 (m, 3H), 7.58 (br s, 1H), 7.48-7.45 (m, 2H), 7.35 (d, J=8.5 Hz, 1H), 6.78 (s, 1H), 6.58 (br s, 2H), 4.43 (d, J=8.3 Hz, 1H), 4.00-3.84 (m, 1H), 3.77 (s, 3H), 3.77-3.75 (m, 1H), 3.21-3.05 (m, 1H), 3.03-2.89 (m, 1H), 2.47-2.31 (m, 1H), 2.40 (s, 3H), 2.21-2.10 (m, 1H). (The two enantiomers of the undesired regioisomer were also isolated.)

Step D: To a solution of the (+)-enantiomer (39 mg, 0.12 mmol) in methanol (2 mL), was added maleic acid (14 mg, 0.12 mmol), and the mixture was stirred for 3 hours. Water (10 mL) was added to the mixture, which was then lyophilized to give (+)-8-methoxy-2-methyl-5-naphthalen-2-yl-2,3,4,5-tetrahydro-1H-benzo[c]azepine, maleate salt as a pale yellow solid (52 mg, 99%, 96.0% AUC HPLC): $^1$H NMR (500 MHz, CD$_3$OD) δ 7.95-7.84 (m, 2H), 7.78 (br s, 1H), 7.65-7.49 (br m, 1H), 7.49-7.47 (m, 2H), 7.37 (d, J=8.5 Hz, 1H), 7.08 (s, 1H), 7.05-6.85 (m, 2H), 6.25 (s, 2H), 4.79-4.47 (m, 2H), 4.46-4.21 (m, 1H), 3.81 (s, 3H), 3.68-3.42 (br m, 2H), 3.05-2.26 (br m, 5H).

Step E (SAM-1-174): To a solution of the (−)-enantiomer (38 mg, 0.12 mmol) in methanol (2 mL), was added maleic acid (14 mg, 0.12 mmol), and the mixture was stirred for 3 hours. Water (10 mL) was added to the mixture, which was then lyophilized to give (−)-8-methoxy-2-methyl-5-naphthalen-2-yl-2,3,4,5-tetrahydro-1H-benzo[c]azepine, maleate sal as a pale yellow solid (50 mg, 95%, 95.8% AUC HPLC): $^1$H NMR (500 MHz, CD$_3$OD) δ 7.95-7.84 (m, 2H), 7.78 (br s, 1H), 7.65-7.49 (br m, 1H), 7.49-7.47 (m, 2H), 7.37 (d, J=8.5 Hz, 1H), 7.08 (s, 1H), 7.05-6.85 (m, 2H), 6.25 (s, 2H), 4.79-4.47 (m, 2H), 4.46-4.21 (m, 1H), 3.81 (s, 3H), 3.68-3.42 (br m, 2H), 3.05-2.26 (br m, 5H).

Example 50

Preparation of (+)-2-methyl-5-naphthalen-2-yl-8-pyridazin-3-yl-2,3,4,5-tetrahydro-1H-benzo[c]azepine, maleate salt Step A: A mixture of (+)-8-methoxy-2-methyl-5-naphthalen-2-yl-2,3,4,5-tetrahydro-1H-benzo[c]azepine (592 mg, 1.9 mmol) and HBr (48% solution in H$_2$O, 15 mL) was heated to reflux and allowed to stir for 3 hours. The solvent and excess HBr were removed under reduced pressure and the resulting solid was partitioned between ethyl acetate and saturated NaHCO$_3$ (aq). After separating the two layers, the aqueous phase was extracted with ethyl acetate (3×). The combined extracts were dried over sodium sulfate, filtered, and concentrated in vacuo to provide the desired phenol (540 mg, 95%) as a tan solid.: $^1$H NMR (500 MHz, CDCl$_3$) δ 7.85-7.83 (m, 1H), 7.82 (s, 1H), 7.77-7.75 (m, 1H), 7.59-7.56 (br, 1H), 7.48-7.45 (m, 2H), 7.34 (dd, J=8.5, 1.5 Hz, 1H), 6.61 (s, 1H), 6.47-6.43 (m, 2H), 4.40 (d, J=9.0 Hz, 1H), 3.91-3.83 (br, 1H), 3.69 (d, J=13.5 Hz, 1H), 3.17-3.10 (m, 1H), 2.96 (ddd, J=12.8, 10.0, 2.5 Hz, 1H), 2.49-2.41 (m, 1H), 2.44 (s, 3H), 2.26-2.19 (m, 1H); ESI MS m/z=304 [C$_{21}$H$_{21}$NO+H]$^+$.

Step B: To a stirred mixture of the product of Step A (539 mg, 1.8 mmol) and pyridine (0.17 mL, 2.1 mmol) in anhydrous CH$_2$Cl$_2$ (18 mL) at 0° C. under N$_2$ was added triflic anhydride (0.36 mL, 2.1 mmol). Stirring was continued at 0° C. for one hour at which time TLC analysis indicated the reaction had gone to completion. The mixture was then diluted with CH$_2$Cl$_2$, washed with saturated NaHCO$_3$ (aq) and brine, dried over sodium sulfate, filtered, and concentrated in vacuo. Purification via flash column chromatography (1:1 ethyl acetate/hexanes) provided the desired triflate (640 mg, 83%) as a yellow oil: $^1$H NMR (500 MHz, CDCl$_3$) δ 7.88-7.85 (m, 2H), 7.80-7.78 (m, 1H), 7.62-7.58 (br, 1H), 7.50-7.47 (m, 2H), 7.33 (dd, J=8.5, 1.5 Hz, 1H), 7.11 (d, J=2.5 Hz, 1H), 6.93-6.91 (m, 1H), 6.71-6.66 (br, 1H), 4.49 (d, J=10.0 Hz, 1H), 4.05-4.03 (m, 1H), 3.77 (d, J=14.0 Hz, 1H), 3.20-3.17 (m, 1H), 3.06 (ddd, J=13.0, 10.5, 2.5 Hz, 1H), 2.48-2.40 (m, 1H), 2.38 (s, 3H), 2.21-2.15 (m, 1H); ESI MS m/z=436 [C$_{22}$H$_{20}$F$_3$NO$_3$S+H]$^+$.

Step C: To a disposable sealed tube were added bis(pinacolato)diboron (200 mg, 0.72 mmol), potassium acetate (211 mg, 2.2 mmol), and the product of Step B (312 mg, 0.72 mmol) as a solution in anhydrous DMSO (3 mL). The reaction mixture was degassed by a subsurface sparge with Ar for 2 minutes. PdCl$_2$(dppf).CH$_2$Cl$_2$ (18 mg, 0.022 mmol) was then added under Ar. The reaction was heated to 80° C. and allowed to stir for 3 hours, at which time ESI MS showed that the reaction had gone to completion. After cooling to room temperature, the reaction mixture was diluted with H$_2$O, and then extracted with ethyl acetate (3×). The combined extracts were dried over sodium sulfate, filtered, and concentrated in vacuo. Partial purification via flash column chromatography (95:5 CH$_2$Cl$_2$/MeOH) provided the desired boronate ester as a dark brown oil: ESI MS m/z=414 [C$_{27}$H$_{32}$BNO$_2$+H]$^+$.

Step D: To a disposable sealed tube were added the product of Step C (296 mg, 0.72 mmol) as a solution in anhydrous DMF (3 mL), sodium carbonate (228 mg, 2.2 mmol) as a solution in H$_2$O (1.4 mL), and 3-chloropyridazine (188 mg, 1.6 mmol). The reaction mixture was degassed by a subsurface sparge with Ar for 2 minutes. PdCl$_2$(dppf).CH$_2$Cl$_2$ (35 mg, 0.043 mmol) was then added under Ar. The reaction was heated to 100° C. and allowed to stir overnight. TLC analysis showed that the reaction had gone to completion. After cooling to room temperature, the reaction mixture was diluted with H$_2$O, then extracted with ethyl acetate (3×). The combined extracts were dried over sodium sulfate, filtered, and concentrated in vacuo. Purification via flash column chromatography (95:5 CH$_2$Cl$_2$/MeOH) yielded the desired pyridazine (128 mg, 49% over two steps) as a light brown oil: [α]$^{25}_D$ −2.9° (c 0.07, methanol); $^1$H NMR (500 MHz, CDCl$_3$) δ 9.14 (dd, J=5.0, 2.0 Hz, 1H), 8.03 (d, J=2.0 Hz, 1H), 7.88-7.86 (m, 2H), 7.82 (dd, J=8.5, 1.5 Hz, 1H), 7.80-7.79 (m, 1H), 7.72-7.70 (m, 1H), 7.64-7.61 (m, 1H), 7.52-7.50 (m, 1H), 7.50-7.48 (m, 2H), 7.40 (dd, J=8.5, 1.5 Hz, 1H), 6.87-6.80 (br, 1H), 4.57 (d, J=9.5 Hz, 1H), 4.11-4.05 (m, 1H), 3.92 (d, J=14.5 Hz, 1H), 3.21-3.16 (m, 1H), 3.09-3.03 (m, 1H), 2.53-2.46 (m, 1H), 2.41 (s, 3H), 2.28-2.22 (m, 1H); ESI MS m/z=366 [C$_{25}$H$_{23}$N$_3$+H]$^+$.

Step E: To a stirred solution of the product of Step D (126 mg, 0.35 mmol) in absolute ethanol (3 mL) at room temperature was added maleic acid (40 mg, 0.35 mmol). Stirring was continued for one hour, and the solvents were then removed under reduced pressure. After dissolving in methanol (1 mL) and diluting with H$_2$O (3 mL), the mixture was lyophilized overnight to provide (+)-2-methyl-5-naphthalen-2-yl-8-pyridazin-3-yl-2,3,4,5-tetrahydro-1H-benzo[c]azepine, maleate salt (162 mg, 98%, >99% AUC HPLC) as a light purple solid: mp 99-102° C.; $^1$H NMR (500 MHz, CD$_3$OD) δ 9.18 (dd, J=4.5, 1.0 Hz, 1H), 8.30 (s, 1H), 8.20 (d, J=8.0 Hz, 1H), 8.03-7.98 (br, 1H), 7.96 (d, J=8.5 Hz, 1H), 7.91-7.89 (m, 1H), 7.83-7.80 (m, 2H), 7.72-7.65 (br, 1H), 7.52-7.50 (m, 2H), 7.44 (d, J=8.5 Hz, 1H), 7.24-6.93 (br, 1H), 6.24 (s, 2H), 4.90-4.80 (m, 1H), 4.57-4.55 (m, 1H), 3.75-3.65 (m, 2H), 3.35-3.25 (m, 1H), 3.03-2.97 (br, 3H), 2.85-2.70 (br, 1H), 2.62-2.56 (m, 1H); ESI MS m/z=366 [C$_{25}$H$_{23}$N$_3$+H]$^+$;

Example 51

Preparation of (+)-2-methyl-8-morpholin-4-yl-5-naphthalen-2-yl-2,3,4,5-tetrahydro-1H-benzo[c]azepine, maleate salt Step A: To a stirred solution of trifluoromethanesulfonic acid 2-methyl-5-naphthalen-2-yl-2,5-tetrahydro-1H-benzo[c]azepine-8-yl ester (325 mg, 0.75 mmol) in anhydrous toluene (4.5 mL) were added morpholine (0.13 mL, 1.5 mmol), cesium carbonate (729 mg, 2.2 mmol), and (2-biphenyl)di-tert-butylphosphine (67 mg, 0.22 mmol). The reaction mixture was degassed with argon, then palladium(II)acetate (25 mg, 0.11 mmol) was added and the reaction mixture was degassed again. The reaction was heated to reflux and stirred for 24 hours. After cooling to room temperature, the reaction mixture was diluted with methylene chloride and filtered through Celite. The filtrate was then washed with saturated NH$_4$Cl (aq) and brine, dried over Na$_2$SO$_4$, filtered, and concentrated in vacuo. Purification via MPLC (95:5 methylene chloride/methanol) yielded the desired morpholine distinctive (121 mg, 44%) as a yellow foam: [α]$^{25}_D$ +2.00 (c 0.4, methanol); $^1$H NMR (500 MHz, CDCl$_3$) δ 7.85-7.83 (m, 2H), 7.78-7.76 (m, 1H), 7.60-7.56 (br, 1H), 7.47-7.45 (m, 2H), 7.36 (d, J=8.5 Hz, 1H), 6.79 (s, 1H), 6.61-6.56 (br, 2H), 4.42 (d, J=9.0 Hz, 1H), 3.99-3.90 (m, 1H), 3.84 (t, J=4.5 Hz, 4H), 3.75 (d, J=13.5 Hz, 1H), 3.18-3.11 (m, 1H), 3.12 (t, J=4.5 Hz, 4H), 3.03-2.99 (m, 1H), 2.46-2.39 (m, 1H), 2.39 (s, 3H), 2.22-2.15 (m, 1H); ESI MS m/z=373 [C$_{25}$H$_{28}$N$_2$O+H]$^+$.

Step B: To a stirred solution of the product of Step A (72 mg, 0.19 mmol) in absolute ethanol (2 mL) at room temperature was added maleic acid (22 mg, 0.19 mmol). Stirring was continued for one hour, and the solvents were then removed under reduced pressure. After dissolving in methanol (1 mL) and diluting with H$_2$O (3 mL), the mixture was lyophilized overnight to provide (+)-2-methyl-8-morpholin-4-yl-5-naphthalen-2-yl-2,3,4,5-tetrahydro-1H-benzo[c]azepine, maleate salt (92 mg, 98%, 99.0% AUC HPLC) as an off-white solid: mp=110-112° C.; ¹H NMR (500 MHz, CD₃OD) δ 7.90 (d, J=8.5 Hz, 1H), 7.88-7.86 (m, 1H), 7.82-7.76 (m, 1H), 7.68-7.50 (br, 1H), 7.49-7.47 (m, 2H), 7.37 (d, J=8.5 Hz, 1H), 7.09 (s, 1H), 7.00-6.82 (br, 1H), 6.75-6.55 (br, 1H), 6.25 (s, 2H), 4.68-4.65 (m, 2H), 4.39-4.26 (br, 1H), 3.83 (m, 4H), 3.66-3.57 (br, 2H), 3.17 (m, 4H), 3.02-2.79 (m, 4H), 2.57-2.45 (br, 1H); ESI MS m/z=373 [C₂₅H₂₈N₂O+H];

Example 52

Preparation of (+)-5-benzo[b]thiophen-5-yl-8-methoxy-2-methyl-2,3,4,5-tetrahydro-1H-benzo[c]azepine, maleate salt and (−)-5-benzo[b]thiophen-5-yl-8-methoxy-2-methyl-2,3,4,5-tetrahydro-1H-benzo[c]azepine, maleate salt Step A: To a solution of 5-bromobenzo[b]thiophene (5.0 g, 23.5 mmol) in N,N-dimethylformamide (50 mL) at room temperature were added tri-o-tolylphosphine (0.64 g, 2.1 mmol) and triethylamine (9.9 mL, 70.4 mmol). The reaction mixture was degreased with argon and then ethyl acrylate (7.7 mL, 70.4 mmol) and tris(dibenzylideneacetone)dipalladium (0) (0.65 g, 0.7 mmol) were added to it. The resultant solution was degreased with argon and then heated at 100° C. overnight. The reaction solution was then cooled to room temperature, diluted with ethyl acetate, washed with water (2×), saturated ammonium chloride and brine, dried over sodium sulfate and concentrated under reduced pressure. The crude product obtained was purified by flash column chromatography (95:5 to 93:7 hexanes/ethyl acetate) to give the desired product (2.5 g, 46%) as a light yellow oil: ¹H NMR (CDCl₃, 500 MHz) δ 7.94 (d, J=1.5 Hz, 1H), 7.87 (d, J=8.5 Hz, 1H), 7.81 (d, J=16.0 Hz, 1H), 7.54 (dd, J=8.4 and 1.6 Hz, 1H), 7.49 (d, J=5.4 Hz, 1H), 7.36 (d, J=5.4 Hz, 1H), 6.50 (d, J=15.9 Hz, 1H), 4.28 (q, J=7.2 Hz, 2H), 1.35 (t, J=7.2 Hz, 3H).

Step B: To a solution of the ethyl ester (1.76 g, 7.6 mmol) from step A above in a mixture of tetrahydrofuran (30 mL) and methanol (15 mL) was added aqueous sodium hydroxide (15 mL, 1 M). The reaction solution was stirred at room temperature overnight and then acidified with aqueous hydrochloric acid (3 mL, 6 M). The resultant solution was concentrated under reduced pressure and the residue obtained was diluted with water, and then extracted with a 3:1 mixture of chloroform and 2-propanol (3×). The combined organic extract was dried over sodium sulfate and concentrated under reduced pressure to give the crude acid (1.85 g), which was used in the next step without any purification: ¹H NMR (DMSO-d₆, 500 MHz) δ 12.37 (br s, 1H), 8.17 (s, 1H), 8.05 (d, J=8.4 Hz, 1H), 7.83 (d, J=5.4 Hz, 1H), 7.73-7.69 (m, 2H), 7.48 (d, J=5.3 Hz, 1H), 6.59 (d, J=16.0 Hz, 1H).

Step C: To a solution of the acid (1.85 g, 7.6 mmol) from step B above and N-methyl morpholine (1.5 mL, 13.7 mmol) in dichloromethane (50 mL) at −20° C. was added isobutyl chloroformate (1.2 mL, 9.1 mmol) dropwise. The reaction solution was stirred at −20° C. for 45 minutes and then a solution of 3-(methoxybenzyl) methylamine (1.3 g, 8.4 mmol) in dichloromethane (10 mL) was added to it dropwise. The resultant solution was warmed to room temperature and stirred overnight. The reaction solution was then washed with water, saturated sodium bicarbonate and brine, dried over sodium sulfate and concentrated under reduced pressure. The crude product obtained was purified by flash column chromatography (95:5 to 50:50 hexanes/ethyl acetate) to give the desired product (2.0 g, 78%) as a yellow oil: ¹H NMR (CDCl₃, 500 MHz) δ 7.96-7.86 (m, 3H), 7.59-7.37 (m, 2H), 7.34-7.26 (m, 2H), 7.04-6.78 (m, 4H), 4.70 (d, J=13.5 Hz, 2H), 3.80 (s, 3H), 3.10 (d, J=17.9 Hz, 3H).

Step D: To a solution of the amide (2.8 g, 8.3 mmol) from step C above in dichloroethane (200 mL) was added Eaton's reagent (20 mL, 126 mmol) and the resultant solution was heated at 90° C. for 16 hours. The reaction solution was then cooled to room temperature and diluted with dichloromethane (100 mL) and water (300 mL). To this solution was then added sodium hydroxide (110 mL, 2 M) dropwise. After the addition, the organic layer was separated and the aqueous layer was extracted with dichloromethane (3×). The combined organic extract was washed with brine, dried over sodium sulfate and concentrated under reduced pressure. The crude product obtained was purified by flash column chromatography (60:40:2 hexanes/ethyl acetate/methanol) to give the desired product (1.08 g, 38%) as a light yellow oil: ¹H NMR (CDCl₃, 500 MHz) δ 7.78 (d, J=8.4 Hz, 1H), 7.54 (d, J=1.5 Hz, 1H), 7.43 (d, J=5.5 Hz, 1H), 7.26-7.24 (m, 1H), 7.06 (dd, J=8.4, 1.7 Hz, 1H), 6.89 (d, J=8.2 Hz, 1H), 6.71-6.69 (m, 2H), 5.08 (d, J=16.1 Hz, 1H), 4.59 (dd, J=11.5, 5.2 Hz, 1H), 4.12 (dd, J=11.4, 4.2 Hz, 1H), 3.79 (s, 3H), 3.32 (dd, J=13.7, 11.6 Hz, 1H), 3.07 (s, 3H), 2.99 (dd, J=13.8, 5.4 Hz, 1H); ESI-MS m/z 338 [M+H]⁺.

Step E: To a solution of the lactam (0.90 g, 2.7 mmol) from step D above in tetrahydrofuran (40 mL) was added borane-tetrahydrofuran complex (5.4 mL, 5.4 mmol, 1M in tetrahydrofuran) at room temperature. The resultant solution was heated under reflux for 1 hour and then cooled to room temperature. To this solution was then added an aqueous solution of hydrochloric acid (17 mL, 6 M). The resultant solution was heated under reflux for 1 hour, and then was cooled to room temperature and concentrated under reduced pressure. The residue obtained was basified with an aqueous solution of sodium hydroxide (2 M) to pH ~9 and then extracted with ethyl acetate (3×). The combined organic extract was washed with brine, dried over sodium sulfate and concentrated under reduced pressure. The crude product obtained was purified by flash column chromatography (96:3.6:0.4 dichloromethane/methanol/concentrated ammonium hydroxide) to give the desired product (0.55 g, 64%) as a white foam: ¹H NMR (CDCl₃, 300 MHz) δ 7.85 (d, J=8.3 Hz, 1H), 7.60 (s, 1H), 7.44 (d, J=5.4 Hz, 1H), 7.29-7.26 (m, 1H), 7.20 (d, J=8.3 Hz, 1H), 6.77 (s, 1H), 6.58 (br s, 2H), 4.39 (d, J=9.0 Hz, 1H), 3.92 (d, J=13.8 Hz, 1H), 3.77-3.70 (m, 1H), 3.77 (s, 3H), 3.17-3.12 (m, 1H), 2.99 (t, J=10.4 Hz, 1H), 2.44-2.33 (m, 1H), 2.40 (s, 3H), 2.18-2.14 (m, 1H).

Step F: The 8-methoxy benzoazepine (0.55 g) from step E above was resolved by preparative chiral HPLC (CHIRALCEL OJ column, using 80:20:0.1 heptane/ethanol/diethylamine as the eluent) to give the (+)-enantiomer [[α]²⁵_D+ 22.3° (c 0.13, methanol)] and the (−)-enantiomer [[α]²⁵_D+ 21.4° (c 0.14, methanol)].

Step G: The (+)-enantiomer (40 mg, 0.12 mmol) was dissolved in methanol (3 mL) and maleic acid (14 mg, 0.12 mmol) was added to it. To this solution was then added water (15 mL) and the resultant solution was lyophilized overnight to provide (+)-5-benzo[b]thiophen-5-yl-8-methoxy-2-methyl-2,3,4,5-tetrahydro-1H-benzo[c]azepine, maleate salt (49 mg, 91%, >99% AUC HPLC) as a white solid: mp 92-96° C.; ¹H NMR (CD₃OD, 500 MHz) δ 7.93 (d, J=8.4 Hz, 1H), 7.62-7.58 (m, 2H), 7.33 (d, J=5.3 Hz, 1H), 7.21 (d, J=8.4 Hz, 1H), 7.05 (d, J=2.5 Hz, 1H), 6.87 (br s, 2H), 6.24 (s, 2H), 4.66-4.54 (m, 2H), 4.30 (d, J=14.0 Hz, 1H), 3.81 (s, 3H), 3.56 (br s, 2H), 2.89 (br s, 3H), 2.68-2.44 (m, 2H); ESI-MS m/z 324 [M+H]⁺.

Step H: The (−)-enantiomer (38 mg, 0.12 mmol) was dissolved in methanol (3 mL) and maleic acid (14 mg, 0.12 mmol) was added to it. To this solution was then added water (15 mL) and the resultant solution was lyophilized overnight to provide (−)-5-benzo[b]thiophen-5-yl-8-methoxy-2-methyl-2,3,4,5-tetrahydro-1H-benzo[c]azepine, maleate salt (48 mg, 92%, >99% AUC HPLC) as a white solid: mp 92-95° C.; $^1$H NMR (CD$_3$OD, 500 MHz) δ 7.93 (d, J=8.4 Hz, 1H), 7.62-7.58 (m, 2H), 7.33 (d, J=5.3 Hz, 1H), 7.21 (d, J=8.4 Hz, 1H), 7.05 (d, J=2.5 Hz, 1H), 6.87 (br s, 2H), 6.24 (s, 2H), 4.66-4.54 (m, 2H), 4.30 (d, J=14.0 Hz, 1H), 3.81 (s, 3H), 3.56 (br s, 2H), 2.91 (br s, 3H), 2.90-2.44 (m, 2H); ESI-MS m/z 324 [M+H]$^+$.

Example 53

Preparation of (+/−)-8-methoxy-5-phenyl-2,3,4,5-tetrahydro-1H-benzo[c]azepine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 h and then cooled to room temperature. The resultant reaction mixture was acidified with 6 N hydrochloric acid to pH 1 and extracted with dichloromethane (3×). The combined organic extracts were dried over sodium sulfate and concentrated in vacuo to give the desired acid (18.0 g, 80%) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-methoxybenzylamine (7.8 g, 57 mmol) and the acid (7.6 g, 57 mmol) from step A above in dichloromethane (400 mL) at room temperature was added 1-(3-(dimethylamino)propyl)-3-ethylcarbodiimide hydrochloride (12.0 g, 62.7 mmol). The reaction solution was stirred at room temperature for 16 hours. The resultant reaction mixture was washed with water, aqueous 1 N hydrochloric acid, water and aqueous saturated sodium bicarbonate, dried over sodium sulfate and concentrated in vacuo. The crude acetal (13.3 g, 92%) as a light yellow was used in the next step without further purification: $^1$H NMR (CDCl$_3$, 500 MHz) δ 7.24 (d, J=8.0 Hz, 1H), 6.86 (dd, J=7.5, 0.5 Hz, 1H), 6.83-6.80 (m, 2H), 6.40 (br, 1H), 4.73 (t, J=5.5 Hz, 1H), 4.44 (d, J=5.5 Hz, 2H), 3.80 (s, 3H), 3.39 (s, 6H), 2.59 (d, J=5.5 Hz, 2H).

Step C: A solution of the acetal (12.2 g, 48.2 mmol) from step B above in concentrated hydrochloric acid (120 mL) was stirred at room temperature for 2 hours. The resultant reaction mixture was diluted with water, saturated with sodium chloride and extracted with chloroform. The combined organic extracts were dried over sodium sulfate and concentrated in vacuo to give the crude product, which was purified by crystallization from dichloromethane to give the desired lactam (5.9 g, 59%) as a light yellow solid: $^1$H NMR (CDCl$_3$, 500 MHz) δ 7.29 (d, J=8.5 Hz, 1H), 7.08 (d, J=12.0 Hz, 1H), 6.89 (dd, J=8.0, 2.5 Hz, 1H), 6.78 (d, J=2.5 Hz, 1H), 6.29 (br, 1H), 6.17 (dd, J=12.0, 2.0 Hz, 1H), 4.13 (d, J=5.5 Hz, 2H), 3.84 (s, 3H).

Step D: To a mixture of the lactam (3.0 g, 16 mmol) from step C above and benzene (9.0 mL, 0.10 mol) was added triflic acid (24.0 mL, 0.27 mol). The reaction solution was stirred at room temperature for 5 hours and then it was diluted with water and extracted with dichloromethane (3×). The combined organic extracts were dried over sodium sulfate and concentrated in vacuo to give the desired 5-phenyllactam (4.4 g, quantitative) as a white solid: $^1$H NMR (CDCl$_3$, 500 MHz) δ 7.30 (t, J=7.0 Hz, 2H), 7.22 (t, J=7.0 Hz, 1H), 7.12 (d, J=7.0 Hz, 2H), 6.86 (d, J=8.5 Hz, 1H), 6.72 (d, J=8.5, 2.5 Hz, 1H), 6.64 (d, J=2.5 Hz, 1H), 6.30 (br, 1H), 4.56 (dd, J=16.0, 6.0 Hz, 1H), 4.49 (dd, J=10.5, 4.5 Hz, 1H), 4.27 (dd, J=16.0, 5.0 Hz, 1H), 3.78 (s, 3H), 3.15 (dd, J=14.5, 10.5 Hz, 1H), 3.00 (dd, J=14.5, 4.5 Hz, 1H).

Step E: To a solution of the 5-phenyllactam (4.2 g, 19.5 mmol) from step D above in THF (120 mL) was added borane-dimethylsulfide (24.5 mL of 2M in tetrahydrofuran, 49 mmol) in batches. The reaction solution was stirred at room temperature for 16 h and then additional borane-dimethylsulfide (5.0 mL of 2M in tetrahydrofuran, 10 mmol) was added to it. The reaction solution was stirred at room temperature for 5 hours and then quenched with methanol. The resultant mixture was concentrated in vacuo and the residue obtained was dissolved in dioxane (80 mL) and 6 N hydrochloric acid (40 mL) and heated under reflux for 1 hour. The resultant solution was cooled to room temperature, neutralized with aqueous sodium hydroxide and extracted with dichloromethane (3×). The combined organic extracts were washed with brine, dried over sodium sulfate and concentrated in vacuo. The crude product obtained was purified by flash column chromatography (99:0.9:0.1 to 90:9:1 dichloromethane/methanol/concentrated ammonium hydroxide) to give the desired benzazepine (2.7 g, 54%) as a light yellow oil: $^1$H NMR (CDCl$_3$, 500 MHz) δ 7.34 (t, J=7.5 Hz, 2H), 7.25 (t, J=7.5 Hz, 1H), 7.16 (d, J=7.5 Hz, 2H), 6.74 (d, J=2.5 Hz, 1H), 6.66-6.54 (m, 2H), 4.36 (d, J=9.5 Hz, 1H), 4.00 (d, J=15.0 Hz, 1H), 3.87 (d, J=14.5 Hz, 1H), 3.77 (s, 3H), 3.29-3.22 (m, 1H), 3.19-3.14 (m, 1H), 2.27-2.13 (m, 2H), 1.69 (br, 1H).

Step F: To a solution of the newly obtained benzazepine (0.60 g, 2.4 mmol) from step E above in methanol (10 mL) were added maleic acid (0.28 g, 2.4 mmol). The resultant solution was sonicated for 5 minutes and concentrated in vacuo. The residue obtained was dissolved in ethyl acetate and sonicated. The precipitation formed was collected by filtration to give (+/−)-8-methoxy-5-phenyl-2,3,4,5-tetrahydro-1H-benzo[c]azepine, maleate salt (0.59 g, 67%, >99% AUC HPLC) as a white solid: mp 154-156° C.; $^1$H NMR (CD$_3$OD, 500 MHz) δ 7.38 (t, J=7.5 Hz, 2H), 7.29 (t, J=7.5 Hz, 1H), 7.18 (d, J=7.5 Hz, 2H), 7.01 (d, J=2.5 Hz, 1H), 6.85 (dd, J=8.5, 2.5 Hz, 1H); 6.82-6.79 (m, 1H), 6.24 (s, 2H), 4.53 (d, J=8.5 Hz, 1H), 4.42 (d, J=14.0 Hz, 1H), 4.17 (d, J=14.0 Hz, 1H), 3.80 (s, 3H), 3.52-3.41 (m, 2H), 2.59-2.50 (m, 1H), 2.40-2.35 (m, 1H); ESI MS m/z 254 [M+H]$^+$.

Example 54

Preparation of (+/−)-2-ethyl-8-methoxy-5-phenyl-2,3,4,5-tetrahydro-1H-benzo[c]azepine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane (3×). The combined organic extracts were dried over sodium sulfate and concentrated in vacuo to give the desired acid (18.0 g, 80%) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-methoxybenzylamine (7.8 g, 57 mmol) and the acid (7.6 g, 57 mmol) from step A above in dichloromethane (400 mL) at room temperature was added 1-(3-(dimethylamino)propyl)-3-ethylcarbodiimide hydrochloride (12.0 g, 62.7 mmol). The reaction solution was stirred at room temperature for 16 hours. The resultant reaction mixture was washed with water, aqueous 1 N hydrochloric acid, water and aqueous saturated sodium bicarbonate, dried over sodium sulfate and concentrated in vacuo. The crude acetal (13.3 g, 92%) as a light yellow was used in the next step without further purification: $^1$H NMR (CDCl$_3$, 500 MHz) δ 7.24 (d, J=8.0 Hz, 1H), 6.86 (dd, J=7.5, 0.5 Hz, 1H), 6.83-6.80 (m, 2H), 6.40 (br, 1H), 4.73 (t, J=5.5 Hz, 1H), 4.44 (d, J=5.5 Hz, 2H), 3.80 (s, 3H), 3.39 (s, 6H), 2.59 (d, J=5.5 Hz, 2H).

Step C: A solution of the acetal (12.2 g, 48.2 mmol) from step B above in concentrated hydrochloric acid (120 mL) was stirred at room temperature for 2 hours. The resultant reaction mixture was diluted with water, saturated with sodium chloride and extracted with chloroform. The combined organic extracts were dried over sodium sulfate and concentrated in vacuo to give the crude product, which was purified by crystallization from dichloromethane to give the desired lactam (5.9 g, 59%) as a light yellow solid: $^1$H NMR (CDCl$_3$, 500 MHz) δ 7.29 (d, J=8.5 Hz, 1H), 7.08 (d, J=12.0 Hz, 1H), 6.89 (dd, J=8.0, 2.5 Hz, 1H), 6.78 (d, J=2.5 Hz, 1H), 6.29 (br, 1H), 6.17 (dd, J=12.0, 2.0 Hz, 1H), 4.13 (d, J=5.5 Hz, 2H), 3.84 (s, 3H).

Step D: To a mixture of the lactam (3.0 g, 16 mmol) from step C above and benzene (9.0 mL, 0.10 mol) was added triflic acid (24.0 mL, 0.27 mol). The reaction solution was stirred at room temperature for S hours and then it was diluted with water and extracted with dichloromethane (3×). The combined organic extracts were dried over sodium sulfate and concentrated in vacuo to give the desired 5-phenyllactam (4.4 g, quantitative) as a white solid: $^1$H NMR (CDCl$_3$, 500 MHz) δ 7.30 (t, J=7.0 Hz, 2H), 7.22 (t, J=7.0 Hz, 1H), 7.12 (d, J=7.0 Hz, 2H), 6.86 (d, J=8.5 Hz, 1H), 6.72 (d, J=8.5, 2.5 Hz, 1H), 6.64 (d, J=2.5 Hz, 1H), 6.30 (br, 1H), 4.56 (dd, J=16.0, 6.0 Hz, 1H), 4.49 (dd, J=10.5, 4.5 Hz, 1H), 4.27 (dd, J=16.0, 5.0 Hz, 1H), 3.78 (s, 3H), 3.15 (dd, J=14.5, 10.5 Hz, 1H), 3.00 (dd, J=14.5, 4.5 Hz, 1H).

Step E: To a solution of the 5-phenyllactam (4.2 g, 19.5 mmol) from step D above in THF (120 mL) was added borane-dimethylsulfide (24.5 mL of 2M in tetrahydrofuran, 49 mmol) in batches. The reaction solution was stirred at room temperature for 16 hours and then additional borane-dimethylsulfide (5.0 mL of 2M in tetrahydrofuran, 10 mmol) was added to it. The reaction solution was stirred at 30 room temperature for 5 hours and then quenched with methanol. The resultant mixture was concentrated in vacuo and the residue obtained was dissolved in dioxane (80 mL) and 6N hydrochloric acid (40 mL) and heated under reflux for 1 hour. The resultant solution was cooled to room temperature, neutralized with aqueous sodium hydroxide and extracted with dichloromethane (3×). The combined organic extracts were washed with brine, dried over sodium sulfate and concentrated in vacuo. The crude product obtained was purified by flash column chromatography (99:0.9:0.1 to 90:9:1 dichloromethane/methanol/concentrated ammonium hydroxide) to give the desired benzazepine (2.7 g, 54%) as a light yellow oil: $^1$H NMR (CDCl$_3$, 500 MHz) δ 7.34 (t, J=7.5 Hz, 2H), 7.25 (t, J=7.5 Hz, 1H), 7.16 (d, J=7.5 Hz, 2H), 6.74 (d, J=2.5 Hz, 1H), 6.66-6.54 (m, 2H), 4.36 (d, J=9.5 Hz, 1H), 4.00 (d, J=15.0 Hz, 1H), 3.87 (d, J=14.5 Hz, 1H), 3.77 (s, 3H), 3.29-3.22 (m, 1H), 3.19-3.14 (m, 1H), 2.27-2.13 (m, 2H), 1.69 (br, 1H).

Step F: To a solution of the secondary benzazepine (0.98 g, 3.9 mmol) from step E above in dichloromethane (50 mL) were added acetaldehyde (0.44 mL, 7.7 mmol), sodium triacetoxyborohydride (1.8 g, 8.3 mmol), acetic acid (0.2 mL), and 3 Å molecular sieves (1.0 g). The reaction solution was stirred at room temperature for 24 h and then it was diluted with dichloromethane, washed with aqueous 1 N sodium carbonate, dried over sodium sulfate and concentrated in vacuo. The crude product obtained was purified by flash column chromatography (dichloromethane to 95:4.5:0.5 dichloromethane/methanol/concentrated ammonium hydroxide) to give the desired N-ethyl benzazepine (0.53 g, 48%) as a yellow oil: $^1$H NMR (CDCl$_3$, 500 MHz) δ 7.34 (t, J=7.5 Hz, 2H), 7.25 (t, J=7.5 Hz, 1H), 7.17 (d, J=7.5 Hz, 2H), 6.75 (d, J=2.5 Hz, 1H), 6.68-6.40 (br, 2H), 4.27 (d, J=8.5 Hz, 1H), 3.94 (d, J=13.5 Hz, 1H), 3.81 (d, J=14.5 Hz, 1H), 3.77 (s, 3H), 3.27-3.16 (br, 1H), 3.06-3.01 (m, 1H), 2.55-2.45 (m, 2H), 2.32-2.24 (m, 1H), 2.13-2.04 (br, 1H), 1.11 (t, J=7.0 Hz, 3H); ESI MS m/z 282 [M+H]$^+$.

Step G: To a solution of the newly obtained N-ethyl benzazepine (61 mg, 0.22 mmol) from step F above in methanol (2 mL) were added maleic acid (25 mg, 0.22 mmol) and water (10 mL). The resultant solution was lypholized overnight to give (+/−)-2-ethyl-8-methoxy-5-phenyl-2,3,4,5-tetrahydro-1H-benzo[c]azepine, maleate salt (86 mg, 97.4% AUC HPLC) as a white solid: $^1$H NMR (CD$_3$OD, 500 MHz) δ 7.42-7.11 (br, 5H), 7.06 (s, 1H), 6.98-6.50 (br, 2H), 6.25 (s, 2H), 4.67-4.16 (br, 5H), 3.81 (s, 3H), 3.70-3.42 (br, 2H), 3.20-2.95 (br, 1H), 2.51-2.21 (br, 1H), 1.43-1.38 (br, 3H); ESI MS m/z 282 [M+H]$^+$.

Example 55

Preparation of (+/−)-2-isopropyl-8-methoxy-5-phenyl-2,3,4,5-tetrahydro-1H-benzo[c]azepine, maleate salt Pursuant to the general method described above in Example 54, the following product was prepared: (+/−)-2-isopropyl-8-methoxy-5-phenyl-2,3,4,5-tetrahydro-1H-benzo[c]azepine, maleate salt: mp 172-175° C.; $^1$H NMR (CD$_3$OD, 500 MHz) δ 7.40-6.32 (br, 8H), 6.24 (s, 2H), 4.63-4.02 (br, 3H), 3.80 (s, 3H), 3.75-3.44 (br, 3H), 2.94-2.23 (br, 2H), 1.29 (br, 6H); ESI MS m/z 296 [M+H]$^+$.

Example 56

Preparation of 4-(5-phenyl-2-(2,2,2-trifluoroethyl)-2,3,4,5,-tetrahydro-1H-benzo[c]-azepin-8-yl)morpholine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane (3×). The combined organic extracts were dried over sodium sulfate and concentrated in vacuo to give the desired acid (18.0 g, 80%) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-methoxybenzylamine (7.8 g, 57 mmol) and the acid (7.6 g, 57 mmol) from step A above in dichloromethane (400 mL) at room temperature was added 1-(3-(dimethylamino)propyl)-3-ethylcarbodiimide hydrochloride (12.0 g, 62.7 mmol). The reaction solution was stirred at room temperature for 16 hours. The resultant reaction mixture was washed with water, aqueous 1N hydrochloric acid, water and aqueous saturated sodium bicarbonate, dried over sodium sulfate and concentrated in vacuo. The crude acetal (13.3 g, 92%) as a light yellow was used in the next step without further purification: $^1$H NMR (CDCl$_3$, 500 MHz) δ 7.24 (d, J=8.0 Hz, 1H), 6.86 (dd, J=7.5, 0.5 Hz, 1H), 6.83-6.80 (m, 2H), 6.40 (br, 1H), 4.73 (t, J=5.5 Hz, 1H), 4.44 (d, J=5.5 Hz, 2H), 3.80 (s, 3H), 3.39 (s, 6H), 2.59 (d, J=5.5 Hz, 2H).

Step C: A solution of the acetal (12.2 g, 48.2 mmol) from step B above in concentrated hydrochloric acid (120 mL) was stirred at room temperature for 2 hours. The resultant reaction mixture was diluted with water, saturated with sodium chloride and extracted with chloroform. The combined organic extracts were dried over sodium sulfate and concentrated in vacuo to give the crude product, which was purified by crystallization from dichloromethane to give the desired lactam (5.9 g, 59%) as a light yellow solid: $^1$H NMR (CDCl$_3$, 500 MHz) δ 7.29 (d, J=8.5 Hz, 1H), 7.08 (d, J=12.0 Hz, 1H), 6.89 (dd, J=8.0, 2.5 Hz, 1H), 6.78 (d, J=2.5 Hz, 1H), 6.29 (br, 1H), 6.17 (dd, J=12.0, 2.0 Hz, 1H), 4.13 (d, J=5.5 Hz, 2H), 3.84 (s, 3H).

Step D: To a mixture of the lactam (3.0 g, 16 mmol) from step C above and benzene (9.0 mL, 0.10 mol) was added triflic acid (24.0 mL, 0.27 mol). The reaction solution was stirred at room temperature for 5 hours and then it was diluted with water and extracted with dichloromethane (3×). The combined organic extracts were dried over sodium sulfate and concentrated in vacuo to give the desired 5-phenyllactam (4.4 g, quantitative) as a white solid: $^1$H NMR (CDCl$_3$, 500 MHz) δ 7.30 (t, J=7.0 Hz, 2H), 7.22 (t, J=7.0 Hz, 1H), 7.12 (d, J=7.0 Hz, 2H), 6.86 (d, J=8.5 Hz, 1H), 6.72 (d, J=8.5, 2.5 Hz, 1H), 6.64 (d, J=2.5 Hz, 1H), 6.30 (br, 1H), 4.56 (dd, J=16.0, 6.0 Hz, 1H), 4.49 (dd, J=10.5, 4.5 Hz, 1H), 4.27 (dd, J=16.0, 5.0 Hz, 1H), 3.78 (s, 3H), 3.15 (dd, J=14.5, 10.5 Hz, 1H), 3.00 (dd, J=14.5, 4.5 Hz, 1H).

Step E: To a solution of the 5-phenyllactam (4.2 g, 19.5 mmol) from step D above in THF (120 mL) was added borane-dimethyl sulfide (24.5 mL of 2M in tetrahydrofuran, 49 mmol) in batches. The reaction solution was stirred at room temperature for 16 hours and then additional borane-dimethyl sulfide (5.0 mL of 2M in tetrahydrofuran, 10 mmol) was added to it. The reaction solution was stirred at room temperature for 5 hours and then quenched with methanol. The resultant mixture was concentrated in vacuo and the residue obtained was dissolved in dioxane (80 mL) and 6N hydrochloric acid (40 mL) and heated under reflux for 1 hour. The resultant solution was cooled to room temperature, neutralized with aqueous sodium hydroxide and extracted with dichloromethane (3×). The combined organic extracts were washed with brine, dried over sodium sulfate and concentrated in vacuo. The crude product obtained was purified by flash column chromatography (99:0.9:0.1 to 90:9:1 dichloromethane/methanol/concentrated ammonium hydroxide) to give the desired benzazepine (2.7 g, 54%) as a light yellow oil: $^1$H NMR (CDCl$_3$, 500 MHz) δ 7.34 (t, J=7.5 Hz, 2H), 7.25 (t, J=7.5 Hz, 1H), 7.16 (d, J=7.5 Hz, 2H), 6.74 (d, J=2.5 Hz, 1H), 6.66-6.54 (m, 2H), 4.36 (d, J=9.5 Hz, 1H), 4.00 (d, J=15.0 Hz, 1H), 3.87 (d, J=14.5 Hz, 1H), 3.77 (s, 3H), 3.29-3.22 (m, 1H), 3.19-3.14 (m, 1H), 2.27-2.13 (m, 2H), 1.69 (br, 1H).

Step F: To a solution of the 2H-benzazepine (2.9 g, 11.4 mmol) from step E above in dichloromethane (120 mL) were added pyridine (1.8 mL, 23 mmol), 4-dimethylaminopyridine (0.14 g, 1.1 mmol) and acetic anhydride (1.3 mL, 14.2 mmol) at 0° C. The reaction solution was let to warm to room temperature and stirred for 15 hours. The resultant reaction mixture was quenched with aqueous ammonium chloride, washed with 1 N hydrochloric acid and aqueous saturated sodium bicarbonate, dried over sodium sulfate and concentrated in vacuo. The crude product obtained (3.2 g, 95%) as a light yellow oil, was used in the next step without further purification: $^1$H NMR (CDCl$_3$, 500 MHz) δ 7.34 (t, J=7.5 Hz, 2H), 7.24 (t, J=7.5 Hz, 1H), 7.09 (d, J=8.0 Hz, 2H), 6.95 (d, J=2.5 Hz, 1H), 6.82-6.63 (m, 2H), 4.69-4.30 (m, 3H), 3.83-3.47 (m, 5H), 2.41-1.92 (m, 5H).

Step G: To a solution of the 8-methoxybenzazepine (3.2 g, 10.8 mmol) from step F above in dichloromethane (90 mL) at −78° C. was added boron tribromide (10 mL, 0.11 mol) slowly. After the addition, the reaction solution was stirred at −78° C. for 4 hours and at room temperature for 1 hour. The resultant reaction mixture was cooled to 0° C., quenched by slow addition of methanol and concentrated in vacuo. The residue obtained (3.2 g, quantitative) as an off-white solid, was used in the next step without further purification: $^1$H NMR (CDCl$_3$, 500 MHz) δ 7.99-7.56 (br, 1H), 7.32 (t, J=7.5 Hz, 2H), 7.23 (t, J=7.5 Hz, 1H), 7.12 (d, J=2.5 Hz, 1H), 7.09 (d, J=7.5 Hz, 2H), 6.73-6.06 (m, 2H), 4.68-4.31 (m, 3H), 3.83-3.54 (m, 2H), 2.47-2.12 (m, 2H), 2.12-1.93 (m, 3H); ESI MS m/z 282 [M+H]$^+$.

Step H: To a solution of the phenol (0.85 g, 3.0 mmol) from step G above in chloroform (30 mL) at 0° C. was added triethylamine (5.1 mL, 36 mmol) followed by triflic anhydride (1.0 mL, 6.0 mmol) dropwise. The resultant reaction solution was stirred at room temperature for 12 h and then additional triethylamine (1.0 mL, 7.0 mmol) and triflic anhydride (1.0 mL, 6.0 mmol) were added. The reaction solution was stirred at room temperature for 1 h and then quenched with aqueous saturated sodium bicarbonate. The resultant mixture was extracted with dichlormethane (2×), washed with aqueous saturated ammonium chloride, dried over sodium sulfate and concentrated in vacuo. The residue obtained was purified by flash column chromatography (66:33 to 33:66 hexanes/ethyl acetate) to give the desired triflate (0.52 g, 42%) as an orange solid: ESI MS m/z 414 [M+H]$^+$.

Step I: To a solution of the triflate (0.20 g, 0.48 mmol) from step H above in toluene (5 mL) were added cesium carbonate (0.49 g, 1.5 mmol), 2-(dicyclohexylphosphino)-2',4',6'-tri-i-propyl-1,1'-biphenyl (24 g, 0.05 mmol) and morpholine (0.042 mL, 1.0 mmol). The resultant mixture was flushed with argon for 10 minutes, and then palladium(II) acetate (11 mg, 0.05 mmol) was added to it. The reaction solution was heated at 100° C. under argon for 13 hours and then cooled to room temperature. The resultant mixture was diluted with dichloromethane, washed with water and brine, dried over sodium sulfate and concentrated in vacuo. The crude product obtained was purified by flash column chromatography (99:0.9:0.1 to 97:2.7:0.3 dichloromethane/methanol/concentrated ammonium hydroxide) to give the desired 8-morpholinyl benzazepine (0.13 g, 83%) as a white foam: $^1$H NMR (CDCl$_3$, 500 MHz) δ 7.32 (t, J=8.0 Hz, 2H), 7.23 (t, J=7.5 Hz, 1H), 7.09 (d, J=7.5 Hz, 2H), 6.95-6.65 (m, 3H), 4.78-4.30 (m, 3H), 3.90-3.41 (m, 6H), 3.20-3.13 (m, 4H), 2.43-2.17 (m, 2H), 2.20-1.74 (m, 3H); ESI MS m/z 351 [M+H]$^+$.

Step J: To a solution of the N-acetyl benzazepine (0.14 g, 0.40 mmol) from step I above in methanol (10 mL) was added an aqueous 2N solution of sodium hydroxide (10 mL). The reaction solution was heated under reflux for 72 hours and then cooled to room temperature. The resultant reaction mixture was extracted with dichloromethane, washed with water and aqueous saturated sodium bicarbonate, dried over sodium sulfate and concentrated in vacuo. The residue obtained was purified by flash column chromatography (dichloromethane to 90:9:1 dichloromethane/methanol/concentrated ammonium hydroxide) to give the desired 2H-benzazepine (0.11 g, 89%) as a white foam: $^1$H NMR (DMSO-d$_6$, 500 MHz) δ 7.35 (t, J=7.5 Hz, 2H), 7.24 (t, J=7.5 Hz, 1H), 7.14 (d, J=7.5 Hz, 2H), 6.84 (d, J=2.5 Hz, 1H), 6.65-6.60 (m, 1H), 6.49-6.38 (br, 1H), 4.33 (d, J=8.5 Hz, 1H), 3.95 (d, J=14.5 Hz, 1H), 3.77 (d, J=14.5 Hz, 1H), 3.71 (t, J=5.0 Hz, 4H), 3.10-2.87 (m, 6H), 2.21-2.12 (m, 1H), 2.03-1.85 (m, 1H).

Step K: To a solution of the 2H-benzazepine (80 mg, 0.26 mmol) from step J above in acetone (5 mL) were added triethylamine (0.06 mL, 0.43 mmol), N,N-diisopropylethylamine (0.025 mL, 0.26 mmol) and 2,2,2-trifluoroethyl methanesulfonate (60 mg, 0.26 mmol). The reaction solution was heated under reflux for 1 hour and then cooled to room temperature and concentrated in vacuo. The residue obtained was purified by flash column chromatography (90:10 to 80:20 hexanes/ethyl acetate) to give the N-trifluoroethyl benzazepine (70 mg, 69%) as a white foam: $^1$H NMR (CDCl$_3$, 500 MHz) δ 7.34 (t, J=7.5 Hz, 2H), 7.25 (t, J=7.5 Hz, 1H), 7.15 (d, J=7.5 Hz, 2H), 6.72 (s, 1H), 6.67-6.50 (br, 2H), 4.29 (d, J=8.0 Hz, 1H), 4.19-4.07 (br, 1H), 3.90 (d, J=15.0 Hz, 1H), 3.87-3.84 (m, 4H), 3.32-3.26 (br, 2H), 3.16-3.12 (m, 4H), 3.03-2.89 (m, 2H), 2.26-2.19 (m, 1H), 2.09-2.00 (m, 1H). To a solution of the N-trifluoroethyl benzazepine (65 mg, 0.17 mmol) in methanol (2 mL) were added maleic acid (19 mg, 0.17 mmol) and water (10 mL). The resultant solution was lypholized overnight to give 4-(5-phenyl-2-(2,2,2-trifluoroethyl)-2,3,4,5,-tetrahydro-1H-benzo[c]-azepin-8-yl)morpholine, maleate salt (84 mg, >99.0% AUC HPLC) as a light pink solid: $^1$H NMR (CD$_3$OD, 500 MHz) δ 7.32 (t, J=7.5 Hz, 2H), 7.23 (t, J=7.5 Hz, 1H), 7.15 (d, J=7.5 Hz, 2H), 6.84 (d, J=2.5 Hz, 1H), 6.75 (d, J=6.5 Hz, 1H), 6.71-6.54 (br, 1H), 6.30 (s, 2H), 4.35 (d, J=7.5 Hz, 1H), 4.21-4.04 (br, 1H), 3.92 (d, J=15.0 Hz, 1H), 3.84 (t, J=5.0 Hz, 4H), 3.29-3.25 (m, 2H), 3.22-3.07 (m, 6H), 2.34-2.27 (m, 1H), 2.06 (d, J=13.5 Hz, 1H); ESI MS m/z 391 [M+H]$^+$.

Example 57

Preparation of (−)-4-(2-ethyl-5-phenyl-2,3,4,5-tetrahydro-1H-benzo[c]azepin-8-yl)morpholine, maleate salt and (+)-4-(2-ethyl-5-phenyl-2,3,4,5-tetrahydro-1H-benzo[c]azepin-8-yl)morpholine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane (3×). The combined organic extracts were dried over sodium sulfate and concentrated in vacuo to give the desired acid (18.0 g, 80%) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-methoxybenzylamine (7.8 g, 57 mmol) and the acid (7.6 g, 57 mmol) from step A above in dichloromethane (400 mL) at room temperature was added 1-(3-(dimethylamino)propyl)-3-ethylcarbodiimide hydrochloride (12.0 g, 62.7 mmol). The reaction solution was stirred at room temperature for 16 hours. The resultant reaction mixture was washed with water, aqueous 1 N hydrochloric acid, water and aqueous saturated sodium bicarbonate, dried over sodium sulfate and concentrated in vacuo. The crude acetal (13.3 g, 92%) as a light yellow was used in the next step without further purification: $^1$H NMR (CDCl$_3$, 500 MHz) δ 7.24 (d, J=8.0 Hz, 1H), 6.86 (dd, J=7.5, 0.5 Hz, 1H), 6.83-6.80 (m, 2H), 6.40 (br, 1H), 4.73 (t, J=5.5 Hz, 1H), 4.44 (d, J=5.5 Hz, 2H), 3.80 (s, 3H), 3.39 (s, 6H), 2.59 (d, J=5.5 Hz, 2H).

Step C: A solution of the acetal (12.2 g, 48.2 mmol) from step B above in concentrated hydrochloric acid (120 mL) was stirred at room temperature for 2 hours. The resultant reaction mixture was diluted with water, saturated with sodium chloride and extracted with chloroform. The combined organic extracts were dried over sodium sulfate and concentrated in vacuo to give the crude product, which was purified by crystallization from dichloromethane to give the desired lactam (5.9 g, 59%) as a light yellow solid: $^1$H NMR (CDCl$_3$, 500 MHz) δ 7.29 (d, J=8.5 Hz, 1H), 7.08 (d, J=12.0 Hz, 1H), 6.89 (dd, J=8.0, 2.5 Hz, 1H), 6.78 (d, J=2.5 Hz, 1H), 6.29 (br, 1H), 6.17 (dd, J=12.0, 2.0 Hz, 1H), 4.13 (d, J=5.5 Hz, 2H), 3.84 (s, 3H).

Step D: To a mixture of the lactam (3.0 g, 16 mmol) from step C above and benzene (9.0 mL, 0.10 mol) was added triflic acid (24.0 mL, 0.27 mol). The reaction solution was stirred at room temperature for 5 hours and then it was diluted with water and extracted with dichloromethane (3×). The combined organic extracts were dried over sodium sulfate and concentrated in vacuo to give the desired 5-phenyllactam (4.4 g, quantitative) as a white solid: $^1$H NMR (CDCl$_3$, 500 MHz) δ 7.30 (t, J=7.0 Hz, 2H), 7.22 (t, J=7.0 Hz, 1H), 7.12 (d, J=7.0 Hz, 2H), 6.86 (d, J=8.5 Hz, 1H), 6.72 (d, J=8.5, 2.5 Hz, 1H), 6.64 (d, J=2.5 Hz, 1H), 6.30 (br, 1H), 4.56 (dd, J=16.0, 6.0 Hz, 1H), 4.49 (dd, J=10.5, 4.5 Hz, 1H), 4.27 (dd, J=16.0, 5.0 Hz, 1H), 3.78 (s, 3H), 3.15 (dd, J=14.5, 10.5 Hz, 1H), 3.00 (dd, J=14.5, 4.5 Hz, 1H).

Step E: To a solution of the 5-phenyllactam (4.2 g, 19.5 mmol) from step D above in THF (120 mL) was added borandimethyl sulfide (24.5 mL of 2M in tetrahydrofuran, 49 mmol) in batches. The reaction solution was stirred at room temperature for 16 hours and then additional borane-dimethyl sulfide (5.0 mL of 2M in tetrahydrofuran, 10 mmol) was added to it. The reaction solution was stirred at room temperature for 5 hours and then quenched with methanol. The resultant mixture was concentrated in vacuo and the residue obtained was dissolved in dioxane (80 mL) and 6N hydrochloric acid (40 mL) and heated under reflux for 1 hour. The resultant solution was cooled to room temperature, neutralized with aqueous sodium hydroxide and extracted with dichloromethane (3×). The combined organic extracts were washed with brine, dried over sodium sulfate and concentrated in vacuo. The crude product obtained was purified by flash column chromatography (99:0.9:0.1 to 90:9:1 dichloromethane/methanol/concentrated ammonium hydroxide) to give the desired benzazepine (2.7 g, 54%) as a light yellow oil: $^1$H NMR (CDCl$_3$, 500 MHz) δ 7.34 (t, J=7.5 Hz, 2H), 7.25 (t, J=7.5 Hz, 1H), 7.16 (d, J=7.5 Hz, 2H), 6.74 (d, J=2.5 Hz, 1H), 6.66-6.54 (m, 2H), 4.36 (d, J=9.5 Hz, 1H), 4.00 (d, J=15:0 Hz, 1H), 3.87 (d, J=14.5 Hz, 1H), 3.77 (s, 3H), 3.29-3.22 (m, 1H), 3.19-3.14 (m, 1H), 2.27-2.13 (m, 2H), 1.69 (br, 1H).

Step F: To a solution of the benzazepine (0.98 g, 3.9 mmol) from step E above in dichloromethane (50 mL) were added acetaldehyde (0.44 mL, 7.7 mmol), sodium triacetoxyborohydride (1.8 g, 8.3 mmol), acetic acid (0.2 mL), and 3 Å molecular sieves (1.0 g). The reaction solution was stirred at room temperature for 24 hours and then it was diluted with dichloromethane, washed with aqueous 1N sodium carbonate, dried over sodium sulfate and concentrated in vacuo. The crude product obtained was purified by flash column chromatography (dichloromethane to 95:4.5:0.5 dichloromethane/methanol/concentrated ammonium hydroxide) to give the desired N-ethyl benzazepine (0.53 g, 48%) as a yellow oil: $^1$H NMR (CDCl$_3$, 500 MHz) δ 7.34 (t, J=7.5 Hz, 2H), 7.25 (t, J=7.5 Hz, 1H), 7.17 (d, J=7.5 Hz, 2H), 6.75 (d, J=2.5 Hz, 1H), 6.68-6.40 (br, 2H), 4.27 (d, J=8.5 Hz, 1H), 3.94 (d, J=13.5 Hz, 1H), 3.81 (d, J=14.5 Hz, 1H), 3.77 (s, 3H), 3.27-3.16 (br, 1H), 3.06-3.01 (m, 1H), 2.55-2.45 (m, 2H), 2.32-2.24 (m, 1H), 2.13-2.04 (br, 1H), 1.11 (t, J=7.0 Hz, 3H); ESI MS m/z 282 [M+H]⁺.

Step G: To a solution of the N-ethyl benzazepine (0.47 g, 1.7 mmol) from step F above in acetic acid (25 mL) was added hydrobromic acid (48% solution in water, 25 mL). The reaction solution was heated at 100° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol, which was used in the next step without purification: $^1$H NMR (CDCl$_3$, 500 MHz) δ 7.34 (t, J=7.5 Hz, 2H), 7.25 (t, J=7.5 Hz, 1H), 7.16 (d, J=7.5 Hz, 2H), 6.63 (s, 1H), 6.58-6.38 (br, 2H), 4.25 (d, J=8.0 Hz, 1H), 3.88 (d, J=13.0 Hz, 1H), 3.76 (d, J=14.5 Hz, 1H), 3.24-3.13 (br, 1H), 3.03-2.98 (m, 1H), 2.57-2.50 (m, 2H), 2.34-2.27 (m, 1H), 2.14-2.07 (m, 1H), 1.13 (t, J=7.0 Hz, 3H); ESI MS m/z 268 [M+H]⁺.

Step H: To a solution of the phenol (1.7 mmol) from step G above in dichloromethane (20 mL) at 0° C. were added pyridine (0.24 mL, 3.0 mmol) and triflic anhydride (0.34 mL, 2.0 mmol). The resultant reaction solution was stirred at 0° C. for 2 hours, and then it was diluted with dichloromethane, washed with aqueous saturated sodium bicarbonate, dried over sodium sulfate and concentrated in vacuo. The desired triflate obtained as a reddish oil was used in the next step without purification: $^1$H NMR (CDCl$_3$, 500 MHz) δ 7.38 (t, J=7.5 Hz, 2H), 7.29 (t, J=7.5 Hz, 1H), 7.17 (d, J=7.5 Hz, 2H), 7.08 (d, J=2.5 Hz, 1H), 6.95 (dd, J=8.5, 2.0 Hz, 1H), 6.77-6.45 (br, 1H), 4.34 (d, J=10.0 Hz, 1H), 4.02 (d, J=15.0 Hz, 1H), 3.85 (d, J=14.5 Hz, 1H), 3.25 (d, J=10.5 Hz, 1H), 3.10-3.05 (m, 1H), 2.54-2.46 (m, 2H), 2.34-2.26 (m, 1H), 2.07 (d, J=11.5 Hz, 1H), 1.11 (t, J=7.0 Hz, 3H); ESI MS m/z 400 [M+H]⁺.

Step I: To a solution of the triflate (1.7 mmol) from step H above in toluene (14 mL) were added cesium carbonate (1.6 g, 5.0 mmol), 2-(dicyclohexylphosphino)-2',4',6'-tri-i-propyl-1,1'-biphenyl (0.16 g, 0.34 mmol) and morpholine (0.29 mL, 3.3 mmol). The resultant mixture was flushed with argon for 5 minutes, and then palladium(II) acetate (38 mg, 0.17 mmol) was added to it. The reaction solution was capped and heated at 100° C. under argon for 4 hours, and then cooled to room temperature. The resultant mixture was diluted with dichloromethane, washed with water and brine, dried over sodium sulfate and concentrated in vacuo. The crude product obtained was purified by flash column chromatography (dichloromethane to 95:4.5:0.5 dichloromethane/methanol/concentrated ammonium hydroxide) to give the desired 8-morpholinyl benzazepine (0.25 g, 45%) as a yellow oil: $^1$H NMR (CDCl$_3$, 500 MHz) δ 7.34 (t, J=7.5 Hz, 2H), 7.25 (t, J=7.5 Hz, 1H), 7.17 (d, J=7.5 Hz, 2H), 6.76 (d, J=2.5 Hz, 1H), 6.61 (d, J=6.0 Hz, 1H), 6.58-6.38 (br, 1H), 4.26 (d, J=9.0 Hz, 1H), 3.95 (d, J=14.0 Hz, 1H), 3.85 (t, J=4.5 Hz, 4H), 3.81 (d, J=14.5 Hz, 1H), 3.27-3.18 (br, 1H), 3.12 (t, J=4.5 Hz, 4H), 3.06-3.00 (m, 1H), 2.56-2.47 (m, 2H), 2.32-2.25 (m, 1H), 2.12-2.03 (br, 1H), 1.12 (t, J=7.0 Hz, 3H); ESI MS m/z 337 [M+H]⁺.

Step J: The 8-morpholinyl benzazepine (0.31 g) from step I above was resolved by preparative chiral HPLC (CHIRALPAK AD column, using 85:15:0.1 heptane/ethanol/trifluoroacetic acid as the eluent) to give the (+)-enantiomer [[α]$^{25}_D$+2.7° (c 0.15, methanol)] (0.14 g) and the (−)-enantiomer [[α]$^{25}_D$−2.9° (c 0.21, methanol)] (0.15 g). To a solution of the (+)-enantiomer (0.14 g, 0.42 mmol) in methanol (3 mL) were added maleic acid (49 mg, 0.42 mmol) and water (15 mL). The resultant solution was lyophilized overnight to provide the maleate salt (+)-4-(2-ethyl-5-phenyl-2,3,4,5-tetrahydro-1H-benzo[c]azepin-8-yl)morpholine, maleate salt (0.19 g, 98.6% AUC HPLC) as a light yellow solid: mp 64-66° C.; $^1$H NMR (CD$_3$OD, 500 MHz) δ 7.38 (t, J=7.5 Hz, 2H), 7.29 (t, J=7.5 Hz, 1H), 7.19 (br, 2H), 7.07 (d, J=2.5 Hz, 1H), 6.98-6.53 (br, 2H), 6.25 (s, 2.1H), 4.52-4.09 (br, 3H), 3.82 (t, J=4.5 Hz, 4H), 3.70-3.47 (m, 2H), 3.29-3.00 (m, 6H), 2.80-2.21 (br, 2H), 1.48-1.31 (br, 3H); ESI MS m/z 337 [M+H]⁺.

To a solution of the (−)-enantiomer (0.14 g, 0.42 mmol) in methanol (3 mL) were added maleic acid (49 mg, 0.42 mmol) and water (15 mL). The resultant solution was lyophilized overnight to provide (−)-4-(2-ethyl-5-phenyl-2,3,4,5-tetrahydro-1H-benzo[c]azepin-8-yl)morpholine, maleate salt (0.19 g, 98.9% AUC HPLC) as a yellow solid: mp 68-72° C.; $^1$H NMR (CD$_3$OD, 500 MHz) δ 7.38 (t, J=7.5 Hz, 2H), 7.29 (t, J=7.5 Hz, 1H), 7.19 (br, 2H), 7.07 (d, J=2.5 Hz, 1H), 6.98-6.53 (br, 2H), 6.25 (s, 2H), 4.52-4.09 (br, 3H), 3.82 (t, J=4.5 Hz, 4H), 3.70-3.47 (m, 2H), 3.29-3.00 (m, 6H), 2.80-2.21 (br, 2H), 1.48-1.31 (br, 3H); ESI MS m/z 337 [M+H]⁺.

Example 58

Preparation of (+)-4-(2-isopropyl-5-phenyl-2,3,4,5-tetrahydro-1H-benzo[c]azepin-8-yl)morpholine, maleate salt Pursuant to the general method described above in Example 57, the following products were prepared: (+)-4-(2-isopropyl-5-phenyl-2,3,4,5-tetrahydro-1H-benzo[c]azepin-8-yl)morpholine, maleate salt: mp 96-99° C.; $^1$H NMR (CD$_3$OD, 500 MHz) δ 7.49-6.32 (br, 8H), 6.24 (s, 2H), 4.72-4.10 (br, 3H), 3.82 (t, J=4.5 Hz, 4H), 3.71-3.40 (br, 3H), 3.15 (app s, 4H), 2.92-2.20 (br, 2H), 1.72-1.20 (br, 6H); ESI MS m/z 352 [M+H]⁺; (−)-4-(2-isopropyl-5-phenyl-2,3,4,5-tetrahydro-1H-benzo[c]azepin-8-yl)morpholine, maleate salt: mp 195-197° C.; $^1$H NMR (CD$_3$OD, 500 MHz) δ 7.49-6.32 (br, 8H), 6.24 (s, 2H), 4.72-4.10 (br, 3H), 3.82 (t, J=4.5 Hz, 4H), 3.71-3.40 (br, 3H), 3.15 (app s, 4H), 2.92-2.20 (br, 2H), 1.72-1.20 (br, 6H); ESI MS m/z 352 [M+H]⁺.

Example 59

Preparation of (+)-2-(8-morpholino-5-phenyl-4,5-dihydro-1H-benzo[c]azepin-2(3H)-yl)ethanol, L-tartrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane (3×). The combined organic extracts were dried over sodium sulfate and concentrated in vacuo to give the desired acid (18.0 g, 80%) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-methoxybenzylamine (7.8 g, 57 mmol) and the acid (7.6 g, 57 mmol) from step A above in dichloromethane (400 mL) at room temperature was added 1-(3-(dimethylamino)propyl)-3-ethylcarbodiimide hydrochloride (12.0 g, 62.7 mmol). The reaction solution was stirred at room temperature for 16 hours. The resultant reaction mixture was washed with water, aqueous 1 N hydrochloric acid, water and aqueous saturated sodium bicarbonate, dried over sodium sulfate and concentrated in vacuo. The crude acetal (13.3 g, 92%) as a light yellow was used in the next step without further purification: ¹H NMR (CDCl₃, 500 MHz) δ 7.24 (d, J=8.0 Hz, 1H), 6.86 (dd, J=7.5, 0.5 Hz, 1H), 6.83-6.80 (m, 2H), 6.40 (br, 1H), 4.73 (t, J=5.5 Hz, 1H), 4.44 (d, J=5.5 Hz, 2H), 3.80 (s, 3H), 3.39 (s, 6H), 2.59 (d, J=5.5 Hz, 2H).

Step C: A solution of the acetal (12.2 g, 48.2 mmol) from step B above in concentrated hydrochloric acid (120 mL) was stirred at room temperature for 2 hours. The resultant reaction mixture was diluted with water, saturated with sodium chloride and extracted with chloroform. The combined organic extracts were dried over sodium sulfate and concentrated in vacuo to give the crude product, which was purified by crystallization from dichloromethane to give the desired lactam (5.9 g, 59%) as a light yellow solid: ¹H NMR (CDCl₃, 500 MHz) δ 7.29 (d, J=8.5 Hz, 1H), 7.08 (d, J=12.0 Hz, 1H), 6.89 (dd, J=8.0, 2.5 Hz, 1H), 6.78 (d, J=2.5 Hz, 1H), 6.29 (br, 1H), 6.17 (dd, J=12.0, 2.0 Hz, 1H), 4.13 (d, J=5.5 Hz, 2H), 3.84 (s, 3H).

Step D: To a mixture of the lactam (3.0 g, 16 mmol) from step C above and benzene (9.0 mL, 0.10 mol) was added triflic acid (24.0 mL, 0.27 mol). The reaction solution was stirred at room temperature for 5 hours and then it was diluted with water and extracted with dichloromethane (3×). The combined organic extracts were dried over sodium sulfate and concentrated in vacuo to give the desired 5-phenyllactam (4.4 g, quantitative) as a white solid: ¹H NMR (CDCl₃, 500 MHz) δ 7.30 (t, J=7.0 Hz, 2H), 7.22 (t, J=7.0 Hz, 1H), 7.12 (d, J=7.0 Hz, 2H), 6.86 (d, J=8.5 Hz, 1H), 6.72 (d, J=8.5, 2.5 Hz, 1H), 6.64 (d, J=2.5 Hz, 1H), 6.30 (br, 1H), 4.56 (dd, J=16.0, 6.0 Hz, 1H), 4.49 (dd, J=10.5, 4.5 Hz, 1H), 4.27 (dd, J=16.0, 5.0 Hz, 1H), 3.78 (s, 3H), 3.15 (dd, J=14.5, 10.5 Hz, 1H), 3.00 (dd, J=14.5, 4.5 Hz, 1H).

Step E: To a solution of the 5-phenyllactam (4.2 g, 19.5 mmol) from step D above in THF (120 mL) was added borane-dimethyl sulfide (24.5 mL of 2M in tetrahydrofuran, 49 mmol) in batches. The reaction solution was stirred at room temperature for 16 hours and then additional borane-dimethyl sulfide (5.0 mL of 2M in tetrahydrofuran, 10 mmol) was added to it. The reaction solution was stirred at room temperature for 5 hours and then quenched with methanol. The resultant mixture was concentrated in vacuo and the residue obtained was dissolved in dioxane (80 mL) and 6N hydrochloric acid (40 mL) and heated under reflux for 1 hour. The resultant solution was cooled to room temperature, neutralized with aqueous sodium hydroxide and extracted with dichloromethane (3×). The combined organic extracts were washed with brine, dried over sodium sulfate and concentrated in vacuo. The crude product obtained was purified by flash column chromatography (99:0.9:0.1 to 90:9:1 dichloromethane/methanol/concentrated ammonium hydroxide) to give the desired benzazepine (2.7 g, 54%) as a light yellow oil: ¹H NMR (CDCl₃, 500 MHz) δ 7.34 (t, J=7.5 Hz, 2H), 7.25 (t, J=7.5 Hz, 1H), 7.16 (d, J=7.5 Hz, 2H), 6.74 (d, J=2.5 Hz, 1H), 6.66-6.54 (m, 2H), 4.36 (d, J=9.5 Hz, 1H), 4.00 (d, J=15.0 Hz, 1H), 3.87 (d, J=14.5 Hz, 1H), 3.77 (s, 3H), 3.29-3.22 (m, 1H), 3.19-3.14 (m, 1H), 2.27-2.13 (m, 2H), 1.69 (br, 1H).

Step F: To a solution of the 2H-benzazepine (2.9 g, 11.4 mmol) from step E above in dichloromethane (120 mL) were added pyridine (1.8 mL, 23 mmol), 4-dimethylaminopyridine (0.14 g, 1.1 mmol) and acetic anhydride (1.3 mL, 14.2 mmol) at 0° C. The reaction solution was let to warm to room temperature and stirred for 15 hours. The resultant reaction mixture was quenched with aqueous ammonium chloride, washed with 1 N hydrochloric acid and aqueous saturated sodium bicarbonate, dried over sodium sulfate and concentrated in vacuo. The crude product obtained (3.2 g, 95%) as a light yellow oil, was used in the next step without further purification: ¹H NMR (CDCl₃, 500 MHz) δ 7.34 (t, J=7.5 Hz, 2H), 7.24 (t, J=7.5 Hz, 1H), 7.09 (d, J=8.0 Hz, 2H), 6.95 (d, J=2.5 Hz, 1H), 6.82-6.63 (m, 2H), 4.69-4.30 (m, 3H), 3.83-3.47 (m, 5H), 2.41-1.92 (m, 5H).

Step G: To a solution of the 8-methoxybenzazepine (3.2 g, 10.8 mmol) from step F above in dichloromethane (90 mL) at −78° C. was added boron tribromide (10 mL, 0.11 mol) slowly. After the addition, the reaction solution was stirred at −78° C. for 4 h and at room temperature for 1 hour. The resultant reaction mixture was cooled to 0° C., quenched by slow addition of methanol and concentrated in vacuo. The residue obtained (3.2 g, quantitative) as an off-white solid, was used in the next step without further purification: ¹H NMR (CDCl₃, 500 MHz) δ 7.99-7.56 (br, 1H), 7.32 (t, J=7.5 Hz, 2H), 7.23 (t, J=7.5 Hz, 1H), 7.12 (d, J=2.5 Hz, 1H), 7.09 (d, J=7.5 Hz, 2H), 6.73-6.06 (m, 2H), 4.68-4.31 (m, 3H), 3.83-3.54 (m, 2H), 2.47-2.12 (m, 2H), 2.12-1.93 (m, 3H); ESI MS m/z 282 [M+H]⁺.

Step H: To a solution of the phenol (0.85 g, 3.0 mmol) from step G above in chloroform (30 mL) at 0° C. was added triethylamine (5.1 mL, 36 mmol) followed by triflic anhydride (1.0 mL, 6.0 mmol) dropwise. The resultant reaction solution was stirred at room temperature for 12 hours and then additional triethylamine (1.0 mL, 7.0 mmol) and triflic anhydride (1.0 mL, 6.0 mmol) were added. The reaction solution was stirred at room temperature for 1 hour and then quenched with aqueous saturated sodium bicarbonate. The resultant mixture was extracted with dichlormethane (2×), washed with aqueous saturated ammonium chloride, dried over sodium sulfate and concentrated in vacuo. The residue obtained was purified by flash column chromatography (66:33 to 33:66 hexanes/ethyl acetate) to give the desired triflate (0.52 g, 42%) as an orange solid: ESI MS m/z 414 [M+H]⁺.

Step I: To a solution of the triflate (0.20 g, 0.48 mmol) from step H above in toluene (5 mL) were added cesium carbonate (0.49 g, 1.5 mmol), 2-(dicyclohexylphosphino)-2',4',6'-tri-i-propyl-1,1'-biphenyl (24 g, 0.05 mmol) and morpholine (0.042 mL, 1.0 mmol). The resultant mixture was flushed with argon for 10 minutes, and then palladium(II) acetate (11 mg, 0.05 mmol) was added to it. The reaction solution was heated at 100° C. under argon for 13 hours and then cooled to room temperature. The resultant mixture was diluted with dichloromethane, washed with water and brine, dried over sodium sulfate and concentrated in vacuo. The crude product obtained was purified by flash column chromatography (99:0.9:0.1 to 97:2.7:0.3 dichloromethane/methanol/concentrated ammonium hydroxide) to give the desired 8-morpholinyl benzazepine (0.13 g, 83%) as a white foam: ¹H NMR (CDCl₃, 500 MHz) δ 7.32 (t, J=8.0 Hz, 2H), 7.23 (t, J=7.5 Hz, 1H), 7.09 (d, J=7.5 Hz, 2H), 6.95-6.65 (m, 3H), 4.78-4.30 (m, 3H), 3.90-3.41 (m, 6H), 3.20-3.13 (m, 4H), 2.43-2.17 (m, 2H), 2.20-1.74 (m, 3H); ESI MS m/z 351 [M+H]⁺.

Step J: To a solution of the N-acetyl benzazepine (0.14 g, 0.40 mmol) from step I above in methanol (10 mL) was added an aqueous 2 N solution of sodium hydroxide (10 mL). The reaction solution was heated under reflux for 72 hours and then cooled to room temperature. The resultant reaction mixture was extracted with dichloromethane, washed with water and aqueous saturated sodium bicarbonate, dried over sodium sulfate and concentrated in vacuo. The residue obtained was purified by flash column chromatography (dichloromethane to 90:9:1 dichloromethane/methanol/concentrated ammonium hydroxide) to give the desired 2H-benzazepine (0.11 g, 89%) as a white foam: ¹H NMR (DMSO-d₆, 500 MHz) δ 7.35 (t, J=7.5 Hz, 2H), 7.24 (t, J=7.5 Hz, 1H), 7.14 (d, J=7.5 Hz, 2H), 6.84 (d, J=2.5 Hz, 1H), 6.65-6.60 (m, 1H), 6.49-6.38 (br, 1H), 4.33 (d, J=8.5 Hz, 1H), 3.95 (d, J=14.5 Hz, 1H), 3.77 (d, J=14.5 Hz, 1H), 3.71 (t, J=5.0 Hz, 4H), 3.10-2.87 (m, 6H), 2.21-2.12 (m, 1H), 2.03-1.85 (m, 1H).

Step K: The free base of the benzazepine from step J (800 mg) was resolved by preparative chiral HPLC (CHIRALPAK AD column, using 85:15:0.1 heptane/isopropanol/diethylamine as the eluent) to give the (+)-enantiomer $[[\alpha]^{25}_D+4.98°$ (c 0.18, methanol)] and the (−)-enantiomer $[[\alpha]^{25}_D-6.83°$ (c 0.18, methanol)].

Step L: To a solution of the (+)-enantiomer of the benzazepine (72 mg, 0.23 mmol) from step K above in acetonitrile (5 mL) were added potassium carbonate (0.13 g, 0.92 mmol) and 2-bromoethanol (0.032 mL, 0.46 mmol). The reaction solution was stirred under reflux for 3 hours and then cooled to room temperature and concentrated in vacuo. The residue obtained was purified by preparative thin layer chromatography (92:7.2:0.8 dichloromethane/methanol/concentrated ammonium hydroxide) to give the N-hydroxyethanol benzazepine $[[\alpha]^{25}_D+0.71°$ (c 0.14, methanol)] (64 mg, 79%) as a white solid: $^1$H NMR (CDCl$_3$, 500 MHz) δ 7.34 (t, J=7.5 Hz, 2H), 7.25 (t, J=7.5 Hz, 1H), 7.15 (d, J=7.5 Hz, 2H), 6.72 (s, 1H), 6.68-6.47 (br, 2H), 4.29 (d, J=8.0 Hz, 1H), 4.03-3.95 (br, 1H), 3.85 (t, J=4.5 Hz, 4H), 3.80 (d, J=14.5 Hz, 1H), 3.58 (t, J=5.0 Hz, 2H), 3.20-3.05 (m, 2H), 3.12 (t, J=4.5 Hz, 4H), 2.63-2.57 (m, 2H), 2.32-2.25 (m, 1H), 2.09 (d, J=14.0 Hz, 1H).

To a solution of the N-hydroxyethanol benzazepine (58 mg, 0.16 mmol) in methanol (2 mL) were added L-tartaric acid (24 mg, 0.16 mmol) and water (10 mL). The resultant solution was lypholized overnight to give (+)-2-(8-morpholino-5-phenyl-4,5-dihydro-1H-benzo[c]azepin-2(3H)-yl)ethanol, L-tartrate salt (80 mg, 97.1% AUC HPLC) as a white solid: mp 93-96° C.; $^1$H NMR (CD$_3$OD, 500 MHz) δ 7.37 (t, J=7.5 Hz, 2H), 7.28 (t, J=7.5 Hz, 1H), 7.18 (d, J=7.5 Hz, 2H), 7.03 (d, J=1.5 Hz, 1H), 6.89 (d, J=8.5 Hz, 1H), 6.85-6.49 (br, 1H), 4.60-4.49 (br, 1H), 4.48 (d, J=8.5 Hz, 1H), 4.40 (s, 2.3H), 4.34 (d, J=13.0 Hz, 1H), 3.87 (t, J=5.0 Hz, 2H), 3,82 (t, J=4.5 Hz, 4H), 3.57 (app s, 2H), 3.16-3.14 (m, 6H), 2.62-2.36 (br, 2H); ESI MS m/z 353 [M+H]$^+$.

Example 60

Preparation of (+)-4-(2-(2-fluoroethyl)-5-phenyl-2,3,4,5-tetrahydro-1H-benzo[c]azepin-8-yl)morpholine, L-tartrate salt Pursuant to the general method described above in Example 59, the following products were prepared: (+)-4-(2-(2-fluoroethyl)-5-phenyl-2,3,4,5-tetrahydro-1H-benzo[c]azepin-8-yl)morpholine, L-tartrate salt: mp 102-105° C.; $^1$H NMR (CD$_3$OD, 500 MHz) δ 7.36 (t, J=7.5 Hz, 2H), 7.27 (t, J=7.5 Hz, 1H), 7.18 (d, J=7.5 Hz, 2H), 7.00 (d, J=2.5 Hz, 1H), 6.84 (d, J=7.5 Hz, 1H), 6.82-6.54 (br, 1H), 4.77 (dt, J=47.5, 4.5 Hz, 2H), 4.46-4.38 (m, 2H), 4.43 (s, 2H), 4.23 (d, J=14.0 Hz, 1H), 3.82 (t, J=5.0 Hz, 4H), 3.50 (app s, 2H), 3.34-3.20 (m, 2H), 3.18-3.13 (m, 4H), 2.57-2.24 (br, 2H); ESI MS m/z 355 [M+H]$^+$.

Example 61

Preparation of (+)-4-(2-benzyl-5-phenyl-2,3,4,5-tetrahydro-1H-benzo[c]azepin-8-yl)morpholine, maleate salt Pursuant to the general method described above in Example 59, the following product was prepared: (+)-4-(2-benzyl-5-phenyl-2,3,4,5-tetrahydro-1H-benzo[c]azepin-8-yl)morpholine, maleate salt: mp 108-110° C.; $^1$H NMR (CD$_3$OD, 500 MHz) δ 7.51 (app s, 5H), 7.37 (t, J=7.5 Hz, 2H), 7.28 (t, J=7.5 Hz, 1H), 7.18 (d, J=7.0 Hz, 2H), 7.06-7.54 (br, 2H), 6.87 (d, J=2.5 Hz, 1H), 6.25 (s, 2H), 4.67-4.07 (br, 5H), 3.82 (t, J=4.5 Hz, 4H), 3.54-3.43 (br, 2H), 3.13 (t, J=4.5 Hz, 4H), 2.79-2.12 (br, 2H); ESI MS m/z 399 [M+H]$^+$.

Example 62

Preparation of 2,6-difluoro-4-(8-methoxy-2-methyl-2,3,4,5-tetrahydro-1H-benzo[c]azepin-5-yl)phenol, citrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-0.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 h and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To a solution of the lactam (2.0 g, 9.84 mmol) from step D in trifluoromethanesulfonic acid (20 mL) was added 2,6-difluorophenol (3.84 g, 29.5 mmol). The reaction mixture was stirred at room temperature for 4 hours. The reaction mixture was diluted with cold water, basified with sodium hydroxide until pH 8-9 and extracted with dichloromethane (3×300 mL). The extracts were dried other sodium sulfate, filtered and concentrated under reduced pressure. The residue was triturated with ethanol to afford the 5-aryllactam (2.04 g, 62%) as a white solid: $^1$H NMR (CDCl$_3$, 500 MHz) δ 9.93 (s, 1H), 6.87 (d, J=2.6 Hz, 1H), 6.81 (d, J=8.6 Hz, 1H), 6.78-6.73 (m, 3H), 4.87 (d, J=16.4 Hz, 1H), 4.42 (d, J=16.4 Hz, 1H), 4.34 (dd, J=9.8, 4.9 Hz, 1H), 3.73 (s, 3H), 3.09 (dd, J=13.4, 9.9 Hz, 1H), 2.92-2.86 (m, 1H), 2.87 (s, 3H).

Step F: To a solution of the 5-aryllactam (2.0 g, 6.0 mmol) from step E in tetrahydrofuran (18 mL) was added borane-dimethylsulfide complex in THF (6 mL, 12.0 mmol, 2M solution). The reaction mixture was heated to reflux for one hour then was concentrated to dryness under reduced pressure. The residue was dissolved in 1,4-dioxane (40 mL) and treated with an aqueous solution of hydrochloric acid (6N, 20 mL) and the mixture was heated to reflux for 3 hours, then concentrated under reduced pressure. The residue was diluted with water (20 mL) and basified until pH 8-9 with a saturated sodium bicarbonate. The solution was extracted with dichloromethane (3×), the combined extracts was dried other sodium sulfate, filtered and concentrated to dryness under reduced pressure to afford the 5-arylbenzazepine (2.04 g, quantitative) as an off-white solid.

Step G: An analytical sample of the 5-arylbenzazepine (0.32 g) was triturated with a mixture of methanol and ethyl acetate to afford a white solid (0.19 g). To a solution of the 5-arylbenzazepine (0.19 g, 0.59 mmol) in a mixture of water and methanol was added citric acid (0.112 g, 0.59 mmol). The solution was lyophilized overnight to afford 2,6-difluoro-4-(8-methoxy-2-methyl-2,3,4,5-tetrahydro-1H-benzo[c]azepin-5-yl)phenol, citrate salt (0.25 g, 85%, AUC HPLC >99%) as a white solid: mp 88-90° C.; $^1$H NMR (CD$_3$OD, 500 MHz) δ 7.02 (d, J=2.6 Hz, 1H), 6.90-6.87 (m, 1H), 6.85-6.78 (m, 1H), 6.72 (d, J=8.9 Hz, 2H), 4.50-4.43 (m, 1H), 4.41 (dd, J=8.6, 2.2 Hz, 1H), 4.24 (d, J=14.0 Hz, 1H), 3.81 (s, 3H), 3.53-3.47 (m, 2H), 3.34 (s, 1H), 2.81 (s, 2H), 2.80 (d, J=15.4 Hz, 2H), 2.72 (d, J=15.4 Hz, 2H), 2.58-2.47 (m, 1H), 2.35-2.32 (m, 1H); ESI MS m/z 320 [M+H]$^+$.

Example 63

Preparation of 2-fluoro-4-(8-methoxy-2-methyl-2,3,4,5-tetrahydro-1H-benzo[c]azepin-5-yl)phenol, maleate salt Pursuant to the general method described above in Example 62, the following product was prepared: 2-fluoro-4-(8-methoxy-2-methyl-2,3,4,5-tetrahydro-1H-benzo[c]azepin-5-yl)phenol, maleate salt: mp 50-54° C.; $^1$H NMR (CD$_3$OD, 500 MHz) δ 7.05-7.01 (m, 1H), 6.95-6.82 (m, 3H), 6.79-6.73 (m, 2H), 6.25 (s, 2H), 4.70-4.48 (m, 1H) 4.46-4.39 (m, 1H), 4.35-4.22 (m, 1H), 3.80 (s, 3H), 3.60-3.51 (m, 2H), 2.99-2.81 (m, 3H), 2.43-2.29 (m, 1H); ESI MS m/z 302 [M+H]$^+$.

Example 64

Preparation of (+)-3-(2-methyl-5-phenyl-2,3,4,5-tetrahydro-1H-benzo[c]azepin-8-yl)benzonitrile, L-tartrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR (CDCl$_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6 N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR (CDCl$_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer [[α]$^{25}$$_D$+3.66° (c 0.41, methanol)] and (−)-enantiomer [[α]$^{25}$$_D$−1.16° (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step I: To a stirred mixture of the phenol from Step H above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a sealed tube were added 3-cyanophenylboronic acid (79 mg, 0.54 mmol), potassium bromide (149 mg, 1.3 mmol), potassium hydroxide (70 mg, 1.3 mmol), and a solution of the triflate from Step I above (160 mg, 0.42 mmol) in toluene (4 mL). The reaction mixture was degassed with argon for 1 minute, then tetrakis(triphenylphosphine)palladium(0) (24 mg, 0.021 mmol) was added. After degassing briefly with argon again, the reaction was heated to 80° C. and stirred for 5 hours. Additional 3-cyanophenylboronic acid (79 mg, 0.54 mmol) and tetrakis(triphenylphosphine)palladium (0) (24 mg, 0.021 mmol) were then added and the reaction was stirred for 2 hours, at which time ESI MS indicated the reaction went to completion. After cooling to room temperature, the mixture was diluted with 90:10 methylene chloride/methanol and filtered through silica gel, then concentrated in vacuo. Purification by flash column chromatography (1%-10% methanol/methylene chloride) yielded the desired benzazepine (41 mg, 29%) as a yellow oil: [α]$^{23}$$_D$−10.0° (c 0.04, methanol); $^1$H NMR (500 MHz, CDCl$_3$) δ 7.83 (s, 1H), 7.78 (d, J=8.0 Hz, 1H), 7.60 (d, J=8.0 Hz, 1H), 7.52 (d, J=8.0 Hz, 1H), 7.40-7.38 (m, 3H), 7.31-7.29 (m, 2H), 7.22-7.21 (m, 2H), 6.79-6.72 (br, 1H), 4.39-4.37 (m, 1H), 4.01-3.99 (m, 1H), 3.83-3.80 (m, 1H), 3.19-3.14 (m, 1H), 3.01-2.97 (m, 1H), 2.41 (s, 3H), 2.44-2.34 (m, 1H), 2.20-2.15 (m, 1H); ESI MS m/z 339 [M+H]$^+$.

Step K: To a stirred solution of the benzazepine from Step J above (40 mg, 0.12 mmol) in methanol (2 mL) at room temperature was added L-tartaric acid (18 mg, 0.12 mmol). The mixture was stirred at room temperature for 1 hour and then the solvent was concentrated to approximately 0.5 mL. After diluting with water (2 mL), the mixture was lyophilized for 15 hours to provide (+)-3-(2-methyl-5-phenyl-2,3,4,5-tetrahydro-1H-benzo[c]azepin-8-yl)benzonitrile, L-tartrate salt (60 mg, 99%, 97.4% AUC HPLC) as a light yellow powder: $^1$H NMR (500 MHz, CD$_3$OD) δ 8.03 (s, 1H), 7.97 (d, J=8.0 Hz, 1H), 7.79-7.78 (m, 1H), 7.73 (d, J=7.5 Hz, 1H), 7.64 (t, J=8.0 Hz, 2H), 7.42 (t, J=7.5 Hz, 2H), 7.33 (t, J=7.5 Hz, 1H), 7.25 (d, J=7.5 Hz, 2H), 7.00-6.94 (br, 1H), 4.73-4.67 (m, 1H), 4.65 (d, J=8.5 Hz, 1H), 4.44-4.41 (m, 1H), 4.41 (s, 2H), 3.65-3.57 (m, 2H), 2.89 (s, 3H), 2.65-2.59 (m, 1H), 2.46-2.43 (m, 1H); ESI MS m/z 339 [M+H]$^+$.

Example 65

Preparation of (+)-4-(2-methyl-5-phenyl-2,3,4,5-tetrahydro-1H-benzo[c]azepin-8-yl)benzonitrile, L-tartrate salt Pursuant to the general method described above in Example 64, the following product was prepared: (+)-4-(2-methyl-5-phenyl-2,3,4,5-tetrahydro-1H-benzo[c]azepin-8-yl)benzonitrile, L-tartrate salt: $^1$H NMR (500 MHz, CD$_3$OD) δ 7.84 (d, J=8.5 Hz, 2H), 7.81 (d, J=8.5 Hz, 2H), 7.80-7.79 (m, 1H), 7.64 (d, J=7.0 Hz, 1H), 7.42 (t, J=7.5 Hz, 2H), 7.32 (t, J=7.5 Hz, 1H), 7.24 (d, J=7.5 Hz, 2H), 7.00-6.93 (br, 1H), 4.69-4.63 (m, 1H), 4.64 (d, J=8.0 Hz, 1H), 4.40 (s, 2H), 4.40-4.38 (m, 1H), 3.59-3.54 (m, 2H), 2.87 (s, 3H), 2.64-2.58 (m, 1H), 2.45-2.41 (m, 1H); ESI MS m/z 339 [M+H]$^+$.

Example 66

Preparation of (+)-2-methyl-8-(4-(methylsulfonyl) phenyl)-5-phenyl-2,3,4,5-tetrahydro-1H-benzo[c] azepine, L-tartrate salt Pursuant to the general method described above in Example 64, the following product was prepared: (+)-2-methyl-8-(4-(methylsulfonyl)phenyl)-5-phenyl-2,3,4,5-tetrahydro-1H-benzo[c]azepine, L-tartrate salt: $^1$H NMR (500 MHz, CD$_3$OD) δ 8.03 (d, J=8.0 Hz, 2H), 7.92 (d, J=8.5 Hz, 2H), 7.84 (s, 1H), 7.67 (d, J=7.5 Hz, 1H), 7.42 (t, J=7.5 Hz, 2H), 7.33 (t, J=7.0 Hz, 1H), 7.25 (d, J=7.5 Hz, 2H), 7.02-6.95 (br, 1H), 4.74-4.68 (m, 1H), 4.66 (d, J=9.0 Hz, 1H), 4.45-4.41 (m, 1H), 4.41 (s, 2H), 3.64-3.58 (m, 2H), 3.15 (s, 3H), 2.91 (s, 3H), 2.67-2.59 (m, 1H), 2.47-2.44 (m, 1H); ESI MS m/z 392 [M+H]$^+$.

Example 67

Preparation of (+)-2-methyl-8-(4-methylpiperazin-1-yl)-5-phenyl-2,3,4,5-tetrahydro-1H-benzo[c]azepine and (−)-2-methyl-8-(4-methylpiperazin-1-yl)-5-phenyl-2,3,4,5-tetrahydro-1H-benzo[c]azepine, L-tartrate salts Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E. To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR (CDCl$_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR (CDCl$_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer $[[\alpha]^{25}_D+3.66°$ (c 0.41, methanol)] and (−)-enantiomer $[[\alpha]^{25}_D-1.16°$ (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step I: To a stirred mixture of the phenol from Step H above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a stirred solution of the triflate from Step I above (298 mg, 0.77 mmol) in anhydrous toluene (7 mL) at room temperature under N$_2$ were added 1-methylpiperazine (0.17 mL, 1.6 mmol), sodium tert-butoxide (223 mg, 2.3 mmol), and 2-(dicyclohexylphosphino)-2',4',6'-tri-i-isopropyl-1,1'-biphenyl (111 mg, 0.23 mmol). The reaction mixture was degassed with argon for 2 minutes, then palladium(II) acetate (26 mg, 0.12 mmol) was added under argon. A reflux condenser was attached and the reaction was heated to 100° C. and stirred for 4 hours, at which time ESI MS indicated the reaction went to completion. After cooling to room temperature, the reaction mixture was diluted with methylene chloride and filtered through Celite. The filtrate was then washed with saturated ammonium chloride and brine, dried over sodium sulfate, filtered, and concentrated in vacuo. Purification by flash column chromatography (9.4:0.5:0.1 methylene chloride/methanol/concentrated ammonium hydroxide) yielded the desired piperazine (137 mg, 53%) as a light yellow oil: $[\alpha]^{23}_D-4.44°$ (c 0.045, methanol); $^1$H NMR (500 MHz, CDCl$_3$) δ 7.34 (t, J=7.5 Hz, 2H), 7.26-7.23 (m, 1H), 7.17 (d, J=7.5 Hz, 2H), 6.77-6.76 (m, 1H), 6.63-6.61 (m, 1H), 6.56-6.49 (br, 1H), 4.24-4.23 (m, 1H), 3.93-3.85 (m, 1H), 3.70-3.67 (m, 1H), 3.17 (t, J=5.0 Hz, 4H), 3.13-3.08 (m, 1H), 2.96-2.92 (m, 1H), 2.55 (t, J=5.0 Hz, 4H), 2.35 (s, 3H), 2.34 (s, 3H), 2.34-2.26 (m, 1H), 2.11-2.05 (m, 1H); ESI MS m/z 336 [M+H]$^+$.

Step K: To a stirred solution of the piperazine from Step J above (132 mg, 0.39 mmol) in methanol (4 mL) at room temperature was added L-tartaric acid (59 mg, 0.39 mmol). The mixture was stirred at room temperature for 1 hour and then the solvent was concentrated to approximately 0.5 mL. After diluting with water (2 mL), the mixture was lyophilized for 15 h to provide (+)-2-methyl-8-(4-methylpiperazin-1-yl)-5-phenyl-2,3,4,5-tetrahydro-1H-benzo[c]azepine, L-tartrate salt (190 mg, 99%, 95.2% AUC HPLC) as a light yellow powder: $^1$H NMR (500 MHz, CD$_3$OD) δ 7.37 (t, J=7.5 Hz, 2H), 7.27 (t, J=7.5 Hz, 1H), 7.17 (d, J=7.5 Hz, 2H), 7.07-7.06 (m, 1H), 6.89 (d, J=7.0 Hz, 1H), 6.79-6.67 (br, 1H), 4.46-4.45 (m, 2H), 4.33 (s, 2H), 4.24-4.21 (m, 1H), 3.51-3.47 (m, 2H), 3.38-3.34 (m, 4H), 3.05-3.02 (m, 4H), 2.81 (s, 3H), 2.66 (s, 3H), 2.59-2.50 (m, 1H), 2.39-2.33 (m, 1H); ESI MS m/z 336 [M+H]$^+$.

Step L: A mixture of the (−)-enantiomer from Step G above (2.76 g, 10.3 mmol) and hydrobromic acid (48% solution in H$_2$O, 70 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (2.23 g, 85%) as a light brown solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step M: To a stirred mixture of the phenol from Step L above (2.21 g, 8.7 mmol) and pyridine (0.85 mL, 10.5 mmol) in anhydrous methylene chloride (50 mL) at 0° C. under N$_2$ was added triflic anhydride (1.8 mL, 10.5 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (1.67 g, 50%) as an orange oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step N: To a stirred solution of the triflate from Step M above (300 mg, 0.78 mmol) in anhydrous toluene (8 mL) at room temperature under N$_2$ were added 1-methylpiperazine (0.17 mL, 1.6 mmol), sodium tert-butoxide (224 mg, 2.3 mmol), and 2-(dicyclohexylphosphino)-2',4',6'-tri-i-isopropyl-1,1'-biphenyl (111 mg, 0.23 mmol). The reaction mixture was degassed with argon for 2 minutes, then palladium(II) acetate (26 mg, 0.12 mmol) was added under argon. A reflux condenser was attached and the reaction was heated to 100° C. and stirred for 4 hours, at which time ESI MS indicated the reaction went to completion. After cooling to room temperature, the reaction mixture was diluted with methylene chloride and filtered through Celite. The filtrate was then washed with saturated ammonium chloride and brine, dried over sodium sulfate, filtered, and concentrated in vacuo. Purification by flash column chromatography (9.4:0.5:0.1 methylene chloride/methanol/concentrated ammonium hydroxide) yielded the desired piperazine (124 mg, 48%) as a light brown oil: [α]$^{23}_D$+3.08° (c 0.065, methanol); $^1$H NMR (500 MHz, CDCl$_3$) δ 7.34 (t, J=7.5 Hz, 2H), 7.26-7.23 (m, 1H), 7.17 (d, J=7.5 Hz, 2H), 6.77-6.76 (m, 1H), 6.63-6.61 (m, 1H), 6.56-6.49 (br, 1H), 4.24-4.23 (m, 1H), 3.93-3.85 (m, 1H), 3.70-3.67 (m, 1H), 3.17 (t, J=5.0 Hz, 4H), 3.13-3.08 (m, 1H), 2.96-2.92 (m, 1H), 2.55 (t, J=5.0 Hz, 4H), 2.35 (s, 3H), 2.34 (s, 3H), 2.34-2.26 (m, 1H), 2.11-2.05 (m, 1H); ESI MS m/z 336 [M+H]$^+$.

Step O: To a stirred solution of the piperazine from Step N above (124 mg, 0.37 mmol) in methanol (4 mL) at room temperature was added L-tartaric acid (55 mg, 0.37 mmol). The mixture was stirred at room temperature for 1 hour and then the solvent was concentrated to approximately 0.5 mL. After diluting with water (2 mL), the mixture was lyophilized for 15 h to provide (−)-2-methyl-8-(4-methylpiperazin-1-yl)-5-phenyl-2,3,4,5-tetrahydro-H-benzo[c]azepine, L-tartrate salt (180 mg, 99%, 98.6% AUC HPLC) as a light brown powder: $^1$H NMR (500 MHz, CD$_3$OD) δ 7.37 (t, J=7.5 Hz, 2H), 7.27 (t, J=7.5 Hz, 1H), 7.17 (d, J=7.5 Hz, 2H), 7.07-7.06 (m, 1H), 6.89 (d, J=7.0 Hz, 1H), 6.79-6.67 (br, 1H), 4.46-4.45 (m, 2H), 4.33 (s, 2H), 4.24-4.21 (m, 1H), 3.51-3.47 (m, 2H), 3.38-3.34 (m, 4H), 3.05-3.02 (m, 4H), 2.81 (s, 3H), 2.66 (s, 3H), 2.59-2.50 (m, 1H), 2.39-2.33 (m, 1H); ESI MS m/z 336 [M+H]$^+$.

Example 68

Preparation of (+)-2-methyl-5-phenyl-8-(4-(pyridin-2-yl)piperazin-1-yl)-2,3,4,5-tetrahydro-1H-benzo[c]azepine, L-tartrate salt Pursuant to the general method described above in Example 67, the following product was prepared: (+)-2-methyl-5-phenyl-8-(4-(pyridin-2-yl)piperazin-1-yl)-2,3,4,5-tetrahydro-1H-benzo[c]azepine, L-tartrate salt: mp 117-119° C.; $^1$H NMR (500 MHz, CD$_3$OD) δ 8.12-8.10 (m, 1H), 7.61-7.57 (m, 1H), 7.38 (t, J=7.5 Hz, 2H), 7.29 (t, J=7.5 Hz, 1H), 7.19 (d, J=7.5 Hz, 2H), 7.12-7.11 (m, 1H), 6.95-6.94 (m, 1H), 6.88 (d, J=8.5 Hz, 1H), 6.80-6.72 (br, 1H), 6.72-6.70 (m, 1H), 4.59-4.49 (m, 1H), 4.49 (d, J=8.0 Hz, 1H), 4.41 (s, 2H), 4.30-4.27 (m, 1H), 3.67-3.65 (m, 4H), 3.59-3.49 (m, 2H), 3.31-3.29 (m, 4H), 2.87 (s, 3H), 2.61-2.52 (m, 1H), 2.42-2.36 (m, 1H); ESI MS m/z 399 [M+H]$^+$; (−)-2-methyl-5-phenyl-8-(4-(pyridine-2-yl)piperazin-1-yl)-2,3,4,5-tetrahydro-1H-benzo[c]azepine, L-tartrate salt: mp 112-115° C.; $^1$H NMR (500 MHz, CD$_3$OD) δ 8.12-8.10 (m, 1H), 7.61-7.57 (m, 1H), 7.38 (t, J=7.5 Hz, 2H), 7.29 (t, J=7.5 Hz, 1H), 7.19 (d, J=7.5 Hz, 2H), 7.12-7.11 (m, 1H), 6.95-6.94 (m, 1H), 6.88 (d, J=8.5 Hz, 1H), 6.80-6.72 (br, 1H), 6.72-6.70 (m, 1H), 4.59-4.49 (m, 1H), 4.49 (d, J=8.0 Hz, 1H), 4.41 (s, 2H), 4.30-4.27 (m, 1H), 3.67-3.65 (m, 4H), 3.59-3.49 (m, 2H), 3.31-3.29 (m, 4H), 2.87 (s, 3H), 2.61-2.52 (m, 1H), 2.42-2.36 (m, 1H); ESI MS m/z 399 [M+H]$^+$.

Example 69

Preparation of (+)-2-methyl-5-phenyl-8-(4-(pyrimidin-2-yl)piperazin-1-yl)-2,3,4,5-tetrahydro-1H-benzo[c]azepine, L-tartrate salt Pursuant to the general method described above in Example 67, the following product was prepared: (+)-2-methyl-5-phenyl-8-(4-(pyrimidin-2-yl)piperazin-1-yl)-2,3,4,5-tetrahydro-1H-benzo[c]azepine, L-tartrate salt: mp 119-121° C.; $^1$H NMR (500 MHz, CD$_3$OD) δ 8.34 (d, J=4.5 Hz, 2H), 7.38 (t, J=7.5 Hz, 2H), 7.28 (t, J=7.5 Hz, 1H), 7.19 (d, J=7.0 Hz, 2H), 7.11-7.10 (m, 1H), 6.94 (d, J=7.5 Hz, 1H), 6.80-6.73 (br, 1H), 6.62 (t, J=5.0 Hz, 1H), 4.57-4.49 (m, 1H), 4.49-4.47 (m, 1H), 4.40 (s, 2H), 4.29-4.26 (m, 1H), 3.95 (t, J=5.0 Hz, 4H), 3.55-3.51 (m, 2H), 3.26 (t, J=5.0 Hz, 4H), 2.86 (br, 3H), 2.60-2.52 (m, 1H), 2.42-2.35 (m, 1H); ESI MS m/z 400 [M+H]$^+$.

Example 70

Preparation of (+)-8-(4-(ethylsulfonyl)piperazin-1-yl)-2-methyl-5-phenyl-2,3,4,5-tetrahydro-1H-benzo[c]azepine, L-tartrate salt Pursuant to the general method described above in Example 67, the following product was prepared: (+)-8-(4-(ethylsulfonyl)piperazin-1-yl)-2-methyl-5-phenyl-2,3,4,5-tetrahydro-1H-benzo[c]azepine, L-tartrate salt: $^1$H NMR (500 MHz, CD$_3$OD) δ 7.37 (t, J=7.5 Hz, 2H), 7.28 (t, J=7.0 Hz, 1H), 7.18 (d, J=7.0 Hz, 2H), 7.08-7.07 (m, 1H), 6.91-6.90 (m, 1H), 6.78-6.71 (br, 1H), 4.54-4.46 (m, 1H), 4.48-4.46 (m, 1H), 4.38 (s, 2H), 4.27-4.24 (m, 1H), 3.55-3.49 (m, 2H), 3.42 (t, J=5.0 Hz, 4H), 3.26 (t, J=5.0 Hz, 4H), 3.08 (q, J=7.5 Hz, 2H), 2.83 (s, 3H), 2.59-2.52 (m, 1H), 2.40-2.35 (m, 1H), 1.34 (t, J=7.5 Hz, 3H), ESI MS m/z 414 [M+H]$^+$.

Example 71

Preparation of (+)-N-isopropyl-2-(4-(2-methyl-5-phenyl-2,3,4,5-tetrahydro-1H-benzo[c]azepin-8-yl)piperazin-1-yl)acetamide, L-tartrate salt Pursuant to the general method described above in Example 67, the following product was prepared: (+)-N-isopropyl-2-(4-(2-methyl-5-phenyl-2,3,4,5-tetrahydro-1H-benzo[c]azepin-8-yl)piperazin-1-yl)acetamide, L-tartrate salt: $^1$H NMR (500 MHz, CD$_3$OD) δ 7.37 (t, J=7.5 Hz, 2H), 7.28 (t, J=7.5 Hz, 1H), 7.18 (d, J=7.5 Hz, 2H), 7.06-7.05 (m, 1H), 6.89-6.87 (m, 1H), 6.77-6.70 (br, 1H), 4.53-4.46 (m, 1H), 4.47-4.46 (m, 1H), 4.39 (s, 2H), 4.27-4.24 (m, 1H), 4.02 (sep, J=6.5 Hz, 1H), 3.55-3.48 (m, 2H), 3.26 (t, J=5.0 Hz, 4H), 3.08 (s, 2H), 2.84 (s, 3H), 2.70 (t, J=5.0 Hz, 4H), 2.60-2.51 (m, 1H), 2.39-2.36 (m, 1H), 1.16 (d, J=6.5 Hz, 6H), ESI MS m/z 421 [M+H]$^+$.

Example 72

Preparation of 1-(2-methyl-5-phenyl-2,3,4,5-tetrahydro-1H-benzo[c]azepin-8-yl)pyridin-2(1H)-one, tartrate salt and N1,N2-dimethyl-N1-(2-methyl-5-phenyl-2,3,4,5-tetrahydro-1H-benzo[c]azepin-8-yl)ethane-1,2-diamine, tartrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of 3-bromobenzaldehyde (47.5 mL, 0.4 mol) in methanol (460 mL) at room temperature was added a solution of methylamine in water (35 mL, 0.4 mol, 40 wt. % solution). The resultant solution was cooled to 0° C. and sodium borohydride (22 g, 0.6 mol) was added to it in portions. The reaction solution was stirred at 0° C. for 3 hours and 30 minutes, and then warmed to room temperature. The resultant reaction mixture was concentrated in vacuo and partitioned between dichloromethane and water. The aqueous layer was separated and washed with dichloromethane (3×). The combined organic extract was washed with saturated sodium bicarbonate and brine, dried over magnesium sulfate, filtered and concentrated in vacuo to give the desired benzylamine (76 g, 81%) as a clear oil: $^1$H NMR (300 MHz, CDCl$_3$) δ 7.48 (d, J=1.5 Hz, 1H), 7.40-7.37 (m, 1H), 7.24-7.16 (m, 2H), 3.73 (s, 2H), 2.45 (s, 3H).

Step C: To a mixture of the benzylamine (31.9 g, 159 mmol) from Step B above, 3,3-dimethoxypropanoic acid (21.4 g, 159 mmol) and dichloromethane (150 mL) at 0° C. was added 1-(3-dimethylaminopropyl)-3-ethylcarbodiimide hydrochloride (33.6 g, 175 mmol). The mixture was stirred at room temperature overnight, and then washed with water, 2 N sodium carbonate and 1 N HCl. The resulting solution was dried over sodium sulfate, filtered and concentrated in vacuo to give the acetal (40.7 g, 81%) as a yellow oil: $^1$H NMR (300 MHz, CDCl$_3$) δ 7.45-7.35 (m, 2H), 7.23-7.09 (m, 2H), 4.92-4.87 (m, 1H), 4.57, 4.54 (s, 2H, rotamers), 3.45, 3.40 (s, 6H, rotamers), 2.96, 2.94 (s, 3H, rotamers), 2.74, 2.68 (d, J=5.6 Hz, 2H, rotamers). The crude product was used without further purification in the next reaction.

Step D: To a suspension of aluminum chloride (21 g, 158 mmol) in dichloromethane (600 mL) at 0° C. was added a solution of the acetal (10 g, 31.6 mmol) in dichloromethane (50 mL) over 30 minutes. The reaction mixture was maintained at 0° C. for 1 hour and 30 minutes, and then allowed to warm to room temperature overnight. The mixture was then cooled to 0° C., and 6 N HCl (300 mL) was added to the solution slowly. The mixture was stirred at 0° C. for 1 hour, and the aqueous layer was separated and washed with dichloromethane. The combined organic extract was washed with brine, dried over sodium sulfate, filtered and concentrated under reduced pressure. Purification by flash column chromatography (1:1 ethyl acetate/hexanes to ethyl acetate) gave the lactam (2.58 g, 32%) as a pale yellow oil: $^1$H NMR (500 MHz, CDCl$_3$) δ 7.52 (dd, J=8.2, 1.9 Hz, 1H), 7.46 (d, J=1.8 Hz, 1H), 7.23 (d, J=8.1 Hz, 1H), 6.99 (d, J=12.1 Hz, 1H), 6.42 (d, J=12.1 Hz, 1H), 4.20 (s, 2H), 3.10 (s, 3H).

Step E: To a mixture of the lactam (1.04 g, 4.13 mmol) from step D and benzene (5 mL) was added trifluoromethanesulfonic acid (20 mL). The reaction mixture was warmed to room temperature and stirred for 48 hours. The reaction mixture was then poured on ice and stirred until the ice melted. The product was extracted into dichloromethane (3×), and the combined organic extract was washed with saturated sodium bicarbonate and brine, dried over sodium sulfate, filtered and concentrated under reduced pressure. Purification of the crude product by flash column chromatography (1:1 ethyl acetate/hexanes to ethyl acetate) gave the aryl lactam (1.24 g, 76%) as a white solid: $^1$H NMR (CDCl$_3$, 500 MHz) δ 7.30-7.20 (m, 5H), 7.05 (d, J=7.2 Hz, 1H), 6.83 (d, J=8.3 Hz, 1H), 5.01 (d, J=16.3 Hz, 1H), 4.45 (dd, J=11.3, 5.1 Hz, 1H), 4.12 (d, J=16.3 Hz, 1H), 3.26 (dd, J=13.8, 11.5 Hz, 1H), 3.05 (s, 3H), 2.96 (dd, J=13.9, 5.1 Hz, 1H).

Step F: To an ice-cold mixture of the lactam (2.61 g, 7.91 mmol) from step E and THF (61 mL) was added a solution of borane-dimethylsulfide complex in THF (8.3 mL, 16.6 mmol, 2M solution). The mixture was warmed to room temperature and then heated in an oil bath at 50° C. for 1 hour. The reaction mixture was cooled to 0° C., quenched with methanol (50 mL) and concentrated under reduced pressure. To the residue was added 1,4-dioxane (75 mL) followed by 6N HCl (25 mL) and the mixture was heated under reflux for 3 hours and 30 minutes. The mixture was cooled in an ice-bath, and a solution of 30-40% sodium hydroxide was added until pH 10. The benzazepine product was extracted into dichloromethane (3×), and the combined organic extract was dried over magnesium sulfate, filtered and concentrated under reduced pressure. The crude product was combined with the product obtained from a second run (0.2 g scale). Purification of the combined crude material by flash column chromatography (dichloromethane, then 99:0.9:0.1 to 90:9:1 dichloromethane/methanol/concentrated ammonium hydroxide) gave the amine (2.55 g, 95%) as a yellow oil: $^1$H NMR (500 MHz, CDCl$_3$) δ 7.60-7.26 (m, 5H), 7.20-7.10 (m, 2H), 6.51 (br, 1H), 4.26 (d, J=9.4 Hz, 1H), 3.89 (d, J=12.2 Hz, 1H), 3.68 (d, J=14.3 Hz, 1H), 3.15-3.00 (m, 1H), 2.99-2.94 (m, 1H), 2.34 (s, 3H), 2.34-2.27 (m, 1H), 2.15-2.05 (m, 1H).

Step G: To a mixture of the amine (0.30 g, 0.95 mmol) from step F, 2-hydroxypyridine (0.11 g, 1.14 mmol), dimethylethylene diamine (40 µL, 0.4 mmol) and potassium phosphate (0.40 g, 1.90 mmol) in a sealed tube was added 1,4-dioxane (1.2 mL), followed by copper(I) iodide (36 mg, 0.19 mmol). The mixture was flushed with argon and heated at 110° C. for 17 hours. The reaction was then cooled to room temperature and partitioned between dichloromethane and water. The aqueous layer was separated and re-extracted with dichloromethane (3×), and the combined organic extract was dried over sodium sulfate, filtered and concentrated under reduced pressure. Purification of the crude product by preparative thin layer chromatography (90:9:1 dichloromethane/methanol/concentrated ammonium hydroxide) gave the pyridone product (0.19 g, 61%) as a white foam: $^1$H NMR (500 MHz, CDCl$_3$) δ 7.39-7.35 (m, 3H), 7.31-7.28 (m, 2H), 7.21-7.04 (m, 3H), 7.10-7.00 (m, 1H), 6.74 (br, 1H), 6.63 (d, J=9.3 Hz, 1H), 6.26-6.16 (m, 1H), 4.35 (d, J=9.6 Hz, 1H), 3.97 (d, J=14.4 Hz, 1H), 3.74 (d, J=14.2 Hz, 1H), 3.20-3.10 (m, 1H), 3.05-2.95 (m, 1H), 2.39 (s, 3H), 2.39-2.30 (m, 1H), 2.20-2.10 (m, 1H). A by-product (DMEDA coupled to bromide; 49 mg, 16%) was also isolated as pale yellow oil: $^1$H NMR (500 MHz, CDCl$_3$) δ 7.36-7.30 (m, 2H), 7.29-7.21 (m, 2H), 7.18 (d, J=7.5 Hz, 2H), 6.60 (d, J=1.8 Hz, 1H), 6.58-6.42 (m, 2H), 4.22 (d, J=8.9 Hz, 1H), 3.88 (d, J=12.6 Hz, 1H), 3.69 (d, J=14.0 Hz, 1H), 3.41 (t, J=6.4 Hz, 2H), 3.15-3.05 (m, 1H), 2.98-2.90 (m, 1H), 2.90 (s, 3H), 2.78 (t, J=6.5 Hz, 2H), 2.45 (s, 3H), 2.37 (s, 3H), 2.37-2.25 (m, 1H), 2.15-2.05 (m, 1H).

Step H: To a solution of the pyridone (0.19 g, 0.57 mmol) from step G in methanol (1 mL) was added L-tartaric acid (86 mg, 0.57 mmol) followed by water (10 mL). The resultant solution was lyophilized overnight to give 1-(2-methyl-5-phenyl-2,3,4,5-tetrahydro-1H-benzo[c]azepin-8-yl)pyridin-2(1H)-one, tartrate salt (268 mg, 97%, AUC HPLC >99%) as a an off-white solid: $^1$H NMR (500 MHz, CD$_3$OD) δ 7.64-7.60 (m, 2H), 7.52 (d, J=2.2 Hz, 1H), 7.44-7.24 (m, 6H), 7.00 (br, 1H), 6.64 (d, J=9.0 Hz, 1H), 6.70-6.50 (m, 1H), 4.68-4.60 (m, 1H), 4.66 (d, J=8.2 Hz, 1H), 4.40 (s, 2H), 4.33 (d, J=14.2 Hz, 1H), 3.65-3.50 (m, 2H), 2.88 (s, 3H), 2.75-2.30 (m, 2H); ESI MS m/z 363 [M+H+ CH$_3$OH]$^+$.

Step I: To a solution of the amine by-product (49 mg, 0.15 mmol) from step G in methanol (1 mL) was added L-tartaric acid (23 mg, 0.15 mmol) followed by water (10 mL). The resultant solution was lyophilized overnight to give N1,N2-dimethyl-N1-(2-methyl-5-phenyl-2,3,4,5-tetrahydro-1H-benzo[c]azepin-8-yl)ethane-1,2-diamine, tartrate salt (72 mg, 100%, AUC HPLC 98.9%) as a brown solid: $^1$H NMR (500 MHz, CD$_3$OD) δ 7.40-7.34 (m, 2H), 7.27-7.25 (m, 1H), 7.20-7.15 (m, 2H), 6.99 (s, 1H), 6.68 (br, 2H), 4.45-4.40 (m, 2H), 4.30 (s, 2H), 4.30-4.18 (m, 1H), 3.64 (t, J=6.1 Hz, 2H), 3.53-3.42 (m, 2H), 3.20 (t, J=6.3 Hz, 2H), 2.95 (d, J=2.6 Hz, 3H), 2.87 (d, J=5.2 Hz, 3H), 2.73 (s, 3H), 2.66-2.47 (m, 1H), 2.45-2.26 (m, 1H); ESI MS m/z 324 [M+H]+.

Example 73

Preparation of (+)-8-(imidazo[1,2-a]pyridin-6-yl)-2-methyl-5-phenyl-2,3,4,5-tetrahydro-1H-benzo[c]azepine, L-tartrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR (CDCl$_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6 N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR (CDCl$_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer [[α]$^{25}_D$+3.66° (c 0.41, methanol)] and (−)-enantiomer [[α]$^{25}_D$−1.16° (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]+.

Step I: To a stirred mixture of the phenol from Step H above (581 mg, 2.3 mmol) and pyridine (0.22 mL, 2.8 mmol) in anhydrous methylene chloride (23 mL) at 0° C. under $N_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, $CDCl_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a disposable sealed tube were added bis(pinacolato)diboron (471 mg, 1.7 mmol), potassium acetate (498 mg, 5.1 mmol), and the triflate from Step I above (650 mg, 1.7 mmol) as a solution in anhydrous DMSO (8 mL). The reaction mixture was degassed with argon for 1 minute, then dichloro[1,1'-bis(diphenylphosphino)ferrocene]palladium (II) dichloromethane adduct (41 mg, 0.051 mmol) was added under argon. The reaction was heated to 80° C. and stirred for 3 hours, at which time ESI MS indicated the reaction went to completion. After cooling to room temperature, the reaction mixture was diluted with water, then extracted with ethyl acetate (3×). The combined extracts were dried over sodium sulfate, filtered, and concentrated in vacuo to provide the desired boronate ester as a dark brown oil, which was taken on to the next step without further purification: ESI MS m/z 364 [M+H]$^+$.

Step K: To a sealed tube were added 6-bromoimidazo[1,2-a]pyridine (251 mg, 1.3 mmol), the boronate ester from Step J above (386 mg, 1.1 mmol, theoretical) as a solution in anhydrous DMF (7 mL), and sodium carbonate (337 mg, 3.2 mmol) as a solution in water (1.7 mL). The reaction mixture was degassed with argon for 3 minutes, then dichloro[1,1'-bis(diphenylphosphino)ferrocene]palladium(II) dichloromethane adduct (52 mg, 0.064 mmol) was added under argon. The reaction was heated to 100° C. and stirred for 15 hours, at which time ESI MS indicated the reaction went to completion. After cooling to room temperature, the reaction mixture was diluted with ethyl acetate and filtered through Celite. After washing with water, the aqueous phase was extracted with additional ethyl acetate (3×). The combined extracts were washed with brine, dried over sodium sulfate, filtered, and concentrated in vacuo. Purification by flash column chromatography (95:5 methylene chloride/methanol) yielded the desired imidazopyridine (244 mg, 65% for two steps) as a light brown oil: $[α]^{23}_D$ –3.75° (c 0.32, methanol); $^1$H NMR (500 MHz, $CDCl_3$) δ 8.28 (s, 1H), 7.67-7.62 (m, 4H), 7.41-7.37 (m, 4H), 7.31-7.28 (m, 1H), 7.22-7.21 (m, 2H), 6.82-6.72 (br, 1H), 4.39-4.38 (m, 1H), 4.04-3.99 (m, 1H), 3.85-3.83 (m, 1H), 3.22-3.16 (m, 1H), 3.03-2.99 (m, 1H), 2.43 (s, 3H), 2.43-2.35 (m, 1H), 2.22-2.17 (m, 1H); ESI MS m/z 354 [M+H]$^+$.

Step L: To a stirred solution of the imidazopyridine from Step K above (224 mg, 0.63 mmol) in methanol (6 mL) at room temperature was added L-tartaric acid (95 mg, 0.63 mmol). The mixture was stirred at room temperature for 1 hour and then the solvent was concentrated to approximately 1.5 mL. After diluting with water (5 mL), the mixture was lyophilized for 15 hours to provide (+)-8-(imidazo [1,2-a]pyridin-6-yl)-2-methyl-5-phenyl-2,3,4,5-tetrahydro-1H-benzo[c]azepine, L-tartrate salt (318 mg, 99%, 99.2% AUC HPLC) as an off-white powder: mp 142-144° C.; $^1$H NMR (500 MHz, $CD_3OD$) δ 8.79 (s, 1H), 7.92 (s, 1H), 7.78 (s, 1H), 7.68-7.62 (m, 4H), 7.42 (t, J=7.5 Hz, 2H), 7.34-7.31 (m, 1H), 7.25 (d, J=7.5 Hz, 2H), 7.03-6.93 (br, 1H), 4.72-4.62 (m, 1H), 4.65-4.64 (m, 1H), 4.44-4.36 (m, 1H), 4.41 (s, 2H), 3.63-3.55 (m, 2H), 2.92-2.86 (br, 3H), 2.67-2.59 (m, 1H), 2.47-2.42 (m, 1H); ESI MS m/z 354 [M+H]$^+$.

Example 74

Preparation of (+)-2-methyl-5-phenyl-8-(1-H-pyrazol-4-yl)-2,3,4,5-tetrahydro-1H-benzo[c]azepine, L-tartrate salt and (−)-2-methyl-5-phenyl-8-(1-H-pyrazol-4-yl)-2,3,4,5-tetrahydro-1H-benzo[c]azepine, L-tartrate salt Pursuant to the general method described above in Example 73, the following products were prepared: (+)-2-methyl-5-phenyl-8-(1-H-pyrazol-4-yl)-2,3,4,5-tetrahydro-1H-benzo[c]azepine, L-tartrate salt: mp 125-127° C.; $^1$H NMR (500 MHz, $CD_3OD$) δ 7.99 (s, 2H), 7.69-7.68 (m, 1H), 7.53 (d, J=8.0 Hz, 1H), 7.40 (t, J=7.0 Hz, 2H), 7.31 (t, J=7.5 Hz, 1H), 7.22 (d, J=7.5 Hz, 2H), 6.91-6.82 (br, 1H), 4.64-1.55 (m, 1H), 4.58-4.57 (m, 1H), 4.40 (s, 2H), 4.36-4.33 (m, 1H), 3.61-3.55 (m, 2H), 2.88 (s, 3H), 2.65-2.56 (m, 1H), 2.4-2.39 (m, 1H); ESI MS m/z 304 [M+H]$^+$; (−)-2-methyl-5-phenyl-8-(1-H-pyrazol-4-yl)-2,3,4,5-tetrahydro-1H-benzo[c]azepine, L-tartrate salt: mp 129-131° C.; $^1$H NMR (500 MHz, $CD_3OD$) δ 7.99 (s, 2H), 7.69-7.68 (m, 1H), 7.53 (d, J=8.0 Hz, 1H), 7.40 (t, J=7.0 Hz, 2H), 7.31 (t, J=7.5 Hz, 1H), 7.22 (d, J=7.5 Hz, 2H), 6.91-6.82 (br, 1H), 4.64-4.55 (m, 1H), 4.58-4.57 (m, 1H), 4.40 (s, 2H), 4.36-4.33 (m, 1H), 3.61-3.55 (m, 2H), 2.88 (s, 3H), 2.65-2.56 (m, 1H), 2.4-2.39 (m, 1H); ESI MS m/z 304 [M+H]$^+$.

Example 75

Preparation of 2-methyl-8-(6-methylpyridazin-3-yl)-5-phenyl-2,3,4,5-tetrahydro-1H-benzo[c]azepine, L-tartrate salt, single enantiomer Pursuant to the general method described above in Example 73, the following product was prepared: 2-methyl-8-(6-methylpyridazin-3-yl)-5-phenyl-2,3,4,5-tetrahydro-1H-benzo[c]azepine, L-tartrate salt, single enantiomer: $^1$H NMR (500 MHz, $CD_3OD$) δ 8.20 (br, 1H), 8.09 (d, J=8.5 Hz, 1H), 7.97 (d, J=8.0 Hz, 1H), 7.69 (d, J=8.5 Hz, 1H), 7.42 (t, J=7.5 Hz, 2H), 7.33 (t, J=7.5 Hz, 1H), 7.26 (d, J=7.5 Hz, 2H), 7.05-6.98 (br, 1H), 4.79-4.67 (m, 1H), 4.68 (d, J=8.5 Hz, 1H), 4.49-4.42 (m, 1H), 4.40 (s, 2H), 3.65-3.56 (m, 2H), 2.91 (br, 3H), 2.73 (s, 3H), 2.68-2.59 (m, 1H), 2.47-2.44 (m, 1H); ESI MS m/z 330 [M+H]$^+$.

Example 76

Preparation of 2-methyl-5-phenyl-8-(pyridazin-3-yl)-2,3,4,5-tetrahydro-1H-benzo[c]azepine, L-tartrate salt, single enantiomer Pursuant to the general method described above in Example 73, the following product was prepared: 2-methyl-5-phenyl-8-(pyridazin-3-yl)-2,3,4,5-tetrahydro-1H-benzo[c]azepine, L-tartrate salt, single enantiomer: $^1$H NMR (500 MHz, $CD_3OD$) δ 9.16 (d, J=4.5 Hz, 1H), 8.22 (s, 1H), 8.20 (d, J=8.5 Hz, 1H), 8.00 (d, J=7.5 Hz, 1H), 7.81 (dd, J=9.0, 5.0 Hz, 1H), 7.43 (t, J=7.5 Hz, 2H), 7.34 (t, J=7.5 Hz, 1H), 7.26 (d, J=7.5 Hz, 2H), 7.07-6.98 (br, 1H), 4.76-4.70 (m, 1H), 4.69 (d, J=9.0 Hz, 1H), 4.48-4.45 (m, 1H), 4.40 (s, 2H), 3.64-3.56 (m, 2H), 2.91 (s, 3H), 2.68-2.60 (m, 1H), 2.47-2.44 (m, 1H); ESI MS m/z 316 [M+H]$^+$.

Example 77

Preparation of (+)-4-(6-(2-methyl-5-phenyl-2,3,4,5-tetrahydro-1H-benzo[c]azepin-8-yl)pyridazin-3-yl)morpholine, L-tartrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR (CDCl$_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR (CDCl$_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer [[α]$^{25}_D$+3.66° (c 0.41, methanol)] and (−)-enantiomer [[α]$^{25}_D$−1.16° (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step I: To a stirred mixture of the phenol from Step H above (581 mg, 2.3 mmol) and pyridine (0.22 mL, 2.8 mmol) in anhydrous methylene chloride (23 mL) at 0° C. under $N_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a disposable sealed tube were added bis(pinacolato)diboron (471 mg, 1.7 mmol), potassium acetate (498 mg, 5.1 mmol), and the triflate from Step I above (650 mg, 1.7 mmol) as a solution in anhydrous DMSO (8 mL). The reaction mixture was degassed with argon for 1 minute, then dichloro[1,1'-bis(diphenylphosphino)ferrocene]palladium (II) dichloromethane adduct (41 mg, 0.051 mmol) was added under argon. The reaction was heated to 80° C. and stirred for 3 hours, at which time ESI MS indicated the reaction went to completion. After cooling to room temperature, the reaction mixture was diluted with water, then extracted with ethyl acetate (3×). The combined extracts were dried over sodium sulfate, filtered, and concentrated in vacuo to provide the desired boronate ester as a dark brown oil, which was taken on to the next step without further purification: ESI MS m/z 364 [M+H]$^+$.

Step K: To a sealed tube were added 3,6-dichloropyridazine (320 mg, 2.2 mmol), the boronate ester from Step J above (650 mg, 1.8 mmol, theoretical) as a solution in anhydrous DMF (11 mL), and cesium carbonate (1.75 g, 5.4 mmol) as a solution in water (2.8 mL). The reaction mixture was degassed with argon for 3 minutes, then dichloro[1,1'-bis(diphenylphosphino)ferrocene]palladium(II) dichloromethane adduct (87 mg, 0.11 mmol) was added under argon. The reaction was heated to 100° C. and stirred for 4 hours, at which time ESI MS indicated the reaction went to completion. After cooling to room temperature, the reaction mixture was diluted with ethyl acetate and filtered through Celite. After washing with water, the aqueous phase was extracted with additional ethyl acetate (3×) and then the combined extracts were washed with brine, dried over sodium sulfate, filtered, and concentrated in vacuo. Purification via flash column chromatography (2%-10% methanol/methylene chloride) yielded the desired chloropyridazine (408 mg, 65% for two steps) as a brown oil: $^1$H NMR (500 MHz, CDCl$_3$) δ 7.94-7.93 (m, 1H), 7.79 (d, J=9.0 Hz, 1H), 7.72 (d, J=8.0 Hz, 1H), 7.53 (d, J=9.0 Hz, 1H), 7.38 (t, J=7.5 Hz, 2H), 7.29 (d, J=7.5 Hz, 1H), 7.21 (d, J=7.5 Hz, 2H), 6.86-6.79 (br, 1H), 4.41-4.39 (m, 1H), 4.05-4.02 (m, 1H), 3.89-3.86 (m, 1H), 3.19-3.15 (m, 1H), 3.04-2.99 (m, 1H), 2.41 (s, 3H), 2.41-2.34 (m, 1H), 2.20-2.15 (m, 1H); ESI MS m/z 350 [M+H]$^+$.

Step L: To a sealed tube were added the chloropyridazine from Step K above (200 mg, 0.57 mmol) as a solution in 1,4-dioxane (5 mL) and morpholine (0.50 mL, 5.7 mmol). The reaction was heated to 80° C. and stirred for 15 hours. Additional morpholine (0.50 mL, 5.7 mmol) was then added and the reaction was stirred 24 hours, at which time ESI MS indicated the reaction went to completion. After cooling to room temperature, the reaction mixture was diluted with ethyl acetate and washed with water. The aqueous phase was extracted with additional ethyl acetate (3×) and the combined extracts were washed with brine, dried over sodium sulfate, filtered, and concentrated in vacuo. Purification by flash column chromatography (9:0.9:0.1 methylene chloride/methanol/concentrated ammonium hydroxide) yielded the desired pyridazine (134 mg, 58%) as a light yellow solid: $[\alpha]^{23}_D$ –8.33° (c 0.12, methanol); $^1$H NMR (500 MHz, CDCl$_3$) δ 7.93-7.92 (m, 1H), 7.66-7.63 (m, 1H), 7.64 (d, J=9.5 Hz, 1H), 7.38 (d, J=7.0 Hz, 2H), 7.29 (d, J=7.0 Hz, 1H), 7.21 (d, J=7.5 Hz, 2H), 6.95 (d, J=9.5 Hz, 1H), 6.79-6.73 (br, 1H), 4.39-4.37 (m, 1H), 4.04-4.01 (m, 1H), 3.87 (t, J=5.0 Hz, 4H), 3.88-3.85 (m, 1H), 3.67 (t, J=5.0 Hz, 4H), 3.19-3.14 (m, 1H), 3.04-2.98 (m, 1H), 2.41-2.34 (m, 1H), 2.38 (s, 3H), 2.18-2.13 (m, 1H); ESI MS m/z 401 [M+H]$^+$.

Step M: To a stirred solution of the pyridazine from Step L above (126 mg, 0.32 mmol) in methanol (5 mL) at room temperature was added L-tartaric acid (47 mg, 0.32 mmol). The mixture was stirred at room temperature for 1 hour and then the solvent was concentrated to approximately 0.5 mL. After diluting with water (1.5 mL), the mixture was lyophilized for 2 days to provide (+)-4-(6-(2-methyl-5-phenyl-2,3,4,5-tetrahydro-1H-benzo[c]azepin-8-yl)pyridazin-3-yl)morpholine, L-tartrate salt (167 mg, 96%, >99% AUC HPLC) as an off-white powder: $^1$H NMR (500 MHz, CD$_3$OD) δ 8.08 (br, 1H), 7.95-7.93 (m, 1H), 7.88 (d, J=7.0 Hz, 1H), 7.45 (t, J=7.5 Hz, 2H), 7.39-7.34 (m, 2H), 7.27 (d, J=7.5 Hz, 2H), 7.04-6.96 (br, 1H), 4.75-4.65 (m, 1H), 4.68-4.67 (m, 1H), 4.47-4.42 (m, 1H), 4.43 (s, 2H), 3.87 (t, J=5.0 Hz, 4H), 3.69 (t, J=5.0 Hz, 4H), 3.63-3.58 (m, 2H), 2.92 (br, 3H), 2.70-2.60 (m, 1H), 2.49-2.45 (m, 1H); ESI MS m/z 401 [M+H]$^+$.

Example 78

Preparation of (+)-N-methyl-6-(2-methyl-5-phenyl-2,3,4,5-tetrahydro-1H-benzo[c]azepin-8-yl)pyridazin-3-amine, L-tartrate salt Pursuant to the general method described above in Example 77, the following product was prepared: (+)-N-methyl-6-(2-methyl-5-phenyl-2,3,4,5-tetrahydro-1H-benzo[c]azepin-8-yl)pyridazin-3-amine, L-tartrate salt: $^1$H NMR (500 MHz, CD$_3$OD) δ 8.06 (s, 1H), 7.85 (d, J=8.0 Hz, 1H), 7.81 (d, J=9.5 Hz, 1H), 7.44 (t, J=7.5 Hz, 2H), 7.35 (t, J=7.5 Hz, 1H), 7.27 (d, J=7.5 Hz, 2H), 7.00 (d, J=9.5 Hz, 1H), 7.02-6.94 (br, 1H), 4.73-4.68 (m, 1H), 4.66 (d, J=8.0 Hz, 1H), 4.44-4.42 (m, 1H), 4.42 (s, 2H), 3.65-3.56 (m, 2H), 3.05 (s, 3H), 2.92 (s, 3H), 2.68-2.61 (m, 1H), 2.49-2.44 (m, 1H); ESI MS m/z 345 [M+H]$^+$.

Example 79

Preparation of 2-methyl-5-phenyl-8-(piperidin-2-yl)-2,3,4,5-tetrahydro-1H-benzo[c]azepine, L-tartrate salt (diastereomers A and B)

Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: ¹H NMR (CDCl₃, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: ¹H NMR (300 MHz, CDCl₃) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: ¹H NMR (500 MHz, CDCl₃) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: ¹H NMR (300 MHz, CDCl₃) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: ¹H NMR (CDCl₃, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6 N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): ¹H NMR (CDCl₃, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer [[α]$^{25}_D$+3.66° (c 0.41, methanol)] and (−)-enantiomer [[α]$^{25}_D$−1.16° (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: ¹H NMR (500 MHz, CDCl₃) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]⁺.

Step I: To a stirred mixture of the phenol from Step H above (581 mg, 2.3 mmol) and pyridine (0.22 mL, 2.8 mmol) in anhydrous methylene chloride (23 mL) at 0° C. under N₂ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: ¹H NMR (500 MHz, CDCl₃) δ 7.38 (t, J=7.5 Hz, 2H), 7.31-7.28 (m, 1H), 7.17 (d, J=7.0 Hz, 2H), 7.09-7.08 (m, 1H), 6.97-6.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a disposable sealed tube were added bis(pinacolato)diboron (471 mg, 1.7 mmol), potassium acetate (498 mg, 5.1 mmol), and the triflate from Step I above (650 mg, 1.7 mmol) as a solution in anhydrous DMSO (8 mL). The reaction mixture was degassed with argon for 1 minute, then dichloro[1,1'-bis(diphenylphosphino)ferrocene]palladium (II) dichloromethane adduct (41 mg, 0.051 mmol) was added under argon. The reaction was heated to 80° C. and stirred for 3 hours, at which time ESI MS indicated the reaction went to completion. After cooling to room temperature, the reaction mixture was diluted with water, then extracted with ethyl acetate (3×). The combined extracts were dried over sodium sulfate, filtered, and concentrated in vacuo to provide the desired boronate ester as a dark brown oil, which was taken on to the next step without further purification: ESI MS m/z 364 [M+H]$^+$.

Step K: To a sealed tube were added 6-bromopyridine (0.14 mL, 1.5 mmol), the boronate ester from Step J above (446 mg, 1.2 mmol, theoretical) as a solution in anhydrous DMF (8 mL), and cesium carbonate (1.2 g, 3.7 mmol) as a solution in water (2 mL). The reaction mixture was degassed with argon for 3 minutes, then dichloro[1,1'-bis(diphenylphosphino)ferrocene]palladium(II) dichloromethane adduct (60 mg, 0.074 mmol) was added under argon. The reaction was heated to 100° C. and stirred for 3.5 hours, at which time ESI MS indicated the reaction went to completion. After cooling to room temperature, the reaction mixture was diluted with ethyl acetate, washed with water (2×), and then dried over sodium sulfate, filtered, and concentrated in vacuo. Purification by flash column chromatography (2%-10% methanol/methylene chloride) yielded the desired pyridine (290 mg, 75% for two steps) as a brown solid: $^1$H NMR (500 MHz, CDCl$_3$) δ 8.68-8.67 (m, 1H), 7.86-7.85 (m, 1H), 7.74-7.68 (m, 3H), 7.41-7.34 (m, 3H), 7.29-7.25 (m, 1H), 7.22-7.19 (n, 2H), 6.83-6.77 (br, 1H), 4.40-4.38 (m, 1H), 4.04-4.01 (m, 1H), 3.91-3.88 (m, 1H), 3.18-3.14 (m, 1H), 3.04-2.99 (m, 1H), 2.42-2.35 (m, 1H), 2.37 (s, 3H), 2.20-2.15 (m, 1H); ESI MS m/z 315 [M+H]$^+$.

Step L: To a solution of the pyridine from Step K above (260 mg, 0.83 mmol) in absolute ethanol (20 mL) in a Parr bottle was added concentrated hydrochloric acid (2.5 mL). The solution was degassed with argon for 5 minutes, then platinum(IV) oxide (20 mg) was added and the mixture was hydrogenated at 50 psi for 15 hours. The catalyst was removed by filtration over Celite and the filtrate was concentrated in vacuo. Purification by preparative HPLC yielded the desired piperidine (66 mg, 25%) as a light yellow oil: $^1$H NMR (500 MHz, CDCl$_3$) δ 7.35 (t, J=7.5 Hz, 2H), 7.27-7.24 (m, 1H), 7.22-7.20 (m, 1H), 7.17 (d, J=7.0 Hz, 2H), 7.04-7.00 (m, 1H), 6.60-6.53 (br, 1H), 4.30-4.28 (m, 1H), 3.90-3.88 (m, 1H), 3.74-3.71 (m, 1H), 3.54-3.51 (m, 1H), 3.18 (d, J=11.5 Hz, 1H), 3.13-3.08 (m, 1H), 2.95-2.90 (m, 1H), 2.78 (t, J=11.0 Hz, 1H), 2.35 (d, J=3.5 Hz, 3H), 2.35-2.38 (m, 1H), 2.13-2.08 (m, 1H), 1.88-1.84 (m, 1H), 1.76-1.74 (m, 1H), 1.77-1.63 (m, 2H), 1.65-1.63 (m, 1H), 1.58-1.45 (m, 2H); ESI MS m/z 321 [M+H]$^+$.

Step M: The free base of the benzazepine from Step L above (65 mg) was resolved by preparative chiral HPLC (CHIRALCEL OD column, using 95:5:0.1 heptane/ethanol/diethylamine as the eluent) to give diastereomer A [[α]$^{23}_D$+ 8.00° (c 0.065, methanol)] and diastereomer B [[α]$^{23}_D$− 16.90° (c 0.065, methanol).

Step N: To a stirred solution of diastereomer A from Step M above (21 mg, 0.066 mmol) in methanol (2 mL) at room temperature was added L-tartaric acid (10 mg, 0.066 mmol). The mixture was stirred at room temperature for 1 hour and then the solvent was concentrated to approximately 0.5 mL. After diluting with water (1.5 mL), the mixture was lyophilized for 15 h to provide 2-methyl-5-phenyl-8-(piperidin-2-yl)-2,3,4,5-tetrahydro-1H-benzo[c]azepine, L-tartrate salt (diastereomer A, 30 mg, 97%, >99% AUC HPLC) a white powder: $^1$H NMR (500 MHz, CD$_3$OD) δ 7.58 (s, 1H), 7.38 (t, J=7.5 Hz, 2H), 7.32-7.28 (m, 1H), 7.30 (d, J=7.5 Hz, 1H), 7.19 (d, J=7.5 Hz, 2H), 6.89-6.78 (br, 1H), 4.56-4.54 (m, 1H), 4.49-4.42 (m, 1H), 4.23-4.16 (m, 2H), 4.13 (s, 2H), 3.51-3.49 (m, 1H), 3.46-3.43 (m, 2H), 3.18-3.12 (m, 1H), 2.83 (s, 3H), 2.61-2.52 (m, 1H), 2.38-2.34 (m, 1H), 2.09-2.06 (m, 1H), 2.04-2.01 (m, 2H), 1.95-1.90 (m, 1H), 1.87-1.82 (m, 1H), 1.77-1.69 (m, 1H); ESI MS m/z 321 [M+H]$^+$.

Step O: To a stirred solution of diastereomer B from Step M above (22 mg, 0.069 mmol) in methanol (2 mL) at room temperature was added L-tartaric acid (10 mg, 0.069 mmol). The mixture was stirred at room temperature for 1 hour and then the solvent was concentrated to approximately 0.5 mL. After diluting with water (1.5 mL), the mixture was lyophilized for 15 h to provide 2-methyl-5-phenyl-8-(piperidin-2-yl)-2,3,4,5-tetrahydro-1H-benzo[c]azepine, L-tartrate salt (diastereomer B, 32 mg, 99%, >99% AUC HPLC) a white powder: $^1$H NMR (500 MHz, CD$_3$OD) δ 7.53 (s, 1H), 7.38 (t, J=7.0 Hz, 2H), 7.34-7.32 (m, 1H), 7.29 (d, J=7.0 Hz, 1H), 7.19 (d, J=6.5 Hz, 2H), 6.88-6.79 (br, 1H), 4.56-4.54 (m, 1H), 4.50-4.43 (m, 1H), 4.21-4.16 (m, 2H), 4.11 (s, 2H), 3.51-3.44 (m, 3H), 3.19-3.14 (m, 1H), 2.84 (s, 3H), 2.62-2.54 (m, 1H), 2.39-2.34 (m, 1H), 2.05-2.01 (m, 3H), 1.96-1.93 (m, 1H), 1.88-1.81 (m, 1H), 1.78-1.71 (m, 1H); ESI MS m/z 321 [M+H]$^+$.

Example 80

Preparation of (+)-1-(2-methyl-5-phenyl-2,3,4,5-tetrahydro-1H-benzo[c]azepin-8-yl)ethanone, L-tartrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) from Step A above and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 h and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (20.3 g, 100 mmol) from step D above and benzene (80 mL) was added trifluoromethanesulfonic acid (100 mL). The reaction mixture was warmed to room temperature and stirred for 3 hours. The reddish-brown mixture was then poured into ice-water mixture, and stirred until the ice melted. The product was extracted into dichloromethane (4×), and the combined organic extracts were washed with saturated sodium bicarbonate and brine, dried over magnesium sulfate, filtered and concentrated under reduced pressure. The crude product was dissolved in ethyl acetate and filtered through a plug of silica gel. The silica gel was washed with ethyl acetate to give the aryl lactam (26.8 g, 95%) as a white foam: $^1$H NMR (CDCl$_3$, 500 MHz) δ 7.28-7.25 (m, 2H), 7.22-7.18 (m, 1H), 7.08-7.06 (m, 2H), 6.86 (d, J=8.6 Hz, 1H), 6.71 (dd, J=8.5, 2.7 Hz, 1H), 6.66 (d, J=2.7 Hz, 1H), 5.02 (d, J=16.1 Hz, 1H), 4.46 (dd, J=11.3, 5.2 Hz, 1H), 4.10 (d, J=16.1 Hz, 1H), 3.79 (s, 3H), 3.25 (dd, J=13.4, 11.5 Hz, 1H), 3.04 (s, 3H), 2.95 (dd, J=13.4, 5.2 Hz, 1H).

Step F: To an ice-cold mixture of the lactam (26.8 g, 95.4 mmol) from step E and THF (980 mL) was added borane-dimethylsulfide complex (19.0 mL, 200 mmol). The mixture was warmed to room temperature, and then heated in an oil bath at 50° C. for 75 minutes. The reaction mixture was then cooled to 0° C., quenched with methanol (100 mL), and concentrated under reduced pressure. To the residue was added 1,4-dioxane (200 mL) followed by 6N HCl (100 mL) and the mixture was heated under reflux for 2 hours. Additional volumes of 1,4-dioxane (60 mL) and 6 N HCl (30 mL) were added to the reaction mixture, which was heated under reflux for 1 hour. The mixture was cooled to room temperature and then in an ice-bath, and a solution of 2 N NaOH (20 mL) followed by a solution of 32% sodium hydroxide was added until pH 10. The crude product was extracted into dichloromethane (4×), and the combined organic extracts were dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the amine (19.4 g, 76%): $^1$H NMR (CDCl$_3$, 500 MHz) δ 7.37-7.32 (m, 2H), 7.26-7.23 (m, 1H), 7.17 (d, J=7.5 Hz, 2H), 6.74 (d, J=2.7 Hz, 1H), 6.65-6.55 (m, 2H), 4.26 (d, J=8.6 Hz, 1H), 3.95-3.84 (m, 1H), 3.76 (s, 3H), 3.69 (d, J=14.1 Hz, 1H), 3.16-3.05 (m, 1H), 2.98-2.90 (m, 1H), 2.35 (s, 3H), 2.35-2.27 (m, 1H), 2.13-2.00 (m, 1H).

Step G: The free base of the benzazepine from step F (19.4 g) was resolved by preparative chiral HPLC (CHIRALCEL OJ column, using 80:20:0.1 heptanes/ethanol/diethylamine as the eluent) to give the (+)-enantiomer [[α]$^{25}_D$+3.66° (c 0.41, methanol)] and (−)-enantiomer [[Q]$^{25}_D$−1.16° (c 0.43, methanol)].

Step H: A mixture of the (+)-enantiomer from Step G above (1.19 g, 4.5 mmol) and hydrobromic acid (48% solution in water, 34 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.10 g, 86%) as a tan solid: $^1$H NMR (500 MHz, CDCl$_3$) δ 7.34 (t, J=7.5 Hz, 2H), 7.28-7.23 (m, 1H), 7.16 (d, J=7.5 Hz, 2H), 6.54 (s, 1H), 6.48-6.35 (m, 2H), 4.24-4.22 (m, 1H), 3.87-3.77 (m, 1H), 3.66-3.63 (m, 1H), 3.17-3.08 (m, 1H), 2.94-2.89 (m, 1H), 2.42 (s, 3H), 2.35-2.31 (m, 1H), 2.18-2.09 (m, 1H); ESI MS m/z 254 [M+H]$^+$.

Step I: To a stirred mixture of the phenol from Step H above (581 mg, 2.3 mmol) and pyridine (0.22 mL, 2.8 mmol) in anhydrous methylene chloride (23 mL) at 0° C. under N$_2$ was added triflic anhydride (0.46 mL, 2.8 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification by flash column chromatography (1:1 ethyl acetate/hexanes) provided the desired triflate (650 mg, 74%) as a yellow oil: $^1$H NMR (500 MHz, CDCl$_3$) δ 7.38 (t, J=7.5 Hz, 2H), 7.31-7.28 (m, 1H), 7.17 (d, J=7.0 Hz, 2H), 7.09-7.08 (m, 1H), 6.97-0.93 (m, 1H), 6.70-6.64 (br, 1H), 4.33-4.31 (m, 1H), 4.03-3.94 (m, 1H), 3.75-3.72 (m, 1H), 3.18-3.13 (m, 1H), 3.03-2.98 (m, 1H), 2.36 (s, 3H), 2.34-2.29 (m, 1H), 2.12-2.06 (m, 1H); ESI MS m/z 386 [M+H]$^+$.

Step J: To a stirred solution of the triflate from Step I above (516 mg, 1.3 mmol) in anhydrous DMF (6.5 mL) was added lithium chloride (170 mg, 4.0 mmol). The mixture was degassed with argon for 2 minutes, then dichlorobis(triphenylphosphine)palladium(II) (47 mg, 0.067 mmol) was added. After degassing briefly with argon again, tributyl(1-ethoxyvinyl)tin (0.54 mL, 1.6 mmol) was added and the mixture was degassed briefly with argon one more time. The reaction was heated to 90° C. and stirred for 3.5 hours, at which time TLC and ESI MS analyses both indicated complete consumption of the starting material and formation of the desired intermediate. The solvent was removed in vacuo and the crude material was purified by flash column chromatography (50%-100% ethyl acetate/hexanes) to provide the desired intermediate as a yellow oil. The oil was stirred in 1 N HCl (20 mL) at room temperature for 1 hour, solid potassium carbonate was added to adjust the pH to 9, and then the solution was extracted with ethyl acetate (3×). The combined extracts were washed with water and brine, dried over sodium sulfate, filtered, and concentrated in vacuo to provide the desired methyl ketone (354 mg, 95%) as a yellow oil: $^1$H NMR (500 MHz, CDCl$_3$) δ 7.78 (s, 1H), 7.67-7.65 (m, 1H), 7.37 (t, J=7.5 Hz, 2H), 7.30-7.29 (m, 1H), 7.17 (d, J=7.5 Hz, 2H), 6.78-6.70 (br, 1H), 4.38-4.36 (m, 1H), 4.01-3.95 (m, 1H), 3.82-3.79 (m, 1H), 3.17-3.11 (m, 1H), 3.00-2.95 (m, 1H), 2.56 (s, 3H), 2.37 (s, 3H), 2.37-2.30 (m, 1H), 2.17-2.11 (m, 1H).

Step K: To a stirred solution of the ketone from Step J above (22 mg, 0.079 mmol) in methanol (2 mL) at room temperature was added L-tartaric acid (12 mg, 0.079 mmol). The mixture was stirred at room temperature for 1 hour and then the solvent was concentrated to approximately 0.5 mL. After diluting with water (1.5 mL), the mixture was lyophilized for 15 h to provide (+)-1-(2-methyl-5-phenyl-2,3,4,5-tetrahydro-1H-benzo[c]azepin-8-yl)ethanone, L-tartrate salt (33 mg, 98%, 98.3% AUC HPLC) as a white powder: $^1$H NMR (500 MHz, CD$_3$OD) δ 8.06 (s, 1H), 7.91 (d, J=7.5 Hz, 1H), 7.41 (t, J=7.5 Hz, 2H), 7.33 (t, J=7.5 Hz, 1H), 7.22 (d, J=7.5 Hz, 2H), 7.00-6.91 (br, 1H), 4.66-4.64 (m, 2H), 4.41 (s, 2H), 4.39-4.34 (m, 1H), 3.57-3.52 (m, 2H), 2.85 (s, 3H), 2.60 (s, 3H), 2.62-2.53 (m, 1H), 2.44-2.37 (m, 1H); ESI MS m/z 280 [M+H]$^+$.

Example 81

Preparation of (+)-N-methyl-2-(2-methyl-5-phenyl-2,3,4,5-tetrahydro-1H-benzo[c]azepin-8-yl)ethane-sulfonamide, L-tartrate salt and (−)-N-methyl-2-(2-methyl-5-phenyl-2,3,4,5-tetrahydro-1H-benzo[c]azepin-8-yl)ethanesulfonamide, L-tartrate salt Step A: To a solution of 3-bromobenzaldehyde (47.5 mL, 0.4 mol) in methanol (460 mL) at room temperature was added a solution of methylamine in water (35 mL, 0.4 mol, 40 wt % solution). The resultant solution was cooled to 0° C. and sodium borohydride (22 g, 0.60 mol) was added to it in portions. The reaction solution was stirred at 0° C. for 3 hours and 30 minutes, and then warmed to room temperature. The resultant reaction mixture was concentrated in vacuo and partitioned between dichloromethane and water. The aqueous layer was separated and washed with dichloromethane (3×). The combined organic extracts were washed with saturated sodium bicarbonate and brine, dried over magnesium sulfate, filtered and concentrated in vacuo to give the benzylamine (76 g, 81%) as a clear oil: $^1$H NMR (300 MHz, CDCl$_3$) δ 7.48 (d, J=1.5 Hz, 1H), 7.40-7.37 (m, 1H), 7.24-7.16 (m, 2H), 3.73 (s, 2H), 2.45 (s, 3H).

Step B: A solution of benzylamine (0.33 g, 46.6 mmol) from Step A above and 3,3-dimethoxypropanoic acid (6.25 g, 46.6 mmol) in anhydrous dichloromethane (180 mL) was cooled to 0° C., and then 1-(3-dimethylaminopropyl)-3-ethylcarbodiimide hydrochloride (9.82 g, 51.2 mmol) was added. The reaction was allowed to warm to room temperature and stirred for 14 hours. The mixture was diluted with dichloromethane (200 mL), washed with water (200 mL), 1 N HCl (200 mL) and saturated sodium bicarbonate, dried over sodium sulfate, filtered, and concentrated in vacuo to yield the desired amide (14.4 g, 98%) as a yellow oil: $^1$H NMR (500 MHz, CDCl$_3$) δ 7.45-7.35 (m, 2H), 7.23-7.09 (m, 2H), 4.92-4.87 (m, 1H), 4.57, 4.54 (s, 2H, rotamers), 3.45, 3.40 (s, 6H, rotamers), 2.96, 2.94 (s, 3H, rotamers), 2.74, 2.68 (d, J=5.6 Hz, 2H, rotamers). The crude product was used without further purification in the next reaction.

Step C: Aluminum chloride (13.50 g, 101.2 mmol) was mixed with anhydrous 1,2-dichloroethane (500 mL) and the resulting slurry stirred and cooled in an ice bath. A solution of the amide from Step B in dichloromethane (100 mL) was added dropwise over approximately 20 minutes. After the addition was complete the reaction mixture was stirred at room temperature for 2.5 hours before being placed in a refrigerator (−20° C.) for 60 hours. After warming to room temperature 6 N HCl (200 mL) was added and the mixture stirred for 30 minutes before water (200 mL) was added. The organic phase was separated and the residual aqueous phase extracted with dichloromethane (200 mL). The combined organic layers were washed with brine, dried over Na$_2$SO$_4$ and concentrated in vacuo. Purification by flash column chromatography (50-75% ethyl acetate/hexanes) yielded the desired product (1.88 g, 34%) as a white solid: $^1$H NMR (300 MHz, CDCl$_3$) δ 7.52 (dd, J=8.2, 1.9 Hz, 1H), 7.46 (d, J=1.8 Hz, 1H), 7.23 (d, J=8.1 Hz, 1H), 6.99 (d, J=12.1 Hz, 1H), 6.42 (d, J=12.1 Hz, 1H), 4.20 (s, 2H), 3.10 (s, 3H).

Step D: To a stirred solution bromobenzene (4.71 mL, 44.7 mmol) in THF (100 mL) at −78° C. was added n-BuLi (2.5M solution in hexanes, 17.9 mL, 44.7 mmol) dropwise over 10 minutes. After a further 30 minutes the solution was transferred to a stirred slurry of copper(I) iodide (4.26 g, 22.3 mmol) in THF (25 mL) at −50° C. under N$_2$. Stirring was continued for 1 hour to produce an orange solution whereupon a solution of lactam (1.88 g, 7.5 mmol) from Step C above in THF (25 mL) followed by iodotrimethylsilane (1.25 mL, 8.75 mmol). The reaction mixture was allowed to warm slowly to room temperature over 16 hours then quenched with saturated ammonium chloride (30 mL). The mixture was diluted with diethyl ether (200 mL), water (170 mL) and the organic phase separated. The aqueous phase was extracted with diethyl ether (200 mL) and the combined organic extracts washed with brine, dried over Na$_2$SO$_4$ and concentrated in vacuo. Purification by flash column chromatography (1-5% methanol/dichloromethane) yielded the lactam (1.73 g, 70%) as a yellow solid: $^1$H NMR (300 MHz, CDCl$_3$) δ 7.33-7.18 (m, 5H), 7.06 (d, J=8.4 Hz, 2H), 6.83 (d, J=8.1 Hz, 1H), 5.02 (d, J=16.3 Hz, 1H), 4.45 (dd, J=11.4, 5.1 Hz, 1H), 4.12 (d, J=16.3 Hz, 1H), 3.30-3.22 (m, 1H), 3.05 (s, 3H), 2.99-2.93 (m, 1H).

Step E: To a stirred solution of lactam (500 mg, 1.51 mmol) from Step D in THF (2.5 mL) at 0° C. under N$_2$ was added borane-dimethylsulfide complex (2.25 mL, 4.53 mmol, 2.0M in THF). After 10 minutes the reaction mixture was allowed to warm to room temperature for 1 hour before heating at 50° C. for 2 hours. The reaction mixture was cooled in an ice bath before slowly adding methanol (2 mL). After 10 minutes of stirring at room temperature the mixture was concentrated in vacuo, taken up in methanol (3 mL) and treated with concentrated hydrochloric acid (1 mL). The mixture was heated at 80° C. for 3 hours before concentrating in vacuo. The remaining residue was partitioned with 2 N NaOH and dichloromethane (30 mL) and the organic layer collected. The aqueous phase was further extracted with dichloromethane (30 mL) and the combined organic extracts were washed with brine, dried over Na$_2$SO$_4$ and concentrated in vacuo. Purification by flash column chromatography (0-5% methanol/dichloromethane) yielded the aryl bromide (339 mg, 71%) as a colorless oil: $^1$H NMR (300 MHz, CDCl$_3$) δ 7.37-7.22 (m, 5H), 7.18-7.11 (m, 2H), 6.49 (d, J=7.3 Hz, 1H), 4.24 (d, J=8.9 Hz, 1H), 3.94-3.82 (m, 1H), 3.67 (d, J=14.2 Hz, 1H), 3.15-3.05 (m, 1H), 3.00-2.90 (m, 1H), 2.32 (s, 3H), 2.32-2.22 (m, 1H), 2.13-2.03 (m, 1H).

Step F: To a solution of 2-chloroethanesulfonyl chloride (1.52 g, 9.27 mmol) in THF (15 mL) cooled at 0° C. was added a solution of methylamine (5.0 mL of a 2 N solution in THF, 10.0 mmol) and triethylamine (2.84 mL, 20.4 mmol) in THF (10 mL) dropwise. The reaction was stirred at 0° C. for 3 hours then stored at −20° C. for approximately 60 hours before partitioning with dichloromethane (400 mL) and 1N HCl (200 mL). The organic extract was washed with brine and dried over Na$_2$SO$_4$ before concentrating in vacuo. The residue was purified by flash column chromatography (20-100% dichloromethane/hexanes) to give N-methylethenesulfonamide (210 mg, 17%) as a colorless liquid: $^1$H NMR (300 MHz, CDCl$_3$) δ 6.56-6.47 (m, 1H), 6.24 (d, J=16.6 Hz, 1H), 6.02 (d, J=9.9 Hz, 1H), 4.96 (br, 1H), 2.69 (d, J=5.3 Hz, 3H).

Step G: A mixture of aryl bromide (370 mg, 1.17 mmol) from Step E above, N-methylethenesulfonamide (210 mg, 1.74 mmol) from Step F above, tri-o-tolylphosphine (120 mg, 0.39 mmol), triethylamine (0.98 mL, 7.02 mmol) and palladium(II) acetate (22 mg, 0.10 mmol) in anhydrous DMF (4 mL) was heated in a sealed glass tube under N$_2$ at 125° C. for 16 hours. After cooling to room temperature, the reaction mixture was partitioned with ethyl acetate (150 mL) and water (150 mL) and the layers separated. The organic layer was washed with water and brine then concentrated in vacuo. The residue was purified by flash column chromatography (0-10% methanol/dichloromethane) to give the vinyl sulfonamide (234 mg. 56%) as a yellow oil: $^1$H NMR (300 MHz, CDCl$_3$) δ 7.48-7.27 (m, 5H), 7.21-7.14 (m, 1H), 6.73-6.63 (m, 1H), 6.61 (d, J=15.4 Hz, 1H), 4.71-4.60 (m, 1H), 4.34 (d, J=9.0 Hz, 1H), 3.99-3.89 (m, 1H), 3.73 (d, J=14.1 Hz, 1H), 3.19-3.08 (m, 1H), 3.02-2.89 (m, 1H), 2.71 (d, J=4.6 Hz, 3H), 2.37 (s, 3H), 3.37-2.27 (m, 1H); ESI MS m/z 357 [M+H]$^+$.

Step H: To a solution of vinyl sulfonamide (230 mg, 0.65 mmol) from Step G above in absolute ethanol (50 mL) in a hydrogenation flask was added 10% palladium on carbon (0.4 g). The flask was flushed with N$_2$ then hydrogen (30 psi) using a Parr hydrogenation apparatus. The flask was shaken for 5 hours before the reaction mixture filtered through Celite and the filtrate was concentrated in vacuo. The crude material was dissolved in dichloromethane and eluted through a short column of silica gel (10% methanol/dichloromethane) to give the benzazepine (186 mg, 82%) as a yellow solid: $^1$H NMR (500 MHz, CDCl$_3$) δ 7.39-7.33 (m, 2H), 7.30-7.27 (m, 1H), 7.16 (d, J=7.0 Hz, 2H), 7.06 (s, 1H), 6.94 (d, J=7.5 Hz, 1H), 6.67-6.56 (m, 1H), 4.31 (d, J=9.0 Hz, 1H), 4.04-3.86 (m, 2H), 3.72 (d, J=14.0 Hz, 1H), 3.28-3.23 (m, 2H), 3.18-3.10 (m, 1H), 3.08-3.03 (m, 2H), 3.01-2.88 (m, 1H), 2.74 (d, J=5.0 Hz, 3H), 2.39 (s, 3H), 2.37-2.27 (m, 1H), 2.18-2.10 (m, 1H); ESI MS m/z 359 [M+H]$^+$.

Step I: The racemic benzazepine from Step H above (175 mg) was resolved by preparative chiral HPLC (CHIRALPAK AD column, using 85:15:0.1 heptane/isopropanol/diethylamine as the eluent) to give the (+)-enantiomer (60 mg) [[α]$^{25}{}_D$+3.8° (c 0.10, methanol)] and the (−)-enantiomer (62 mg) [[α]$^{25}{}_D$−3.2° (c 0.06, methanol)].

Step J: To a solution of the (+)-enantiomer (60 mg, 0.17 mmol) from step I in methanol (15 mL) at room temperature was added L-(+)-tartaric acid (25 mg, 0.17 mmol). The mixture was stirred until the tartaric acid had dissolved before concentrating in vacuo. The residue was then dissolved in methanol (2 mL), diluted with water (20 mL) and lyophilized for 24 h to provide (+)-N-methyl-2-(2-methyl-5-phenyl-2,3,4,5-tetrahydro-1H-benzo[c]azepin-8-yl)ethanesulfonamide, L-tartrate salt (88 mg, 98.5% AUC HPLC) as a white solid: $^1$H NMR (500 MHz, CDCl$_3$) δ 7.42-7.26 (m, 7H), 6.87-6.74 (m, 1H), 4.63-4.53 (m, 2H), 4.42 (s, 2H), 4.37-4.26 (m, 1H), 3.62-3.50 (m, 2H), 3.40-3.30 (m, 2H), 3.10-3.05 (m, 2H), 2.87 (s, 3H), 2.72 (s, 3H), 2.63-2.52 (m, 1H), 2.44-2.36 (m, 1H); ESI MS m/z 359 [M+H]$^+$.

Step K: To a solution of the (−)-enantiomer (62 mg, 0.17 mmol) from Step I above in methanol (15 mL) at room temperature was added L-(+)-tartaric acid (26 mg, 0.17 mmol). The mixture was stirred until the tartaric acid had dissolved before concentrating in vacuo. The residue was then dissolved in methanol (2 mL), diluted with water (20 mL) and lyophilized for 24 h to provide (−)-N-methyl-2-(2-methyl-5-phenyl-2,3,4,5-tetrahydro-1H-benzo[c]azepin-8-yl)ethanesulfonamide, L-tartrate salt (88 mg, 97.3% AUC HPLC) as a white solid: $^1$H NMR (500 MHz, CD$_3$OD) δ 7.41-7.35 (m, 3H), 7.32-7.28 (m, 1H), 7.26-7.15 (m, 2H), 6.87-6.73 (m, 1H), 4.60-4.53 (m, 2H), 4.41 (s, 2H), 4.33-4.25 (m, 1H), 3.59-3.50 (m, 2H), 3.40-3.30 (m, 2H), 3.10-3.04 (m, 2H), 2.85 (s, 3H), 2.71 (s, 3H), 2.63-2.52 (m, 1H), 2.43-2.36 (m, 1H); ESI MS m/z 359 [M+H]$^+$.

Example 82

Preparation of (+)-6-(5-(4-chlorophenyl)-2-methyl-2,3,4,5-tetrahydro-1H-benzo[c]azepin-8-yl)-N-methylpyridazin-3-amine, L-tartrate salt and (−)-6-(5-(4-chlorophenyl)-2-methyl-2,3,4,5-tetrahydro-1H-benzo[c]azepin-8-yl)-N-methylpyridazin-3-amine, L-tartrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C.

over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (4 g, 19.7 mmol) from step D and chlorobenzene (4 mL) was added trifluoromethanesulfonic acid (32 mL). The reaction mixture was warmed to room temperature and stirred for 3 hours and 45 minutes. The reaction mixture was then poured on ice and stirred until the ice melted. The product was extracted into ethyl acetate (4×), and the combined organic extract was washed with saturated sodium bicarbonate and brine, dried over magnesium sulfate, filtered and concentrated under reduced pressure. The crude product from this reaction was combined with the product from a second run (1 g scale). Purification of the combined crude material by flash column chromatography (40:60 ethyl acetate/hexanes to ethyl acetate) gave the aryl lactam (2.26 g, 29%) as an off-white foam: $^1$H NMR (CDCl$_3$, 500 MHz) δ 7.26-7.23 (m, 2H), 7.00 (dd, J=6.5, 1.9 Hz, 2H), 6.83 (d, J=8.6 Hz, 1H), 6.74-6.70 (m, 1H), 6.66 (d, J=2.7 Hz, 1H), 4.91 (d, J=16.2 Hz, 1H), 4.47-4.37 (m, 1H), 4.18 (d, J=16.3 Hz, 1H), 3.79 (s, 3H), 3.16 (dd, J=13.6, 10.9 Hz, 1H), 3.95 (s, 3H), 2.97 (dd, J=13.7, 5.1 Hz, 1H).

Step F: To an ice-cold mixture of the lactam (2.26 g, 7.19 mmol) from step E in THF (74 mL) was added a solution of borane-dimethylsulfide complex in THF (7.6 mL, 15.1 mmol, 2M solution). The mixture was warmed to room temperature and then heated in an oil bath at 50° C. for 1. The reaction mixture was cooled to 0° C., quenched with methanol (50 mL) and concentrated under reduced pressure. To the residue was added 1,4-dioxane (30 mL) followed by 6 N HCl (10 mL) and the mixture was heated under reflux for 1 hour and 30 minutes. The mixture was cooled in an ice-bath and a solution of 2 N sodium hydroxide was added until pH 10. The crude product was extracted into dichloromethane (4×), and the combined organic extract was dried over magnesium sulfate, filtered and concentrated under reduced pressure. Purification of the crude product by flash column chromatography (dichloromethane, then 99:1 to 95:5 dichloromethane/methanol) gave the amine (1.77 g, 82%) as a clear oil: $^1$H NMR (CDCl$_3$, 300 MHz) δ 7.31 (d, J=8.5 Hz, 2H), 7.10 (d, J=8.3 Hz, 2H), 6.74 (d, J=2.7 Hz, 1H), 6.64-6.50 (m, 2H), 4.23 (d, J=7.9 Hz, 1H), 3.95-3.80 (m, 1H), 3.77 (s, 3H), 3.67 (d, J=14.2 Hz, 1H), 3.15-3.00 (m, 1H), 2.98-2.94 (m, 1H), 2.34 (s, 3H), 2.34-2.20 (m, 1H), 2.15-2.00 (m, 1H).

Step G: A mixture of the amine from Step F above (1.40 g, 4.6 mmol) and hydrobromic acid (48% solution in water, 30 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.09 g, 82%) as a tan solid: $^1$H NMR (500 MHz, CDCl$_3$) δ 7.31 (d, J=8.0 Hz, 2H), 7.09 (d, J=8.5 Hz, 2H), 6.57-6.56 (m, 1H), 6.48-6.47 (m, 1H), 6.48-6.39 (m, 1H), 4.20 (d, J=8.5 Hz, 1H), 3.84-3.74 (m, 1H), 3.64-3.61 (m, 1H), 3.12-3.05 (m, 1H), 2.93-2.88 (m, 1H), 2.41 (s, 3H), 2.34-2.26 (m, 1H), 2.14-2.06 (m, 1H); ESI MS m/z 288 [M+H]$^+$.

Step H: To a stirred mixture of the phenol from Step G above (552 mg, 1.9 mmol) and pyridine (0.2 mL, 2.3 mmol) in anhydrous methylene chloride (19 mL) at 0° C. under N$_2$ was added triflic anhydride (0.4 mL, 2.3 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification via flash column chromatography (1:1 ethyl acetate/hexanes) provided the desired triflate (457 mg, 57%) as a yellow oil: $^1$H NMR (500 MHz, CDCl$_3$) δ 7.35 (d, J=8.5 Hz, 2H), 7.10 (d, J=10.0 Hz, 2H), 7.09 (s, 1H), 6.97 (dd, J=8.5, 2.5 Hz, 1H), 6.70-6.63 (m, 1H), 4.30 (d, J=9.5 Hz, 1H), 3.96 (d, J=14.0 Hz, 1H), 3.72 (d, J=14.5 Hz, 1H), 3.14-3.11 (m, 1H), 2.99 (ddd, J=13.3, 10.0, 3.0 Hz, 1H), 2.35 (s, 3H), 2.28 (m, 1H), 2.09-2.03 (m, 1H); ESI MS m/z 420 [M+H]$^+$.

Step I: To a mixture of the triflate (1.40 g, 3.34 mmol) from step H, potassium acetate (0.98 g, 10 mmol) and bis(pinacolato)diboron (0.93 g, 3.67 mmol) was added DMSO (21.5 mL). The solution was purged with argon for 10 minutes, and dichloro[1,1'-bis(diphenylphosphine)ferrocene]palladium (II) dichloromethane adduct (82 mg, 0.10 mmol) was added to it. The mixture was heated at 80° C. for 3 hours, cooled to room temperature and poured into water. The product was extracted into dichloromethane (3×), and the combined organic layer was washed with water and brine, dried over sodium sulfate, filtered and concentrated under reduced pressure to give the boronate ester, which was used immediately without further purification. To a mixture of the crude boronate ester (1.67 mmol), 3,6-dichloropyridazine (0.50 g, 3.34 mmol), sodium carbonate (0.53 g, 5.01 mmol) and water (3.3 mL) was added DMF (14.3 mL), and the mixture was purged with argon for 10 minutes. To this degassed solution was added dichloro[1,1'-bis(diphenylphosphine)ferrocene]palladium(II) dichloromethane adduct (0.11 mg, 0.13 mmol), and the mixture was heated at 80° C. for 2 hours and 30 minutes. The reaction was then cooled to room temperature, and partitioned between dichloromethane and water. The aqueous layer was separated and re-extracted with dichloromethane (2×), and the combined organic extract was dried over magnesium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the pyridazine product (0.28 mg, 44%) as a brown oil: $^1$H NMR (500 MHz, CDCl$_3$) δ 7.94 (d, J=1.9 Hz, 1H), 7.78 (d, J=9.0 Hz, 1H), 7.72 (d, J=9.4 Hz, 1H), 7.53 (d, J=9.0 Hz, 1H), 7.35 (d, J=8.4 Hz, 2H), 7.14 (d, J=8.2 Hz, 2H), 7.05 (br, 1H), 4.37 (d, J=8.9 Hz, 1H), 4.00 (d, J=15.5 Hz, 1H), 3.84 (d, J=13.8 Hz, 1H), 3.20-3.10 (m, 1H), 3.05-2.95 (m, 1H), 2.38 (s, 3H), 2.38-2.29 (m, 1H), 2.20-2.10 (m, 1H).

Step J: To a mixture of the pyridazine (0.28 g, 0.73 mmol) from step I and methylamine (5 mL, 40 wt. % in water) in a sealed tube was added 1,4-dioxane (10 mL), and the mixture was heated at 80° C. for 24 hours. The cooled reaction mixture was concentrated under reduced pressure. Purification by flash column chromatography (dichloromethane, then 99:0.9:0.1 to 90:9:1 dichloromethane/methanol/concentrated ammonium hydroxide) gave the pyridazine derivative (175 mg, 63%) as a pale brown foam: $^1$H NMR (500 MHz, CDCl$_3$) δ 7.89 (d, J=1.8 Hz, 1H), 7.72 (br, 1H), 7.59 (d, J=9.3 Hz, 1H), 7.34 (d, J=8.4 Hz, 2H), 7.12 (d, J=8.0 Hz, 2H), 6.89-6.74 (br, 1H), 6.72 (d, J=9.3 Hz, 1H), 4.87 (br, 1H), 4.37 (d, J=9.0 Hz, 1H), 4.20-3.85 (m, 2H), 3.28-3.08 (m, 2H), 3.09 (d, J=5.0 Hz, 3H), 2.45 (s, 3H), 2.48-2.33 (m, 1H), 2.29-2.14 (m, 1H).

Step K: The free base of the benzazepine from step J (175 mg) was resolved by preparative chiral HPLC (CHIRALCEL OD column, using 80:20:0.1 heptanes/ethanol/diethylamine as the eluent) to give the (+)-enantiomer [[α]$^{25}_D$+5.94° (c 0.16, methanol)] and the (–)-enantiomer [[α]$^{25}_D$–3.36° (c 0.19, methanol)]. Both enantiomers were washed with water to remove residual diethylamine.

To a solution of the (+)-enantiomer (42 mg, 0.11 mmol) in methanol (3 mL) was added L-tartaric acid (17 mg, 0.11 mmol) followed by water (10 mL). The resultant solution was lyophilized overnight to give (+)-6-(5-(4-chlorophenyl)-2-methyl-2,3,4,5-tetrahydro-1H-benzo[c]azepin-8-yl)-N-methylpyridazin-3-amine, L-tartrate salt (63 mg, >100%, AUC HPLC 99.0%) as an off-white solid: $^1$H NMR (500 MHz, CD$_3$OD) δ 8.04 (d, J=1.6 Hz, 1H), 7.83 (d, J=7.8 Hz, 1H), 7.77 (d, J=9.4 Hz, 1H), 7.42 (d, J=8.4 Hz, 2H), 7.23 (d, J=8.1 Hz, 2H), 6.98-6.95 (m, 1H), 6.97 (d, J=9.4 Hz, 1H), 4.65-4.60 (m, 1H), 4.63 (d, J=8.1 Hz, 1H), 4.41 (s, 2H), 4.41-4.34 (m, 1H), 3.63-3.47 (m, 2H), 3.02 (s, 3H), 2.89 (s, 3H), 2.68-2.47 (m, 2H); ESI MS m/z 379 [M+H]$^+$.

To a solution of the (–)-enantiomer (30 mg, 0.08 mmol) in methanol (3 mL) was added L-tartaric acid (12 mg, 0.08 mmol) followed by water (10 mL). The resultant solution was lyophilized overnight to give (–)-6-(5-(4-chlorophenyl)-2-methyl-2,3,4,5-tetrahydro-1H-benzo[c]azepin-8-yl)-N-methylpyridazin-3-amine, L-tartrate salt (41 mg, 98%, AUC HPLC >99%) as an off-white solid: $^1$H NMR (500 MHz, CD$_3$OD) δ 8.04 (d, J=1.6 Hz, 1H), 7.83 (d, J=7.8 Hz, 1H), 7.77 (d, J=9.4 Hz, 1H), 7.42 (d, J=8.4 Hz, 2H), 7.23 (d, J=8.1 Hz, 2H), 6.98-6.95 (m, 1H), 6.97 (d, J=9.4 Hz, 1H), 4.65-4.60 (m, 1H), 4.63 (d, J=8.1 Hz, 1H), 4.41 (s, 2H), 4.41-4.34 (m, 1H), 3.63-3.47 (m, 2H), 3.02 (s, 3H), 2.89 (s, 3H), 2.68-2.47 (m, 2H); ESI MS m/z 379 [M+H]$^+$.

Example 83

Preparation of (+/–)-6-(5-(4-chlorophenyl)-2-methyl-2,3,4,5-tetrahydro-1H-benzo[c]azepin-8-yl) pyridazin-3-amine, maleate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (4 g, 19.7 mmol) from step D and chlorobenzene (4 mL) was added trifluoromethanesulfonic acid (32 mL). The reaction mixture was warmed to room temperature and stirred for 3 hours and 45 minutes. The reaction mixture was then poured on ice and stirred until the ice melted. The product was extracted into ethyl acetate (4×), and the combined organic extract was washed with saturated sodium bicarbonate and brine, dried over magnesium sulfate, filtered and concentrated under reduced pressure. The crude product from this reaction was combined with the product from a second run (1 g scale). Purification of the combined crude material by flash column chromatography (40:60 ethyl acetate/hexanes to ethyl acetate) gave the aryl lactam (2.26 g, 29%) as an off-white foam: $^1$H NMR (CDCl$_3$, 500 MHz) δ 7.26-7.23 (m, 2H), 7.00 (dd, J=6.5, 1.9 Hz, 2H), 6.83 (d, J=8.6 Hz, 1H), 6.74-6.70 (m, 1H), 6.66 (d, J=2.7 Hz, 1H), 4.91 (d, J=16.2 Hz, 1H), 4.47-4.37 (m, 1H), 4.18 (d, J=16.3 Hz, 1H), 3.79 (s, 3H), 3.16 (dd, J=13.6, 10.9 Hz, 1H), 3.95 (s, 3H), 2.97 (dd, J=13.7, 5.1 Hz, 1H).

Step F: To an ice-cold mixture of the lactam (2.26 g, 7.19 mmol) from step E in THF (74 mL) was added a solution of borane-dimethylsulfide complex in THF (7.6 mL, 15.1 mmol, 2M solution). The mixture was warmed to room temperature and then heated in an oil bath at 50° C. for 1 hour. The reaction mixture was cooled to 0° C., quenched with methanol (50 mL) and concentrated under reduced pressure. To the residue was added 1,4-dioxane (30 mL) followed by 6 N HCl (10 mL) and the mixture was heated under reflux for 1 hour and 30 minutes. The mixture was cooled in an ice-bath and a solution of 2 N sodium hydroxide was added until pH 10. The crude product was extracted into dichloromethane (4×), and the combined organic extract was dried over magnesium sulfate, filtered and concentrated under reduced pressure. Purification of the crude product by flash column chromatography (dichloromethane, then 99:1 to 95:5 dichloromethane/methanol) gave the amine (1.77 g, 82%) as a clear oil: $^1$H NMR (CDCl$_3$, 300 MHz) δ 7.31 (d, J=8.5 Hz, 2H), 7.10 (d, J=8.3 Hz, 2H), 6.74 (d, J=2.7 Hz, 1H), 6.64-6.50 (m, 2H), 4.23 (d, J=7.9 Hz, 1H), 3.95-3.80 (m, 1H), 3.77 (s, 3H), 3.67 (d, J=14.2 Hz, 1H), 3.15-3.00 (m, 1H), 2.98-2.94 (m, 1H), 2.34 (s, 3H), 2.34-2.20 (m, 1H), 2.15-2.00 (m, 1H).

Step G: A mixture of the amine from Step F above (1.40 g, 4.6 mmol) and hydrobromic acid (48% solution in water, 30 mL) was heated to reflux and stirred for 2 hours. The solvent and excess hydrobromic acid were removed under reduced pressure and the resulting solid was partitioned between ethyl acetate and saturated sodium bicarbonate. After separating the two layers, the aqueous phase was extracted with ethyl acetate (3×). The combined extracts were dried over sodium sulfate, filtered, and concentrated in vacuo to provide the desired phenol (1.09 g, 82%) as a tan solid: $^1$H NMR (500 MHz, CDCl$_3$) δ 7.31 (d, J=8.0 Hz, 2H), 7.09 (d, J=8.5 Hz, 2H), 6.57-6.56 (m, 1H), 6.48-6.47 (m, 1H), 6.48-6.39 (m, 1H), 4.20 (d, J=8.5 Hz, 1H), 3.84-3.74 (m, 1H), 3.64-3.61 (m, 1H), 3.12-3.05 (m, 1H), 2.93-2.88 (m, 1H), 2.41 (s, 3H), 2.34-2.26 (m, 1H), 2.14-2.06 (m, 1H); ESI MS m/z 288 [M+H]$^+$.

Step H: To a stirred mixture of the phenol from Step G above (552 mg, 1.9 mmol) and pyridine (0.2 mL, 2.3 mmol) in anhydrous methylene chloride (19 mL) at 0° C. under N$_2$ was added triflic anhydride (0.4 mL, 2.3 mmol). The reaction was stirred at 0° C. for 1 hour, at which time TLC analysis indicated the reaction went to completion. The mixture was then diluted with methylene chloride, washed with saturated sodium bicarbonate and brine, dried over sodium sulfate, filtered, and concentrated in vacuo. Purification via flash column chromatography (1:1 ethyl acetate/hexanes) provided the desired triflate (457 mg, 57%) as a yellow oil: $^1$H NMR (500 MHz, CDCl$_3$) δ 7.35 (d, J=8.5 Hz, 2H), 7.10 (d, J=10.0 Hz, 2H), 7.09 (s, 1H), 6.97 (dd, J=8.5, 2.5 Hz, 1H), 6.70-6.63 (m, 1H), 4.30 (d, J=9.5 Hz, 1H), 3.96 (d, J=14.0 Hz, 1H), 3.72 (d, J=14.5 Hz, 1H), 3.14-3.11 (m, 1H), 2.99 (ddd, J=13.3, 10.0, 3.0 Hz, 1H), 2.35 (s, 3H), 2.28 (m, 1H), 2.09-2.03 (m, 1H); ESI MS m/z 420 [M+H]$^+$.

Step I: To a mixture of the triflate (1.40 g, 3.34 mmol) from step H, potassium acetate (0.98 g, 10 mmol) and bis(pinacolato)diboron (0.93 g, 3.67 mmol) was added DMSO (21.5 mL). The solution was purged with argon for 10 minutes, and dichloro[1,1'-bis(diphenylphosphine)ferrocene]palladium (II) dichloromethane adduct (82 mg, 0.10 mmol) was added to it. The mixture was heated at 80° C. for 3 hours, and then cooled to room temperature and poured into water. The product was extracted into dichloromethane (3×), and the combined organic layer was washed with water and brine, dried over sodium sulfate, filtered and concentrated under reduced pressure to give the boronate ester, which was used immediately without further purification.

Step J: To a mixture of the crude boronate ester (1.67 mmol) from step I, 6-chloropyridazin-3-amine (0.43 g, 3.34 mmol), sodium carbonate (0.53 g, 5.01 mmol) and water (3.3 mL) was added DMF (14.3 mL), and the mixture was purged with argon for 10 minutes. To this degassed solution was added dichloro[1,1'-bis(diphenylphosphine)ferrocene]palladium(II) dichloromethane adduct (0.11 mg, 0.13 mmol), and the mixture was heated at 80° C. overnight. The reaction was then cooled to room temperature, and partitioned between dichloromethane and water. The aqueous layer was separated and re-extracted with dichloromethane (2×), and the combined organic extract was dried over magnesium sulfate, filtered and concentrated under reduced pressure. Purification of the crude product by preparative thin layer chromatography (Analtech 1 mm plates; 90:9:1 dichloromethane/methanol/concentrated ammonium hydroxide) gave the pyridazine product (54 mg, 9%), as a brown solid: $^1$H NMR (CDCl$_3$, 500 MHz) δ 7.85 (s, 1H), 7.64-7.58 (m, 2H), 7.33 (d, J=8.2 Hz, 2H), 7.13 (d, J=8.1 Hz, 2H), 6.80 (dd, J=9.2, 1.0 Hz, 1H), 6.73 (br, 1H), 4.80-4.70 (m, 2H), 4.34 (d, J=9.0 Hz, 1H), 3.98 (d, J=13.4 Hz, 1H), 3.82 (d, J=14.2 Hz, 1H), 3.15-3.09 (m, 1H), 3.05-2.95 (m, 1H), 2.36 (s, 3H), 2.35-2.31 (m, 1H), 2.23-2.07 (m, 1H).

Step K: To a solution of the benzazepine (53 mg, 0.14 mmol) from step J in methanol (2 mL) was added maleic acid (17 mg, 0.14 mmol) followed by water (10 mL). The resultant solution was lyophilized overnight to give (+/−)-6-(5-(4-chlorophenyl)-2-methyl-2,3,4,5-tetrahydro-1H-benzo[c]azepin-8-yl)pyridazin-3-amine, maleate salt (70 mg, 100%, AUC HPLC 96.8%) as a tan powder: $^1$H NMR (CD$_3$OD, 500 MHz) δ 8.06 (s, 1H), 7.87-7.80 (m, 2H), 7.43 (d, J=8.2 Hz, 2H), 7.25-7.20 (m, 2H), 7.05 (d, J=9.3 Hz, 1H), 6.98-6.88 (m, 1H), 6.24 (s, 2H), 4.75-4.65 (m, 1H), 4.66 (d, J=9.2 Hz, 1H), 4.47-4.40 (m, 1H), 3.70-3.50 (m, 2H), 2.95 (s, 3H), 2.70-2.30 (m, 2H); ESI MS m/z 365 [M+H]$^+$.

Example 84

Preparation of (−)-5-(3-fluorophenyl)-2-methyl-8-(6-methylpyridazin-3-yl)-2,3,4,5-tetrahydro-1H-benzo[c]azepine, citrate salt and (+)-5-(3-fluorophenyl)-2-methyl-8-(6-methylpyridazin-3-yl)-2,3,4,5-tetrahydro-1H-benzo[c]azepine, citrate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To a solution of the lactam (1.0 g, 4.92 mmol) from step D in trifluoromethanesulfonic acid (10 mL) was added 2-fluorophenol (1.32 mL, 14.8 mmol). The reaction mixture was stirred at room temperature for 45 minutes. The reaction mixture was poured into ice-water, basified with a concentrated ammonium hydroxide until pH 8-9 and extracted with dicloromethane (3×100 mL). The organic extracts were dried other sodium sulfate, filtered and concentrated under reduced pressure. The residue was triturated with ethanol to afford the 5-aryllactam (1.3 g, 84%) as a white solid: $^1$H NMR (CDCl$_3$, 500 MHz) δ 7.02 (d, J=1.5 Hz, 1H), 6.89 (d, J=8.6 Hz, 1H), 6.74 (dd, J=8.6, 2.7 Hz, 1H), 6.69-6.65 (m, 2H), 6.65 (d, J=2.7 Hz, 1H), 6.58-6.52 (m, 1H), 4.56 (d, J=16.4 Hz, 1H), 4.51 (d, J=16.4 Hz, 1H), 3.79 (s, 3H), 3.19 (dd, J=13.8, 4.6 Hz, 1H), 3.07 (s, 3H), 3.04 (dd, J=13.8, 8.5 Hz, 1H), 1.59 (s, 1H).

Step F: To a solution of the 5-aryllactam (1.00 g, 3.17 mmol) from step E above in tetrahydrofuran (10 mL) was added borane-dimethylsulfide complex in THF (3.17 mL, 6.34 mmol, 2M solution). The reaction mixture was heated to reflux for 1 h then was concentrated under reduced pressure. The reaction mixture was dissolved in 1,4-dioxane (120 mL) and was treated with an aqueous solution of hydrochloric acid (6 N, 9 mL) and the mixture was heated to reflux for 3 hours, then was concentrated to dryness under reduced pressure. The residue was diluted with water (20 mL) and basified until pH 8-9 with a saturated sodium bicarbonate. The solution thus obtained was extracted with dichloromethane (3×80 mL), the combined extracts was dried other sodium sulfate, filtered and concentrated under reduced pressure to afford the 5-arylbenzazepine (1.07 g, quantitative) as a white foam.

Step G: To a solution of the aryl benzazepine (2.01 g, 6.66 mmol) in dichloromethane (33 mL) was successively added pyridine (3.23 mL, 39.93 mmol) and trifluoromethansulfonic anhydride (1.68 mL, 9.99 mmol). The reaction mixture was stirred at 0° C. for 30 minutes and diluted with water (20 mL). The aqueous phase was extracted with dichloromethane (3×60 mL) and the combined extracts were dried over sodium sulfate, filtered and concentrated to afford the triflate as a yellow oil.

Step H: A dry flask was loaded with the triflate (~6.66 mmol) from step G, palladium(II) acetate (0.06 g, 0.26 mmol), triphenylphosphine (0.14 g, 0.53 mmol), triethylamine (5.57 mL, 39.96 mmol), DMF (33 mL) and formic acid (1.36 g, 26.6 mmol, 90% solution). The reaction mixture was heated to 70° C. for 2 hours. The cooled reaction mixture was diluted with water (20 mL) and extracted with dichloromethane (3×60 mL). The combined organic phase was dried over sodium sulfate, filtered and concentrated under reduce pressure. The residue was purified by flash column chromatography (95:4.5:0.5 dichloromethane/methanol/concentrated ammonium hydroxide) to afford the benzazepine (2.13 g): $^1$H NMR (CDCl$_3$, 500 MHz) δ 7.32-7.27 (m, 1H), 7.01-6.91 (m, 2H), 6.87 (d, J=10.3 Hz, 1H), 6.75 (d, J=2.6 Hz, 1H), 6.67-6.52 (m, 2H), 4.25 (dd, J=8.9, 1.4 Hz, 1H), 3.89-3.78 (m, 1H), 3.77 (s, 3H), 3.68 (d, J=14.2 Hz, 1H), 3.15-3.04 (m, 1H), 3.01-2.90 (m, 1H), 2.34 (s, 3H), 2.31-2.22 (m, 1H), 2.17-2.05 (m, 1H).

Step I: A solution of the benzazepine (1.95 g, 6.6 mmol) from Step H above in acetic acid (10 mL) and 48% hydrobromic acid (20 mL) was heated to reflux for 40 hours and the mixture was concentrated to a smaller volume under reduced pressure. The residue was basified with 2 N sodium hydroxide and extracted with dichloromethane (3×100 mL). The combined organic phases were dried over sodium sulfate, filtered and concentrated under reduced pressure to afford the phenol (1.52 g, 85% yield) as a brown foam. $^1$H NMR (CDCl$_3$, 500 MHz) δ 7.29-7.26 (m, 1H), 7.01-6.89 (m, 2H), 6.84 (d, J=10.0 Hz, 1H), 6.51 (br, 3H), 4.22 (d, J=8.4 Hz, 1H), 3.80-3.69 (m, 1H), 3.63 (d, J=14.0 Hz, 1H), 3.26-3.09 (m, 1H), 3.01-2.90 (m, 1H), 2.41 (s, 3H), 2.38-2.27 (m, 1H), 2.21-2.14 (m, 1H).

Step J: To a solution of the phenol (0.34 g, 1.27 mmol) in dichloromethane (10 mL) was successively added pyridine (0.20 mL, 2.53 mmol) and trifluoromethanesulfonic anhydride (0.32 mL, 1.90 mmol). The reaction mixture was stirred at 0° C. for 1 hour, then diluted with water (20 mL). The aqueous phase was extracted with dichloromethane (3×60 mL) and the combined extracts were dried over sodium sulfate, filtered and concentrated to afford the triflate as a yellow foam.

Step K: A dry flask was loaded with the triflate (~1.27 mmol) from Step J above, bis(pinacolato)diboron (0.35 g, 1.39 mmol), potassium acetate (0.37 g, 3.81 mmol), dichloro[1,1'-bis(diphenylphosphino)ferrocene]palladium(II) (0.08 g, 0.10 mmol) and DMSO (7.0 mL). The mixture was heated to 100° C. under argon for 2 hours. The cooled reaction mixture was diluted with ethyl acetate (150 mL), washed successively with water (3×15 mL) and brine (2×10 mL), dried over sodium sulfate, filtered and concentrated to give the boronate ester, which was used as it is in the next step without further purification.

Step L: A dry flask was loaded with the boronate ester (~1.27 mmol) from step K above, 3-chloro-6-methylpyridazine (0.24 g, 1.90 mmol), sodium carbonate (0.33 g, 3.17 mmol) and dichloro[1,1'-bis(diphenylphosphino)ferrocene]palladium(II) (0.08 g, 0.10 mmol). The flask was flushed with argon prior to the addition of N,N-dimethylformamide (16 mL) and water (3.2 mL). The reaction mixture was heated to 120° C. under argon for 1 hour. The cooled reaction mixture was diluted with water (50 mL) and extracted with dichloromethane (3×150 mL). The combined organic phase was dried over sodium sulfate, filtered and concentrated. The residue was purified by flash column chromatography (first purification 90:9:1 dichloromethane/methanol/concentrated ammonium hydroxide; second purification 90:9:1 ethyl acetate/methanol/concentrated ammonium hydroxide) to afford the pyridazinyl benzazepine (150 mg, 34% yield other 4 steps).

Step M: The free base of the pyridazinyl benzazepine (0.15 g) from Step L above was resolved by preparative chiral HPLC (CHIRALCEL OD column, using 70:30:0.1 heptane/isopropanol/diethylamine as the eluent) to give the (+)-enantiomer [[α]$^{25}$$_D$+2.3° (c 0.013, methanol)] and the (−)-enantiomer [[α]$^{25}$$_D$−9.2° (c 0.013, methanol)].

Step N: The mixture of the (+)-enantiomer (0.047 g, 0.13 mmol) from Step M above and citric acid (26 mg, 0.13 mmol) was dissolved in a mixture of methanol and water, frozen and lyophilized to afford (+)-5-(3-fluorophenyl)-2-methyl-8-(6-methylpyridazin-3-yl)-2,3,4,5-tetrahydro-1H-benzo[c]azepine, citrate salt (0.068 g, 87%, AUC HPLC >99%) as a white solid: mp 90-95° C.; $^1$H NMR (CD$_3$OD, 500 MHz) δ 8.26 (s, 1H), 8.08 (d, J=8.7 Hz, 1H), 7.99 (d, J=8.1 Hz, 1H), 7.69 (d, J=8.7 Hz, 1H), 7.48-7.39 (m, 1H), 7.14-6.99 (m, 4H), 4.70 (d, J=8.6 Hz, 2H), 4.44 (d, J=13.2 Hz, 1H), 3.65-3.55 (m, 2H), 2.90 (s, 3H), 2.84 (d, J=9.5 Hz, 2H), 2.75-2.69 (m, 5H), 2.67-2.58 (m, 1H), 2.49-2.41 (m, 1H); ESI MS m/z 348 [M+H]$^+$.

Step O: The mixture of the (−)-enantiomer (0.053 g, 0.15 mmol) from Step M above and citric acid (29 mg, 0.15 mmol) was dissolved in a mixture of methanol and water, frozen and lyophilized to afford (−)-5-(3-fluorophenyl)-2-methyl-8-(6-methylpyridazin-3-yl)-2,3,4,5-tetrahydro-1H-benzo[c]azepine, citrate salt (0.072 g, 73%, AUC HPLC 98.5%) as a white solid: mp 107-110° C.; $^1$H NMR (CD$_3$OD, 500 MHz) δ 8.26 (s, 1H), 8.08 (d, J=8.7 Hz, 1H), 7.99 (d, J=8.1 Hz, 1H), 7.69 (d, J=8.7 Hz, 1H), 7.48-7.39 (m, 1H), 7.14-6.99 (m, 4H), 4.70 (d, J=8.6 Hz, 2H), 4.44 (d, J=13.2 Hz, 1H), 3.65-3.55 (m, 2H), 2.90 (s, 3H), 2.84 (d, J=9.5 Hz, 2H), 2.75-2.69 (m, 5H), 2.67-2.58 (m, 1H), 2.49-2.41 (m, 1H); ESI MS m/z 348 [M+H]$^+$.

Example 85

Preparation of (+)-4-(5-(4-fluorophenyl)-2-methyl-2,3,4,5-tetrahydro-1H-benzo[c]azepin-8-yl)morpholine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (8.0 g, 39.4 mmol) from step D and fluorobenzene (32 mL) was added trifluoromethanesulfonic acid (50 mL). The reaction mixture was warmed to room temperature and stirred for 3 h and 30 minutes. The reddish-brown mixture was then poured on ice and stirred until the ice melted. The product was extracted into ethyl acetate (3×), and the combined organic extract was washed with saturated sodium bicarbonate and brine, dried over magnesium sulfate, filtered and concentrated under reduced pressure. Purification of the crude product by flash column chromatography (1:1 ethyl acetate/hexanes to ethyl acetate) gave both pure and impure fractions. The impure fractions were repurified by flash column chromatography (1:1 ethyl acetate/hexanes to ethyl acetate), and combined with the pure fraction obtained previously to give the aryl lactam (6.8 g, 57%) as a yellow oil: $^1$H NMR (CDCl$_3$, 300 MHz) δ 7.05-6.92 (m, 4H), 6.84 (d, J=8.6 Hz, 1H), 6.75-6.69 (m, 1H), 6.66 (d, J=2.7 Hz, 1H), 4.91 (d, J=16.2 Hz, 1H), 4.46 (dd, J=10.8, 5.1 Hz, 1H), 4.19 (d, J=16.2 Hz, 1H), 3.79 (s, 3H), 3.17 (dd, J=13.6, 10.9 Hz, 1H), 3.04 (s, 3H), 2.98 (dd, J=13.7, 5.1 Hz, 1H).

Step F: To an ice-cold mixture of the lactam (6.8 g, 22.7 mmol) from step E and THF (178 mL) was added a solution of borane-dimethylsulfide complex in THF (24 mL, 47.7 mmol, 2 M solution). The mixture was warmed to room temperature, and then heated in an oil bath at 50° C. for 45 minutes. The reaction mixture was cooled to 0° C., quenched with methanol (50 mL), and concentrated under reduced pressure. To the residue was added 1,4-dioxane (75 mL), followed by 6 N HCl (25 mL), and the mixture was heated under reflux for 3 hours and 30 minutes. The mixture was cooled in an ice-bath, and a solution of 30-40% sodium hydroxide was added until pH 10. The crude product was extracted into dichloromethane (3×), and the combined organic extract was dried over magnesium sulfate, filtered and concentrated under reduced pressure. Purification of the crude product by flash column chromatography (dichloromethane, then 99:1 to 90:10 dichloromethane/solvent A; solvent A=90:9:1 dichloromethane/methanol/triethylamine) gave the amine (4.89 g, 75%) as a yellowish-brown oil: $^1$H NMR (CDCl$_3$, 300 MHz) δ 7.16-7.00 (m, 4H), 6.74 (d, J=2.7 Hz, 1H), 6.64-6.50 (m, 2H), 4.24 (d, J=9.2 Hz, 1H), 3.95-3.80 (m, 1H), 3.77 (s, 3H), 3.67 (d, J=14.1 Hz, 1H), 3.15-3.05 (m, 1H), 3.00-2.90 (m, 1H), 2.34 (s, 3H), 2.32-2.20 (m, 1H), 2.15-1.95 (m, 1H).

Step G: To a solution of the amine (1.24 g, 4.35 mmol) from step F in acetic acid (20 mL) was added an aqueous solution of hydrobromic acid (20 mL, 48 wt. % solution), and the mixture was heated under reflux for 20 hours. The mixture was cooled to room temperature, and then in an ice bath, and was quenched with 2 N NaOH, followed by saturated sodium bicarbonate. The crude product was extracted into dichloromethane (4×), and the combined organic extract was dried over sodium sulfate, filtered and concentrated under reduced pressure. Coevaporation of the residue with toluene yielded the phenol (1.17 g) as a pale brown foam containing some acetic acid. The product was dissolved in dichloromethane, washed with saturated sodium bicarbonate, dried over magnesium sulfate, filtered and concentrated under reduced pressure to give the phenol (0.94 g, 80%, crude) as a pale brown foam: $^1$H NMR (CDCl$_3$, 300 MHz) δ 7.25-6.98 (m, 4H), 6.57 (d, J=2.5 Hz, 1H), 6.55-6.45 (m, 2H), 4.21 (d, J=8.9 Hz, 1H), 3.85-3.75 (m, 1H), 3.61 (d, J=13.9 Hz, 1H), 3.15-3.05 (m, 1H), 3.00-2.85 (m, 1H), 2.40 (s, 3H), 2.35-2.20 (m, 1H), 2.15-2.00 (m, 1H).

Step H: To a solution of the phenol (0.32 g, 1.2 mmol) from step G above in dichloromethane (20 mL) at 0° C. were added pyridine (0.20 mL, 2.4 mmol) and triflic anhydride (0.24 mL, 1.4 mmol). The resultant reaction solution was stirred at 0° C. for 2 hours, and then it was diluted with dichloromethane, washed with aqueous saturated sodium bicarbonate, dried over sodium sulfate and concentrated in vacuo. The crude product obtained (0.37 g, 78%) as a yellow oil was used in the next step without purification: $^1$H NMR (CDCl$_3$, 500 MHz) δ 7.15-7.02 (m, 5H), 6.97 (dd, J=9.0, 2.5 Hz, 1H), 6.81-6.35 (m, 1H), 4.31 (d, J=9.5 Hz, 1H), 3.97 (d, J=12.0 Hz, 1H), 3.72 (d, J=14.5 Hz, 1H), 3.20-2.93 (m, 2H), 2.35 (s, 3H), 2.32-2.25 (m, 1H), 2.13-2.04 (m, 1H).

Step I: To a solution of the triflate (0.37 g, 0.92 mmol) from step H above in toluene (8 mL) were added cesium carbonate (0.90 g, 2.8 mmol), 2-(dicyclohexylphosphino)-2',4',6'-tri-i-propyl-1,1'-biphenyl (88 mg, 0.18 mmol) and morpholine (0.16 mL, 1.8 mmol). The resultant mixture was flushed with argon for 5 minutes, and then palladium(II) acetate (21 mg, 0.09 mmol) was added to it. The reaction solution was heated at 100° C. under argon for 5 hours, and then additional palladium(II) acetate (21 mg, 0.09 mmol), 2-(dicyclohexylphosphino)-2',4',6'-tri-1-propyl-1,1'-biphenyl (40 mg, 0.08 mmol) and morpholine (0.15 mL, 1.7 mmol) were added to the reaction solution. The reaction mixture was heated at 100° C. for 14 hours and then cooled to room temperature. The resultant mixture was diluted with dichloromethane, washed with water and brine, dried over sodium sulfate and concentrated in vacuo. The crude product was purified by using the flash column chromatography (dichloromethane to 94:5.4:0.6 dichloromethane/methanol/concentrated ammonium hydroxide) to give the desired benzazepine [[α]$^{25}_D$−2.64° (c 0.11, methanol)] (0.15 g, 27%): $^1$H NMR (CDCl$_3$, 500 MHz) δ 7.12 (dd, J=8.5, 6.0 Hz, 2H), 7.03 (t, J=9.0 Hz, 2H), 6.75 (d, J=2.5 Hz, 1H), 6.61 (dd, J=8.5, 2.0 Hz, 1H), 6.58-6.40 (m, 1H), 4.22 (d, J=9.0 Hz, 1H), 3.93-3.83 (m, 1H), 3.84 (t, J=5.0 Hz, 4H), 3.67 (d, J=14.0 Hz, 1H), 3.12 (t, J=5.0 Hz, 4H), 3.12-3.08 (m, 1H), 2.96-2.91 (m, 1H), 2.35 (s, 3H), 2.30-2.23 (m, 1H), 2.13-2.05 (m, 1H). To a solution of the freshly prepared benzazepine (0.15 g, 0.45 mmol) in methanol (3 mL) were added maleic acid (52 mg, 0.45 mmol) and water (15 mL). The resultant solution was lyophilized overnight to provide (+)-4-(5-(4-fluorophenyl)-2-methyl-2,3,4,5-tetrahydro-1H-benzo[c]azepin-8-yl)morpholine, maleate salt (0.20 g, 96.4% AUC HPLC) as a light yellow solid: mp 87-90° C.; $^1$H NMR (CD$_3$OD, 500 MHz) δ 7.19 (br s, 2H), 7.12 (t, J=8.5 Hz, 2H), 7.05 (d, J=2.5 Hz, 1H), 6.96-6.43 (m, 2H), 6.25 (s, 2H), 4.67-4.46 (m, 1H), 4.49 (d, J=11.0 Hz, 1H), 4.37-4.13 (m, 1H), 3.82 (t, J=5.0 Hz, 4H), 3.63-3.45 (m, 2H), 3.15 (t, J=5.0 Hz, 4H), 2.90 (br, 3H), 2.69-2.30 (m, 2H); ESI MS m/z 341 [M+H]$^+$.

Example 86

Preparation of 5-(4-fluorophenyl)-2-methyl-8-(pyrimidin-5-yl)-2,3,4,5-tetrahydro-1H-benzo[c]azepine, L-tartrate salt (Enantiomers 1 and 2)

Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: ¹H NMR (300 MHz, CDCl₃) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (8.0 g, 39.4 mmol) from step D and fluorobenzene (32 mL) was added trifluoromethanesulfonic acid (50 mL). The reaction mixture was warmed to room temperature and stirred for 3 hours and 30 minutes. The reddish-brown mixture was then poured on ice and stirred until the ice melted. The product was extracted into ethyl acetate (3×), and the combined organic extract was washed with saturated sodium bicarbonate and brine, dried over magnesium sulfate, filtered and concentrated under reduced pressure. Purification of the crude product by flash column chromatography (1:1 ethyl acetate/hexanes to ethyl acetate) gave both pure and impure fractions. The impure fractions were repurified by flash column chromatography (1:1 ethyl acetate/hexanes to ethyl acetate), and combined with the pure fraction obtained previously to give the aryl lactam (6.8 g, 57%) as a yellow oil: ¹H NMR (CDCl₃, 300 MHz) δ 7.05-6.92 (m, 4H), 6.84 (d, J=8.6 Hz, 1H), 6.75-6.69 (m, 1H), 6.66 (d, J=2.7 Hz, 1H), 4.91 (d, J=16.2 Hz, 1H), 4.46 (dd, J=10.8, 5.1 Hz, 1H), 4.19 (d, J=16.2 Hz, 1H), 3.79 (s, 3H), 3.17 (dd, J=13.6, 10.9 Hz, 1H), 3.04 (s, 3H), 2.98 (dd, J=13.7, 5.1 Hz, 1H).

Step F: To an ice-cold mixture of the lactam (6.8 g, 22.7 mmol) from step E and THF (178 mL) was added a solution of borane-dimethylsulfide complex in THF (24 mL, 47.7 mmol, 2 M solution). The mixture was warmed to room temperature, and then heated in an oil bath at 50° C. for 45 minutes. The reaction mixture was cooled to 0° C., quenched with methanol (50 mL), and concentrated under reduced pressure. To the residue was added 1,4-dioxane (75 mL), followed by 6 N HCl (25 mL), and the mixture was heated under reflux for 3 hours and 30 minutes. The mixture was cooled in an ice-bath, and a solution of 30-40% sodium hydroxide was added until pH 10. The crude product was extracted into dichloromethane (3×), and the combined organic extract was dried over magnesium sulfate, filtered and concentrated under reduced pressure. Purification of the crude product by flash column chromatography (dichloromethane, then 99:1 to 90:10 dichloromethane/solvent A; solvent A=90:9:1 dichloromethane/methanol/triethylamine) gave the amine (4.89 g, 75%) as a yellowish-brown oil: ¹H NMR (CDCl₃, 300 MHz) δ 7.16-7.00 (m, 4H), 6.74 (d, J=2.7 Hz, 1H), 6.64-6.50 (m, 2H), 4.24 (d, J=9.2 Hz, 1H), 3.95-3.80 (m, 1H), 3.77 (s, 3H), 3.67 (d, J=14.1 Hz, 1H), 3.15-3.05 (m, 1H), 3.00-2.90 (m, 1H), 2.34 (s, 3H), 2.32-2.20 (m, 1H), 2.15-1.95 (m, 1H).

Step G: To a solution of the amine (1.24 g, 4.35 mmol) from step F in acetic acid (20 mL) was added an aqueous solution of hydrobromic acid (20 mL, 48 wt. % solution), and the mixture was heated under reflux for 20 hours. The mixture was cooled to room temperature, and then in an ice bath, and was quenched with 2 N NaOH, followed by saturated sodium bicarbonate. The crude product was extracted into dichloromethane (4×), and the combined organic extract was dried over sodium sulfate, filtered and concentrated under reduced pressure. Coevaporation of the residue with toluene yielded the phenol (1.17 g) as a pale brown foam containing some acetic acid. The product was dissolved in dichloromethane, washed with saturated sodium bicarbonate, dried over magnesium sulfate, filtered and concentrated under reduced pressure to give the phenol (0.94 g, 80%, crude) as a pale brown foam: ¹H NMR (CDCl₃, 300 MHz) δ 7.25-6.98 (m, 4H), 6.57 (d, J=2.5 Hz, 1H), 6.55-6.45 (m, 2H), 4.21 (d, J=8.9 Hz, 1H), 3.85-3.75 (m, 1H), 3.61 (d, J=13.9 Hz, 1H), 3.15-3.05 (m, 1H), 3.00-2.85 (m, 1H), 2.40 (s, 3H), 2.35-2.20 (m, 1H), 2.15-2.00 (m, 1H).

Step H: To a solution of the phenol (0.7 g, 2.6 mmol) from step G above in dichloromethane (30 mL) at 0° C. was added pyridine (0.4 mL, 5.2 mmol) followed by triflic anhydride (0.55 mL, 3.2 mmol). The reaction mixture was stirred at 0° C. for 2 hours, and then was diluted with dichloromethane, washed with aqueous saturated sodium bicarbonate, dried over sodium sulfate and concentrated under reduced pressure. The crude product obtained (0.82 g, 79%) as a yellow oil was used in the next step without purification: ¹H NMR (CDCl₃, 500 MHz) δ 7.15-7.02 (m, 5H), 6.97 (dd, J=9.0, 2.5 Hz, 1H), 6.81-6.35 (m, 1H), 4.31 (d, J=9.5 Hz, 1H), 3.97 (d, J=12.0 Hz, 1H), 3.72 (d, J=14.5 Hz, 1H), 3.20-2.93 (m, 2H), 2.35 (s, 3H), 2.32-2.25 (m, 1H), 2.13-2.04 (m, 1H).

Step I: To a mixture of the triflate (0.82 g, 2.04 mmol) from step H, potassium acetate (0.60 g, 6.11 mmol) and bis(pinacolato)diboron (0.62 g, 2.44 mmol) was added DMSO (13 mL). The solution was purged with argon for 10 minutes, and dichloro[1,1'-bis(diphenylphosphine)ferrocene]palladium (II) dichloromethane adduct (0.05 g, 0.06 mmol) was added to it. The mixture was heated at 80° C. overnight, and then cooled to room temperature and poured into water. The product was extracted into dichloromethane (3×), and the combined organic layer was washed with water and brine, dried over sodium sulfate, filtered and concentrated under reduced pressure to give the boronate ester, which was used immediately without further purification. To a mixture of the crude boronate ester, 5-bromopyrimidine (0.32 g, 2.04 mmol), sodium carbonate (0.32 g, 3.06 mmol) and water (2 mL) was added DMF (8.7 mL), and the mixture was purged with argon for 10 minutes. To this degassed solution was added dichloro[1,1'-bis(diphenylphosphine)ferrocene]palladium(II) dichloromethane adduct (67 mg, 82 μmol), and the mixture was heated at 80° C. for 4 hours. The reaction was then cooled to room temperature, and partitioned between dichloromethane and water. The aqueous layer was separated and re-extracted with dichloromethane (2×), and the combined organic extract was dried over sodium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave two fractions of the pyrimidine product (91 mg and 166 mg, 38% yield in total over 2 steps), both pale brown foams: ¹H NMR (CDCl₃,₃₀₀ MHz) δ 9.19 (s, 1H), 8.92 (s, 2H), 7.40 (d, J=2.0 Hz, 1H), 7.32-7.28 (m, 1H), 7.20-7.15 (m, 2H), 7.11-7.05 (m, 2H), 6.76 (d, J=5.9 Hz, 1H), 4.37 (d, J=9.2 Hz, 1H), 3.99 (d, J=14.3 Hz, 1H), 3.79 (d, J=14.1 Hz, 1H), 3.21-3.05 (m, 1H), 3.01-2.94 (m, 1H), 2.41 (s, 3H), 2.37-2.30 (m, 1H), 2.21-2.05 (m, 1H).

Step J: The two fractions of the free base of the benzazepine from step I (91 mg and 166 mg) were resolved separately by preparative chiral HPLC (CHIRALCEL OJ column, using 80:20:0.1 heptanes/ethanol/diethylamine as the eluent) to give enantiomer 1 and enantiomer 2.

To a solution of enantiomer 1 (102 mg, 0.31 mmol) in methanol (4 mL) was added L-tartaric acid (46 mg, 0.31 mmol) followed by water (15 mL). The resultant solution was lyophilized overnight to give 5-(4-fluorophenyl)-2-methyl-8-(pyrimidin-5-yl)-2,3,4,5-tetrahydro-1H-benzo[c]azepine, L-tartrate salt, enantiomer 1 (146 mg, 98%, AUC HPLC >99%) as an off-white solid: $[[\alpha]^{25}_D+9.71°$ (c 0.22, methanol)]; ¹H NMR (CD₃OD, 500 MHz) δ 9.15 (s, 1H), 9.09 (s, 2H), 7.83 (s, 1H), 7.69 (d, J=7.5 Hz, 1H), 7.32-7.21 (m, 2H), 7.20-7.10 (m, 2H), 6.94 (br, 1H), 4.66 (d, J=8.9 Hz, 2H), 4.40

(s, 2H), 4.40-4.35 (m, 1H), 3.56 (s, 2H), 2.86 (s, 3H), 2.63-2.47 (m, 1H), 2.45-2.26 (m, 1H); ESI MS m/z 334 [M+H]$^+$.

To a solution of enantiomer 2 (98 mg, 0.29 mmol) in methanol (6 mL) was added L-tartaric acid (44 mg, 0.29 mmol), followed by water (25 mL). The resultant solution was lyophilized overnight to give 5-(4-fluorophenyl)-2-methyl-8-(pyrimidin-5-yl)-2,3,4,5-tetrahydro-1H-benzo[c]azepine, L-tartrate salt, enantiomer 2 (135 mg, 95%, AUC HPLC 98.2%) as an off-white solid: $[[\alpha]^{25}{}_D +1.93°$ (c 0.18, methanol)]; $^1$H NMR (CD$_3$OD, 500 MHz) δ 9.15 (s, 1H), 9.09 (s, 2H), 7.83 (s, 1H), 7.69 (d, J=7.5 Hz, 1H), 7.32-7.21 (m, 2H), 7.20-7.10 (m, 2H), 6.94 (br, 1H), 4.66 (d, J=8.9 Hz, 2H), 4.40 (s, 2H), 4.40-4.35 (m, 1H), 3.56 (s, 2H), 2.86 (s, 3H), 2.63-2.47 (m, 1H), 2.45-2.26 (m, 1H); ESI MS m/z 334 [M+H]$^+$.

Example 87

Preparation of (+)-5-(5-(4-fluorophenyl)-2-methyl-2,3,4,5-tetrahydro-1H-benzo[c]azepin-8-yl)-3,3-dimethylindolin-2-one L-tartrate salt and (−)-5-(5-(4-fluorophenyl)-2-methyl-2,3,4,5-tetrahydro-1H-benzo[c]azepin-8-yl)-3,3-dimethylindolin-2-one L-tartrate salt Pursuant to the general method described above in Example 86, the following products were prepared: (+)-5-(5-(4-fluorophenyl)-2-methyl-2,3,4,5-tetrahydro-1H-benzo[c]azepin-8-yl)-3,3-dimethylindolin-2-one L-tartrate salt: $^1$H NMR (CD$_3$OD, 500 MHz) δ 7.70 (s, 1H), 7.56-7.54 (m, 2H), 7.50 (d, J=8.0 Hz, 1H), 7.25 (br, 2H), 7.15 (t, J=8.5 Hz, 2H), 7.00 (d, J=8.0 Hz, 1H), 6.99-6.62 (br, 1H), 4.61 (d, J=8.0 Hz, 2H), 4.40 (s, 2H), 4.36 (d, J=15.0 Hz, 1H), 3.55 (br, 2H), 2.87 (s, 3H), 2.67-2.35 (br, 2H), 1.39 (s, 6H); ESI MS m/z 415 [M+H]$^+$; (−)-5-(5-(4-fluorophenyl)-2-methyl-2,3,4,5-tetrahydro-1H-benzo[c]azepin-8-yl)-3,3-dimethylindolin-2-one L-tartrate salt: $^1$H NMR (CD$_3$OD, 500 MHz) δ 7.70 (s, 1H), 7.56-7.54 (m, 2H), 7.50 (d, J=8.0 Hz, 1H), 7.25 (br, 2H), 7.15 (t, J=8.5 Hz, 2H), 7.00 (d, J=8.0 Hz, 1H), 6.99-6.62 (br, 1H), 4.61 (d, J=8.0 Hz, 2H), 4.40 (s, 2H), 4.36 (d, J=15.0 Hz, 1H), 3.55 (br, 2H), 2.88 (s, 3H), 2.67-2.35 (br, 2H), 1.39 (s, 6H); ESI MS m/z 415 [M+H]$^+$.

Example 88

Preparation of (−)-5-(4-fluorophenyl)-8-(imidazo[1,2-α]pyrazin-3-yl)-2-methyl-2,3,4,5-tetrahydro-1H-benzo[c]azepine, L-tartrate salt and (+)-5-(4-fluorophenyl)-8-(imidazo[1,2-α]pyrazin-3-yl)-2-methyl-2,3,4,5-tetrahydro-1H-benzo[c]azepine, L-tartrate salt Pursuant to the general method described above in Example 86, the following products were prepared: (−)-5-(4-fluorophenyl)-8-(imidazo[1,2-α]pyrazin-3-yl)-2-methyl-2,3,4,5-tetrahydro-1H-benzo[c]azepine, L-tartrate salt: $^1$H NMR (CD$_3$OD, 500 MHz) δ 9.08 (s, 1H), 8.59 (d, J=4.5 Hz, 1H), 8.00 (s, 1H), 7.96 (d, J=4.5 Hz, 1H), 7.80 (s, 1H), 7.66 (d, J=7.5 Hz, 1H), 7.30 (br, 2H), 7.17 (t, J=8.5 Hz, 2H), 7.11-6.83 (br, 1H), 4.69 (d, J=9.0 Hz, 1H), 4.69-4.55 (br, 1H), 4.41 (s, 2H), 4.41-4.37 (m, 1H), 3.57 (br, 2H), 2.88 (s, 3H), 2.67-2.54 (br, 1H), 2.43 (d, J=15.5 Hz, 1H); ESI MS m/z 373 [M+H]$^+$; (+)-5-(4-fluorophenyl)-8-(imidazo[1,2-α]pyrazin-3-yl)-2-methyl-2,3,4,5-tetrahydro-1H-benzo[c]azepine, L-tartrate salt: $^1$H NMR (CD$_3$OD, 500 MHz) δ 9.08 (s, 1H), 8.59 (d, J=5.0 Hz, 1H), 8.00 (s, 1H), 7.96 (d, J=4.5 Hz, 1H), 7.80 (s, 1H), 7.66 (d, J=7.5 Hz, 1H), 7.31 (t, J=6.5 Hz, 2H), 7.17 (t, J=8.5 Hz, 2H), 7.11-6.83 (br, 1H), 4.68 (d, J=8.5 Hz, 1H), 4.68-4.59 (br, 1H), 4.40 (s, 2H), 4.36 (d, J=13.0 Hz, 1H), 3.57 (br, 2H), 2.88 (s, 3H), 2.67-2.54 (br, 1H), 2.43 (d, J=15.5 Hz, 1H); ESI MS m/z 373 [M+H]$^+$.

Example 89

Preparation of (+)-5-(4-fluorophenyl)-2-methyl-8-(6-methylpyridazin-3-yl)-2,3,4,5-tetrahydro-1H-benzo[c]azepine, maleate salt Pursuant to the general method described above in Example 86, the following product was prepared: (+)-5-(4-fluorophenyl)-2-methyl-8-(6-methylpyridazin-3-yl)-2,3,4,5-tetrahydro-1H-benzo[c]azepine, maleate salt: mp 173-176° C.; $^1$H NMR (CD$_3$OD, 500 MHz) δ 8.23 (d, J=2.0 Hz, 1H), 8.07 (d, J=9.0 Hz, 1H), 7.99 (d, J=7.5 Hz, 1H), 7.70 (d, J=9.0 Hz, 1H), 7.28 (br, 2H), 7.17 (t, J=8.5 Hz, 2H), 7.09-6.74 (m, 1H), 6.24 (s, 2.2H), 4.93-4.72 (m, 1H), 4.71 (d, J=10.0 Hz, 1H), 4.50 (d, J=12.0 Hz, 1H), 3.72-3.60 (m, 2H), 2.98 (s, 3H), 2.73 (s, 3H), 2.67-2.43 (m, 2H); ESI MS m/z 348 [M+H]$^+$.

Example 90

Preparation of 1-(6-(5-(4-fluorophenyl)-2-methyl-2,3,4,5-tetrahydro-1H-benzo[c]azepin-8-yl)pyridazin-3-yl)piperidin-4-ol, tartrate salt (Enantiomers 1 and 2)

Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (8.0 g, 39.4 mmol) from step D and fluorobenzene (32 mL) was added trifluoromethanesulfonic acid (50 mL). The reaction mixture was warmed to room temperature and stirred for 3 hours and 30 minutes. The reddish-brown mixture was then poured on ice and stirred until the ice melted. The product was extracted into ethyl acetate (3x), and the combined organic extract was washed with saturated sodium bicarbonate and brine, dried over magnesium sulfate, filtered and concentrated under reduced pressure. Purification of the crude product by flash column chromatography (1:1 ethyl acetate/hexanes to ethyl acetate) gave both pure and impure fractions. The impure fractions were repurified by flash column chromatography (1:1 ethyl acetate/hexanes to ethyl acetate), and combined with the pure fraction obtained previously to give the aryl lactam (6.8 g, 57%) as a yellow oil: $^1$H NMR (CDCl$_3$, 300 MHz) δ 7.05-6.92 (m, 4H), 6.84 (d, J=8.6 Hz, 1H), 6.75-6.69 (m, 1H), 6.66 (d, J=2.7 Hz, 1H), 4.91 (d, J=16.2 Hz, 1H), 4.46 (dd, J=10.8, 5.1 Hz, 1H), 4.19 (d, J=16.2 Hz, 1H), 3.79 (s, 3H), 3.17 (dd, J=13.6, 10.9 Hz, 1H), 3.04 (s, 3H), 2.98 (dd, J=13.7, 5.1 Hz, 1H).

Step F: To an ice-cold mixture of the lactam (6.8 g, 22.7 mmol) from step E and THF (178 mL) was added a solution of borane-dimethylsulfide complex in THF (24 mL, 47.7 mmol, 2M solution). The mixture was warmed to room temperature, and then heated in an oil bath at 50° C. for 45 minutes. The reaction mixture was cooled to 0° C., quenched with methanol (50 mL), and concentrated under reduced pressure. To the residue was added 1,4-dioxane (75 mL), followed by 6 N HCl (25 mL), and the mixture was heated under reflux for 3 hours and 30 minutes. The mixture was cooled in an ice-bath, and a solution of 30-40% sodium hydroxide was added until pH 10. The crude product was extracted into dichloromethane (3x), and the combined organic extract was dried over magnesium sulfate, filtered and concentrated under reduced pressure. Purification of the crude product by flash column chromatography (dichloromethane, then 99:1 to 90:10 dichloromethane/solvent A; solvent A=90:9:1 dichloromethane/methanol/triethylamine) gave the amine (4.89 g, 75%) as a yellowish-brown oil: $^1$H NMR (CDCl$_3$, 300 MHz) δ 7.16-7.00 (m, 4H), 6.74 (d, J=2.7 Hz, 1H), 6.64-6.50 (m, 2H), 4.24 (d, J=9.2 Hz, 1H), 3.95-3.80 (m, 1H), 3.77 (s, 3H), 3.67 (d, J=14.1 Hz, 1H), 3.15-3.05 (m, 1H), 3.00-2.90 (m, 1H), 2.34 (s, 3H), 2.32-2.20 (m, 1H), 2.15-1.95 (m, 1H).

Step G: To a solution of the amine (1.24 g, 4.35 mmol) from step F in acetic acid (20 mL) was added an aqueous solution of hydrobromic acid (20 mL, 48 wt. % solution), and the mixture was heated under reflux for 20 hours. The mixture was cooled to room temperature, and then in an ice bath, and was quenched with 2N NaOH, followed by saturated sodium bicarbonate. The crude product was extracted into dichloromethane (4x), and the combined organic extract was dried over sodium sulfate, filtered and concentrated under reduced pressure. Coevaporation of the residue with toluene yielded the phenol (1.17 g) as a pale brown foam containing some acetic acid. The product was dissolved in dichloromethane, washed with saturated sodium bicarbonate, dried over magnesium sulfate, filtered and concentrated under reduced pressure to give the phenol (0.94 g, 80%, crude) as a pale brown foam: $^1$H NMR (CDCl$_3$, 300 MHz) δ 7.25-6.98 (m, 4H), 6.57 (d, J=2.5 Hz, 1H), 6.55-6.45 (m, 2H), 4.21 (d, J=8.9 Hz, 1H), 3.85-3.75 (m, 1H), 3.61 (d, J=13.9 Hz, 1H), 3.15-3.05 (m, 1H), 3.00-2.85 (m, 1H), 2.40 (s, 3H), 2.35-2.20 (m, 1H), 2.15-2.00 (m, 1H).

Step H: To a solution of the phenol (0.7 g, 2.6 mmol) from step G above in dichloromethane (30 mL) at 0° C. was added pyridine (0.4 mL, 5.2 mmol) followed by triflic anhydride (0.55 mL, 3.2 mmol). The reaction mixture was stirred at 0° C. for 2 hours, and then was diluted with dichloromethane, washed with aqueous saturated sodium bicarbonate, dried over sodium sulfate and concentrated under reduced pressure. The crude product obtained (0.82 g, 79%) as a yellow oil was used in the next step without purification: $^1$H NMR (CDCl$_3$, 500 MHz) δ 7.15-7.02 (m, 5H), 6.97 (dd, J=9.0, 2.5 Hz, 1H), 6.81-6.35 (m, 1H), 4.31 (d, J=9.5 Hz, 1H), 3.97 (d, J=12.0 Hz, 1H), 3.72 (d, J=14.5 Hz, 1H), 3.20-2.93 (m, 2H), 2.35 (s, 3H), 2.32-2.25 (m, 1H), 2.13-2.04 (m, 1H).

Step I: To a mixture of the triflate (0.82 g, 2.04 mmol) from step H, potassium acetate (0.60 g, 6.11 mmol) and bis(pinacolato)diboron (0.62 g, 2.44 mmol) was added DMSO (13 mL). The solution was purged with argon for 10 minutes, and dichloro[1,1'-bis(diphenylphosphine)ferrocene]palladium (II) dichloromethane adduct (0.05 g, 0.06 mmol) was added to it. The mixture was heated at 80° C. overnight, and then cooled to room temperature and poured into water. The product was extracted into dichloromethane (3x), and the combined organic layer was washed with water and brine, dried over sodium sulfate, filtered and concentrated under reduced pressure to give the boronate ester, which was used immediately without further purification.

Step J: To a mixture of the crude boronate ester (1.0 g, 2.6 mmol) from step I, 3,6-dichloropyridazine (1.48 g, 3.14 mmol), cesium carbonate (2.56 g, 7.87 mmol) and water (4 mL) was added DMF (16.1 mL), and the mixture was purged with argon for 10 minutes. To this degassed solution was added dichloro[1,1'-bis(diphenylphosphine)ferrocene]palladium(II) dichloromethane adduct (0.13 g, 0.15 mmol), and the mixture was heated at 100° C. for 3 hours and 30 minutes. The reaction was then cooled to room temperature, and partitioned between dichloromethane and water. The aqueous layer was separated and re-extracted with dichloromethane (2x), and the combined organic extract was dried over sodium sulfate, filtered and concentrated under reduced pressure. Purification of the crude product by flash column chromatography (dichloromethane, then 99:0.9:0.1 to 90:9:1 dichloromethane/methanol/concentrated ammonium hydroxide) gave the pyridazine product (0.33 g, 34%) as a brown foam: $^1$H NMR (CDCl$_3$, 300 MHz) δ 7.94 (d, J=1.9 Hz, 1H), 7.79 (d, J=9.0 Hz, 1H), 7.72 (dd, J=8.9, 1.7 Hz, 1H), 7.20-7.04 (m, 5H), 6.85-6.70 (m, 1H), 4.38 (d, J=8.2 Hz, 1H), 4.02 (d, J=14.1 Hz, 1H), 3.85 (d, J=14.3 Hz, 1H), 3.11-3.05 (m, 1H), 3.04-2.94 (m, 1H), 2.40 (s, 3H), 2.40-2.25 (m, 1H), 2.05-2.20 (m, 1H).

Step K: To a mixture of the pyridazine (0.16 g, 0.43 mmol) from step J and 1-methylpiperazine (0.48 mL, 4.36 mmol) in a sealed tube was added 1,4-dioxane (5 mL), and the mixture was heated at 80° C. for 24 hours. An additional quantity of 1-methylpiperazine (0.48 mL, 4.36 mmol) was added to the reaction mixture, which was then heated at 95° C. for 24 hours more. The cooled reaction mixture was partitioned between dichloromethane and water, and the organic layer was separated out. The aqueous layer was re-extracted with dichloromethane (3×), and the combined organic extract was dried over sodium sulfate, filtered and concentrated under reduced pressure. Purification by flash column chromatography (dichloromethane, then 99:0.9:0.1 to 90:9:1 dichloromethane/methanol/concentrated ammonium hydroxide) gave the pyridazine derivative (0.14 g, 74%) as a pale brown foam: $^1$H NMR (CDCl$_3$, 500 MHz) δ 7.92 (d, J=1.8 Hz, 1H), 7.66 (d, J=7.8 Hz, 1H), 7.61 (d, J=9.6 Hz, 1H), 7.18-7.15 (m, 2H), 7.08-7.04 (m, 2H), 6.96 (d, J=9.6 Hz, 1H), 7.00 (br, 1H), 4.35 (d, J=9.1 Hz, 1H), 4.10-3.92 (m, 1H), 3.84 (d, J=14.8 Hz, 1H), 3.73 (t, J=5.0 Hz, 4H), 3.21-3.05 (m, 1H), 3.04-2.86 (m, 1H), 2.56 (t, J=5.1 Hz, 4H), 2.37 (s, 3H), 2.36 (s, 3H), 2.36-2.23 (m, 1H), 2.21-2.05 (m, 1H).

Step L: The free base of the benzazepine from step K (0.14 g) was resolved by preparative chiral HPLC (CHIRALCEL OD column, using 80:20:0.1 heptanes/ethanol/diethylamine as the eluent) to give enantiomer 1 and enantiomer 2. Enantiomer A was further purified by preparative thin layer chromatography (Analtech 1 mm plates, 90:9:1 dichloromethane/methanol/concentrated ammonium hydroxide).

To a solution of enantiomer 1 (45 mg, 0.10 mmol) in methanol (2 mL) was added L-tartaric acid (16 mg, 0.10 mmol) followed by water (10 mL). The resultant solution was lyophilized overnight to give 1-(6-(5-(4-fluorophenyl)-2-methyl-2,3,4,5-tetrahydro-1H-benzo[c]azepin-8-yl)pyridazin-3-yl)piperidin-4-ol, tartrate salt, enantiomer 1 (58 mg, 96%, AUC HPLC 97.3%) as a pale yellow solid: $[\alpha]^{25}_D$+11.6° (c 0.21, methanol)]; $^1$H NMR (CD$_3$OD, 500 MHz) δ 8.03 (d, J=1.6 Hz, 1H), 7.91 (d, J=9.6 Hz, 1H), 6.84 (d, J=7.4 Hz, 1H), 7.39 (d, J=9.6 Hz, 1H), 7.29-7.24 (m, 2H), 7.18-7.10 (m, 2H), 6.89 (br, 1H), 4.64-4.60 (m, 1H), 4.63 (d, J=9.0 Hz, 1H), 4.39 (s, 2H), 4.34 (d, J=13.8 Hz, 1H), 3.84-3.74 (m, 4H), 3.53-3.47 (m, 2H), 2.85-2.79 (m, 4H), 2.65-2.52 (m, 1H), 2.52 (s, 3H), 2.45-2.31 (m, 1H); ESI MS m/z 432 [M+H]$^+$.

To a solution of enantiomer 2 (45 mg, 0.10 mmol) in methanol (2 mL) was added L-tartaric acid (16 mg, 0.10 mmol) followed by water (10 mL). The resultant solution was lyophilized overnight to give 1-(6-(5-(4-fluorophenyl)-2-methyl-2,3,4,5-tetrahydro-1H-benzo[c]azepin-8-yl)pyridazin-3-yl)piperidin-4-ol, tartrate salt, enantiomer 2 (60 mg, 98%, AUC HPLC >99%) as a brown solid: $[\alpha]^{25}_D$+6.00° (c 0.15, methanol)]; $^1$H NMR (CD$_3$OD, 500 MHz) δ 8.03 (d, J=1.6 Hz, 1H), 7.91 (d, J=9.6 Hz, 1H), 6.84 (d, J=7.4 Hz, 1H), 7.39 (d, J=9.6 Hz, 1H), 7.29-7.24 (m, 2H), 7.18-7.10 (m, 2H), 6.89 (br, 1H), 4.64-4.60 (m, 1H), 4.63 (d, J=9.0 Hz, 1H), 4.39 (s, 2H), 4.34 (d, J=13.8 Hz, 1H), 3.84-3.74 (m, 4H), 3.53-3.47 (m, 2H), 2.85-2.79 (m, 4H), 2.65-2.52 (m, 1H), 2.52 (s, 3H), 2.45-2.31 (m, 1H); ESI MS m/z 432 [M+H]$^+$.

Example 91

Preparation of 4-(2-(5-(4-fluorophenyl)-2-methyl-2,3,4,5-tetrahydro-1H-benzo[c]azepin-8-yloxy)ethyl)morpholine (enantiomers 1 and 2)

Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To an ice-cold mixture of the lactam (8.0 g, 39.4 mmol) from step D and fluorobenzene (32 mL) was added trifluoromethanesulfonic acid (50 mL). The reaction mixture was warmed to room temperature and stirred for 3 hours and 30 minutes. The reddish-brown mixture was then poured on ice and stirred until the ice melted. The product was extracted into ethyl acetate (3×), and the combined organic extract was washed with saturated sodium bicarbonate and brine, dried over magnesium sulfate, filtered and concentrated under reduced pressure. Purification of the crude product by flash column chromatography (1:1 ethyl acetate/hexanes to ethyl acetate) gave both pure and impure fractions. The impure fractions were repurified by flash column chromatography (1:1 ethyl acetate/hexanes to ethyl acetate), and combined with the pure fraction obtained previously to give the aryl lactam (6.8 g, 57%) as a yellow oil: $^1$H NMR (CDCl$_3$, 300 MHz) δ 7.05-6.92 (m, 4H), 6.84 (d, J=8.6 Hz, 1H), 6.75-6.69 (m, 1H), 6.66 (d, J=2.7 Hz, 1H), 4.91 (d, J=16.2 Hz, 1H), 4.46 (dd, J=10.8, 5.1 Hz, 1H), 4.19 (d, J=16.2 Hz, 1H), 3.79 (s, 3H), 3.17 (dd, J=13.6, 10.9 Hz, 1H), 3.04 (s, 3H), 2.98 (dd, J=13.7, 5.1 Hz, 1H).

Step F: To an ice-cold mixture of the lactam (6.8 g, 22.7 mmol) from step E and THF (178 mL) was added a solution of borane-dimethylsulfide complex in THF (24 mL, 47.7 mmol, 2 M solution). The mixture was warmed to room temperature, and then heated in an oil bath at 50° C. for 45 minutes. The reaction mixture was cooled to 0° C., quenched with methanol (50 mL), and concentrated under reduced pressure. To the residue was added 1,4-dioxane (75 mL), followed by 6 N HCl (25 mL), and the mixture was heated under reflux for 3 hours and 30 minutes. The mixture was cooled in an ice-bath, and a solution of 30-40% sodium hydroxide was added until pH 10. The crude product was extracted into dichloromethane (3×), and the combined organic extract was dried over magnesium sulfate, filtered and concentrated under reduced pressure. Purification of the crude product by flash column chromatography (dichloromethane, then 99:1 to 90:10 dichloromethane/solvent A; solvent A=90:9:1 dichloromethane/methanol/triethylamine) gave the amine (4.89 g, 75%) as a yellowish-brown oil: $^1$H NMR (CDCl$_3$, 300 MHz) δ 7.16-7.00 (m, 4H), 6.74 (d, J=2.7 Hz, 1H), 6.64-6.50 (m, 2H), 4.24 (d, J=9.2 Hz, 1H), 3.95-3.80 (m, 1H), 3.77 (s, 3H), 3.67 (d, J=14.1 Hz, 1H), 3.15-3.05 (m, 1H), 3.00-2.90 (m, 1H), 2.34 (s, 3H), 2.32-2.20 (m, 1H), 2.15-1.95 (m, 1H).

Step G: To a solution of the amine (1.24 g, 4.35 mmol) from step F in acetic acid (20 mL) was added an aqueous solution of hydrobromic acid (20 mL, 48 wt. % solution), and the mixture was heated under reflux for 20 hours. The mixture was cooled to room temperature, and then in an ice bath, and was quenched with 2 N NaOH, followed by saturated sodium bicarbonate. The crude product was extracted into dichloromethane (4×), and the combined organic extract was dried over sodium sulfate, filtered and concentrated under reduced pressure. Coevaporation of the residue with toluene yielded the phenol (1.17 g) as a pale brown foam containing some acetic acid. The product was dissolved in dichloromethane, washed with saturated sodium bicarbonate, dried over magnesium sulfate, filtered and concentrated under reduced pressure to give the phenol (0.94 g, 80%, crude) as a pale brown foam: $^1$H NMR (CDCl$_3$, 300 MHz) δ 7.25-6.98 (m, 4H), 6.57 (d, J=2.5 Hz, 1H), 6.55-6.45 (m, 2H), 4.21 (d, J=8.9 Hz, 1H), 3.85-3.75 (m, 1H), 3.61 (d, J=13.9 Hz, 1H), 3.15-3.05 (m, 1H), 3.00-2.85 (m, 1H), 2.40 (s, 3H), 2.35-2.20 (m, 1H), 2.15-2.00 (m, 1H).

Step H: To a mixture of the phenol (0.35 g, 1.29 mmol) from step G, cesium carbonate (0.63 g, 1.94 mmol) and 4-(2-chloroethyl)morpholine (0.29 g, 1.94 mmol) was added 1,4-dioxane (10 mL), and the mixture was heated under reflux for 24 hours. The cooled reaction mixture was partitioned between dichloromethane and water, and the organic layer was separated. The aqueous layer was re-extracted with dichloromethane (3×), and the combined organic extract was dried over sodium sulfate, filtered and concentrated under reduced pressure. Purification by flash column chromatography (dichloromethane, then 99:0.9:0.1 to 90:9:1 dichloromethane/methanol/concentrated ammonium hydroxide) gave the morpholine derivative (0.22 g, 44%) as a pale yellow oil: $^1$H NMR (CDCl$_3$, 500 MHz) δ 7.14-7.09 (m, 2H), 7.05-7.00 (m, 2H), 6.76 (d, J=2.5 Hz, 1H), 6.62-6.59 (m, 1H), 6.52 (br s, 1H), 4.23 (d, J=9.0 Hz, 1H), 4.07 (t, J=5.7 Hz, 2H), 3.90-3.80 (m, 1H), 3.72 (t, J=4.7 Hz, 4H), 3.66 (d, J=14.1 Hz, 1H), 3.15-3.05 (m, 1H), 3.00-2.90 (m, 1H), 2.78 (t, J=5.7 Hz, 2H), 2.56 (t, J=4.3 Hz, 4H), 2.34 (s, 3H), 2.30-2.20 (m, 1H), 2.10-2.00 (m, 1H).

Step I: The free base of the benzazepine from step H (0.22 g) was resolved by preparative chiral HPLC (CHIRALCEL OJ column, using 80:20:0.1 heptanes/ethanol/diethylamine as the eluent) to give enantiomer 1 and enantiomer 2. Both enantiomers were converted into the corresponding tartrate salts, which were found to be of insufficient purity. The salts were converted into the corresponding free bases by washing with sodium bicarbonate solution, and each enantiomer was further purified by preparative thin layer chromatography (Analtech 1 mm plates, 90:9:1 dichloromethane/methanol/concentrated ammonium hydroxide).

To a solution of enantiomer 1 (58 mg, 0.15 mmol) in methanol (2 mL) was added L-tartaric acid (23 mg, 0.15 mmol) followed by water (10 mL). The resultant solution was lyophilized overnight to give 4-(2-(5-(4-fluorophenyl)-2-methyl-2,3,4,5-tetrahydro-1H-benzo[c]azepin-8-yloxy)ethyl)morpholine, L-tartrate salt, enantiomer 1 (58 mg, 96%, AUC HPLC 95.4%) as an off-white solid: $[[\alpha]^{25}_D$+9.93° (c 0.15, methanol)]; $^1$H NMR (CD$_3$OD, 500 MHz) δ 7.22-7.18 (m, 2H), 7.14-7.09 (m, 2H), 7.06 (d, J=2.3 Hz, 1H), 6.88 (d, J=7.4 Hz, 1H), 6.75 (br, 1H), 4.50 (d, J=8.1 Hz, 2H), 4.37 (s, 2H), 4.22-4.18 (m, 3H), 3.75 (t, J=4.6 Hz, 4H), 3.53-3.42 (m, 2H), 2.94 (t, J=5.2 Hz, 2H), 2.84 (s, 3H), 2.74 (d, J=4.2 Hz, 4H), 2.58-2.42 (m, 1H), 2.37-2.26 (m, 1H); ESI MS m/z 385 [M+H]$^+$.

To a solution of enantiomer 2 (48 mg, 0.12 mmol) in methanol (2 mL) was added L-tartaric acid (19 mg, 0.12 mmol) followed by water (10 mL). The resultant solution was lyophilized overnight to give 4-(2-(5-(4-fluorophenyl)-2-methyl-2,3,4,5-tetrahydro-1H-benzo[c]azepin-8-yloxy)ethyl)morpholine, L-tartrate salt, enantiomer 2 (63 mg, 95%, AUC HPLC 97.7%) as an off-white solid.: $[[\alpha]^{25}_D$+2.04° (c 0.15, methanol)]; $^1$H NMR (CD$_3$OD, 500 MHz) δ 7.22-7.18 (m, 2H), 7.14-7.09 (m, 2H), 7.06 (d, J=2.3 Hz, 1H), 6.88 (d, J=7.4 Hz, 1H), 6.75 (br, 1H), 4.50 (d, J=8.1 Hz, 2H), 4.37 (s, 2H), 4.22-4.18 (m, 3H), 3.75 (t, J=4.6 Hz, 4H), 3.53-3.42 (m, 2H), 2.94 (t, J=5.2 Hz, 2H), 2.84 (s, 3H), 2.74 (d, J=4.2 Hz, 4H), 2.58-2.42 (m, 1H), 2.37-2.26 (m, 1H); ESI MS m/z 385 [M+H]$^+$.

Example 92

Preparation of (+)- and (−)-2-fluoro-4-(2-methyl-8-(6-methylpyridazin-3-yl)-2,3,4,5-tetrahydro-1H-benzo[c]azepin-5-yl)benzonitrile, L-tartrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To a solution of the lactam (1.0 g, 4.92 mmol) from step D in trifluoromethanesulfonic acid (10 mL) was added 2-fluorophenol (1.32 mL, 14.8 mmol). The reaction mixture was stirred at room temperature for 45 minutes. The reaction mixture was poured into ice-water, basified with a concentrated ammonium hydroxide till pH 8-9 and extracted with dicloromethane (3×100 mL). The organic extracts were dried other sodium sulfate, filtered and concentrated under reduced pressure. The residue was triturated with ethanol to afford the 5-aryllactam (1.3 g, 84%) as a white solid: $^1$H NMR (CDCl$_3$, 500 MHz) δ 7.02 (d, J=1.5 Hz, 1H), 6.89 (d, J=8.6 Hz, 1H), 6.74 (dd, J=8.6, 2.7 Hz, 1H), 6.69-6.65 (m, 2H), 6.65 (d, J=2.7 Hz, 1H), 6.58-6.52 (m, 1H), 4.56 (d, J=16.4 Hz, 1H), 4.51 (d, J=16.4 Hz, 1H), 3.79 (s, 3H), 3.19 (dd, J=13.8, 4.6 Hz, 1H), 3.07 (s, 3H), 3.04 (dd, J=13.8, 8.5 Hz, 1H), 1.59 (s, 1H).

Step F: To a solution of the 5-aryllactam (1.00 g, 3.17 mmol) from step E above in tetrahydrofuran (10 mL) was added borane-dimethylsulfide complex in THF (3.17 mL, 6.34 mmol, 2M solution). The reaction mixture was heated to reflux for 1 h then was concentrated under reduced pressure. The reaction mixture was dissolved in 1,4-dioxane (120 mL) and was treated with an aqueous solution of hydrochloric acid (6 N, 9 mL) and the mixture was heated to reflux for 3 hours, then was concentrated to dryness under reduced pressure. The residue was diluted with water (20 mL) and basified until pH 8-9 with a saturated sodium bicarbonate. The solution thus obtained was extracted with dichloromethane (3×80 mL), the combined extracts was dried other sodium sulfate, filtered and concentrated under reduced pressure to afford the 5-arylbenzazepine (1.07 g, quantitative) as a white foam.

Step G: To a solution of the aryl benzazepine (3.0 g, 9.95 mmol) in dichloromethane (50 mL) was successively added pyridine (1.6 mL, 19.9 mmol) and trifluoromethansulfonic anhydride (2.5 mL, 14.86 mmol). The reaction mixture was stirred at 0° C. for 1 hour then diluted with water (50 mL). The aqueous phase was extracted with dichloromethane (3×150 mL) and the combined extracts were dried over sodium sulfate, filtered and concentrated to afford the desired triflate as a yellow oil.

Step H: To the crude triflate (~9.95 mmol) from step G was successively added 1,1'-bis(diphenylphosphino)ferrocene (0.87 g, 1.19 mmol), zinc(II) cyanide (2.34 g, 19.93 mmol), tris(dibenzylideneacetone)dipalladium(0) (273 mg, 0.29 mmol) and DMF (50 mL). The reaction mixture was heated to 130° C. for 1 hour under argon. The cooled reaction mixture was diluted with water (50 mL) and extracted with dichloromethane (3×150 mL). The combined organic phase was dried over sodium sulfate, filtered and concentrated under reduced pressure. The crude product was purified by flash chromatography (98:1.8:0.2 to 94:5.4:0.6 dichloromethane/methanol/concentrated ammonium hydroxide) to afford the benzonitrile benzazepine (2.29 g, 74% yield over 2 steps) as a white solid. $^1$H NMR (CD$_3$OD, 500 MHz) δ 7.60-7.54 (m, 1H), 7.07 (d, J=8.0 Hz, 1H), 7.01 (d, J=10.2 Hz, 1H), 6.76 (d, J=2.7 Hz, 1H), 6.65 (dd J=8.3, 2.5 Hz, 1H), 6.60-6.55 (m, 1H), 4.30 (dd, J=8.5, 1.7 Hz, 1H), 3.83-3.72 (m, 1H), 3.78 (s, 3H), 3.63 (d, J=14.4 Hz, 1H), 3.04-2.96 (m, 1H), 2.95-2.87 (m, 1H), 2.33 (s, 3H), 2.31-2.22 (m, 1H), 2.20-2.10 (m, 1H).

Step I: To a solution of the benzonitrilebenzazepine (1.01 g, 3.25 mmol) from step H above in dichloromethane (20 mL) was added boron tribomide (1.5 mL, 15.9 mmol). The reaction mixture was stirred at −78° C. overnight and concentrated under reduced pressure. The residue was diluted with methanol (20 mL) then concentrated in vacuo (3×). The residue was next diluted in dichloromethane (60 mL) and treated with a saturated sodium bicarbonate (20 mL). The aqueous phase was extracted with dichloromethane (2×60 mL). The combined organic phase was dried over sodium sulfate, filtered and concentrated under reduced pressure. The residue was purified by flash column chromatography (97.5:2.5 to 92.5:7.5 dichloromethane/methanol) to afford the 8-hydroxybenzazepine (0.55 g, 57%). $^1$H NMR (CDCl$_3$, 500 MHz) δ 7.62-7.56 (m, 1H), 7.06 (d, J=7.9 Hz, 1H), 6.99 (d, J=9.9 Hz, 1H), 6.58-6.53 (m, 1H), 6.49 (s, 2H), 4.27 (d, J=8.2 Hz, 1H), 3.80-3.69 (m, 1H), 3.58 (d, J=14.0 Hz, 1H), 3.05-2.89 (m, 2H), 2.43 (s, 3H), 2.40-2.29 (m, 1H), 2.24-2.18 (m, 1H).

Step J: To a solution of the 8-hydroxybenzazepine (0.53 g, 1.81 mmol) from Step I above in dichloromethane (10 mL) was successively added pyridine (0.29 mL, 19.9 mmol) and trifluoromethansulfonic anhydride (0.45 mL, 2.71 mmol). The reaction mixture was stirred at 0° C. for 40 minutes then, was diluted with water (6 mL) and a saturated ammonium chloride (2 mL). The aqueous phase was extracted with dichloromethane (3×20 mL) and the combined extracts were dried over sodium sulfate, filtered and concentrated to afford the triflate as a brown foam.

Step K: A dry flask was loaded with the triflate (~1.81 mmol) from step J above, bis(pinacolato)diboron (0.55 g, 2.17 mmol), potassium acetate (0.53 g, 5.43 mmol), dichloro [1,1'-bis(diphenylphosphino)ferrocene]palladium(II) (0.12 g, 0.14 mmol) and DMSO (10 mL). The mixture was heated to 87° C. under argon for 1 hour. The cooled reaction mixture was diluted with ethyl acetate (100 mL), washed successively with water (3×20 mL) and brine (2×20 mL), dried over sodium sulfate, filtered and concentrated under reduced pressure to give boronate ester, which was used as it is in the next step without further purification.

Step L: A dry flask was loaded with the boronate ester (~1.81 mmol) from step K above, 3-chloro-6-methylpyridazine (0.34 g, 2.76 mmol), sodium carbonate (0.48 g, 4.52 mmol) and dichloro[1,1'-bis(diphenylphosphino)ferrocene]palladium(II) (0.12 g, 0.14 mmol). The flask was flushed with argon prior to the addition of DMF (16 mL) and water (3.2 mL). The reaction mixture was heated to 90° C. under argon for 2 hours. The cooled reaction mixture was diluted with water (50 mL) and extracted with dichloromethane (3×100 mL). The combined organic phases were dried over sodium sulfate, filtered and concentrated. The residue was purified by flash column chromatography (95:5 to 85:15 dichloromethane/methanol) to afford the pyridazinyl benzazepine (420 mg, 62% yield over 3 steps).

Step M: The free base of the pyridazinyl benzazepine (0.42 g) from Step L above was resolved by preparative chiral HPLC (CHIRALCEL OD column, using 70:30:0.1 heptane/isopropanol/diethylamine as the eluent) to give the (+)-enantiomer $[[\alpha]^{25}_D+6.00$ (c 0.02, chloroform)] and the (−)-enantiomer $[[\alpha]^{25}_D-6.0°$ (c 0.03, chloroform)].

Step N: The mixture of the (+)-enantiomer (0.104 g, 0.27 mmol) from Step M above and L-tartaric acid (42 mg, 0.27 mmol) was dissolved in a mixture of methanol and water, frozen and lyophilized to afford (+)-2-fluoro-4-(2-methyl-8-(6-methylpyridazin-3-yl)-2,3,4,5-tetrahydro-1H-benzo[c]azepin-5-yl)benzonitrile, L-tartrate salt as a brown solid: mp 112-115° C.; $^1$H NMR (CD$_3$OD, 500 MHz) δ 8.20 (s, 1H), 8.08 (d, J=8.7 Hz, 1H), 8.00 (d, J=7.9 Hz, 1H), 7.84-7.78 (m, 1H), 7.69 (d, J=8.7 Hz, 1H), 7.31 (d, J=10.5 Hz, 1H), 7.27 (d, J=7.9 Hz, 1H), 7.04-6.94 (m, 1H), 4.80-4.76 (m, 1H), 4.18-4.09 (m, 1H), 4.40 (s, 2H), 4.39-4.32 (m, 1H), 3.59-3.46 (m, 2H), 2.77 (s, 3H), 2.72 (s, 3H), 2.78-2.55 (m, 1H), 2.48-2.38 (m, 1H); ESI MS m/z 373 [M+H]$^+$.

Step O: The mixture of the (−)-enantiomer (0.100 g, 0.27 mmol) from Step M above and L-tartaric acid (40 mg, 0.27 mmol) was dissolved in a mixture of methanol and water, frozen and lyophilized to afford (−)-2-fluoro-4-(2-methyl-8-(6-methylpyridazin-3-yl)-2,3,4,5-tetrahydro-1H-benzo[c]azepin-5-yl)benzonitrile, L-tartrate salt (0.136 g, 90%, AUC HPLC >99%) as a brown solid: mp 122-127° C.; $^1$H NMR (CD$_3$OD, 500 MHz) δ 8.20 (s, 1H), 8.08 (d, J=8.7 Hz, 1H), 8.00 (d, J=7.9 Hz, 1H), 7.84-7.78 (m, 1H), 7.69 (d, J=8.7 Hz, 1H), 7.31 (d, J=10.5 Hz, 1H), 7.27 (d, J=7.9 Hz, 1H), 7.04-6.94 (m, 1H), 4.80-4.76 (m, 1H), 4.18-4.09 (m, 1H), 4.40 (s, 2H), 4.39-4.32 (m, 1H), 3.59-3.46 (m, 2H), 2.77 (s, 3H), 2.72 (s, 3H), 2.78-2.55 (m, 1H), 2.48-2.38 (m, 1H); ESI MS m/z 373 [M+H]$^+$.

Example 93

Preparation of 2,6-difluoro-4-(8-methoxy-2-methyl-2,3,4,5-tetrahydro-1H-benzo[c]azepin-5-yl)benzonitrile, citrate salt Step A: To a solution of aqueous 2 N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: $^1$H NMR (CDCl$_3$, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added a solution of methylamine in water (130 mL, 1.5 mol, 40 wt. % solution). The resultant solution was cooled to 0° C. and sodium borohydride (83 g, 2.3 mol) was added to it in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined dichloromethane extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (26.3 g, 174 mmol) from Step B above, 3,3-dimethoxypropanoic acid (23.4 g, 174 mmol) and dichloromethane (182 mL) at 0° C. was added 1-(3-dimethylaminopropyl)-3-ethylcarbodiimide hydrochloride (36.8 g, 192 mmol). The mixture was stirred at room temperature overnight, and then washed with water and saturated sodium bicarbonate. The resulting solution was dried over magnesium sulfate, filtered and concentrated in vacuo to give the acetal (42 g, 90%) as a yellow oil: $^1$H NMR (500 MHz, CDCl$_3$) δ 7.30-7.20 (m, 1H), 6.84-6.70 (m, 3H), 4.93-4.89 (m, 1H), 4.58, 4.53 (s, 2H, rotamers), 3.79 (s, 3H), 3.44, 3.39 (s, 6H, rotamers), 2.94 (s, 3H), 2.73, 2.70 (d, J=5.5 Hz, 2H, rotamers). The crude product was used without further purification in the next reaction.

Step D: To the acetal (42.0 g, 157 mmol) from step C above was added pre-cooled concentrated hydrochloric acid (200 mL) at 0° C. The mixture was gradually warmed to 10° C. over 2 hours and 30 minutes. The cold reaction mixture was diluted with ice-cold water, and the white precipitate formed was filtered, washed with cold water and dried. The solid obtained was taken up in dichloromethane and washed with saturated sodium bicarbonate. The resultant solution was dried over magnesium sulfate, filtered and concentrated in vacuo to yield the lactam (20.3 g, 63%) as a white solid: $^1$H NMR (300 MHz, CDCl$_3$) δ 7.30 (d, J=8.4 Hz, 1H), 7.01 (d, J=12.1 Hz, 1H), 6.90 (dd, J=8.4, 2.7 Hz, 1H), 6.82 (d, J=2.6 Hz, 1H), 6.29 (d, J=12.1 Hz, 1H), 4.19 (s, 2H), 3.86 (s, 3H), 3.09 (s, 3H).

Step E: To a solution of the lactam (2.0 g, 9.84 mmol) from step D in trifluoromethanesulfonic acid (20 mL) was added 2,6-difluorophenol (3.84 g, 29.5 mmol). The reaction mixture was stirred at room temperature for 4 hours. The reaction mixture was diluted with cold water, basified with sodium hydroxide till pH 8-9 and extracted with dichloromethane (3×300 mL). The extracts were dried other sodium sulfate, filtered and concentrated under reduced pressure. The residue was triturated with ethanol to afford the 5-aryllactam (2.04 g, 62%) as a white solid: $^1$H NMR (CDCl$_3$, 500 MHz) δ 9.93 (s, 1H), 6.87 (d, J=2.6 Hz, 1H), 6.81 (d, J=8.6 Hz, 1H), 6.78-6.73 (m, 3H), 4.87 (d, J=16.4 Hz, 1H), 4.42 (d, J=16.4 Hz, 1H), 4.34 (dd, J=9.8, 4.9 Hz, 1H), 3.73 (s, 3H), 3.09 (dd, J=13.4, 9.9 Hz, 1H), 2.92-2.86 (m, 1H), 2.87 (s, 3H).

Step F: To a solution of the 5-aryllactam (2.0 g, 6.0 mmol) from step E in tetrahydrofuran (18 mL) was added borane-dimethylsulfide complex in THF (6 mL, 12.0 mmol, 2M solution). The reaction mixture was heated to reflux for one hour then was concentrated to dryness under reduced pressure. The residue was dissolved in 1,4-dioxane (40 mL) and treated with an aqueous solution of hydrochloric acid (6 N, 20 mL) and the mixture was heated to reflux for 3 hours, then concentrated under reduced pressure. The residue was diluted with water (20 mL) and basified until pH 8-9 with a saturated sodium bicarbonate. The solution was extracted with dichloromethane (3×), the combined extracts was dried other sodium sulfate, filtered and concentrated to dryness under reduced pressure to afford the 5-arylbenzazepine (2.04 g, quantitative) as an off-white solid.

Step 6: To a solution of the aryl benzazepine (0.50 g, 1.56 mmol) from step F in dichloromethane was successively added pyridine (0.25 mL, 3.18 mmol) and trifluoromethansulfonic anhydride (0.39 mL, 2.33 mmol). The reaction mixture was stirred at 0° C. for 1 hour and diluted with water (20 mL). The aqueous phase was extracted with dichloromethane (3×60 mL) and the combined extracts were dried over sodium sulfate, filtered and concentrated to afford the desired triflate as a yellow foam.

Step H: To the crude triflate (~0.78 mmol) from step G was successively added 1,1'-bis(diphenylphosphino)ferrocene (0.068 mg, 0.09 mmol), zinc(II) cyanide (0.18 g, 1.55 mmol), tris(dibenzylideneacetone)dipalladium(0) (0.02 mg, 0.02 mmol) and DMF (6.0 mL). The reaction mixture was heated to 130° C. for 1 hour under argon. The cooled reaction mixture was diluted with water (20 mL) and extracted with dichloromethane (3×80 mL). The combined organic phases were dried over sodium sulfate, filtered and concentrated under reduced pressure. The crude product was purified flash chromatography column (25:25:45:5 dichloromethane/hexanes/ethyl acetate/concentrated ammonium hydroxide) to afford the benzazepine (0.08 g, 31% yield over 2 steps) as a white solid.

To a solution of the benzazepine (76 mg, 0.23 mmol) in methanol (2 mL) was added citric acid (44 mg, 0.22 mmol) followed by slow addition of water (10 mL). The resultant reaction solution was lyophilized overnight to give 2,6-difluoro-4-(8-methoxy-2-methyl-2,3,4,5-tetrahydro-1H-benzo[c]azepin-5-yl)benzonitrile, citrate salt (121 mg, 100%, AUC HPLC >99%) as an off-white solid: mp 82-86° C.; $^1$H NMR (CD$_3$OD, 500 M) δ 7.10-7.03 (m, 3H), 6.93-6.90 (m, 1H), 6.85-6.74 (m, 1H), 4.61 (d, J=7.5 Hz, 1H), 4.45-4.39 (m, 1H) 4.22 (d, J=13.1 Hz, 1H), 3.81 (s, 3H), 3.52-3.41 (m, 2H), 2.84-2.78 (m, 5H), 2.73 (d, J=15.4 Hz, 2H), 2.61-2.51 (m, 1H), 2.42-2.29 (m, 1H); ESI MS m/z 329 [M+H]$^+$.

Example 94

Preparation of (+/−)-5-(5-chlorothiophen-2-yl)-8-methoxy-2-methyl-2,3,4,5-tetrahydro-1H-benzo[c]azepine, citrate salt Step A: To a solution of m-anisaldehyde (205 g, 1.5 mol) in methanol (800 mL) at room temperature was added 40% methylamine in water (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of benzylamine (25.6 g, 169 mmol) from Step B above, 3,3-dimethoxypropanoic acid (22.5 g, 168 mmol) and methylene chloride (200 mL) was added 1-(3-dimethylaminopropyl)-3-ethylcarbodiimide hydrochloride (32.9 g, 171 mmol) at 0° C. The mixture was stirred at room temperature overnight, and then washed with water (150 mL), 1N hydrochloric acid (100 mL) and saturated sodium bicarbonate (60 mL). The resulting solution was dried over sodium sulfate, filtered and concentrated in vacuo to give the acetal (44.9 g, 99%) as a brown oil. The crude product was used directly in the next reaction.

Step C: The acetal (44.9 g, 168 mmol) from step C above was treated with pre-cooled concentrated hydrochloric acid (200 mL) at 0° C. The mixture was stirred at 0° C. for 2 hours. The reaction was quenched with 2 N NaOH (the pH was adjusted to 7). The mixture was extracted with methylene chloride (2×500 mL). The combined extracts were dried over sodium sulfate, filtered and concentrated in vacuo. The residue was recrystallized with hexanes/ethyl acetate followed by another recrystallization to yield the lactam (12.1 g) as a colorless solid. Another crop of the lactam (6.80 g) was obtained from the mother liquid by column chromatography (1:1 hexanes/ethyl acetate). The combined yield was 55%: $^1$H NMR (500 MHz, CDCl$_3$) δ 7.30 (d, J=8.0 Hz, 1H), 7.01 (d, J=12.1 Hz, 1H), 6.90 (dd, J=8.3, 2.6 Hz, 1H), 6.82 (d, J=2.6 Hz, 1H), 6.29 (d, J=12.1 Hz, 1H), 4.19 (s, 2H), 3.86 (s, 3H), 3.10 (s, 3H); ESI MS m/z 204 [M+H]$^+$.

Step D: To a solution of lactam product from Step C above (0.50 g, 2.46 mmol) in dichloromethane (10 mL) was added 3-chlorothiophene (0.91 mL, 9.84 mmol) followed by aluminum chloride (0.65 g, 4.92 mmol). The reaction was allowed to stir for a further 6 hours, diluted with dichloromethane (50 mL) and quenched with water (20 mL). The mixture was made basic by addition of 2 N NaOH before the organic layer was separated, dried over Na$_2$SO$_4$ and concentrated in vacuo. Purification by flash column chromatography (50-70% ethyl acetate/hexanes) yielded the desired product (564 mg, 71%) as a yellow foam: $^1$H NMR (500 MHz, CDCl$_3$) δ 7.12 (d, J=5.4 Hz, 1H), 6.99 (d, J=8.6 Hz, 1H), 6.86 (d, J=5.4 Hz, 1H), 6.76 (dd, J=8.6, 2.7 Hz, 1H), 6.64 (d, J=2.7 Hz, 1H), 4.90 (m, 1H), 4.81 (d, J=16.3 Hz, 1H), 4.28 (d, J=16.3 Hz, 1H), 3.79 (s, 3H), 3.28-3.23 (m, 1H), 3.12-3.07 (m, 1H), 3.05 (s, 3H); ESI MS m/z 322 [M+H]$^+$.

Step E: To a stirred solution of lactam from Step D above (270 mg, 0.84 mmol) in THF (3.5 mL) at 0° C. under N$_2$ was added borane-dimethylsulfide complex (1.26 mL of a 2N solution in THF, 2.52 mmol). After 30 minutes the reaction mixture was allowed to warm to room temperature for 3 hours before cooling back to 0° C. The reaction was quenched by slow addition of saturated ammonium chloride (3 mL), extracted with dichloromethane (30 mL) and the organic layer dried over Na$_2$SO$_4$ before concentrating in vacuo. The residue was dissolved in dioxane (20 mL) and 6 N HCl (10 mL) and the solution heated at 60° C. for 3 hours. After cooling to room temperature the mixture was made basic by addition of 2 N NaOH and concentrated in vacuo. The residue was purified by flash chromatography (dry loading, 0-15% methanol/ethyl acetate) to afford the desired product (156 mg, 60%) as a yellow oil: $^1$H NMR (300 MHz, CDCl$_3$) δ 7.23 (d, J=5.4 Hz, 1H), 6.94 (d, J=5.4 Hz, 1H), 6.73 (d, J=2.6 Hz, 1H), 6.65-6.55 (m, 2H), 4.63 (dd, J=9.8, 1.9 Hz, 1H), 4.02 (d, J=14.4 Hz, 1H), 3.83-3.75 (m, 4H), 3.17-3.07 (m, 1H), 3.04-2.94 (m, 1H), 2.37-2.25 (m, 4H), 2.13-2.03 (m, 1H); ESI MS m/z 308 [M+H]$^+$.

Step F: To a solution of product from Step E above (143 mg, 0.46 mmol) in methanol (2 mL) was added citric acid (96 mg, 0.50 mmol). The mixture was stirred until a homogeneous solution was obtained then concentrated in vacuo to give (+/−)-5-(5-chlorothiophen-2-yl)-8-methoxy-2-methyl-2,3,4,5-tetrahydro-1H-benzo[c]azepine, citrate salt (239 mg, 100%, AUC HPLC 96.9%) as an off-white foam: $^1$H NMR (300 MHz, CD$_3$OD) δ 7.48 (d, J=5.4 Hz, 1H), 7.06-7.02 (m, 2H), 6.91-6.85 (m, 1H), 6.76-6.70 (m, 1H), 4.92-4.81 (m, 4H), 4.67 (d, J=14.3 Hz, 1H), 4.45 (d, J=14.3 Hz, 1H), 3.81 (s, 3H), 3.63-3.53 (m, 2H), 2.88-2.69 (m, 7H), 2.57-2.40 (m, 2H); ESI MS m/z 308 [M+H]$^+$.

Example 95

Preparation of trans-2-methyl-5-phenyl-2,3,4,5-tetrahydro-1H-benzo[c]azepin-4-ol, L-tartrate salt and trans-2-methyl-5-phenyl-2,3,4,5-tetrahydro-1H-benzo[c]azepin-4-ol, L-tartrate salt, diasteromers A and B Step A: To a mixture of N-methylbenzylamine (20.2 g, 167 mmol), 3,3-dimethoxypropanoic acid (22.4 g, 167 mmol) in methylene chloride (200 mL) was added 1-(3-dimethylaminopropyl)-3-ethylcarbodiimide hydrochloride (32.6 g, 170 mmol) at 0° C. The mixture was stirred at room temperature overnight, and then washed with water (150 mL), 1 N HCl (100 mL) and saturated NaHCO$_3$ (60 mL). The resulting solution was dried over Na$_2$SO$_4$, filtered and concentrated in vacuo to give the acetal (36.7 g, 93%) as a brown oil: $^1$H NMR (300 MHz, CDCl$_3$) δ 7.36-7.16 (m, 5H), 4.94-4.66 (m, 1H), 4.59 (d, J=12.0 Hz, 2H), 3.44 (s, 3H), 3.40 (s, 3H), 2.95 (s, 3H), 2.75-2.70 (m, 2H).

Step B: To a suspension of aluminum chloride (42.7 g, 320 mmol) in methylene chloride (700 mL) was added a solution of the acetal (19.0 g, 80 mmol) from step A above in methylene chloride (100 mL) dropwise. After the addition was completed, the mixture was stirred at room temperature for 3 hours and then poured into ice-water (1 L) carefully. The two phases were separated and the methylene chloride phase was washed with saturated NaHCO$_3$, dried over Na$_2$SO$_4$, filtered and concentrated in vacuo. The residue was triturated with diethyl ether. After filtration, the unsaturated lactam (3.20 g) was obtained as an off-white solid. The mother liquid was concentrated and the residue was purified by column chromatography (1:1 to 1:2 hexanes/ethyl acetate) to yield another crop of the product (3.70 g). The combined yield was 50%: $^1$H NMR (500 MHz, CDCl$_3$) δ 7.38-7.15 (m, 4H), 7.08 (d, J=12.0 Hz, 1H), 6.41 (d, J=12.0 Hz, 1H), 4.24 (s, 2H), 3.11 (s, 3H).

Step C: To a suspension of copper(I) iodide (4.13 g, 21.7 mmol) in THF (70 mL) at −30 to −40° C. was added 1.8 M PhLi in di-n-butyl ether (24.0 mL, 43.2 mmol) dropwise. The mixture was stirred at that temperature for 1 hour before a solution of the unsaturated lactam (1.88 g, 10.9 mmol) from step B above in THF (20 mL) was added dropwise followed by iodotrimethylsilane (2.3 mL, 16.3 mmol). The resulting mixture was allowed to warm slowly to room temperature and stirred overnight. Triethylamine (5 mL) followed by saturated ammonium chloride (10 mL) was added to quench the reaction at −78° C. The mixture was partitioned between methylene chloride and water. The aqueous phase was extracted with methylene chloride three times. The combined extracts were dried over Na$_2$SO$_4$, filtered and concentrated in vacuo. The residue was purified by column chromatography (2:1 to 1:1 hexanes/ethyl acetate) to yield the lactam (2.31 g, 85%) as an off-white solid: $^1$H NMR (500 MHz, CDCl$_3$) δ 7.47-7.08 (m, 8H), 6.96 (d, J=7.0 Hz, 1H), 5.05 (d, J=16 Hz, 1H), 4.52 (dd, J=11.0, 5.0 Hz, 1H), 4.17 (d, J=16.0 Hz, 1H), 3.28 (dd, J=14.0, 11.0 Hz, 1H), 3.05 (s, 3H), 2.98 (dd, J=14.0, 5.0 Hz, 1H).

Step D: To a solution of lithium hexamethyldisilazane (8.6 mL, 8.6 mmol, 1.0 M in THF) from Step C above in THF (8 mL) at −78° C. under N$_2$ was added dropwise a solution of the lactam (0.72 g, 2.87 mmol) in THF (30 mL). The resulting mixture was stirred and allowed to warm up to 0° C. The mixture was stirred at 0° C. for 10 minutes and re-cooled to −78° C. Oxodiperoxymolybdenum-pyridine-hexamethylphosphoric triamide (2.49 g, 5.74 mmol) was added in one portion. The resulting mixture was stirred at −55° C. for 1 hour and allowed to warm to room temperature overnight. The mixture was cooled at −78° C. and quenched with saturated ammonium chloride (5 mL). The mixture was partitioned between ethyl acetate (60 mL) and water (40 mL). After separation, the aqueous phase was acidified to pH 4 with 3N HCl and extracted with methylene chloride (2×100 mL). The combined organic phases were dried over Na$_2$SO$_4$, filtered and concentrated in vacuo. The residue was purified by column chromatography (1:1 hexanes/ethyl acetate) to yield the hydroxylactam (286 mg, 37%) as an off-white solid: $^1$H NMR (500 MHz, CDCl$_3$) δ 7.35-7.10 (m, 8H), 6.96 (d, J=7.0 Hz, 1H), 5.22 (d, J=16.0 Hz, 1H), 5.06 (dd, J=10.0, 5.0 Hz, 1H), 4.26 (d, J=5.0 Hz, 1H), 4.08 (d, J=10.0 Hz, 1H), 3.83 (d, J=16.0 Hz, 1H), 3.10 (s, 3H); ESI MS m/z 268 [M+H]$^+$.

Step E: To a mixture of the hydroxylactam (369 mg, 1.38 mmol) from step D above in THF (10 mL) at room temperature was added dropwise 2.0M borane-dimethylsulfide in THF (2.1 mL, 4.2 mmol). The mixture was refluxed for 2 hours. After cooling, the mixture was concentrated in vacuo. To the residue was added tetramethylenediamine (1.5 mL, 9.66 mmol) and methanol (10 mL). The mixture was refluxed for 2 hours. After cooling, the mixture was concentrated in vacuo. The residue was purified by column chromatography (20:1 methylene chloride/methanol) to yield the hydroxybenzazepine (350 mg, 98%, trans-isomer based on NOESY spectrum) as a white solid: $^1$H NMR (500 MHz, CDCl$_3$) δ 7.35-7.10 (m, 8H), 6.96 (d, J=7.0 Hz, 1H), 4.59 (d, J=6.0 Hz, 1H), 4.40 (br, 1H), 3.70 (br, 1H), 3.67 (d, J=15.6 Hz, 1H), 3.61 (d, J=13.0 Hz, 1H), 2.87-2.85 (m, 1H), 2.70 (d, J=7.0 Hz, 1H), 2.42 (s, 3H); ESI MS m/z 254 [M+H]$^+$.

Step F: The free base of the hydroxybenzazepine from Step E above (0.13 g) was resolved by preparative chiral HPLC (CHIRALCEL OJ column, using 80:20:0.1 heptane/ethanol/diethylamine as the eluent) to give diastereomer A [[α]$^{25}_D$+40° (c 0.065, methanol)] and diastereomer B [[α]$^{25}_D$−48° (c 0.075, methanol)].

Step G: To a solution of the diastereomer A (53 mg, 0.21 mmol) from Step F above in methanol (1 mL) was added L-tartaric acid (31 mg, 0.21 mmol). After the mixture was stirred at room temperature for 10 minutes, water (20 mL) was added. The resultant solution was lyophilized overnight to give trans-2-methyl-5-phenyl-2,3,4,5-tetrahydro-1H-benzo[c]azepin-4-ol, tartrate salt, diastereomer A (73 mg, 87%, AUC HPLC 96.7%) as an white solid: $^1$H NMR (CD$_3$OD, 500 MHz) δ 7.44-7.09 (m, 9H), 4.78 (br, 1H), 4.65 (d, J=6.5 Hz, 1H), 4.40 (s, 2H), 4.35 (d, J=14.1 Hz, 1H), 4.29 (d, J=14.1 Hz, 1H), 3.41-3.39 (m, 1H), 3.32-3.30 (m, 1H), 2.88 (s, 3H); ESI MS m/z 254 [M+H]$^+$.

Step H: To a solution of the diastereomer B (56 mg, 0.22 mmol) from Step F above in methanol (1 mL) was added L-tartaric acid (33 mg, 0.22 mmol). After the mixture was stirred at room temperature for 10 minutes, water (20 mL)

was added. The resultant solution was lyophilized overnight to give trans-2-methyl-5-phenyl-2,3,4,5-tetrahydro-1H-benzo[c]azepin-4-ol, L-tartrate salt, diastereomer B (72 mg, 81%, AUC HPLC 96.1%) as an white solid: $^1$H NMR (CD$_3$OD, 500 MHz) δ 7.44-7.09 (m, 9H), 4.78 (br, 1H), 4.65 (d, J=6.5 Hz, 1H), 4.40 (s, 2H), 4.35 (d, J=14.1 Hz, 1H), 4.29 (d, J=14.1 Hz, 1H), 3.41-3.39 (m, 1H), 3.32-3.30 (m, 1H), 2.88 (s, 3H); ESI MS m/z 254 [M+H]$^+$.

Example 96

Preparation of cis-2-methyl-5-phenyl-2,3,4,5-tetrahydro-1H-benzo[c]azepin-4-ol, L-tartrate salt and cis-2-methyl-5-phenyl-2,3,4,5-tetrahydro-1H-benzo[c]azepin-4-ol, L-tartrate salt, diastereomers A and B Step A: To a mixture of N-methylbenzylamine (20.2 g, 167 mmol), 3,3-dimethoxypropanoic acid (22.4 g, 167 mmol) in methylene chloride (200 mL) was added 1-(3-dimethylaminopropyl)-3-ethylcarbodiimide hydrochloride (32.6 g, 170 mmol) at 0° C. The mixture was stirred at room temperature overnight, and then washed with water (150 mL), 1 N HCl (100 mL) and saturated NaHCO$_3$ (60 mL). The resulting solution was dried over Na$_2$SO$_4$, filtered and concentrated in vacuo to give the acetal (36.7 g, 93%) as a brown oil: $^1$H NMR (300 MHz, CDCl$_3$) δ 7.36-7.16 (m, 5H), 4.94-4.66 (m, 1H), 4.59 (d, J=12.0 Hz, 2H), 3.44 (s, 3H), 3.40 (s, 3H), 2.95 (s, 3H), 2.75-2.70 (m, 2H).

Step B: To a suspension of aluminum chloride (42.7 g, 320 mmol) in methylene chloride (700 mL) was added a solution of the acetal (19.0 g, 80 mmol) from step A above in methylene chloride (100 mL) dropwise. After the addition was completed, the mixture was stirred at room temperature for 3 hours and then poured into ice-water (1 L) carefully. The two phases were separated and the methylene chloride phase was washed with saturated NaHCO$_3$, dried over Na$_2$SO$_4$, filtered and concentrated in vacuo. The residue was triturated with diethyl ether. After filtration, the unsaturated lactam (3.20 g) was obtained as an off-white solid. The mother liquid was concentrated and the residue was purified by column chromatography (1:1 to 1:2 hexanes/ethyl acetate) to yield another crop of the product (3.70 g). The combined yield was 50%: $^1$H NMR (500 MHz, CDCl$_3$) δ 7.38-7.15 (m, 4H), 7.08 (d, J=12.0 Hz, 1H), 6.41(d, J=12.0 Hz, 1H), 4.24 (s, 2H), 3.11 (s, 3H).

Step C: To a suspension of copper(I) iodide (4.13 g, 21.7 mmol) in THF (70 mL) at −30 to −40° C. was added 1.8 M PhLi in di-n-butyl ether (24.0 mL, 43.2 mmol) dropwise. The mixture was stirred at that temperature for 1 hour before a solution of the unsaturated lactam (1.88 g, 10.9 mmol) from step B above in THF (20 mL) was added dropwise followed by iodotrimethylsilane (2.3 mL, 16.3 mmol). The resulting mixture was allowed to warm slowly to room temperature and stirred overnight. Triethylamine (5 mL) followed by saturated ammonium chloride (10 mL) was added to quench the reaction at −78° C. The mixture was partitioned between methylene chloride and water. The aqueous phase was extracted with methylene chloride three times. The combined extracts were dried over Na$_2$SO$_4$, filtered and concentrated in vacuo. The residue was purified by column chromatography (2:1 to 1:1 hexanes/ethyl acetate) to yield the lactam (2.31 g, 85%) as an off-white solid: $^1$H NMR (500 MHz, CDCl$_3$) δ 7.47-7.08 (m, 8H), 6.96 (d, J=7.0 Hz, 1H), 5.05 (d, J=16 Hz, 1H), 4.52 (dd, J=11.0, 5.0 Hz, 1H), 4.17 (d, J=16.0 Hz, 1H), 3.28 (dd, J=14.0, 11.0 Hz, 1H), 3.05 (s, 3H), 2.98 (dd, J=14.0, 5.0 Hz, 1H).

Step D: To a solution of lithium hexamethyldisilazane (8.6 mL, 8.6 mmol, 1.0 M in THF) in THF (8 mL) at −78° C. under N$_2$ was added dropwise a solution of the lactam (0.72 g, 2.87 mmol) from Step C above in THF (30 mL). The resulting mixture was stirred and allowed to warm up to 0° C. The mixture was stirred at 0° C. for 10 minutes and re-cooled to −78° C. Oxodiperoxymolybdenum-pyridine-hexamethylphosphoric triamide (2.49 g, 5.74 mmol) was added in one portion. The resulting mixture was stirred at −55° C. for 1 hour and allowed to warm to room temperature overnight. The mixture was cooled at −78° C. and quenched with saturated ammonium chloride (5 mL). The mixture was partitioned between ethyl acetate (60 mL) and water (40 mL). After separation, the aqueous phase was acidified to pH 4 with 3 N HCl and extracted with methylene chloride (2×100 mL). The combined organic phases were dried over Na$_2$SO$_4$, filtered and concentrated in vacuo. The residue was purified by column chromatography (1:1 hexanes/ethyl acetate) to yield the hydroxylactam (286 mg, 37%) as an off-white solid: $^1$H NMR (500 MHz, CDCl$_3$) δ 7.35-7.10 (m, 8H), 6.96 (d, J=7.0 Hz, 1H), 5.22 (d, J=16.0 Hz, 1H), 5.06 (dd, J=10.0, 5.0 Hz, 1H), 4.26 (d, J=5.0 Hz, 1H), 4.08 (d, J=10.0 Hz, 1H), 3.83 (d, J=16.0 Hz, 1H), 3.10 (s, 3H); ESI MS m/z 268 [M+H]$^+$.

Step E: To a mixture of the hydroxylactam (369 mg, 1.38 mmol) from step D above in THF (10 mL) at room temperature was added dropwise 2.0 M borane-dimethylsulfide in THF (2.1 mL, 4.2 mmol). The mixture was refluxed for 2 hours. After cooling, the mixture was concentrated in vacuo. To the residue was added tetramethylenediamine (1.5 mL, 9.66 mmol) and methanol (10 mL). The mixture was refluxed for 2 hours. After cooling, the mixture was concentrated in vacuo. The residue was purified by column chromatography (20:1 methylene chloride/methanol) to yield the hydroxybenzazepine (350 mg, 98%, trans-isomer based on NOESY spectrum) as a white solid: $^1$H NMR (500 MHz, CDCl$_3$) δ 7.35-7.10 (m, 8H), 6.96 (d, J=7.0 Hz, 1H), 4.59 (d, J=6.0 Hz, 1H), 4.40 (br, 1H), 3.70 (br, 1H), 3.67 (d, J=15.6 Hz, 1H), 3.61 (d, J=13.0 Hz, 1H), 2.87-2.85 (m, 1H), 2.70 (d, J=7.0 Hz, 1H), 2.42 (s, 3H); ESI MS m/z 254 [M+H]$^+$.

Step F: To a solution of dimethyl sulfoxide (0.14 g, 1.8 mmol) in methylene chloride (3 mL) at −78° C. was added dropwise trifluoroacetic anhydride (0.21 g, 1.0 mmol). The mixture was stirred at that temperature for 30 minutes before a solution of the hydroxybenzazepine (0.13 g, 0.51 mmol) from step E above was added. The resulting mixture was stirred at −78° C. for 15 minutes. Triethylamine (0.20 g, 2.0 mmol) was added and the mixture was stirred at −78° C. for 4 hours. Water (1 mL) was added to quench the reaction and the resulting mixture was stirred and warmed to room temperature. The mixture was partitioned between methylene chloride (20 mL) and saturated sodium bicarbonate (20 mL). The aqueous phase was extracted with methylene chloride (10 mL). The combined extracts were dried over Na$_2$SO$_4$, filtered and concentrated in vacuo to give the ketone as a white solid (0.13 g). The crude residue was used directly in the next reaction.

Step G: To a solution of the ketone (0.13 g, 0.51 mmol) from step F above in methanol (10 mL) was added sodium borohydride (76 mg, 2.0 mmol). The mixture was stirred at room temperature for 4 hours. Most solvents were evaporated in vacuo and the residue was partitioned between methylene chloride (20 mL) and water (10 mL). The aqueous phase was extracted with methylene chloride (10 mL). The combined extracts were dried over Na$_2$SO$_4$, filtered and concentrated in vacuo. The residue was purified by column chromatography (20:1 to 10:1 methylene chloride/methanol) to yield the cis-hydroxybenzazepine (72 mg, 56% two steps) as a white solid: $^1$H NMR (CD$_3$OD, 500 MHz) δ 7.52-7.08 (m, 8H), 6.54 (d, J=7.7 Hz, 1H), 4.42 (s, 1H), 4.32 (br, 1H), 3.80 (d, J=13.8 Hz, 1H), 3.64 (d, J=13.8 Hz, 1H), 3.24-3.22 (m, 1H), 2.82 (d, J=12.3 Hz, 1H), 2.54 (s, 3H); ESI MS m/z 254 [M+H]$^+$.

Step H: The free base of the cis-hydroxybenzazepine from Step G above (0.50 mg) was resolved by preparative chiral HPLC (CHIRALCEL OD column, using 97:3:0.1 heptane/1-propanol/diethylamine as the eluent) to give diastereomer A [[α]$^{25}_D$+19.2° (c 0.12, methanol)] and diastereomer B [[α]$^{25}_D$−17.9° (c 0.14, methanol)].

Step I: To a solution of the diastereomer A (6.0 mg, 0.024 mmol) from step H above in methanol (1 mL) was added L-tartaric acid (3.6 mg, 0.024 mmol). After the mixture was stirred at room temperature for 10 minutes, water (10 mL) was added. The resultant solution was lyophilized overnight to give cis-2-methyl-5-phenyl-2,3,4,5-tetrahydro-1H-benzo[c]azepin-4-ol, L-tartrate salt, diastereomer A (7.6 mg, 79%, AUC HPLC >99%) as an white solid: $^1$H NMR (CD$_3$OD, 500 MHz) δ 7.50-7.24 (m, 8H), 6.69 (br, 1H), 4.72 (s, 1H), 4.52 (s, 1H), 4.42 (s, 2H), 4.34 (d, J=13.6 Hz, 1H), 3.70 (d, J=12.4 Hz, 1H), 3.37 (d, J=10.8 Hz, 1H), 2.98 (s, 3H); ESI MS m/z 254 [M+H]$^+$.

Step J: To a solution of the diastereomer B (7.0 mg, 0.028 mmol) from step H above in methanol (1 mL) was added L-tartaric acid (4.1 mg, 0.028 mmol). After the mixture was stirred at room temperature for 10 minutes, water (10 mL) was added. The resultant solution was lyophilized overnight to give cis-2-methyl-5-phenyl-2,3,4,5-tetrahydro-1H-benzo[c]azepin-4-ol, L-tartrate salt, diastereomer B (7.6 mg, 68%, AUC HPLC 96%) as an white solid: $^1$H NMR (CD$_3$OD, 500 MHz) δ 7.50-7.24 (m, 8H), 6.69 (br, 1H), 4.72 (s, 1H), 4.52 (s, 1H), 4.42 (s, 2H), 4.34 (d, J=13.6 Hz, 1H), 3.70 (d, J=12.4 Hz, 1H), 3.37 (d, J=10.8 Hz, 1H), 2.98 (s, 3H); ESI MS m/z 254 [M+H]$^+$.

Example 97

Preparation of trans-4-fluoro-2-methyl-5-phenyl-2,3,4,5-tetrahydro-1H-benzo[c]azepine, L-tartrate salt and trans-4-fluoro-2-methyl-5-phenyl-2,3,4,5-tetrahydro-1H-benzo[c]azepine, L-tartrate salt, diastereomers A and B Step A: To a mixture of N-methylbenzylamine (20.2 g, 167 mmol), 3,3-dimethoxypropanoic acid (22.4 g, 167 mmol) in methylene chloride (200 mL) was added 1-(3-dimethylaminopropyl)-3-ethylcarbodiimide hydrochloride (32.6 g, 170 mmol) at 0° C. The mixture was stirred at room temperature overnight, and then washed with water (150 mL), 1N HCl (100 mL) and saturated NaHCO$_3$ (60 mL). The resulting solution was dried over Na$_2$SO$_4$, filtered and concentrated in vacuo to give the acetal (36.7 g, 93%) as a brown oil: $^1$H NMR (300 MHz, CDCl$_3$) δ 7.36-7.16 (m, 5H), 4.94-4.66 (m, 1H), 4.59 (d, J=12.0 Hz, 2H), 3.44 (s, 3H), 3.40 (s, 3H), 2.95 (s, 3H), 2.75-2.70 (m, 2H).

Step B: To a suspension of aluminum chloride (42.7 g, 320 mmol) in methylene chloride (700 mL) was added a solution of the acetal (18.98 g, 80 mmol) from step A above in methylene chloride (100 mL) dropwise. After the addition was completed, the mixture was stirred at room temperature for 3 hours and then poured into ice-water (1 L) carefully. The two phases were separated and the methylene chloride phase was washed with saturated NaHCO$_3$, dried over Na$_2$SO$_4$, filtered and concentrated in vacuo. The residue was triturated with diethyl ether. After filtration, the unsaturated lactam (3.20 g) was obtained as an off-white solid. The mother liquid was concentrated and the residue was purified by column chromatography (1:1 to 1:2 hexanes/ethyl acetate) to yield another crop of the product (3.70 g). The combined yield was 50%: $^1$H NMR (500 MHz, CDCl$_3$) δ 7.38-7.15 (m, 4H), 7.08 (d, J=12.0 Hz, 1H), 6.41(d, J=12.0 Hz, 1H), 4.24 (s, 2H), 3.11 (s, 3H).

Step C: To a suspension of copper(I) iodide (4.13 g, 21.7 mmol) in THF (70 mL) at −30 to −40° C. was added 1.8 M PhLi in di-n-butyl ether (24.0 mL, 43.2 mmol) dropwise. The mixture was stirred at that temperature for 1 hour before a solution of the unsaturated lactam (1.88 g, 10.9 mmol) from step B above in THF (20 mL) was added dropwise followed by iodotrimethylsilane (2.3 mL, 16.3 mmol). The resulting mixture was allowed to warm slowly to room temperature and stirred overnight. Triethylamine (5 mL) followed by saturated ammonium chloride (10 mL) was added to quench the reaction at −78° C. The mixture was partitioned between methylene chloride and water. The aqueous phase was extracted with methylene chloride three times. The combined extracts were dried over Na$_2$SO$_4$, filtered and concentrated in vacuo. The residue was purified by column chromatography (2:1 to 1:1 hexanes/ethyl acetate) to yield the lactam (2.31 g, 85%) as an off-white solid: $^1$H NMR (500 MHz, CDCl$_3$) δ 7.47-7.08 (m, 8H), 6.96 (d, J=7.0 Hz, 1H), 5.05 (d, J=16 Hz, 1H), 4.52 (dd, J=11.0, 5.0 Hz, 1H), 4.17 (d, J=16.0 Hz, 1H), 3.28 (dd, J=14.0, 11.0 Hz, 1H), 3.05 (s, 3H), 2.98 (dd, J=14.0, 5.0 Hz, 1H).

Step D: To a solution of lithium hexamethyldisilazane (3.0 mL, 3.0 mmol, 1.0 M in THF) in THF (9.0 mL) at −78° C. under N$_2$ was added dropwise a solution of the lactam (0.50 g, 2.0 mmol) from Step C above in THF (13 mL). The resulting mixture was stirred and allowed to warm to room temperature. The mixture was stirred at room temperature for 10 minutes and recooled to −78° C. A solution of N-fluorobenzenesulfonimide (0.95 g, 3.0 mmol) in THF (3 mL) was added dropwise. The mixture was stirred and allowed to warm to room temperature overnight. The reaction was quenched by saturated ammonium chloride and the mixture was extracted with methylene chloride (3×20 mL). The residue was purified by column chromatography (2:1 hexanes/ethyl acetate) to yield the fluorolactam (0.36 g, 66%) as a white solid: $^1$H NMR (500 MHz, CDCl$_3$) δ 7.32-7.13 (m, 8H), 6.99 (d, J=7.0 Hz, 1H), 5.78 (dd, J=48.2, 10.1 Hz, 1H), 5.00 (d, J=16.3 Hz, 1H), 4.53 (dd, J=20.2, 10.1 Hz, 1H), 3.99 (d, J=16.3 Hz, 1H), 3.05 (s, 3H); ESI MS m/z 270 [M+H]$^+$.

Step E: To a mixture of the fluorolactam (0.15 g, 0.56 mmol) from Step D above in THF (4 mL) at room temperature was added a 2 M borane dimethylsulfide in THF (1.2 mL, 2.4 mmol). The mixture was stirred at 80° C. for 2 hours. Volatiles were evaporated in vacuo. The residue was treated with 6 N HCl (3 mL) and dioxane (3 mL). The mixture was stirred at 80° C. for 1 hour. After cooling, the mixture was treated with saturated NaHCO$_3$ and 2 N NaOH to bring the pH to 9. The mixture was extracted with methylene chloride (3×20 mL). The combined extracts were dried over Na$_2$SO$_4$, filtered and concentrated in vacuo. The residue was purified by column chromatography (10:1 methylene chloride/methanol) to yield the fluorobenzazepine (0.11 g, 76%, trans-isomer based on NOESY spectrum) as a colorless oil: $^1$H NMR (500 MHz, CDCl$_3$) δ 7.37-7.16 (m, 8H), 6.91 (d, J=7.2 Hz, 1H), 5.28-5.09 (m, 1H), 4.67 (t, J=7.8 Hz, 1H), 3.88 (d, J=14.4 Hz, 1H), 3.79 (d, J=14.3 Hz, 1H), 3.20-3.07 (m, 2H), 2.43 (s, 3H); ESI MS m/z 256 [M+H]$^+$.

Step F: The free base of the fluorobenzazepine (0.10 g) from Step E above was resolved by preparative chiral HPLC (CHIRALCEL OJ column, using 80:20:0.1 heptane/EtOH/diethylamine as the eluent) to give diastereomer A [[α]$^{25}_D$+38.4° (c 0.042, methanol)] and diastereomer B [[α]$^{25}_D$−30.0° (c 0.083, methanol)].

Step G: To a solution of the diastereomer B (37 mg, 0.15 mmol) from Step F above in methanol (1 mL) was added L-tartaric acid (43 mg, 0.21 mmol). After the mixture was stirred at room temperature for 10 minutes, water (20 mL) was added. The resultant solution was lyophilized overnight to give trans-4-fluoro-2-methyl-5-phenyl-2,3,4,5-tetrahydro-1H-benzo[c]azepine, L-tartrate salt, diastereomer B (52 mg, 85%, AUC HPLC 94.6%) as an white solid: $^1$H NMR (CD$_3$OD, 500 MHz) δ 7.44-7.13 (m, 9H), 5.60 (d, J=41 Hz, 1H), 4.94-4.89 (m, 1H), 4.43 (s, 2H), 4.25 (d, J=14.2 Hz, 1H), 4.19 (d, J=14.2 Hz, 1H), 3.60-3.55 (m, 1H), 3.39-3.30 (m, 1H), 2.76 (s, 3H); ESI MS m/z 256 [M+H]$^+$.

Step H: To a solution of the diastereomer A (28 mg, 0.11 mmol) from Step F above in methanol (1 mL) was added L-tartaric acid (17 mg, 0.11 mmol). After the mixture was stirred at room temperature for 10 minutes, water (20 mL) was added. The resultant solution was lyophilized overnight to give trans-4-fluoro-2-methyl-5-phenyl-2,3,4,5-tetrahydro-1H-benzo[c]azepine, tartrate salt, diastereomer A (42 mg, 93%, AUC HPLC 96.2%) as an white solid: $^1$H NMR (CD$_3$OD, 500 MHz) δ 7.44-7.13 (m, 9H), 5.60 (d, J=41 Hz, 1H), 4.94-4.89 (m, 1H), 4.43 (s, 2H), 4.25 (d, J=14.2 Hz, 1H), 4.19 (d, J=14.2 Hz, 1H), 3.60-3.55 (m, 1H), 3.39-3.30 (m, 1H), 2.76 (s, 3H); ESI MS m/z 256 [M+H]$^+$.

Example 98

Preparation of trans-2,4-dimethyl-5-phenyl-2,3,4,5-tetrahydro-1H-benzo[c]azepine, L-tartrate salt and trans-2,4-dimethyl-5-phenyl-2,3,4,5-tetrahydro-1H-benzo[c]azepine, L-tartrate salt, diastereomers A and B Step A: To a mixture of N-methylbenzylamine (20.2 g, 167 mmol), 3,3-dimethoxypropanoic acid (22.4 g, 167 mmol) in methylene chloride (200 mL) was added 1-(3-dimethylaminopropyl)-3-ethylcarbodiimide hydrochloride (32.6 g, 170 mmol) at 0° C. The mixture was stirred at room temperature overnight, and then washed with water (150 mL), 1 N HCl (100 mL), and saturated NaHCO$_3$ (60 mL). The resulting solution was dried over Na$_2$SO$_4$, filtered and concentrated in vacuo to give the acetal (36.7 g, 93%) as a brown oil: $^1$H NMR (300 MHz, CDCl$_3$) δ 7.36-7.16 (m, 5H), 4.94-4.66 (m, 1H), 4.59 (d, J=12.0 Hz, 2H), 3.44 (s, 3H), 3.40 (s, 3H), 2.95 (s, 3H), 2.75-2.70 (m, 2H).

Step B: To a suspension of aluminum chloride (42.7 g, 320 mmol) in methylene chloride (700 mL) was added a solution of the acetal (19.0 g, 80 mmol) from step A above in methylene chloride (100 mL) dropwise. After the addition was completed, the mixture was stirred at room temperature for 3 h and then poured into ice-water (1 L) carefully. The two phases were separated and the methylene chloride phase was washed with saturated NaHCO$_3$, dried over Na$_2$SO$_4$, filtered and concentrated in vacuo. The residue was triturated with diethyl ether. After filtration, the unsaturated lactam (3.20 g) was obtained as an off-white solid. The mother liquid was concentrated and the residue was purified by column chromatography (1:1 to 1:2 hexanes/ethyl acetate) to yield another crop of the product (3.70 g). The combined yield was 50%: $^1$H NMR (500 MHz, CDCl$_3$) δ 7.38-7.15 (m, 4H), 7.08 (d, J=12.0 Hz, 1H), 6.41(d, J=12.0 Hz, 1H), 4.24 (s, 2H), 3.11 (s, 3H).

Step C: To a suspension of copper(I) iodide (4.13 g, 21.7 mmol) in THF (70 mL) at −30 to −40° C. was added 1.8 M PhLi in di-n-butyl ether (24.0 mL, 43.2 mmol) dropwise. The mixture was stirred at that temperature for 1 hour before a solution of the unsaturated lactam (1.88 g, 10.9 mmol) from step B above in THF (20 mL) was added dropwise followed by iodotrimethylsilane (2.3 mL, 16.3 mmol). The resulting mixture was allowed to warm slowly to room temperature and stirred overnight. Triethylamine (5 mL) followed by saturated ammonium chloride (10 mL) was added to quench the reaction at −78° C. The mixture was partitioned between methylene chloride and water. The aqueous phase was extracted with methylene chloride three times. The combined extracts were dried over Na$_2$SO$_4$, filtered and concentrated in vacuo. The residue was purified by column chromatography (2:1 to 1:1 hexanes/ethyl acetate) to yield the lactam (2.31 g, 85%) as an off-white solid: $^1$H NMR (500 MHz, CDCl$_3$) δ 7.47-7.08 (m, 8H), 6.96 (d, J=7.0 Hz, 1H), 5.05 (d, J=16 Hz, 1H), 4.52 (dd, J=11.0, 5.0 Hz, 1H), 4.17 (d, J=16.0 Hz, 1H), 3.28 (dd, J=14.0, 11.0 Hz, 1H), 3.05 (s, 3H), 2.98 (dd, J=14.0, 5.0 Hz, 1H).

Step D: To a stirred solution of diisopropylamine (0.42 mL, 3.0 mmol) in THF (12 mL) at −78° C. was added dropwise 2.5 M n-butyllithium (1.2 mL, 3.0 mmol). The resulting mixture was stirred at 0° C. for 10 min and then cooled to −78° C. for another 30 minutes. A suspension of the lactam (502 mg, 2.0 mmol) from Step C above in THF (20 mL) was added dropwise. After the mixture was stirred at −55° C. for 2 hours, iodomethane (0.19 mL, 3.0 mmol) was added. The resulting mixture was stirred from −55° C. to room temperature overnight. The mixture was cooled at −78° C. and quenched with saturated ammonium chloride (5 mL). The mixture was diluted with ethyl acetate (50 mL) and washed with brine (20 mL). The ethyl acetate phase was dried over Na$_2$SO$_4$ and concentrated in vacuo. The residue was purified by column chromatography (2:1 to 1:1 hexanes/ethyl acetate) to yield the methyllactam (214 mg, 40%) as colorless oil: $^1$H NMR (500 MHz, CDCl$_3$) δ 7.29-7.04 (m, 8H), 6.92 (d, J=7.8 Hz, 1H), 5.54 (d, J=15.9 Hz, 1H), 3.90 (d, J=11.9 Hz, 1H), 3.82 (d, J=16.0 Hz, 1H), 3.62-3.60 (m, 1H), 3.01 (s, 3H), 1.05 (d, J=6.4 Hz, 3H).

Step E: To a mixture of the lactam (0.27 g, 1.0 mmol) from step D above in THF (8 mL) at room temperature was added a 2M solution borane-dimethylsulfide in THF (1 mL, 2.0 mmol). The mixture was stirred at 50° C. for 2 hours. Volatiles were evaporated in vacuo. The residue was treated with 6 N HCl (3 mL) and dioxane (3 mL). The mixture was stirred at 70° C. for 1 hour. After cooling, the mixture was treated with saturated NaHCO$_3$ and 2 N NaOH to bring the pH to 9. The mixture was extracted with methylene chloride (3×30 mL). The combined extracts were dried over Na$_2$SO$_4$, filtered and concentrated in vacuo. The residue was purified by column chromatography (20:1 to 10:1 methylene chloride/methanol) to yield the methylbenzazepine (0.18 g, 72%) as a colorless oil: $^1$H NMR (500 MHz, CDCl$_3$) δ 7.31-7.10 (m, 8H), 6.99 (d, J=7.0 Hz, 1H), 4.02 (d, J=6.5 Hz, 1H), 3.75 (d, J=13.3 Hz, 1H), 3.61 (d, J=14.0 Hz, 1H), 2.73 (d, J=10.5 Hz, 1H), 2.60-2.58 (m, 2H), 2.32 (s, 3H), 1.00 (d, J=6.5 Hz, 3H).

Step F: The free base of the methylbenzazepine (0.18 g) from step E above was resolved by preparative chiral HPLC (CHIRALCEL OJ column, using 90:10:0.1 heptane/2-propanol/diethylamine as the eluent) to give diastereomer A [[α]$^{25}_D$+70.3° (c 0.117, methanol)] and diastereomer B [[α]$^{25}_D$ −94.8° (c 0.083, methanol)].

Step G: To a solution of the diastereomer A (80 mg, 0.32 mmol) from step F in methanol (1 mL) was added L-tartaric acid (48 mg, 0.32 mmol). After the mixture was stirred at room temperature for 10 minutes, water (20 mL) was added. The resultant solution was lyophilized overnight to give trans-2,4-dimethyl-5-phenyl-2,3,4,5-tetrahydro-1H-benzo [c]azepine, L-tartrate salt, diastereomer A (72 mg, 81%, AUC HPLC 96.1%) as an white solid: $^1$H NMR (CD$_3$OD, 500 MHz) δ 7.40-7.17 (m, 9H), 4.56 (br, 1H), 4.40 (s, 2H), 4.30 (d, J=12.0 Hz, 1H), 4.16 (d, J=7.4 Hz, 1H), 3.35-3.33 (m, 1H), 3.16 (br, 1H), 2.84 (br, 1H), 2.84 (s, 3H), 1.11 (d, J=6.9 Hz, 3H); ESI MS m/z 252[M+H]+.

Step H: To a solution of the diastereomer B (76 mg, 0.30 mmol) from step F in methanol (1 mL) was added L-tartaric acid (43 mg, 0.21 mmol). After the mixture was stirred at room temperature for 10 minutes, water (20 mL) was added. The resultant solution was lyophilized overnight to give trans-2,4-dimethyl-5-phenyl-2,3,4,5-tetrahydro-1H-benzo[c]azepine, L-tartrate salt, diastereomer B (115 mg, 85%, AUC HPLC >99%) as an white solid: $^1$H NMR (CD$_3$OD, 500 MHz) δ 7.40-7.17 (m, 9H), 4.56 (br, 1H), 4.40 (s, 2H), 4.30 (d, J=12.0 Hz, 1H), 4.16 (d, J=7.4 Hz, 1H), 3.35-3.33 (m, 1H), 3.16 (br, 1H), 2.84 (br, 1H), 2.84 (s, 3H), 1.11 (d, J=6.9 Hz, 3H); ESI MS m/z 252[M+H]+.

Example 99

Preparation of (+)-2-methyl-5-phenyl-2,3,4,5-tetrahydro-1H-benzo[c]azepine, L-tartrate salt and (−)-2-methyl-5-phenyl-2,3,4,5-tetrahydro-1H-benzo[c]azepine, L-tartrate salt Step A: To a mixture of N-methylbenzylamine (20.2 g, 167 mmol), 3,3-dimethoxypropanoic acid (22.4 g, 167 mmol) in methylene chloride (200 mL) was added 1-(3-dimethylaminopropyl)-3-ethylcarbodiimide hydrochloride (32.6 g, 170 mmol) at 0° C. The mixture was stirred at room temperature overnight, and then washed with water (150 mL), 1N HCl (100 mL), and saturated NaHCO$_3$ (60 mL). The resulting solution was dried over Na$_2$SO$_4$, filtered and concentrated in vacuo to give the acetal (36.7 g, 93%) as a brown oil: $^1$H NMR (300 MHz, CDCl$_3$) δ 7.36-7.16 (m, 5H), 4.94-4.66 (m, 1H), 4.59 (d, J=12.0 Hz, 2H), 3.44 (s, 3H), 3.40 (s, 3H), 2.95 (s, 3H), 2.75-2.70 (m, 2H).

Step B: To a suspension of aluminum chloride (42.7 g, 320 mmol) in methylene chloride (700 mL) was added a solution of the acetal (19.0 g, 80 mmol) from step A above in methylene chloride (100 mL) dropwise. After the addition was completed, the mixture was stirred at room temperature for 3 hours and then poured into ice-water (1 L) carefully. The two phases were separated and the methylene chloride phase was washed with saturated NaHCO$_3$, dried over Na$_2$SO$_4$, filtered and concentrated in vacuo. The residue was triturated with diethyl ether. After filtration, the unsaturated lactam (3.20 g) was obtained as an off-white solid. The mother liquid was concentrated and the residue was purified by column chromatography (1:1 to 1:2 hexanes/ethyl acetate) to yield another crop of the product (3.70 g). The combined yield was 50%: $^1$H NMR (500 MHz, CDCl$_3$) δ 7.38-7.15 (m, 4H), 7.08 (d, J=12.0 Hz, 1H), 6.41 (d, J=12.0 Hz, 1H), 4.24 (s, 2H), 3.11 (s, 3H).

Step C: To a suspension of copper(I) iodide (4.13 g, 21.7 mmol) in THF (70 mL) at −30 to −40° C. was added 1.8 M PhLi in di-n-butyl ether (24.0 mL, 43.2 mmol) dropwise. The mixture was stirred at that temperature for 1 hour before a solution of the unsaturated lactam (1.88 g, 10.9 mmol) from step B above in THF (20 mL) was added dropwise followed by iodotrimethylsilane (2.3 mL, 16.3 mmol). The resulting mixture was allowed to warm slowly to room temperature and stirred overnight. Triethylamine (5 mL) followed by saturated ammonium chloride (10 mL) was added to quench the reaction at −78° C. The mixture was partitioned between methylene chloride and water. The aqueous phase was extracted with methylene chloride three times. The combined extracts were dried over Na$_2$SO$_4$, filtered and concentrated in vacuo. The residue was purified by column chromatography (2:1 to 1:1 hexanes/ethyl acetate) to yield the lactam (2.31 g, 85%) as an off-white solid: $^1$H NMR (500 MHz, CDCl$_3$) δ 7.47-7.08 (m, 8H), 6.96 (d, J=7.0 Hz, 1H), 5.05 (d, J=16 Hz, 1H), 4.52 (dd, J=11.0, 5.0 Hz, 1H), 4.17 (d, J=16.0 Hz, 1H), 3.28 (dd, J=14.0, 11.0 Hz, 1H), 3.05 (s, 3H), 2.98 (dd, J=14.0, 5.0 Hz, 1H).

Step D: To a suspension of the lactam (0.35 g, 1.4 mmol) from step C above in either at room temperature was added lithium aluminum hydride (52 mg, 1.4 mmol). The mixture was stirred at room temperature for 1 hour. Water (0.1 mL), 2 N NaOH (0.3 mL) and water (0.1 mL) were added successively. The mixture was filtered through a Celite pad and the filtrate was concentrated in vacuo. The residue was mainly the enamine intermediate based on the proton NMR spectrum. The residue was dissolved in a mixture of THF (12 mL) and methanol (3 mL). 1.0 M HCl in dioxane (4N, 0.4 mL) was added followed by the addition of sodium cyanoborohydride (86 mg, 1.4 mmol). The resulting mixture was stirred at room temperature for 30 minutes and then basified with 2 N NaOH. The mixture was extracted with methylene chloride (2×20 mL). The combined organic phases were dried over Na$_2$SO$_4$, filtered and concentrated in vacuo. The residue was purified by column chromatography (1:1 methylene chloride/methanol) to yield the benzazepine (100 mg, 31%) as an off-white solid: $^1$H NMR (500 MHz, CDCl$_3$) δ 7.37-7.06 (m, 8H), 6.80 (br, 1H), 4.33 (d, J=9.3 Hz, 1H), 3.90 (br, 1H), 3.74 (d, J=14.1 Hz, 1H), 3.12 (br, 1H), 2.99-2.93 (m, 1H), 2.36 (s, 3H), 2.36-2.34 (m, 1H), 2.15-2.09 (m, 1H); ESI MS m/z 238 [M+H]+.

Step E: The free base of the benzazepine (0.10 g) from Step D above was resolved by preparative chiral HPLC (CHIRALCEL OJ column, using 80:20:0.1 heptane/ethanol/diethylamine as the eluent) to give the (+)-enantiomer [[α]$^{25}_D$+13.3° (c 0.075, methanol)] and the (−)-enantiomer [[α]$^{25}_D$−7.5° (c 0.067, methanol)].

Step F: To a solution of the (+)-enantiomer (26 mg, 0.11 mmol) from Step E above in methanol (1 mL) was added L-tartaric acid (16 mg, 0.11 mmol). After the mixture was stirred at room temperature for 10 minutes, water (20 mL) was added. The resultant solution was lyophilized overnight to give (+)-2-methyl-5-phenyl-2,3,4,5-tetrahydro-1H-benzo[c]azepine, L-tartrate salt (38 mg, 89%, AUC HPLC >99%) as an white solid: $^1$H NMR (CD$_3$OD, 500 MHz) δ 7.44-7.19 (m, 8H), 6.86 (br, 1H), 4.59 (br, 2H), 4.39 (s, 2H), 4.32 (d, J=14.0 Hz, 1H), 3.56 (br, 2H), 2.83 (s, 3H), 2.58 (br, 1H), 2.41-2.39 (m, 1H); ESI MS m/z 238 [M+H]+.

Step G: To a solution of the (−)-enantiomer (25 mg, 0.11 mmol) from Step E above in methanol (1 mL) was added L-tartaric acid (16 mg, 0.11 mmol). After the mixture was stirred at room temperature for 10 minutes, water (20 mL) was added. The resultant solution was lyophilized overnight to give (−)-2-methyl-5-phenyl-2,3,4,5-tetrahydro-1H-benzo[c]azepine, L-tartrate salt (39 mg, 89%, AUC HPLC >99%) as an white solid: $^1$H NMR (CD$_3$OD, 500 MHz) δ 7.44-7.19 (m, 8H), 6.86 (br, 1H), 4.59 (br, 2H), 4.39 (s, 2H), 4.32 (d, J=14.0 Hz, 1H), 3.56 (br, 2H), 2.83 (s, 3H), 2.58 (br, 1H), 2.41-2.39 (m, 1H); ESI MS m/z 238 [M+H]+.

Example 100

Preparation of (+/−)-5-(3,4-difluorophenyl)-2-methyl-2,3,4,5-tetrahydro-1H-benzo[c]azepine, fumarate salt Pursuant to the general method described above in Example 99, the following product was prepared: (+/−)-5-(3,4-difluorophenyl)-2-methyl-2,3,4,5-tetrahydro-1H-benzo[c]azepine, fumarate salt: $^1$H NMR (CD$_3$OD, 500 MHz) δ 7.47 (d, J=1.6 Hz, 1H), 7.36-7.29 (m, 3H), 7.14 (t, J=8.8 Hz, 1H), 7.00 (s, 1H), 6.90 (br, 1H), 6.24 (s, 2H), 4.62 (d, J=9.9 Hz, 1H), 4.36 (d, J=14.0 Hz, 1H), 3.64-3.56 (m, 2H), 2.91 (s, 3H), 2.57 (br, 1H), 2.43-2.40 (m, 1H); ESI MS m/z 274 [M+H]$^+$.

Example 101

Preparation of 4-(2-methyl-8-(6-methylpyridazin-3-yl)-2,3,4,5-tetrahydro-1H-benzo[c]azepin-5-yl)benzonitrile, L-tartrate salt and 4-(2-methyl-8-(6-methylpyridazin-3-yl)-2,3,4,5-tetrahydro-1H-benzo[c]azepin-5-yl)benzonitrile, L-tartrate salt (enantiomers 1 and 2)

Step A: To a mixture of 1-(3-methoxyphenyl)-N-methylmethanamine (25.6 g, 169 mmol), 3,3-dimethoxypropanoic acid (22.5 g, 168 mmol) and methylene chloride (200 mL) was added 1-(3-dimethylaminopropyl)-3-ethylcarbodiimide hydrochloride (32.9 g, 171 mmol) at 0° C. The mixture was stirred at room temperature overnight, and then washed with water (150 mL), 1 N hydrochloric acid (100 mL) and saturated sodium bicarbonate (60 mL). The resulting solution was dried over sodium sulfate, filtered and concentrated in vacuo to give the acetal (44.9 g, 99%) as a brown oil. The crude product was used directly in the next reaction.

Step B: The acetal (44.9 g, 168 mmol) from step A above was treated with pre-cooled concentrated hydrochloric acid (200 mL) at 0° C. The mixture was stirred at 0° C. for 2 hours. The reaction was quenched with 2 N NaOH (the pH was adjusted to 7). The mixture was extracted with methylene chloride (2×500 mL). The combined extracts were dried over sodium sulfate, filtered and concentrated in vacuo. The residue was recrystallized with hexanes/ethyl acetate followed by another recrystallization to yield the lactam (12.1 g) as a colorless solid. Another crop of the lactam (6.80 g) was obtained from the mother liquid by column chromatography (1:1 hexanes/ethyl acetate). The combined yield was 55%: $^1$H NMR (500 MHz, CDCl$_3$) δ 7.30 (d, J=8.0 Hz, 1H), 7.01 (d, J=12.1 Hz, 1H), 6.90 (dd, J=8.3, 2.6 Hz, 1H), 6.82 (d, J=2.6 Hz, 1H), 6.29 (d, J=12.1 Hz, 1H), 4.19 (s, 2H), 3.86 (s, 3H), 3.10 (s, 3H); ESI MS m/z 204 [M+H]$^+$.

Step C: To a solution of 1,4-dibromobenzene (9.4 g, 40 mmol) in THF (100 mL) at –78° C. under nitrogen was added 2.5 M nBuLi (16 mL, 40 mmol) dropwise. The addition rate was adjusted to keep the internal temperature below –60° C. After the addition was completed, some white precipitate was formed and copper(I) iodide (3.8 g, 20 mmol) was added. The mixture was stirred at –30 to –40° C. for 1 hour before a solution of the unsaturated lactam (2.0 g, 10 mmol) from step B above in THF (20 mL) followed by iodotrimethylsilane (4.0 g, 2.9 mL, 20 mmol) was added dropwise. The resulting mixture was stirred and allowed to warm up to room temperature overnight. Triethylamine (5 mL) followed by saturated ammonium chloride (10 mL) was added to quench the reaction at –78° C. The mixture was partitioned between methylene chloride and water. The aqueous phase was extracted with methylene chloride three times. The combined extracts were dried over sodium sulfate, filtered and concentrated in vacuo. The residue was purified by column chromatography (1:1 to 1:2 hexanes/ethyl acetate) to yield the lactam (1.8 g, 49%) as an off-white solid: $^1$H NMR (500 MHz, CDCl$_3$) δ 7.39 (d, J=6.5 Hz, 2H), 6.93 (d, J=6.5 Hz, 2H), 6.82 (d, J=8.5 Hz, 1H), 6.72 (d, J=8.5 Hz, 1H), 6.66 (s, 1H), 4.90 (d, J=16.2 Hz, 1H), 4.42 (br, 1H), 4.19 (d, J=16.3 Hz, 1H), 3.79 (s, 3H), 3.15 (dd, J=13.7, 10.9 Hz, 1H), 3.05 (s, 3H), 2.98 (dd, J=13.8, 5.0 Hz, 1H).

Step D: To a mixture of the lactam (1.7 g, 4.9 mmol) from step C above and THF (20 mL) at room temperature was added a 2 M solution borane-dimethylsulfide in THF (4.9 mL, 9.8 mmol). The mixture was stirred at 50° C. for 2 hours. Volatiles were evaporated in vacuo. The residue was treated with 6 N HCl (3 mL) and dioxane (3 mL). The mixture was refluxed for 3 hours. After cooling, the mixture was treated with saturated sodium bicarbonate and 2N NaOH to bring pH to 9. The mixture was extracted with methylene chloride (3×40 mL). The combined extracts were dried over sodium sulfate, filtered and concentrated in vacuo. The residue was purified by column chromatography (20:1 to 10:1 methylene chloride/methanol) to yield the benzazepine (1.6 g, 95%) as colorless oil: $^1$H NMR (500 MHz, CDCl$_3$) δ 7.47 (d, J=8.4 Hz, 2H), 7.04 (d, J=8.2 Hz, 2H), 6.74 (s, 1H), 6.60 (br, 1H), 6.52 (br, 1H), 4.21 (d, J=8.0 Hz, 1H), 3.82 (br, 1H), 3.77 (s, 3H), 3.67 (d, J=14.2 Hz, 1H), 3.07 (br, 1H), 2.96-2.91 (m, 1H), 2.34 (s, 3H), 2.27-2.24 (m, 1H), 2.07 (br, 1H); ESI MS m/z 346 [M+H]$^+$.

Step E: A mixture of the benzazepine (1.4 g, 4.1 mmol), zinc cyanide (0.29 g, 2.5 mmol), tetrakis(triphenylphosphine) palladium (0.24 g, 0.21 mmol) in DMF (6 mL) was stirred at 80° C. under nitrogen for 6 hours. After cooling, the resulting mixture was partitioned between ethyl acetate (60 mL) and 1N NaOH (30 mL). The ethyl acetate phase was dried over sodium sulfate, filtered and concentrated in vacuo. The residue was purified by column chromatography (10:1 methylene chloride/methanol) to yield the cyanobenzazepine (0.99 g, 83%) as an off-white solid: $^1$H NMR (500 MHz, CDCl$_3$) δ 7.63 (d, J=8.3 Hz, 2H), 7.28 (d, J=8.2 Hz, 2H), 6.76 (s, 1H), 6.63-6.61 (m, 1H), 6.53 (br, 1H), 4.31 (d, J=7.5 Hz, 1H), 3.81 (br, 1H), 3.78 (s, 3H), 3.65 (d, J=14.3 Hz, 1H), 3.03 (br, 1H), 2.96-2.91 (m, 1H), 2.35 (s, 3H), 2.35-2.28 (m, 1H), 2.08 (br, 1H); ESI MS m/z 293 [M+H]$^+$.

Step F: To a solution of the cyanobenzazepine (0.99, 3.4 mmol) from step E above in methylene chloride (15 mL) at –78° C. under nitrogen was added 1 M boron tribromide in methylene chloride (33 mL, 33 mmol). The mixture was stirred at –78° C. for 30 minutes and allowed to warm up to room temperature. After stirring at room temperature for 1 hour, the mixture was cooled at –78° C. and quenched with saturated sodium bicarbonate. The two phases were separated and aqueous phase was extracted with a mixed methylene chloride/methanol (10/1). The combined extracts were dried over sodium sulfate, filtered and concentrated in vacuo. The residue was purified by column chromatography (10:1 methylene chloride/methanol) to yield the hydroxybenzazepine (0.24 g, 25%) as an off-white solid: $^1$H NMR (500 MHz, CDCl$_3$) δ 7.26 (d, J=8.3 Hz, 2H), 7.28 (d, J=8.3 Hz, 2H), 6.78 (br, 1H), 6.67 (s, 1H), 6.59 (s, 1H), 4.35 (d, J=6.6 Hz, 1H), 4.00 (br, 1H), 3.83 (d, J=14.3 Hz, 1H), 3.20 (br, 2H), 2.52 (s, 3H), 2.44 (br, 1H), 2.36 (br, 1H); ESI MS m/z 279 [M+H]$^+$.

Step G: To a mixture of the hydroxybenzazepine from step F above (0.23 g, 0.84 mmol), triethylamine (0.59 mL, 4.21 mmol) in chloroform (8 mL) at 0° C. was added trifluoromethanesulfonic anhydride (0.22 mL, 1.3 mmol). The mixture was stirred at room temperature overnight and quenched with saturated sodium bicarbonate. The two phases were separated and aqueous phase was extracted with methylene chloride. The combined extracts were dried over sodium sulfate, filtered and concentrated in vacuo. The residue was purified by column chromatography (20:1 to 10:1 methylene chloride/methanol) to yield the triflate (0.20 g, 48%) as colorless oil: $^1$H NMR (500 MHz, CDCl$_3$) δ 7.68 (d, J=8.3 Hz, 2H), 7.30 (d, J=8.1 Hz, 2H), 7.11 (s, 1H), 7.00 (d, J=8.5 Hz, 1H), 6.66 (br, 1H), 4.38 (d, J=8.9 Hz, 1H), 3.93 (br, 1H), 3.71 (d, J=14.6 Hz, 1H), 3.05 (br, 1H), 3.00-2.95 (m, 1H), 2.35 (s, 3H), 2.35-2.29 (m, 1H), 2.08 (br, 1H); ESI MS m/z 411 [M+H]$^+$.

Step H: A round bottomed flask was charged with the triflate (0.20 g, 0.44 mmol) from step G above, bis(pinacolato)diboron (0.12 g, 0.48 mmol) and potassium acetate (0.13 g, 1.33 mmol) and dichloro[1,1'-bis(diphenylphosphino)ferrocene]palladium(II) dichloromethane adduct (36 mg, 0.04 mmol) in DMF (3 mL). The mixture was refilled with nitrogen three times and then stirred at 80° C. for 1 hour. The mixture was cooled to room temperature. Cesium carbonate (0.43 g, 1.33 mmol), 3-chloro-6-methylpyridazine (0.10 g, 0.67 mmol) and water (2 mL) were added. The mixture was refilled with nitrogen three times and then stirred at 60° C. for 2 hours. After cooling, the mixture was partitioned between methylene chloride and water. The aqueous phase was extracted with methylene chloride. The combined extracts were dried over sodium sulfate, filtered and concentrated in vacuo. The residue was purified by column chromatography (10:1 methylene chloride/methanol) to yield the desired benzazepine (70 mg, 46%) as an off-white solid.

Step I: The free base of the methylbenzazepine (70 mg) from step H above was resolved by preparative chiral HPLC (CHIRALCEL OD column, using 80:20:0.1 heptane/ethanol/diethylamine as the eluent) to give the enantiomer 1 [[α]$^{25}_D$-3.7° (c 0.108, methanol)] (25 mg) and enantiomer 2 [[α]$^{25}_D$-1.8° (c 0.109, methanol)] (29 mg).

Step J: To a solution of enantiomer 1 (25 mg, 0.07 mmol) from step I above in methanol (1 mL) was added L-tartaric acid (11 mg, 0.07 mmol). After the mixture was stirred at room temperature for 10 minutes, water (20 mL) was added. The resultant solution was lyophilized overnight to give 4-(2-methyl-8-(6-methylpyridazin-3-yl)-2,3,4,5-tetrahydro-1H-benzo[c]azepin-5-yl)benzonitrile, L-tartrate salt, enantiomer 1 (30 mg, 83%, AUC HPLC >99%) as a white solid: $^1$H NMR (CD$_3$OD, 500 MHz) δ 8.22 (s, 1H), 8.09 (d, J=14.7 Hz, 1H), 7.99 (d, J=12.6 Hz, 1H), 7.80 (d, J=15.2 Hz, 2H), 7.70 (d, J=14.6 Hz, 1H), 7.46 (d, J=13.5 Hz, 2H), 7.00 (br, 1H), 4.85-4.76 (m, 2H), 4.42 (br, 1H), 4.41 (s, 2H), 3.58 (br, 2H), 2.89 (s, 3H), 2.72 (s, 3H), 2.70 (br, 1H), 2.51 (br, 1H); ESI MS m/z 355 [M+H]$^+$.

Step K: To a solution of enantiomer 2 (29 mg, 0.08 mmol) in methanol (1 mL) was added L-tartaric acid (12 mg, 0.08 mmol). After the mixture was stirred at room temperature for 10 minutes, water (20 mL) was added. The resultant solution was lyophilized overnight to give 4-(2-methyl-8-(6-methylpyridazin-3-yl)-2,3,4,5-tetrahydro-1H-benzo[c]azepin-5-yl)benzonitrile, L-tartrate salt, enantiomer 2 (31 mg, 76%, AUC HPLC >99%) as a white solid: $^1$H NMR (CD$_3$OD, 500 MHz) δ 8.22 (s, 1H), 8.09 (d, J=14.7 Hz, 1H), 7.99 (d, J=12.6 Hz, 1H), 7.80 (d, J=15.2 Hz, 2H), 7.70 (d, J=14.6 Hz, 1H), 7.46 (d, J=13.5 Hz, 2H), 7.00 (br, 1H), 4.85-4.76 (m, 2H), 4.42 (br, 1H), 4.41 (s, 2H), 3.58 (br, 2H), 2.89 (s, 3H), 2.72 (s, 3H), 2.70 (br, 1H), 2.51 (br, 1H); ESI MS m/z 355 [M+H]$^+$.

Example 102

Preparation of (+/−)-8-methoxy-2-methyl-5-(thiophen-2-yl)-2,3,4,5-tetrahydro-1H-benzo[c]azepine, citrate salt Step A: To a solution of m-anisaldehyde (205 g, 1.5 mol) in methanol (800 mL) at room temperature was added 40% methylamine in water (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined organic extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: Ethyl acrylate (33.0 mL, 298 mmol) was added to a stirred mixture of benzylamine (15.0 g, 99.2 mmol) from Step A above and acetic acid (3 mL) at 0° C. The mixture was heated at 80° C. for 4 hours and allowed to cool to room temperature before diluting with dichloromethane (300 mL). The reaction mixture was washed with saturated NaHCO$_3$, dried over Na$_2$SO$_4$ and concentrated in vacuo. The residue was treated with toluene and the resulting solution concentrated in vacuo in order to remove residual ethyl acrylate, affording the ester (25.0 g, 100%) as a colorless oil: $^1$H NMR (500 MHz, CDCl$_3$) δ 7.22 (t, J=8.0 Hz, 1H), 6.89-6.86 (m, 2H), 6.78 (dd, J=8.2, 2.5 Hz, 1H), 4.13 (q, J=7.1 Hz, 2H), 3.80 (s, 3H), 3.48 (s, 2H), 2.74 (t, J=7.2 Hz, 2H), 2.51 (t, J=7.2 Hz, 2H), 2.21 (s, 3H), 1.25 (t, J=7.1 Hz, 3H).

Step C: To a stirred solution of ester (25.0 g, 99.2 mmol) from Step B above in methanol (210 mL) at room temperature was added a solution of NaOH (4.0 g, 100.0 mmol) in water (90 mL). After 16 h the reaction mixture was concentrated in vacuo. The residue was treated with toluene and the resulting solution concentrated in vacuo in order to remove residual water, affording the sodium salt (24.5 g, 100%) as a white solid: $^1$H NMR (300 MHz, CD$_3$OD) δ 7.20 (t, J=7.9 Hz, 1H), 6.93-6.85 (m, 2H), 6.79 (dd, J=8.2, 1.7 Hz, 1H), 4.91 (s, 2H), 3.78 (s, 3H), 2.78-2.72 (m, 2H), 2.45-2.38 (m, 2H), 2.20 (s, 3H).

Step D: A mixture of the sodium salt (24.3 g, 99.2 mmol) from Step C above and 85% polyphosphoric acid (200 g) was heated at 100-110° C. for 16 hours with slow stirring under N$_2$. The reaction flask was cooled in an ice bath and water was added until the viscous reaction mixture dissolved. The solution was adjusted to pH 8-9 by slow addition of 6 N NaOH and the aqueous phase extracted with dichloromethane (3×500 mL). The combined extracts were dried over Na$_2$SO$_4$ and concentrated in vacuo to afford the ketone (12.05 g, 60%) as a brown oil which was stored at −20° C.: $^1$H NMR (300 MHz, CDCl$_3$) δ 7.82 (d, J=8.6 Hz, 1H), 6.87 (dd, J=8.6, 2.5 Hz, 1H), 6.69 (d, J=2.5 Hz, 1H), 3.92 (s, 2H), 3.87 (s, 3H), 2.87-2.78 (m, 4H), 2.43 (s, 3H); ESI MS m/z 206 [M+H]$^+$.

Step E: To a solution of ketone (550 mg, 2.68 mmol) from Step D above in THF (6 ml) under N$_2$ at −78° C. was added thienyl lithium (4 mL of a 1 M solution in THF, 4.00 mmol). After 1 hour, the reaction was allowed to warm to room temperature, quenched with 6N HCl (1.5 mL) and methanol (3 mL) then stirred for a further 1 hour. The mixture was made basic by addition of 2 N NaOH and extracted with dichloromethane (2×). The combined extracts were dried over Na$_2$SO$_4$, concentrated in vacuo and the residue passed through a short plug of silica gel using 10% dichloromethane/methanol as eluent. After concentration in vacuo, the resulting oil was dissolved in ethanol (100 mL) and acetic acid (0.2 mL) was hydrogenated over palladium(II) hydroxide (300 mg) at 40 psi for 16 hours using a Parr hydrogenation apparatus. The reaction mixture was filtered through Celite, concentrated in vacuo and partitioned with dichloromethane and saturated NaHCO$_3$. The organic layer was separated, dried over Na$_2$SO$_4$ and concentrated in vacuo. Purification by flash column chromatography (0-10% methanol/dichloromethane) afforded the benzazepine (126 mg, 17%) as a yellow oil: ¹H NMR (300 MHz, CDCl₃) δ 7.20 (d, J=5.0 Hz, 1H), 6.98-6.81 (m, 2H), 6.74-6.60 (m, 3H), 4.47 (dd, J=6.6, 2.6 Hz, 1H), 3.86-3.60 (m, 2H), 3.78 (s, 3H), 3.25-3.13 (m, 1H), 3.02-2.90 (m, 1H), 2.34-2.15 (m, 2H), 2.32 (s, 3H).

Step F: To a solution of the benzazepine (124 mg, 0.45 mmol) from Step E above in methanol (3 mL) was added citric acid (87 mg, 0.45 mmol). The mixture was stirred until a homogeneous solution was obtained then concentrated in vacuo to give (+/−)-8-methoxy-2-methyl-5-(thiophen-2-yl)-2,3,4,5-tetrahydro-1H-benzo[c]azepine, citrate salt (211 mg, 100%) as a purple solid: ¹H NMR (500 MHz, CD₃OD) δ 7.34 (d, J=5.1 Hz, 1H), 7.17-7.08 (m, 1H), 7.02-7.00 (m, 2H), 6.95 (dd, J=8.5, 2.2 Hz, 1H), 6.77-6.73 (m, 1H), 4.72-4.68 (m, 1H), 4.34-4.28 (m, 2H), 3.83 (s, 3H), 3.66-3.59 (m, 1H), 3.55-3.49 (m, 1H), 2.83 (s, 3H), 2.83-2.71 (m, 4H), 2.61-2.45 (m, 2H); ESI MS m/z 274 [M+H]⁺.

Example 103

Preparation of (+)-5-(5-(benzo[b]thiophen-5-yl)-2-methyl-8-(morpholine-4-yl)-2,3,4,5-tetrahydro-1H-benzo[c]azepine, maleate salt and (−)-5-(5-(benzo[b]thiophen-5-yl)-2-methyl-8-(morpholine-4-yl)-2,3,4,5-tetrahydro-1H-benzo[c]azepine, maleate salt Step A: To a solution of aqueous 2N sodium hydroxide (100 mL) was added methyl 3,3-dimethoxy propionate (25.0 g, 0.17 mol). The reaction solution was stirred at 50° C. for 1 hour and then cooled to room temperature. The resultant reaction mixture was acidified with 6 N hydrochloric acid to pH 1 and extracted with dichloromethane three times. The combined organic extracts were dried over sodium sulfate and concentrated in vacuo to give the desired acid (22.5 g, quantitative) as a clear colorless oil, which was used in the next step without further purification: ¹H NMR (CDCl₃, 300 MHz) δ 4.83 (t, J=5.7 Hz, 1H), 3.39 (s, 6H), 2.71 (d, J=5.7 Hz, 2H).

Step B: To a solution of m-anisaldehyde (205 g, 1.5 mol) in methanol (800 mL) at room temperature was added 40% methylamine in water (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined methylene chloride extracts were washed with 1:1 water/brine, dried over sodium sulfate and concentrated in vacuo to give the desired benzylamine (66.7 g, 29%) as a clear oil: ¹H NMR (300 MHz, CDCl₃) δ 7.24 (t, J=8.4 Hz, 1H), 6.91-6.78 (m, 3H), 3.81 (s, 3H), 3.73 (s, 2H), 2.46 (s, 3H).

Step C: To a mixture of benzylamine (25.6 g, 169 mmol) from Step B above, 3,3-dimethoxypropanoic acid (22.5 g, 168 mmol) and methylene chloride (200 mL) was added 1-(3-dimethylaminopropyl)-3-ethylcarbodiimide hydrochloride (32.9 g, 171 mmol) at 0° C. The mixture was stirred at room temperature overnight, and then washed with water (150 mL), 1N hydrochloric acid (100 mL), and saturated sodium bicarbonate (60 mL). The resulting solution was dried over sodium sulfate, filtered and concentrated in vacuo to give the acetal (44.9 g, 99%) as a brown oil. The crude product was used directly in the next reaction.

Step D: The acetal (44.9 g, 168 mmol) from step C above was treated with pre-cooled concentrated hydrochloric acid (200 mL) at 0° C. The mixture was stirred at 0° C. for 2 hours. The reaction was quenched with 2 N NaOH (the pH was adjusted to 7). The mixture was extracted with methylene chloride (2×500 mL). The combined extracts were dried over sodium sulfate, filtered and concentrated in vacuo. The residue was recrystallized with hexanes/ethyl acetate followed by another recrystallization to yield the lactam (12.1 g) as a colorless solid. Another crop of the lactam (6.80 g) was obtained from the mother liquid by column chromatography (1:1 hexanes/ethyl acetate). The combined yield was 55%: ¹H NMR (500 MHz, CDCl₃) δ 7.30 (d, J=8.0 Hz, 1H), 7.01 (d, J=12.1 Hz, 1H), 6.90 (dd, J=8.3, 2.6 Hz, 1H), 6.82 (d, J=2.6 Hz, 1H), 6.29 (d, J=12.1 Hz, 1H), 4.19 (s, 2H), 3.86 (s, 3H), 3.10 (s, 3H); ESI MS m/z 204 [M+H]⁺.

Step E: To a solution of diisopropylamine (15.5 mL, 110 mmol) in THF (100 mL) at 0° C. was added n-butyllithium (40 mL of 2.5M in hexanes, 100 mmol). The resultant reaction solution was stirred at 0° C. for 30 minutes and then cooled to −40° C., before it was cannulated to a solution of 5-bromobenzothiophene (10.5 g, 50.0 mmol) and chlorotrimethylsilane (12.7 mL, 100 mmol) in THF (150 mL) at −78° C. The reaction solution was stirred at −78° C. for 1 hour, and then it was quenched with aqueous ammonium chloride at −78° C. and warmed to room temperature. The resultant mixture was extracted with ethyl acetate and the organic extract obtained was washed with brine, dried over sodium sulfate and concentrated in vacuo. The residue obtained was purified by flash column chromatography (hexanes to 98:2 hexanes/ethyl acetate) to give the desired 5-bromo-2-trimethylsilylbenzothiophene (14.1 g, 98%) as a clear colorless oil: ¹H NMR (500 MHz, CDCl₃) δ 7.93 (d, J=2.0 Hz, 1H), 7.72 (d, J=8.5 Hz, 1H), 7.39 (dd, J=8.5, 2.0 Hz, 1H), 7.37 (s, 1H), 0.38 (s, 9H).

Step F: To a solution of the 5-bromo-2-trimethylsilylbenzothiophene (3.0 g, 10.5 mmol) from step E above in THF (25 mL) at −78° C. was added n-butyllithium (4.0 mL of 2.5M in hexanes, 10.0 mmol). The reaction solution was stirred at −78° C. for 15 minutes and then it was cannulated to a slurry of copper(I) iodide (0.95 g, 5.0 mmol) in THF (5.0 mL) at −78° C. The resultant reaction mixture was stirred at −40° C. for 90 minutes and then a solution of the lactam (1.02 g, 5.0 mmol) from step D above in THF (12 mL) was added to it, followed by iodotrimethylsilane (0.73 mL, 5.0 mmol). The reaction solution was slowly warmed to room temperature and stirred for 12 hours. To this reaction mixture was then added triethylamine (0.8 mL) followed by aqueous saturated ammonium chloride. The resultant mixture was extracted with ethyl acetate and the organic extract obtained was washed with brine, dried over sodium sulfate and concentrated in vacuo. The crude product was purified by flash column chromatography (90:10 to 33:66 hexanes/ethyl acetate) to give the desired lactam (0.96 g, 47%) as a white solid: ¹H NMR (500 MHz, CDCl₃) δ 7.77 (d, J=8.0 Hz, 1H), 7.51 (d, J=1.5 Hz, 1H), 7.38 (s, 1H), 7.04 (dd, J=8.0, 2.0 Hz, 1H), 6.87 (d, J=9.5 Hz, 1H), 6.70-6.68 (m, 2H), 5.08 (d, J=16.0 Hz, 1H), 4.57 (dd, J=11.5, 5.5 Hz, 1H), 4.10 (d, J=16.5 Hz, 1H), 3.79 (s, 3H), 3.31 (dd, J=13.5, 6.5 Hz, 1H), 3.07 (s, 3H), 2.98 (dd, J=14.0, 5.0 Hz, 1H), 0.35 (s, 9H).

Step G: To a solution of the lactam (0.96 g, 2.3 mmol) from step F above in tetrahydrofuran (20 mL) at 0° C. was added borane-dimethylsulfide (2.5 mL of 2M in tetrahydrofuran, 5.0 mmol). The reaction solution was stirred at 0° C. for 5 minutes and at 50° C. for 90 minutes and then it was cooled to room temperature and quenched with methanol. The resultant mixture was concentrated in vacuo and the residue obtained was dissolved in dioxane (30 mL) and aqueous hydrochloric acid (6 N, 10 mL) and heated under reflux for 1 hour. After cooling to room temperature, the reaction mixture was neutralized with aqueous sodium hydroxide to pH 9 and extracted with dichloromethane (3×). The combined organic extracts were washed with brine, dried over sodium sulfate and concentrated in vacuo. The crude product obtained was purified by flash column chromatography (25:75 hexanes/ethyl acetate to 25:75:10 hexanes/ethyl acetate/methanol) to give the desired benzazepine (0.94 g, 85%) as a light yellow oil: $^1$H NMR (CDCl$_3$, 500 MHz) δ 7.85 (d, J=8.5 Hz, 1H), 7.60 (s, 1H), 7.44 (d, J=5.5 Hz, 1H), 7.29 (d, J=5.5 Hz, 1H), 7.20 (dd, J=8.5, 1.5 Hz, 1H), 6.77-6.76 (m, 1H), 6.64-6.45 (br, 2H), 4.39 (d, J=8.5 Hz, 1H), 3.99-3.86 (br, 1H), 3.77 (s, 3H), 3.72 (d, J=14.0 Hz, 1H), 3.17-3.10 (br, 1H), 3.01-2.95 (m, 1H), 2.42-2.34 (m, 1H), 2.36 (s, 3H), 2.21-2.12 (br, 1H).

Step H: The racemic benzazepine (0.95 g) from Step G above was resolved by preparative chiral HPLC (CHIRALCEL OJ column, using 80:20:0.1 heptane/ethanol/diethylamine as the eluent) to give the (+)-enantiomer [[α]$^{25}_D$+ 20.00 (c 0.12, methanol)] (0.44 g) as an off-white solid and the (+)-enantiomer [[α]$^{25}_D$−20.0° (c 0.11, methanol)] (0.45 g) as an off-white solid.

Step I: To a solution of the (+)-enantiomer of the 8-methoxybenzazepine (0.44 g, 1.4 mmol) from step H above in acetic acid (25 mL) was added hydrobromic acid (48% solution in water, 25 mL). The reaction solution was heated at 100° C. for 16 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (0.48 g, quantitative) as a yellow foam. The crude product was used in the next step without purification: $^1$H NMR (CDCl$_3$, 500 MHz) δ 7.85 (d, J=8.5 Hz, 1H), 7.58 (s, 1H), 7.44 (d, J=5.0 Hz, 1H), 7.28 (d, J=5.5 Hz, 1H), 7.18 (d, J=8.5 Hz, 1H), 6.61-6.37 (br, 3H), 4.36 (d, J=9.0 Hz, 1H), 3.93-3.78 (br, 1H), 3.69 (d, J=14.0 Hz, 1H), 3.20-3.10 (br, 1H), 2.98 (t, J=10.5 Hz, 1H), 2.46-2.36 (m, 1H), 2.44 (s, 3H), 2.28-2.14 (br, 1H); ESI MS m/z 310 [M+H]$^+$.

Step J: To a solution of the phenol (0.48 g, 1.4 mmol) from step I above in dichloromethane (20 mL) at 0° C. were added pyridine (0.22 mL, 2.8 mmol) and triflic anhydride (0.30 mL, 1.8 mmol). The reaction solution was let to warm to room temperature and stirred for 1 hour. The resultant reaction mixture was diluted with dichloromethane, washed with aqueous saturated sodium bicarbonate and water, dried over sodium sulfate and concentrated in vacuo. The residue was purified by column chromatography (1:1 hexane/ethyl acetate to pure ethyl acetate) to yield the triflate (0.47 g, 78% over two steps) as an off-white foam: $^1$H NMR (CDCl$_3$, 500 MHz) δ 7.88 (d, J=8.5 Hz, 1H), 7.61 (s, 1H), 7.48 (d, J=5.0 Hz, 1H), 7.31 (d, J=5.5 Hz, 1H), 7.18 (dd, J=8.5, 1.5 Hz, 1H), 7.10 (d, J=2.5 Hz, 1H), 6.93 (dd, J=8.5, 2.0 Hz, 1H), 6.82-6.47 (br, 1H), 4.45 (d, J=9.5 Hz, 1H), 4.02 (d, J=12.5 Hz, 1H), 3.76 (d, J=14.0 Hz, 1H), 3.22-3.14 (m, 1H), 3.06-3.01 (m, 1H), 2.43-2.36 (m, 1H), 2.37 (s, 3H), 2.19-2.02 (m, 1H).

Step K: To a solution of the triflate (0.26 g, 0.58 mmol) from step J above in xylene (6 mL) were added cesium carbonate (0.55 g, 1.7 mmol), 2-(dicyclohexylphosphino)-2',4',6'-tri-i-propyl-1,1'-biphenyl (54 mg, 0.11 mmol) and morpholine (0.10 mL, 1.1 mmol). The resultant mixture was flushed with nitrogen for 5 minutes, and then palladium (II) acetate (13 mg, 0.06 mmol) was added to it. The reaction solution was heated at 135° C. in a sealed tube for 2.5 hours, and then cooled to room temperature. The resultant mixture was diluted with dichloromethane, washed with water and brine, dried over sodium sulfate and concentrated in vacuo. The crude product obtained was purified by column chromatography (20:1 to 10:1 dichloromethane/methanol) to give the desired 8-morpholinylbenzazepine [[α]$^{20}_D$+13.3° (c 0.06, methanol)] (204 mg, 93%) as an off-white foam: $^1$H NMR (CDCl$_3$, 500 MHz) δ 7.85 (d, J=8.5 Hz, 1H), 7.59 (s, 1H), 7.44 (d, J=5.5 Hz, 1H), 7.28 (d, J=5.0 Hz, 1H), 7.20 (dd, J=8.5, 1.5 Hz, 1H), 6.78 (d, J=2.0 Hz, 1H), 6.65-6.49 (br, 2H), 4.38 (d, J=8.5 Hz, 1H), 4.01-3.90 (br, 1H), 3.84 (t, J=4.5 Hz, 4H), 3.75 (d, J=14.0 Hz, 1H), 3.19-3.10 (m, 1H), 3.12 (t, J=4.5 Hz, 4H), 3.03-2.98 (m, 1H), 2.43-2.36 (m, 1H), 2.39 (s, 3H), 2.21-2.14 (br, 1H).

Step L: To a solution of the newly obtained 8-morpholinylbenzazepine (200 mg, 0.53 mmol) from Step K above in methanol (4 mL) were added maleic acid (61 mg, 0.53 mmol) and water (20 mL). The resultant solution was lyophilized overnight to give the (+)-5-(5-(benzo[b]thiophen-5-yl)-2-methyl-8-(morpholine-4-yl)-2,3,4,5-tetrahydro-1H-benzo[c]azepine, maleate salt (215 mg, 79% AUC HPLC) as an off-white solid: mp 116-122° C.; $^1$H NMR (CD$_3$OD, 500 MHz) δ 7.92 (d, J=8.5 Hz, 1H), 7.73-7.48 (br, 1H), 7.59 (d, J=5.0 Hz, 1H), 7.33 (s, 1H), 7.21 (d, J=8.0 Hz, 1H), 7.07 (s, 1H), 7.03-6.52 (br, 2H), 6.26 (s, 2.3H), 4.64-4.20 (br, 3H), 3.83 (br s, 4H), 3.74-3.51 (br, 2H), 3.20-3.10 (br, 4H), 3.05-2.27 (br, 5H); ESI MS m/z 379 [M+H]$^+$.

Step M: To a solution of the (−)-enantiomer of the 8-methoxybenzazepine (0.45 g, 1.4 mmol) from step H above in acetic acid (25 mL) was added hydrobromic acid (48% solution in water, 25 mL). The reaction solution was heated at 100° C. for 16 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (0.51 g, quantitative) as a yellow foam. The crude product was used in the next step without purification: $^1$H NMR (CDCl$_3$, 500 MHz) δ 7.85 (d, J=8.5 Hz, 1H), 7.58 (s, 1H), 7.44 (d, J=5.0 Hz, 1H), 7.28 (d, J=5.5 Hz, 1H), 7.18 (d, J=8.5 Hz, 1H), 6.61-6.37 (br, 3H), 4.36 (d, J=9.0 Hz, 1H), 3.93-3.78 (br, 1H), 3.69 (d, J=14.0 Hz, 1H), 3.20-3.10 (br, 1H), 2.98 (t, J=10.5 Hz, 1H), 2.46-2.36 (m, 1H), 2.44 (s, 3H), 2.28-2.14 (br, 1H); ESI MS m/z 310 [M+H]$^+$.

Step N: To a solution of the phenol (0.51 g, 1.4 mmol) from step M above in dichloromethane (20 mL) at 0° C. were added pyridine (0.22 mL, 2.8 mmol) and triflic anhydride (0.30 mL, 1.8 mmol). The reaction solution was let to warm to room temperature and stirred for 1 hour. The resultant reaction mixture was diluted with dichloromethane, washed with aqueous saturated sodium bicarbonate and water, dried over sodium sulfate and concentrated in vacuo. The crude product obtained (0.51 g, 83% over two steps) as a dark brown foam was used in the next step without purification: $^1$H NMR (CDCl$_3$, 500 MHz) δ 7.88 (d, J=8.5 Hz, 1H), 7.61 (s, 1H), 7.48 (d, J=5.0 Hz, 1H), 7.31 (d, J=5.5 Hz, 1H), 7.18 (dd, J=8.5, 1.5 Hz, 1H), 7.10 (d, J=2.5 Hz, 1H), 6.93 (dd, J=8.5, 2.0 Hz, 1H), 6.82-6.47 (br, 1H), 4.45 (d, J=9.5 Hz, 1H), 4.02 (d, J=12.5 Hz, 1H), 3.76 (d, J=14.0 Hz, 1H), 3.22-3.14 (m, 1H), 3.06-3.01 (m, 1H), 2.43-2.36 (m, 1H), 2.37 (s, 3H), 2.19-2.02 (m, 1H).

Step O: To a solution of the triflate (0.25 g, 0.56 mmol) from step N above in xylene (6 mL) were added cesium carbonate (0.55 g, 1.7 mmol), 2-(dicyclohexylphosphino)-2',4',6'-tri-i-propyl-1,1'-biphenyl (54 mg, 0.11 mmol) and morpholine (0.10 mL, 1.1 mmol). The resultant mixture was flushed with argon for 5 minutes, and then palladium(II) acetate (13 mg, 0.06 mmol) was added to it. The reaction solution was heated at 100° C. under argon for 16 hours, and then cooled to room temperature. The resultant mixture was diluted with dichloromethane, washed with water and brine, dried over sodium sulfate and concentrated in vacuo. The crude product obtained was purified by flash column chromatography (98:2 to 60:40 dichloromethane/methanol) followed by preparative thin layer chromatography (92:8 dichloromethane/methanol) to give the desired 8-morpholinylbenzazepine [[α]$^{24}_D$ −7.8° (c 0.09, methanol)] (89 mg, 42%) as an off-white foam: $^1$H NMR (CDCl$_3$, 500 MHz) δ 7.85 (d, J=8.5 Hz, 1H), 7.59 (s, 1H), 7.44 (d, J=5.5 Hz, 1H), 7.28 (d, J=5.0 Hz, 1H), 7.20 (dd, J=8.5, 1.5 Hz, 1H), 6.78 (d, J=2.0 Hz, 1H), 6.65-6.49 (br, 2H), 4.38 (d, J=8.5 Hz, 1H), 4.01-3.90 (br, 1H), 3.84 (t, J=4.5 Hz, 4H), 3.75 (d, J=14.0 Hz, 1H), 3.19-3.10 (m, 1H), 3.12 (t, J=4.5 Hz, 4H), 3.03-2.98 (m, 1H), 2.43-2.36 (m, 1H), 2.39 (s, 3H), 2.21-2.14 (br, 1H). To a solution of the newly obtained 8-morpholinylbenzazepine (80 mg, 0.21 mmol) in methanol (3 mL) were added maleic acid (24.6 mg, 0.21 mmol) and water (15 mL). The resultant solution was lyophilized overnight to give the (−)-5-(5-(benzo[b]thiophen-5-yl)-2-methyl-8-(morpholine-4-yl)-2,3,4,5-tetrahydro-1H-benzo[c]azepine, maleate salt (103 mg, 98.8% AUC HPLC) as an off-white solid: mp 107-111° C.; $^1$H NMR (CD$_3$OD, 500 MHz) δ 7.92 (d, J=8.5 Hz, 1H), 7.73-7.48 (br, 1H), 7.59 (d, J=5.0 Hz, 1H), 7.33 (s, 1H), 7.21 (d, J=8.0 Hz, 1H), 7.07 (s, 1H), 7.03-6.52 (br, 2H), 6.26 (s, 2.3H), 4.64-4.20 (br, 3H), 3.83 (br s, 4H), 3.74-3.51 (br, 2H), 3.20-3.10 (br, 4H), 3.05-2.27 (br, 5H); ESI MS m/z 379 [M+H]$^+$.

Example 104

Preparation of (+)-5-(benzo[b]thiophen-5-yl)-2-methyl-8-(pyrimidin-5-yl)-2,3,4,5-tetrahydro-1H-benzo[c]azepine, maleate salt Pursuant to the general method described above in Example 103, the following product was prepared: (+)-5-(benzo[b]thiophen-5-yl)-2-methyl-8-(pyrimidin-5-yl)-2,3,4,5-tetrahydro-1H-benzo[c]azepine maleate salt: mp 111-117° C.; $^1$H NMR (CD$_3$OD, 500 MHz) δ 9.17 (s, 1H), 9.10 (s, 2H), 7.97 (d, J=8.5 Hz, 1H), 7.87 (d, J=2.0 Hz, 1H), 7.76-7.63 (m, 2H), 7.62 (d, J=5.5 Hz, 1H), 7.36 (d, J=5.0 Hz, 1H), 7.27 (d, J=8.0 Hz, 1H), 7.24-6.80 (br, 1H), 6.41-6.15 (br, 2H), 4.77-4.21 (br, 3H), 3.75-3.52 (br, 2H), 3.07-2.40 (br, 5H); ESI MS m/z 372 [M+H]$^+$.

Example 105

Preparation of (+)-5-(benzo[b]thiophen-5-yl)-2-methyl-8-(pyrazin-2-yl)-2,3,4,5-tetrahydro-1H-benzo[c]azepine, maleate salt Pursuant to the general method described above in Example 103, the following product was prepared: (+)-5-(benzo[b]thiophen-5-yl)-2-methyl-8-(pyrazin-2-yl)-2,3,4,5-tetrahydro-1H-benzo[c]azepine maleate salt: mp 102-108° C.; $^1$H NMR (CD$_3$OD, 500 MHz) δ 9.14 (s, 1H), 8.69 (d, J=1.5 Hz, 1H), 8.56 (d, J=2.5 Hz, 1H), 8.26 (d, J=1.5 Hz, 1H), 8.12-8.00 (br, 1H), 7.98 (d, J=8.5 Hz, 1H), 7.74-7.63 (br, 1H), 7.62 (d, J=5.5 Hz, 1H), 7.36 (d, J=5.5 Hz, 1H), 7.27 (d, J=8.0 Hz, 1H), 7.27-6.75 (br, 1H), 6.26 (s, 2.3H), 4.79-4.31 (br, 3H), 3.73-3.54 (br, 2H), 3.10-2.73 (br, 4H), 2.61-2.48 (br, 1H); ESI MS m/z 372 [M+H]$^+$.

Example 106

Preparation of (+)-5-(benzo[b]thiophen-5-yl)-2-methyl-8-(6-methylpyridazin-3-yl)-2,3,4,5-tetrahydro-1H-benzo[c]azepine, maleate salt Pursuant to the general method described above in Example 103, the following product was prepared: (+)-5-(benzo[b]thiophen-5-yl)-2-methyl-8-(6-methylpyridazin-3-yl)-2,3,4,5-tetrahydro-1H-benzo[c]azepine maleate salt: mp 105-109° C.; $^1$H NMR (CD$_3$OD, 500 MHz) δ 8.26 (s, 1H), 8.08 (d, J=8.5 Hz, 1H), 7.98 (d, J=8.0 Hz, 2H), 7.70 (d, J=8.0 Hz, 2H), 7.62 (d, J=5.0 Hz, 1H), 7.36 (s, 1H), 7.28 (d, J=7.0 Hz, 1H), 7.24-6.80 (br, 1H), 6.25 (s, 2.3H), 4.77-4.22 (br, 3H), 3.82-3.54 (br, 2H), 3.12-2.42 (br, 5H), 2.73 (s, 3H); ESI MS m/z 386 [M+H]$^+$.

Example 107

Preparation of (+)-5-(benzo[b]thiophen-5-yl)-2-methyl-8-(pyridazin-3-yl)-2,3,4,5-tetrahydro-1H-benzo[c]azepine, maleate salt Pursuant to the general method described above in Example 103, the following product was prepared: (+)-5-(benzo[b]thiophen-5-yl)-2-methyl-8-(pyridazin-3-yl)-2,3,4,5-tetrahydro-1H-benzo[c]azepine maleate salt: mp 117-121° C.; $^1$H NMR (CD$_3$OD, 500 MHz) δ 9.18 (d, J=5.0 Hz, 1H), 8.29 (d, J=2.0 Hz, 1H), 8.19 (d, J=8.0 Hz, 1H), 8.08-7.95 (br, 1H), 7.98 (d, J=8.5 Hz, 1H), 7.81 (dd, J=8.5, 5.0 Hz, 1H), 7.76-7.62 (br, 1H), 7.63 (d, J=5.5 Hz, 1H), 7.37-6.87 (m, 2H), 7.28 (d, J=7.5 Hz, 1H), 6.25 (s, 2.3H), 4.71-4.32 (br, 3H), 3.82-3.50 (br, 2H), 3.12-2.73 (br, 4H), 2.64-2.45 (br, 1H); ESI MS m/z 372 [M+H]$^+$.

Example 108

Preparation of 2-methyl-5-phenyl-8-(trifluoromethyl)-2,3,4,5-tetrahydro-1H-benzo[c]azepine, L-tartrate salt Step A: To a solution of the 2-bromo-5-trifluoromethylbenzonitrile (2.6 g, 10.4 mmol) in toluene (20 mL) at −78° C. was added diisobutylaluminium hydride (21 mL, 21 mmol, 1.0 M in toluene) cooled to −78° C. by cannula. The solution was stirred at −78 to −50° C. for 2 hours. Water (5 mL) was added slowly to the reaction and the reaction was allowed to warm up to room temperature. The mixture was adjusted to pH 10 with NaOH. The product was extracted with dichloromethane, washed with saturated sodium bicarbonate and brine, dried over sodium sulfate and concentrated. The residue was purified by flash chromatography (hexanes/ether 90:10) to give the desired aldehyde (2.0 g, 76%) as a dark solid: $^1$H NMR (CDCl$_3$, 300 MHz) δ 10.38 (s, 1H), 8.18 (s, 1H), 7.68 (d, J=8.7 Hz, 1H), 7.54 (d, J=8.7 Hz, 1H).

Step B: To a solution of the aldehyde (2.0 g, 7.9 mmol) from step A above, methylamine hydrochloride (1.4 g, 21 mmol) and triethylamine (2.1 g, 21 mmol) in ethanol (60 mL) were added titanium(IV) isopropoxide (18.4 g, 64.8 mmol) at room temperature. The mixture was stirred at room temperature overnight. Sodium borohydride (590 mg, 15.6 mmol) was added to the mixture and the reaction mixture was stirred at room temperature for 2 hours. To the reaction mixture was added saturated ammonium chloride (mL) and the resulting mixture was stirred at room temperature for 10 minutes. The precipitate was filtered and the filtrate was concentrated to give the desired benzylamine (1.4 g, 66%) as a colorless oil: $^1$H NMR (CDCl$_3$, 300 MHz) δ 7.71-7.65 (m, 2H), 7.37 (dd, J=8.3, 2.0 Hz, 1H), 3.87 (s, 2H), 2.48 (s, 3H); ESI MS m/z 269 [M+H]$^+$.

Step C: Preparation of the N-methoxy-N-methylacrylamide: To a solution of methoxy methylamine hydrochloride (10.8 g, 111 mmol), triethylamine (11.3 g, 111 mmol) in dichloromethane (50 mL) at 0° C. was added acrylic chloride (10 g, 111 mmol) in dichloromethane (50 mL) dropwise. The mixture was stirred at 0° C. for 2 hours. The reaction mixture was diluted with dichloromethane, washed with saturated sodium bicarbonate and brine, dried over sodium sulfate and concentrated to give the desired acrylamide (8.2 g, 64%) as a light yellow oil: $^1$H NMR (CDCl$_3$, 300 MHz) δ 6.73 (dd, J=17.1, 6.7 Hz, 1H), 6.43 (dd, J=17.1, 2.0 Hz, 1H), 5.75 (dd, J=6.7, 2.0 Hz, 1H), 3.71 (s, 3H), 3.26 (s, 3H); ESI MS m/z 116 [M+H]$^+$.

Step D: The benzylamine (1.4 g, 5.2 mmol) from step B above, acetic acid (0.5 mL), and the acrylamide (1.2 g 10.4 mmol) from step C above in dioxane (15 mL) were heated at reflux for 2 hours. The solvent was removed under vacuum. The residue was diluted with dichloromethane, washed with saturated sodium bicarbonate and brine, dried over sodium sulfate and concentrated to give the desired amide (1.9 g, crude) as a light yellow oil: $^1$H NMR (CDCl$_3$, 300 MHz) δ 7.80 (s, 1H), 7.64 (d, J=8.3 Hz, 1H), 7.34 (d, J=8.3 Hz, 1H), 3.67 (s, 3H), 3.65 (s, 2H), 3.18 (s, 3H), 2.85 (t, J=7.2 Hz, 2H), 2.66 (t, J=7.2 Hz, 2H), 2.30 (s, 3H); ESI MS m/z 384 [M+H]$^+$.

Step E: To a solution of the amide (1.9 g, crude) from step D above in THF (20 mL) at –78° C. was added n-butyllithium (13 mL, 32 mmol, 2.5 M in hexanes) dropwise. The resultant solution was stirred at –78° C. for 20 minutes. The reaction was quenched with methanol/water (3 mL+3 mL). The mixture was diluted with dichloromethane, washed with water, saturated sodium bicarbonate and brine, dried over sodium sulfate and concentrated. The residue was purified by flash chromatography (98:1.8:0.2 to 95:4.5:0.5 dichloromethane/methanol/concentrated ammonium hydroxide) to give the desired ketone (400 mg, 32% two steps): $^1$H NMR (CDCl$_3$, 300 MHz) δ 7.85 (d, J=8.0 Hz, 1H), 7.62 (d, J=8.0 Hz, 1H), 7.46 (s, 1H), 3.97 (s, 2H), 2.91-2.87 (m, 4H), 2.46 (s, 3H); ESI MS m/z 244 [M+H]$^+$.

Step F: To a solution of the ketone (400 mg, 1.6 mmol) from step E above in THF (5 mL) cooled at –78° C. was added phenyllithium generated from bromobenzene (775 mg, 4.9 mmol) and n-butyllithium (2.0 mL, 5.0 mmol, 2.5 M in hexanes) in situ at –78° C. by cannula. The reaction mixture was stirred at –78° C. for 1 hour. The reaction was quenched with methanol (0.5 mL) at this temperature. After warming up to room temperature, the reaction mixture was diluted with dichloromethane, washed with saturated ammonium chloride and brine, dried over sodium sulfate and concentrated. The residue was purified by flash chromatography (95:1.8:0.2 to 95:4.5:0.5 dichloromethane/methanol/concentrated ammonium hydroxide) to give the desired 5-benzazepinol (250 mg, 49%) as a gum-like solid: $^1$H NMR (CDCl$_3$, 300 MHz) δ 7.39-7.27 (m, 8H), 3.87 (d, J=15.5 Hz, 1H), 3.76 (d, J=15.5 Hz, 1H) 3.20-3.10 (m, 1H), 2.77-2.72 (m, 1H), 2.62-2.52 (m, 1H), 2.42 (s, 3H), 2.40-2.33 (m, 1H); ESI MS m/z 322 [M+H]$^+$.

Step G: The alcohol (250 mg, 0.78 mmol) from step F above was dissolved in trifluoroacetic acid (2 mL) and the solution was stirred at room temperature for 5 minutes. The solution was transferred to a Parr bottle and methanol (20 mL) was added to the bottle. Palladium(II) hydroxide on carbon (10 wt %, 0.5 g) was added to the bottle. The mixture was hydrogenated (25 psi) at room temperature for 25 minutes. The catalyst was filtered over a pad of Celite and the filtrate was concentrated. The filtrate was adjusted to pH 9 with saturated NaHCO$_3$ and the product was extracted with dichloromethane. The organic layer was washed with brine, dried over sodium sulfate and concentrated. The residue was purified by flash chromatography (95:1.8:0.2 to 95:4.5:0.5 dichloromethane/methanol/concentrated ammonium hydroxide) to give the desired benzazepine (230 mg, 97%) as a colorless oil.

Step H: To a solution of the benzazepine (20.6 mg, 0.067 mmol) in methanol (0.5 mL) was added L-tartaric acid (11 mg, 0.073 mmol) followed by slow addition of water (5 mL). The resultant solution was lyophilized overnight to give 2-methyl-5-phenyl-8-(trifluoromethyl)-2,3,4,5-tetrahydro-1H-benzo[c]azepine, L-tartrate salt (31 mg, 100%, AUC HPLC >98.1%) as a white solid: mp 134-136° C.; $^1$H NMR (CD$_3$OD, 500 MHz) δ 7.80 (s, 1H), 7.61 (d, J=7.6 Hz, 1H), 7.43-7.40 (m, 2H), 7.33 (t, J=7.4 Hz, 1H), 7.22 (d, J=7.4 Hz, 2H), 7.00 (br, 1H), 4.68-4.66 (m, 2H), 4.45 (s, 4H), 4.41-4.38 (m, 1H), 3.64-3.55 (m, 2H), 2.88 (s, 3H), 2.62-2.55 (m, 1H), 2.42-2.39 (m, 1H); ESI MS m/z 306 [M+H]$^+$.

Example 109

Preparation of 7-fluoro-8-methoxy-2-methyl-5-phenyl-2,3,4,5-tetrahydro-1H-benzo[c]azepine, L-tartrate salt Step A: To a solution of 3-methoxy-4-fluorobenzaldehyde (8.4 g, 54.5 mmol) in methanol (150 mL) was added methylamine (40% in water, 7.2 mL, 82 mmol) at room temperature. The reaction mixture was cooled to 0° C., sodium borohydride (2.07 g, 82 mmol) was added to the solution portionwise. The reaction mixture was stirred at 0° C. for 2 hours. The solvent was removed. The residue was dissolved in water, and the product was extracted with dichloromethane. The organic layer was washed with brine, dried over sodium sulfate and concentrated to give the benzylamine (9.2 g, quantitative) as a colorless liquid: $^1$H NMR (CDCl$_3$, 300 MHz) δ 7.04-6.95 (m, 2H), 6.83-6.78 (m, 1H), 3.90 (s, 3H), 3.70 (s, 2H), 2.45 (s, 3H); ESI MS m/z 170 [M+H]$^+$.

Step B: A solution of the benzylamine (9.2 g, 22 mmol) from step A above, acetic acid (2 mL) and ethyl acrylate (50 mL, 250 mmol) was heated at 100° C. for 2 hours. The solvent was removed under vacuum. The residue was diluted with dichloromethane, washed with sodium bicarbonate, brine, dried over sodium sulfate and concentrated to give the desired ester (14.0 g, crude) as a light yellow oil: $^1$H NMR (CDCl$_3$, 300 MHz) δ 7.02-6.95 (m, 2H), 6.80-6.75 (m, 1H), 4.13 (q, J=7.1 Hz, 2H), 3.89 (s, 3H), 3.46 (s, 2H), 2.73 (t, J=7.2 Hz, 2H), 2.51 (t, J=7.2 Hz, 2H), 2.21 (s, 3H), 1.26 (t, J=7.1 Hz, 3H); ESI MS m/z 270 [M+H]$^+$.

Step C: To a solution of the ester (14.0 g, crude) from step B in methanol (100 mL) was added NaOH solution (2.5 g, 62.5 mmol, 31 ml H$_2$O) at room temperature. The solution was stirred at room temperature overnight. The solvent was removed and the residue was azeotroped with benzene. The residue was dried under vacuum to give a white solid (15.0 g, crude). The white solid (9.0 g, crude) and polyphosphorous acid (80 g) were combined and heated at 130° C. overnight. After cooling to room temperature, the reaction mixture was diluted with water, and then adjusted to pH 9 with NaOH. The product was extracted with dichloromethane. The organic layer was washed with brine, dried over sodium sulfate, and concentrated to give the desired ketone (3.3 g, 45% for three steps): ¹H NMR (CDCl₃, 300 MHz) δ 7.57 (d, J=11.6 Hz, 1H), 6.74 (d, J=7.7 Hz, 1H), 3.95 (s, 3H), 3.89 (s, 2H), 2.86-2.80 (m, 4H), 2.43 (s, 3H); ESI MS m/z 224 [M+H]⁺.

Step D: To a solution of the ketone (820 mg, 3.8 mmol) from step C above in THF (10 mL) cooled to −78° C. was added phenyllithium, which was freshly prepared from bromobenzene (1.8 g, 11.5 mmol) and n-butyllithium (4.6 mL, 11.5 mmol, 2.5 M in hexanes) at −78° C. The reaction mixture was stirred at −78° C. for 1 hour. The reaction was quenched with methanol (1 mL) at this temperature. After warming up to room temperature, the reaction mixture was diluted with dichloromethane, washed with saturated ammonium chloride and brine, dried over sodium sulfate and concentrated. The residue was purified by flash chromatography (98:1.8:0.2 to 95:4.5:0.5 dichloromethane/methanol/concentrated ammonium hydroxide) to give the desired benzazepinol (850 mg, 74%) as a light yellow solid: ESI MS m/z 302 [M+H]⁺.

Step E: The alcohol (850 mg, 2.82 mmol) from step D above was dissolved in trifluoroacetic acid (3 mL) and the solution was stirred at room temperature for 5 minutes. The solution was transferred to a Parr bottle and methanol (20 mL) was added to the bottle. Palladium(II) hydroxide on carbon (10 wt %, 300 mg) was added to the bottle. The reaction mixture was hydrogenated (25 psi) at room temperature for 30 minutes. The catalyst was filtered over a pad of Celite. The filtrate was concentrated and the residue was adjusted to pH 9 with NaOH. The product was extracted with dichloromethane. The organic layer was washed with brine, dried over sodium sulfate and concentrated. The residue was purified by flash chromatography (98:1.8:0.2 to 95:4.5:0.5 dichloromethane/methanol/concentrated ammonium hydroxide) to give the benzazepine (820 mg, quant.) as a light-brown oil: ¹H NMR (CDCl₃, 300 MHz) δ 7.39-7.29 (m, 3H), 7.17 (d, J=7.2 Hz, 2H), 6.79 (d, J=8.6 Hz, 1H), 6.35-6.31 (m, 1H), 4.21 (d, J=9.8 Hz, 1H), 3.89 (d, J=14.0 Hz, 1H), 3.87 (s, 2H), 3.66 (d, J=14.0 Hz, 1H), 3.15-3.10 (m, 1H), 2.91-2.84 (m, 1H), 2.36 (s, 3H), 2.32-2.27 (m, 1H), 2.08-2.04 (m, 1H); ESI MS m/z 286. The compound (80 mg) was further purified by HPLC to give 27 mg pure material.

Step F: To a solution of the material from step E (27 mg, 0.095 mmol) in methanol (1 mL) was added L-tartaric acid (14 mg, 0.095 mmol) followed by slow addition of water (5 mL). The resultant solution was lyophilized overnight to give 7-fluoro-8-methoxy-2-methyl-5-phenyl-2,3,4,5-tetrahydro-1H-benzo[c]azepine, L-tartrate salt (36 mg, 88%, AUC HPLC 98.1%) as a white solid: mp 110-112° C.; ¹H NMR (CD₃OD, 500 MHz) δ 7.42-7.39 (m, 2H), 7.33-7.31 (m, 1H), 7.22-7.20 (m, 3H), 6.48 (br, 1H), 4.60-4.45 (m, 2H), 4.42 (s, 3H), 4.28 (d, J=9.2 Hz, 1H), 3.89 (s, 3H), 2.59-2.50 (m, 2H), 2.86 (s, 3H), 2.60-2.50 (m, 1H), 2.38-2.35 (m, 1H); ESI MS m/z 286 [M+H].

Example 110

Preparation of 9-fluoro-8-methoxy-2-methyl-5-phenyl-2,3,4,5-tetrahydro-1H-benzo[c]azepin-5-ol, L-tartrate salt Step A: To a solution of 2-fluoro-3-methoxybenzaldehyde (5.0 g, 32 mmol), methylamine hydrochloride (4.38 g, 63.8 mmol) and triethylamine (6.54 g, 63.8 mmol) in ethanol (100 ml) were added titanium(IV) isopropoxide (18.4 g, 64.8 mmol) at room temperature. The mixture was stirred at room temperature overnight. Sodium borohydride (1.84 g, 48.6 mmol) was added to the mixture and reaction mixture was stirred at room temperature for 2 hours. To the reaction mixture was added saturated ammonium chloride (100 mL), and the resulting mixture was stirred at room temperature for 10 minutes. The precipitate was filtered and the filtrate was concentrated to give a light brown oil: ¹H NMR (CDCl₃, 300 MHz) δ 7.13-7.07 (m, 2H), 6.98-6.91 (m, 1H), 4.01 (s, 2H), 3.89 (s, 3H), 2.51 (s, 3H); ESI MS m/z 170 [M+H]⁺.

Step B: The benzylamine (3.7 g, 22 mmol) from step A above, acetic acid (1 mL) and ethyl acrylate (40 mL, 200 mmol) were heated at 100° C. for 2 hours. The solvent was removed under vacuum. The residue was diluted with dichloromethane, washed with saturated sodium bicarbonate and brine, dried over sodium sulfate and concentrated to give the desired ester (4.5 g, crude) as a light yellow oil: ¹H NMR (CDCl₃, 300 MHz) δ 7.07-6.83 (m, 3H), 4.13 (q, J=7.1 Hz, 2H), 3.91 (s, 3H), 3.60 (s, 2H), 2.75 (t, J=7.2 Hz, 2H), 2.53 (t, J=7.2 Hz, 2H), 2.23 (s, 3H), 1.24 (t, J=7.1 Hz, 3H); ESI MS m/z 270 [M+H]⁺.

Step C: To a solution of the ester (4.5 g, crude) from step B in methanol (50 mL) was added 2N NaOH (50 mL) at room temperature. The solution was stirred at room temperature overnight. The solvent was removed and the residue was azeotroped with benzene. The residue was dried under vacuum to give a white solid. The white solid and polyphosphorous acid (60 g) was heated at 130° C. overnight. After cooling to room temperature, the reaction mixture was diluted with water and then adjusted to pH 9 with NaOH. The product was extracted with dichloromethane. The organic layer was washed with brine, dried over sodium sulfate, and concentrated. The residue was purified by flash chromatography (95:4.5:0.5 dichloromethane/methanol/concentrated ammonium hydroxide) to give the desired ketone (720 mg, 19% for two steps): ¹H NMR (CDCl₃, 500 MHz) δ 7.60-7.58 (m, 1H), 6.95-6.91 (m, 1H), 4.04 (s, 2H), 3.94 (s, 3H), 2.85-2.75 (m, 4H), 2.44 (s, 3H); ESI MS m/z 224 [M+H]⁺.

Step D: To a solution of the ketone (720 mg, 3.22 mmol) from step C above in THF (6 mL) cooled at −78° C. was added phenyllithium (3.6 mL, 6.4 mmol, 1.8 M in THF) dropwise. The reaction mixture was stirred at −78° C. for 1 h. The reaction was quenched with methanol (0.5 mL) at this temperature. After warming up to room temperature, the reaction mixture was diluted with dichloromethane, washed with saturated ammonium chloride and brine, dried over sodium sulfate and concentrated. The residue was purified by flash chromatography (95:1.8:0.2 to 95:4.5:0.5 dichloromethane/methanol/concentrated ammonium hydroxide) to give the desired 5-benzazepinol (760 mg, 78%) as a gum-like solid. To a solution of the 5-benzazepinol (50 mg, 0.16 mmol) in methanol (1 mL) was added L-tartaric acid (24 mg, 0.16 mmol) followed by slow addition of water (5 mL). The resultant solution was lyophilized overnight to give 9-fluoro-8-methoxy-2-methyl-5-phenyl-2,3,4,5-tetrahydro-1H-benzo[c]azepin-5-ol, tartrate salt (62 mg, 84%, AUC HPLC >99%) as a white solid: mp 130-132° C.; ¹H NMR (CD₃OD, 500 MHz) δ 7.42-7.33 (m, 5H), 7.06-6.92 (m, 2H), 4.91-4.74 (m, 2H), 4.42 (s, 3H), 4.19-4.16 (m, 1H), 3.87 (s, 3H), 3.75 3.65 (m, 1H), 3.38-3.32 (m, 1H), 2.88-2.83 (m, 4H), 2.39-2.34 (m, 1H); ESI MS m/z 302 [M+H]⁺.

Example 111

Preparation of 8-methoxy-2-methyl-5-(4-(trifluoromethyl)phenyl)-2,3,4,5-tetrahydro-1H-benzo[c]azepin-5-ol, L-tartrate salt Pursuant to the general method described above in Example 110, the following product was prepared: 8-methoxy-2-methyl-5-(4-(trifluoromethyl)phenyl)-2,3,4,5-tetrahydro-1H-benzo[c]azepin-5-ol, tartrate salt: ¹H NMR (CD₃OD, 500 MHz) δ 7.23 (d, J=8.5 Hz, 2H), 7.60-7.59 (m, 2H), 7.02-6.89 (m, 3H), 4.87-4.79 (m, 2H), 4.42 (s, 2H), 4.28-4.19 (m, 1H), 3.85-3.80 (m, 4H), 3.38-3.32 (m, 1H), 2.94-2.88 (m, 4H), 2.20-2.14 (m, 1H); ESI MS m/z 352 [M+H]⁺.

Example 112

Preparation of 5-(3,4-difluorophenyl)-8-methoxy-2-methyl-2,3,4,5-tetrahydro-1H-benzo[c]azepin-5-ol, citrate salt Pursuant to the general method described above in Example 110, the following product was prepared: 5-(3,4-difluorophenyl)-8-methoxy-2-methyl-2,3,4,5-tetrahydro-1H-benzo[c]azepin-5-ol, citrate salt: mp 75-77° C.; ¹H NMR (500 MHz, CD₃OD) δ 7.40-7.24 (m, 2H), 7.15-7.10 (m, 1H), 7.05-7.00 (m, 1H), 6.99 (d, J=2.6 Hz, 1H), 6.91-6.86 (m, 1H), 4.72-4.58 (m, 1H), 4.25 (d, J=13.9 Hz, 1H), 3.90 (s, 3H), 3.83-3.80 (m, 1H), 3.45-3.39 (m, 1H), 2.88 (s, 2H), 2.86-2.82 (m, 3H), 2.82 (d, J=15.5 Hz, 2H), 2.73 (d, J=15.5 Hz, 2H), 2.70-2.66 (m, 1H), 2.34-2.28 (m, 1H); ESI MS m/z 320 [M+H]⁺.

Example 113

Preparation of (+)-5-(2-fluorophenyl)-2-methyl-8-(6-methylpyridazin-3-yl)-2,3,4,5-tetrahydro-1H-benzo[c]azepine, L-tartrate salt and (−)-5-(2-fluorophenyl)-2-methyl-8-(6-methylpyridazin-3-yl)-2,3,4,5-tetrahydro-1H-benzo[c]azepine, L-tartrate salt Step A: To a solution of m-anisaldehyde (205 g, 1.5 mol) in methanol (800 mL) at room temperature was added methylamine (130 mL of 40% in water, 1.5 mol). The resultant solution was cooled to 0° C. and sodium borohydride (83 g, 2.3 mol) was added to it in batches. The reaction solution was stirred at 0° C. for 2 hours and then it was warmed to room temperature, concentrated in vacuo and diluted with water. The organic phase was separated, diluted with ethyl acetate, washed with 1:1 water/brine, dried over sodium sulfate and concentrated in vacuo to give the desired benzylamine (158.5 g, 70% yield) as a clear oil. The combined aqueous extracts were extracted with dichloromethane (3×). The combined methylene chloride extracts were washed with 1:1 water/brine, dried over sodium sulfate and concentrated in vacuo to give the desired benzylamine (66.7 g, 29% yield) as a clear oil: ¹H NMR (300 MHz, CDCl₃) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 min and then cooled to room temperature and concentrated in vacuo. The residue obtained was dissolved in dichloromethane, washed with aqueous sodium bicarbonate, dried over sodium sulfate and concentrated in vacuo. The crude product obtained was used in the next step without further purification: ¹H NMR (500 MHz, CDCl₃) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 h and then concentrated in vacuo. The residue obtained was dissolved in water, adjusted to pH 7, extracted with chloroform (3×) and 3:1 chloroform/2-propanol (3×). The combined organic extract were dried over sodium sulfate and concentrated in vacuo to give the desired acid (25 g, 56% yield) as a light green oil, which was used in the next step without further purification.

Step D: A mixture of the acid (24.0 g, 107 mmol) from step C above and polyphosphoric acid (180 g) was heated at 100-110° C. for 18 hours. The resultant slurry was dissolved in dichloromethane and water, basified with sodium bicarbonate and sodium carbonate to pH>8 and then extracted with dichloromethane (5×). The combined organic extract were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: ¹H NMR (500 MHz, CDCl₃) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]⁺.

Step E: To a solution of 2-bromofluorobenzene (0.66 mL, 6.0 mmol) in THF (25 mL) at −78° C. was added n-BuLi (2.4 mL, 6.0 mmol, 2.5 M in hexanes) dropwise. After the addition, the reaction solution was stirred at −78° C. for 30 minutes. To this solution was then added a cold (−78° C.) solution of the ketone (1.0 g, 5.0 mmol) from step D above in THF (5 mL) quickly. The reaction solution was stirred at −78° C. for 3 hours and then quenched with saturated aqueous solution of sodium bicarbonate. The resultant mixture was warmed to room temperature, extracted with dichloromethane (3×), dried over sodium sulfate and concentrated in vacuo. The crude product obtained was purified by flash column chromatography (99:0.9:0.1 to 88:10.8:1.2 dichloromethane/methanol/concentrated ammonium hydroxide) to give the desired tertiary alcohol (0.76 g, 50%) as a reddish oil: ¹H NMR (500 MHz, CDCl₃) δ 7.71 (t, J=7.5 Hz, 1H), 7.32-7.27 (m, 1H), 7.19 (td, J=7.5, 1.0 Hz, 1H), 7.01 (ddd, J=12.0, 8.5, 1.0 Hz, 1H), 6.81 (d, J=8.5 Hz, 1H), 6.67 (d, J=2.5 Hz, 1H), 6.59 (dd, J=8.5, 2.5 Hz, 1H), 5.25-4.70 (br, 1H), 3.95 (d, J=16.0 Hz, 1H), 3.76 (d, J=15.5 Hz, 1H), 3.76 (s, 3H), 3.18 (td, J=11.0, 6.5 Hz, 1H), 2.88-2.80 (m, 1H), 2.65 (ddd, J=11.5, 6.5, 3.0 Hz, 1H), 2.47 (s, 3H), 2.19 (ddd, J=14.5, 6.0, 3.0 Hz, 1H); ESI MS m/z 302 [M+H]⁺.

Step F: T a solution of the tertiary alcohol (0.76 g, 2.5 mmol) from step E above in trifluoroacetic acid (3 mL) and ethanol (30 mL) was added palladium(II) hydroxide (0.5 g). The reaction solution was shaken under hydrogen (30 psi) for 15 hours. The resultant reaction mixture was filtered through a pad of Celite and the filtrate was concentrated in vacuo. The crude 8-methoxy benzazepine obtained was used in the next step without further purification: ESI MS m/z 286 [M+H]⁺.

Step G: To a solution of the 8-methoxybenzazepine (2.5 mmol) from step F above in acetic acid (30 mL) was added hydrobromic acid (48% solution in water, 30 mL). The reaction solution was heated at 100° C. for 16 hours, cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (0.58 g, 85% yield) as a brown solid, which was used in the next step without further purification: ¹H NMR (CDCl₃, 500 MHz) δ 7.28-7.22 (m, 1H), 7.18-7.04 (m, 3H), 6.56 (d, J=2.5 Hz, 1H), 6.45 (dd, J=8.5, 2.5 Hz, 1H), 6.43-6.31 (m, 1H), 4.50 (d, J=9.0 Hz, 1H), 3.95 (d, J=13.5 Hz, 1H), 3.67 (d, J=9.0 Hz, 1H), 3.16-3.08 (m, 1H), 2.95-2.90 (m, 1H), 2.43 (s, 3H), 2.42-2.34 (m, 1H), 2.05-2.01 (m, 1H); ESI MS m/z 272 [M+H]⁺.

Step H: To a solution of the phenol (0.57 g, 2.1 mmol) from step G above in dichloromethane (30 mL) at 0° C. were added pyridine (0.34 mL, 4.2 mmol) and triflic anhydride (0.39 mL, 2.3 mmol). The resultant reaction mixture was stirred at 0° C. for 2 hours, and then it was diluted with dichloromethane, washed with aqueous saturated sodium bicarbonate, dried over sodium sulfate and concentrated in vacuo. The crude product obtained was purified by flash column chromatography (ethyl acetate to 97:3 ethyl acetate/methanol) to give the desired triflate (0.66 g, 77% yield) as a yellow oil: $^1$H NMR (CDCl$_3$, 500 MHz) δ 7.33-7.28 (m, 1H), 7.23-7.04 (m, 4H), 6.95 (dd, J=8.5, 2.5 Hz, 1H), 6.63 (d, J=8.5 Hz, 1H), 4.59 (d, J=10.0 Hz, 1H), 4.11 (d, J=14.5 Hz, 1H), 3.76 (d, J=14.5 Hz, 1H), 3.17-3.13 (m, 1H), 3.06-3.00 (m, 1H), 2.40-2.32 (m, 1H), 2.37 (s, 3H), 2.00-1.97 (m, 1H).

Step I: To a solution of the triflate (0.66 g, 1.6 mmol) from step H above and bis(pinacolato)diboron (0.51 g, 2.0 mmol) in DMSO (18 mL) was added potassium acetate (0.48 g, 4.9 mmol). The resultant mixture was flushed with argon for 10 minutes, and then dichloro[1,1'-bis(diphenylphosphino)ferrocene]palladium(II) dichloromethane adduct (0.13 g, 0.16 mmol) was added to it. The reaction solution was degassed again with argon for 5 minutes and then heated at 80° C. for 1 hour. The resultant reaction solution was then cooled to room temperature, diluted with ethyl acetate, washed with water (2×) and brine, dried over sodium sulfate and concentrated in vacuo. The crude boronate ester was used in the next step without further purification.

Step J: To a mixture of the boronate ester (1.6 mmol) from step I above, 3-chloro-6-methylpyridazine (0.41 g, 3.2 mmol) and sodium carbonate (0.51 g, 4.8 mmol) were added DMF (12 mL) and water (3 mL). The resultant solution was flushed with argon for 10 minutes, and then dichloro[1,1'-bis(diphenylphosphino)ferrocene]palladium(II) dichloromethane adduct (65 mg, 0.08 mmol) was added to it. The reaction mixture was flushed with argon for 5 minutes and then heated at 80° C. for 2 hours. The reaction solution was then cooled to room temperature, diluted with ethyl acetate, washed with water (2×), dried over sodium sulfate and concentrated in vacuo. The crude product obtained was purified by flash column chromatography (dichloromethane to 90:9:1 dichloromethane/methanol/concentrated ammonium hydroxide) and preparative thin layer chromatography (90:9:1 dichloromethane/methanol/concentrated ammonium hydroxide) to give the desired benzazepine (0.15 g, 27%) as a brown foam: $^1$H NMR (CDCl$_3$, 500 MHz) δ 7.96 (d, J=2.0 Hz, 1H), 7.73-7.71 (m, 1H), 7.70 (d, J=9.0 Hz, 1H), 7.34 (d, J=9.0 Hz, 1H), 7.32-7.24 (m, 2H), 7.18 (t, J=7.0 Hz, 1H), 7.13-7.05 (m, 1H), 6.73 (d, J=8.0 Hz, 1H), 4.66 (d, J=9.5 Hz, 1H), 4.15 (d, J=14.5 Hz, 1H), 3.90 (d, J=14.5 Hz, 1H), 3.16 (d, J=11.0 Hz, 1H), 3.06-3.01 (m, 1H), 2.74 (s, 3H), 2.43-2.37 (m, 1H), 2.40 (s, 3H), 2.06-2.03 (m, 1H).

Step K: The racemic benzazepine (0.15 g) from step J above was resolved by preparative chiral HPLC (CHIRALPAK AD column, using 80:20:0.1 heptane/2-propanol/diethylamine as the eluent) to give the (+)-enantiomer [[α]$^{25}_D$+12.8° (c 0.13, methanol)] (50 mg) and the (−)-enantiomer [[α]$^{25}_D$−23.0° (c 0.21, methanol)] (59 mg).

Step L: To a solution of the (+)-enantiomer (50 mg, 0.14 mmol) from step K above in methanol (2 mL) were added L-tartaric acid (21 mg, 0.14 mmol) and water (10 mL). The resultant solution was lyophilized overnight to provide (+)-5-(2-fluorophenyl)-2-methyl-8-(6-methylpyridazin-3-yl)-2,3,4,5-tetrahydro-1H-benzo[c]azepine, L-tartrate salt (70 mg, >99.0% AUC HPLC) as an off-white solid: $^1$H NMR (CD$_3$OD, 500 MHz) δ 8.19 (s, 1H), 8.06 (d, J=8.5 Hz, 1H), 7.91 (dd, J=8.0, 1.5 Hz, 1H), 7.68 (d, J=9.0 Hz, 1H), 7.44-7.30 (m, 2H), 7.28 (t, J=7.0 Hz, 1H), 7.20 (t, J=9.5 Hz, 1H), 6.86 (d, J=6.5 Hz, 1H), 4.93-4.76 (m, 2H), 4.46 (d, J=14.5 Hz, 1H), 4.40 (s, 2H), 3.57-3.53 (br 2H), 2.87 (s, 3H), 2.72 (s, 3H), 2.62-2.52 (br, 1H), 2.37 (d, J=13.5 Hz, 1H); ESI MS m/z 348 [M+H]$^+$. To a solution of the (−)-enantiomer (59 mg, 0.17 mmol) from step K above in methanol (2 mL) were added L-tartaric acid (25 mg, 0.17 mmol) and water (10 mL). The resultant solution was lyophilized overnight to provide (−)-5-(2-fluorophenyl)-2-methyl-8-(6-methylpyridazin-3-yl)-2,3,4,5-tetrahydro-1H-benzo[c]azepine, L-tartrate salt (82 mg, >99.0% AUC HPLC) as an off-white solid: $^1$H NMR (CD$_3$OD, 500 MHz) δ 8.19 (s, 1H), 8.06 (d, J=8.5 Hz, 1H), 7.91 (dd, J=8.0, 1.5 Hz, 1H), 7.68 (d, J=9.0 Hz, 1H), 7.44-7.30 (m, 2H), 7.28 (t, J=7.0 Hz, 1H), 7.20 (t, J=9.5 Hz, 1H), 6.86 (d, J=6.5 Hz, 1H), 4.93-4.76 (m, 2H), 4.46 (d, J=14.5 Hz, 1H), 4.40 (s, 2H), 3.57-3.53 (br, 2H), 2.87 (s, 3H), 2.72 (s, 3H), 2.62-2.52 (br, 1H), 2.37 (d, J=13.5 Hz, 1H); ESI MS m/z 348 [M+H]$^+$.

Example 114

Preparation of 9-fluoro-2-methyl-8-(6-methylpyridazin-yl)-5-phenyl-2,3,4,5-tetrahydro-1H-benzo[c]azepine, citrate salt (enantiomers 1 and 2)

Pursuant to the general method described above in Example 110, the following product was prepared: 9-fluoro-2-methyl-8-(6-methylpyridazin-yl)-5-phenyl-2,3,4,5-tetrahydro-1H-benzo[c]azepine, citrate salt, enantiomer 1: mp 123-125° C.; $^1$H NMR (DMSO-d$_6$, 500 MHz) δ 7.97 (d, J=8.7 Hz, 1H), 7.82 (t, J=8.0 Hz, 1H), 7.71 (d, J=8.7 Hz, 1H), 7.46-7.42 (m, 2H), 7.36-7.33 (m, 1H), 7.27 (d, J=7.5 Hz, 1H), 6.82 (br, 1H), 4.72-4.68 (m, 2H), 4.60-4.58 (m, 1H), 3.64-3.61 (m, 2H), 2.92 (s, 3H), 2.87-2.74 (m, 10H), 2.74 (s, 3H), 2.61-2.64 (m, 1H), 2.48-2.44 (m, 1H); ESI MS m/z 348 [M+H]; 9-fluoro-2-methyl-8-(6-methylpyridazin-yl)-5-phenyl-2,3,4,5-tetrahydro-1H-benzo[c]azepine, citrate salt, enantiomer 2: mp 96-98° C.; $^1$H NMR (DMSO-d$_6$, 500 MHz) δ 7.97 (d, J=8.7 Hz, 1H), 7.82 (t, J=8.0 Hz, 1H), 7.71 (d, J=8.7 Hz, 1H), 7.46-7.42 (m, 2H), 7.36-7.33 (m, 1H), 7.27 (d, J=7.5 Hz, 1H), 6.82 (br, 1H), 4.72-5.68 (m, 2H), 4.60-4.58 (m, 1H), 3.64-3.61 (m, 2H), 2.92 (s 3H), 2.87-2.74 (m, 10H), 2.74 (s, 3H), 2.61-2.64 (m, 1H), 2.48-2.44 (m, 1H); ESI MS m/z 348 [M+H]. (The extra protons are to account for the 2.5 equivalents of citric acid.)

Example 115

Preparation of 9-fluoro-2-methyl-5-phenyl-8-(pyridazin-3-yl)-2,3,4,5-tetrahydro-1H-benzo[c]azepine, L-tartrate salt (enantiomers 1 and 2)

Pursuant to the general method described above in Example 110, the following products were prepared: 9-fluoro-2-methyl-5-phenyl-8-(pyridazin-3-yl)-2,3,4,5-tetrahydro-1H-benzo[c]azepine, tartrate salt, enantiomer 1: mp 106-108° C.; $^1$H NMR (CD$_3$OD, 500 MHz) δ 9.20 (d, J=4.5 Hz, 1H), 8.09 (d, J=8.6 Hz, 1H), 7.83-7.81 (m, 2H), 7.43 (t, J=7.4 Hz, 2H), 7.34 (t, J=7.3 Hz, 1H), 7.28 (d, J=7.9 Hz, 1H), 6.82 (br, 1H), 4.70 (d, J=9.2 Hz, 1H), 4.63-4.60 (m, 2H), 4.43 (s, 3H), 3.60-3.50 (m, 2H), 2.86 (s, 3H), 2.65-2.55 (m, 1H), 2.49-2.38 (m, 1H); ESI MS m/z 334 [M+H]; 9-fluoro-2-methyl-5-phenyl-8-(pyridazin-3-yl)-2,3,4,5-tetrahydro-1H-benzo[c]azepine, tartrate salt, enantiomer 2: mp 98-100° C.; $^1$H NMR (CD$_3$OD, 500 MHz) δ 9.20 (d, J=4.5 Hz, 1H), 8.09 (d, J=8.6 Hz, 1H), 7.83-7.81 (m, 2H), 7.43 (t, J=7.4 Hz, 2H), 7.34 (t, J=7.3 Hz, 1H), 7.28 (d, J=7.9 Hz, 1H), 6.82 (br, 1H), 4.70 (d, J=9.2 Hz, 1H), 4.63-4.60 (m, 2H), 4.43 (s, 3H), 3.60-3.50 (m, 2H), 2.86 (s, 3H), 2.65-2.55 (m, 1H), 2.49-2.38 (m, 1H); ESI MS m/z 334 [M+H].

Example 116

Preparation of (+)-7-fluoro-2-methyl-8-(6-methylpyridazin-3-yl)-5-phenyl-2,3,4,5-tetrahydro-1H-benzo[c]azepine, tartrate salt and (−)-7-fluoro-2-methyl-8-(6-methylpyridazin-3-yl)-5-phenyl-2,3,4,5-tetrahydro-1H-benzo[c]azepine, L-tartrate salt Pursuant to the general method described above in Example 110, the following products were prepared: (+)-7-fluoro-2-methyl-8-(6-methylpyridazin-3-yl)-5-phenyl-2,3,4,5-tetrahydro-1H-benzo[c]azepine, tartrate salt: mp 112-114° C.; $^1$H NMR (CD$_3$OD, 500 MHz) δ 8.10 (d, J=7.2 Hz, 1H), 7.97 (d, J=8.7 Hz, 1H), 7.69 (d, J=8.7 Hz, 1H), 7.47-7.44 (m, 2H), 7.38-7.35 (m, 1H), 7.29 (d, J=7.2 Hz, 1H), 6.65 (br, 1H), 4.78-4.65 (m, 2H), 4.45-4.43 (m, 1H), 4.40 (s, 2H), 3.69-3.60 (m, 2H), 2.86 (s, 3H), 2.74 (s, 3H), 2.65-2.58 (m, 1H), 2.44-2.41 (m, 1H); ESI MS m/z 334 [M+H]; (−)-7-fluoro-2-methyl-8-(6-methylpyridazin-3-yl)-5-phenyl-2,3,4,5-tetrahydro-1H-benzo[c]azepine, tartrate salt: mp 102-104° C.; $^1$H NMR (CD$_3$OD, 500 MHz) δ 8.10 (d, J=7.2 Hz, 1H), 7.97 (d, J=8.7 Hz, 1H), 7.69 (d, J=8.7 Hz, 1H), 7.47-7.44 (m, 2H), 7.38-7.35 (m, 1H), 7.29 (d, J=7.2 Hz, 1H), 6.65 (br, 1H), 4.78-4.65 (m, 2H), 4.45-4.43 (m, 1H), 4.40 (s, 2H), 3.69-3.60 (m, 2H), 2.86 (s, 3H), 2.74 (s, 3H), 2.65-2.58 (m, 1H), 2.44-2.41 (m, 1H); ESI MS m/z 334 [M+H].

Example 117

Preparation of 2-methyl-8-(6-methylpyridazin-3-yl)-5-(3-(trifluoromethyl)phenyl)-2,3,4,5-tetrahydro-1H-benzo[c]azepine, L-tartrate salt (enantiomers 1 and 2)

Pursuant to the general method described above in Example 110, the following products were prepared: 2-methyl-8-(6-methylpyridazin-3-yl)-5-(3-(trifluoromethyl)phenyl)-2,3,4,5-tetrahydro-1H-benzo[c]azepine, tartrate salt, enantiomer 1: mp 100-102° C.; $^1$H NMR (CD$_3$OD, 500 MHz) δ 8.23 (s, 1H), 8.07 (d, J=8.8 Hz, 1H), 7.97 (d, J=8.2 Hz, 1H), 7.70-7.63 (m, 3H), 7.57-7.55 (m, 2H), 4.87-4.73 (m, 2H), 4.50-4.40 (m, 5H), 3.65-3.50 (m, 2H), 2.92 (s, 3H), 2.72 (s, 3H), 2.66-2.64 (m, 1H), 2.46-2.43 (m, 1H); ESI MS m/z 398 [M+H]; 2-methyl-8-(6-methylpyridazin-3-yl)-5-(3-(trifluoromethyl)phenyl)-2,3,4,5-tetrahydro-1H-benzo[c]azepine, tartrate salt, enantiomer 2: mp 108-110° C.; $^1$H NMR (CD$_3$OD, 500 MHz) δ 8.23 (s, 1H), 8.07 (d, J=8.8 Hz, 1H), 7.97 (d, J=8.2 Hz, 1H), 7.70-7.63 (m, 3H), 7.57-7.55 (m, 2H), 4.87-4.73 (m, 2H), 4.50-4.40 (m, 4H), 3.65-3.50 (m, 2H), 2.92 (s, 3H), 2.72 (s, 3H), 2.66-2.64 (m, 1H), 2.46-2.43 (m, 1H); ESI MS m/z 398 [M+H].

Example 118

Preparation of (+)-2-methyl-8-(6-methylpyridazin-3-yl)-5-(4-trifluoromethoxy)phenyl-2,3,4,5-tetrahydro-1H-benzo[c]azepine, L-tartrate salt and (−)-2-methyl-8-(6-methylpyridazin-3-yl)-5-(4-trifluoromethoxy)phenyl-2,3,4,5-tetrahydro-1H-benzo[c]azepine, L-tartrate salt Pursuant to the general method described above in Example 110, the following products were prepared: (+)-2-methyl-8-(6-methylpyridazin-3-yl)-5-(4-trifluoromethoxy)phenyl-2,3,4,5-tetrahydro-1H-benzo[c]azepine, tartrate salt: mp 116-118° C.; $^1$H NMR (CD$_3$OD, 500 MHz) δ 8.21 (s, 1H), 8.08 (d, J=8.6 Hz, 1H), 7.98 (d, J=8.0 Hz, 1H), 7.69 (d, J=8.6 Hz, 1H), 7.38-7.33 (m, 4H), 6.99 (br, 1H), 4.73-4.71 (m, 2H), 4.45-4.41 (m, 3H), 3.65-3.55 (m, 2H), 2.90 (s, 3H), 2.72 (s, 3H), 2.61-2.59 (m, 1H), 2.48-2.40 (m, 1H); ESI MS m/z 414 [M+H]; (−)-2-methyl-8-(6-methylpyridazin-3-yl)-5-(4-trifluoromethoxy)phenyl-2,3,4,5-tetrahydro-1H-benzo[c]azepine, tartrate salt: mp 118-120° C.; $^1$H NMR (CD$_3$OD, 500 MHz) δ 8.21 (s, 1H), 8.08 (d, J=8.6 Hz, 1H), 7.98 (d, J=8.0 Hz, 1H), 7.69 (d, J=8.6 Hz, 1H), 7.38-7.33 (m, 4H), 6.99 (br, 1H), 4.73-4.71 (m, 2H), 4.45-4.41 (m, 3H), 3.65-3.55 (m, 2H), 2.90 (s, 3H), 2.72 (s, 3H), 2.61-2.59 (m, 1H), 2.48-2.40 (m, 1H); ESI MS m/z 414 [M+H].

Example 119

Preparation of (+)-5-(3,4-difluorophenyl)-2-methyl-8-(6-methylpyridazin-3-yl)-2,3,4,5-tetrahydro-1H-benzo[c]azepine, L-tartrate salt and (−)-5-(3,4-difluorophenyl)-2-methyl-8-(6-methylpyridazin-3-yl)-2,3,4,5-tetrahydro-1H-benzo[c]azepine, L-tartrate salt Pursuant to the general method described above in Example 110, the following products were prepared: (+)-5-(3,4-difluorophenyl)-2-methyl-8-(6-methylpyridazin-3-yl)-2,3,4,5-tetrahydro-1H-benzo[c]azepine, L-tartrate salt: mp 100-102° C.; $^1$H NMR (CD$_3$OD, 500 MHz) δ 8.19 (s, 1H), 8.09 (d, J=8.7 Hz, 1H), 8.00 (d, J=7.8 Hz, 1H), 7.69 (d, J=8.7 Hz, 1H), 7.36-7.28 (m, 1H), 7.24-7.16 (m, 1H), 7.07-6.95 (m, 2H), 4.68 (d, J=8.3 Hz, 2H), 4.45 (d, J=11.7 Hz, 1H), 4.40 (s, 2H), 3.59 (br, 2H), 2.89 (s, 3H), 2.72 (s, 3H), 2.53-2.50 (m, 1H), 2.49-2.47 (m, 1H); ESI MS m/z 366 [M+H]$^+$; (−)-5-(3,4-difluorophenyl)-2-methyl-8-(6-methylpyridazin-3-yl)-2,3,4,5-tetrahydro-1H-benzo[c]azepine, L-tartrate salt: mp 100-104° C.; $^1$H NMR (CD$_3$OD, 500 MHz) δ 8.19 (s, 1H), 8.09 (d, J=8.7 Hz, 1H), 8.00 (d, J=7.8 Hz, 1H), 7.69 (d, J=8.7 Hz, 1H), 7.36-7.28 (m, 1H), 7.24-7.16 (m, 1H), 7.07-6.95 (m, 2H), 4.68 (d, J=8.3 Hz, 2H), 4.45 (d, J=11.7 Hz, 1H), 4.40 (s, 2H), 3.59 (br, 2H), 2.89 (s, 3H), 2.72 (s, 3H), 2.53-2.50 (m, 1H), 2.49-2.47 (m, 1H); ESI MS m/z 366 [M+H]$^+$.

Example 120

Preparation of (+/−)-2-(8-methoxy-2-methyl-2,3,4,5-tetrahydro-1H-benzo[c]azepin-5-yl)thiazole, citrate salt Step A: To a solution of m-anisaldehyde (205 g, 1.5 mol) in methanol (800 mL) at room temperature was added 40% methylamine in water (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The resultant reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined organic extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: Ethyl acrylate (33.0 mL, 298 mmol) was added to a stirred mixture of benzylamine (15.0 g, 99.2 mmol) from Step A above and acetic acid (3 mL) at 0° C. The mixture was heated at 80° C. for 4 hours and allowed to cool to room temperature before diluting with dichloromethane (300 mL). The reaction mixture was washed with saturated NaHCO$_3$, dried over Na$_2$SO$_4$ and concentrated in vacuo. The residue was treated with toluene and the resulting solution concentrated in vacuo in order to remove residual ethyl acrylate, affording the ester (25.0 g, 100%) as a colorless oil: $^1$H NMR (500 MHz, CDCl$_3$) δ 7.22 (t, J=8.0 Hz, 1H), 6.89-6.86 (m, 2H), 6.78 (dd, J=8.2, 2.5 Hz, 1H), 4.13 (q, J=7.1 Hz, 2H), 3.80 (s, 3H), 3.48 (s, 2H), 2.74 (t, J=7.2 Hz, 2H), 2.51 (t, J=7.2 Hz, 2H), 2.21 (s, 3H), 1.25 (t, J=7.1 Hz, 3H).

Step C: To a stirred solution of ester (25.0 g, 99.2 mmol) from Step B above in methanol (210 mL) at room temperature was added a solution of NaOH (4.0 g, 100.0 mmol) in water (90 mL). After 16 hours the reaction mixture was concentrated in vacuo. The residue was treated with toluene and the resulting solution concentrated in vacuo in order to remove residual water, affording the sodium salt (24.5 g, 100%) as a white solid: $^1$H NMR (300 MHz, CD$_3$OD) δ 7.20 (t, J=7.9 Hz, 1H), 6.93-6.85 (m, 2H), 6.79 (dd, J=8.2, 1.7 Hz, 1H), 4.91 (s, 2H), 3.78 (s, 3H), 2.78-2.72 (m, 2H), 2.45-2.38 (m, 2H), 2.20 (s, 3H).

Step D: A mixture of the sodium salt (24.3 g, 99.2 mmol) from Step C above and 85% polyphosphoric acid (200 g) was heated at 100-110° C. for 16 hours with slow stirring under N$_2$. The reaction flask was cooled in an ice bath and water was added until the viscous reaction mixture dissolved. The solution was adjusted to pH 8-9 by slow addition of 6 N NaOH and the aqueous phase extracted with dichloromethane (3×500 mL). The combined extracts were dried over Na$_2$SO$_4$ and concentrated in vacuo to afford the ketone (12.05 g, 60%) as a brown oil which was stored at −20° C.: $^1$H NMR (300 MHz, CDCl$_3$) δ 7.82 (d, J=8.6 Hz, 1H), 6.87 (dd, J=8.6, 2.5 Hz, 1H), 6.69 (d, J=2.5 Hz, 1H), 3.92 (s, 2H), 3.87 (s, 3H), 2.87-2.78 (m, 4H), 2.43 (s, 3H); ESI MS m/z 206 [M+H]$^+$.

Step E: To a stirred solution of thiazole (0.69 mL, 9.72 mmol) in THF (15 mL) at −78° C. under N$_2$ was added dropwise n-butyllithium (3.90 mL of a 2.5 M solution in hexanes, 9.72 mmol). After 30 minutes a solution of ketone (0.50 g, 2.43 mmol) from Step D above in THF (5 mL) was added and the mixture stirred for 2 h before addition of methanol (5 mL). The reaction mixture was allowed to warm to room temperature before partitioning with diethyl ether and brine. The organic layer was dried over Na$_2$SO$_4$ and concentrated in vacuo. Purification by flash column chromatography (50-100% dichloromethane/(dichloromethane/methanol/concentrated ammonium hydroxide; 90:9:1 v/v)) yielded the alcohol (475 mg, 67%) as a purple solid: $^1$H NMR (300 MHz, CDCl$_3$) δ 7.82 (d, J=3.3 Hz, 1H), 7.33 (d, J=3.3 Hz, 1H), 6.95-6.85 (m, 1H), 6.68-6.63 (m, 2H), 3.94-3.77 (m, 2H), 3.77 (s, 3H), 3.19-3.08 (m, 1H), 2.90-2.80 (m, 1H), 2.75-2.65 (m, 1H), 2.45-2.35 (m, 1H), 2.43 (s, 3H); ESI MS m/z 291 [M+H]$^+$.

Step F: To a solution of alcohol (50 mg, 0.17 mmol) from Step E above in toluene (2 mL) was added p-toluenesulfonic acid (33 mg, 0.19 mmol) followed by 1,2-dichloroethane to aid dissolution. The mixture was heated at 85° C. for 3 hours, allowed to cool to room temperature, washed with saturated NaHCO$_3$ and concentrated in vacuo. The crude alkene intermediate was dissolved in methanol (15 mL) and trifluoroacetic acid (1 mL) and hydrogenated over palladium(II) hydroxide (75 mg) at 30 psi for 2 hours using a Parr hydrogenation apparatus. The reaction mixture was filtered through Celite, concentrated in vacuo and partitioned with dichloromethane and saturated NaHCO$_3$. The organic layer was separated, dried over Na$_2$SO$_4$ and concentrated in vacuo. Purification by flash column chromatography (0-10% methanol/dichloromethane) afforded the benzazepine (24 mg, 51%) as a colorless oil: $^1$H NMR (300 MHz, CDCl$_3$) δ 7.78 (d, J=3.3 Hz, 1H), 7.23 (d, J=3.3 Hz, 1H), 7.04-6.93 (m, 1H), 6.77-6.68 (m, 2H), 4.54 (dd, J=6.5, 2.6 Hz, 1H), 3.81 (s, 3H), 3.81-3.60 (m, 2H), 3.20-3.10 (m, 1H), 3.01-2.92 (m, 1H), 2.58-2.46 (m, 1H), 2.39-2.26 (m, 1H), 2.31 (s, 3H); ESI MS m/z 275 [M+H]$^+$.

Step G: To a solution of the benzazepine (24 mg, 0.09 mmol) from Step F above in methanol (3 mL) was added citric acid (17 mg, 0.09 mmol). The mixture was stirred until a homogeneous solution was obtained then concentrated in vacuo to give (+/−)-2-(8-methoxy-2-methyl-2,3,4,5-tetrahydro-1H-benzo[c]azepin-5-yl)thiazole, citrate salt (41 mg, 100%) as a white solid: $^1$H NMR (300 MHz CD$_3$OD) δ 7.82 (d, J=3.3 Hz, 1H), 7.52 (d, J=3.3 Hz, 1H), 7.26-7.14 (m, 1H), 7.04-6.93 (m, 2H), 4.75-4.85 (m, 1H), 4.37-4.22 (m, 2H), 3.83 (s, 3H), 3.75-3.63 (m, 1H), 3.55-3.43 (m, 1H), 2.85-2.67 (m, 8H), 2.58-2.43 (m, 1H); ESI MS m/z 275 [M+H]$^+$.

Example 121

Preparation of (+/−)-2-Methyl-8-morpholino-5-(4-methyl-3,4-dihydro-2H-benzo[b][1,4]-oxazin-7-yl)-2,3-dihydro-1H-benzo[c]azepine, L-tartrate salt Step A: A mixture of 5-bromophthalide (21.7 g, 0.10 mol) and dichlorotriphenylphosphorane (45.6 g, 0.13 mol) was heated at 180° C. for 2 hours. The mixture was allowed to cool to 0° C. and then methanol (26 mL) and pyridine (26 mL) were added. The reaction mixture was stirred at room temperature for 1 hour. Hexanes (520 mL) and water (260 mL) were added to the mixture. The resultant precipitate was removed by filtration. The organic layer of the filtrate was separated and washed with brine, dried over sodium sulfate and concentrated under reduced pressure to give the desired benzyl chloride (25.8 g, 98%), which was used in the next step without further purification.

Step B: To a mixture of the benzyl chloride (25.8 g, 97.9 mmol) from step A above and ethyl 3-(methylamino)-propionate (14.0 g, 107 mmol) was added potassium carbonate (40.6 g, 294 mmol). The reaction mixture was heated under reflux for 6 hours. The solvent was removed under reduced pressure. The residue was partitioned between ethyl acetate and water. The organic layer was separated and the aqueous layer was extracted with ethyl acetate (2×). The combined organic extracts were washed with brine, dried over sodium sulfate and concentrated under reduced pressure to provide the desired benzylamine (34.5 g, 98%), which was used in the next step without further purification: $^1$H NMR (500 MHz, CDCl$_3$) δ 7.73 (d, J=1.7 Hz, 1H), 7.64 (d, J=8.3 Hz, 1H), 7.42 (dd, J=8.3, 1.9 Hz, 1H), 4.14 (q, J=7.1 Hz, 2H), 3.87 (s, 2H), 3.80 (s, 2H), 2.76 (t, J=7.2 Hz, 2H), 2.48 (t, J=7.2 Hz, 2H), 2.20 (s, 3H), 1.24 (t, J=7.1 Hz, 3H); ESI MS m/z 358, 360 [M+H]$^+$.

Step C: To a solution of the benzylamine (34.5 g, 96.3 mmol) from step B above in tetrahydrofuran (500 mL) at −30° C. was added 1M solution of potassium t-butoxide (203 mL, 203 mmol). The reaction mixture was stirred between −30° C. to −20° C. for 10 minutes and then quenched with saturated ammonium chloride solution. The mixture was extracted with ethyl acetate (3×). The combined organic extracts were washed with brine, dried over sodium sulfate and concentrated under reduced pressure to give a mixture of the desired ethyl and methyl esters (32.2 g, 99%), which was used in the next step without further purification.

Step D: To a mixture of the esters (32.0 g, 100 mmol) from step C above and acetic acid (75 mL) in concentrated hydrochloric acid (150 mL) was added sodium iodide (22.5 g, 0.15 mmol). The reaction mixture was heated at 110° C. for 20 hours. Most of solvent was removed under reduced pressure. The residue was neutralized to pH>8 and then extracted with dichloromethane (3×). The combined organic extracts were washed with brine, dried over sodium sulfate and concentrated under reduced pressure. The residue obtained was purified by flash column chromatography (3-5% methanol/dichloromethane) to give the desired ketone (14.8 g, 48% over 4 steps) as a dark brown semi-solid: $^1$H NMR (500 MHz, CDCl$_3$) δ 7.64 (d, J=8.2 Hz, 1H), 7.50 (dd, J=8.2, 1.9 Hz, 1H), 7.37 (d, J=1.8 Hz, 1H), 3.89 (s, 2H), 2.87-2.82 (m, 4H), 2.43 (s, 3H); ESI MS m/z 254, 256 [M+H]$^+$.

Step E: To a solution of 7-bromo-benzoxazine (1.01, 4.41 mmol) in tetrahydrofuran (10 mL) at −78° C. was added 2.5M n-butyllithium in hexanes (1.7 mL, 4.25 mmol). The reaction mixture was stirred at −78° C. for 20 minutes and then transferred into a −78° C. cooled solution of the ketone from step D (1.02 g, 4.01 mmol) in tetrahydrofuran (10 mL). The reaction mixture was stirred at −78° C. for 3 hours and then allowed to warm to room temperature overnight. The mixture was quenched with saturated ammonium chloride solution and extracted with ethyl acetate (3×). The combined organic extracts were washed with brine, dried over sodium sulfate and concentrated under reduced pressure. The residue was purified by flash column chromatography (3 to 5% methanol/dichloromethane) to give the desired tertiary alcohol (300 mg, 37%): $^1$H NMR (500 MHz, CDCl$_3$) δ 7.32 (br, 2H), 7.25 (s, 1H), 6.67 (d, J=8.3 Hz, 1H), 6.63 (d, J=1.8 Hz, 1H), 6.60 (d, J=8.4 Hz, 1H), 4.28 (t, J=4.4 Hz, 2H), 3.72 (d, J=14.9 Hz, 1H), 3.54 (d, J=14.9 Hz, 1H), 3.27 (t, J=4.4 Hz, 2H), 3.04-2.99 (m, 1H), 2.88 (s, 3H), 2.88-2.84 (m, 1H), 2.46-2.33 (m, 2H), 2.31 (s, 3H); ESI MS m/z 403, 405 [M+H]$^+$.

Step F: A mixture of the tertiary alcohol (300 mg, 0.744 mmol) from step E above and trifluoroacetic acid (2 mL) in dichloromethane (10 mL) was stirred at room temperature for 30 minutes. The resultant mixture was diluted with dichloromethane (100 mL) and neutralized with saturated sodium bicarbonate. The organic layer was separated and washed with brine, dried over sodium sulfate and concentrated under reduced pressure to give (Z)-7-(8-bromo-2-methyl-2,3-dihydro-1H-benzo[c]azepin-5-yl)-4-methyl-3,4-dihydro-2H-benzo[b][1,4]oxazine (270 mg, 94%), which was used in the next step without further purification: $^1$H NMR (500 MHz, CDCl$_3$) δ 7.56 (d, J=1.8 Hz, 1H), 7.47 (dd, J=8.3, 1.8 Hz, 1H), 7.11 (d, J=8.3 Hz, 1H), 6.75 (dd, J=8.3, 2.0 Hz, 1H), 6.71 (d, J=2.0 Hz, 1H), 6.60 (d, J=8.3 Hz, 1H), 6.37 (t, J=7.3 Hz, 1H), 4.29 (t, J=4.4 Hz, 2H), 3.64 (s, 2H), 3.30 (t, J=4.4 Hz, 2H), 2.95 (d, J=6.8 Hz, 2H), 2.91 (s, 3H), 2.53 (s, 3H); ESI MS m/z 385, 387 [M+H]$^+$.

Step G: To a solution of the dihydrobenzazepine (270 mg, 0.70 mmol) from step F above in pyridine (15 mL) were added potassium carbonate (967 mg, 7.0 mmol) and p-toluenesulfonylhydrazide (672 mg, 3.5 mmol) in batches. The reaction solution was heated under reflux for 24 hours and then cooled to room temperature. The resultant reaction mixture was filtered through Celite. The Celite bed was washed with ethyl acetate. The filtrate was concentrated under reduced pressure. The residue dissolved in ethyl acetate was washed with water and brine, dried over sodium sulfate and concentrated under reduced pressure. The residue obtained was purified by flash column chromatography (3% methanol/dichloromethane) to give the desired 8-bromotetrahydrobenzazepine (176 mg, 65%): $^1$H NMR (500 MHz, CDCl$_3$) δ 7.28 (d, J=2.1 Hz, 1H), 7.19 (dd, J=8.2, 1.7 Hz, 1H), 6.64 (d, J=8.2 Hz, 2H), 6.60-6.56 (m, 2H), 4.31 (t, J=4.4 Hz, 2H), 4.12 (d, J=9.9 Hz, 1H), 3.83 (br, 1H), 3.69 (d, J=14.2 Hz, 1H), 3.26 (t, J=4.4 Hz, 2H), 3.13-3.10 (m, 1H), 2.95-2.90 (m, 1H), 2.89 (s, 3H), 2.32 (s, 3H), 2.24-2.17 (m, 1H), 2.06-2.04 (m, 1H); ESI MS m/z 387, 389 [M+H]$^+$.

Step H: To a solution of the 8-bromotetrahydrobenzazepine (72 mg, 0.186 mmol) from step G above in toluene (2 mL) was added morpholine (33 mg, 0.372 mmol), cesium carbonate (182 mg, 0.558 mmol), and 2-(dicyclohexylphosphino)-2',4',6'-tri-i-propyl-1,1'-biphenyl (18 mg, 0.037 mmol). The resultant mixture was degassed with argon for 5 minutes, and then added palladium(II) acetate (5 mg, 0.019 mmol). The reaction solution was heated at reflux under argon for 2 hours, and then cooled to room temperature. The resultant mixture was partitioned between ethyl acetate and water. The combined organic extracts were washed with brine, dried over sodium sulfate and concentrated under reduced pressure. The crude product obtained was purified by flash column chromatography [3% to 5% methanol (containing 10% concentrated ammonium hydroxide)/dichloromethane] to give the 8-morpholinobenzazepine (40 mg, 55%): $^1$H NMR (CDCl$_3$, 500 MHz) δ 6.72 (d, J=2.5 Hz, 1H), 6.65-6.59 (m, 5H), 4.31 (t, J=4.4 Hz, 2H), 4.11 (d, J=8.8 Hz, 1H), 3.85-3.83 (m, 5H), 3.69 (d, J=13.8 Hz, 1H), 3.25 (t, J=4.4 Hz, 2H), 3.12-3.08 (m, 5H), 2.93-2.90 (m, 1H), 2.88 (s, 3H), 2.33 (s, 3H), 2.24-2.17 (m, 1H), 2.07 (br, 1H); ESI MS m/z 394 [M+H]$^+$.

Step I: To a solution of the 8-morpholinobenzazepine from step H (40 mg, 0.102 mmol) in methanol (1 mL) was added L-tartaric acid (15.3 mg, 0.102 mmol). The solvent was removed under reduced pressure. The residue was dissolved with acetonitrile (1 mL) and water (0.5 mL). The resultant solution was lyophilized overnight to give (+/−)-2-methyl-8-morpholino-5-(4-methyl-3,4-dihydro-2H-benzo[b][1,4]-oxazin-7-yl)-2,3-dihydro-1H-benzo[c]azepine, L-tartrate salt (45 mg, 99%, AUC HPLC 96.8%) as an off-white solid: $^1$H NMR (CD$_3$OD, 500 MHz) δ 7.01 (d, J=1.9 Hz, 1H), 6.91-6.87 (m, 2H), 6.69 (d, J=8.3 Hz, 1H), 6.56 (d, J=8.0 Hz, 1H), 4.43-4.40 (m, 1H), 4.39 (s, 2H), 4.30-4.28 (m, 2H), 4.25 (t, J=4.4 Hz, 2H), 3.82 (t, J=4.7 Hz, 4H), 3.50-3.44 (m, 2H), 3.22 (t, J=4.4 Hz, 2H), 3.15 (t, J=4.7 Hz, 4H), 2.86 (s, 3H), 2.82 (s, 3H), 2.48 (br, 1H), 2.34-2.31 (m, 1H); ESI MS m/z 394 [M+H]$^+$.

Example 122

Preparation of (+/−)-2-Methyl-8-(6-methylpyridazin-3-yl)-5-(4-methyl-3,4-dihydro-2H-benzo[b][1,4]-oxazin-7-yl)-2,3-dihydro-1H-benzo[c]azepine, L-tartrate salt Pursuant to the general method described above in Example 121, the following product was prepared: (+/−)-2-Methyl-8-(6-methylpyridazin-3-yl)-5-(4-methyl-3,4-dihydro-2H-benzo[b][1,4]-oxazin-7-yl)-2,3-dihydro-1H-benzo[c]azepine, L-tartrate salt: $^1$H NMR (CD$_3$OD, 500 MHz) δ 8.17 (s, 1H), 8.09 (d, J=8.8 Hz, 1H), 7.99 (d, J=6.1 Hz, 1H), 7.69 (d, J=8.8 Hz, 1H), 7.13 (br, 1H), 6.73 (d, J=8.2 Hz, 1H), 6.63 (d, J=7.7 Hz, 1H), 6.55 (s, 1H), 4.67 (br, 1H), 4.51-4.47 (m, 1H), 4.44 (s, 3H), 4.27 (t, J=4.3 Hz, 2H), 3.60 (br, 2H), 3.24 (t, J=4.3 Hz, 2H), 2.91 (s, 3H), 2.88 (s, 3H), 2.73 (s, 3H), 2.60-2.55 (m, 1H), 2.42-2.39 (m, 1H); ESI MS m/z 401 [M+H]$^+$.

Example 123

Preparation of (+/−)-2-Methyl-8-morpholino-5-(2,3-dihydrobenzo[b][1,4]-dioxin-6-yl)-2,3-dihydro-1H-benzo[c]azepine, L-tartrate salt Pursuant to the general method described above in Example 121, the following product was prepared: (+/−)-2-Methyl-8-morpholino-5-(2,3-dihydrobenzo[b][1,4]-dioxin-6-yl)-2,3-dihydro-1H-benzo[c]azepine, L-tartrate salt: $^1$H NMR (CD$_3$OD, 500 MHz) δ 7.02 (s, 1H), 6.90 (d, J=7.9 Hz, 1H), 6.83-6.81(m, 2H), 6.61 (br, 2H), 4.42 (br, 1H), 4.41 (s, 2H), 4.35 (d, J=8.4 Hz, 1H), 4.27 (d, J=13.8 Hz, 1H), 4.22 (d, J=1.6 Hz, 4H), 3.83-3.81 (m, 4H), 3.51 (br, 2H), 3.16-3.14 (m, 4H), 2.83 (s, 3H), 2.48 (br, 1H), 2.35-2.32 (m, 1H); ESI MS m/z 381 [M+H]$^+$.

Example 124

Preparation of (−)-2-Methyl-8-(6-methylpyridazin-3-yl)-5-(2,3-dihydrobenzo[b][1,4]-dioxin-6-7-yl)-2,3-dihydro-1H-benzo[c]azepine, L-tartrate salt and (+)-2-Methyl-8-(6-methylpyridazin-3-yl)-5-(2,3-dihydrobenzo[b][1,4]-dioxin-6-7-yl)-2,3-dihydro-1H-benzo[c]azepine, L-tartrate salt Pursuant to the general method described above in Example 121, the following products were prepared: (−)-2-Methyl-8-(6-methylpyridazin-3-yl)-5-(2,3-dihydrobenzo[b][1,4]-dioxin-6-7-yl)-2,3-dihydro-1H-benzo[c]azepine, L-tartrate salt: $^1$H NMR (CD$_3$OD, 500 MHz) δ 8.17 (br, 1H), 8.09 (d, J=8.6 Hz, 1H), 7.99 (d, J=7.5 Hz, 1H), 7.69 (d, J=8.6 Hz, 1H), 7.08 (br, 1H), 6.87 (d, J=8.1 Hz, 1H), 6.68 (d, J=7.9 Hz, 2H), 4.69 (br, 1H), 4.55 (d, J=7.7 Hz, 1H), 4.46 (d, J=13.3 Hz, 1H), 4.41 (s, 2H), 4.25 (s, 4H), 3.60 (br, 2H), 2.90 (s, 3H), 2.73 (s, 3H), 2.55 (br, 1H), 2.42-2.39 (m, 1H); ESI MS m/z 388 [M+H]$^+$; (+)-2-Methyl-8-(6-methylpyridazin-3-yl)-5-(2,3-dihydrobenzo[b][1,4]-dioxin-6-7-yl)-2,3-dihydro-1H-benzo[c]azepine, L-tartrate salt: $^1$H NMR (CD$_3$OD, 500 MHz) δ 8.16 (br, 1H), 8.09 (d, J=8.7 Hz, 1H), 7.99 (d, J=7.6 Hz, 1H), 7.69 (d, J=8.7 Hz, 1H), 7.08 (br, 1H), 6.87 (d, J=8.2 Hz, 1H), 6.69-6.67 (m, 2H), 4.67 (br, 1H), 4.55 (d, J=8.1 Hz, 1H), 4.45 (d, J=13.3 Hz, 1H), 4.40 (s, 2H), 3.59 (br, 2H), 2.89 (s, 3H), 2.72 (s, 3H), 2.55 (br, 1H), 2.42-2.39 (m, 1H); ESI MS m/z 388 [M+H]$^+$.

Example 125

Preparation of (Z)-8-methoxy-2-methyl-5-p-tolyl-2,3-dihydro-1H-benzo[c]azepine, L-tartrate salt Step A: To a solution of m-anisaldehyde (205 g, 1.5 mol) in methanol (800 mL) at room temperature was added methylamine (40% in water, 130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extract was extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 minutes, cooled to room temperature and concentrated in vacuo. The residue obtained was dissolved in dichloromethane, washed with aqueous sodium bicarbonate, dried over sodium sulfate and concentrated in vacuo. The crude product obtained was used in the next step without further purification: $^1$H NMR (500 MHz, CDCl$_3$) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 h and then concentrated in vacuo. The residue obtained was dissolved in water, adjusted to pH 7 and extracted with chloroform (3×) and mixture of 3:1 chloroform/2-propanol (3×). The combined organic extracts were dried over sodium sulfate and concentrated in vacuo to give the desired acid (25 g, 56%) as a light green oil, which was used in the next step without further purification.

Step D: A mixture of the acid (24 g, 107 mmol) from step C above and polyphosphoric acid (180 g) was heated at 100-110° C. for 18 hours. The resultant slurry was dissolved in dichloromethane and water, neutralized to pH>8 and then extracted with dichloromethane (5×). The combined organic extracts were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: $^1$H NMR (500 MHz, CDCl$_3$) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]$^+$.

Step E: To a solution of the ketone (2.6 g, 12.7 mmol) in THF (100 mL) at −78° C. was added a solution of lithium bis(trimethylsilyl)amide (14 mL, 14 mmol, 1M in THF) slowly. The reaction solution was stirred at −78° C. for 30 minutes and then a solution of N-phenyl trifluoromethanesulfonimide (5.0 g, 14 mmol) in THF (20 mL) was added to it slowly. The reaction solution was allowed to warm to room temperature, stirred for 10 hours, quenched with aqueous saturated sodium bicarbonate and then extracted with ethyl acetate (3×). The combined organic extracts were washed with brine, dried over sodium sulfate and concentrated in vacuo. The crude product obtained was purified by flash column chromatography (dichloromethane to 97:3 dichloromethane/methanol) to give the desired vinyl triflate (3.8 g, 89%) as a dark black oil: $^1$H NMR (500 MHz, CDCl$_3$) δ 7.50 (d, J=8.5 Hz, 1H), 6.90 (dd, J=8.5, 2.5 Hz, 1H), 6.78 (d, J=2.5 Hz, 1H), 6.02 (t, J=5.5 Hz, 1H), 3.84 (s, 3H), 3.70 (s, 2H), 3.34 (d, J=5.5 Hz, 2H), 2.43 (s, 3H).

Step F: To a solution of the vinyl triflate (3.0 g, 8.9 mmol) from step E above in THF (100 mL) and water (15 mL) were added 4-tolylboronic acid (1.5 g, 10.7 mmol), cesium carbonate (8.7 g, 26.7 mmol) and tricyclohexylphosphine (0.30 g, 1.07 mmol). The resultant mixture was flushed with argon for 10 minutes and then palladium(II) acetate (0.20 g, 0.9 mmol) was added to it. The reaction solution was purged with argon for 5 minutes and then stirred at 75° C. for 3 hours. The reaction mixture was cooled to room temperature, diluted with ethyl acetate, washed with aqueous saturated sodium bicarbonate and brine, dried over sodium sulfate and concentrated in vacuo. The residue obtained was purified by flash column chromatography (99:0.9:0.1 to 92:7.2:0.8 dichloromethane/methanol/concentrated ammonium hydroxide) to give the desired 8-methoxydihydrobenzazepine (1.2 g, 48%) as a dark oil: $^1$H NMR (500 MHz, CDCl$_3$) δ 7.21 (d, J=8.0 Hz, 2H), 7.14 (d, J=8.0 Hz, 2H), 7.03 (d, J=8.5 Hz, 1H), 6.92 (d, J=3.0 Hz, 1H), 6.83 (dd, J=8.5, 2.5 Hz, 1H), 6.37 (t, J=7.0 Hz, 1H), 3.85 (s, 3H), 3.54 (s, 2H), 2.86 (d, J=7.0 Hz, 1H), 2.44 (s, 3H), 2.37 (s, 3H); ESI MS m/z 280 [M+H]$^+$.

Step G: To a solution of the 8-methoxydihydrobenzazepine (42 mg, 0.15 mmol) from step F above in methanol (2 mL) were added L-tartaric acid (22.5 mg, 0.15 mmol) and water (10 mL). The resultant solution was lyophilized overnight to provide (Z)-8-methoxy-2-methyl-5-p-tolyl-2,3-dihydro-1H-benzo[c]azepine, L-tartrate salt (64 mg, 99.7% AUC HPLC) as an off-white solid: $^1$H NMR (CD$_3$OD, 500 MHz) δ 7.24-7.21 (m, 5H), 7.15-7.09 (m, 2H), 6.37 (t, J=7.0 Hz, 1H), 4.40 (s, 2H), 4.10 (s, 2H), 3.90 (s, 3H), 3.39-3.38 (m, 2H), 2.91 (s, 2H), 2.37 (s, 3H); ESI MS m/z 280 [M+H]$^+$.

Example 126

Preparation of (Z)-2-methyl-8-(6-methylpyridazin-3-yl)-5-p-tolyl-2,3-dihydro-1H-benzo[c]azepine, L-tartrate salt Step A: To a solution of m-anisaldehyde (205 g, 1.5 mol) in methanol (800 mL) at room temperature was added methylamine (40% in water) (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extract was extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 minutes and then cooled to room temperature, concentrated in vacuo. The residue obtained was dissolved in dichloromethane, washed with aqueous sodium bicarbonate, dried over sodium sulfate and concentrated in vacuo. The crude product was used in the next step without further purification: $^1$H NMR (500 MHz, CDCl$_3$) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 h and then concentrated in vacuo. The residue obtained was dissolved in water, adjusted to pH 7 and extracted with chloroform (3×) and mixture of 3:1 chloroform/2-propanol (3×). The combined organic extracts were dried over sodium sulfate and concentrated in vacuo to give the desired acid (25 g, 56%) as a light green oil, which was used in the next step without further purification.

Step D: A mixture of the acid (24 g, 107 mmol) from step C above and polyphosphoric acid (180 g) was heated at 100-110° C. for 18 hours. The resultant slurry was dissolved in dichloromethane and water, neutralized to pH>8 and then extracted with dichloromethane (5×). The combined organic extracts were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: $^1$H NMR (500 MHz, CDCl$_3$) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]$^+$.

Step E: To a solution of the ketone (2.6 g, 12.7 mmol) in THF (100 mL) at −78° C. was added a solution of lithium bis(trimethylsilyl)amide (14 mL, 14 mmol, 1M in THF) slowly. The reaction solution was stirred at −78° C. for 30 minutes and then a solution of N-phenyl trifluoromethanesulfonimide (5.0 g, 14 mmol) in THF (20 mL) was added to it slowly. The reaction solution was let to warm to room temperature, stirred for 10 hours, quenched with aqueous saturated sodium bicarbonate and then extracted with ethyl acetate (3×). The combined organic extracts were washed with brine, dried over sodium sulfate and concentrated in vacuo. The crude product obtained was purified by flash column chromatography (dichloromethane to 97:3 dichloromethane/methanol) to give the desired vinyl triflate (3.8 g, 89%) as a dark black oil: $^1$H NMR (500 MHz, CDCl$_3$) δ 7.50 (d, J=8.5 Hz, 1H), 6.90 (dd, J=8.5, 2.5 Hz, 1H), 6.78 (d, J=2.5 Hz, 1H), 6.02 (t, J=5.5 Hz, 1H), 3.84 (s, 3H), 3.70 (s, 2H), 3.34 (d, J=5.5 Hz, 2H), 2.43 (s, 3H).

Step F: To a solution of the vinyl triflate (3.0 g, 8.9 mmol) from step E above in THF (100 mL) and water (15 mL) were added 4-tolylboronic acid (1.5 g, 10.7 mmol), cesium carbonate (8.7 g, 26.7 mmol) and tricyclohexylphosphine (0.30 g, 1.07 mmol). The resultant mixture was flushed with argon for 10 minutes and then palladium(II) acetate (0.20 g, 0.9 mmol) was added to it. The reaction solution was purged with argon for 5 minutes and then stirred at 75° C. for 3 hours. The reaction mixture was cooled to room temperature, diluted with ethyl acetate, washed with aqueous saturated sodium bicarbonate and brine, dried over sodium sulfate and concentrated in vacuo. The residue obtained was purified by flash column chromatography (99:0.9:0.1 to 92:7.2:0.8 dichloromethane/methanol/concentrated ammonium hydroxide) to give the desired 8-methoxydihydrobenzazepine (1.2 g, 48%) as a dark oil: $^1$H NMR (500 MHz, CDCl$_3$) δ 7.21 (d, J=8.0 Hz, 2H), 7.14 (d, J=8.0 Hz, 2H), 7.03 (d, J=8.5 Hz, 1H), 6.92 (d, J=3.0 Hz, 1H), 6.83 (dd, J=8.5, 2.5 Hz, 1H), 6.37 (t, J=7.0 Hz, 1H), 3.85 (s, 3H), 3.54 (s, 2H), 2.86 (d, J=7.0 Hz, 1H), 2.44 (s, 3H), 2.37 (s, 3H); ESI MS m/z 280 [M+H]$^+$.

Step G: To a solution of the 8-methoxydihydrobenzazepine (1.2 g, 4.3 mmol) from step F above in acetic acid (40 mL) was added hydrobromic acid (48% solution in water, 40 mL). The reaction solution was heated at 105° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (1.1 g, 96%) as a brown solid. The crude product was used in the next step without further purification: $^1$H NMR (CDCl$_3$, 500 MHz) δ 7.23 (d, J=8.0 Hz, 2H), 7.15 (d, J=8.0 Hz, 2H), 6.98 (d, J=8.5 Hz, 1H), 6.88 (d, J=2.5 Hz, 1H), 6.81 (dd, J=8.5, 2.5 Hz, 1H), 6.35 (t, J=7.0 Hz, 1H), 3.44 (s, 2H), 3.05 (d, J=7.5 Hz, 2H), 2.49 (s, 3H), 2.37 (s, 3H); ESI MS m/z 266 [M+H]$^+$.

Step H: To a solution of the phenol (1.1 g, 4.1 mmol) from step G above in dichloromethane (50 mL) at 0° C. were added pyridine (0.66 mL, 8.2 mmol) and triflic anhydride (0.77 mL, 4.6 mmol). The resultant reaction mixture was allowed to warm to room temperature and stirred for 16 hours. The reaction solution was then diluted with dichloromethane, washed with aqueous saturated sodium bicarbonate, dried over sodium sulfate and concentrated in vacuo to give the desired triflate (1.8 g, quantitative) as a reddish oil: $^1$H NMR (CDCl$_3$, 500 MHz) δ 7.28 (d, J=1.0 Hz, 1H), 7.19 (d, J=1.5 Hz, 2H), 7.16 (s, 4H), 6.50 (t, J=7.0 Hz, 1H), 3.57 (s, 2H), 2.84 (d, J=7.0 Hz, 2H), 2.43 (s, 3H), 2.38 (s, 3H); ESI MS m/z 398 [M+H]$^+$.

Step I: To a solution of the triflate (1.1 g, 2.8 mmol) from step H above and bis(pinacolato)diboron (0.84 g, 3.3 mmol) in DMSO (20 mL) was added potassium acetate (0.83 g, 8.5 mmol). The resultant solution was purged with argon for 10 minutes, and then dichloro[1,1'-bis(diphenylphosphino)ferrocene]palladium(II) dichloromethane adduct (0.23 g, 0.28 mmol) was added. The reaction solution was degassed again with argon for 5 minutes and heated at 80° C. for 90 minutes. The reaction solution was then cooled to room temperature, diluted with ethyl acetate, washed with water (2×) and brine, dried over sodium sulfate and concentrated in vacuo. The crude product obtained was used in the next step without further purification: ESI MS m/z 376 [M+H]$^+$.

Step J: To a mixture of the boronate ester (2.8 mmol) from step I above, 3-chloro-6-methylpyridazine (0.72 g, 5.6 mmol) and sodium carbonate (0.89 g, 8.4 mmol) were added DMF (32 mL) and water (8 mL). The resultant solution was flushed with argon for 10 minutes, and then dichloro[1,1'-bis(diphenylphosphino)ferrocene]palladium(II) dichloromethane adduct (0.11 g, 0.14 mmol) was added to it. The reaction mixture was flushed with argon for 5 minutes and then heated at 80° C. for 2 hours. The reaction solution was then cooled to room temperature, diluted with ethyl acetate, washed with 1:1 water/brine (2×), dried over sodium sulfate and concentrated in vacuo. The crude product obtained was purified by flash column chromatography (dichloromethane to 92:7.2:0.8 dichloromethane/methanol/concentrated ammonium hydroxide) to give the desired dihydrobenzazepine (0.58 g, 61%) as a brown solid: $^1$H NMR (CDCl$_3$, 500 MHz) δ 8.09 (d, J=1.5 Hz, 1H), 8.01 (dd, J=8.0, 2.0 Hz, 1H), 7.80 (d, J=9.0 Hz, 1H), 7.40 (d, J=8.5 Hz, 1H), 7.30-7.26 (m, 1H), 7.23 (d, J=8.0 Hz, 2H), 7.17 (d, J=8.5 Hz, 2H), 6.51 (t, J=7.0 Hz, 1H), 3.68 (s, 2H), 2.92 (d, J=7.0 Hz, 2H), 2.78 (s, 3H), 2.48 (s, 3H), 2.38 (s, 3H); ESI MS m/z 342 [M+H]$^+$.

Step K (MHU-H-90): To a solution of the dihydrobenzazepine (29 mg, 0.08 mmol) from step J above in methanol (2 mL) were added L-tartaric acid (12.7 mg, 0.08 mmol) and water (10 mL). The resultant solution was lyophilized overnight to provide (Z)-2-methyl-8-(6-methylpyridazin-3-yl)-5-p-tolyl-2,3-dihydro-1H-benzo[c]azepine, L-tartrate salt (41 mg, 98.4% AUC HPLC) as an off-white solid: $^1$H NMR (CD$_3$OD, 500 MHz) δ 8.38 (s, 1H), 8.18 (t, J=8.5 Hz, 2H), 7.74 (d, J=9.0 Hz, 1H), 7.38 (d, J=8.0 Hz, 1H), 7.28 (d, J=8.0 Hz, 2H), 7.24 (d, J=8.0 Hz, 2H), 6.56 (br s, 1H), 4.40 (s, 2H), 4.22 (s, 2H), 3.44 (br, 2H), 2.94 (s, 3H), 2.76 (s, 3H), 2.39 (s, 3H); ESI MS m/z 342 [M+H]$^+$.

Example 127

Preparation of (Z)-2-methyl-8-(4-(pyrimidin-2-yl)piperazin-1-yl)-5-p-tolyl-2,3-dihydro-1H-benzo[c]azepine, L-tartrate salt Pursuant to the general method described above in Example 126, the following product was prepared: (Z)-2-methyl-8-(4-(pyrimidin-2-yl)piperazin-1-yl)-5-p-tolyl-2,3-dihydro-1H-benzo[c]azepine, L-tartrate salt: $^1$H NMR (CD$_3$OD, 500 MHz) δ 8.36 (d, J=5.0 Hz, 2H), 7.24-7.19 (m, 5H), 7.16 (dd, J=8.5, 2.5 Hz, 1H), 7.09 (d, J=8.5 Hz, 1H), 6.64 (t, J=5.0 Hz, 1H), 6.31 (t, J=7.0 Hz, 1H), 4.40 (s, 2.4H), 4.11 (br s, 2H), 3.99 (t, J=5.0 Hz, 4H), 3.47-3.41 (m, 6H), 2.92 (s, 3H), 2.37 (s, 3H); ESI MS m/z 412 [M+H]$^+$.

Example 128

Preparation of (E)-5-(2,4-difluorophenyl)-2-methyl-8-(4-methylpiperazin-1-yl)-2,3-dihydro-1H-benzo[c]azepine, L-tartrate salt Pursuant to the general method described above in Example 126, the following product was prepared: (E)-5-(2,4-difluorophenyl)-2-methyl-8-(4-methylpiperazin-1-yl)-2,3-dihydro-1H-benzo[c]azepine, L-tartrate salt: $^1$H NMR (CD$_3$OD, 500 MHz) δ 7.37 (td, J=8.5, 6.0 Hz, 1H), 7.20 (d, J=2.5 Hz, 1H), 7.07 (dd, J=8.5, 2.5 Hz, 1H), 7.04-6.98 (m, 2H), 6.95 (d, J=9.0 Hz, 1H), 6.31 (t, J=7.0 Hz, 1H), 4.38 (s, 2H), 4.09 (s, 2H), 3.45-3.41 (m, 6H), 2.90-2.88 (m, 7H), 2.56 (s, 3H); ESI MS m/z 370 [M+H]$^+$.

Example 129

Preparation of (E)-5-(2,4-difluorophenyl)-2-methyl-8-(6-methylpyridazin-3-yl)-2,3-dihydro-1H-benzo[c]azepine, L-tartrate salt Pursuant to the general method described above in Example 126, the following product was prepared: (E)-5-(2,4-difluorophenyl)-2-methyl-8-(6-methylpyridazin-3-yl)-2,3-dihydro-1H-benzo[c]azepine, L-tartrate salt: $^1$H NMR (CD$_3$OD, 500 MHz) δ 8.36 (s, 1H), 8.17-8.14 (m, 2H), 7.72 (d, J=8.5 Hz, 1H), 7.47 (q, J=8.0 Hz, 1H), 7.27 (d, J=8.5 Hz, 1H), 7.10-7.01 (m, 2H), 6.54 (br s, 1H), 4.41 (s, 2H), 4.23 (s, 2H), 3.44 (s, 2H), 2.92 (s, 3H), 2.75 (s, 3H); ESI MS m/z 364 [M+H]$^+$.

Example 130

Preparation of (Z)-8-methoxy-2-methyl-5-(pyridine-4-yl)-2,3-dihydro-1H-benzo[c]azepine, L-tartrate salt Pursuant to the general method described above in Example 126, the following product was prepared: (Z)-8-methoxy-2-methyl-5-(pyridine-4-yl)-2,3-dihydro-1H-benzo[c]azepine, L-tartrate salt: $^1$H NMR (CD$_3$OD, 500 MHz) δ 8.57 (d, J=6.0 Hz, 2H), 7.40 (dd, J=4.8, 1.3 Hz, 2H), 7.28 (s, 1H), 7.13 (s, 2H), 6.65 (t, J=7.1 Hz, 1H), 4.43 (s, 2H), 4.15 (s, 2H), 3.91 (s, 3H), 3.47 (d, J=6.8 Hz, 2H), 2.93 (s, 3H); ESI MS m/z 267 [M+H]$^+$.

Example 131

Preparation of (+)-5-(2-fluorophenyl)-2-methyl-8-(4-methylpiperazin-1-yl)-2,3,4,5-tetrahydro-1H-benzo[c]azepine, L-tartrate salt and (−)-5-(2-fluorophenyl)-2-methyl-8-(4-methylpiperazin-1-yl)-2,3,4,5-tetrahydro-1H-benzo[c]azepine, L-tartrate salt Step A: To a solution of m-anisaldehyde (205 g, 1.5 mol) in methanol (800 mL) at room temperature was added methylamine (130 mL of 40% in water, 1.5 mol). The resultant solution was cooled to 0° C. and sodium borohydride (83 g, 2.3 mol) was added to it in batches. The reaction solution was stirred at 0° C. for 2 hours and then it was warmed to room temperature, concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extracts were extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 minutes and then cooled to room temperature and concentrated in vacuo. The residue obtained was dissolved in dichloromethane, washed with aqueous sodium bicarbonate, dried over sodium sulfate and concentrated in vacuo. The crude product obtained was used in the next step without further purification: $^1$H NMR (500 MHz, CDCl$_3$) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 hours and then concentrated in vacuo. The residue obtained was dissolved in water, adjusted to pH 7, extracted with chloroform (3×) and 3:1 chloroform/2-propanol (3×). The combined organic extract were dried over sodium sulfate and concentrated in vacuo to give the desired acid (25 g, 56%) as a light green oil, which was used in the next step without further purification.

Step D: A mixture of the acid (24.0 g, 107 mmol) from step C above and polyphosphoric acid (180 g) was heated at 100-110° C. for 18 hours. The resultant slurry was dissolved in dichloromethane and water, basified with sodium bicarbonate and sodium carbonate to pH>8 and then extracted with dichloromethane (5×). The combined organic extract were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: $^1$H NMR (500 MHz, CDCl$_3$) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]$^+$.

Step E: To a solution of 2-bromofluorobenzene (0.66 mL, 6.0 mmol) in THF (25 mL) at −78° C. was added n-BuLi (2.4 mL, 6.0 mmol, 2.5 M in hexanes) dropwise. After the addition, the reaction solution was stirred at −78° C. for 30 minutes. To this solution was then added a cold (−78° C.) solution of the ketone (1.0 g, 5.0 mmol) from step D above in THF (5 mL) quickly. The reaction solution was stirred at −78° C. for 3 hours h and then quenched with saturated aqueous solution of sodium bicarbonate. The resultant mixture was warmed to room temperature, extracted with dichloromethane (3×), dried over sodium sulfate and concentrated in vacuo. The crude product obtained was purified by flash column chromatography (99:0.9:0.1 to 88:10.8:1.2 dichloromethane/methanol/concentrated ammonium hydroxide) to give the desired tertiary alcohol (0.76 g, 50%) as a reddish oil: $^1$H NMR (500 MHz, CDCl$_3$) δ 7.71 (t, J=7.5 Hz, 1H), 7.32-7.27 (m, 1H), 7.19 (td, J=7.5, 1.0 Hz, 1H), 7.01 (ddd, J=12.0, 8.5, 1.0 Hz, 1H), 6.81 (d, J=8.5 Hz, 1H), 6.67 (d, J=2.5 Hz, 1H), 6.59 (dd, J=8.5, 2.5 Hz, 1H), 5.25-4.70 (br, 1H), 3.95 (d, J=16.0 Hz, 1H), 3.76 (d, J=15.5 Hz, 1H), 3.76 (s, 3H), 3.18 (td, J=11.0, 6.5 Hz, 1H), 2.88-2.80 (m, 1H), 2.65 (ddd, J=11.5, 6.5, 3.0 Hz, 1H), 2.47 (s, 3H), 2.19 (ddd, J=14.5, 6.0, 3.0 Hz, 1H); ESI MS m/z 302 [M+H]$^+$.

Step F: To a solution of the tertiary alcohol (1.5 g, 5.0 mmol) from step E above in dichloromethane (150 mL) was added p-toluenesulfonic acid monohydrate (2.4 g, 12.5 mmol). The reaction solution was heated under reflux for 90 minutes and then cooled to room temperature, quenched with aqueous 2 N sodium hydroxide to pH>8 and extracted with dichloromethane (3×). The combined organic extracts were dried over sodium sulfate, filtered and concentrated in vacuo to give the desired dihydrobenzazepine (1.4 g, 99%) as a dark black oil: $^1$H NMR (CD$_3$OD, 500 MHz) δ 7.31-7.26 (m, 1H), 7.24 (td, J=7.5, 1.5 Hz, 1H), 7.12 (td, J=7.5, 1.0 Hz, 1H), 7.04 (ddd, J=10.0, 8.0, 1.0 Hz, 1H), 6.91 (s, 1H), 6.90 (d, J=6.0 Hz, 1H), 6.79 (dd, J=8.5, 2.5 Hz, 1H), 6.32 (t, J=7.5 Hz, 1H), 3.84 (s, 3H), 3.61 (s, 2H), 2.96 (d, J=7.0 Hz, 2H), 2.45 (s, 3H).

Step G: To a solution of the dihydrobenzazepine (1.3 g, 4.6 mmol) from step F above in acetic acid (70 mL) was added hydrobromic acid (48% solution in water, 70 mL). The reaction solution was heated at 105° C. for 40 hours, cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (1.1 g, 89%) as a brown solid. The crude product was used in the next step without further purification: $^1$H NMR (CDCl$_3$, 500 MHz) δ 7.32-7.24 (m, 2H), 7.13 (td, J=7.5, 1.0 Hz, 1H), 7.06 (dd, J=5.0, 3.5 Hz, 1H), 6.88 (dd, J=3.0, 2.5 Hz, 1H), 6.85 (s, 1H), 6.78 (dd, J=8.5, 2.5 Hz, 1H), 6.33 (t, J=7.0 Hz, 1H), 3.50 (s, 2H), 3.11 (d, J=7.0 Hz, 2H), 2.51 (s, 3H); ESI MS m/z 270 [M+H]$^+$.

Step H: To a solution of the phenol (0.70 g, 2.6 mmol) from step G above in dichloromethane (30 mL) at 0° C. were added pyridine (0.42 mL, 5.2 mmol) and triflic anhydride (0.49 mL, 2.9 mmol). The resultant reaction mixture was stirred at 0° C. for 30 minutes and then room temperature for 16 hours. The reaction solution was then diluted with dichloromethane, washed with aqueous saturated sodium bicarbonate, dried over sodium sulfate and concentrated in vacuo. The crude product obtained was purified by flash column chromatography (dichloromethane to 97:3 dichloromethane/methanol) to give the desired triflate (0.62 g, 60%) as a yellow oil: $^1$H NMR (CDCl$_3$, 500 MHz) δ 7.35-7.31 (m, 1H), 7.27 (d, J=2.5 Hz, 1H), 7.24 (dd, J=7.5, 2.0 Hz, 1H), 7.17-7.14 (m, 2H), 7.08-7.04 (m, 2H), 6.45 (t, J=6.5 Hz, 1H), 3.65 (s, 2H), 2.97 (d, J=7.0 Hz, 2H), 2.46 (s, 3H); ESI MS m/z 402 [M+H]$^+$.

Step I: To a solution of the triflate (0.62 g, 1.5 mmol) from step H above in toluene (15 mL) were added 2-(dicyclohexylphosphino)-2',4',6'-tri-i-propyl-1,1'-biphenyl (73 mg, 0.15 mmol) and 1-methylpiperazine (0.34 mL, 3.1 mmol). The resultant mixture was flushed with argon for 5 minutes, and then palladium(II) acetate (17 mg, 0.08 mmol) and sodium tert-butoxide (0.30 g, 3.1 mmol) were added to it. The reaction solution was vacuumed and backfilled with argon (3×) and then heated at 100° C. for 14 hours. After cooling to room temperature, the resultant reaction mixture was diluted with dichloromethane, washed with water and brine, dried over sodium sulfate and concentrated in vacuo. The crude product obtained was purified by flash column chromatography (dichloromethane to 94:5.4:0.6 dichloromethane/methanol/concentrated ammonium hydroxide) and followed by preparative thin layer chromatography (98:1.8:0.2 dichloromethane/methanol/concentrated ammonium hydroxide) to give (E)-5-(2-fluorophenyl)-2-methyl-8-(4-methylpiperazin-1-yl)-2,3-dihydro-1H-benzo[c]azepine (0.23 g, 42%) as a reddish oil: $^1$H NMR (CDCl$_3$, 500 MHz) δ 7.30-7.25 (m, 1H), 7.23 (dd, J=7.5, 2.0 Hz, 1H), 7.11 (dt, J=7.5, 1.0 Hz, 1H), 7.04 (ddd, J=9.5, 8.0, 1.0 Hz, 1H), 6.90 (d, J=2.5 Hz, 1H), 6.86 (d, J=8.5 Hz, 1H), 6.79 (dd, J=8.5, 2.5 Hz, 1H), 6.28 (t, J=7.0 Hz, 1H), 3.60 (s, 2H), 3.27 (t, J=5.0 Hz, 4H), 2.98 (d, J=7.0 Hz, 2H), 2.57 (t, J=5.0 Hz, 4H), 2.46 (s, 3H), 2.35 (s, 3H); ESI MS m/z 352 [M+H]$^+$.

Step J: To a solution of the dihydrobenzazepine (0.23 g, 0.65 mmol) from step I above in pyridine (12 mL) were added potassium carbonate (0.9 g, 6.5 mmol) and p-toluenesulfonyl hydrazide (0.61 g, 3.3 mmol). The reaction solution was heated under reflux for 20 hours, and then additional p-toluenesulfonyl hydrazide (0.30 g, 1.7 mmol) was added. The resultant reaction solution was heated under reflux for 14 hours and then it was cooled to room temperature, diluted with dichloromethane, washed with water, dried over sodium sulfate and concentrated in vacuo. The crude product obtained was purified by flash column chromatography (dichloromethane to 99:9:1 dichloromethane/methanol/concentrated ammonium hydroxide) to give the desired benzazepine (0.14 g, 61%) as a dark oil: $^1$H NMR (CDCl$_3$, 500 MHz) δ 7.27-7.05 (m, 4H), 6.78 (d, J=2.5 Hz, 1H), 6.60 (dd, J=8.5, 2.5 Hz, 1H), 6.47 (d, J=8.0 Hz, 1H), 4.51 (d, J=10.0 Hz, 1H), 4.01 (d, J=14.5 Hz, 1H), 3.72 (d, J=14.0 Hz, 1H), 3.16 (t, J=5.0 Hz, 4H), 3.12-2.93 (m, 2H), 2.55 (t, J=5.0 Hz, 4H), 2.37 (s, 3H), 2.37-2.30 (m, 1H), 2.34 (s, 3H), 2.01-1.93 (m, 1H); ESI MS m/z 354 [M+H]$^+$.

Step K: The racemic benzazepine (0.13 g) from step J above was resolved by preparative chiral HPLC (CHIRALCEL OD column, using 85:15:0.1 heptane/2-propanol/diethylamine as the eluent) to give the (+)-enantiomer [[α]$^{25}_D$+ 8.0° (c 0.10, methanol)] (60 mg) as a light yellow oil and the (−)-enantiomer [[α]$^{25}_D$−16.2° (c 0.12, methanol)] (67 mg) as a light yellow oil.

Step L: To a solution of the (+)-enantiomer (57 mg, 0.16 mmol) from step K above in methanol (2 mL) were added L-tartaric acid (24 mg, 0.16 mmol) and water (10 mL). The resultant solution was lyophilized overnight to provide (+)-5-(2-fluorophenyl)-2-methyl-8-(4-methylpiperazin-1-yl)-2,3,4,5-tetrahydro-1H-benzo[c]azepine, L-tartrate salt (80 mg, >99.0% AUC HPLC) as a white solid: $^1$H NMR (CD$_3$OD, 500 MHz) δ 7.38-7.33 (m, 1H), 7.28-7.20 (m, 2H), 7.15 (dd, J=11.0, 8.5 Hz, 1H), 7.07 (d, J=2.5 Hz, 1H), 6.84 (dd, J=8.5, 2.5 Hz, 1H), 6.62-6.54 (br, 1H), 4.67 (dd, J=10.0, 1.5 Hz, 1H), 4.59 (d, J=14.0 Hz, 1H), 4.35 (s, 2H), 4.27 (d, J=14.0 Hz, 1H), 3.52-3.45 (br, 4H), 2.91 (t, J=5.0 Hz, 4H), 2.82 (s, 3H), 2.57 (s, 3H), 2.53-2.42 (m, 1H), 2.28 (dd, J=15.0, 2.0 Hz, 1H); ESI MS m/z 354 [M+H]$^+$.

Step M: To a solution of the (−)-enantiomer (63 mg, 0.18 mmol) from step K above in methanol (2 mL) were added L-tartaric acid (27 mg, 0.18 mmol) and water (10 mL). The resultant solution was lyophilized overnight to provide (−)-5-(2-fluorophenyl)-2-methyl-8-(4-methylpiperazin-1-yl)-2,3,4,5-tetrahydro-1H-benzo[c]azepine, L-tartrate salt (89 mg, >99.0% AUC HPLC) as a white solid: $^1$H NMR (CD$_3$OD, 500 MHz) δ 7.38-7.33 (m, 1H), 7.28-7.20 (m, 2H), 7.15 (dd, J=11.0, 8.5 Hz, 1H), 7.07 (d, J=2.5 Hz, 1H), 6.84 (dd, J=8.5, 2.5 Hz, 1H), 6.62-6.54 (br, 1H), 4.67 (dd, J=10.0, 1.5 Hz, 1H), 4.59 (d, J=14.0 Hz, 1H), 4.35 (s, 2H), 4.27 (d, J=14.0 Hz, 1H), 3.52-3.45 (br, 4H), 2.91 (t, J=5.0 Hz, 4H), 2.82 (s, 3H), 2.57 (s, 3H), 2.53-2.42 (m, 1H), 2.28 (dd, J=15.0, 2.0 Hz, 1H); ESI MS m/z 354 [M+H]$^+$.

Example 132

Preparation of (−)-2-methyl-8-(6-methylpyridazin-3-yl)-5-p-tolyl-2,3,4,5-tetrahydro-1H-benzo[c]azepine, L-tartrate salt and (+)-2-methyl-8-(6-methylpyridazin-3-yl)-5-p-tolyl-2,3,4,5-tetrahydro-1H-benzo[c]azepine, L-tartrate salt Pursuant to the general method described above in Example 131, the following products were prepared: (−)-2-methyl-8-(6-methylpyridazin-3-yl)-5-p-tolyl-2,3,4,5-tetrahydro-1H-benzo[c]azepine, L-tartrate salt: $^1$H NMR (CD$_3$OD, 500 MHz) δ 8.18 (d, J=1.5 Hz, 1H), 8.08 (d, J=9.0 Hz, 1H), 7.96 (d, J=8.0 Hz, 1H), 7.69 (d, J=9.0 Hz, 1H), 7.24 (d, J=8.0 Hz, 2H), 7.12 (d, J=7.5 Hz, 2H), 7.12-6.80 (br, 1H), 4.73-4.64 (br, 1H), 4.62 (d, J=8.0 Hz, 1H), 4.43 (d, J=13.0 Hz, 1H), 4.40 (s, 2H), 3.56 (br, 2H), 2.88 (s, 3H), 2.73 (s, 3H), 2.67-2.54 (br, 1H), 2.42 (d, J=15.0 Hz, 1H), 2.36 (s, 3H); ESI MS m/z 344 [M+H]$^+$; (+)-2-methyl-8-(6-methylpyridazin-3-yl)-5-p-tolyl-2,3,4,5-tetrahydro-1H-benzo[c]azepine, L-tartrate salt: $^1$H NMR (CD$_3$OD, 500 MHz) δ 8.18 (d, J=1.5 Hz, 1H), 8.08 (d, J=9.0 Hz, 1H), 7.96 (d, J=8.0 Hz, 1H), 7.69 (d, J=8.5 Hz, 1H), 7.24 (d, J=8.0 Hz, 2H), 7.12 (d, J=7.5 Hz, 2H), 7.12-6.80 (br, 1H), 4.73-4.64 (br, 1H), 4.62 (d, J=8.0 Hz, 1H), 4.43 (d, J=13.0 Hz, 1H), 4.40 (s, 2H), 3.58 (br, 2H), 2.89 (s, 3H), 2.73 (s, 3H), 2.67-2.54 (br, 1H), 2.42 (d, J=14.5 Hz, 1H), 2.36 (s, 3H); ESI MS m/z 344 [M+H]$^+$.

Example 133

Preparation of (+)-5-(2,4-difluorophenyl)-2-methyl-8-(6-methylpyridazin-3-yl)-2,3,4,5-tetrahydro-1H-benzo[c]azepine, L-tartrate salt and (−)-5-(2,4-difluorophenyl)-2-methyl-8-(6-methylpyridazin-3-yl)-2,3,4,5-tetrahydro-1H-benzo[c]azepine, L-tartrate salt Pursuant to the general method described above in Example 131, the following products were prepared: (+)-5-(2,4-difluorophenyl)-2-methyl-8-(6-methylpyridazin-3-yl)-2,3,4,5-tetrahydro-1H-benzo[c]azepine, L-tartrate salt: $^1$H NMR (CD$_3$OD, 500 MHz) δ 8.21 (s, 1H), 8.06 (d, J=8.5 Hz, 1H), 7.94 (d, J=8.0 Hz, 1H), 7.68 (d, J=9.0 Hz, 1H), 7.36 (q, J=7.0 Hz, 1H), 7.08 (t, J=9.0 Hz, 2H), 6.86 (d, J=7.5 Hz, 1H), 4.90-4.75 (m, 2H), 4.48 (d, J=13.5 Hz, 1H), 4.42 (s, 2H), 3.64-3.53 (br, 2H), 2.90 (s, 3H), 2.73 (s, 3H), 2.60-2.49 (br, 1H), 2.37 (d, J=13.0 Hz, 1H); ESI MS m/z 366 [M+H]$^+$; (−)-5-(2,4-difluorophenyl)-2-methyl-8-(6-methylpyridazin-3-yl)-2,3,4,5-tetrahydro-1H-benzo[c]azepine, L-tartrate salt: $^1$H NMR (CD$_3$OD, 500 MHz) δ 8.20 (d, J=1.5 Hz, 1H), 8.06 (d, J=8.5 Hz, 1H), 7.94 (d, J=8.0 Hz, 1H), 7.68 (d, J=9.0 Hz, 1H), 7.36 (q, J=7.0 Hz, 1H), 7.07 (t, J=9.0 Hz, 2H), 6.86 (d, J=7.5 Hz, 1H), 4.90-4.75 (m, 2H), 4.48 (d, J=13.5 Hz, 1H), 4.41 (s, 2H), 3.64-3.53 (br, 2H), 2.88 (s, 3H), 2.72 (s, 3H), 2.60-2.49 (br, 1H), 2.38-2.23 (br, 1H); ESI MS m/z 366 [M+H]$^+$.

Example 134

Preparation of (+/−)-8-Methoxy-2-methyl-5-(4-pyridin-4-yl)-2,3,4,5-tetrahydro-1H-benzo[c]azepine, L-tartrate salt Pursuant to the general method described above in Example 131, the following product was prepared: (+/−)-8-Methoxy-2-methyl-5-(4-pyridin-4-yl)-2,3,4,5-tetrahydro-1H-benzo[c]azepine, L-tartrate salt: $^1$H NMR (CD$_3$OD, 500 MHz) δ 8.53 (s, 2H), 7.27 (s, 2H), 7.06 (d, J=2.3 Hz, 1H), 6.92-6.81 (m, 2H), 4.57 (d, J=8.3 Hz, 1H), 4.52-4.40 (m, 1H), 4.40 (s, 2H), 4.23 (d, J=13.6 Hz, 1H), 3.82 (s, 3H), 3.57-3.49 (m, 2H), 2.82 (s, 3H), 2.60 (br, 1H), 2.51-2.39 (m, 1H); ESI MS m/z 269 [M+H]$^+$.

Example 135

Preparation of (+)-2-methyl-8-(6-methylpyridazin-3-yl)-5-o-tolyl-2,3,4,5-tetrahydro-1H-benzo[e]azepine, L-tartrate salt and (−)-2-methyl-8-(6-methylpyridazin-3-yl)-5-o-tolyl-2,3,4,5-tetrahydro-1H-benzo[c]azepine, L-tartrate salt Step A: To a solution of m-anisaldehyde (205 g, 1.5 mol) in methanol (800 mL) at room temperature was added methylamine (40% in water) (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extract was extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 minutes and then cooled to room temperature, concentrated in vacuo. The residue obtained was dissolved in dichloromethane, washed with aqueous sodium bicarbonate, dried over sodium sulfate and concentrated in vacuo. The crude product obtained was used in the next step without further purification: $^1$H NMR (500 MHz, CDCl$_3$) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 hours and then concentrated in vacuo. The residue obtained was dissolved in water, adjusted to pH 7 and extracted with chloroform (3×) and mixture of 3:1 chloroform/2-propanol (3×). The combined organic extracts were dried over sodium sulfate and concentrated in vacuo to give the desired acid (25 g, 56%) as a light green oil, which was used in the next step without further purification.

Step D: A mixture of the acid (24 g, 107 mmol) from step C above and polyphosphoric acid (180 g) was heated at 100-110° C. for 18 hours. The resultant slurry was dissolved in dichloromethane and water, neutralized to pH>8 and then extracted with dichloromethane (5×). The combined organic extracts were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: $^1$H NMR (500 MHz, CDCl$_3$) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]$^+$.

Step E: To a solution of the ketone (2.6 g, 12.7 mmol) in THF (100 mL) at −78° C. was added a solution of lithium bis(trimethylsilyl)amide (14 mL, 14 mmol, 1M in THF) slowly. The reaction solution was stirred at −78° C. for 30 minutes and then a solution of N-phenyl trifluoromethanesulfonimide (5.0 g, 14 mmol) in THF (20 mL) was added to it slowly. The reaction solution was let to warm to room temperature, stirred for 10 h, quenched with aqueous saturated sodium bicarbonate and then extracted with ethyl acetate (3×). The combined organic extracts were washed with brine, dried over sodium sulfate and concentrated in vacuo. The crude product obtained was purified by flash column chromatography (dichloromethane to 97:3 dichloromethane/methanol) to give the desired vinyl triflate (3.8 g, 89%) as a dark black oil: $^1$H NMR (500 MHz, CDCl$_3$) δ 7.50 (d, J=8.5 Hz, 1H), 6.90 (dd, J=8.5, 2.5 Hz, 1H), 6.78 (d, J=2.5 Hz, 1H), 6.02 (t, J=5.5 Hz, 1H), 3.84 (s, 3H), 3.70 (s, 2H), 3.34 (d, J=5.5 Hz, 2H), 2.43 (s, 3H).

Step F: To a solution of the vinyl triflate (0.80 g, 2.4 mmol) from step E above in toluene (24 mL) were added 2-tolylboronic acid (0.65 g, 4.8 mmol), ethanol (4.8 mL) and aqueous 2M sodium carbonate (11 mL). The resultant mixture was flushed with argon for 10 minutes and then palladium(0) tetrakistriphenylphosphine (0.28 g, 0.24 mmol) was added to it. The reaction solution was purged with argon for 5 minutes and then stirred at 70° C. for 16 hours. The reaction mixture was cooled to room temperature, diluted with ethyl acetate, washed with aqueous saturated sodium bicarbonate and brine, dried over sodium sulfate and concentrated in vacuo. The residue obtained was purified by flash column chromatography (dichloromethane to 94:5.4:0.6 dichloromethane/methanol/concentrated ammonium hydroxide) to give the desired 8-methoxydihydrobenzazepine (0.45 g, 67%) as a dark oil: $^1$H NMR (500 MHz, CDCl$_3$) δ 7.25-7.20 (m, 3H), 7.15 (d, J=7.0 Hz, 1H), 6.89 (d, J=2.5 Hz, 1H), 6.76 (d, J=8.5 Hz, 1H), 6.73 (dd, J=8.5, 2.5 Hz, 1H), 6.08 (t, J=6.5 Hz, 1H), 3.82 (s, 3H), 3.66 (s, 2H), 3.00 (d, J=6.5 Hz, 2H), 2.47 (s, 3H), 2.04 (s, 3H); ESI MS m/z 280 [M+H]$^+$.

Step G: To a solution of the 8-methoxydihydrobenzazepine (0.45 g, 1.6 mmol) from step F above in ethanol (60 mL) were added trifluoroacetic acid (0.8 mL) and palladium(II) hydroxide (0.15 g, 0.21 mmol). The reaction solution was shaken under hydrogen (35 psi) for 16 hours. The resultant reaction mixture was filtered through a pad of Celite and the filtrate obtained was concentrated in vacuo to give the desired 8-methoxybenzazepine (0.47 g, quantitative), which was used in the next step without purification: ESI MS m/z 282 [M+H]$^+$.

Step H: To a solution of the 8-methoxybenzazepine (0.47 g, 1.67 mmol) from step G above in acetic acid (30 mL) was added hydrobromic acid (48% solution in water, 30 mL). The reaction solution was heated at 105° C. for 20 hours, and then cooled to room temperature and concentrated in vacuo. The residue obtained was dissolved in methylene chloride and water, and then carefully neutralized with aqueous saturated sodium bicarbonate to pH ~9. The organic extract was separated, washed with water and brine, dried over sodium sulfate and concentrated in vacuo. The crude product obtained was purified by flash column chromatography (dichloromethane to 90:9:1 dichloromethane/methanol/concentrated ammonium hydroxide) to give the desired phenol (0.21 g, 47%) as a white solid: $^1$H NMR (CDCl$_3$, 500 MHz) δ 7.27-7.18 (m, 4H), 6.60 (d, J=2.5 Hz, 1H), 6.39 (dd, J=8.5, 2.5 Hz, 1H), 6.14 (d, J=8.5 Hz, 1H), 4.34 (d, J=10.5 Hz, 1H), 4.07 (d, J=14.0 Hz, 1H), 3.64 (d, J=14.0 Hz, 1H), 3.15 (d, J=13.0 Hz, 1H), 2.94 (td, J=12.5, 2.0 Hz, 1H), 2.44 (s, 3H), 2.34-2.21 (m, 1H), 2.14 (s, 3H), 2.02 (d, J=12.0 Hz, 1H).

Step I: To a solution of the phenol (0.21 g, 0.78 mmol) from step H above in dichloromethane (10 mL) at 0° C. were added pyridine (0.13 mL, 1.6 mmol) and triflic anhydride (0.15 mL, 0.86 mmol). The reaction solution was stirred at 0° C. for 30 minutes and room temperature for 30 minutes. The resultant reaction mixture was then quenched with aqueous saturated sodium bicarbonate and extracted with dichloromethane (2×). The combined organic extract was dried over sodium sulfate and concentrated in vacuo to give the desired triflate (0.37 g, quantitative) as a yellow oil, which was used in the next step without purification.

Step J: To a solution of the triflate (0.78 mmol) from step I above and bis(pinacolato)diboron (0.24 g, 0.94 mmol) in DMSO (8 mL) was added potassium acetate (0.24 g, 2.4 mmol). The resultant solution was purged with argon for 10 minutes, and then dichloro[1,1'-bis(diphenylphosphino)ferrocene]palladium(II) dichloromethane adduct (65 mg, 0.08 mmol) was added. The reaction solution was degassed again with argon for 5 minutes and heated at 80° C. for 90 minutes. The reaction solution was then cooled to room temperature, diluted with ethyl acetate, washed with water (2×) and brine, dried over sodium sulfate and concentrated in vacuo. The crude product obtained was used in the next step without further purification: ESI MS m/z 378 [M+H]+.

Step K: To a mixture of the boronate ester (0.78 mmol) from step J above, 3-chloro-6-methylpyridazine (0.21 g, 1.6 mmol) and sodium carbonate (0.25 g, 2.4 mmol) were added DMF (8 mL) and water (2 mL). The resultant solution was flushed with argon for 10 minutes, and then dichloro[1,1'-bis(diphenylphosphino)ferrocene]palladium(II) dichloromethane adduct (65 mg, 0.08 mmol) was added to it. The reaction mixture was flushed with argon for 5 minutes and then heated at 80° C. for 2 hours. The resultant reaction solution was then cooled to room temperature, diluted with ethyl acetate, washed with 1:1 water/brine (2×), dried over sodium sulfate and concentrated in vacuo. The crude product obtained was purified by flash column chromatography (dichloromethane to 90:9:1 dichloromethane/methanol/concentrated ammonium hydroxide) to give the desired benzazepine (0.14 g, 52%): $^1$H NMR (CDCl$_3$, 500 MHz) δ 7.96 (d, J=1.5 Hz, 1H), 7.68 (d, J=9.0 Hz, 1H), 7.63 (d, J=8.0 Hz, 1H), 7.34-7.21 (m, 5H), 6.50 (d, J=8.0 Hz, 1H), 4.51 (d, J=10.5 Hz, 1H), 4.23 (d, J=14.0 Hz, 1H), 3.88 (d, J=14.0 Hz, 1H), 3.27 (d, J=13.5 Hz, 1H), 3.06 (t, J=12.5 Hz, 1H), 2.74 (s, 3H), 2.42 (s, 3H), 2.42-2.35 (m, 1H), 2.16 (s, 3H), 2.08 (d, J=13.5 Hz, 1H); ESI MS m/z 344 [M+H]+.

Step L: The racemic benzazepine (0.14 g) from step K above was resolved by preparative chiral HPLC (CHIRALPAK AD column, using 80:20:0.1 heptane/2-propanol/diethylamine as the eluent) to give the (+)-enantiomer [[α]$^{25}_D$+19.5° (c 0.13, methanol)] (64 mg, 91%) as an off-white solid and the (−)-enantiomer [[α]$^{25}_D$−22.5° (c 0.13, methanol)] (65 mg, 92%) as an off-white solid.

Step M: To a solution of the (+)-enantiomer (62.0 mg, 0.18 mmol) from step L above in methanol (3 mL) were added L-tartaric acid (27.0 mg, 0.18 mmol) and water (10 mL). The resultant solution was lyophilized overnight to provide (+)-2-methyl-8-(6-methylpyridazin-3-yl)-5-o-tolyl-2,3,4,5-tetrahydro-1H-benzo[c]azepine, L-tartrate salt (88 mg, 98.9% AUC HPLC) as an off-white solid: $^1$H NMR (CD$_3$OD, 500 MHz) δ 8.20 (s, 1H), 8.05 (d, J=8.5 Hz, 1H), 7.84 (dd, J=8.0, 1.5 Hz, 1H), 7.67 (d, J=8.5 Hz, 1H), 7.34-7.26 (m, 4H), 6.63 (d, J=8.0 Hz, 1H), 4.97-4.76 (m, 2H), 4.49 (d, J=13.0 Hz, 1H), 4.40 (s, 2H), 3.67 (br s, 2H), 2.92 (s, 3H), 2.72 (s, 3H), 2.53-2.39 (br, 2H), 2.18 (s, 3H); ESI MS m/z 344 [M+H]+.

Step N: To a solution of the (−)-enantiomer (63.0 mg, 0.18 mmol) from step L above in methanol (3 mL) were added L-tartaric acid (27.5 mg, 0.18 mmol) and water (10 mL). The resultant solution was lyophilized overnight to provide (−)-2-methyl-8-(6-methylpyridazin-3-yl)-5-o-tolyl-2,3,4,5-tetrahydro-1H-benzo[c]azepine, L-tartrate salt (85 mg, 100% AUC HPLC) as a light yellow solid: $^1$H NMR (CD$_3$OD, 500 MHz) δ 8.20 (s, 1H), 8.05 (d, J=8.5 Hz, 1H), 7.84 (d, J=8.0 Hz, 1H), 7.67 (d, J=8.5 Hz, 1H), 7.34-7.26 (m, 4H), 6.63 (d, J=8.0 Hz, 1H), 4.97-4.76 (m, 2H), 4.49 (d, J=13.0 Hz, 1H), 4.40 (s, 2H), 3.67 (br s, 2H), 2.92 (s, 3H), 2.72 (s, 3H), 2.53-2.39 (br, 2H), 2.18 (s, 3H); ESI MS m/z 344 [M+H]+.

Example 136

Preparation of (−)-5-(2,6-difluorophenyl)-2-methyl-8-(6-methylpyridazin-3-yl)-2,3,4,5-tetrahydro-1H-benzo[c]azepine, L-tartrate salt and (+)-5-(2,6-difluorophenyl)-2-methyl-8-(6-methylpyridazin-3-yl)-2,3,4,5-tetrahydro-1H-benzo[c]azepine, L-tartrate salt Pursuant to the general method described above in Example 135, the following products were prepared: (−)-5-(2,6-difluorophenyl)-2-methyl-8-(6-methylpyridazin-3-yl)-2,3,4,5-tetrahydro-1H-benzo[c]azepine, L-tartrate salt: $^1$H NMR (CD$_3$OD, 500 MHz) δ 8.21 (s, 1H), 8.07 (d, J=9.0 Hz, 1H), 7.94 (dd, J=8.0, 2.0 Hz, 1H), 7.68 (d, J=9.0 Hz, 1H), 7.49-7.43 (m, 1H), 7.12 (t, J=9.0 Hz, 2H), 6.91 (d, J=8.0 Hz, 1H), 5.05-4.76 (m, 2H), 4.49 (d, J=14.0 Hz, 1H), 4.41 (s, 2H), 3.59 (br, 2H), 2.90 (s, 3H), 2.73-2.64 (br, 1H), 2.72 (s, 3H), 2.30 (d, J=16.0 Hz, 1H); ESI MS m/z 366 [M+H]+; (+)-5-(2,6-difluorophenyl)-2-methyl-8-(6-methylpyridazin-3-yl)-2,3,4,5-tetrahydro-1H-benzo[c]azepine, L-tartrate salt: $^1$H NMR (CD$_3$OD, 500 MHz) δ 8.21 (s, 1H), 8.07 (d, J=9.0 Hz, 1H), 7.94 (dd, J=8.0, 2.0 Hz, 1H), 7.68 (d, J=9.0 Hz, 1H), 7.49-7.43 (m, 1H), 7.12 (t, J=9.0 Hz, 2H), 6.91 (d, J=8.0 Hz, 1H), 5.05-4.76 (m, 2H), 4.49 (d, J=14.0 Hz, 1H), 4.41 (s, 2H), 3.59 (br, 2H), 2.90 (s, 3H), 2.73-2.64 (s, 1H), 2.72 (s, 3H), 2.30 (d, J=16.0 Hz, 1H); ESI MS m/z 366 [M+H]+.

Example 137

Preparation of (+)-2-methyl-8-(4-(pyrimidin-2-yl)piperazin-1-yl)-5-p-tolyl-2,3,4,5-tetrahydro-1H-benzo[c]azepine, L-tartrate salt and (−)-2-methyl-8-(4-(pyrimidin-2-yl)piperazin-1-yl)-5-p-tolyl-2,3,4,5-tetrahydro-1H-benzo[c]azepine, L-tartrate salt Step A: To a solution of m-anisaldehyde (205 g, 1.5 mol) in methanol (800 mL) at room temperature was added methylamine (40% in water) (130 mL, 1.5 mol). The resultant solution was cooled to 0° C. and then sodium borohydride (83 g, 2.3 mol) was added in portions. The reaction solution was stirred at 0° C. for 2 hours and then warmed to room temperature. The reaction mixture was concentrated in vacuo and diluted with water. The organic phase was separated, diluted with ethyl acetate, washed with 1:1 water/brine, dried over sodium sulfate and concentrated in vacuo to give the desired benzylamine (158.5 g, 70%) as a clear oil. The combined aqueous extract was extracted with dichloromethane (3×). The combined methylene chloride extracts were washed with 1:1 water/brine, dried over sodium sulfate and concentrated in vacuo to give the desired benzylamine (66.7 g, 29%) as a clear oil: $^1$H NMR (300 MHz, CDCl$_3$) δ 7.24 (t, J=8.4 Hz, 1H), 6.91-6.78 (m, 3H), 3.81 (s, 3H), 3.73 (s, 2H), 2.46 (s, 3H).

Step B: To a mixture of the benzylamine (30 g, 198 mmol) from step A above and ethyl acrylate (65 mL, 600 mmol) was added acetic acid (6 mL). The resultant mixture was heated under reflux for 90 min and then cooled to room temperature, concentrated in vacuo. The residue obtained was dissolved in dichloromethane, washed with aqueous sodium bicarbonate, dried over sodium sulfate and concentrated in vacuo. The crude product obtained was used in the next step without further purification: $^1$H NMR (500 MHz, CDCl$_3$) δ 7.21 (t, J=8.0 Hz, 1H), 6.88-6.87 (m, 2H), 6.79 (dd, J=8.0, 2.5 Hz, 1H), 4.14 (q, J=7.0 Hz, 2H), 3.80 (s, 3H), 3.49 (s, 2H), 2.74 (t, J=7.0 Hz, 2H), 2.51 (t, J=7.0 Hz, 2H), 2.21 (s, 3H), 1.25 (t, J=7.0 Hz, 3H).

Step C: To a solution of the ester (198 mmol) from step B above in methanol (500 mL) was added aqueous sodium hydroxide (200 mL, 2M). The resultant mixture was stirred at room temperature for 3 hours and then concentrated in vacuo. The residue obtained was dissolved in water, adjusted to pH 7 and extracted with chloroform (3×) and mixture of 3:1 chloroform/2-propanol (3×). The combined organic extracts were dried over sodium sulfate and concentrated in vacuo to give the desired acid (25 g, 56%) as a light green oil, which was used in the next step without further purification.

Step D: A mixture of the acid (24 g, 107 mmol) from step C above and polyphosphoric acid (180 g) was heated at 100-110° C. for 18 hours. The resultant slurry was dissolved in dichloromethane and water, neutralized to pH>8 and then extracted with dichloromethane (5×). The combined organic extracts were dried over sodium sulfate and concentrated in vacuo. The residue obtained was purified by flash column chromatography (99:0.9:0.1 to 95:4.5:0.5 dichloromethane/methanol/concentrated ammonium hydroxide) to give the desired ketone (8.5 g, 39%) as a dark reddish oil: $^1$H NMR (500 MHz, CDCl$_3$) δ 7.81 (d, J=8.5 Hz, 1H), 6.87 (dd, J=8.5, 2.5 Hz, 1H), 6.90 (d, J=2.5 Hz, 1H), 3.91 (s, 2H), 3.86 (s, 3H), 2.86-2.80 (m, 4H), 2.42 (s, 3H); ESI MS m/z 206 [M+H]$^+$.

Step E: To a solution of the ketone (2.6 g, 12.7 mmol) in THF (100 mL) at −78° C. was added a solution of lithium bis(trimethylsilyl)amide (14 mL, 14 mmol, 1M in THF) slowly. The reaction solution was stirred at −78° C. for 30 minutes and then a solution of N-phenyl trifluoromethanesulfonimide (5.0 g, 14 mmol) in THF (20 mL) was added to it slowly. The reaction solution was let to warm to room temperature, stirred for 10 hours, quenched with aqueous saturated sodium bicarbonate and then extracted with ethyl acetate (3×). The combined organic extracts were washed with brine, dried over sodium sulfate and concentrated in vacuo. The crude product obtained was purified by flash column chromatography (dichloromethane to 97:3 dichloromethane/methanol) to give the desired vinyl triflate (3.8 g, 89%) as a dark black oil: $^1$H NMR (500 MHz, CDCl$_3$) δ 7.50 (d, J=8.5 Hz, 1H), 6.90 (dd, J=8.5, 2.5 Hz, 1H), 6.78 (d, J=2.5 Hz, 1H), 6.02 (t, J=5.5 Hz, 1H), 3.84 (s, 3H), 3.70 (s, 2H), 3.34 (d, J=5.5 Hz, 2H), 2.43 (s, 3H).

Step F: To a solution of the vinyl triflate (3.0 g, 8.9 mmol) from step E above in THF (100 mL) and water (15 mL) were added 4-tolylboronic acid (1.5 g, 10.7 mmol), cesium carbonate (8.7 g, 26.7 mmol) and tricyclohexylphosphine (0.30 g, 1.07 mmol). The resultant mixture was flushed with argon for 10 minutes and then palladium(II) acetate (0.20 g, 0.9 mmol) was added to it. The reaction solution was purged with argon for 5 minutes and then stirred at 75° C. for 3 hours. The reaction mixture was cooled to room temperature, diluted with ethyl acetate, washed with aqueous saturated sodium bicarbonate and brine, dried over sodium sulfate and concentrated in vacuo. The residue obtained was purified by flash column chromatography (99:0.9:0.1 to 92:7.2:0.8 dichloromethane/methanol/concentrated ammonium hydroxide) to give the desired 8-methoxydihydrobenzazepine (1.2 g, 48%) as a dark oil: $^1$H NMR (500 MHz, CDCl$_3$) δ 7.21 (d, J=8.0 Hz, 2H), 7.14 (d, J=8.0 Hz, 2H), 7.03 (d, J=8.5 Hz, 1H), 6.92 (d, J=3.0 Hz, 1H), 6.83 (dd, J=8.5, 2.5 Hz, 1H), 6.37 (t, J=7.0 Hz, 1H), 3.85 (s, 3H), 3.54 (s, 2H), 2.86 (d, J=7.0 Hz, 1H), 2.44 (s, 3H), 2.37 (s, 3H); ESI MS m/z 280 [M+H]$^+$.

Step G: To a solution of the 8-methoxydihydrobenzazepine (1.2 g, 4.3 mmol) from step F above in acetic acid (40 mL) was added hydrobromic acid (48% solution in water, 40 mL). The reaction solution was heated at 105° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (1.1 g, 96%) as a brown solid. The crude product was used in the next step without further purification: $^1$H NMR (CDCl$_3$, 500 MHz) δ 7.23 (d, J=8.0 Hz, 2H), 7.15 (d, J=8.0 Hz, 2H), 6.98 (d, J=8.5 Hz, 1H), 6.88 (d, J=2.5 Hz, 1H), 6.81 (dd, J=8.5, 2.5 Hz, 1H), 6.35 (t, J=7.0 Hz, 1H), 3.44 (s, 2H), 3.05 (d, J=7.5 Hz, 2H), 2.49 (s, 3H), 2.37 (s, 3H); ESI MS m/z 266 [M+H]$^+$.

Step H: To a solution of the phenol (1.1 g, 4.1 mmol) from step G above in dichloromethane (50 mL) at 0° C. were added pyridine (0.66 mL, 8.2 mmol) and triflic anhydride (0.77 mL, 4.6 mmol). The resultant reaction mixture was allowed to warm to room temperature and stirred for 16 hours. The reaction solution was then diluted with dichloromethane, washed with aqueous saturated sodium bicarbonate, dried over sodium sulfate and concentrated in vacuo to give the desired triflate (1.8 g, quantitative) as a reddish oil: $^1$H NMR (CDCl$_3$, 500 MHz) δ 7.28 (d, J=1.0 Hz, 1H), 7.19 (d, J=1.5 Hz, 2H), 7.16 (s, 4H), 6.50 (t, J=7.0 Hz, 1H), 3.57 (s, 2H), 2.84 (d, J=7.0 Hz, 2H), 2.43 (s, 3H), 2.38 (s, 3H); ESI MS m/z 398 [M+H]$^+$.

Step I: To a solution of the triflate (0.67 g, 1.7 mmol) from step H above in toluene (20 mL) were added 2-(dicyclohexylphosphino)-2',4',6'-tri-i-propyl-1,1'-biphenyl (95 mg, 0.20 mmol) and 2-(piperazin-1-yl)pyrimidine (0.42 g, 2.5 mmol). The resultant mixture was flushed with argon for 5 minutes, and then palladium(II) acetate (22.4 mg, 0.10 mmol) and sodium tert-butoxide (0.33 g, 3.4 mmol) were added to it. The reaction solution was vacuumed and backfilled with argon (3×) and then heated at 100° C. for 3 hours. After cooling to room temperature, the reaction mixture was diluted with dichloromethane, washed with water and brine, dried over sodium sulfate and concentrated in vacuo. The crude product obtained was purified by flash column chromatography (98:1.8:0.2 to 94:5.4:0.6 dichloromethane/methanol/concentrated ammonium hydroxide) to give (Z)-2-methyl-8-(4-(pyrimidin-2-yl)piperazin-1-yl)-5-p-tolyl-2,3-dihydro-1H-benzo[c]azepine (0.25 g, 36%) as a brown oil: $^1$H NMR (CDCl$_3$, 500 MHz) δ 8.34 (d, J=4.5 Hz, 2H), 7.23 (d, J=8.0 Hz, 2H), 7.14 (d, J=8.0 Hz, 2H), 7.20 (d, J=8.5 Hz, 1H), 6.96 (d, J=2.5 Hz, 1H), 6.80 (dd, J=8.5, 3.0 Hz, 1H), 6.53 (t, J=5.0 Hz, 1H), 6.34 (t, J=7.5 Hz, 1H), 3.40 (t, J=5.5 Hz, 4H), 2.53 (s, 2H), 3.34 (t, J=5.5 Hz, 4H), 2.88 (d, J=7.0 Hz, 2H), 2.44 (s, 3H), 2.37 (s, 3H); ESI MS m/z 412 [M+H]$^+$.

Step J: To a solution of the dihydrobenzazepine (0.20 g, 0.49 mmol) from step I above in ethanol (30 mL) was added palladium(II) hydroxide (0.20 g, 0.28 mmol). The reaction solution was shaken under hydrogen (35 psi) for 1 h. The resultant reaction mixture was filtered through a pad of Celite and concentrated in vacuo. The crude product was purified by preparative HPLC to give the desired racemic benzazepine (85 mg, 42%) as an off-white foam: $^1$H NMR (CDCl$_3$, 500 MHz) δ 8.33 (d, J=5.0 Hz, 2H), 7.15 (d, J=8.0 Hz, 2H), 7.06 (d, J=8.0 Hz, 2H), 6.81 (d, J=2.5 Hz, 1H), 6.65 (d, J=7.5 Hz, 1H), 6.62-6.53 (br, 1H), 6.51 (t, J=5.0 Hz, 1H), 4.21 (d, J=9.0

Hz, 1H), 3.96 (t, J=5.0 Hz, 4H), 3.89 (br d, J=12.5 Hz, 1H), 3.70 (d, J=14.0 Hz, 1H), 3.20 (t, J=5.5 Hz, 4H), 3.15-3.08 (br, 1H), 2.93 (t, J=10.5 Hz, 1H), 2.36 (s, 3H), 2.35 (s, 3H), 2.32-2.25 (m, 1H), 2.12-2.04 (br, 1H); ESI MS m/z 414 [M+H]+.

Step K: The racemic benzazepine (84 mg) was resolved by preparative chiral HPLC (CHIRALPAK AD column, using 80:20:0.1 heptane/2-propanol/diethylamine as the eluent) to give the (+)-enantiomer [[α]$^{25}_D$+2.00° (c 0.10, methanol)] (39 mg, 93%) as a light yellow oil and the (−)-enantiomer [[α]$^{25}_D$−3.00° (c 0.10, methanol)] (39 mg, 93%) as a light yellow oil.

Step L: To a solution of the (+)-enantiomer (36 mg, 0.087 mmol) from step K above in methanol (3 mL) were added L-tartaric acid (13.0 mg, 0.087 mmol) and water (9 mL). The resultant solution was lyophilized overnight to provide (+)-2-methyl-8-(4-(pyrimidin-2-yl)piperazin-1-yl)-5-p-tolyl-2,3,4,5-tetrahydro-1H-benzo[c]azepine, L-tartrate salt (47 mg, 99.3% AUC HPLC) as a yellow solid: $^1$H NMR (CD$_3$OD, 500 MHz) δ 8.34 (dd, J=4.5, 2.0 Hz, 2H), 7.19 (d, J=7.5 Hz, 2H), 7.09 (d, J=2.5 Hz, 1H), 7.05 (d, J=7.0 Hz, 2H), 6.96-6.65 (br, 2H), 6.63-6.60 (m, 1H), 4.60-4.33 (br, 1H), 4.43 (d, J=8.5 Hz, 1H), 4.39 (s, 2H), 4.24 (d, J=14.0 Hz, 1H), 3.95 (t, J=5.0 Hz, 4H), 3.50 (br, 2H), 3.26 (t, J=5.0 Hz, 4H), 2.85 (s, 3H), 2.62-2.34 (br, 2H), 2.34 (s, 3H); ESI MS m/z 414 [M+H]+.

Step M: To a solution of the (−)-enantiomer (38 mg, 0.092 mmol) from step K above in methanol (3 mL) were added L-tartaric acid (13.8 mg, 0.092 mmol) and water (9 mL). The resultant solution was lyophilized overnight to provide (−)-2-methyl-8-(4-(pyrimidin-2-yl)piperazin-1-yl)-5-p-tolyl-2,3,4,5-tetrahydro-1H-benzo[c]azepine, L-tartrate salt (48 mg, 99.4% AUC HPLC) as a yellow solid: $^1$H NMR (CD$_3$OD, 500 MHz) δ 8.34 (d, J=5.0 Hz, 2H), 7.19 (d, J=7.5 Hz, 2H), 7.09 (d, J=2.5 Hz, 1H), 7.05 (d, J=8.0 Hz, 2H), 6.94 (d, J=8.0 Hz, 1H), 6.89-6.65 (br, 1H), 6.62 (t, J=4.5 Hz, 1H), 4.60-4.33 (br, 1H), 4.43 (d, J=10.0 Hz, 1H), 4.40 (s, 2H), 4.25 (d, J=14.0 Hz, 1H), 3.95 (t, J=5.0 Hz, 4H), 3.51 (br, 2H), 3.26 (t, J=5.0 Hz, 4H), 2.86 (s, 3H), 2.62-2.34 (br, 2H), 2.34 (s, 3H); ESI MS m/z 414 [M+H]+.

Example 138

Preparation of (+)-5-(2,4-difluorophenyl)-2-methyl-8-(4-methylpiperazin-1-yl)-2,3,4,5-tetrahydro-1H-benzo[c]azepine, L-tartrate salt and (−)-5-(2,4-difluorophenyl)-2-methyl-8-(4-methylpiperazin-1-yl)-2,3,4,5-tetrahydro-1H-benzo[c]azepine, L-tartrate salt Pursuant to the general method described above in Example 137, the following products were prepared: (+)-5-(2,4-difluorophenyl)-2-methyl-8-(4-methylpiperazin-1-yl)-2,3,4,5-tetrahydro-1H-benzo[c]azepine, L-tartrate salt: $^1$H NMR (CD$_3$OD, 500 MHz) δ 7.32-7.16 (br, 1H), 7.07 (d, J=2.5 Hz, 1H), 7.04-6.97 (br, 2H), 6.86 (dd, J=8.5, 2.0 Hz, 1H), 6.63-6.48 (br, 1H), 4.65 (d, J=10.0 Hz, 1H), 4.58 (d, J=14.0 Hz, 1H), 4.35 (s, 2H), 4.26 (d, J=14.0 Hz, 1H), 3.50-3.42 (br, 2H), 3.37-3.30 (br, 4H), 2.98-2.92 (br, 4H), 2.81 (s, 3H), 2.61 (s, 3H), 2.50-2.21 (br, 2H); ESI MS m/z 372 [M+H]+; (−)-5-(2,4-difluorophenyl)-2-methyl-8-(4-methylpiperazin-1-yl)-2,3,4,5-tetrahydro-1H-benzo[c]azepine, L-tartrate salt: $^1$H NMR (CD$_3$OD, 500 MHz) δ 7.32-7.16 (br, 1H), 7.07 (d, J=2.5 Hz, 1H), 7.04-6.97 (br, 2H), 6.86 (dd, J=8.5, 2.0 Hz, 1H), 6.63-6.48 (br, 1H), 4.65 (d, J=10.0 Hz, 1H), 4.58 (d, J=14.0 Hz, 1H), 4.35 (s, 2H), 4.26 (d, J=14.0 Hz, 1H), 3.50-3.42 (br, 2H), 3.37-3.30 (br, 4H), 2.98-2.92 (br, 4H), 2.81 (s, 3H), 2.61 (s, 3H), 2.50-2.21 (br, 2H); ESI MS m/z 372 [M+H]+.

Example 139

Preparation of (+/−)-8-methoxy-2-methyl-5-(pyridin-3-yl)-2,3,4,5-tetrahydro-1H-benzo[c]azepine, L-tartrate salt Pursuant to the general method described above in Example 137, the following products were prepared: (+/−)-8-methoxy-2-methyl-5-(pyridin-3-yl)-2,3,4,5-tetrahydro-1H-benzo[c]azepine, L-tartrate salt: mp 102-105° C.; $^1$H NMR (CD$_3$OD, 500 MHz) δ 8.50-8.49 (m, 1H), 8.38 (s, 1H), 7.72-7.71 (m, 1H), 7.50-7.47 (m, 1H), 7.06-7.05 (m, 1H), 6.89-6.88 (m, 1H), 6.70 (br, 1H), 4.61-4.59 (m, 1H), 4.43 (s, 3H), 4.29-4.26 (m, 1H), 3.80 (s, 3H), 3.60-3.50 (m, 2H), 2.87 (s, 3H), 2.65-2.55 (m, 2H), 2.40-2.37 (m, 1H); ESI MS m/z 269 [M+H].

Example 140

Preparation of (+)-5-(4-Fluorophenyl)-2-methyl-8-[6-(trifluoromethyl)-pyridazin-3-yl]-2,3,4,5-tetrahydro-1H-benzo[c]azepine, L-tartrate salt and (−)-5-(4-Fluorophenyl)-2-methyl-8-[6-(trifluoromethyl)-pyridazin-3-yl]-2,3,4,5-tetrahydro-1H-benzo[c]azepine, L-tartrate salt Step A: A mixture of 5-bromophthalide (21.7 g, 0.10 mol) and dichlorotriphenylphosphorane (45.6 g, 0.13 mol) was heated at 180° C. for 2 hours. The mixture was allowed to cool to 0° C. and then methanol (26 mL) and pyridine (26 mL) were added. The reaction mixture was stirred at room temperature for 1 hour. Hexanes (520 mL) and water (260 mL) were added to the mixture. The resultant precipitate was removed by filtration. The organic layer of the filtrate was separated and washed with brine, dried over sodium sulfate and concentrated under reduced pressure to give the desired benzyl chloride (25.8 g, 98%), which was used in the next step without further purification.

Step B: To a mixture of the benzyl chloride (25.8 g, 97.9 mmol) from step A above and ethyl 3-(methylamino)-propionate (14.0 g, 107 mmol) was added potassium carbonate (40.6 g, 294 mmol). The reaction mixture was heated under reflux for 6 hours. The solvent was removed under reduced pressure. The residue was partitioned between ethyl acetate and water. The organic layer was separated and the aqueous layer was extracted with ethyl acetate (2×). The combined organic extracts were washed with brine, dried over sodium sulfate and concentrated under reduced pressure to provide the desired benzylamine (34.5 g, 98%), which was used in the next step without further purification: $^1$H NMR (500 MHz, CDCl$_3$) δ 7.73 (d, J=1.7 Hz, 1H), 7.64 (d, J=8.3 Hz, 1H), 7.42 (dd, J=8.3, 1.9 Hz, 1H), 4.14 (q, J=7.1 Hz, 2H), 3.87 (s, 2H), 3.80 (s, 2H), 2.76 (t, J=7.2 Hz, 2H), 2.48 (t, J=7.2 Hz, 2H), 2.20 (s, 3H), 1.24 (t, J=7.1 Hz, 3H); ESI MS m/z 358, 360 [M+H]+.

Step C: To a solution of the benzylamine (34.5 g, 96.3 mmol) from step B above in tetrahydrofuran (500 mL) at −30° C. was added 1M solution of potassium t-butoxide (203 mL, 203 mmol). The reaction mixture was stirred between −30° C. to −20° C. for 10 minutes and then quenched with saturated ammonium chloride solution. The mixture was extracted with ethyl acetate (3×). The combined organic extracts were washed with brine, dried over sodium sulfate and concentrated under reduced pressure to give a mixture of the desired ethyl and methyl esters (32.2 g, 99%), which was used in the next step without further purification.

Step D: To a mixture of the esters (32.0 g, 100 mmol) from step C above and acetic acid (75 mL) in concentrated hydrochloric acid (150 mL) was added sodium iodide (22.5 g, 0.15 mmol). The reaction mixture was heated at 110° C. for 20 hours. Most of solvent was removed under reduced pressure. The residue was neutralized to pH>8 and then extracted with dichloromethane (3×). The combined organic extracts were washed with brine, dried over sodium sulfate and concentrated under reduced pressure. The residue obtained was purified by flash column chromatography (3-5% methanol/dichloromethane) to give the desired ketone (14.8 g, 48% over 4 steps) as a dark brown semi-solid: $^1$H NMR (500 MHz, CDCl$_3$) δ 7.64 (d, J=8.2 Hz, 1H), 7.50 (dd, J=8.2, 1.9 Hz, 1H), 7.37 (d, J=1.8 Hz, 1H), 3.89 (s, 2H), 2.87-2.82 (m, 4H), 2.43 (s, 3H); ESI MS m/z 254, 256 [M+H]$^+$.

Step E: To a solution of 1-bromo-4-fluorobenzene (8.71 g, 49.8 mmol) in tetrahydrofuran (50 mL) at −78° C. was added 2.5M n-butyllithium in hexanes (19.9 mL, 49.8 mmol). The reaction mixture was stirred at −78° C. for 20 minutes and then transferred into a −78° C. cooled solution of the ketone (6.33 g, 24.9 mmol) from step D above in tetrahydrofuran (50 mL). The reaction mixture was stirred at −78° C. for 3 hours and then allowed to warm to room temperature overnight. The mixture was quenched with saturated ammonium chloride solution and extracted with ethyl acetate (3×). The combined organic extracts were washed with brine, dried over sodium sulfate and concentrated under reduced pressure. The residue was purified by flash column chromatography (3 to 5% methanol/dichloromethane) to give the desired tertiary alcohol (3.3 g, 38%): $^1$H NMR (500 MHz, CDCl$_3$) δ 7.32-7.23 (m, 4H), 7.05-7.00 (m, 2H), 6.92 (br, 1H), 3.78 (d, J=15.5 Hz, 1H), 3.67 (d, J=15.5 Hz, 1H), 3.10-3.05 (m, 1H), 2.72-2.67 (m, 1H), 2.51-2.46 (m, 1H), 2.40 (s, 3H), 2.31-2.26 (m, 1H); ESI MS m/z 350, 352 [M+H]$^+$.

Step F: A mixture of the tertiary alcohol (3.30 g, 9.42 mmol) from step E above and trifluoroacetic acid (3 mL) was stirred at room temperature for 10 minutes. The resultant mixture was diluted with dichloromethane (100 mL) and neutralized with saturated sodium bicarbonate. The organic layer was separated and washed with brine, dried over sodium sulfate and concentrated under reduced pressure. The residue was purified by flash column chromatography (2 to 5% methanol/dichloromethane) to give (Z)-8-bromo-5-(4-fluorophenyl)-2-methyl-2,3-dihydro-1H-benzo[c]azepine (2.43 g, 78%): $^1$H NMR (300 MHz, CDCl$_3$) δ 7.53 (d, J=2.1 Hz, 1H), 7.43 (dd, J=8.3, 2.1 Hz, 1H), 7.26-7.22 (m, 2H), 7.05-6.99 (m, 2H), 6.95 (d, J=8.3 Hz, 1H), 6.43 (t, J=7.1 Hz, 1H), 3.52 (s, 2H), 2.84 (d, J=7.1 Hz, 2H), 2.43 (s, 3H); ESI MS m/z 332, 334 [M+H]$^+$.

Step G: To a solution of the dihydrobenzazepine (2.43 g, 7.31 mmol) from step F above in pyridine (50 mL) were added potassium carbonate (8.08 g, 58.5 mmol) and p-toluenesulfonylhydrazide (5.45 g, 29.3 mmol) in batches. The reaction solution was heated under reflux for 48 h and then cooled to room temperature. The resultant reaction mixture was filtered through Celite. The Celite bed was washed with ethyl acetate. The filtrate was concentrated under reduced pressure. The residue dissolved in ethyl acetate was washed with water and brine, dried over sodium sulfate and concentrated under reduced pressure. The residue obtained was purified by flash column chromatography (3 to 5% methanol/dichloromethane) to give the desired 8-bromotetrahydrobenzazepine (1.74 g, 71%): $^1$H NMR (500 MHz, CDCl$_3$) δ 7.31 (d, J=2.1 Hz, 1H), 7.20-7.16 (m, 1H), 7.13-7.10 (m, 2H), 7.04 (t, J=8.6 Hz, 2H), 6.49 (br, 1H), 4.24 (d, J=9.3 Hz, 1H), 3.88 (d, J=12.2 Hz, 1H), 3.67 (d, J=14.3 Hz, 1H), 3.12-3.09 (m, 1H), 2.98-2.93 (m, 1H), 2.34 (s, 3H), 2.30-2.23 (m, 1H), 2.08-2.04 (m, 1H); ESI MS m/z 334, 336 [M+H]$^+$.

Step H: Bis(pinacolato)diboron (682 mg, 2.68 mmol) was added to a mixture of the 8-bromo-tetrahydrobenzazepine (816 mg, 2.44 mmol)from step G above and potassium acetate (719 mg, 7.32 mmol) in DMSO (10 mL). The reaction mixture was degassed with argon. Dichloro[1,1'-bis(diphenylphosphino)ferrocene]palladium(II) dichloromethane adduct (120 mg, 0.146 mmol) was added and the reaction mixture was stirred at 80° C. for 2 hours, cooled, diluted with water and extracted with ethyl acetate (3×). The combined organic extracts were washed with brine, dried over anhydrous sodium sulfate and concentrated to give the desired boronate ester (1.2 g, >99% crude yield), which was used in the next step without further purification: ESI MS m/z=382 [M+H]$^+$.

Step I: 3-Chloro-6-trifluoromethylpyridazine (223 mg, 1.22 mmol) was added to a mixture of the crude boronate ester from step H (400 mg, 0.813 mmol) and cesium carbonate (795 mg, 2.44 mmol) in DMF (10 mL) and water (1.5 mL). The reaction mixture was degassed with argon. Dichloro[1,1'-bis(diphenylphosphino)ferrocene]palladium(II) dichloromethane adduct (66 mg, 0.081 mmol) was added and the reaction mixture was stirred at 100° C. for 2 hours, cooled, diluted with water and extracted with ethyl acetate (3×). The combined organic extracts were washed with brine, dried over anhydrous sodium sulfate and concentrated. Purification by flash column chromatography (5% methanol/dichloromethane) gave the desired pyridazinyl benzazepine product (178 mg, 55% over 2 steps): $^1$H NMR (CDCl$_3$, 500 MHz) δ 8.03 (d, J=1.7 Hz, 1H), 7.99 (d, J=8.9 Hz, 1H), 7.85-7.82 (m, 2H), 7.19-7.16 (m, 2H), 7.08 (t, J=8.6 Hz, 2H), 6.82 (br, 1H), 4.40 (d, J=9.3 Hz, 1H), 4.04 (d, J=13.6 Hz, 1H), 3.86 (d, J=14.3 Hz, 1H), 3.16-3.15 (m, 1H), 3.03-2.98 (m, 1H), 2.40 (s, 3H), 2.38-2.31 (m, 1H), 2.16-2.14 (m, 1H); ESI MS m/z 402 [M+H]$^+$.

Step J: The pyridazinyl benzazepine from Step I (178 mg) was resolved by preparative chiral HPLC (ChiralCel OJ column, using 80:20:0.1 heptane/ethanol/diethylamine as the eluent) to give the (+)-enantiomer [[α]$^{25}_D$+8.3° (c 0.12, methanol)] and the (−)-enantiomer [[α]$^{25}_D$−6.7° (c 0.12, methanol)].

Step K: To a solution of the (+)-enantiomer from Step J (80 mg, 0.199 mmol) in methanol (1 mL) was added maleic acid (30 mg, 0.199 mmol). The solvent was removed under reduced pressure. The residue was dissolved with acetonitrile (1 mL) and water (0.5 mL). The resultant solution was lyophilized overnight to give (+)-5-(4-fluorophenyl)-2-Methyl-8-[6-(trifluoromethyl)-pyridazin-3-yl]- -2,3,4,5-tetrahydro-1H-benzo[c]azepine, L-tartrate salt (110 mg, 99%, AUC HPLC 98.0%) as an off-white solid: $^1$H NMR (CD$_3$OD, 500 MHz) δ 8.43 (d, J=8.8 Hz, 1H), 8.33 (br, 1H), 8.18 (d, J=8.9 Hz, 1H), 8.12 (d, J=7.4 Hz, 1H), 7.28 (d, J=4.3 Hz, 2H), 7.18-7.15 (m, 2H), 7.02 (br, 1H), 4.77-4.70 (m, 2H), 4.49 (d, J=13.5 Hz, 1H), 4.39 (s, 2H), 3.61 (br, 2H), 2.90 (s, 3H), 2.61 (br, 1H), 2.45 (br, 1H); ESI MS m/z 402 [M+H]$^+$.

Step L: To a solution of the (−)-enantiomer from Step J (80 mg, 0.199 mmol) in methanol (1 mL) was added maleic acid (30 mg, 0.199 mmol). The solvent was removed under reduced pressure. The residue was dissolved with acetonitrile (1 mL) and water (0.5 mL). The resultant solution was lyophilized overnight to give (−)-5-(4-fluorophenyl)-2-methyl-8-[6-(trifluoromethyl)-pyridazin-3-yl]- -2,3,4,5-tetrahydro-1H-benzo[c]azepine, L-tartrate salt (110 mg, 99%, AUC HPLC >99%) as an off-white solid: $^1$H NMR (CD$_3$OD, 500 MHz) δ 8.42 (d, J=8.9 Hz, 1H), 8.33 (br, 1H), 8.18 (d, J=8.9 Hz, 1H), 8.12 (d, J=7.3 Hz, 1H), 7.28 (d, J=4.9 Hz, 2H), 7.18-7.15 (m, 2H), 7.02 (br, 1H), 4.79-4.70 (m, 2H), 4.49 (d, J=13.9 Hz, 1H), 4.40 (s, 2H), 3.61 (br, 2H), 2.90 (s, 3H), 2.61 (br, 1H), 2.45-2.42 (m, 1H); ESI MS m/z 402 [M+H]$^+$.

Example 141

Preparation of 8-methoxy-2-methyl-5-(4-(trifluoromethyl)phenyl)-2,3,4,5-tetrahydro-1H-benzo[c]azepine, L-tartrate salt Step A: To a solution of 3-methoxybenzaldehyde (31.2 g, 229 mmol) in DMF (500 ml) were added N-bromosuccinimide (48.9 g, 275 mmol) at room temperature. The mixture was stirred at room temperature overnight. The solution was poured into water. The precipitate was filtered to give the desired bromide (50.7 g, quantitative) as a white solid: $^1$H NMR (CDCl$_3$, 300 MHz) δ 10.31 (s, 1H), 7.53 (d, J=8.7 Hz, 1H), 7.42 (s, 1H), 7.04 (d, J=8.7 Hz, 1H), 3.84 (s, 3H).

Step B: To a solution of the bromide (20 g, 93 mmol) from step A in toluene (200 mL) was added glycol (31 g, 465 mmol) and camphorsulfonic acid (1.07 g, 4.6 mmol). The mixture was refluxed with Dean-Stark trap for 4 hours. After cooling to room temperature, the excess glycol was separated. The toluene layer was washed with saturated NaHCO$_3$, water, brine, dried over sodium sulfate and concentrated to give the desired dioxolane (24 g, quantitative) as a light colorless oil: $^1$H NMR (CDCl$_3$, 300 MHz) δ 7.44 (d, J=8.7 Hz, 1H), 7.16 (d, J=3.1 Hz, 1H), 6.79 (dd, J=8.7, 3.1 Hz, 1H), 6.04 (s, 1H), 4.17-4.06 (m, 4H), 3.80 (s, 3H).

Step C: To a solution of the dioxolane (5.05 g, 19.5 mmol) from step B above in THF (50 mL) cooled to −78° C. was added n-BuLi (2.5 M in hexane, 10.1 mL, 25.4 mmol) cooled to −78° C. by cannula. After stirring at this temperature for 0.5 hour, 4-(trifluoromethyl)benzaldehyde (4.41 g, 25.4 mmol) was added to the resulting mixture dropwise. The reaction mixture was stirred at −78° C. for 1 hour. It was quenched at −78° C. with methanol (3 mL) and warmed up to room temperature. The mixture was diluted with dichloromethane. The organic layer was washed with brine, dried over sodium sulfate, and concentrated to give the desired alcohol (9.8 g, crude): $^1$H NMR (CDCl$_3$, 500 MHz) δ 7.59 (d, J=8.3 Hz, 2H), 7.53 (d, J=8.3 Hz, 2H), 7.16 (d, J=2.7 Hz, 1H), 7.00 (d, J=8.5 Hz, 1H), 6.82 (dd, J=8.5, 2.7 Hz, 1H), 6.20 (d, J=3.7 Hz, 1H), 5.92 (s, 1H), 4.18-4.04 (m, 4H), 3.81(s, 3H), 3.45 (d, J=4.3 Hz, 1H).

Step D: To a solution of the alcohol (9.8 g, crude) from step C above and triethylamine (5.0 g, 49.5 mmol) in dichloromethane cooled to 0° C. was added methanesulfonyl chloride (7.5 g, 65 mmol) slowly. The reaction mixture was stirred at 0° C. for 1 hour. The reaction mixture was diluted with dichloromethane, washed with water, saturated NaHCO$_3$, brine, dried over sodium sulfate and concentrated to give the desired chloride (10 g crude) as a thick oil.

Step E: To a suspension of zinc powder (3.92 g, 60 mmol) in THF (5 mL) was added chlorotrimethylsilane (0.5 mL). The mixture was stirred at room temperature for 2 minutes. The solvent was poured off. The operation was repeated another time. To the suspension of the activated zinc in dichloromethane (80 mL) was added iodine (20 mg) and the mixture was heated to reflux. To the refluxing mixture was added a small portion of ethyl 2-bromoacetate (6.7 g, 40 mmol) and methylmagnesium bromide (5 drops, 3.0 M in ether). Once the reaction was initiated, the rest of the ethyl 2-bromoacetate was continuously added to the refluxing mixture. The mixture was further refluxed for 2 hours, cooled to 0° C. and a solution of the chloride (10 g, crude) from step D above in dichloromethane (100 mL) was added slowly. The reaction mixture was stirred at 0° C. to room temperature overnight. The reaction was washed with saturated ammonium chloride (zinc stayed in aqueous phase), brine, dried over sodium sulfate and concentrated. The residue was purified by column chromatography (10:90 to 40:60 ethyl acetate/hexanes) to give the desired ester (6.6 g, 80% for three steps): $^1$H NMR (CDCl$_3$, 300 MHz) δ 7.51 (d, J=8.2 Hz, 2H), 7.41 (d, J=8.2 Hz, 2H), 7.14 (d, J=2.8 Hz, 1H), 7.06 (d, J=8.5 Hz, 1H), 6.84 (dd, J=8.5, 2.8 Hz, 1H), 6.04 (s, 1H), 5.10 (t, J=7.8 Hz, 1H), 4.17-4.00 (m, 6H), 3.77 (s, 3H), 3.03 (d, J=7.8 Hz, 2H), 1.12 (t, J=7.1 Hz, 3H).

Step F: To a solution of the ester (6.6 g, 15.6 mmol) from step E above in THF (60 mL) at 0° C. was added concentrated hydrochloric acid (12 M, 144 mmol). The solution was stirred at 0° C. for 2 hours. The solution was diluted with dichloromethane, washed with saturated NaHCO$_3$, brine, dried over sodium sulfate and concentrated to give the desired aldehyde (5.9 g, crude) as a colorless oil: $^1$H NMR (CDCl$_3$, 300 MHz) δ 10.27 (s, 1H), 7.53 (d, J=8.1 Hz, 2H), 7.35-7.28 (m, 4H), 7.13 (dd, J=8.6, 2.9 Hz, 1H), 5.64 (t, J=7.9 Hz, 1H), 4.04 (q, J=7.1 Hz, 2H), 3.85 (s, 3H), 3.06 (d, J=7.9 Hz, 2H), 1.12 (t, J=7.1 Hz, 3H).

Step G: To a solution of the aldehyde (5.9 g, 15.5 mmol) from step F above, methylamine hydrochloride (2.1 g, 31 mmol) and triethylamine (3.2 g, 31 mmol) in ethanol (60 ml) were added titanium (IV) isopropoxide (8.8 g, 31 mmol) at room temperature. The mixture was stirred at room temperature overnight. Sodium borohydride (880 mg, 23.2 mmol) was added to the mixture portionwise, and reaction mixture was stirred at room temperature for 2 hours. To the reaction mixture was added saturated ammonium chloride (60 mL), and the resulting mixture was stirred at room temperature for 10 minutes. The precipitate was filtered and the filtrate was concentrated to give the benzylamine (5.5 g, 90%) as colorless oil: $^1$H NMR (CDCl$_3$, 300 MHz) δ 7.50 (d, J=8.2 Hz, 2H), 7.34 (d, J=8.2 Hz, 2H), 7.16 (d, J=8.5 Hz, 1H), 6.90 (d, J=2.7 Hz, 1H), 6.80 (dd, J=8.5, 2.7 Hz, 1H), 4.92 (t, J=7.9 Hz, 1H), 4.04 (q, J=7.1 Hz, 2H), 3.79 (s, 3H), 3.74-3.66 (m, 2H), 3.06-2.98 (m, 2H), 2.44 (s, 3H), 1.12 (t, J=7.1 Hz, 3H); ESI MS m/z 396 [M+H]$^+$.

Step H: To a solution of the benzylamine (4.6 g, 12 mmol) from step G above in toluene (100 mL) was added camphorsulfonic acid (150 mg). The solution was refluxed for 36 hours. After cooling to room temperature, the reaction was washed with saturated NaHCO$_3$, brine, dried over sodium sulfate and concentrated to give the desired lactam (3.0 g, 75%) as light yellow oil: $^1$H NMR (CDCl$_3$, 300 MHz) δ 7.53 (d, J=8.1 Hz, 2H), 7.18 (d, J=8.1 Hz, 2H), 6.81 (d, J=8.5 Hz, 1H), 6.74-6.68 (m, 2H), 4.94 (d, J=16.2 Hz, 1H), 4.56-4.51 (m, 1H), 4.21 (d, J=16.2 Hz, 1H), 3.23-3.15 (m, 1H), 3.06 (s, 3H), 3.03-2.97 (m, 1H), 2.04 (s, 3H); ESI MS m/z 350 [M+H]$^+$.

Step I: To a solution of the lactam (3.0 g, 8.6 mmol) from step H above in THF (40 mL) cooled to 0° C. was added boron-dimethylsulfide (13 mL, 26.0 mmol, 2.0 M in THF) dropwise. The resulting solution was allowed to warm up to room temperature and heated at 50° C. for 1 hour. After cooling to room temperature, HCl (6 N, 15 mL) was slowly added to the solution. It was refluxed at 70° C. for 1 hour and at room temperature overnight. After cooling to room temperature, the solution was adjusted to pH 9 with NaOH. The product was extracted with dichloromethane, washed with and dried over sodium sulfate and concentrated. The residue was purified by column chromatography (98:1.8:0.2 to 90:4.5:0.5 dichloromethane/methanol/concentrated ammonium hydroxide) to give the benzazepine (2.1 g, 73%) as a gel-like semi-solid. To a solution of the benzazepine (43 mg, 0.128 mg) in methanol (1 mL) was added L-tartaric acid (19 mg, 0.127 mmol) followed by slow addition of water (5 mL). The resultant solution was lyophilized overnight to give 8-methoxy-2-methyl-5-(4-(trifluoromethyl)phenyl)-2,3,4,5-tetrahydro-1H-benzo[c]azepine, tartrate salt (25 mg, 81%, AUC HPLC >99%) as a white solid: mp 78-81° C.; $^1$H NMR (CD$_3$OD, 500 MHz) δ 7.69 (d, J=8.1 Hz, 2H), 7.39 (d, J=8.1 Hz, 1H), 7.05 (s, 1H), 6.88 (d, J=7.0 Hz, 1H), 6.75 (br, 1H), 4.61 (d, J=8.1 Hz, 1H), 4.53 (br, 1H), 4.41 (s, 3H), 4.27-4.26 (m, 1H), 3.80 (s, 3H), 3.54-3.44 (m, 2H), 2.85 (s, 3H), 2.63-2.56 (m, 1H), 2.41-2.39 (m, 1H); MS m/z 336 [M+H].

Example 142

Preparation of (+) 4-(2-methyl-5-(4-(trifluoromethyl) phenyl-2,3,4,5-tetrahydro-1H-benzo[c]azepine-8-yl) morpholine, L-tartrate salt, and (−) 4-(2-methyl-5-(4-(trifluoromethyl)phenyl-2,3,4,5-tetrahydro-1H-benzo [c]azepine-8-yl)morpholine, L-tartrate salt Step A: To a solution of 3-methoxybenzaldehyde (31.2 g, 229 mmol) in DMF (500 ml) were added N-bromosuccinimide (48.9 g, 275 mmol) at room temperature. The mixture was stirred at room temperature overnight. The solution was poured into water. The precipitate was filtered to give the desired bromide (50.7 g, quant.) as a white solid: $^1$H NMR (CDCl$_3$, 300 MHz) δ 10.31 (s, 1H), 7.53 (d, J=8.7 Hz, 1H), 7.42 (s, 1H), 7.04 (d, J=8.7 Hz, 1H), 3.84 (s, 3H).

Step B: To a solution of the bromide (20 g, 93 mmol) from step A in toluene (200 mL) was added glycol (31 g, 465 mmol) and camphorsulfonic acid (1.07 g, 4.6 mmol). The mixture was refluxed with Dean-Stark trap for 4 hours. After cooling to room temperature, the excess glycol was separated. The toluene layer was washed with saturated NaHCO$_3$, water, brine, dried over sodium sulfate and concentrated to give the desired dioxolane (24 g, quant.) as a light colorless oil: $^1$H NMR (CDCl$_3$, 300 MHz) δ 7.44 (d, J=8.7 Hz, 1H), 7.16 (d, J=3.1 Hz, 1H), 6.79 (dd, J=8.7, 3.1 Hz, 1H), 6.04 (s, 1H), 4.17-4.06 (m, 4H), 3.80 (s, 3H).

Step C: To a solution of the dioxolane (5.05 g, 19.5 mmol) from step B above in THF (50 mL) cooled to −78° C. was added n-BuLi (2.5 M in hexane, 10.1 mL, 25.4 mmol) cooled to −78° C. by cannula. After stirring at this temperature for 0.5 hour, 4-(trifluoromethyl)benzaldehyde (4.41 g, 25.4 mmol) was added to the resulting mixture dropwise. The reaction mixture was stirred at −78° C. for 1 hour. It was quenched at −78° C. with methanol (3 mL) and warmed up to room temperature. The mixture was diluted with dichloromethane. The organic layer was washed with brine, dried over sodium sulfate, and concentrated to give the desired alcohol (9.8 g, crude): $^1$H NMR (CDCl$_3$, 500 MHz) δ 7.59 (d, J=8.3 Hz, 2H), 7.53 (d, J=8.3 Hz, 2H), 7.16 (d, J=2.7 Hz, 1H), 7.00 (d, J=8.5 Hz, 1H), 6.82 (dd, J=8.5, 2.7 Hz, 1H), 6.20 (d, J=3.7 Hz, 1H), 5.92 (s, 1H), 4.18-4.04 (m, 4H), 3.81(s, 3H), 3.45 (d, J=4.3 Hz, 1H).

Step D: To a solution of the alcohol (9.8 g, crude) from step C above and triethylamine (5.0 g, 49.5 mmol) in dichloromethane cooled to 0° C. was added methanesulfonyl chloride (7.5 g, 65 mmol) slowly. The reaction mixture was stirred at 0° C. for 1 hour. The reaction mixture was diluted with dichloromethane, washed with water, saturated NaHCO$_3$, brine, dried over sodium sulfate and concentrated to give the desired chloride (10 g crude) as a thick oil.

Step E: To a suspension of zinc powder (3.92 g, 60 mmol) in THF (5 mL) was added chlorotrimethylsilane (0.5 mL). The mixture was stirred at room temperature for 2 minutes. The solvent was poured off. The operation was repeated another time. To the suspension of the activated zinc in dichloromethane (80 mL) was added iodine (20 mg) and the mixture was heated to reflux. To the refluxing mixture was added a small portion of ethyl 2-bromoacetate (6.7 g, 40 mmol) and methylmagnesium bromide (5 drops, 3.0 M in ether). Once the reaction was initiated, the rest of the ethyl 2-bromoacetate was continuously added to the refluxing mixture. The mixture was further refluxed for 2 hours, cooled to 0° C. and a solution of the chloride (10 g, crude) from step D above in dichloromethane (100 mL) was added slowly. The reaction mixture was stirred at 0° C. to room temperature overnight. The reaction was washed with saturated ammonium chloride (zinc stayed in aqueous phase), brine, dried over sodium sulfate and concentrated. The residue was purified by column chromatography (10:90 to 40:60 ethyl acetate/hexanes) to give the desired ester (6.6 g, 80% for three steps): $^1$H NMR (CDCl$_3$, 300 MHz) δ 7.51 (d, J=8.2 Hz, 2H), 7.41 (d, J=8.2 Hz, 2H), 7.14 (d, J=2.8 Hz, 1H), 7.06 (d, J=8.5 Hz, 1H), 6.84 (dd, J=8.5, 2.8 Hz, 1H), 6.04 (s, 1H), 5.10 (t, J=7.8 Hz, 1H), 4.17-4.00 (m, 6H), 3.77 (s, 3H), 3.03 (d, J=7.8 Hz, 2H), 1.12 (t, J=7.1 Hz, 3H).

Step F: To a solution of the ester (6.6 g, 15.6 mmol) from step E above in THF (60 mL) at 0° C. was added concentrated hydrochloric acid (12 M, 144 mmol). The solution was stirred at 0° C. for 2 hours. The solution was diluted with dichloromethane, washed with saturated NaHCO$_3$, brine, dried over sodium sulfate and concentrated to give the desired aldehyde (5.9 g, crude) as a colorless oil: $^1$H NMR (CDCl$_3$, 300 MHz) δ 10.27 (s, 1H), 7.53 (d, J=8.1 Hz, 2H), 7.35-7.28 (m, 4H), 7.13 (dd, J=8.6, 2.9 Hz, 1H), 5.64 (t, J=7.9 Hz, 1H), 4.04 (q, J=7.1 Hz, 2H), 3.85 (s, 3H), 3.06 (d, J=7.9 Hz, 2H), 1.12 (t, J=7.1 Hz, 3H).

Step G: To a solution of the aldehyde (5.9 g, 15.5 mmol) from step F above, methylamine hydrochloride (2.1 g, 31 mmol) and triethylamine (3.2 g, 31 mmol) in ethanol (60 ml) were added titanium (IV) isopropoxide (8.8 g, 31 mmol) at room temperature. The mixture was stirred at room temperature overnight. Sodium borohydride (880 mg, 23.2 mmol) was added to the mixture portionwise, and reaction mixture was stirred at room temperature for 2 hours. To the reaction mixture was added saturated ammonium chloride (60 mL), and the resulting mixture was stirred at room temperature for 10 minutes. The precipitate was filtered and the filtrate was concentrated to give the benzylamine (5.5 g, 90%) as colorless oil: $^1$H NMR (CDCl$_3$, 300 MHz) δ 7.50 (d, J=8.2 Hz, 2H), 7.34 (d, J=8.2 Hz, 2H), 7.16 (d, J=8.5 Hz, 1H), 6.90 (d, J=2.7 Hz, 1H), 6.80 (dd, J=8.5, 2.7 Hz, 1H), 4.92 (t, J=7.9 Hz, 1H), 4.04 (q, J=7.1 Hz, 2H), 3.79 (s, 3H), 3.74-3.66 (m, 2H), 3.06-2.98 (m, 2H), 2.44 (s, 3H), 1.12 (t, J=7.1 Hz, 3H); ESI MS m/z 396 [M+H]$^+$.

Step H: To a solution of the benzylamine (4.6 g, 12 mmol) from step G above in toluene (100 mL) was added camphorsulfonic acid (150 mg). The solution was refluxed for 36 hours. After cooling to room temperature, the reaction was washed with saturated NaHCO$_3$, brine, dried over sodium sulfate and concentrated to give the desired lactam (3.0 g, 75%) as light yellow oil: $^1$H NMR (CDCl$_3$, 300 MHz) δ 7.53 (d, J=8.1 Hz, 2H), 7.18 (d, J=8.1 Hz, 2H), 6.81 (d, J=8.5 Hz, 1H), 6.74-6.68 (m, 2H), 4.94 (d, J=16.2 Hz, 1H), 4.56-4.51 (m, 0.1H), 4.21 (d, J=16.2 Hz, 1H), 3.23-3.15 (m, 1H), 3.06 (s, 3H), 3.03-2.97 (m, 1H), 2.04 (s, 3H); ESI MS m/z 350 [M+H]$^+$.

Step I: To a solution of the lactam (3.0 g, 8.6 mmol) from step H above in THF (40 mL) cooled to 0° C. was added boron-dimethylsulfide (13 mL, 26.0 mmol, 2.0 M in THF) dropwise. The resulting solution was allowed to warm up to room temperature and heated at 50° C. for 1 hour. After cooling to room temperature, HCl (6 N, 15 mL) was slowly added to the solution. It was refluxed at 70° C. for 1 hour and at room temperature overnight. After cooling to room temperature, the solution was adjusted to pH 9 with NaOH. The product was extracted with dichloromethane, washed with and dried over sodium sulfate and concentrated. The residue was purified by column chromatography (98:1.8:0.2 to 90:4.5:0.5 dichloromethane/methanol/concentrated ammonium hydroxide) to give benzazepine (2.1 g, 73%) as a gel-like semi-solid: $^1$H NMR (CDCl$_3$, 300 MHz) δ 7.60 (d, J=8.1 Hz, 2H), 7.29 (d, J=8.1 Hz, 2H), 6.76 (d, J=2.7 Hz, 1H), 6.63-6.59 (m, 1H), 6.52 (br, 1H), 4.31 (d, J=7.9 Hz, 1H), 3.87 (d, J=13.8 Hz, 1H), 3.80 (s, 3H), 3.67 (d, J=13.8 Hz, 1H), 3.11-2.90 (m, 2H), 2.37-2.26 (m, 4H), 2.12 (m, 1H); MS m/z 336 [M+H].

Step J: To a solution of the benzazepine (460 mg, 1.37 mmol) from step I above in dichloromethane (5 mL) cooled to −78° C. was added boron bromide (1.5 mL, 1.5 mmol, 1.0 M in dichloromethane) dropwise. The dry-ice bath was removed, and the reaction was allowed to warm up to room temperature. After stirring for 1 hour, the reaction was cooled by ice-water bath and water (5 mL) was added dropwise to quench the reaction. The mixture was stirred at 0° C. for 5 minutes. The mixture was then adjusted to pH 8 with saturated NaHCO$_3$. The organic layer was separated, washed with brine, dried over sodium sulfate and concentrated to give the desired phenol (417 mg, crude) as a gum-like solid: $^1$H NMR (CDCl$_3$, 300 MHz) δ 7.60 (d, J=8.0 Hz, 2H), 7.30-7.25 (m, 2H), 6.66-6.50 (m, 3H), 4.30 (d, J=7.9 Hz, 1H), 3.86 (d, J=11.1 Hz, 1H), 3.68 (d, J=11.1 Hz, 1H), 3.08-2.99 (m, 2H), 2.47-2.15 (m, 5H); MS m/z 322 [M+H].

Step K: To a solution of the phenol (417 mg, 1.92 mmol) from step J above in dichloromethane (5 mL) and pyridine (0.5 mL) was added triflic anhydride (528 mg, 1.9 mmol) dropwise at 0° C. After stirring at this temperature for 1 hour, the solution was washed with water, saturated NaHCO$_3$, brine and dried over sodium sulfate and concentrated to give the desired triflate (730 mg, crude) as a thick oil: $^1$H NMR (CDCl$_3$, 300 MHz) δ 7.68-7.63 (m, 4H), 7.13 (d, J=2.7 Hz, 1H), 7.03-6.99 (m, 1H), 6.68 (br, 1H), 4.40 (d, J=8.8 Hz, 1H), 4.04 (d, J=15.4 Hz, 1H), 3.79 (d, J=15.4 Hz, 1H), 3.19-3.03 (m, 2H), 2.42-2.12 (m, 5H); MS m/z 454 [M+H].

Step L: To a solution of the triflate (730 mg, crude) from step K above in xylene (6 mL) was added dicyclohexyl(2′,4′,6′-triisopropylbiophenyl-2-yl)phosphine (177 mg, 0.37 mmol) and cesium carbonate (1.2 g, 3.7 mmol). The system was purged with argon. Palladium (II) acetate (42 mg, 0.19 mmol) and morpholine (0.7 mL, 6.2 mmol) were added to the mixture. The reaction mixture was heated at 130° C. overnight. After cooling to room temperature, the reaction mixture was diluted with dichloromethane, and filtered through a pad of Celite. The filtrate was concentrated. The residue was purified by flash chromatography (98:1.8:0.2 to 90:4.5:0.5 dichloromethane/methanol/ammonium hydroxide) to the desired benzazepine (300 mg, 62% for two steps) as a gum-like solid.

Step M: The free base of the benzazepine was resolved by preparative chiral HPLC (CHIRALCEL OD column, using 80:20:0.1 heptane/isopropanol/diethylamine as the eluent) to give the enantiomer 1 [[α]$^{25}_D$ −4.6° (c 0.065, methanol)] and the enantiomer 2 [[α]$^{25}_D$ −5.5° (c 0.073, methanol)].

Step N: To a solution of the enantiomer 1 (37 mg, 0.095 mmol) from Step M above in methanol (1 mL) was added L-tartaric acid (17 mg, 0.11 mmol) followed by slow addition of water (5 mL). The resultant solution was lyophilized overnight to give (+) 4-(2-methyl-5-(4-(trifluoromethyl)phenyl-2,3,4,5-tetrahydro-1H-benzo[c]azepine-8-yl)morpholine, tartrate salt (42 mg, 78%, AUC HPLC >99%) as a white solid: mp 126-128° C.; $^1$H NMR (CD$_3$OD, 500 MHz) δ 7.69 (d, J=8.1 Hz, 1H), 7.39 (d, J=8.1 Hz, 1H), 7.06 (s, 1H), 6.90 (d, J=7.5 Hz, 1H), 6.62 (br, 1H), 4.58-4.49 (m, 2H), 4.41 (s, 3H), 4.24 (br, 1H), 3.83-3.81 (m, 4H), 3.52-3.43 (m, 2H), 3.16-3.15 (m, 4H), 2.86 (s, 3H), 2.59-2.25 (m, 2H); ESI MS m/z 392 [M+H].

Step O: To a solution of the enantiomer 2 (2, 37 mg, 0.095 mmol) from Step M above in methanol (1 mL) was added L-tartaric acid (17 mg, 0.11 mmol), followed by slow addition of water (5 mL). The resultant solution was lyophilized overnight to give (+) 4-(2-methyl-5-(4-(trifluoromethyl)phenyl-2,3,4,5-tetrahydro-1H-benzo[c]azepine-8-yl)morpholine, tartrate salt (43 mg, 79%, AUC HPLC >99%) as a white solid: mp 125-127° C.; $^1$H NMR (CD$_3$OD, 500 MHz) δ 7.69 (d, J=8.1 Hz, 1H), 7.39 (d, J=8.1 Hz, 1H), 7.06 (s, 1H), 6.90 (d, J=7.5 Hz, 1H), 6.62 (br, 1H), 4.58-4.49 (m, 2H), 4.41 (s, 3H), 4.24 (br, 1H), 3.83-3.81 (m, 4H), 3.52-3.43 (m, 2H), 3.16-3.15 (m, 4H), 2.86 (s, 3H), 2.59-2.25 (m, 2H); ESI MS m/z 392 [M+H].

Example 143

Preparation of 5-(3,5-difluorophenyl)-2-methyl-8-(pyridazin-3-yl)-2,3,4,5-tetrahydro-1H-benzo[c]azepine, L-tartrate salt and 5-(3,5-difluorophenyl)-2-methyl-8-(pyridazin-3-yl)-2,3,4,5-tetrahydro-1H-benzo[c]azepine, L-tartrate salt, enantiomers 1 and 2

Step A: To a solution of m-anisaldehyde (55.4 g, 0.41 mol) in DMF (400 mL) was added a solution of N-bromosuccinimide (124.0 g, 0.69 mol) dropwise at room temperature. After the addition, the reaction solution was stirred at room temperature for 12 hours, then poured into a mixture of ice and water and stirred for 10 minutes. The precipitate was collected by filtration and dissolved in ethyl acetate. The resultant solution was washed with water (2×) and brine, dried over sodium sulfate and concentrated in vacuo to give the desired aldehyde (76.4 g, 87%) as an off-white solid: $^1$H NMR (CDCl$_3$, 500 MHz) δ 10.32 (s, 1H), 7.53 (d, J=8.5 Hz, 1H), 7.42 (d, J=3.5 Hz, 1H), 7.04 (dd, J=9.0, 3.0 Hz, 1H), 3.85 (s, 3H).

Step B: To a solution of the aldehyde (50.0 g, 0.23 mol) from step A above in toluene (650 mL) were added ethylene glycol (14.2 mL, 0.26 mol) and camphorsulfonic acid (10.7 g, 46 mmol). The reaction solution was heated under reflux with a Dean-Stark trap for 6 hours and then it was cooled to room temperature and diluted with ethyl acetate (300 mL). The resultant solution was washed with aqueous saturated sodium bicarbonate and brine, dried over sodium sulfate and concentrated in vacuo to give the desired acetal (61.5 g, quantitative) as a yellow oil: $^1$H NMR (CDCl$_3$, 500 MHz) δ 7.44 (d, J=8.5 Hz, 1H), 7.15 (d, J=3.5 Hz, 1H), 6.79 (dd, J=8.5, 3.0 Hz, 1H), 6.04 (s, 1H), 4.18-4.06 (m, 4H), 3.81 (s, 3H).

Step C: To a solution of the acetal (13.0 g, 50.3 mmol) from step B above in tetrahydrofuran (120 mL) at −78° C. was added a cold (−78° C.) solution n-BuLi (22.0 mL, 55.0 mmol, 2.5M in hexanes). The resultant solution was stirred at −78° C. for 2 hours and then a cold (0° C.) solution of 3,5-difluorobenzaldehyde (7.0 g, 49.3 mmol) in THF (30 mL) was added to it. The reaction solution was stirred at −78° C. for 2 hours and then it was warmed to room temperature, quenched with a saturated solution of ammonium chloride and extracted with ethyl acetate (3×). The combined organic extracts were washed with brine, dried over sodium sulfate and concentrated in vacuo. The crude product obtained was purified by flash column chromatography (90:10 to 75:25 hexanes/ethyl acetate) to give the desired alcohol (13.4 g, 82%) as a yellow oil: $^1$H NMR (CDCl$_3$, 500 MHz) δ 7.15 (d, J=3.0 Hz, 1H), 7.05 (d, J=8.5 Hz, 1H), 6.97-6.93 (m, 2H), 6.85 (dd, J=8.5, 3.0 Hz, 1H), 6.70 (tt, J=9.0, 2.5 Hz, 1H), 6.09 (d, J=4.5 Hz, 1H), 5.90 (s, 1H), 4.10-4.03 (m, 4H), 3.82 (s, 3H), 3.43 (d, J=4.5 Hz, 1H).

Step D: To a solution of the alcohol (1.7 g, 5.2 mmol) from step C above in dichloromethane (20 mL) at 0° C. were added triethylamine (1.8 mL, 13 mmol) and methanesulfonyl chloride (1.2 g, 10.6 mmol). The resultant reaction solution was stirred at 0° C. for 45 minutes and then diluted with ethyl acetate. The mixture obtained was washed with aqueous sodium bicarbonate and brine, dried over sodium sulfate and concentrated in vacuo to give the crude chloride, which was used in the next step without further purification: $^1$H NMR (CDCl$_3$, 500 MHz) δ 7.31 (d, J=8.5 Hz, 1H), 7.13 (d, J=3.0 Hz, 1H), 7.04-6.99 (m, 2H), 6.89 (dd, J=8.5, 3.0 Hz, 1H), 6.72 (tt, J=8.5, 2.0 Hz, 1H), 6.64 (s, 1H), 6.02 (s, 1H), 4.11-4.04 (m, 4H), 3.82 (s, 3H).

Step E: To a dry flask with zinc (4.3 g, 65.0 mmol) under nitrogen were added tetrahydrofuran (25 mL) and trimethylsilyl chloride (0.1 mL). The resultant mixture was stirred at room temperature for 5 minutes and then the solvent was removed by syringe. To this activated zinc were then added dichloromethane (150 mL), ethyl 2-bromoacetate (6.0 mL, 54.5 mmol), iodine (0.1 g) and methylmagnesium bromide (0.1 mL of 3M in diethyl ether, 0.3 mmol). The resultant reaction mixture was heated under reflux for 1 hour and then cooled to 0° C. To this milky solution was added a solution of the chloride (12.2 g, 36.0 mmol) from step D above in dichloromethane (50 mL) and the resultant mixture was stirred at 0° C. for 20 minutes and room temperature for 90 minutes. The reaction solution was then washed with aqueous ammonium chloride and brine, dried over sodium sulfate and concentrated in vacuo. The crude product obtained was purified by flash column chromatography (95:5 to 83:17 hexanes/ethyl acetate) to give the desired ester (10.8 g, 76%) as a light yellow oil: $^1$H NMR (CDCl$_3$, 500 MHz) δ 7.13 (d, J=3.0 Hz, 1H), 7.06 (d, J=8.5 Hz, 1H), 6.86-6.79 (m, 3H), 6.61 (tt, J=9.0, 2.5 Hz, 1H), 6.03 (s, 1H), 5.01 (t, J=7.5 Hz, 1H), 4.21-4.03 (m, 6H), 3.79 (s, 3H), 2.97 (d, J=7.5 Hz, 2H), 1.14 (t, J=7.0 Hz, 3H).

Step F: To a solution of the ester (1.5 g, 3.9 mmol) from step E above in dioxane (80 mL) at 0° C. was added concentrated hydrochloric acid (15 mL). The reaction solution was stirred at 0° C. for 20 minutes and room temperature for 1 hour. The resultant reaction solution was diluted with ethyl acetate, washed with water and brine, dried over sodium sulfate and concentrated in vacuo to give the desired aldehyde (1.6 g, quantitative), which was used in the next step without further purification: $^1$H NMR (CDCl$_3$, 500 MHz) δ 10.25 (s, 1H), 7.34 (d, J=3.0 Hz, 1H), 7.28 (d, J=8.5 Hz, 1H), 7.11 (dd, J=8.5, 2.5 Hz, 1H), 6.76-6.72 (m, 2H), 6.63 (tt, J=9.0, 2.5 Hz, 1H), 5.58 (t, J=8.0 Hz, 1H), 4.05 (q, J=7.0 Hz, 2H), 3.86 (s, 3H), 3.01 (d, J=8.0 Hz, 2H), 1.14 (t, J=7.0 Hz, 3H).

Step G: To a solution of methylamine (0.60 mL, 4.9 mmol, 33% in ethanol) and the aldehyde (1.6 g, 3.9 mmol) from step F above was added titanium(IV) isopropoxide (1.5 mL, 5.1 mmol). The resultant reaction solution was stirred at room temperature for 16 h and then sodium borohydride (0.16 g, 4.3 mmol) was added to it. The reaction solution was stirred at room temperature for 1 hour, and then quenched with water. The precipitate formed was removed by filtration, and the filtrate obtained was diluted with dichloromethane, washed with water, dried over sodium sulfate and concentrated in vacuo to give the crude amine (1.4 g, 98%) as a light yellow oil, which was used in the next step without purification: $^1$H NMR (CDCl$_3$, 500 MHz) δ 7.13 (d, J=8.5 Hz, 1H), 6.90 (d, J=3.0 Hz, 1H), 6.80 (dd, J=8.5, 3.0 Hz, 1H), 6.78-6.75 (m, 2H), 6.61 (tt, J=9.0, 2.5 Hz, 1H), 4.87 (t, J=8.0 Hz, 1H), 4.05 (q, J=7.0 Hz, 2H), 3.79 (s, 3H), 3.75 (d, J=13.0 Hz, 1H), 3.67 (d, J=13.0 Hz, 1H), 3.04-2.92 (m, 2H), 2.45 (s, 3H), 1.70-1.30 (br, 1H), 1.14 (t, J=7.0 Hz, 3H); ESI MS m/z 364 [M+H]$^+$.

Step H: To a solution of the amine (4.0 g, 11.0 mmol) from step G above in toluene (100 mL) at −78° C. was added a solution of diisobutylaluminium hydride (27.5 mL, 27.5 mmol, 1M in toluene) slowly. The reaction solution was stirred at −78° C. for 2 hours, and then cold (−78° C.) methanol (80 mL) was added to it via cannula. The resultant reaction mixture was stirred at −40° C. for 10 minutes and then sodium borohydride (1.6 g, 44 mmol) was added to it in batches. The reaction solution was stirred at −40° C. for 30 minutes, then it was warmed to room temperature, stirred for 1 hour and concentrated in vacuo. The residue obtained was dissolved in a mixture of dichloromethane and aqueous saturated Rochelle's salt and the resultant solution was vigorously stirred for 30 minutes. The organic extract was then separated, dried over sodium sulfate and concentrated in vacuo. The crude product obtained was purified by flash column chromatography (99:0.9:0.1 to 90:9:1 dichloromethane/methanol/concentrated ammonium hydroxide) to give the desired 8-methoxybenzazepine (3.0 g, 89%) as a light yellow oil: $^1$H NMR (CDCl$_3$, 500 MHz) δ 6.83-6.51 (m, 6H), 4.23 (dd, J=9.0, 2.0 Hz, 1H), 3.82-3.72 (m, 1H), 3.79 (s, 3H), 3.67 (d, J=14.5 Hz, 1H), 3.08-3.02 (br, 1H), 2.95-2.90 (m, 1H), 2.33 (s, 3H), 2.27-2.20 (m, 1H), 2.17-2.06 (br, 1H); ESI MS m/z 304 [M+H]$^+$.

Step I: To a solution of the 8-methoxybenzazepine (2.8 g, 9.1 mmol) from step H above in acetic acid (60 mL) was added hydrobromic acid (60 mL, 48% solution in water). The reaction solution was heated at 100° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (2.8 g, quantitative) as a brown solid, which was used in the next step without purification: $^1$H NMR (CDCl$_3$, 500 MHz) δ 6.79-6.40 (m, 6H), 4.20 (d, J=8.5 Hz, 1H), 3.82-3.64 (br, 1H), 3.61 (d, J=14.0 Hz, 1H), 3.23-2.76 (br, 2H), 2.41 (s, 3H), 2.32-2.03 (br, 2H).

Step J: To a solution of the phenol (1.8 g, 6.2 mmol) from step I above in dichloromethane (60 mL) at 0° C. were added pyridine (1.0 mL, 12.4 mmol) and triflic anhydride (1.2 mL, 6.9 mmol). The resultant reaction solution was stirred at 0° C. for 2 hours, and then it was diluted with dichloromethane, washed with aqueous saturated sodium bicarbonate, dried over sodium sulfate and concentrated in vacuo. The triflate obtained (2.5 g, 96%) as a dark reddish oil was used in the next step without purification: $^1$H NMR (CDCl$_3$, 500 MHz) δ 7.11 (d, J=2.5 Hz, 1H), 7.02 (dd, J=8.5, 2.5 Hz, 1H), 6.87-6.56 (m, 4H), 4.31 (d, J=9.0 Hz, 1H), 3.93 (d, J=13.0 Hz, 1H), 3.72 (d, J=14.5 Hz, 1H), 3.18-2.94 (m, 2H), 2.35 (s, 3H), 2.29-2.01 (m, 2H).

Step K: To a mixture of the triflate (1.7 g, 4.1 mmol) from step J above, bis(pinacolato)diboron (1.3 g, 5.0 mmol) and potassium acetate (1.2 g, 12.3 mmol) was added DMSO (30 mL). The resultant solution was purged with argon for 10 minutes, and then dichloro[1,1'-bis(diphenylphosphino)ferrocene]palladium(II) dichloromethane adduct (0.33 g, 0.41 mmol) was added. The reaction solution was degassed again with argon for 5 minutes and heated at 80° C. for 1 hour. The resultant reaction solution was then cooled to room temperature, diluted with ethyl acetate, washed with water (2×) and brine, dried over sodium sulfate and concentrated in vacuo. The crude product obtained was used in the next step without further purification.

Step L: To a mixture of the boronate ester (1.3 g, 3.2 mmol) from step K above, 3,6-dichloropyridazine (0.97 g, 6.5 mmol) and sodium carbonate (1.02 g, 10.0 mmol) were added DMF (50 mL) and water (12.5 mL). The reaction solution was flushed with argon for 10 minutes, and then dichloro[1,1'-bis(diphenylphosphino)ferrocene]palladium(II) dichloromethane adduct (0.21 g, 0.26 mmol) was added. The resultant mixture was flushed with argon for 5 minutes and heated at 80° C. for 2 hours. The reaction solution was then cooled to room temperature, diluted with ethyl acetate, washed with 1:1 brine and water (2×), dried over sodium sulfate and concentrated in vacuo. The crude product obtained was purified by flash column chromatography (99:0.9:0.1 to 94:5.4:0.6 dichloromethane/methanol/concentrated ammonium hydroxide) to give the desired 8-(3-chloropyridazin-3-yl) benzazepine (0.77 g, 62%) as a brown oil: $^1$H NMR (CDCl$_3$, 500 MHz) δ 7.95 (d, J=2.0 Hz, 1H), 7.80 (d, J=9.0 Hz, 1H), 7.76 (d, J=8.0 Hz, 1H), 7.55 (d, J=8.5 Hz, 1H), 6.96-6.79 (br, 1H), 6.78-6.67 (m, 3H), 4.37 (d, J=8.0 Hz, 1H), 3.96 (d, J=13.0 Hz, 1H), 3.83 (d, J=14.0 Hz, 1H), 3.14-2.95 (m, 2H), 2.38 (s, 3H), 2.34-2.15 (m, 2H).

Step M: To a solution of the 8-(3-chloropyridazin-3-yl) benzazepine (0.77 g, 2.0 mmol) from step L above in ethanol (50 mL) were added hydrazine (1.0 mL, 20 mmol) and palladium on carbon (0.11 g). The reaction solution was heated under reflux for 16 h, and then it was cooled to room temperature, filtered through a plug of Celite and concentrated under reduced pressure. The crude product was purified by flash column chromatography (dichloromethane to 90:9:1 dichloromethane/methanol/concentrated ammonium hydroxide) to give the racemic benzazepine (0.20 g, 28%) as a yellow foam: $^1$H NMR (CDCl$_3$, 500 MHz) δ 9.15 (dd, J=4.5, 1.5 Hz, 1H), 8.00 (d, J=2.0 Hz, 1H), 7.84 (dd, J=8.5, 1.5 Hz, 1H), 7.80 (d, J=8.0 Hz, 1H), 7.53 (dd, J=8.5, 5.0 Hz, 1H), 6.92-6.80 (br, 1H), 6.77-6.70 (m, 3H), 4.38 (d, J=8.5 Hz, 1H), 3.98 (d, J=13.0 Hz, 1H), 3.85 (d, J=14.0 Hz, 1H), 3.14-3.08 (m, 1H), 3.01-2.96 (m, 1H), 2.38 (s, 3H), 2.87-2.14 (m, 2H).

Step N: The racemic benzazepine (0.20 g) was resolved by preparative chiral HPLC (CHIRALCEL OD column, using 80:20:0.1 heptane/ethanol/diethylamine as the eluent) to give enantiomer 1 [[α]$^{25}_D$ –1.67° (c 0.12, methanol)] (98 mg) and enantiomer 2 [[α]$^{25}_D$ –4.17° (c 0.12, methanol)] (73 mg).

Step O: To a solution of the enantiomer 1 (95 mg, 0.27 mmol) from step N above in methanol (2 mL) were added L-tartaric acid (40.5 mg, 0.27 mmol) and water (10 mL). The resultant solution was lyophilized overnight to provide 5-(3,5-difluorophenyl)-2-methyl-8-(pyridazin-3-yl)-2,3,4,5-tetrahydro-1H-benzo[c]azepine, L-tartrate salt, enantiomer 1 (0.13 g, >99.0% AUC HPLC) as an off-white solid: $^1$H NMR (CD$_3$OD, 500 MHz) δ 9.17 (dd, J=5.0, 1.5 Hz, 1H), 8.22-8.19 (m, 2H), 8.03 (d, J=7.5 Hz, 1H), 7.81 (dd, J=8.5, 5.0 Hz, 1H), 7.11-6.82 (m, 4H), 4.70 (d, J=8.5 Hz, 1H), 4.65-4.56 (br, 1H), 4.41 (s, 2H), 4.36 (d, J=14.5 Hz, 1H), 3.56-3.50 (br, 2H), 2.84 (s, 3H), 2.63-2.52 (br, 1H), 2.41 (br d, J=15.5 Hz, 1H); ESI MS m/z 352 [M+H]$^+$.

Step P (MHU-H-48): To a solution of the enantiomer 2 (71 mg, 0.20 mmol) from step N above in methanol (2 mL) were added L-tartaric acid (30.3 mg, 0.20 mmol) and water (10 mL). The resultant solution was lyophilized overnight to provide 5-(3,5-difluorophenyl)-2-methyl-8-(pyridazin-3-yl)-2,3,4,5-tetrahydro-1H-benzo[c]azepine, L-tartrate salt, enantiomer 2 (98 mg, >99% AUC HPLC) as a white solid: $^1$H NMR (CD$_3$OD, 500 MHz) δ 9.17 (dd, J=5.0, 1.5 Hz, 1H), 8.22 (s, 1H), 8.20 (d, J=8.5 Hz, 1H), 8.03 (d, J=8.0 Hz, 1H), 7.81 (dd, J=8.5, 5.0 Hz, 1H), 7.11-6.82 (m, 4H), 4.70 (d, J=8.5 Hz, 1H), 4.65-4.56 (br, 1H), 4.41 (s, 2H), 4.37 (d, J=14.5 Hz, 1H), 3.56-3.50 (br, 2H), 2.84 (s, 3H), 2.63-2.52 (br, 1H), 2.41 (br d, J=15.5 Hz, 1H); ESI MS m/z 352 [M+H]$^+$.

Example 144

Preparation of (+)-5-(3,5-difluorophenyl)-2-methyl-8-(6-methylpyridazin-3-yl)-2,3,4,5-tetrahydro-1H-benzo[c]azepine, L-tartrate salt and (−)-5-(3,5-difluorophenyl)-2-methyl-8-(6-methylpyridazin-3-yl)-2,3,4,5-tetrahydro-1H-benzo[c]azepine, L-tartrate salt Pursuant to the general method described above in Example 143, the following products were prepared: (+)-5-(3,5-difluorophenyl)-2-methyl-8-(6-methylpyridazin-3-yl)-2,3,4,5-tetrahydro-1H-benzo[c]azepine, L-tartrate salt: mp 116-118° C.; $^1$H NMR (CD$_3$OD, 500 MHz) δ 8.24 (d, J=1.5 Hz, 1H), 8.09 (d, J=9.0 Hz, 1H), 8.02 (d, J=8.0 Hz, 1H), 7.70 (d, J=8.5 Hz, 1H), 7.13-6.71 (m, 4H), 4.80-4.60 (m, 2H), 4.48 (s, 2.5H), 4.48-4.40 (m, 1H), 3.69-3.54 (m, 2H), 2.96 (s, 3H), 2.74 (s, 3H), 2.68-2.37 (m, 2H); ESI MS m/z 366 [M+H]$^+$; (−)-5-(3,5-difluorophenyl)-2-methyl-8-(6-methylpyridazin-3-yl)-2,3,4,5-tetrahydro-1H-benzo[c]azepine, L-tartrate salt: mp 108-110° C.; $^1$H NMR (CD$_3$OD, 500 MHz) δ 8.24 (d, J=1.5 Hz, 1H), 8.09 (d, J=9.0 Hz, 1H), 8.02 (d, J=8.0 Hz, 1H), 7.70 (d, J=8.5 Hz, 1H), 7.13-6.71 (m, 4H), 4.80-4.60 (m, 2H), 4.48 (s, 3.5H), 4.48-4.40 (m, 1H), 3.69-3.54 (m, 2H), 2.96 (s, 3H), 2.74 (s, 3H), 2.68-2.37 (m, 2H); ESI MS m/z 366 [M+H]$^+$.

Example 145

Preparation of (+)-5-(3,5-difluorophenyl)-2-methyl-8-(piperazin-1-yl)-2,3,4,5-tetrahydro-1H-benzo[c]azepine, L-tartrate salt and (−)-5-(3,5-difluorophenyl)-2-methyl-8-(piperazin-1-yl)-2,3,4,5-tetrahydro-1H-benzo[c]azepine, L-tartrate salt Step A: To a solution of m-anisaldehyde (55.4 g, 0.41 mol) in DMF (400 mL) was added a solution of N-bromosuccinimide (124.0 g, 0.69 mol) dropwise at room temperature. After the addition, the reaction solution was stirred at room temperature for 12 hours, then poured into a mixture of ice and water and stirred for 10 minutes. The precipitate was collected by filtration and dissolved in ethyl acetate. The resultant solution was washed with water (2×) and brine, dried over sodium sulfate and concentrated in vacuo to give the desired aldehyde (76.4 g, 87%) as an off-white solid: $^1$H NMR (CDCl$_3$, 500 MHz) δ 10.32 (s, 1H), 7.53 (d, J=8.5 Hz, 1H), 7.42 (d, J=3.5 Hz, 1H), 7.04 (dd, J=9.0, 3.0 Hz, 1H), 3.85 (s, 3H).

Step B: To a solution of the aldehyde (50.0 g, 0.23 mol) from step A above in toluene (650 mL) were added ethylene glycol (14.2 mL, 0.26 mol) and camphorsulfonic acid (10.7 g, 46 mmol). The reaction solution was heated under reflux with a Dean-Stark trap for 6 h and then it was cooled to room temperature and diluted with ethyl acetate (300 mL). The resultant solution was washed with aqueous saturated sodium bicarbonate and brine, dried over sodium sulfate and concentrated in vacuo to give the desired acetal (61.5 g, quantitative) as a yellow oil: $^1$H NMR (CDCl$_3$, 500 MHz) δ 7.44 (d, J=8.5 Hz, 1H), 7.15 (d, J=3.5 Hz, 1H), 6.79 (dd, J=8.5, 3.0 Hz, 1H), 6.04 (s, 1H), 4.18-4.06 (m, 4H), 3.81 (s, 3H).

Step C: To a solution of the acetal (13.0 g, 50.3 mmol) from step B above in tetrahydrofuran (120 mL) at −78° C. was added a cold (−78° C.) solution n-BuLi (22.0 mL, 55.0 mmol, 2.5M in hexanes). The resultant solution was stirred at −78° C. for 2 hours and then a cold (0° C.) solution of 3,5-difluorobenzaldehyde (7.0 g, 49.3 mmol) in THF (30 mL) was added to it. The reaction solution was stirred at −78° C. for 2 hours and then it was warmed to room temperature, quenched with a saturated solution of ammonium chloride and extracted with ethyl acetate (3×). The combined organic extracts were washed with brine, dried over sodium sulfate and concentrated in vacuo. The crude product obtained was purified by flash column chromatography (90:10 to 75:25 hexanes/ethyl acetate) to give the desired alcohol (13.4 g, 82%) as a yellow oil: $^1$H NMR (CDCl$_3$, 500 MHz) δ 7.15 (d, J=3.0 Hz, 1H), 7.05 (d, J=8.5 Hz, 1H), 6.97-6.93 (m, 2H), 6.85 (dd, J=8.5, 3.0 Hz, 1H), 6.70 (tt, J=9.0, 2.5 Hz, 1H), 6.09 (d, J=4.5 Hz, 1H), 5.90 (s, 1H), 4.10-4.03 (m, 4H), 3.82 (s, 3H), 3.43 (d, J=4.5 Hz, 1H).

Step D: To a solution of the alcohol (1.7 g, 5.2 mmol) from step C above in dichloromethane (20 mL) at 0° C. were added triethylamine (1.8 mL, 13 mmol) and methanesulfonyl chloride (1.2 g, 10.6 mmol). The resultant reaction solution was stirred at 0° C. for 45 minutes and then diluted with ethyl acetate. The mixture obtained was washed with aqueous sodium bicarbonate and brine, dried over sodium sulfate and concentrated in vacuo to give the crude chloride, which was used in the next step without further purification: $^1$H NMR (CDCl$_3$, 500 MHz) δ 7.31 (d, J=8.5 Hz, 1H), 7.13 (d, J=3.0 Hz, 1H), 7.04-6.99 (m, 2H), 6.89 (dd, J=8.5, 3.0 Hz, 1H), 6.72 (tt, J=8.5, 2.0 Hz, 1H), 6.64 (s, 1H), 6.02 (s, 1H), 4.14-4.04 (m, 4H), 3.82 (s, 3H).

Step E: To a dry flask with zinc (4.3 g, 65.0 mmol) under nitrogen were added tetrahydrofuran (25 mL) and trimethylsilyl chloride (0.1 mL). The resultant mixture was stirred at room temperature for 5 minutes and then the solvent was removed by syringe. To this activated zinc were then added dichloromethane (150 mL), ethyl 2-bromoacetate (6.0 mL, 54.5 mmol), iodine (0.1 g) and methylmagnesium bromide (0.1 mL of 3M in diethyl ether, 0.3 mmol). The resultant reaction mixture was heated under reflux for 1 hour and then cooled to 0° C. To this milky solution was added a solution of the chloride (12.2 g, 36.0 mmol) from step D above in dichloromethane (50 mL) and the resultant mixture was stirred at 0° C. for 20 minutes and room temperature for 90 minutes. The reaction solution was then washed with aqueous ammonium chloride and brine, dried over sodium sulfate and concentrated in vacuo. The crude product obtained was purified by flash column chromatography (95:5 to 83:17 hexanes/ethyl acetate) to give the desired ester (10.8 g, 76%) as a light yellow oil: $^1$H NMR (CDCl$_3$, 500 MHz) δ 7.13 (d, J=3.0 Hz, 1H), 7.06 (d, J=8.5 Hz, 1H), 6.86-6.79 (m, 3H), 6.61 (tt, J=9.0, 2.5 Hz, 1H), 6.03 (s, 1H), 5.01 (t, J=7.5 Hz, 1H), 4.21-4.03 (m, 6H), 3.79 (s, 3H), 2.97 (d, J=7.5 Hz, 2H), 1.14 (t, J=7.0 Hz, 3H).

Step F: To a solution of the ester (1.5 g, 3.9 mmol) from step E above in dioxane (80 mL) at 0° C. was added concentrated hydrochloric acid (15 mL). The reaction solution was stirred at 0° C. for 20 minutes and room temperature for 1 hour. The resultant reaction solution was diluted with ethyl acetate, washed with water and brine, dried over sodium sulfate and concentrated in vacuo to give the desired aldehyde (1.6 g, quantitative), which was used in the next step without further purification: $^1$H NMR (CDCl$_3$, 500 MHz) δ 10.25 (s, 1H), 7.34 (d, J=3.0 Hz, 1H), 7.28 (d, J=8.5 Hz, 1H), 7.11 (dd, J=8.5, 2.5 Hz, 1H), 6.76-6.72 (m, 2H), 6.63 (tt, J=9.0, 2.5 Hz, 1H), 5.58 (t, J=8.0 Hz, 1H), 4.05 (q, J=7.0 Hz, 2H), 3.86 (s, 3H), 3.01 (d, J=8.0 Hz, 2H), 1.14 (t, J=7.0 Hz, 3H).

Step G: To a solution of methylamine (0.60 mL, 4.9 mmol, 33% in ethanol) and the aldehyde (1.6 g, 3.9 mmol) from step F above was added titanium isopropoxide (1.5 mL, 5.1 mmol). The resultant reaction solution was stirred at room temperature for 16 hours and then sodium borohydride (0.16 g, 4.3 mmol) was added to it. The reaction solution was stirred at room temperature for 1 hour, and then quenched with water. The precipitate formed was removed by filtration, and the filtrate obtained was diluted with dichloromethane, washed with water, dried over sodium sulfate and concentrated in vacuo to give the crude amine (1.4 g, 98%) as a light yellow oil, which was used in the next step without purification: $^1$H NMR (CDCl$_3$, 500 MHz) δ 7.13 (d, J=8.5 Hz, 1H), 6.90 (d, J=3.0 Hz, 1H), 6.80 (dd, J=8.5, 3.0 Hz, 1H), 6.78-6.75 (m, 2H), 6.61 (tt, J=9.0, 2.5 Hz, 1H), 4.87 (t, J=8.0 Hz, 1H), 4.05 (q, J=7.0 Hz, 2H), 3.79 (s, 3H), 3.75 (d, J=13.0 Hz, 1H), 3.67 (d, J=13.0 Hz, 1H), 3.04-2.92 (m, 2H), 2.45 (s, 3H), 1.70-1.30 (br, 1H), 1.14 (t, J=7.0 Hz, 3H); ESI MS m/z 364 [M+H]$^+$.

Step H: To a solution of the amine (4.0 g, 11.0 mmol) from step G above in toluene (100 mL) at −78° C. was added a solution of diisobutylaluminium hydride (27.5 mL, 27.5 mmol, 1M in toluene) slowly. The reaction solution was stirred at −78° C. for 2 hours, and then cold (−78° C.) methanol (80 mL) was added to it via cannula. The resultant reaction mixture was stirred at −40° C. for 10 minutes and then sodium borohydride (1.6 g, 44 mmol) was added to it in batches. The reaction solution was stirred at −4° C. for 30 minutes, and then it was warmed to room temperature, stirred for 1 hour and concentrated in vacuo. The residue obtained was dissolved in a mixture of dichloromethane and aqueous saturated Rochelle's salt and the resultant solution was vigorously stirred for 30 minutes. The organic extract was then separated, dried over sodium sulfate and concentrated in vacuo. The crude product obtained was purified by flash column chromatography (99:0.9:0.1 to 90:9:1 dichloromethane/methanol/concentrated ammonium hydroxide) to give the desired 8-methoxybenzazepine (3.0 g, 89%) as a light yellow oil: $^1$H NMR (CDCl$_3$, 500 MHz) δ 6.83-6.51 (m, 6H), 4.23 (dd, J=9.0, 2.0 Hz, 1H), 3.82-3.72 (m, 1H), 3.79 (s, 3H), 3.67 (d, J=14.5 Hz, 1H), 3.08-3.02 (br, 1H), 2.95-2.90 (m, 1H), 2.33 (s, 3H), 2.27-2.20 (m, 1H), 2.17-2.06 (br, 1H); ESI MS m/z 304 [M+H]$^+$.

Step I: To a solution of the 8-methoxybenzazepine (2.8 g, 9.1 mmol) from step H above in acetic acid (60 mL) was added hydrobromic acid (60 mL, 48% solution in water). The reaction solution was heated at 100° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (2.8 g, quantitative) as a brown solid, which was used in the next step without purification: $^1$H NMR (CDCl$_3$, 500 MHz) δ 6.79-6.40 (m, 6H), 4.20 (d, J=8.5 Hz, 1H), 3.82-3.64 (br, 1H), 3.61 (d, J=14.0 Hz, 1H), 3.23-2.76 (br, 2H), 2.41 (s, 3H), 2.32-2.03 (br, 2H).

Step J: To a solution of the phenol (1.8 g, 6.2 mmol) from step I above in dichloromethane (60 mL) at 0° C. were added pyridine (1.0 mL, 12.4 mmol) and triflic anhydride (1.2 mL, 6.9 mmol). The resultant reaction solution was stirred at 0° C. for 2 hours, and then it was diluted with dichloromethane, washed with aqueous saturated sodium bicarbonate, dried over sodium sulfate and concentrated in vacuo. The triflate obtained (2.5 g, 96%) as a dark reddish oil was used in the next step without purification: $^1$H NMR (CDCl$_3$, 500 MHz) δ 7.11 (d, J=2.5 Hz, 1H), 7.02 (dd, J=8.5, 2.5 Hz, 1H), 6.87-6.56 (m, 4H), 4.31 (d, J=9.0 Hz, 1H), 3.93 (d, J=13.0 Hz, 1H), 3.72 (d, J=14.5 Hz, 1H), 3.18-2.94 (m, 2H), 2.35 (s, 3H), 2.29-2.01 (m, 2H).

Step K: To a solution of the triflate (0.45 g, 1.1 mmol) from step J above in o-xylene (10 mL) were added sodium tert-butoxide (0.21 g, 2.1 mmol), 2-(dicyclohexylphosphino)-2',4',6'-tri-i-propyl-1,1'-biphenyl (52 mg, 0.11 mmol) and piperazine (0.18 g, 2.1 mmol). The resultant mixture was flushed with argon for 5 minutes, and then palladium(II) acetate (12 mg, 0.05 mmol) was added to it. The reaction solution was heated at 110° C. under argon for 20 hours, and then cooled to room temperature. The resultant mixture was diluted with dichloromethane, washed with water and brine, dried over sodium sulfate and concentrated in vacuo. The crude product was purified by flash column chromatography (99:0.9:0.1 to 92:7.2:0.8 dichloromethane/methanol/concentrated ammonium hydroxide) to give the desired 8-piperazinyl benzazepine (0.13 g, 35%) as a yellow oil: $^1$H NMR (CDCl$_3$, 500 MHz) δ 6.85-6.50 (m, 6H), 4.20 (d, J=8.5 Hz, 1H), 3.79 (d, J=13.0 Hz, 1H), 3.66 (d, J=14.0 Hz, 1H), 3.13-2.89 (m, 10H), 2.33 (s, 3H), 2.26-2.11 (m, 2H); ESI MS m/z 358 [M+H]$^+$.

Step L: The 8-piperazinyl benzazepine (0.13 g) from step K above was resolved by preparative chiral HPLC (CHIRALCEL OD column, using 90:10:0.1 heptane/ethanol/diethylamine as the eluent) to give the (+)-enantiomer [[α]$_{25}^D$+4.00 (c 0.10, methanol)] and the (−)-enantiomer [[α]$^{25}_D$−6.0° (c 0.10, methanol)].

Step M: To a solution of the (−)-enantiomer (53 mg, 0.15 mmol) from step L above in methanol (2 mL) were added L-tartaric acid (23 mg, 0.15 mmol) and water (10 mL). The resultant solution was lyophilized overnight to provide (−)-5-(3,5-difluorophenyl)-2-methyl-8-(piperazin-1-yl)-2,3,4,5-tetrahydro-1H-benzo[c]azepine, L-tartrate salt (75 mg, 97.6% AUC HPLC) as a light yellow solid: $^1$H NMR (CD$_3$OD, 500 MHz) δ 7.08 (d, J=2.0 Hz, 1H), 6.93 (d, J=7.5 Hz, 1H), 6.87 (tt, J=9.0, 2.0 Hz, 1H), 6.82-6.55 (m, 3H), 4.47 (d, J=8.5 Hz, 1H), 4.39-4.27 (m, 1H), 4.32 (s, 2H), 4.11 (d, J=14.0 Hz, 1H), 3.44-3.30 (m, 10H), 2.73 (s, 3H), 2.57-2.24 (m, 2H); ESI MS m/z 358 [M+H]$^+$.

To a solution of the (+)-enantiomer (51 mg, 0.14 mmol) from step L above in methanol (2 mL) were added L-tartaric acid (21 mg, 0.14 mmol) and water (10 mL). The resultant solution was lyophilized overnight to provide (+)-5-(3,5-difluorophenyl)-2-methyl-8-(piperazin-1-yl)-2,3,4,5-tetrahydro-1H-benzo[c]azepine, L-tartrate salt (70 mg, >99% AUC HPLC) as a white solid: $^1$H NMR (CD$_3$OD, 500 MHz) δ 7.05 (d, J=2.5 Hz, 1H), 6.91 (d, J=8.0 Hz, 1H), 6.86 (tt, J=9.0, 2.0 Hz, 1H), 6.82-6.57 (m, 3H), 4.45 (d, J=8.5 Hz, 1H), 4.33-4.14 (m, 1H), 4.31 (s, 2H), 4.03 (d, J=14.0 Hz, 1H), 3.45-3.30 (m, 10H), 2.67 (s, 3H), 2.54-2.24 (m, 2H); ESI MS m/z 358 [M+H]$^+$.

Example 146

Preparation of (+)-4-(5-(3,5-difluorophenyl)-2-methyl-2,3,4,5-tetrahydro-1H-benzo[c]azepin-8-yl)morpholine, L-tartrate salt and (−)-4-(5-(3,5-difluorophenyl)-2-methyl-2,3,4,5-tetrahydro-1H-benzo[c]azepin-8-yl)morpholine, L-tartrate salt Pursuant to the general method described above in Example 145, the following products were prepared: (+)-4-(5-(3,5-difluorophenyl)-2-methyl-2,3,4,5-tetrahydro-1H-benzo[c]azepin-8-yl)morpholine, L-tartrate salt: $^1$H NMR (CD$_3$OD, 500 MHz) δ 7.04 (d, J=2.5 Hz, 1H), 6.95-7.68 (m, 5H), 4.49 (d, J=8.5 Hz, 1H), 4.43-4.37 (m, 1H), 4.39 (s, 2H), 4.19 (d, J=13.0 Hz, 1H), 3.83 (t, J=5.0 Hz, 4H), 3.46-3.40 (m, 2H), 3.17 (t, J=5.0 Hz, 4H), 2.80 (s, 3H), 2.58-2.27 (m, 2H); ESI MS m/z 359 [M+H]$^+$; (−)-4-(5-(3,5-difluorophenyl)-2-methyl-2,3,4,5-tetrahydro-1H-benzo[c]azepin-8-yl)morpholine, L-tartrate salt: $^1$H NMR (CD$_3$OD, 500 MHz) δ 7.04 (d, J=2.5 Hz, 1H), 6.95-7.68 (m, 5H), 4.49 (d, J=8.5 Hz, 1H), 4.43-4.37 (m, 1H), 4.39 (s, 2H), 4.22 (d, J=13.0 Hz, 1H), 3.83 (t, J=5.0 Hz, 4H), 3.46-3.40 (m, 2H), 3.17 (t, J=5.0 Hz, 4H), 2.82 (s, 3H), 2.58-2.27 (m, 2H); ESI MS m/z 359 [M+H]$^+$.

Example 147

Preparation of (+)-5-(3,5-difluorophenyl)-2-methyl-8-(4-methylpiperazin-1-yl)-2,3,4,5-tetrahydro-1H-benzo[c]azepine, L-tartrate salt and (−)-5-(3,5-difluorophenyl)-2-methyl-8-(4-methylpiperazin-1-yl)-2,3,4,5-tetrahydro-1H-benzo[c]azepine, L-tartrate salt Step A: To a solution of m-anisaldehyde (55.4 g, 0.41 mol) in DMF (400 mL) was added a solution of N-bromosuccinimide (124.0 g, 0.69 mol) dropwise at room temperature. After the addition, the reaction solution was stirred at room temperature for 12 hours, then poured into a mixture of ice and water and stirred for 10 minutes. The precipitate was collected by filtration and dissolved in ethyl acetate. The resultant solution was washed with water (2×) and brine, dried over sodium sulfate and concentrated in vacuo to give the desired aldehyde (76.4 g, 87%) as an off-white solid: $^1$H NMR (CDCl$_3$, 500 MHz) δ 10.32 (s, 1H), 7.53 (d, J=8.5 Hz, 1H), 7.42 (d, J=3.5 Hz, 1H), 7.04 (dd, J=9.0, 3.0 Hz, 1H), 3.85 (s, 3H).

Step B: To a solution of the aldehyde (50.0 g, 0.23 mol) from step A above in toluene (650 mL) were added ethylene glycol (14.2 mL, 0.26 mol) and camphorsulfonic acid (10.7 g, 46 mmol). The reaction solution was heated under reflux with a Dean-Stark trap for 6 h and then it was cooled to room temperature and diluted with ethyl acetate (300 mL). The resultant solution was washed with aqueous saturated sodium bicarbonate and brine, dried over sodium sulfate and concentrated in vacuo to give the desired acetal (61.5 g, quantitative) as a yellow oil: $^1$H NMR (CDCl$_3$, 500 MHz) δ 7.44 (d, J=8.5 Hz, 1H), 7.15 (d, J=3.5 Hz, 1H), 6.79 (dd, J=8.5, 3.0 Hz, 1H), 6.04 (s, 1H), 4.18-4.06 (m, 4H), 3.81 (s, 3H).

Step C: To a solution of the acetal (13.0 g, 50.3 mmol) from step B above in tetrahydrofuran (120 mL) at −78° C. was added a cold (−78° C.) solution n-BuLi (22.0 mL, 55.0 mmol, 2.5M in hexanes). The resultant solution was stirred at −78° C. for 2 hours and then a cold (0° C.) solution of 3,5-difluorobenzaldehyde (7.0 g, 49.3 mmol) in THF (30 mL) was added to it. The reaction solution was stirred at −78° C. for 2 hours and then it was warmed to room temperature, quenched with a saturated solution of ammonium chloride and extracted with ethyl acetate (3×). The combined organic extracts were washed with brine, dried over sodium sulfate and concentrated in vacuo. The crude product obtained was purified by flash column chromatography (90:10 to 75:25 hexanes/ethyl acetate) to give the desired alcohol (13.4 g, 82%) as a yellow oil: $^1$H NMR (CDCl$_3$, 500 MHz) δ 7.15 (d, J=3.0 Hz, 1H), 7.05 (d, J=8.5 Hz, 1H), 6.97-6.93 (m, 2H), 6.85 (dd, J=8.5, 3.0 Hz, 1H), 6.70 (tt, J=9.0, 2.5 Hz, 1H), 6.09 (d, J=4.5 Hz, 1H), 5.90 (s, 1H), 4.10-4.03 (m, 4H), 3.82 (s, 3H), 3.43 (d, J=4.5 Hz, 1H).

Step D: To a solution of the alcohol (1.7 g, 5.2 mmol) from step C above in dichloromethane (20 mL) at 0° C. were added triethylamine (1.8 mL, 13 mmol) and methanesulfonyl chloride (1.2 g, 10.6 mmol). The resultant reaction solution was stirred at 0° C. for 45 minutes and then diluted with ethyl acetate. The mixture obtained was washed with aqueous sodium bicarbonate and brine, dried over sodium sulfate and concentrated in vacuo to give the crude chloride, which was used in the next step without further purification: $^1$H NMR (CDCl$_3$, 500 MHz) δ 7.31 (d, J=8.5 Hz, 1H), 7.13 (d, J=3.0 Hz, 1H), 7.04-6.99 (m, 2H), 6.89 (dd, J=8.5, 3.0 Hz, 1H), 6.72 (tt, J=8.5, 2.0 Hz, 1H), 6.64 (s, 1H), 6.02 (s, 1H), 4.14-1.04 (m, 4H), 3.82 (s, 3H).

Step E: To a dry flask with zinc (4.3 g, 65.0 mmol) under nitrogen were added tetrahydrofuran (25 mL) and trimethylsilyl chloride (0.1 mL). The resultant mixture was stirred at room temperature for 5 minutes and then the solvent was removed by syringe. To this activated zinc were then added dichloromethane (150 mL), ethyl 2-bromoacetate (6.0 mL, 54.5 mmol), iodine (0.1 g) and methylmagnesium bromide (0.1 mL of 3M in diethyl ether, 0.3 mmol). The resultant reaction mixture was heated under reflux for 1 hour and then cooled to 0° C. To this milky solution was added a solution of the chloride (12.2 g, 36.0 mmol) from step D above in dichloromethane (50 mL) and the resultant mixture was stirred at 0° C. for 20 minutes and room temperature for 90 minutes. The reaction solution was then washed with aqueous ammonium chloride and brine, dried over sodium sulfate and concentrated in vacuo. The crude product obtained was purified by flash column chromatography (95:5 to 83:17 hexanes/ethyl acetate) to give the desired ester (10.8 g, 76%) as a light yellow oil: $^1$H NMR (CDCl$_3$, 500 MHz) δ 7.13 (d, J=3.0 Hz, 1H), 7.06 (d, J=8.5 Hz, 1H), 6.86-6.79 (m, 3H), 6.61 (tt, J=9.0, 2.5 Hz, 1H), 6.03 (s, 1H), 5.01 (t, J=7.5 Hz, 1H), 4.21-4.03 (m, 6H), 3.79 (s, 3H), 2.97 (d, J=7.5 Hz, 2H), 1.14 (t, J=7.0 Hz, 3H).

Step F: To a solution of the ester (1.5 g, 3.9 mmol) from step E above in dioxane (80 mL) at 0° C. was added concentrated hydrochloric acid (15 mL). The reaction solution was stirred at 0° C. for 20 minutes and room temperature for 1 hour. The resultant reaction solution was diluted with ethyl acetate, washed with water and brine, dried over sodium sulfate and concentrated in vacuo to give the desired aldehyde (1.6 g, quantitative), which was used in the next step without further purification: $^1$H NMR (CDCl$_3$, 500 MHz) δ 10.25 (s, 1H), 7.34 (d, J=3.0 Hz, 1H), 7.28 (d, J=8.5 Hz, 1H), 7.11 (dd, J=8.5, 2.5 Hz, 1H), 6.76-6.72 (m, 2H), 6.63 (tt, J=9.0, 2.5 Hz, 1H), 5.58 (t, J=8.0 Hz, 1H), 4.05 (q, J=7.0 Hz, 2H), 3.86 (s, 3H), 3.01 (d, J=8.0 Hz, 2H), 1.14 (t, J=7.0 Hz, 3H).

Step G: To a solution of methylamine (0.60 mL, 4.9 mmol, 33% in ethanol) and the aldehyde (1.6 g, 3.9 mmol) from step F above was added titanium isopropoxide (1.5 mL, 5.1 mmol). The resultant reaction solution was stirred at room temperature for 16 h and then sodium borohydride (0.16 g, 4.3 mmol) was added to it. The reaction solution was stirred at room temperature for 1 hour, and then quenched with water. The precipitate formed was removed by filtration, and the filtrate obtained was diluted with dichloromethane, washed with water, dried over sodium sulfate and concentrated in vacuo to give the crude amine (1.4 g, 98%) as a light yellow oil, which was used in the next step without purification: $^1$H NMR (CDCl$_3$, 500 MHz) δ 7.13 (d, J=8.5 Hz, 1H), 6.90 (d, J=3.0 Hz, 1H), 6.80 (dd, J=8.5, 3.0 Hz, 1H), 6.78-6.75 (m, 2H), 6.61 (tt, J=9.0, 2.5 Hz, 1H), 4.87 (t, J=8.0 Hz, 1H), 4.05 (q, J=7.0 Hz, 2H), 3.79 (s, 3H), 3.75 (d, J=13.0 Hz, 1H), 3.67 (d, J=13.0 Hz, 1H), 3.04-2.92 (m, 2H), 2.45 (s, 3H), 1.70-1.30 (br, 1H), 1.14 (t, J=7.0 Hz, 3H); ESI MS m/z 364 [M+H]$^+$.

Step H: To a solution of the amine (4.0 g, 11.0 mmol) from step G above in toluene (100 mL) at −78° C. was added a solution of diisobutylaluminium hydride (27.5 mL, 27.5 mmol, 1M in toluene) slowly. The reaction solution was stirred at −78° C. for 2 hours, and then cold (−78° C.) methanol (80 mL) was added to it via cannula. The resultant reaction mixture was stirred at −40° C. for 10 minutes and then sodium borohydride (1.6 g, 44 mmol) was added to it in batches. The reaction solution was stirred at −40° C. for 30 minutes, then it was warmed to room temperature, stirred for 1 hour and concentrated in vacuo. The residue obtained was dissolved in a mixture of dichloromethane and aqueous saturated Rochelle's salt and the resultant solution was vigorously stirred for 30 minutes. The organic extract was then separated, dried over sodium sulfate and concentrated in vacuo. The crude product obtained was purified by flash column chromatography (99:0.9:0.1 to 90:9:1 dichloromethane/methanol/concentrated ammonium hydroxide) to give the desired 8-methoxybenzazepine (3.0 g, 89%) as a light yellow oil: $^1$H NMR (CDCl$_3$, 500 MHz) δ 6.83-6.51 (m, 6H), 4.23 (dd, J=9.0, 2.0 Hz, 1H), 3.82-3.72 (m, 1H), 3.79 (s, 3H), 3.67 (d, J=14.5 Hz, 1H), 3.08-3.02 (br, 1H), 2.95-2.90 (m, 1H), 2.33 (s, 3H), 2.27-2.20 (m, 1H), 2.17-2.06 (br, 1H); ESI MS m/z 304 [M+H]$^+$.

Step I: To a solution of the 8-methoxybenzazepine (2.8 g, 9.1 mmol) from step H above in acetic acid (60 mL) was added hydrobromic acid (60 mL, 48% solution in water). The reaction solution was heated at 100° C. for 20 hours, and then cooled to room temperature and concentrated in vacuo. The residue obtained was dissolved in methylene chloride and water, and then carefully neutralized with aqueous saturated sodium bicarbonate to pH>8. The organic extract was separated, washed with water and brine, dried over sodium sulfate and concentrated in vacuo to give the desired phenol (2.8 g, quantitative) as a brown solid, which was used in the next step without purification: $^1$H NMR (CDCl$_3$, 500 MHz) δ 6.79-6.40 (m, 6H), 4.20 (d, J=8.5 Hz, 1H), 3.82-3.64 (br, 1H), 3.61 (d, J=14.0 Hz, 1H), 3.23-2.76 (br, 2H), 2.41 (s, 3H), 2.32-2.03 (br, 2H).

Step J: To a solution of the phenol (1.8 g, 6.2 mmol) from step I above in dichloromethane (60 mL) at 0° C. were added pyridine (1.0 mL, 12.4 mmol) and triflic anhydride (1.2 mL, 6.9 mmol). The resultant reaction solution was stirred at 0° C. for 2 hours, and then it was diluted with dichloromethane, washed with aqueous saturated sodium bicarbonate, dried over sodium sulfate and concentrated in vacuo. The triflate obtained (2.5 g, 96%) as a dark reddish oil was used in the next step without purification: $^1$H NMR (CDCl$_3$, 500 MHz) δ 7.11 (d, J=2.5 Hz, 1H), 7.02 (dd, J=8.5, 2.5 Hz, 1H), 6.87-6.56 (m, 4H), 4.31 (d, J=9.0 Hz, 1H), 3.93 (d, J=13.0 Hz, 1H), 3.72 (d, J=14.5 Hz, 1H), 3.18-2.94 (m, 2H), 2.35 (s, 3H), 2.29-2.01 (m, 2H).

Step K: To a solution of the triflate (0.45 g, 1.1 mmol) from step J above in o-xylene (10 mL) were added sodium tert-butoxide (0.21 g, 2.1 mmol), 2-(dicyclohexylphosphino)-2',4',6'-tri-i-propyl-1,1'-biphenyl (52 mg, 0.11 mmol) and piperazine (0.18 g, 2.1 mmol). The resultant mixture was flushed with argon for 5 minutes, and then palladium(II) acetate (12 mg, 0.05 mmol) was added to it. The reaction solution was heated at 110° C. under argon for 20 hours, and then cooled to room temperature. The resultant mixture was diluted with dichloromethane, washed with water and brine, dried over sodium sulfate and concentrated in vacuo. The crude product was purified by flash column chromatography (dichloromethane/methanol/concentrated ammonium hydroxide 99:0.9:0.1 to 92:7.2:0.8) to give the desired 8-piperazinyl benzazepine (0.13 g, 35%) as a yellow oil: $^1$H NMR (CDCl$_3$, 500 MHz) δ ¹H NMR (CDCl₃, 500 MHz) δ 6.85-6.50 (m, 6H), 4.20 (d, J=8.5 Hz, 1H), 3.79 (d, J=13.0 Hz, 1H), 3.66 (d, J=14.0 Hz, 1H), 3.13-2.89 (m, 10H), 2.33 (s, 3H), 2.26-2.11 (m, 2H); ESI MS m/z 358 [M+H]⁺.

Step L: The 8-piperazinyl benzazepine (0.45 g) from step K above was resolved by preparative chiral HPLC (CHIRAL-CEL OD column, using 90:10:0.1 heptane/ethanol/diethylamine as the eluent) to give the (+)-enantiomer [[α]²⁵$_D$+ 1.58° (c 0.10, methanol)] (0.22 g) and the (−)-enantiomer [[α]²⁵$_D$−1.61° (c 0.10, methanol)] (0.19 g).

Step M: To a solution of the (+)-enantiomer (0.14 g, 0.39 mmol) from step L above in methanol (7.0 mL) were added formaldehyde (0.35 mL, 4.7 mmol, 37% in water) and acetic acid (54 μL, 0.94 mmol). The reaction solution was heated at 80° C. for 1 hour, and then cooled to 0° C. To this solution were added dichloromethane (1 mL) and sodium cyanoborohydride (0.36 g, 5.5 mmol). The reaction mixture was stirred at 0° C. for 1 hour, and then warmed to room temperature. The reaction solution was then quenched with aqueous sodium bicarbonate and extracted with dichloromethane (3×). The combined organic extracts were dried over sodium sulfate and concentrated in vacuo. The crude product obtained was purified by flash column chromatography (dichloromethane to 90:9:1 dichloromethane/methanol/triethylamine) to give the desired product (0.12 g, 83%) as a colorless oil: [[α]²⁵$_D$ +3.33° (c 0.12, methanol)]; ¹H NMR (CDCl₃, 500 MHz) δ 6.76 (d, J=2.5 Hz, 1H), 6.69-6.43 (m, 5H), 4.20 (dd, J=8.5, 1.5 Hz, 1H), 3.82-3.74 (br, 1H), 3.66 (d, J=14.0 Hz, 1H), 3.19 (t, J=5.0 Hz, 4H), 3.06-3.02 (br, 1H), 2.94-2.89 (m, 1H), 2.56 (t, J=5.0 Hz, 4H), 2.37 (s, 3H), 2.33 (s, 3H), 2.26-2.19 (m, 1H), 2.13-2.06 (br, 1H).

To a solution of the freshly prepared 8-methylpiperazinyl benzazepine (0.12 g, 0.31 mmol) in methanol (3 mL) were added L-tartaric acid (47 mg, 0.31 mmol) and water (15 mL). The resultant solution was lyophilized overnight to provide (+)-5-(3,5-difluorophenyl)-2-methyl-8-(4-methylpiperazin-1-yl)-2,3,4,5-tetrahydro-1H-benzo[c]azepine, L-tartrate salt (0.16 g, 97.1% AUC HPLC) as a white solid: ¹H NMR (CD₃OD, 500 MHz) δ 7.07 (d, J=2.5 Hz, 1H), 6.93 (d, J=8.5 Hz, 1H), 6.88 (tt, J=9.5, 2.0 Hz, 1H), 6.83-6.67 (br, 3H), 4.48 (d, J=8.0 Hz, 1H), 4.41-4.30 (m, 1H), 4.36 (s, 2H), 4.16 (d, J=14.0 Hz, 1H), 3.46-3.40 (m, 2H), 3.39-3.30 (m, 4H), 2.97 (app s, 4H), 2.78 (s, 3H), 2.61 (s, 3H), 2.57-2.29 (m, 2H); ESI MS m/z 372 [M+H]⁺.

Step N: To a solution of the (−)-enantiomer (0.18 g, 0.50 mmol) from step L above in methanol (8 mL) were added formaldehyde (0.56 mL, 6.1 mmol, 37% in water) and acetic acid (70 μL, 1.2 mmol). The reaction solution was heated at 80° C. for 1 hour, and then cooled to 0° C. To this solution were added dichloromethane (1 mL) and sodium cyanoborohydride (0.45 g, 7.1 mmol). The reaction mixture was stirred at 0° C. for 1 hour, and then warmed to room temperature. The reaction solution was then quenched with aqueous sodium bicarbonate and extracted with dichloromethane (3×). The combined organic extracts were dried over sodium sulfate and concentrated in vacuo. The crude product obtained was purified by flash column chromatography (dichloromethane to dichloromethane/methanol/triethylamine 90:9:1) to give the desired benzazepine (0.15 g, 80%) as a light yellow oil: [[α]²⁵$_D$−2.86° (c 0.14, methanol)]; ¹H NMR (CDCl₃, 500 MHz) δ 6.76 (d, J=2.5 Hz, 1H), 6.69-6.43 (m, 5H), 4.20 (dd, J=8.5, 1.5 Hz, 1H), 3.82-3.74 (br, 1H), 3.66 (d, J=14.0 Hz, 1H), 3.19 (t, J=5.0 Hz, 4H), 3.06-3.02 (br, 1H), 2.94-2.89 (m, 1H), 2.56 (t, J=5.0 Hz, 4H), 2.37 (s, 3H), 2.33 (s, 3H), 2.26-2.19 (m, 1H), 2.13-2.06 (br, 1H).

Step O: To a solution of the freshly prepared benzazepine (0.14 g, 0.38 mmol) from step N above in methanol (3 mL) were added L-tartaric acid (57 mg, 0.38 mmol) and water (15 mL). The resultant solution was lyophilized overnight to provide (−)-5-(3,5-difluorophenyl)-2-methyl-8-(4-methylpiperazin-1-yl)-2,3,4,5-tetrahydro-1H-benzo[c]azepine, L-tartrate salt (0.19 g, >99% AUC HPLC) as a white solid: ¹H NMR (CD₃OD, 500 MHz) δ 7.07 (d, J=2.0 Hz, 1H), 6.93 (d, J=8.5 Hz, 1H), 6.88 (tt, J=9.5, 2.0 Hz, 1H), 6.83-6.67 (br, 3H), 4.48 (d, J=9.0 Hz, 1H), 4.41-4.30 (m, 1H), 4.35 (s, 2H), 4.17 (d, J=14.0 Hz, 1H), 3.46-3.40 (m, 2H), 3.39-3.30 (m, 4H), 3.00 (app s, 4H), 2.79 (s, 3H), 2.64 (s, 3H), 2.57-2.28 (m, 2H); ESI MS m/z 372 [M+H]⁺.

Example 148

Preparation of 5-(3,5-difluorophenyl)-2-methyl-2,3,4,5-tetrahydro-1H-benzo[c]azepine, maleate salt (enantiomers 1 and 2)

Step A: A mixture of 2-bromobenzaldehyde (3.70 g, 20.0 mmol), t-butylacrylate (4.4 mL, 30.0 mmol), allylpalladium chloride dimer (0.37 g, 1.0 mmol), tri-o-tolylphosphine (0.61 g, 2.0 mmol), and sodium acetate (4.92 g, 60.0 mmol) in toluene (80 mL) was refluxed under nitrogen overnight. After cooling, the mixture was filtered through a Celite pad and washed with methylene chloride. The filtrate was concentrated in vacuo and residue was purified by column chromatography (8:1 to 4:1 hexanes/ethyl acetate) to afford the unsaturated ester (4.63 g, 99%): ¹H NMR (500 MHz, CDCl₃) δ 10.3 (s, 1H), 8.41 (d, J=15.8 Hz, 1H), 7.89 (s, 1H), 7.64-7.53 (m, 3H), 6.31 (d, J=15.9 Hz, 1H), 1.55 (s, 9H).

Step B: A mixture of the unsaturated ester (0.70 g, 3.0 mmol) from step A above, (1S,2S)-(+) pseudoephedrine (0.55 g, 3.3 mmol), concentrated hydrochloric acid (1 drop) in toluene (23 mL) was refluxed for 4 hours. After cooling, the mixture was poured into saturated NaHCO₃ (30 mL) and diluted with ethyl acetate (50 mL). The two phases were separated. The ethyl acetate phase was washed with brine, dried over Na₂SO₄, filtered and concentrated in vacuo to give the oxazolidine (0.92 g, quant.) as a yellow solid: ¹H NMR (500 MHz, CDCl₃) δ 8.42 (d, J=16.0 Hz, 1H), 7.88 (s, 1H), 7.59-7.14 (m, 8H), 6.26 (d, J=16.0 Hz, 1H), 5.22 (s, 1H), 4.84 (d, J=8.7 Hz, 1H), 2.57-2.54 (m, 1H), 2.17 (s, 3H), 1.55 (s, 9H), 1.27 (d, J=6.0 Hz, 3H).

Step C: To a solution of 3,5-difluorobromobenzene (1.93 g, 10 mmol) in ether at −78° C. was added 1.7 M tert-butyl lithium (11.8 mL, 20 mmol). The mixture was stirred at −78° C. for 1 hour before it was cannulated into a solution of the oxazolidine from step B above (1.90 g, 5.0 mmol) in ether (30 mL) at −78° C. The resulting mixture was stirred at −78° C. and allowed to warm up to room temperature overnight. Saturated ammonium chloride (10 mL) was added to quench the reaction. The mixture was extracted with methylene chloride (3×20 mL). The combined extracts were dried over Na₂SO₄, filtered and concentrated in vacuo to afford the crude residue (de: 60% based on crude ¹H NMR). The residue was mixed in THF (20 mL), acetic acid (6 mL) and water (3 mL) and stirred at room temperature for 2 hours. The mixture was diluted with ethyl acetate (50 mL) and washed with water and saturated NaHCO₃. The ethyl acetate phase was dried over Na₂SO₄, filtered and concentrated in vacuo and the residue was purified by column chromatography (16:1 to 4:1 hexanes/ethyl acetate) to afford the aldehyde (0.69 g, 40%, two steps) as a colorless oil: ¹H NMR (500 MHz, CDCl₃) δ 10.24 (s, 1H), 7.83 (d, J=7.7 Hz, 1H), 7.59-7.57 (m, 1H), 7.47-7.45 (m, 1H), 7.40 (d, J=7.7 Hz, 1H), 6.79-6.76 (m, 2H), 6.64-6.62 (m, 1H), 5.68 (t, J=8.0 Hz, 1H), 2.96-2.95 (m, 2H), 1.32 (s, 9H).

Step D: To a solution of the aldehyde from step C above (0.69 g, 2.0 mmol) in methanol (11 mL) was added methylamine hydrochloride (0.81 g, 12 mmol). Sodium cyanoborohydride (124 mg, 2.0 mmol) was then added. The resulting mixture was stirred at room temperature for 3 h and then quenched with a few drops of 6 N HCl. The mixture was diluted with water and basified to pH 9 with adding 2 N NaOH. The mixture was extracted with methylene chloride (3×20 mL). The combined extracts were dried over $Na_2SO_4$, filtered and concentrated in vacuo. The residue was purified by column chromatography (20:1 to 10:1 methylene chloride/methanol) to yield the amino ester (0.32 g, 44%) as a colorless oil: $^1$H NMR (500 MHz, $CDCl_3$) δ 7.32-7.22 (m, 4H), 6.80-6.78 (m, 2H), 6.63-6.60 (m, 1H), 4.91 (t, J=8.1 Hz, 1H), 3.80 (d, J=13.0 Hz, 1H), 3.73 (d, J=13.0 Hz, 1H), 2.93-2.88 (m, 2H), 2.46 (s, 3H), 1.29 (s, 9H); ESI MS m/z 362 [M+H]$^+$.

Step E: To a solution of the amino ester (0.31 g, 0.88 mmol) from step D above in toluene (6 mL) was added 1 M diisobutylaluminum hydride in toluene (2.2 mL, 2.2 mmol). The mixture was stirred at −78° C. for 1.5 hours. Methanol (6 mL) was added to quench the reaction. The mixture was stirred at −20° C. for 15 minutes before sodium borohydride (34 mg, 0.90 mmol) was added. Two more portions of sodium borohydride (30 mg, 0.79 mmol) were added at −40° C. at 2 hour and 4 hour intervals. The mixture was allowed to warm to room temperature and stirred overnight. The mixture was concentrated to dryness and the residue was partitioned between water and methylene chloride. The two phases were separated and the methylene chloride phase was washed with saturated $NaHCO_3$, dried over $Na_2SO_4$, filtered and concentrated in vacuo. The residue was purified by column chromatography (20:1 to 10:1 methylene chloride/methanol) to yield the benzazepine (132 mg, 55%) as a colorless oil: $^1$H NMR (500 MHz, $CDCl_3$) δ 7.19-7.12 (m, 3H), 6.72-6.69 (m, 4H), 4.30 (d, J=9.0 Hz, 1H), 3.88 (br, 1H), 3.70 (d, J=14.3 Hz, 1H), 3.07 (br, 1H), 2.97-2.92 (m, 1H), 2.33 (s, 3H), 2.28-2.23 (m, 1H), 2.14 (br, 1H); ESI MS m/z 275 [M+H]$^+$.

Step F: The free base of the benzazepine (0.13 g) from step E was resolved by preparative chiral HPLC (CHIRALCEL OD column, using 80:20:0.1 heptane/ethanol/trifluroacetic acid as the eluent) to give enantiomer I [[α]$^{25}_D$+2.4° (c 0.165, methanol), 18 mg] and enantiomer II [[α]$^{25}_D$+1.73° (c 0.06, methanol), 74 mg].

Step G: To a solution of enantiomer I (16 mg, 0.059 mmol) from step F in methanol (0.5 mL) was added maleic acid (6.8 mg, 0.059 mmol). After the mixture was stirred at room temperature for 10 minutes, water (3 mL) was added. The resultant solution was lyophilized overnight to give 5-(3,5-difluorophenyl)-2-methyl-2,3,4,5-tetrahydro-1H-benzo[c]azepine, maleate salt enantiomer 1 (21 mg, 92%, AUC HPLC 91.6%) as an off-white solid: $^1$H NMR ($CD_3OD$, 500 MHz) δ 7.45 (br, 1H), 7.35 (br, 2H), 6.93-6.81 (m, 4H), 6.24 (s, 2H), 4.61 (d, J=8.8 Hz, 1H), 4.49 (br, 1H), 4.24 (d, J=14.2 Hz, 1H), 3.50 (br, 2H), 2.82 (s, 3H), 2.55 (br, 1H), 2.38 (br, 1H); ESI MS m/z 275 [M+H]$^+$.

Step H: To a solution of enantiomer II (70 mg, 0.26 mmol) in methanol (1 mL) was added maleic acid (29 mg, 0.26 mmol). After the mixture was stirred at room temperature for 10 minutes, water (20 mL) was added. The resultant solution was lyophilized overnight to give 5-(3,5-difluorophenyl)-2-methyl-2,3,4,5-tetrahydro-1H-benzo[c]azepine, maleate salt enantiomer 2 (78 mg, 79%, AUC HPLC 97.0%) as an off-white solid: $^1$H NMR ($CD_3OD$, 500 MHz) δ 7.45 (br, 1H), 7.35-6.81 (m, 4H), 6.24 (s, 2H), 4.61 (d, J=8.8 Hz, 1H), 4.49 (br, 1H), 4.24 (d, J=14.2 Hz, 1H), 3.50 (br, 2H), 2.82 (s, 3H), 2.55 (br, 1H), 2.38 (br, 1H); ESI MS m/z 275 [M+H]$^+$.

Example 149

Preparation of (−)-5-(benzo[b]thiophen-2-yl)-2-methyl-2,3,4,5-tetrahydro-1H-benzo[c]azepine, maleate salt and (+)-5-(benzo[b]thiophen-2-yl)-2-methyl-2,3,4,5-tetrahydro-1H-benzo[c]azepine, L-tartrate salt Step A: A mixture of 2-bromobenzaldehyde (3.70 g, 20.0 mmol), t-butylacrylate (4.4 mL, 30.0 mmol), allylpalladium chloride dimer (0.37 g, 1.0 mmol), tri-o-tolylphosphine (0.61 g, 2.0 mmol), and sodium acetate (4.92 g, 60.0 mmol) in toluene (80 mL) was refluxed under nitrogen overnight. After cooling, the mixture was filtered through a Celite pad and washed with methylene chloride. The filtrate was concentrated in vacuo and the residue was purified by column chromatography (8:1 to 4:1 hexanes/ethyl acetate) to afford the unsaturated ester (4.63 g, 99%): $^1$H NMR (500 MHz, $CDCl_3$) δ 10.3 (s, 1H), 8.41 (d, J=15.8 Hz, 1H), 7.89 (s, 1H), 7.64-7.53 (m, 3H), 6.31 (d, J=15.9 Hz, 1H), 1.55 (s, 9H).

Step B: A mixture of the unsaturated ester (0.70 g, 3.0 mmol) from step A above, (1S,2S)-(+) pseudoephedrine (0.55 g, 3.3 mmol), concentrated hydrochloric acid (1 drop) in toluene (23 mL) was refluxed for 4 h. After cooling, the mixture was poured into saturated $NaHCO_3$ (30 mL) and diluted with ethyl acetate (50 mL). The two phases were separated. The ethyl acetate phase was washed with brine, dried over $Na_2SO_4$, filtered and concentrated in vacuo to give the oxazolidine (0.92 g, quant.) as a yellow solid: $^1$H NMR (500 MHz, $CDCl_3$) δ 8.42 (d, J=16.0 Hz, 1H), 7.88 (s, 1H), 7.59-7.14 (m, 8H), 6.26 (d, J=16.0 Hz, 1H), 5.22 (s, 1H), 4.84 (d, J=8.7 Hz, 1H), 2.57-2.54 (m, 1H), 2.17 (s, 3H), 1.55 (s, 9H), 1.27 (d, J=6.0 Hz, 3H).

Step C: To a solution of benzothiophene (0.81 g, 6.0 mmol) in THF at −78° C. was added 2.5 M n-butyllithium (2.4 mL, 6.0 mmol). The mixture was allowed to stir at 0° C. for 10 minutes and then cooled to −78° C. A solution of the crude product (0.92 g, 3.0 mmol) from step B above in diethyl ether (10 mL) was added dropwise at −78° C. under nitrogen. The resulting mixture was allowed to warm up to room temperature and stirred overnight. Saturated $NaHCO_3$ (10 mL) was added to quench the reaction. The mixture was extracted with methylene chloride (3×20 mL). The combined extracts were dried over $Na_2SO_4$, filtered and concentrated in vacuo to afford the crude residue (de: 8% based on crude $^1$H NMR). The residue was mixed with THF (20 mL), acetic acid (6 mL) and water (3 mL) and stirred at room temperature for 2 hours. The mixture was diluted with ethyl acetate (50 mL) and washed with water and saturated $NaHCO_3$. The ethyl acetate phase was dried over $Na_2SO_4$, filtered and concentrated in vacuo and the residue was purified by column chromatography (16:1 to 4:1 hexanes/ethyl acetate) to afford the aldehyde (0.25 g, 23%, two steps) as a colorless oil: $^1$H NMR (500 MHz, $CDCl_3$) δ 10.38 (s, 1H), 7.86 (d, J=7.2 Hz, 1H), 7.71 (d, J=8.1 Hz, 1H), 7.65 (d, J=7.7 Hz, 1H), 7.57-7.45 (m, 3H), 7.30-7.23 (m, 2H), 7.24 (s, 1H), 5.96 (t, J=7.9 Hz, 1H), 3.19-3.07 (m, 2H), 1.28 (s, 9H).

Step D: A 8.0 M solution of methylamine in ethanol (0.51 mL) was treated with 4 N HCl in dioxane (1.0 mL) and the resulting solution was added to a solution of the aldehyde (0.25 g, 0.68 mmol) from step C above in methanol (14 mL). Sodium cyanoborohydride (44 mg, 0.70 mmol) was added. The resulting mixture was stirred at room temperature for 3 hours and then quenched with a few drops of 6 N HCl. The mixture was diluted with water and basified to pH 9 with 2 N NaOH. The mixture was extracted with methylene chloride (3×20 mL). The combined extracts were dried over $Na_2SO_4$, filtered and concentrated in vacuo. The residue was purified by column chromatography (20:1 to 10:1 methylene chloride/methanol) to yield the amino ester (0.12 g, 46%) as colorless oil: $^1$H NMR (500 MHz, CDCl$_3$) δ 7.70 (d, J=8.0 Hz, 1H), 7.63 (d, J=7.6 Hz, 1H), 7.37-7.23 (m, 6H), 6.99 (s, 1H), 5.13 (t, J=7.9 Hz, 1H), 3.96 (d, J=13.1 Hz, 1H), 3.87 (d, J=13.1 Hz, 1H), 3.16-3.06 (m, 2H), 2.50 (s, 3H), 1.30 (s, 9H); ESI MS m/z 382 [M+H]$^+$.

Step E: To a solution of the amino ester (0.21 g, 0.54 mmol) from step D above in toluene (4 mL) was added 1 M diisobutylaluminum hydride in toluene (1.35 mL, 1.35 mmol). The mixture was stirred at −78° C. for 1.5 hours. Methanol (6 mL) was added to quench the reaction. The mixture was stirred at −40° C. for 15 minutes before sodium borohydride (20 mg, 0.53 mmol) was added. Two more portions of sodium borohydride (20 mg, 0.30 mmol) were added at −40° C. at 2 hour and 4 hour intervals. The mixture was allowed to warm to room temperature and stirred for another 2 hours. The mixture was concentrated to dryness and the residue was partitioned between water and methylene chloride. The two phases were separated and the methylene chloride phase was washed with saturated NaHCO$_3$, dried over Na$_2$SO$_4$, filtered and concentrated in vacuo. The residue was purified by column chromatography (20:1 to 10:1 methylene chloride/methanol) to yield the benzazepine (130 mg, 82%) as colorless oil: $^1$H NMR (500 MHz, CDCl$_3$) δ 7.78 (d, J=7.7 Hz, 1H), 7.63 (d, J=7.2 Hz, 1H), 7.39-7.28 (m, 6H), 6.77 (s, 1H), 4.69 (br, 1H), 4.32 (d, J=14.3 Hz, 1H), 4.16 (d, J=14.2 Hz, 1H), 3.58 (br, 1H), 3.36 (br, 1H), 2.58 (s, 3H), 2.58-2.51 (m, 2H); ESI MS m/z 294 [M+H]$^+$.

Step F: The free base of the benzazepine (0.18 g) from step E above was resolved by preparative chiral HPLC (CHIRALCEL OD column, using 90:10:0.1 heptane/ethanol/diethylamine as the eluent) to give the (+)-enantiomer [[α]$^{25}_D$+15.00 (c 0.06, methanol)] and the (−)-enantiomer [[α]$^{25}_D$−13.3° (c 0.075, methanol)].

Step G: To a solution of the (+)-enantiomer (42 mg, 0.14 mmol) from step F above in methanol (1 mL) was added L-tartaric acid (21 mg, 0.14 mmol). After the mixture was stirred at room temperature for 10 minutes, water (20 mL) was added. The resultant solution was lyophilized overnight to give (+)-5-(benzo[b]thiophen-2-yl)-2-methyl-2,3,4,5-tetrahydro-1H-benzo[c]azepine, L-tartrate salt (57 mg, 90%, AUC HPLC >99%) as a white solid: $^1$H NMR (CD$_3$OD, 500 MHz) δ 7.80 (d, J=7.9 Hz, 1H), 7.68 (d, J=7.5 Hz, 1H), 7.47-7.28 (m, 6H), 6.96 (s, 1H), 4.41 (br, 4H), 3.68 (br, 1H), 3.60 (br, 1H), 2.83 (s, 3H), 2.62-2.57 (m, 2H); ESI MS m/z 294 [M+H]$^+$.

Step H: To a solution of the (−)-enantiomer (83 mg, 0.28 mmol) from step F above in methanol (1 mL) was added maleic acid (33 mg, 0.28 mmol). After the mixture was stirred at room temperature for 10 minutes, water (20 mL) was added. The resultant solution was lyophilized overnight to give (−)-5-(benzo[b]thiophen-2-yl)-2-methyl-2,3,4,5-tetrahydro-1H-benzo[c]azepine, maleate salt (92 mg, 65%, AUC HPLC 97.0%) as an off-white solid: $^1$H NMR (CD$_3$OD, 500 MHz) δ 7.81 (d, J=7.7 Hz, 1H), 7.70 (d, J=7.3 Hz, 1H), 7.49-7.29 (m, 6H), 6.96 (br, 1H), 6.27 (s, 2H), 4.45 (br, 2H), 3.74 (br, 1H), 3.63 (br, 1H), 2.97 (s, 3H), 2.61 (br, 2H); ESI MS m/z 294 [M+H]$^+$.

Example 150

Preparation of 8-fluoro-2-methyl-5-phenyl-2,3,4,5-tetrahydro-1H-benzo[c]azepine, maleate salt Step A: To a solution of 5-bromo-2-fluorobenzaldehyde (1.67 g, 8.2 mmol) in methanol (15 mL) was added methylamine (1.07 mL, 40 wt % in water, 12.3 mmol) at 0° C. After stirred at 0° C. for 15 minutes, sodium cyanoborohydride (4.34 g, 20.5 mmol) was added followed by methanol (10 mL). The mixture was stirred at room temperature for 1.5 hours. The mixture was diluted with dichloromethane. The organic layer was washed with brine, dried over sodium sulfate, and concentrated. The residue was purified by column chromatography (10:90 methanol/ethyl acetate) to give the desired amine (500 mg, 28%): $^1$H NMR (CDCl$_3$, 300 MHz) δ 7.49 (dd, J=8.7, 3.8 Hz, 1H), 7.16 (dd, J=9.3, 3.1 Hz, 2H), 6.88-6.82 (m, 1H), 3.79 (s, 2H), 2.46 (s, 3H); ESI MS m/z 219 [M+H]$^+$.

Step B: To a solution of the benzylamine (490 mg, 2.23 mmol) from step A above in acetonitrile (5 mL) was added di-t-butyl dicarbonate (584 mg, 2.7 mmol) at room temperature. After stirring at room temperature for 1 hour, the reaction mixture was diluted with dichloromethane, washed with saturated NaHCO$_3$, brine, dried over sodium sulfate and concentrated to give the desired carbamate (700 mg, quant.) as a light colorless oil: $^1$H NMR (CDCl$_3$, 300 MHz) δ 7.51-7.41 (m, 1H), 6.91-6.84 (m, 2H), 4.49-4.44 (m, 2H), 2.91-2.89 (m, 3H), 1.50-1.42 (m, 9H); ESI MS m/z 319 [M+H]$^+$.

Step C: A mixture of (Z)-ethyl 3-iodo-3-phenylacrylate, methyl 3-phenylpropiolate (1 g, 6.2 mmol), sodium iodide (930 mg, 6.2 mmol) and trifluoroacetic acid (10 mL) was heated at 60° C. overnight. After cooling to room temperature, the reaction solution was diluted with dichloromethane, washed with water, saturated NaHCO$_3$, brine, dried over sodium sulfate and concentrated to give (Z)-ethyl 3-iodo-3-phenylacrylate (1.1 g, crude) as a brown oil.

Step D: To a solution of the carbamate (700 mg, crude) from step B above in DMF (10 mL) was added bis(pinacolato)diboron (679 mg, 2.7 mmol) and potassium acetate (656 mg, 6.7 mmol). The mixture was purged with argon. 1,1'-Bis(diphenylphosphino)ferrocenedichloropalladium (273 mg, 0.33 mmol) was added to the mixture. The reaction was heated at 60-90° C. for 2 hours. After cooling to room temperature, (Z)-ethyl 3-iodo-3-phenylacrylate (1.1 g, crude) from Step C above, cesium carbonate (2.2 g, 6.7 mmol) and water (3 mL) were added to the reaction mixture. The resulting mixture was heated at 80° C. for 4 hours. After cooling to room temperature, the reaction mixture was diluted with dichloromethane, and filtered through a pad of Celite. The filtrate was washed with water, brine, dried over sodium sulfate and concentrated. The residue was purified by column chromatography (10:90 to 20:80 ethyl acetate/hexanes) to give the desired alkene (690 mg, crude) as a thick liquid: $^1$H NMR (CDCl$_3$, 500 MHz) δ 7.44 (d, J=8.7 Hz, 1H), 7.16 (d, J=3.1 Hz, 1H), 7.42-7.20 (m, 5H), 7.03-6.94 (m, 2H), 6.88-6.85 (m, 1H), 5.77 (s, 1H), 4.14-4.10 (m, 2H), 3.48 (s, 3H), 2.69-2.59 (m, 3H), 1.47-1.35 (m, 9H); ESI MS m/z 400 [M+H]$^+$.

Step E: The alkene (690 mg, crude) from step D above was dissolved in methanol (15 mL). Palladium on carbon (10 wt %, 0.30 g) was added to the Parr bottle. The mixture was hydrogenated (40 psi) at room temperature for 5 hours. The catalyst was filtered and the filtrate was concentrated to give the desired ester (500 mg, crude) as a colorless oil: $^1$H NMR (CDCl$_3$, 500 MHz) δ 7.35-7.25 (m, 5H), 6.97-6.74 (m, 3H), 4.70-4.55 (m, 2H), 4.12-4.10 (m, 1H), 3.58 (s, 3H), 3.02 (d, J=7.5 Hz, 2H), 2.73-2.63 (m, 3H), 1.46-1.34 (m, 9H); ESI MS m/z 402 [M+H]$^+$.

Step F: The ester (500 mg, crude) from step E above and HCl (4 N in dioxane, 5 mL) were mixed at room temperature. After stirred at room temperature for 1 hour, the reaction solution was neutralized with saturated NaHCO$_3$. The product was extracted with dichloromethane, washed with, brine, dried over sodium sulfate and concentrated, The residue was purified by column chromatography (5:95 methanol/ethyl acetate) to give the desired benzylamine (170 mg,) as a colorless oil: $^1$H NMR (CDCl$_3$, 500 MHz) δ 7.39-7.32 (m, 3H), 7.30-7.24 (m, 2H), 7.16-7.14 (m, 3H), 4.71-4.60 (m, 2H), 4.00-3.95 (m, 1H), 3.62 (s, 3H), 2.28-3.18 (m, 2H), 2.70 (s, 3H); ESI MS m/z 302 [M+H]$^+$.

Step G: To a solution of the benzylamine (170 mg, crude)) from step F above in toluene (20 mL) was added camphorsulfonic acid (10 mg). The solution was refluxed for 16 hours. After cooling to room temperature, the reaction was washed with NaHCO$_3$, brine, dried over sodium sulfate and concentrated to give the desired lactam (70 mg, 75%) as light yellow oil: $^1$H NMR (CDCl$_3$, 300 MHz) δ 7.40-7.35 (m, 1H), 7.32-7.19 (m, 2H), 7.08-7.03 (m, 2H), 6.90-6.84 (m, 3H), 5.03 (d, J=16.3 Hz, 1H), 4.47 (dd, J=11.4, 5.1 Hz, 1H), 4.15-4.08 (m, 2H), 3.26 (dd, J=13.7, 11.4 Hz, 1H), 3.05 (s, 3H), 2.97 (dd, J=13.7, 5.3 Hz, 1H); ESI MS m/z 270 [M+H]$^+$.

Step H: To a solution of the lactam (67 mg, 0.25 mmol) from step G above in THF (5 mL) cooled to 0° C. was added borane-dimethylsulfide (0.51 mL, 2.0 M in THF, 1.0 mmol) dropwise. The resulting solution was then allowed to warm up to room temperature and heated at 50° C. for 2 hours. After cooling to room temperature, HCl (6 N, 1 mL) was slowly added to the solution. It was heated at 60° C. for 1.5 hours. After cooling to room temperature, the solution was adjusted to pH 9. The product was extracted with dichloromethane, washed with brine and dried over sodium sulfate and concentrated. The residue was purified by column chromatography (98:1.8:0.2 to 95:4.5:0.5 dichloromethane/methanol/concentrated ammonium hydroxide) to give the benzazepine (24 mg, 38%) as a thick oil. To a solution of the benzazepine (24 mg, 0.94 mg) in methanol (1 mL) was added maleic acid (11 mg, 0.094 mmol) followed by addition of water (5 mL). The resultant solution was lyophilized overnight to give 8-fluoro-2-methyl-5-phenyl-2,3,4,5-tetrahydro-1H-benzo[c]azepine, maleate salt (25 mg, 71%, AUC HPLC >99%) as a white solid: mp 153-155° C.; $^1$H NMR (CD$_3$OD, 500 MHz) δ 7.42-7.39 (m, 2H), 7.33-7.30 (m, 1H), 7.27 (dd, J=8.9, 2.7 Hz, 1H), 7.20-7.19 (m, 2H), 7.12-7.08 (m, 1H), 6.85 (br, 1H), 6.25 (s, 3H), 4.69-4.52 (m, 3H), 4.36-4.27 (m, 1H), 3.65-3.60 (m, 2H), 2.93 (s, 3H), 2.58-2.40 (m, 2H); MS m/z 256 [M+H].

Example 151

Preparation of (−)-5-(3,4-difluorophenyl)-8-(6-methylpyridazin-3-yl)-2,3,4,5-tetrahydro-1H-benzo[c]azepine, L-tartrate salt Step A: To an ice-cooled solution of 5-(3,4-difluorophenyl)-2-methyl-8-(6-methylpyridazin-3-yl)-2,3,4,5-tetrahydro-1H-benzo[c]azepine (45 mg, 0.123 mmol) and proton sponge (27 mg, 0.123 mmol) in 1,2 dichloroethane (3 mL) was added 1-chloroethyl chloroformate (36 mg, 0.246 mmol). The reaction mixture was heated at reflux for 1 hour. The mixture was concentrated under reduced pressure. The residue was purified by flash column chromatography (3% methanol/dichloromethane). The fractions containing the desired carbamate were concentrated under reduced pressure. The residue was dissolved in methanol (5 mL) and heated at reflux for 1 hour. The solvent was removed under reduced pressure. The residue was partitioned between dichloromethane and saturated sodium bicarbonate solution. The combined organic extracts (3×) were washed with brine, dried over sodium sulfate and concentrated under reduced pressure. The crude product obtained was purified by flash column chromatography [2% to 9% methanol (containing 10% concentrated ammonium hydroxide)/dichloromethane] to give the desired 2-desmethyl benzazepine (15 mg, 35%): $^1$H NMR (CDCl$_3$, 500 MHz) δ 7.94 (d, J=1.8 Hz, 1H), 7.75 (dd, J=7.9, 1.7 Hz, 1H), 7.71 (d, J=8.7 Hz, 1H), 7.37 (d, J=8.7 Hz, 1H), 7.18-7.13 (m, 1H), 7.03-6.98 (m, 1H), 6.91-6.82 (m, 2H), 4.45 (d, J=8.8 Hz, 1H), 4.12 (d, J=14.9 Hz, 1H), 4.02 (d, J=14.9 Hz, 1H), 3.33-3.30 (m, 1H), 3.25-3.20 (m, 1H), 2.75 (s, 3H), 2.24-2.14 (m, 2H); ESI MS m/z 352 [M+H]$^+$.

Step B: To a solution of the 2-desmethyl benzazepine (13 mg, 0.037 mmol) from step A above in methanol (0.5 mL) was added L-tartaric acid (5.6 mg, 0.037 mmol). The solvent was removed under reduced pressure. The residue was dissolved in acetonitrile (1 mL) and water (0.5 mL). The resultant solution was lyophilized overnight to give (−)-5-(3,4-difluorophenyl)-8-(6-methylpyridazin-3-yl)-2,3,4,5-tetrahydro-1H-benzo[c]azepine, L-tartrate salt (19.9 mg, 93%, AUC HPLC 94.7%) as a pink solid: $^1$H NMR (CD$_3$OD, 500 MHz) δ 8.18 (d, J=1.5 Hz, 1H), 8.09 (d, J=8.8 Hz, 1H), 7.99 (dd, J=8.0, 1.6 Hz, 1H), 7.69 (d, J=8.8 Hz, 1H), 7.35-7.29 (m, 1H), 7.22-7.18 (m, 1H), 7.05-7.01 (m, 2H), 4.72 (d, J=8.7 Hz, 1H), 4.61 (d, J=14.3 Hz, 1H), 4.41 (s, 4H), 3.55 (br, 2H), 3.17-3.14 (m, 1H), 2.72 (s, 3H), 2.59-2.54 (m, 1H), 2.44-2.40 (m, 1H); ESI MS m/z 352 [M+H]$^+$.

Example 152

Preparation of (+)-4-(1,1-dimethyl-5-phenyl-2,3,4,5-tetrahydro-1H-benzo[c]azepin-8-yl)morpholine, L-tartrate salt and (−)-4-(1,1-dimethyl-5-phenyl-2,3,4,5-tetrahydro-1H-benzo[c]azepin-8-yl)morpholine, L-tartrate salt Step A: Cerium(III) chloride heptahydrate (59.6 g, 160 mmol) was dried with stirring at 145° C. in vacuo (0.1 mm Hg) overnight. The resulting off-white power was treated with anhydrous THF (320 mL) and the suspension was stirred at room temperature for 2 h and then cooled at −78° C. To the suspension was added dropwise 1.6M methyllithium in THF (100 mL, 160 mmol). After the mixture was stirred at −65° C. for 30 minutes, 3-methoxybenzonitrile was added dropwise. The color turned dark brown. The resulting mixture was stirred at −65° C. for 4 hours, then quenched by adding saturated ammonium chloride (100 mL). The mixture was stirred at room temperature for 20 minutes and filtered through a Celite pad. The filtrate was concentrated in vacuo. The residue was purified by column chromatography (10:1 methylene chloride/methanol) to gave the desired geminal diamine (6.00 g, 90%) as an off-white solid: $^1$H NMR (500 MHz, CD$_3$OD) δ 7.17 (s, 1H), 7.10 (d, J=7.8 Hz, 1H), 6.84 (d, J=7.8 Hz, 1H), 3.75 (s, 3H), 1.80 (s, 6H).

Step B: A solution of the geminal diamine (0.61 g, 3.7 mmol) from step A above in methanol (5 mL) was treated with 4N HCl in dioxane (1.4 mL, 5.5 mmol). The mixture was concentrated in vacuo. The residue was mixed with acetophenone (0.44 g, 3.7 mmol), concentrated hydrochloric acid (19 μL), ethanol (1.9 mL) and paraformaldehyde (0.16 g, 5.2 mmol). The mixture was heated in a sealed tube at 110° C. overnight. More paraformaldehyde (50 mg) was added and the mixture was stirred at 110° C. for another 5 hours. The mixture was concentrated in vacuo. The residue was purified by column chromatography (20:1 methylene chloride/methanol) to give the desired aminoketone as a colorless oil (0.99 g, 71%): $^1$H NMR (300 MHz, CD$_3$OD) δ 7.87-7.84 (m, 2H), 7.49-7.47 (m, 1H), 7.37-7.19 (m, 4H), 6.89 (d, J=3.2 Hz, 1H), 3.88 (s, 3H), 3.61 (br, 2H), 3.00 (br, 2H), 1.86 (s, 6H).

Step C: To a solution of the aminoketone (0.99 g, 3.3 mmol) from step B above in methanol (15 mL) was added sodium borohydride (0.50 g, 13.3 mmol). The mixture was stirred at 0° C. for 1 hour. More sodium borohydride (0.25 g, 6.7 mmol) was added. The mixture was stirred at room temperature overnight. Saturated ammonium chloride (20 mL) was added to quench the reaction and most of the solvent was evaporated in vacuo. The pH was brought to 9-10 by adding 2 N NaOH. The mixture was extracted with methylene chloride (3×20 mL). The combined extracts were dried over $Na_2SO_4$, filtered and concentrated in vacuo. The amino alcohol (1.0 g) was used directly in the next reaction: $^1$H NMR ($CDCl_3$, 500 MHz) δ 7.33-7.24 (m, 5H), 7.03-7.00 (m, 2H), 6.81(br, 1H), 4.89 (dd, J=8.8, 2.8 Hz, 1H), 3.81 (s, 3H), 2.71 (br, 1H), 2.57 (br, 1H), 1.81-1.69 (m, 2H), 1.50 (s, 6H); ESI MS m/z 300 $[M+H]^+$.

Step D: To a solution of the amino alcohol (0.93 g, 3.1 mmol) from step C above in methylene chloride (80 mL) at −15° C. was added aluminum chloride powder (4.15 g, 31.1 mmol). The mixture was stirred at −15° C. for 1 hour. Saturated ammonium chloride (60 mL) was added to quench the excess aluminum chloride. The pH of the aqueous phase was adjusted to 9-10 with 2 N NaOH. The two layers were separated and the aqueous layer was extracted with methylene chloride (3×60 mL). The combined organic layers were dried over $Na_2SO_4$, filtered and concentrated in vacuo. The residue was purified by column chromatography (20:1 methylene chloride/methanol) to give the desired benzazepine (0.23 g, 26%) as an off-white solid: $^1$H NMR (500 MHz, $CDCl_3$) δ 7.34-7.20 (m, 5H), 6.91 (s, 1H), 6.69 (d, J=8.5 Hz, 1H), 6.61 (d, J=8.5 Hz, 1H), 4.60 (dd, J=9.0, 3.0 Hz, 1H), 3.78 (s, 3H), 3.11-3.09 (m, 1H), 2.94-2.89 (m, 1H), 2.28-2.22 (m, 2H), 1.55 (s, 3H), 1.51 (s, 3H); ESI MS m/z 282 $[M+H]^+$.

Step E: A mixture of the benzazepine (0.22 g, 0.78 mmol) from step D above, hydrobromic acid (48% solution in $H_2O$, 6 mL) and acetic acid (5 mL) was heated to reflux and stirred for 12 hours. The volatiles were removed under reduced pressure. The residue was treated with saturated $NaHCO_3$ (20 mL) and extracted with methylene chloride (3×20 mL). The combined extracts were dried over $Na_2SO_4$, filtered and concentrated in vacuo to give the crude phenol (0.21 g) as an off-white solid. The crude phenol was used directly in the next reaction: $^1$H NMR (500 MHz, $CDCl_3$) δ 7.34-7.19 (m, 5H), 6.81 (s, 1H), 6.63 (d, J=8.4 Hz, 1H), 6.46 (d, J=8.0 Hz, 1H), 4.55 (d, J=8.40 Hz, 1H), 3.14-3.10 (m, 1H), 2.93-2.90 (m, 1H), 2.31-2.23 (m, 1H), 1.53 (s, 3H), 1.48 (s, 3H); ESI MS m/z 268 $[M+H]^+$.

Step F: To a mixture of the phenol (0.21 g, 0.74 mmol) from step E above and N,N-diisopropylethylamine (0.37 mL, 2.2 mmol) in methylene chloride (5 mL) at 0° C. was added dropwise trifluoromethanesulfonic anhydride (0.19 mL, 1.1 mmol). The mixture was stirred at 0° C. for 1 hour. Saturated $NaHCO_3$ (10 mL) was added to quench the reaction. The two phases were separated and the aqueous phase was extracted with methylene chloride (2×30 mL). The combined extracts were dried over $Na_2SO_4$, filtered and concentrated in vacuo. The residue was purified by column chromatography (20:1 dichloromethane/methanol) to yield the triflate (0.10 g, 34%) as a colorless oil: $^1$H NMR ($CDCl_3$, 500 MHz) δ 7.38-7.17 (m, 6H), 6.95 (dd, J=8.6, 2.6 Hz, 1H), 6.80 (d, J=8.6 Hz, 1H), 4.71 (dd, J=7.9, 4.7 Hz, 1H), 3.14-3.10 (m, 1H), 2.93-2.90 (m, 1H), 2.30-2.22 (m, 2H), 1.56 (s, 3H), 1.51 (s, 3H); ESI MS m/z 400 $[M+H]^+$.

Step G: To a solution of the triflate (0.10 g, 0.25 mmol) from step F above in xylene (3 mL) were added cesium carbonate (0.24 mg, 0.75 mmol), 2-(dicyclohexylphosphino)-2',4',6'-tri-i-propyl-1,1'-biphenyl (29 mg, 0.06 mmol) and morpholine (44 mg, 0.50 mmol). The mixture was flushed with nitrogen for 5 minutes, and then palladium(II) acetate (7 mg, 0.03 mmol) was added to it. The reaction solution was heated at 135° C. in a sealed tube for 3 hours, and then cooled to room temperature. The resultant mixture was diluted with dichloromethane, washed with water and brine, dried over sodium sulfate and concentrated in vacuo. The crude product obtained was purified by column chromatography (20:1 to 10:1 dichloromethane/methanol) to give the desired 8-morpholinylbenzazepine (48 mg, 57%) as a colorless oil: ESI MS m/z 337 $[M+H]^+$.

Step H: The free base of the benzazepine (48 mg) from Step G above was resolved by preparative chiral HPLC (CHIRALCEL OD column, using 90:10:0.1 heptane/ethanol/diethylamine as the eluent) to give the (+)-enantiomer $[[\alpha]^{25}_D+9.1°$ (c 0.164, methanol)] and the (−)-enantiomer $[[\alpha]^{25}_D-8.5°$ (c 0.130, methanol)].

Step I: To a solution of the (+)-8-morpholinylbenzazepine (16 mg, 0.049 mmol) form step H above in methanol (1 mL) was added L-tartaric acid (7.3 mg, 0.049 mmol). After the mixture was stirred at room temperature for 10 minutes, water (20 mL) was added. The resulting solution was lyophilized overnight to give (+)-4-(1,1-dimethyl-5-phenyl-2,3,4,5-tetrahydro-1H-benzo[c]azepin-8-yl)morpholine, tartrate salt (23.5 mg, 99%, AUC HPLC 98.9%) as an white solid: $^1$H NMR ($CD_3OD$, 500 MHz) δ 7.42-7.24 (m, 5H), 7.07 (s, 1H), 6.74 (d, J=8.7 Hz, 1H), 6.56 (d, J=8.7 Hz, 1H), 4.56 (d, J=10.9 Hz, 1H), 4.39 (s, 2H), 3.81 (t, J=4.7 Hz, 4H), 3.63 (br, 1H), 3.35 (br, 1H), 3.31 (s, 3H), 3.11 (t, J=4.7 Hz, 4H), 2.45 (br, 1H), 2.35 (br, 1H), 1.89 (s, 3H), 1.85 (s, 3H); ESI MS m/z 337 $[M+H]^+$.

Step J: To a solution of the (−)-8-morpholinylbenzazepine (20 mg, 0.058 mmol) form step H above in methanol (1 mL) was added L-tartaric acid (8.6 mg, 0.058 mmol). After the mixture was stirred at room temperature for 10 minutes, water (20 mL) was added. The resulting solution was lyophilized overnight to give (−)-4-(1,1-dimethyl-5-phenyl-2,3,4,5-tetrahydro-1H-benzo[c]azepin-8-yl)morpholine, tartrate salt (23.5 mg, 91%, AUC HPLC >99%) as an white solid: $^1$H NMR ($CD_3OD$, 500 MHz) δ 7.42-7.24 (m, 5H), 7.07 (s, 1H), 6.74 (d, J=8.7 Hz, 1H), 6.56 (d, J=8.7 Hz, 1H), 4.56 (d, J=10.9 Hz, 1H), 4.39 (s, 2H), 3.81 (t, J=4.7 Hz, 4H), 3.63 (br, 1H), 3.35 (br, 1H), 3.31 (s, 3H), 3.11 (t, J=4.7 Hz, 4H), 2.45 (br, 1H), 2.35 (br, 1H), 1.89 (s, 3H), 1.85 (s, 3H); ESI MS m/z 337 $[M+H]^+$.

Example 153

Preparation of (−)-4-(2-methyl-8-morpholino-2,3,4,5-tetrahydro-1H-benzo[c]azepin-5-yl)benzonitrile, L-tartrate salt Step A: To a mixture of 1-(3-methoxyphenyl)-N-methylbenzylamine hydrochloric salt (11.3 g, 60.0 mmol), 4-bromoacetophenone (11.9 g, 60.0 mmol), concentrated hydrochloric acid (0.1 mL) in ethanol (25 mL) was added paraformaldehyde (2.45 g, 81.8 mmol). The mixture was refluxed for 4 hours. A white solid was formed. After cooling, the mixture was mixed with acetone (50 mL) and stored in freezer overnight. Filtration gave the aminoketone HCl salt (14.5 g, 61%) as a white solid: $^1$H NMR (500 MHz, $CD_3OD$) δ 7.94 (d, J=6.7 Hz, 2H), 7.72 (d, J=6.6 Hz, 2H), 7.42 (d, J=7.7 Hz, 1H), 7.15-7.06 (m, 3H), 4.45 (br, 1H), 4.35 (br, 1H), 3.85 (s, 3H), 3.70 (br, 1H), 3.61-3.58 (m, 2H), 3.45 (d, J=11.9 Hz, 1H), 2.87 (s, 3H); ESI MS m/z 362 $[M+H]^+$.

Step B: To a suspension of the aminoketone (10.0 g, 25.1 mmol) from step A above in methanol (200 mL) at 0° C. was added sodium borohydride (2.08 g, 55.0 mmol) in portions over 2 hour period. Saturated ammonium chloride (20 mL)

was added to quench the reaction and the mixture was stirred at room temperature for 15 minutes. Most of the solvent was evaporated in vacuo. The residue was partitioned between methylene chloride (150 mL) and water (150 mL). The two layers were separated and the aqueous layer was extracted with methylene chloride (3×100 mL). The combined organic layers were dried over $Na_2SO_4$, filtered and concentrated in vacuo to give the amino alcohol (9.16 g, quantitative) as a colorless oil: $^1$H NMR (500 MHz, $CDCl_3$) δ 7.43 (d, J=6.7 Hz, 2H), 7.28-7.20 (m, 3H), 6.93-6.83 (m, 3H), 4.85 (t, J=5.8 Hz, 1H), 3.82 (s, 3H), 3.60 (d, J=12.8 Hz, 1H), 3.44 (d, J=12.8 Hz, 1H), 2.81-2.77 (m, 1H), 2.58-2.55 (m, 1H), 2.28 (s, 3H), 1.85-1.81 (m, 2H); ESI MS m/z 364 $[M+H]^+$.

Step C: To a solution of the amino alcohol (8.98 g, 24.6 mmol) from step B above in methylene chloride (540 mL) at 0° C. was added aluminum chloride powder (36.1 g, 271 mmol). The mixture was stirred at 0° C. for 1.5 hours and then poured into ice-water (1 L). The pH of the aqueous phase was adjusted to 9-10 with 2 N NaOH. The two layers were separated and the aqueous layer was extracted with methylene chloride (3×500 mL). The combined organic layers were dried over $Na_2SO_4$, filtered and concentrated in vacuo. The residue was purified by column chromatography (100:5:0.5 ethyl acetate/ethanol/concentrated ammonium hydroxide) to give the benzazepine (6.00 g, 70%) as off-white solid: $^1$H NMR (500 MHz, $CDCl_3$) δ 7.47 (d, J=8.4 Hz, 2H), 7.04 (d, J=8.2 Hz, 2H), 6.74 (s, 1H), 6.60 (br, 1H), 6.52 (br, 1H), 4.21 (d, J=8.0 Hz, 1H), 3.82 (br, 1H), 3.77 (s, 3H), 3.67 (d, J=14.2 Hz, 1H), 3.07 (br, 1H), 2.96-2.91 (m, 1H), 2.34 (s, 3H), 2.27-2.24 (m, 1H), 2.07 (br, 1H); ESI MS m/z 346 $[M+H]^+$.

Step D: The free base of the benzazepine (5.70 g) from Step C above was resolved by preparative chiral HPLC (CHIRALPAK AD column, using 85:15:0.1 heptane/ethanol/diethylamine as the eluent) to give the (+)-enantiomer $[[\alpha]^{25}_D +7.8°$ (c 0.167, methanol)] and the (−)-enantiomer $[[\alpha]^{25}_D -9.3°$ (c 0.150, methanol)].

Step E: A mixture of the (−)-benzazepine from Step D above (1.00 g, 2.9 mmol), hydrobromic acid (48% solution in water, 20 mL) and acetic acid (20 mL) was heated to reflux and stirred for 2 hours. The volatiles were removed under reduced pressure. The residue was treated with saturated $NaHCO_3$ (50 mL) and extracted with 9:1 methylene chloride/methanol. The combined extracts were dried over $Na_2SO_4$, filtered and concentrated in vacuo. The resulting tan solid was triturated with methanol to afford the desired phenol (0.70 g, 73%) as an off-white solid: $^1$H NMR (500 MHz, DMSO-$d_6$) δ 9.16 (s, 1H), 7.52 (d, J=8.3 Hz, 2H), 7.10 (d, J=8.0 Hz, 2H), 6.59 (s, 1H), 6.47 (d, J=6.2 Hz, 1H), 6.39 (br, 1H), 4.21 (d, J=8.5 Hz, 1H), 3.72 (br, 1H), 3.5 (d, J=14.2 Hz, 1H), 2.86-2.2.83 (m, 2H), 2.17 (s, 3H), 2.16 (br, 1H), 1.90 (br, 1H); ESI MS m/z 334 $[M+H]^+$.

Step F: A mixture of the phenol (0.17 g, 0.50 mmol) from step E above, sodium methanesulfonate (61 mg, 0.6 mg), copper iodide (10 mg, 0.05 mmol), L-proline sodium salt (14 mg, 0.10 mmol) in dimethyl sulfoxide (1 mL) was stirred under nitrogen in a sealed tube at 95° C. for 30 hours. After cooling, the mixture was diluted with ethyl acetate (60 mL) and washed with water (2×30 mL). The ethyl acetate phase was dried over $Na_2SO_4$, filtered and concentrated in vacuo. The residue was purified by column chromatography (100:10:1 methylene chloride/methanol/triethylamine) to yield the desired methylsulfonyl benzazepine (0.17 g) as an off-white solid. The material containing the starting material as an impurity based on proton NMR was used directly in the next reaction.

Step G: To a mixture of the methylsulfonyl benzazepine (0.17 g) from step F above and pyridine (0.2 mL, 2 mmol) in methylene chloride (5 mL) at 0° C. was added dropwise trifluoromethanesulfonic anhydride (0.17 mL, 1.0 mmol). The mixture was stirred at 0° C. for 1 hour. Saturated $NaHCO_3$ (10 mL) was added to quench the reaction. The two phases were separated and the aqueous phase was extracted with methylene chloride (2×20 mL). The combined extracts were dried over $Na_2SO_4$, filtered and concentrated in vacuo. The residue was purified by column chromatography (ethyl acetate) to yield the triflate (0.12 g, 53%) as a colorless oil: $^1$H NMR ($CDCl_3$, 500 MHz) δ 7.96 (d, J=8.4 Hz, 2H), 7.39 (d, J=8.2 Hz, 2H), 7.12 (s, 1H), 7.01-6.99 (m, 1H), 6.72 (br, 1H), 4.43 (d, J=8.7 Hz, 1H), 3.95 (br, 1H), 3.73 (d, J=14.5 Hz, 1H), 3.10 (s, 3H), 3.09 (br, 1H), 3.02-2.99 (m, 1H), 2.35 (s, 3H), 2.34 (br, 1H), 2.22 (br, 1H); ESI MS m/z 464 $[M+H]^+$.

Step H: To a solution of the triflate (45 mg, 0.097 mmol) from step G above in xylene (0.5 mL) were added cesium carbonate (95 mg, 0.29 mmol), 2-(dicyclohexylphosphino)-2',4',6'-tri-i-propyl-1,1'-biphenyl (10 mg, 0.02 mmol) and morpholine (20 mg, 0.15 mmol). The resultant mixture was flushed with nitrogen for 5 minutes, and then palladium(II) acetate (2.2 mg, 0.010 mmol) was added to it. The reaction solution was heated at 135° C. in a sealed tube for 2.5 hours, and then cooled to room temperature. The resultant mixture was diluted with dichloromethane, washed with water and brine, dried over sodium sulfate and concentrated in vacuo. The crude product obtained was purified by column chromatography (20:1 to 10:1 dichloromethane/methanol) to give the desired 8-morpholinylbenzazepine $[[\alpha]^{20}_D -10.0°$ (c 0.10, methanol)] (33 mg, 85%) as a colorless oil: $^1$H NMR ($CDCl_3$, 500 MHz) δ 7.92 (d, J=8.3 Hz, 2H), 7.38 (d, J=8.1 Hz, 2H), 6.77 (s, 1H), 6.63 (d, J=8.2 Hz, 1H), 6.51 (br, 1H), 4.33 (d, J=8.9 Hz, 1H), 3.86-3.84 (m, 5H), 3.67 (d, J=14.3 Hz, 1H), 3.14-3.10 (m, 4H), 3.09 (s, 3H), 3.05 (br, 1H), 2.96-2.92 (m, 1H), 2.35 (s, 3H), 2.35-2.13 (m, 1H), 2.30 (br, 1H); ESI MS m/z 401 $[M+H]^+$.

Step I: To a solution of the 8-morpholinylbenzazepine (single enantiomer) (33 mg, 0.082 mmol) in methanol (1 mL) was added L-tartaric acid (12 mg, 0.082 mmol). After the mixture was stirred at room temperature for 10 minutes, water (20 mL) was added. The resultant solution was lyophilized overnight to give (−)-4-(2-methyl-8-morpholino-2,3,4,5-tetrahydro-1H-benzo[c]azepin-5-yl)benzonitrile, L-tartrate salt (39 mg, 87%, AUC HPLC >99%) as a white solid: $^1$H NMR ($CD_3OD$, 500 MHz) δ 7.97 (d, J=7.9 Hz, 2H), 7.47 (d, J=8.0 Hz, 2H), 7.07 (s, 1H), 6.90 (br, 1H), 6.77 (br, 1H), 4.61 (d, J=8.4 Hz, 1H), 4.51 (br, 1H), 4.40 (s, 2H), 4.28 (d, J=13.5 Hz, 1H), 3.83-3.81 (m, 4H), 3.52 (br, 2H), 3.30-3.14 (m, 7H), 2.84 (s, 3H), 2.60 (br, 1H), 2.40 (br, 1H); ESI MS m/z 401 $[M+H]^+$.

Example 154

Preparation of (−)-2-methyl-8-(6-methylpyridazin-3-yl)-5-(4-(methylsulfonyl)phenyl)-2,3,4,5-tetrahydro-1H-benzo[c]azepine, L-tartrate salt Step A: To a mixture of 1-(3-methoxyphenyl)-N-methylbenzylamine hydrochloric salt (11.3 g, 60.0 mmol), 4-bromoacetophenone (11.9 g, 60.0 mmol), concentrated hydrochloric acid (0.1 mL) in ethanol (25 mL) was added paraformaldehyde (2.45 g, 81.8 mmol). The mixture was refluxed for 4 hours. A white solid was formed. After cooling, the mixture was mixed with acetone (50 mL) and stored in freezer overnight. Filtration gave the aminoketone HCl salt (14.5 g, 61%) as a white solid: $^1$H NMR (500 MHz, $CD_3OD$) δ 7.94 (d, J=6.7 Hz, 2H), 7.72 (d, J=6.6 Hz, 2H), 7.42 (d, J=7.7 Hz, 1H), 7.15-7.06 (m, 3H), 4.45 (br, 1H), 4.35 (br, 1H), 3.85

(s, 3H), 3.70 (br, 1H), 3.61-3.58 (m, 2H), 3.45 (d, J=11.9 Hz, 1H), 2.87 (s, 3H); ESI MS m/z 362 [M+H]$^+$.

Step B: To a suspension of the aminoketone (10.0 g, 25.1 mmol) from step A above in methanol (200 mL) at 0° C. was added sodium borohydride (2.08 g, 55.0 mmol) in portions over 2 hour period. Saturated ammonium chloride (20 mL) was added to quench the reaction and the mixture was stirred at room temperature for 15 minutes. Most of the solvent was evaporated in vacuo. The residue was partitioned between methylene chloride (150 mL) and water (150 mL). The two layers were separated and the aqueous layer was extracted with methylene chloride (3×100 mL). The combined organic layers were dried over Na$_2$SO$_4$, filtered and concentrated in vacuo to give the amino alcohol (9.16 g, quantitative) as a colorless oil: $^1$H NMR (500 MHz, CDCl$_3$) δ 7.43 (d, J=6.7 Hz, 2H), 7.28-7.20 (m, 3H), 6.93-6.83 (m, 3H), 4.85 (t, J=5.8 Hz, 1H), 3.82 (s, 3H), 3.60 (d, J=12.8 Hz, 1H), 3.44 (d, J=12.8 Hz, 1H), 2.81-2.77 (m, 1H), 2.58-2.55 (m, 1H), 2.28 (s, 3H), 1.85-1.81 (m, 2H); ESI MS m/z 364 [M+H]$^+$.

Step C: To a solution of the amino alcohol (8.98 g, 24.6 mmol) from step B above in methylene chloride (540 mL) at 0° C. was added aluminum chloride powder (36.1 g, 271 mmol). The mixture was stirred at 0° C. for 1.5 hours and then poured into ice-water (1 L). The pH of the aqueous phase was adjusted to 9-10 with 2 N NaOH. The two layers were separated and the aqueous layer was extracted with methylene chloride (3×500 mL). The combined organic layers were dried over Na$_2$SO$_4$, filtered and concentrated in vacuo. The residue was purified by column chromatography (100:5:0.5 ethyl acetate/ethanol/concentrated ammonium hydroxide) to give the benzazepine (6.00 g, 70%) as off-white solid: $^1$H NMR (500 MHz, CDCl$_3$) δ 7.47 (d, J=8.4 Hz, 2H), 7.04 (d, J=8.2 Hz, 2H), 6.74 (s, 1H), 6.60 (br, 1H), 6.52 (br, 1H), 4.21 (d, J=8.0 Hz, 1H), 3.82 (br, 1H), 3.77 (s, 3H), 3.67 (d, J=14.2 Hz, 1H), 3.07 (br, 1H), 2.96-2.91 (m, 1H), 2.34 (s, 3H), 2.27-2.24 (m, 1H), 2.07 (br, 1H); ESI MS m/z 346 [M+H]$^+$.

Step D: The free base of the benzazepine (5.70 g) from Step C above was resolved by preparative chiral HPLC (CHIRAL-PAK AD column, using 85:15:0.1 heptane/ethanol/diethylamine as the eluent) to give the (+)-enantiomer [[α]$^{25}_D$+7.8° (c 0.167, methanol)] and the (−)-enantiomer [[α]$^{25}_D$−9.3° (c 0.150, methanol)].

Step E: A mixture of the (−)-benzazepine from Step D above (1.00 g, 2.9 mmol), hydrobromic acid (48% solution in water, 20 mL) and acetic acid (20 mL) was heated to reflux and stirred for 2 hours. The volatiles were removed under reduced pressure. The residue was treated with saturated NaHCO$_3$ (50 mL) and extracted with 9:1 methylene chloride/methanol. The combined extracts were dried over Na$_2$SO$_4$, filtered and concentrated in vacuo. The resulting tan solid was triturated with methanol to afford the desired phenol (0.70 g, 73%) as an off-white solid: $^1$H NMR (500 MHz, DMSO-d$_6$) δ 9.16 (s, 1H), 7.52 (d, J=8.3 Hz, 2H), 7.10 (d, J=8.0 Hz, 2H), 6.59 (s, 1H), 6.47 (d, J=6.2 Hz, 1H), 6.39 (br, 1H), 4.21 (d, J=8.5 Hz, 1H), 3.72 (br, 1H), 3.5 (d, J=14.2 Hz, 1H), 2.86-2.2.83 (m, 2H), 2.17 (s, 3H), 2.16 (br, 1H), 1.90 (br, 1H); ESI MS m/z 334 [M+H]$^+$.

Step F: A mixture of the phenol (0.17 g, 0.50 mmol) from step E above, sodium methanesulfonate (61 mg, 0.6 mg), copper iodide (10 mg, 0.05 mmol), L-proline sodium salt (14 mg, 0.10 mmol) in dimethyl sulfoxide (1 mL) was stirred under nitrogen in a sealed tube at 95° C. for 30 hours. After cooling, the mixture was diluted with ethyl acetate (60 mL) and washed with water (2×30 mL). The ethyl acetate phase was dried over Na$_2$SO$_4$, filtered and concentrated in vacuo. The residue was purified by column chromatography (100: 10:1 methylene chloride/methanol/triethylamine) to yield the desired methylsulfonyl benzazepine (0.17 g) as an off-white solid. The material containing the starting material as an impurity based on proton NMR was used directly in the next reaction.

Step G: To a mixture of the methylsulfonyl benzazepine (0.17 g) from step F above and pyridine (0.2 mL, 2 mmol) in methylene chloride (5 mL) at 0° C. was added dropwise trifluoromethanesulfonic anhydride (0.17 mL, 1.0 mmol). The mixture was stirred at 0° C. for 1 hour. Saturated NaHCO$_3$ (10 mL) was added to quench the reaction. The two phases were separated and the aqueous phase was extracted with methylene chloride (2×20 mL). The combined extracts were dried over Na$_2$SO$_4$, filtered and concentrated in vacuo. The residue was purified by column chromatography (ethyl acetate) to yield the triflate (0.12 g, 53%) as a colorless oil: $^1$H NMR (CDCl$_3$, 500 MHz) δ 7.96 (d, J=8.4 Hz, 2H), 7.39 (d, J=8.2 Hz, 2H), 7.12 (s, 1H), 7.01-6.99 (m, 1H), 6.72 (br, 1H), 4.43 (d, J=8.7 Hz, 1H), 3.95 (br, 1H), 3.73 (d, J=14.5 Hz, 1H), 3.10 (s, 3H), 3.09 (br, 1H), 3.02-2.99 (m, 1H), 2.35 (s, 3H), 2.34 (br, 1H), 2.22 (br, 1H); ESI MS m/z 464 [M+H]$^+$.

Step H: A round bottomed flask was charged with the triflate (74 mg, 0.16 mmol) from step G above, bis(pinacolato)diboron (45 mg, 0.18 mmol) and potassium acetate (47 mg, 0.48 mmol) and dichloro[1,1'-bis(diphenylphosphino)ferrocene]palladium(II) dichloromethane adduct (13 mg, 0.016 mmol) in DMF (1.5 mL). The mixture was refilled with nitrogen three times and then stirred at 80° C. for 1 hour. The mixture was cooled to room temperature. Cesium carbonate (156 mg, 0.48 mmol), 3-chloro-6-methylpyridazine (36 mg, 0.24 mmol) and water (1 mL) were added. The mixture was refilled with nitrogen three times and then stirred at 60° C. for 2 hours. After cooling, the mixture was partitioned between methylene chloride and water. The aqueous phase was extracted with methylene chloride. The combined extracts were washed with 2N NaOH (2×10 mL), dried over sodium sulfate, filtered and concentrated in vacuo. The residue was purified by column chromatography (10:1 methylene chloride/methanol) to yield the desired benzazepine [[α]$^{20}_D$+5.00 (c 0.08, methanol)] (16 mg, 25%) as an off-white solid: $^1$H NMR (CDCl$_3$, 500 MHz) δ 7.98-7.94 (m, 3H), 7.76 (d, J=7.9 Hz, 1H), 7.72 (d, J=8.7 Hz, 1H), 7.43-7.36 (m, 3H), 6.77 (br, 1H), 4.48 (d, J=9.0 Hz, 1H), 4.00 (d, J=9.1 Hz, 1H), 3.83 (d, J=14.4 Hz, 1H), 3.10 (s, 3H), 3.08 (br, 1H), 3.02-2.97 (m, 1H), 2.79 (s, 3H), 2.43 (br, 1H), 2.41 (s, 3H), 2.17 (br, 1H); ESI MS m/z 408 [M+H]$^+$.

Step I: To a solution of the benzazepine (single enantiomer) (16 mg, 0.039 mmol) in methanol (1 mL) was added L-tartaric acid (5.9 mg, 0.039 mmol). After the mixture was stirred at room temperature for 10 minutes, water (20 mL) was added. The resultant solution was lyophilized overnight to give (−)-2-methyl-8-(6-methylpyridazin-3L-yl)-5-(4-(methylsulfonyl)phenyl)-2,3,4,5-tetrahydro-1H-benzo[c]azepine, L-tartrate salt (17 mg, 78%, AUC HPLC 96.5%) as an white solid: $^1$H NMR (CD$_3$OD, 500 MHz) δ 8.22 (br, 1H), 8.09 (br, 1H), 8.01 (br, 3H), 7.70 (br, 1H), 7.55 (br, 2H), 6.98 (br, 1H), 4.74 (br, 1H), 4.45 (br, 2H), 4.42 (s, 2H), 3.62 (br, 2H), 3.16 (s, 3H), 2.90 (s, 3H), 2.72 (s, 3H), 2.70 (br, 1H), 2.48 (br, 1H); ESI MS m/z 408 [M+H]$^+$.

Example 155

Preparation of (+)-5-(4-methoxyphenyl)-2-methyl-8-(6-methylpyridazin-3-yl)-2,3,4,5-tetrahydro-1H-benzo[c]azepine, L-tartrate salt and (−)-5-(4-methoxyphenyl)-2-methyl-8-(6-methylpyridazin-3-yl)-2,3,4, 5-tetrahydro-1H-benzo[c]azepine, L-tartrate salt Step A: A mixture of the 3-hydroxybenzaldehyde (10 g, 82 mmol), tert-butyldimethylsilyl chloride (13.6 g, 90.2 mmol), and imidazole (6.7 g, 98 mmol) in DMF (60 mL) were stirred overnight. The reaction mixture was diluted with dichloromethane, washed with water and brine, dried and concentrated. The residue was purified by flash chromatography (90:10 hexane/ethyl acetate) to give the silyl ether (20.8 g, 100%) as a colorless oil: $^1$H NMR (CDCl$_3$, 300 MHz) δ 9.94 (s, 1H), 7.47 (d, J=7.5 Hz, 1H), 7.39 (t, J=7.5 Hz, 1H), 7.32-7.31 (m, 1H), 7.12-7.08 (m, 1H), 0.99 (s, 9H), 0.22 (s, 6H).

Step B: To a solution of the silyl ether (20.8 g, 82 mmol) from step A above in methanol (200 mL) was added methylamine (40% in water, 11 mL, 123 mmol) at room temperature. After stirring for 10 minutes, the reaction mixture was cooled to 0° C., sodium borohydride (4.7 g, 123 mmol) was added to the solution portionwise. The reaction mixture was stirred at 0° C. for 2 hours. The solvent was removed. The residue was dissolved in water and the product was extracted with dichloromethane, washed with brine, dried over sodium sulfate and concentrated to give the benzylamine (19.5 g, 95%) as a colorless liquid: $^1$H NMR (CDCl$_3$, 500 MHz) δ 7.17 (t, J=7.6 Hz, 1H), 6.89 (d, J=7.6 Hz, 1H), 6.79 (s, 1H), 6.72 (d, J=7.6 Hz, 1H), 3.82 (s, 2H), 2.44 (s, 3H), 0.98 (s, 9H), 0.20 (s, 6H); ESI MS m/z 252 [M+H]$^+$.

Step C: The benzylamine (4.56 g, 18.1 mmol) from step B above was dissolved in HCl/dioxane (20 mL, 80 mmol, 4 M in dioxane). The solvent was then removed. To the residue was added paraformaldehyde (1.1 g, 36.2 mmol), 4-methoxyacetophenone (2.73 g, 18.1 mmol), ethanol (25 mL) and a few drops of concentrated hydrochloric acid. The solution was refluxed overnight. After cooling to room temperature, the solvent was removed and the residue was neutralized with saturated NaHCO$_3$. The product was extracted with dichloromethane, washed with brine, dried over sodium sulfate and concentrated. The residue was purified by flash chromatography (90:5 ethyl acetate/methanol) to give the desired ketone (2.57 g, 48%) as a colorless liquid: $^1$H NMR (CDCl$_3$, 300 MHz) δ 7.91 (d, J=7.8 Hz, 2H), 7.15 (t, J=7.8 Hz, 1H), 6.92 (d, J=7.8 Hz, 2H), 6.83 (d, J=7.6 Hz, 1H), 6.78 (s, 1H), 6.69 (d, J=7.8 Hz, 1H), 3.87 (s, 3H), 3.50 (s, 2H), 3.13 (t, J=7.6 Hz, 2H), 2.86 (t, J=7.6 Hz, 2H), 2.26 (s, 3H); ESI MS m/z 300 [M+H]$^+$.

Step D: To a solution of the ketone (2.57 g, crude) from step C above in methanol (25 mL) at 0° C. was added sodium borohydride (490 mg, 13 mmol) portionwise. After stirring at 0° C. for 1 hour, the solvent was removed and the residue was diluted with dichloromethane, washed with water and brine, dried over sodium sulfate and concentrated to give the alcohol (2.3 g, 90%) as a colorless liquid: $^1$H NMR (CDCl$_3$, 300 MHz) δ 7.29-7.28 (m, 2H), 7.18 (t, J=7.8 Hz, 1H), 6.88-6.75 (m, 5H), 4.84 (dd, J=8.8, 2.9 Hz, 1H), 3.80 (s, 3H), 3.62 (d, J=12.9 Hz, 1H), 3.35 (d, J=12.9 Hz, 1H), 2.82-2.77 (m, 1H), 2.57-2.54 (m, 1H), 2.28 (s, 3H), 1.88-1.71 (m, 2H); ESI MS m/z 302 [M+H]$^+$.

Step E: To a solution of the alcohol (2.3 g, 7.6 mmol) from step D above in dichloromethane at −78° C. was added aluminium chloride (5.1 g, 38 mmol). The mixture was allowed to warm up to a range of −40 to −30° C. After stirring at this temperature for 2 hours, water was added to the mixture. The mixture was adjusted to pH 8 with NaOH. The product was extracted with dichloromethane, washed with brine, dried over sodium sulfate and concentrated. The residue was purified by flash chromatography (98:1.8:0.2 to 95:4.5:0.5 dichloromethane/methanol/concentrated ammonium hydroxide) to give the desired benzazepine (1.3 g, 60%) as a light brown semi-solid: $^1$H NMR (CDCl$_3$, 300 MHz) δ 7.06 (d, J=8.7 Hz, 2H), 6.90 (d, J=8.7 Hz, 2H), 6.79-6.53 (m, 3H), 4.18 (d, J=8.7 Hz, 1H), 3.81 (s, 3H), 3.81-3.63 (m, 2H), 3.24-2.95 (m, 2H), 2.37 (s, 3H), 2.31-2.04 (m, 2H); ESI MS m/z 284 [M+H]$^+$.

Step F: To a solution of the phenol (1.3 g, 4.6 mmol) from step E above in dichloromethane (10 mL) and pyridine (2 mL) was added triflic anhydride (1.95 g, 6.9 mmol) dropwise at 0° C. After stirring at this temperature for 1 hour, the solution was washed with water, saturated NaHCO$_3$ and brine, dried over sodium sulfate and concentrated to give the desired triflate (2.1 g, crude) as a thick oil: ESI MS m/z 416 [M+H]$^+$.

Step G: To a solution of the triflate (2.1 g, crude) from step F in DMSO (10 mL) was added bis(pinacolato)diboron (1.4 g, 5.5 mmol) and potassium acetate (1.5 mg, 15.5 mmol). The mixture was purged with argon. 1,1'-Bis(diphenylphosphino)ferrocenedichloropalladium (293 mg, 0.40 mmol) was added to the mixture. The reaction was heated at 85° C. for 1.5 hours. After cooling to room temperature, the reaction mixture was diluted with dichloromethane, and filtered through a pad of Celite. The filtrate was washed with water, brine, dried over sodium sulfate and concentrated to give the desired boronate ester (4.2 g, crude) as a thick black liquid: ESI MS m/z 394 [M+H]$^+$.

Step H: The boronate ester (2.1 g, crude) from step G above, 3-chloro-6-methylpyridazine (660 mg, 5.1 mmol), and cesium carbonate (2.2 g, 6.8 mmol) were suspended in DMF (10 mL) and water (3 mL). The mixture was purged with argon. 1,1'-Bis(diphenylphosphino)ferrocenedichloropalladium (150 mg, 0.21 mmol) was added to the mixture. The mixture was heated at 100° C. for 2 hours. After cooling to room temperature, the reaction mixture was diluted with dichloromethane, and filtered through a pad of Celite. The filtrate was washed with water, brine, dried over sodium sulfate and concentrated. The residue was purified by flash chromatography (98:1.8:0.2 to 95:4.5:0.5 dichloromethane/methanol/concentrated ammonium hydroxide) to give the benzazepine (370 mg, 45% for 3 steps) as an oil.

Step I: The free base of benzazepine from Step H above was resolved by preparative chiral HPLC (CHIRALCEL OD column, using 80:20:0.1 heptane/isopropanol/diethylamine as the eluent) to give (−)-enantiomer and (−)-enantiomer.

Step J: To a solution of the (−)-enantiomer (63 mg, 0.18 mmol) from Step I above in methanol (1 mL) was added L-tartaric acid (27 mg, 0.18 mmol) followed by slow addition of water (8 mL). The resultant solution was lyophilized overnight to give (+)-5-(4-methoxyphenyl)-2-methyl-8-(6-methylpyridazin-3-yl)-2,3,4,5-tetrahydro-1H-benzo[c]azepine, L-tartrate salt (75 mg, 83%, AUC HPLC >99%) as an off-white solid: mp 122-124° C.; $^1$H NMR (CD$_3$OD, 500 MHz) δ 8.19 (s, 1H), 8.08 (d, J=8.9 Hz, 1H), 7.97 (d, J=7.7 Hz, 1H), 7.69 (d, J=8.8 Hz, 1H), 7.15 (d, J=8.3 Hz, 2H), 7.04 (br, 1H), 6.98 (d, J=8.3 Hz, 2H), 4.76-4.61 (m, 2H), 4.47-4.43 (m, 4H), 3.81 (s, 3H), 3.66-3.60 (m, 2H), 2.92 (s, 3H), 2.72 (s, 3H), 2.59-2.44 (m, 1H), 2.43-2.41 (m, 1H); ESI MS m/z 360 [M+H].

Step K: To a solution of the (−)-enantiomer (57 mg, 0.16 mmol) from Step I above in methanol (1 mL) was added L-tartaric acid (24 mg, 0.16 mmol) followed by slow addition of water (8 mL). The resultant solution was lyophilized overnight to give (−)-5-(4-methoxyphenyl)-2-methyl-8-(6-methylpyridazin-3-yl)-2,3,4,5-tetrahydro-1H-benzo[c]azepine, L-tartrate salt (76 mg, 94%, AUC HPLC >98.4%) as a off-white solid: mp 132-134° C.; $^1$H NMR (CD$_3$OD, 500 MHz) δ 8.19 (s, 1H), 8.08 (d, J=8.9 Hz, 1H), 7.97 (d, J=7.7 Hz, 1H), 7.69 (d, J=8.8 Hz, 1H), 7.15 (d, J=8.3 Hz, 2H), 7.04 (br, 1H), 6.98 (d, J=8.3 Hz, 2H), 4.76-4.61 (m, 2H), 4.47-4.43 (m, 4H), 3.81 (s, 3H), 3.66-3.60 (m, 2H), 2.92 (s, 3H), 2.72 (s, 3H), 2.59-2.44 (m, 1H), 2.43-2.41 (m, 1H); ESI MS m/z 360 [M+H].

Example 156

Preparation of 4-(2-methyl-8-(6-methylpyridazin-3-yl)-2,3,4,5-tetrahydro-1H-benzo[c]azepin-5-yl)phenol, L-tartrate salt, enantiomers A and B Step A: A mixture of the 3-hydroxybenzaldehyde (10 g, 82 mmol), tert-butyldimethylsilyl chloride (13.6 g, 90.2 mmol), and imidazole (6.7 g, 98 mmol) in DMF (60 mL) were stirred overnight. The reaction mixture was diluted with dichloromethane, washed with water and brine, dried and concentrated. The residue was purified by flash chromatography (90:10 hexane/ethyl acetate) to give the silyl ether (20.8 g, 100%) as a colorless oil: $^1$H NMR (CDCl$_3$, 300 MHz) δ 9.94 (s, 1H), 7.47 (d, J=7.5 Hz, 1H), 7.39 (t, J=7.5 Hz, 1H), 7.32-7.31 (m, 1H), 7.12-7.08 (m, 1H), 0.99 (s, 9H), 0.22 (s, 6H).

Step B: To a solution of the silyl ether (20.8 g, 82 mmol) from step A above in methanol (200 mL) was added methylamine (40% in water, 11 mL, 123 mmol) at room temperature. After stirring for 10 minutes, the reaction mixture was cooled to 0° C., sodium borohydride (4.7 g, 123 mmol) was added to the solution portionwise. The reaction mixture was stirred at 0° C. for 2 hours. The solvent was removed. The residue was dissolved in water and the product was extracted with dichloromethane, washed with brine, dried over sodium sulfate and concentrated to give the benzylamine (19.5 g, 95%) as a colorless liquid: $^1$H NMR (CDCl$_3$, 500 MHz) 67.17 (t, J=7.6 Hz, 1H), 6.89 (d, J=7.6 Hz, 1H), 6.79 (s, 1H), 6.72 (d, J=7.6 Hz, 1H), 3.82 (s, 2H), 2.44 (s, 3H), 0.98 (s, 9H), 0.20 (s, 6H); ESI MS m/z 252 [M+H]+.

Step C: The benzylamine (4.56 g, 18.1 mmol) from step B above was dissolved in HCl/dioxane (20 mL, 80 mmol, 4M in dioxane). The solvent was then removed. To the residue was added paraformaldehyde (1.1 g, 36.2 mmol), 4-methoxyacetophenone (2.73 g, 18.1 mmol), ethanol (25 mL) and a few drops of concentrated hydrochloric acid. The solution was refluxed overnight. After cooling to room temperature, the solvent was removed and the residue was neutralized with saturated NaHCO$_3$. The product was extracted with dichloromethane, washed with brine, dried over sodium sulfate and concentrated. The residue was purified by flash chromatography (90:5 ethyl acetate/methanol) to give the desired ketone (2.57 g, 48%) as a colorless liquid: $^1$H NMR (CDCl$_3$, 300 MHz) δ 7.91 (d, J=7.8 Hz, 2H), 7.15 (t, J=7.8 Hz, 1H), 6.92 (d, J=7.8 Hz, 2H), 6.83 (d, J=7.6 Hz, 1H), 6.78 (s, 1H), 6.69 (d, J=7.8 Hz, 1H), 3.87 (s, 3H), 3.50 (s, 2H), 3.13 (t, J=7.6 Hz, 2H), 2.86 (t, J=7.6 Hz, 2H), 2.26 (s, 3H); ESI MS m/z 300 [M+H]+.

Step D: To a solution of the ketone (2.57 g, crude) from step C above in methanol (25 mL) at 0° C. was added sodium borohydride (490 mg, 13 mmol) portionwise. After stirring at 0° C. for 1 hour, the solvent was removed and the residue was diluted with dichloromethane, washed with water and brine, dried over sodium sulfate and concentrated to give the alcohol (2.3 g, 90%) as a colorless liquid: $^1$H NMR (CDCl$_3$, 300 MHz) δ 7.29-7.28 (m, 2H), 7.18 (t, J=7.8 Hz, 1H), 6.88-6.75 (m, 5H), 4.84 (dd, J=8.8, 2.9 Hz, 1H), 3.80 (s, 3H), 3.62 (d, J=12.9 Hz, 1H), 3.35 (d, J=12.9 Hz, 1H), 2.82-2.77 (m, 1H), 2.57-2.54 (m, 1H), 2.28 (s, 3H), 1.88-1.71 (m, 2H); ESI MS m/z 302 [M+H]+.

Step E: To a solution of the alcohol (2.3 g, 7.6 mmol) from step D above in dichloromethane at −78° C. was added aluminium chloride (5.1 g, 38 mmol). The mixture was allowed to warm up to a range of −40 to −30° C. After stirring at this temperature for 2 hours, water was added to the mixture. The mixture was adjusted to pH 8 with NaOH. The product was extracted with dichloromethane, washed with brine, dried over sodium sulfate and concentrated. The residue was purified by flash chromatography (98:1.8:0.2 to 95:4.5:0.5 dichloromethane/methanol/concentrated ammonium hydroxide) to give the desired benzazepine (1.3 g, 60%) as a light brown semi-solid: $^1$H NMR (CDCl$_3$, 300 MHz) δ 7.06 (d, J=8.7 Hz, 2H), 6.90 (d, J=8.7 Hz, 2H), 6.79-6.53 (m, 3H), 4.18 (d, J=8.7 Hz, 1H), 3.81 (s, 3H), 3.81-3.63 (m, 2H), 3.24-2.95 (m, 2H), 2.37 (s, 3H), 2.31-2.04 (m, 2H); ESI MS m/z 284 [M+H]+.

Step F: To a solution of the phenol (1.3 g, 4.6 mmol) from step E above in dichloromethane (10 mL) and pyridine (2 mL) was added triflic anhydride (1.95 g, 6.9 mmol) dropwise at 0° C. After stirring at this temperature for 1 hour, the solution was washed with water, saturated NaHCO3 and brine, dried over sodium sulfate and concentrated to give the desired triflate (2.1 g, crude) as a thick oil: ESI MS m/z 416 [M+H]+.

Step G: To a solution of the triflate (2.1 g, crude) from step F in DMSO (10 mL) was added bis(pinacolato)diboron (1.4 g, 5.5 mmol) and potassium acetate (1.5 mg, 15.5 mmol). The mixture was purged with argon. 1,1'-Bis(diphenylphosphino)ferrocenedichloropalladium (293 mg, 0.40 mmol) was added to the mixture. The reaction was heated at 85° C. for 1.5 hours. After cooling to room temperature, the reaction mixture was diluted with dichloromethane, and filtered through a pad of Celite. The filterate was washed with water, brine, dried over sodium sulfate and concentrated to give the desired boronate ester (4.2 g, crude) as a thick black liquid: ESI MS m/z 394 [M+H]+.

Step H: The boronate ester (2.1 g, crude) from step G above, 3-chloro-6-methylpyridazine (660 mg, 5.1 mmol), and cesium carbonate (2.2 g, 6.8 mmol) were suspended in DMF (10 mL) and water (3 mL). The mixture was purged with argon. 1,1'-Bis(diphenylphosphino)ferrocenedichloropalladium (150 mg, 0.21 mmol) was added to the mixture. The mixture was heated at 100° C. for 2 hours. After cooling to room temperature, the reaction mixture was diluted with dichloromethane, and filtered through a pad of Celite. The filtrate was washed with water, brine, dried over sodium sulfate and concentrated. The residue was purified by flash chromatography (98:1.8:0.2 to 95:4.5:0.5 dichloromethane/methanol/concentrated ammonium hydroxide) to give the benzazepine (370 mg, 45% for 3 steps) as an oil.

Step I: The free base of benzazepine from Step H above was resolved by preparative chiral HPLC (CHIRALCEL OD column, using 80:20:0.1 heptane/isopropanol/diethylamine as the eluent) to give enantiomer A and enantiomer B.

Step J: To a solution of the enantiomer A (57 mg, 0.16 mmol) in dichloromethane (5 mL) at −78° C. was added boron tribromide (200 mg, 0.8 mmol) dropwise. The mixture was stirred at −78° C. for 4 hours, at 0° C. for 0.5 hour, and room temperature for 20 minutes. Water was added to the reaction mixture at 0° C., and the resultant mixture was stirred at 0° C. for 10 minutes. The mixture was adjusted to pH 8 with saturated NaHCO$_3$. The product was extracted with dichloromethane, washed with brine, dried over sodium sulfate and concentrated to give the desired phenol (31 mg, 56%).

Step K: To a solution of the phenol (31 mg, 0.090 mmol) from step J above in methanol (0.5 mL) was added L-tartaric acid (16 mg, 0.11 mmol) followed by slow addition of water (5 mL). The resultant solution was lyophilized overnight to give 4-(2-methyl-8-(6-methylpyridazin-3-yl)-2,3,4,5-tetrahydro-1H-benzo[c]azepin-5-yl)phenol, L-tartrate salt, enantiomer A (36 mg, 77%, AUC HPLC >97.8%) as a off-white solid: mp 120-122° C.; $^1$H NMR (CD$_3$OD, 500 MHz) δ8.19 (s, 1H), 8.07 (d, J=8.8 Hz, 1H), 7.97 (d, J=7.4 Hz, 1H), 7.69 (d, J=8.7 Hz, 1H), 7.15-7.04 (m, 3H), 6.83 (d, J=7.5 Hz, 2H), 4.71-4.57 (m, 2H), 4.47-4.43 (m, 4H), 3.66-3.60 (m, 2H), 2.93 (s, 3H), 2.72 (s, 3H), 2.59-2.52 (m, 1H), 2.48-2.40 (m, 1H); ESI MS m/z 346 [M+H].

Step L: To a solution of the enantiomer B (70 mg, 0.19 mmol) in dichloromethane (5 mL) at −78° C. was added boron tribromide (244 mg, 0.98 mmol) dropwise. The mixture was stirred at −78° C. for 4 hours, at 0° C. for 0.5 hour, and room temperature for 20 minutes. Water was added to the reaction mixture at 0° C., and the resultant mixture was stirred at 0° C. for 10 minutes. The mixture was adjusted to pH 8 with saturated NaHCO$_3$. The product was extracted with dichloromethane, washed with brine, dried over sodium sulfate and concentrated to give the desired phenol (31 mg, 46%).

Step M: To a solution of the phenol (31 mg, 0.090 mmol) from step L above in methanol (0.5 mL) was added L-tartaric acid (16 mg, 0.11 mmol) followed by slow addition of water (5 mL). The resultant solution was lyophilized overnight to give 4-(2-methyl-8-(6-methylpyridazin-3-yl)-2,3,4,5-tetrahydro-1H-benzo[c]azepin-5-yl)phenol, L-tartrate salt, enantiomer B (41 mg, 87%, AUC HPLC >97.2%) as a off-white solid: mp 140-142° C.; $^1$H NMR (CD$_3$OD, 500 MHz) δ8.19 (s, 1H), 8.07 (d, J=8.8 Hz, 1H), 7.97 (d, J=7.4 Hz, 1H), 7.69 (d, J=8.7 Hz, 1H), 7.15-7.04 (m, 3H), 6.83 (d, J=7.5 Hz, 2H), 4.71-4.57 (m, 2H), 4.47-4.43 (m, 4H), 3.66-3.60 (m, 2H), 2.93 (s, 3H), 2.72 (s, 3H), 2.59-2.52 (m, 1H), 2.48-2.40 (m, 1H); ESI MS m/z 346 [M+H].

Example 157

Primary Binding Assay

Preparation of Membranes

Recombinant HEK-293 cells expressing either the hSERT, hDAT, or hNET proteins were harvested from T-175 flasks as follows. The medium was removed from the flasks and the cells rinsed with HBSS without Ca and without Mg. The cells were then incubated for 5-10 minutes in 10 mM Tris-Cl, pH 7.5, 5 mM EDTA before the cells were lifted with a combination of pipetting and scraping, as needed. The cell suspension was collected into centrifuge bottles and homogenized for 30 seconds with a Polytron homogenizer. The suspension was centrifuged for 30 minutes at 32,000×g, 4° C. The supernatant was decanted and the pellet resuspended and homogenized in 50 mM Tris-Cl, pH 7.5, 1 mM EDTA for 10 seconds. The suspension was then centrifuged again for 30 minutes at 32,000×g, 4° C. The supernatant was decanted and the pellet resuspended in 50 mM Tris-Cl, pH 7.5, 1 mM EDTA and briefly homogenized. A Bradford assay (Bio-rad) was performed and the membrane preparation diluted to 2 mg/ml with 50 mM Tris-Cl, pH 7.5, 1 mM EDTA. Aliquots were prepared, and then frozen and stored at −80° C.

SERT Radioligand Binding Assay

Compounds were dissolved in 100% DMSO at a concentration 100 times the desired highest assay concentration, serially diluted 1:3 in 100% DMSO, and 0.4 µl/well of each solution esd dispensed to a Nunc polypropylene, round bottom, 384-well plate. 100% inhibition is defined with 0.4 µl/well of 1 mM fluoxetine dissolved in DMSO. 20 µl/well of a 2× membrane preparation (15 ug/ml in 50 mM Tris-Cl, pH 7.5, 120 mM NaCl, 5 mM KCl) and 20 µl/well of a 2× radioligand solution (520 pM [$^{125}$I]RTI-55 in 50 mM Tris-Cl, pH 7.5, 120 mM NaCl, 5 mM KCl) were added to each well and the reaction incubated for 1 hour at room temperature. The contents of the assay plate were then transferred to a Millipore Multiscreen$_{HTS}$ GF/B filter plate which has been pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing was completed in less than 90 seconds. The plates were air-dried overnight, 12 µl/well of MicroScint scintillation fluid added, and the plates counted in a Trilux.

DAT Radioligand Binding Assay

Compounds were dissolved in 100% DMSO at a concentration 100 times the desired highest assay concentration, serially diluted 1:3 in 100% DMSO, and 0.4 µl/well of each solution was dispensed to a Nunc polypropylene, round bottom, 384-well plate. 100% inhibition is defined with 0.4 µl/well of 1 mM GBR-12935 dissolved in DMSO. 20 ul/well of a 2× membrane preparation (12.5 µg/ml in 30 mM sodium phosphate buffer, pH 7.9 at 4° C.) and 20 µl/well of a 2× radioligand solution (250 pM [$^{125}$I]RTI-55 in 30 mM sodium phosphate buffer, pH 7.9 at 4° C.) were added to the well and the reaction incubated for 1 hour at room temperature. The contents of the assay plate were then transferred to a Millipore Multiscreen$_{HTS}$ GF/B filter plate which had been pretreated with 0.5% PEI for at least one hour. The plate was vacuum-filtered and washed with 7 washes of 100 µl/well 50 mM Tris-Cl, pH 7.5, 120 mM NaCl, 5 mM KCl chilled to 4° C. The filtration and washing were completed in less than 90 seconds. The plates were air-dried overnight, 12 µl/well of MicroScint scintillation fluid added, and the plates counted in a Trilux.

NET Radioligand Binding Assay

Compounds were dissolved in 100% DMSO at a concentration 100× the desired highest assay concentration, serially diluted 1:3 in 100% DMSO, and 1.0 µl/well of each solution was dispensed to a Nunc polypropylene, round bottom, 384-well plate. 100% inhibition is defined with 1.0 µl/well of 10 mM desipramine dissolved in DMSO. 50 µl/well of a 2× membrane preparation (0.4 mg/ml in 50 mM Tris-Cl, pH 7.5, 120 mM NaCl, 5 mM KCl) and 50 µl/well of a 2× radioligand solution (4 nM [$^3$H]nisoxetine in 50 mM Tris-Cl, pH 7.5, 120 mM NaCl, 5 mM KCl) were added to the well and the reaction incubated for 1 hour at room temperature. The contents of the assay plate were then transferred to a Millipore Multiscreen$_{HTS}$ GF/B filter plate which had been pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing is completed in less than 90 seconds. The plates were air-dried overnight, 12 µl/well of MicroScint scintillation fluid added, and the plates counted in a Trilux.

Data Analysis

The raw data is normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, $Y=\text{Bottom}+(\text{Top}-\text{Bottom})/(1+10^{\wedge}((\text{LogIC}_{50}-X)*\text{HillSlope}))$ in order to determine the IC$_{50}$ value for each compound. The radioligand concentration chosen for each assay corresponds to the K$_d$ concentration determined through saturation binding analysis for each assay.

Example 158

Occupancy Assay

Male Sprague-Dawley 180-300 g) (Charles River Laboratories, Wilmington, Mass.) were orally dosed with a test compound (suspended in 0.25% methylcellulose in distilled water). After 60 minutes survival post-dose, rats were sacrificed, and the brains were evacuated and rapidly frozen in chilled isopentane. The frozen brain tissues were stored at −80° C. until use.

The brain tissues were thawed and homogenized in 7-10 volumes of incubation buffer using a polytron homogenizer (Kinematica). Sample aliquots were frozen immediately in dry ice/ethanol and stored at −80° C. Protein content was measured for each brain using a Coomassie protein assay kit (Pierce). In a 96 deep-well plate, 100 μg of tissue (0.4 mg/ml) was incubated with an appropriate radioligand under conditions same as for the brain section binding as shown in Table 1. The effect of the incubation time and temperature on occupancy assessment was also evaluated. At the end of the incubation time, the reactions were stopped by filtering through FPXLR-196 filters (Brandel) that had been soaked in 0.5-1.0% polyethyleneimine for 1 hour at 4° C. The filters were washed twice with ice-cold incubation buffer, tritium was measured using a Wallac Microbeta liquid scintillation counter.

TABLE 1

Radioligands and Incubation Conditions for ex vivo Homogenate Binding Assay

| Transporter | Radioligand | Concentration | Nonspecific Drug | Buffer | Incubation time | Temp |
|---|---|---|---|---|---|---|
| SERT | [$^3$H]-citalopram | 2 nM | 10 uM Fluoxetine | 50 mM Tris. 120 mM NaCl. 5 mM KCl (pH 7.4 at 25° C.) | 20 minutes | 4° C. |
| DAT | [$^{125}$I]-RTI-55 | 0.4 nM | 10 uM GBR-12935 | 30 mM sodium phosphate (pH 7.9 at 4° C.) | 10 minutes | 4° C. |
| NET | [$^3$H]-nisoxetine | 5 nM | 10 uM Reboxetine | 50 mM Tris. 300 mM NaCl. 5 mM KCl (pH 7.4 at 25° C.) | 20 minutes | 4° C. |

The radioactivity of the filters was measured as disintegrations per minute on a LKB Trilux liquid scintillation counter or Packard Cobra II gamma counter. Specific binding was calculated by subtracting the value of nonspecific binding density from that of total binding density (non-drug treated tissue) in the corresponding region or tissue homogenate. The percent of specific binding was calculated as the following: percent specific binding=(specific binding in drug treated minus nonspecific binding)/(total binding minus nonspecific binding)×100%. The percentage of specific binding in a drug treated condition is inversely proportional to the percent inhibition or percent receptor occupancy by the drug.

Example 159

In Vivo Behavioral Assays

For All Tests

All animals were maintained in accordance with the guidelines of the Committee on Animals of the Bristol-Myers Squibb Company and *Guide for Care and Use of Laboratory Animals*, Institute of Animal Laboratory Resources, 1996, which are hereby incorporated by reference in their entirety. Research protocols were approved by the Bristol-Myers Squibb Company Institutional Animal Care and Use Committee.

Mouse Tail Suspension Assay

Male Swiss Webster mice are housed 3-4 per cage in rooms maintained at a constant temperature (21-23° C.) and humidity (50±10%) on a 12-hour light/dark cycle. Animals have ad libitum access to water and food throughout studies. On the day of testing, they are brought into the testing room and allowed to acclimate for 1 hour. To begin testing, the tail is attached to a piece of tape which is then attached to a hook on the ceiling of a sound-attenuated chamber. Immobility is automatically recorded using the Med Associates software. Compounds are administered acutely at a fixed pretreatment interval before session.

Rat Forced Swim Assay

Male Sprague Dawley rats are housed in pairs in rooms maintained at a constant temperature (21-23° C.) and humidity (50±10%) on a 12-hour light/dark cycle. Animals have ad libitum access to water and food throughout studies. Animals are handled for two minutes each on the two days prior to the start of the experiment. On the first day of testing, rats are placed in the swim tank (a Pyrex cylinder 46 cm tall×21 cm in diameter, filled with 30 cm of water ranging between 24-26° C.) for 15 minutes (the pre-swim session). At the end of the 15-minute session, rats are dried and replaced in their home cage. Compounds are administered at three time points in the next 24 hour (23.5, 5, and 1 hour), prior to a second test swim. This swim test is 5 minutes in duration and the animals' behavior is videotaped and active behaviors (immobility, swimming, climbing) are scored. At the end of each 5-second period during the 5-minute test session the rat's behavior is scored as one of the following: immobility (the rat remained floating in the water without struggling and made only those movements necessary to keep its head above water), swimming (the rat made active swimming motions, more than necessary to merely maintain its head above water, e.g., moving around in the cylinder), or climbing (the rat made active movements with its forepaws in and out of the water, usually directed against the cylinder wall). Compounds are only identified by a predesignated code and the experimenter remains blinded throughout the experiment (including while scoring videotapes).

Rat and Mouse Locomotor Activity

Animals are housed according to conditioned described above for the two species. The testing apparatus consisted of Plexiglas chambers equipped with Digiscan activity monitors (Omnitech Electronics, Columbus, Ohio) that detect interruptions of eight photobeams. Horizontal activity was recorded in 5-minute bins for a total of 60 minutes and expressed as total distance covered (in cm). Compounds were administered acutely at a fixed pretreatment interval prior to testing.

Example 160

In Vitro Functional Inhibition of Neurotransmitter Uptake in Rat Synaptosomes

[$^3$H] 5-HT Uptake into Rat Brain Synaptosomes
Synaptosome Preparation

Frontal cortices were homogenized in ice-cold 0.32 M sucrose (1:20 w/v) using a loose fitting (clearance: 0.5 mm), glass/Teflon, motor driven homogeniser (12 strokes, 800 rpm). Nuclei and cell debris will be removed by centrifugation at 1,500×g for 10 minutes. The resulting supernatant was be centrifuged at 18,000×g for 10 minutes. The resulting crude synaptosomal pellet was then resuspended in ice-cold Krebs Henseleit buffer, pH 7.4 at 25° C. (equivalent to 8.3 mg wet weight of tissue/ml). All centrifugations will be carried out at 4° C.
Uptake Assay Crude frontal cortical synaptosomes were incubated in a shaking water bath for 15 minutes at 37° C. Aliquots (150 µL; equivalent to 1.25 mg wet weight of tissue/tube) were then added to tubes containing 275 µL of Krebs Henseleit buffer and 50 µL of buffer (total uptake) or 50 µL of drug solution at 10 concentrations ranging from $10^{-11}$-$10^{-4}$ M or 50 µL of zimeldine ($10^{-5}$ M, non-specific uptake). Uptake was initiated by the addition of 25 µL of freshly prepared [$^3$H]5-HT (2 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µl of [$^3$H]5-HT was pipetted into four vials for the accurate determination of the concentration added to each tube. Radioactivity (dpm) was determined by liquid scintillation counting (1 mL Packard MV Gold scintillator).

[$^3$H] Noradrenaline Uptake into Rat Brain Synaptosomes
Synaptosome Preparation Frontal cortices were homogenised in ice-cold 0.32 M sucrose (1:10 w/v) using a loose fitting (clearance: 0.5 mm), glass/Teflon, motor driven homogeniser (12 strokes, 800 rpm). Nuclei and cell debris were removed by centrifugation at 1,500×g for 10 minutes. The supernatant was then centrifuged at 18,000×g for 10 minutes. The resulting crude synaptosomal pellet was resuspended in ice-cold Krebs Physiological buffer, gassed with 95% O$_2$/5% CO$_2$ (equivalent to 16.7 mg wet weight of tissue/ml). All centrifugations were carried out at 4° C.
Uptake Assay Crude frontal cortical synaptosomes were incubated in a shaking water bath for 15 minutes at 37° C. Aliquots (150 µL; equivalent to 2.5 mg wet weight of tissue/tube) were then added to tubes containing 275 µL of Krebs Physiological buffer and 50 µL of buffer (total uptake) or 50 µL of drug solution at 10 concentrations ranging from $10^{-11}$-$10^{-4}$ M or 50 µL of desipramine ($10^{-5}$ M, non-specific uptake). Uptake was initiated by the addition of 25 µL of freshly prepared [$^3$H]noradrenaline (10 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µL of [$^3$H]noradrenaline were pipetted into four vials for the accurate determination of the concentration added to each tube. Radioactivity (dpm) was determined by liquid scintillation counting (1 mL Packard MV Gold scintillator).

[$^3$H] Dopamine uptake into Rat Brain Synaptosomes
Synaptosome Preparation

Striata were homogenized in ice-cold 0.32 M sucrose (1:40 w/v) using a loose fitting (clearance: 0.5 mm), glass/Teflon, motor driven homogenizer (12 strokes, 800 rpm). Nuclei and cell debris were removed by centrifligation at 1,500×g for 10 minutes. The resulting supernatant was then centrifuged at 18,000×g for 10 minutes. The resulting crude synaptosomal pellet was then resuspended in ice-cold Krebs Henseleit buffer, pH 7.4 at 25° C. (equivalent to 4.17 mg wet weight of tissue/ml). All centrifugations were carried out at 4° C.
Uptake Assay Crude striatal synaptosomes were incubated in a shaking water bath for 15 minutes at 37° C. Aliquots (150 µL; equivalent to 0.625 mg wet weight of tissue/tube) were then added to tubes containing 275 µL of Krebs Henseleit buffer and 50 µL of buffer (total uptake) or 50 µL of drug solution at 10 concentrations ranging from $10^{-11}$-$10^{-4}$M or 50 µL of GBR 12909 ($10^{-5}$M, non-specific uptake). Uptake was initiated by the addition of 25 µL of freshly prepared [$^3$H]dopamine (2.5 nM), followed by vortexing and was continued for 5 minutes at 37° C. in the shaking water bath.

Uptake was terminated by filtration under vacuum through Skatron 11734 filters using a Skatron cell harvester. Filters were rapidly washed with ice-cold saline (wash setting 9,9,0). Scored filter paper discs were placed into plastic scintillation vials and 25 µL of [$^3$H]-dopamine was pipetted into four vials for the accurate determination of the concentration added to each tube. Radioactivity (dpm) was determined by liquid scintillation counting (1 mL Packard MV Gold scintillator).
Data Analysis—Inhibition Constants ($K_i$ values)

The concentration of compound required to inhibit 50% of specific uptake (IC$_{50}$) was calculated using Prism into which count data (dpm) is entered directly from the Liquid Scintillation Analyser. This program calculates specific uptake in the absence and presence of a range of concentrations of compound and then converts the specific uptake values in the presence and absence of each concentration of compound into percentages of specific uptake in the absence of compound as described for a single concentration.

The percentage specific uptake at each concentration of compound was then plotted against the logarithm$_{10}$ of the concentration of compound. The IC$_{50}$ was calculated using the following formula:

$$\% \text{ Specific uptake} = \frac{(100 - D^P)}{(D^P + IC_{50}^P)}$$

where 100=maximum binding (i.e., binding in the absence of compound);

P=slope factor which is analogous to the Hill slope;

D=concentration of compound (M).

The Hill slope was calculated to detect deviations from simple one-site interactions. A Hill slope approximating to unity indicates displacement from a single site, significantly less than unity indicates displacement from multiple sites and significantly greater than unity indicates positive co-operativity.

The affinity constant ($K_i$) of the compound for the uptake site will then be calculated using the Cheng and Prusoff equation (Cheng et al., *Biochem. Pharmacol.* 22(23):3099-3108 (1973), which is hereby incorporated by reference in its entirety):

$$K_i = \frac{IC_{50}}{1 + [L]/K_d}$$

where [L]=the concentration of radioligand (M);
$K_d$=the affinity of the uptake site for the radioligand.
The concentration of radioligand [L] nM $$= \frac{dpm \text{ (total assay radioligand)}}{SA \times (2.22 \times 10^{12})} \times \frac{1}{\text{assay volume}}$$

where SA=specific activity of the radioligand (Ci/mmol).

In binding assays based on human dopamine, serotonin, and/or norepinephrine transporters, certain compounds of formulae I(A-E) had $IC_{50}$ values less than 1 µM, more specifically, less than 100 nM, and most specifically, less than 15 nM.

In binding assays based on human dopamine, serotonin, and/or norepinephrine transporters, certain compounds of Formula II had $IC_{50}$ values less than 1 µM, more specifically, less than 100 nM, and most specifically, less than 15 nM.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A compound of formulae I(A-E) having the following structure:

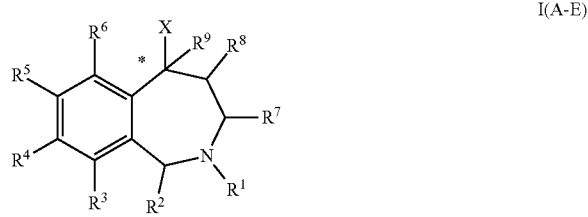

I(A-E)

wherein:
the carbon atom designated * is in the R or S configuration; and

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$; or $R^4$ is a monocyclic or bicyclic aryl or heteroaryl selected from the group consisting of phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxinyl, naphthyl, quinolinyl, isoquinolinyl, quinazolinyl, cinnolinyl, pthalazinyl, quinoxalinyl, 2,3-dihydro-benzo[1,4] dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic carbocycle or heterocycle and $R^4$ is substituted monocyclic or bicyclic aryl or heteroaryl;

provided that for compounds of formula IC, X is substituted phenyl and $R^4$ is H, —$OR^{12}$, —$S(O)_nR^{13}$, $C(O)R^{13}$, —$NR^{10}R^{11}$, —CN, halogen, or $C_1$-$C_6$ alkyl, wherein each of the $C_1$-$C_6$ alkyl is optionally substituted from 1 to 3 times with substituents as defined below in $R^{15}$;

provided that for compounds of formula ID, X is substituted bicyclic carbocycle or heterocycle and $R^4$ is H, —$OR^{12}$, —$S(O)_nR^{13}$, $C(O)R^{13}$, —$NR^{10}R^{11}$, —CN, halogen, or $C_1$-$C_6$ alkyl, wherein each of the $C_1$-$C_6$ alkyl is optionally substituted from 1 to 3 times with substituents as defined below in $R^{15}$; and provided that for compounds of formula IE, X is substituted aromatic monocyclic heterocycle and $R^4$ is substituted monocyclic or bicyclic aryl or heteroaryl;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, —$OR^{12}$, —$S(O)_nR^{13}$, —CN, —$C(O)R^{13}$, —$C_2$-$C_6$ alkenyl, $C_2$-$C_6$ alkynyl, $C_3$-$C_6$ cycloalkyl, and $C_4$-$C_7$ cycloalkylalkyl, wherein each of $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, —$OR^{12}$, —$SR^{10}$, $C_1$-$C_6$ alkyl, —CN or —$NR^{10}R^{11}$, wherein each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-c]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on a ring carbon with from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, or on the additional nitrogen atom from 1 to 3 times with a substituent selected independently at each occurrence thereof from the group consisting of $S(O)_nR^{13}$, —$C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, wherein each of the phenyl, benzyl, and 5- and 6-membered heterocycle is optionally substituted from 1 to 3 times with substituents as defined below in $R^{14}$; or when $R^4$ is —$NR^{10}R^{11}$ or —$C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —C(O)$R^{13}$, and —S(O)$_n R^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —C(O)$R^{13}$, and —S(O)$_n R^{13}$;

$R^{12}$ is selected from the group consisting of H, $C_1$-$C_4$ alkyl, $C_3$-$C_6$ cycloalkyl, $C_4$-$C_7$ cycloalkylalkyl, and —C(O)$R^{13}$, wherein each of —$C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —NR$^{10}$R$^{11}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, wherein the heterocycle is optionally substituted from 1 to 3 times with a substituent selected independently at each occurrence thereof from the group consisting of halogen, cyano, —OR$^{10}$, —S(O)$_n$R$^{10}$, —C(O)R$^{10}$, —C(O)NR$^{10}$R$^{11}$ and $C_1$-$C_4$ alkyl, wherein each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —NO$_2$, —OR$^{12}$, —NR$^{10}$R$^{11}$, —NR$^{12}$C(O)$_2$R$^{13}$, —NR$^{12}$C(O)NR$^{12}$R$^{13}$, —S(O)$_n$R$^{13}$, —CN, —C(O)R$^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, C(O)R$^{13}$, $C_1$-$C_3$ alkyl, —OR$^{12}$, —NR$^{10}$R$^{11}$, —S(O)$_n$R$^{13}$, aryl, and heteroaryl, wherein each of the aryl or heteroaryl groups is optionally substituted from 1 to 4 times with substituents as defined above in $R^{14}$;

with the following provisos that (1) when $R^4$ is H or $C_{1-4}$ alkoxy, X cannot be phenyl; (2) when $R^4$ is (a) $C_{1-6}$ alkyl, (b) $C_{1-4}$ alkoxy, (c) hydroxyl, (d) halogen, or (e) CN, X cannot be a phenyl substituted at the para-position with the same $R^4$; (3) when any one of $R^3$, $R^4$, $R^5$, and $R^6$ is hydrogen, halogen, perhalomethyl, optionally substituted $C_{1-6}$-alkyl, hydroxy, optionally substituted $C_{1-4}$ alkoxy, cyano, amino, optionally substituted mono- or optionally substituted di-$C_{1-4}$ alkylamino, acylamino, or carbamoyl, X cannot be furanyl, thienyl, pyrazolyl, tetrazolyl, isoxazolyl, isothiazolyl, 1,2,3-oxadiazolyl, 1,2,3-thiadiazolyl, 1,2,4-oxadiazolyl, 1,2,4-thiadiazolyl, 1,3,4-oxadiazolyl, 1,3,4-thiadiazolyl, 1,2,5-oxadiazolyl, 1,2,5-thiadiazolyl, benzo[d]isoxazolyl, or benzo[d]isothiazolyl; (4) when $R^4$ is —S(O)$_n$R$^{13}$, n cannot be 0; and (5) when $R^9$ is a substituted alkyl, $R^{15}$ cannot be —NR$^{10}$R$^{11}$;

or an oxide thereof, or a pharmaceutically acceptable salt thereof.

2. The compound according to claim 1, wherein X is substituted phenyl and $R^4$ is substituted monocyclic or bicyclic aryl or heteroaryl.

3. The compound according to claim 1, wherein X is substituted bicyclic carbocycle or heterocycle and $R^4$ is substituted monocyclic or bicyclic aryl or heteroaryl.

4. The compound according to claim 1, wherein X is substituted phenyl and $R^4$ is selected from the group consisting of H, —OR$^{12}$, —S(O)$_n$R$^{13}$, C(O)R$^{13}$, —NR$^{10}$R$^{11}$, —CN, halogen, and $C_1$-$C_6$ alkyl, wherein each of the $C_1$-$C_6$ alkyl is optionally substituted from 1 to 3 times with substituents as defined in $R^{15}$.

5. The compound according to claim 1, wherein X is substituted bicyclic carbocycle or heterocycle and $R^4$ is selected from the group consisting of H, —OR$^{12}$, —S(O)$_n$R$^{13}$, C(O)R$^{13}$, —NR$^{10}$R$^{11}$, —CN, halogen, and $C_1$-$C_6$ alkyl, wherein each of the $C_1$-$C_6$ alkyl is optionally substituted from 1 to 3 times with substituents as defined in $R^{15}$.

6. The compound according to claim 1, wherein X is substituted monocyclic heterocycle and $R^4$ is substituted monocyclic or bicyclic aryl or heteroaryl.

7. The compound according to claim 1, wherein:
X is phenyl, optionally substituted from 1 to 4 times with substituents as defined in $R^{14}$;
$R^1$ is H, methyl, ethyl, or isopropyl;
$R^2$ is H, methyl, or gem-dimethyl;
$R^3$ is H, methyl, hydroxy, methoxy, fluoro, chloro, cyano, trifluoromethyl, or trifluoromethoxy;
$R^5$ is H, fluoro, chloro, methyl, trifluoromethyl, trifluoromethoxy, cyano, hydroxy or methoxy;
$R^6$ is H, fluoro, chloro, methyl, trifluoromethyl, trifluoromethoxy, cyano, hydroxy or methoxy;
$R^7$ is H, gem-dimethyl, or $C_1$-$C_4$ alkyl, wherein each of the $C_1$-$C_4$ alkyl is optionally substituted from 1 to 3 times with substituents as defined in $R^{15}$;
$R^8$ is H, hydroxy, fluoro, or chloro; and
$R^9$ is H, fluoro, chloro, methyl, hydroxyl, or cyano.

8. The compound according to claim 7, wherein:
$R^4$ is H, halogen, —OR$^{12}$, —S(O)$_n$R$^{13}$, —CN, —C(O)R$^{13}$, —NR$^{10}$R$^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined in $R^{15}$; or
$R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —C(O)R$^{13}$, and —S(O)$_n$R$^{13}$.

9. The compound according to claim 7, wherein $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined in $R^{14}$.

10. The compound according to claim 1, wherein:

X represents a 5- or 6-membered monocyclic heterocycle selected from the group consisting of pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, wherein each of the $C_1$-$C_4$ alkyl is optionally substituted from 1 to 3 times with substituents as defined in $R^{15}$;

$R^8$ is H, hydroxy, fluoro, or chloro; and $R^9$ is H, fluoro, chloro, methyl, hydroxyl, or cyano.

11. The compound according to claim 10, wherein:

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined in $R^{15}$; or $R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$.

12. The compound according to claim 10, wherein $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined in $R^{14}$.

13. The compound according to claim 1, wherein:

X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(31/)-yl, optionally substituted from 1 to 4 times with substituents as defined in $R^{14}$;

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, wherein each of the $C_1$-$C_4$ alkyl is optionally substituted from 1 to 3 times with substituents as defined in $R^{15}$;

$R^8$ is H, hydroxy, fluoro, or chloro; and $R^9$ is H, fluoro, chloro, methyl, hydroxyl, or cyano.

14. The compound according to claim 13, wherein:

$R^4$ is H, halogen —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined in $R^{15}$; or $R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —C(O)$R^{13}$, and —S(O)$_n R^{13}$.

15. The compound according to claim 13, wherein $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, optionally substituted from 1 to 4 times with substituents as defined in $R^{14}$.

16. The compound according to claim 1, wherein:
X is thiophenyl, thiazolyl, pyridinyl, phenyl, naphthyl, benzo[b]thiophenyl, benzofuranyl, benzo[d][1,3]dioxolyl, 2,3-dihydrobenzo[b][1,4]dioxinyl, 3,4-dihydro-2H-benzo[b][1,4]oxazinyl, or 4-methyl-3,4-dihydro-2H-benzo[b][1,4]oxazinyl, optionally substituted with from 1 to 3 substituents selected independently from the group consisting of halogen, methoxy, cyano, trifluoromethyl, trifluoromethoxy, difluoromethoxy, substituted $C_1$-$C_3$ alkyl, methanesulfonyl, carbamoyl, $C_1$-$C_3$ alkyl—Substituted carbamoyl, and acetamido;
$R^1$ is H, methyl, ethyl, isopropyl, 2-hydroxyethyl, 2,2,2-trifluoroethyl, 2-fluoroethyl, or benzyl;
$R^2$ is H or gem-dimethyl;
$R^3$ is H or fluoro;
$R^4$ is H, methoxy, hydroxyl, methyl, fluoro, bromo, cyano, trifluoromethyl, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-pyridazin-3-yloxy, 1,2,4-oxadiazol-3-yl, 3,5-dimethylisoxazol-4-yl, 1H-pyrazol-4-yl, 2-cyanophenyl, 3-cyanophenyl, 4-cyanophenyl, (methanesulfonyl)phenyl, pyridinyl, aminopyridinyl, pyridazin-3-yl, 6-methylpyridazin-3-yl, 6-(trifluoromethyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, (6-(hydroxymethyl)pyridazin-3-yl, pyrimidin-2-yl, pyrimidin-4-yl, pyrimidin-5-yl, pyrazin-2-yl, 2-oxopyridin-1(2H)-yl, 6-oxo-1,6-dihydropyridazin-3-yl, imidazo[1,2-a]pyridin-6-yl, imidazo[1,2-a]pyrazin-3-yl, 3-oxo-[1,2,4]triazolo[4,3-a]pyridin-2(3H)-yl, 5,6-dihydroimidazo[1,2-a]pyrazin-7(8H)-yl, 3-(trifluoromethyl)-5,6-dihydro-[1,2,4]triazolo[4,3-a]pyrazin-7 (8H)-yl, [1,2,4]triazolo[1,5-a]pyridin-6-yl, [1,2,4]triazolo[4,3-a]pyridin-6-yl, or 3,3-dimethyl-2-oxoindolin-5-yl;

$R^5$ is H or fluoro;
$R^6$ is H or fluoro;
$R^7$ is H;
$R^8$ is H, fluoro, or hydroxy; and
$R^9$ is H or hydroxy.

17. The compound according to claim 1, wherein the carbon atom designated * is in the R configuration.

18. The compound according to claim 1, wherein the carbon atom designated * is in the S configuration.

19. The compound according to claim 1, wherein the compound is a (+) stereoisomer.

20. The compound according to claim 1, wherein the compound is a (−) stereoisomer.

21. A pharmaceutical composition comprising a pharmaceutically acceptable carrier and a therapeutically effective amount of the compound according to claim 1.

22. A compound of formula (II) having the following structure:

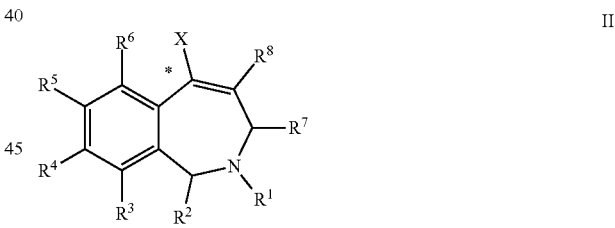

II wherein:
X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$; or
X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$; or $R^4$ is phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(311)-yl, optionally substituted from 1 to 4 times with substituents as defined below in $R^{14}$;

$R^7$ is selected from the group consisting of H, —$S(O)_nR^{13}$, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ is gem-dimethyl;

$R^8$ is H or $C_1$-$C_6$ alkyl, wherein each of $C_1$-$C_6$ alkyl is optionally substituted from 1 to 3 times with substituents as defined below in $R^{15}$;

$R^{10}$ and $R^{11}$ are each independently selected from the group consisting of H, —$C(O)R^{13}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-c]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on a ring carbon with from 1 to 3 times with a substituent selected independently at each occurrence thereof from the group consisting of halogen, cyano, —$OR^{12}$, —$NR^{12}R^{13}$, —$S(O)_nR^{13}$, —$C(O)R^{13}$, and $C_1$-$C_4$ alkyl, or on the additional nitrogen atom from 1 to 3 times with a substituent selected independently at each occurrence thereof from the group consisting of $S(O)_nR^{13}$, —$C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, wherein each of the phenyl, benzyl, and 5- and 6-membered heterocycle is optionally substituted from 1 to 3 times with substituents as defined below in $R^{14}$; or when $R^4$ is —$NR^{10}R^{11}$ or —$C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —$C(O)R^{13}$, and —$S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and —$C(O)R^{13}$, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —$NR^{10}R^{11}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, wherein the heterocycle is optionally substituted from 1 to 3 times with a substituent selected independently at each occurrence thereof from the group consisting of halogen, cyano, —$OR^{10}$, —$S(O)_nR^{10}$, —$C(O)R^{10}$, —$C(O)NR^{10}R^{11}$ and $C_1$-$C_4$ alkyl, wherein each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$NR^{12}C(O)NR^{12}R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, —$NR^{10}R^{11}$, —$S(O)_nR^{13}$, aryl, and heteroaryl, wherein each of the aryl or heteroaryl groups is optionally substituted from 1 to 4 times with substituents as defined above in $R^{14}$;

with the following provisos that (1) when $R^4$ is H, X cannot be phenyl or a phenyl substituted at the para-position with Cl; (2) when $R^4$ is H, OMe, or O-benzyl, X cannot be a phenyl substituted at the para-position with the same $R^4$; and (3) when $R^2$ is a 2-(4-nitrophenoxy)ethyl, $R^5$ cannot be $OC(O)NMe_2$;

or an oxide thereof, or a pharmaceutically acceptable salt thereof.

23. The compound according to claim 22, wherein:

$R^1$ is H, methyl, ethyl, or isopropyl;

$R^2$ is H, methyl, or gem-dimethyl;

$R^3$ is H, methyl, hydroxy, methoxy, fluoro, chloro, cyano, trifluoromethyl, or trifluoromethoxy;

$R^5$ is H, fluoro, chloro, methyl, trifluoromethyl, trifluoromethoxy, cyano, hydroxyl, or methoxy;

$R^6$ is H, fluoro, chloro, methyl, trifluoromethyl, trifluoromethoxy, cyano, hydroxyl, or methoxy;

$R^7$ is H, gem-dimethyl, or $C_1$-$C_4$ alkyl, wherein each of the $C_1$-$C_4$ alkyl is optionally substituted from 1 to 3 times with substituents as defined in $R^{15}$; and $R^8$ is H or $C_1$-$C_3$ alkyl.

24. The compound according to claim 22, wherein:

X is thiophenyl, thiazolyl, pyridinyl, phenyl, naphthyl, benzo[b]thiophenyl, benzofuranyl, benzo[d][1,3]dioxolyl, 2,3-dihydrobenzo[b][1,4]dioxinyl, 3,4-dihydro-2H-benzo[b][1,4]oxazinyl or 4-methyl-3,4-dihydro-2H-benzo[b][1,4]oxazinyl, optionally substituted with from 1 to 3 substituents selected independently from the group consisting of halogen, methoxy, cyano, trifluoromethyl, trifluoromethoxy, difluoromethoxy, substituted $C_1$-$C_3$ alkyl, methanesulfonyl, carbamoyl, $C_1$-$C_3$ alkyl-substituted carbamoyl, and acetamido;

$R^1$ is H, methyl, ethyl, isopropyl, 2-hydroxyethyl, 2,2,2-trifluoroethyl, 2-fluoroethyl, or benzyl;

$R^2$ is H or gem-dimethyl;

$R^3$ is H or fluoro;

$R^4$ is H, methoxy, hydroxyl, methyl, fluoro, bromo, cyano, trifluoromethyl, trifluoromethoxy, acetyl, aminomethyl, 1-aminocyclopropyl, morpholinomethyl, 2-hydroxypropan-2-yl, morpholine-4-carbonyl, 2-morpholinoethoxy, 2-(dimethylamino)ethyl(methyl)amino, 2-hydroxyethylamino, piperidin-1-yl, pyrrolidin-1-yl, piperidin-4-ol, morpholino, piperazin-1-yl, 4-methylpiperazin-1-yl, 4-(ethylsulfonyl)piperazin-1-yl, 4-(2-(isopropylamino)-2-oxoethyl)piperazin-1-yl, 4-(pyridin-2-yl)piperazin-1-yl, 4-(pyrimidin-2-yl)piperazin-1-yl, 2-oxopyrrolidin-1-yl, 2-oxopiperidin-1-yl, 6-methylpyridazin-3-yloxy, 6-pyridazin-3-yloxy, 1,2,4-oxadiazol-3-yl, 3,5-dimethylisoxazol-4-yl, 1H-pyrazol-4-yl, 2-cyanophenyl, 3-cyanophenyl, 4-cyanophenyl, (methanesulfonyl)phenyl, pyridinyl, aminopyridinyl, pyridazin-3-yl, 6-methylpyridazin-3-yl, 6-(trifluoromethyl)pyridazin-3-yl, 6-aminopyridazin-3-yl, 6-(methylamino)pyridazin-3-yl, 6-(dimethylamino)pyridazin-3-yl, 6-morpholinopyridazin-3-yl, 6-(4-hydroxypiperidin-1-yl)pyridazin-3-yl, 6-(4-methylpiperazin-1-yl)pyridazin-3-yl, (6-(hydroxymethyl)pyridazin-3-yl, pyrimidin-2-yl, pyrimidin-4-yl, pyrimidin-5-yl, pyrazin-2-yl, 2-oxopyridin-1(2H)-yl, 6-oxo-1,6-dihydropyridazin-3-yl, imidazo[1,2-a]pyridin-6-yl, imidazo[1,2-a]pyrazin-3-yl, 3-oxo-[1,2,4]triazolo[4,3-a]pyridin-2(3H)-yl, 5,6-dihydroimidazo[1,2-a]pyrazin-7(8H)-yl, 3-(trifluoromethyl)-5,6-dihydro-[1,2,4]triazolo[4,3-a]pyrazin-7(8H)-yl, [1,2,4]triazolo[1,5-a]pyridin-6-yl, [1,2,4]triazolo[4,3-a]pyridin-6-yl, or 3,3-dimethyl-2-oxoindolin-5-yl;

$R^5$ is H or fluoro;

$R^6$ is H or fluoro;

$R^7$ is H; and $R^8$ is H or $C_1$-$C_3$ alkyl.

25. The compound according to claim 22, wherein the compound is a (+) stereoisomer.

26. The compound according to claim 22, wherein the compound is a (−) stereoisomer.

27. A pharmaceutical composition comprising a pharmaceutically acceptable carrier and a therapeutically effective amount of the compound according to claim 22.

28. A process for preparation of a product compound of formulae I(A-E) having the following structure:

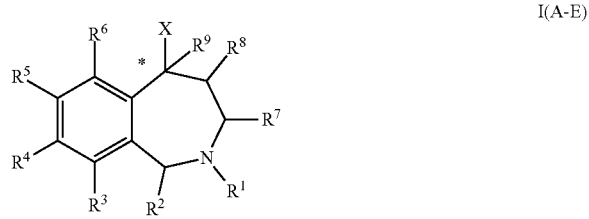

I(A-E)

wherein:

the carbon atom designated * is in the R or S configuration; and

X represents a 5- or 6-membered aromatic or nonaromatic monocyclic carbocycle or heterocycle selected from the group consisting of phenyl, pyridyl, 2-oxo-pyridin-1-yl, pyrimidinyl, pyridazinyl, pyrazinyl, triazinyl, pyranyl, pyrrolyl, furanyl, thiophenyl, oxazolyl, isoxazolyl, thiazolyl, isothiazolyl, pyrazolyl, imidazolyl, oxadiazolyl, thiadiazolyl, triazolyl, and tetrazolyl, optionally substituted from 1 to 4 times with substituents as defined below in $R^{14}$; or X is a [5,5]-, [6,5]-, [6,6]-, or [6,7]-fused bicyclic carbocycle or heterocycle selected from the group consisting of indenyl, indanyl, benzofuranyl, benzothiophenyl, dihydrobenzothiophenyl, dihydrobenzofuranyl, isoindolyl, indolinyl, benzo[1,3]dioxolyl, benzooxazolyl, benzothiazolyl, benzoisothiazolyl, benzoisoxazolyl, indazolyl, benzoimidazolyl, benzotriazolyl, naphthyl, tetrahydronaphthyl, quinolinyl, isoquinolinyl, quinazolinyl, cinnolinyl, phthalazinyl, quinoxalinyl, benzo[1,2,3]triazinyl, benzo[1,2,4]triazinyl, 2,3-dihydro-benzo[1,4]dioxinyl, 4H-chromenyl, dihydrobenzocycloheptenyl, tetrahydrobenzocycloheptenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, benzo[c][1,2,5]oxadiazolyl, benzo[c][1,2,5]thiadiazolyl, 3,4-dihydro-2H-benzo[b][1,4]oxazinyl, imidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$;

$R^1$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$;

$R^2$ is H, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, each of which is optionally substituted from 1 to 3 times with substituents as defined below in $R^{15}$; or $R^2$ is gem-dimethyl;

$R^3$, $R^5$, and $R^6$ are each independently selected from the group consisting of H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^3$, $R^5$, and $R^6$ are each independently a 5- or 6-membered monocyclic carbocycle or heterocycle or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{14}$;

$R^4$ is H, halogen, —$OR^{12}$, —$S(O)_nR^{13}$, —CN, —$C(O)R^{13}$, —$NR^{10}R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, wherein each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^4$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$; or $R^4$ is a monocyclic or bicyclic aryl or heteroaryl selected from the group consisting of phenyl, pyridyl, 2-oxo-pyridin-1-yl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridin-2(3H)-yl, optionally substituted from 1 to 4 times with substituents as defined below in $R^{14}$;

provided that for compounds of formula IA, X is substituted phenyl and $R^4$ is substituted monocyclic or bicyclic aryl or heteroaryl;

provided that for compounds of formula IB, X is substituted bicyclic carbocycle or heterocycle and $R^4$ is substituted monocyclic or bicyclic aryl or heteroaryl;

provided that for compounds of formula IC, X is substituted phenyl and $R^4$ is H, $-OR^{12}$, $-S(O)_nR^{13}$, $C(O)R^{13}$, $-NR^{10}R^{11}$, $-CN$, halogen, or $C_1$-$C_6$ alkyl, wherein each of the $C_1$-$C_6$ alkyl is optionally substituted from 1 to 3 times with substituents as defined below in $R^{15}$;

provided that for compounds of formula ID, X is substituted bicyclic carbocycle or heterocycle and $R^4$ is H, $-OR^{12}$, $-S(O)_nR^{13}$, $C(O)R^{13}$, $-NR^{10}R^{11}$, $-CN$, halogen, or $C_1$-$C_6$ alkyl, wherein each of the $C_1$-$C_6$ alkyl is optionally substituted from 1 to 3 times with substituents as defined below in $R^{15}$; and provided that for compounds of formula IE, X is substituted aromatic monocyclic heterocycle and $R^4$ is substituted monocyclic or bicyclic aryl or heteroaryl;

$R^7$ is selected from the group consisting of H, $-S(O)_nR^{13}$, $-C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$;

$R^8$ is selected from the group consisting of H, halogen, $-OR^{12}$, $-S(O)_nR^{13}$, $-CN$, $-C(O)R^{13}$, $-NR^{10}R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; or $R^7$ and $R^8$ are gem-dimethyl, with the proviso that only one of $R^7$ and $R^8$ is gem-dimethyl;

$R^9$ is H, halogen, $-OR^{12}$, $-SR^{10}$, $C_1$-$C_6$ alkyl, $-CN$, or $-NR^{10}R^{11}$, wherein each of $C_1$-$C_6$ alkyl is optionally substituted from 1 to 3 times with substituents as defined below in $R^{15}$;

$R^{10}$ and $R^{11}$ are each independently selected from the group consisting of H, $-C(O)R^{13}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{10}$ and $R^{11}$ are each independently selected from the group consisting of phenyl, benzyl, and other 5- or 6-membered monocyclic heterocycles, wherein each of the phenyl, benzyl, and 5- or 6-membered monocyclic heterocycle is optionally substituted from 1 to 3 times with substituents as defined below in $R^{14}$;

$R^{10}$ and $R^{11}$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-c]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on a ring carbon with from 1 to 3 times with a substituent selected independently at each occurrence thereof from the group consisting of halogen, cyano, $-OR^{12}$, $-NR^{12}R^{13}$, $-S(O)_nR^{13}$, $-C(O)R^{13}$, and $C_1$-$C_4$ alkyl, or on the additional nitrogen atom from 1 to 3 times with a substituent selected independently at each occurrence thereof from the group consisting of $S(O)_nR^{13}$, $-C(O)R^{13}$, and $C_1$-$C_4$ alkyl, wherein each of $C_1$-$C_4$ alkyl is optionally substituted from 1 to 3 times with substituents as defined below in $R^{15}$;

$R^{10}$ and $R^{11}$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, wherein the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, wherein each of the phenyl, benzyl, and 5- and 6-membered heterocycle is optionally substituted from 1 to 3 times with substituents as defined below in $R^{14}$; or when $R^4$ is —$NR^{10}R^{11}$ or —$C(O)NR^{10}R^{11}$, either $R^{10}$ or $R^{11}$ is a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substituents selected from the group consisting of $C_1$-$C_3$ alkyl, —$C(O)R^{13}$, and —$S(O)_nR^{13}$, or either $R^{10}$ or $R^{11}$ is a $C_1$-$C_3$ alkyl substituted with a bridged bicyclic ring containing 6-12 carbon atoms and optionally containing one or more heteroatoms selected from the group consisting of oxygen, nitrogen, and sulfur, wherein the bridged bicyclic ring is optionally substituted from 1 to 3 times with substitutents selected from the group consisting of $C_1$-$C_3$ alkyl, —$C(O)R^{13}$, and —$S(O)_nR^{13}$;

$R^{12}$ is selected from the group consisting of H, $C_1$-$C_4$ alkyl, $C_3$-$C_6$ cycloalkyl, $C_4$-$C_7$ cycloalkylalkyl, and —$C(O)R^{13}$, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$;

$R^{13}$ is selected from the group consisting of H, —$NR^{10}R^{11}$, $C_1$-$C_4$ alkyl, $C_3$-$C_6$ cycloalkyl, and $C_4$-$C_7$ cycloalkylalkyl, wherein each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{15}$; or $R^{12}$ and $R^{13}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles containing 1-5 heteroatoms selected from the group consisting of oxygen, nitrogen, and sulfur, optionally substituted from 1 to 4 times with substituents as defined below in $R^{14}$; or $R^{12}$ and $R^{13}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, wherein the heterocycle is optionally substituted from 1 to 3 times with a substituent selected independently at each occurrence thereof from the group consisting of halogen, cyano, —$OR^{10}$, —$S(O)_nR^{10}$, —$C(O)R^{10}$, —$C(O)NR^{10}R^{11}$ and $C_1$-$C_4$ alkyl, wherein each of $C_1$-$C_4$ alkyl is optionally substituted from 1 to 3 times with substituents as defined below in $R^{15}$;

n is 0, 1, or 2;

$R^{14}$ is independently selected at each occurrence from a substituent in the group consisting of halogen, —$NO_2$, —$OR^{12}$, —$NR^{10}R^{11}$, —$NR^{12}C(O)_2R^{13}$, —$S(O)_nR^{13}$, —CN, —$C(O)R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{15}$; and $R^{15}$ is independently selected at each occurrence from a substituent in the group consisting of —CN, halogen, $C(O)R^{13}$, $C_1$-$C_3$ alkyl, —$OR^{12}$, —$NR^{10}R^{11}$, —$S(O)_nR^{13}$, aryl, and heteroaryl, wherein each of the aryl or heteroaryl groups is optionally substituted from 1 to 4 times with substituents as defined above in $R^{14}$;

with the following provisos that (1) when $R^4$ is H, X cannot be phenyl; (2) when $R^4$ is (a) $C_{1-6}$ alkyl, (b) $C_{1-4}$ alkoxy, (c) hydroxyl, (d) halogen, or (e) CN, X cannot be a phenyl substituted at the para-position with the same $R^4$; (3) when any one of $R^3$, $R^4$, $R^5$, and $R^6$ is hydrogen, halogen, perhalomethyl, optionally substituted $C_{1-6}$-alkyl, hydroxy, optionally substituted $C_{1-4}$ alkoxy, cyano, amino, optionally substituted mono- or optionally substituted di-$C_{1-4}$ alkylamino, acylamino, or carbamoyl, X cannot be furanyl, thienyl, pyrazolyl, tetrazolyl, isoxazolyl, isothiazolyl, 1,2,3-oxadiazolyl, 1,2,3-thiadiazolyl, 1,2,4-oxadiazolyl, 1,2,4-thiadiazolyl, 1,3,4-oxadiazolyl, 1,3,4-thiadiazolyl, 1,2,5-oxadiazolyl, 1,2,5-thiadiazolyl, benzo[d]isoxazolyl, or benzo[d]isothiazolyl; (4) when $R^4$ is —$S(O)_nR^{13}$, n cannot be 0; and (5) when $R^9$ is a substituted alkyl, $R^{15}$ cannot be —$NR^{10}R^{11}$;

or an oxide thereof, or a pharmaceutically acceptable salt thereof, said process comprising:

treating an intermediate compound of the formula:

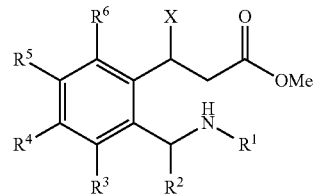

under conditions effective to produce the product compound.

* * * * *

UNITED STATES PATENT AND TRADEMARK OFFICE
CERTIFICATE OF CORRECTION

| | | Page 1 of 1 |
|---|---|---|
| PATENT NO. | : 7,956,050 B2 | |
| APPLICATION NO. | : 11/487884 | |
| DATED | : June 7, 2011 | |
| INVENTOR(S) | : Molino et al. | |

It is certified that error appears in the above-identified patent and that said Letters Patent is hereby corrected as shown below:

Title Page, Item (57) Abstract, ninth line, delete " 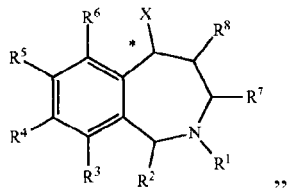 "

and insert -- 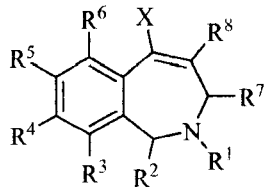 -- in its place.

Signed and Sealed this
Twenty-third Day of August, 2011

David J. Kappos
Director of the United States Patent and Trademark Office

UNITED STATES PATENT AND TRADEMARK OFFICE
CERTIFICATE OF CORRECTION

| | | |
|---|---|---|
| PATENT NO. | : 7,956,050 B2 | Page 1 of 1 |
| APPLICATION NO. | : 11/487884 | |
| DATED | : June 7, 2011 | |
| INVENTOR(S) | : Molino et al. | |

It is certified that error appears in the above-identified patent and that said Letters Patent is hereby corrected as shown below:

Title Page, Item (73) Assignee, third line, insert -- Bristol Myers Squibb Company, Princeton, NJ (US) --

Signed and Sealed this
Sixth Day of December, 2011

David J. Kappos
*Director of the United States Patent and Trademark Office*